US008669266B2

(12) United States Patent
Nazare et al.

(10) Patent No.: US 8,669,266 B2
(45) Date of Patent: Mar. 11, 2014

(54) QUINOLINE-CARBOXAMIDE DERIVATIVES AS P2Y12 ANTAGONISTS

(75) Inventors: Marc Nazare, Wiesbaden (DE); Gernot Zech, Wiesbaden (DE); Melitta Just, Langen (DE); Tilo Weiss, Frankfurt am Main (DE); Gerhard Hessler, Hofheim (DE); Joerg Czech, Marburg (DE)

(73) Assignee: Sanofi, Paris (FR)

( * ) Notice: Subject to any disclaimer, the term of this patent is extended or adjusted under 35 U.S.C. 154(b) by 674 days.

(21) Appl. No.: 12/573,551

(22) Filed: Oct. 5, 2009

(65) Prior Publication Data

US 2010/0135999 A1  Jun. 3, 2010

Related U.S. Application Data

(63) Continuation of application No. PCT/EP2008/002790, filed on Apr. 9, 2008.

(30) Foreign Application Priority Data

Apr. 23, 2007  (EP) .................................... 07008209

(51) Int. Cl.
*A01N 43/42* (2006.01)
*A61K 31/44* (2006.01)

(52) U.S. Cl.
USPC ............ 514/279; 514/247; 514/277; 514/183

(58) Field of Classification Search
None
See application file for complete search history.

(56) References Cited

U.S. PATENT DOCUMENTS

| 5,612,359 | A | 3/1997 | Murugesan et al. |
| 6,043,265 | A | 3/2000 | Murugesan et al. |
| 7,026,323 | B2 * | 4/2006 | Bryant et al. ............... 514/254.1 |
| 2005/0192252 | A1 * | 9/2005 | Sanderink et al. ............... 514/56 |

FOREIGN PATENT DOCUMENTS

| WO | WO 98/57951 | 8/1998 |
| WO | WO 98/37075 | 12/1998 |
| WO | WO 00/01389 | 1/2000 |
| WO | WO 00/76970 A2 | 12/2000 |
| WO | WO 01/40231 A1 | 6/2001 |
| WO | WO 01/47919 A1 | 7/2001 |
| WO | WO 02/44145 A1 | 6/2002 |
| WO | WO 03/026652 A1 | 4/2003 |
| WO | 2004/052366 A1 | 6/2004 |
| WO | WO 2005/009971 A1 | 2/2005 |
| WO | WO 2006/077851 A1 | 7/2006 |
| WO | 2006/114774 A2 | 11/2006 |
| WO | 2007/022241 A2 | 2/2007 |

OTHER PUBLICATIONS

Senear, A.E. et al., "The Synthesis of Potential Antimalarials. 7-Chloro-α-(2-piperidyl)-4-quinolinemethanol," Journal of the American Chemical Society (1946), vol. 68, No. 12, pp. 2695-2697.

Littke, Adam F. et al., "Palladium-Catalyzed Coupling Reactions of Aryl Chlorides," Angewandte Chemie International Edition (2002), vol. 41, pp. 4176-4211.
Muci, Alex R. et al., "Practical Palladium Catalysts for C-N and C-O Bond Formation," Topics in Current Chemistry (2002), vol. 219, pp. 131-209.
Surrey, Alexander R. et al., "Some 7-Substituted 4-Aminoquinoline Derivatives," Journal of the American Chemical Society (1946), vol. 68, No. 1, pp. 113-116.
Tunoori, Ashok Rao et al., "Polymer-Bound Triphenylphosphine as Traceless Reagent for Mitsunobu Reactions in Combinatorial Chemistry: Synthesis of Aryl Ethers from Phenols and Alcohols," Tetrahedron Letters (1998), vol. 39, pp. 8751-8754.
Yang, Bryant H. et al., "Palladium-catalyzed amination of aryl halides and sulfonates," Journal of Organometallic Chemistry (1999), vol. 576, pp. 125-146.
Bryant, Judi A. et al., "Preparation of 2-[(piperazinocarbonylmethl)aminocarbonyl]quinolines as platelet adenosine diphosphate receptor antagonists," Database CA, Chemical Abstracts Service, 2002.

(Continued)

*Primary Examiner* — Jeffrey S. Lundgren
*Assistant Examiner* — Meghan Finn
(74) *Attorney, Agent, or Firm* — Scully, Scott, Murphy & Presser, P.C.

(57) ABSTRACT

The present invention relates to compounds of the formula I,

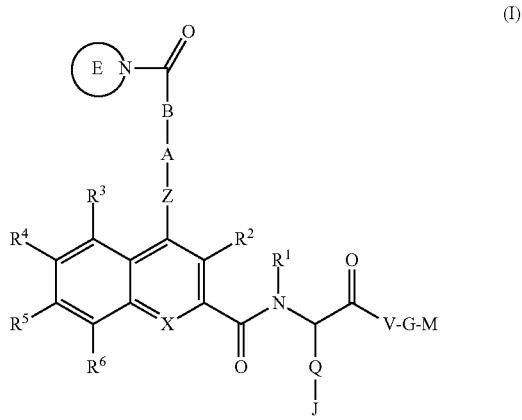

in which $R^1$; $R^2$; $R^3$; $R^4$; $R^5$; $R^6$; Z; A; B; E; X; Q; J; V; G and M have the meanings indicated in the claims. The compounds of the formula I are valuable pharmacologically active compounds. They exhibit a strong anti-aggregating effect on platelets and thus an anti-thrombotic effect and are suitable e.g. for the therapy and prophylaxis of cardio-vascular disorders like thromboembolic diseases or restenoses. They are reversible antagonists of the platelet ADP receptor P2Y12, and can in general be applied in conditions in which an undesired activation of the platelet ADP receptor P2Y12 is present or for the cure or prevention of which an inhibition of the platelet ADP receptor P2Y12 is intended. The invention furthermore relates to processes for the preparation of compounds of the formula I, their use, in particular as active ingredients in pharmaceuticals, and pharmaceutical preparations comprising them.

12 Claims, No Drawings

(56) References Cited

OTHER PUBLICATIONS

Dangelmaier, Carol et al., "Potentiation of Thromboxane $A_2$-induced Platelet Secretion by Gi Signaling through the Phosphoinositide-3 Kinase Pathway," Journal of Thrombosis and Haemostasis (2001), vol. 85, pp. 341-348.
Gachet, Christian et al., "Purinoceptors on blood platelets: further pharmacological and clinical evidence to suggest the presence of two ADP receptors," British Journal of Haematology (1995), vol. 91, pp. 434-444.
Gachet, Christian, "ADP Receptors of Platelets and their Inhibition," Journal of Thrombosis and Haemostasis (2001), vol. 86, pp. 222-232.
Su, De-Bao et al., "Methyl Chlorodifluoroacetate A Convenient Trifluoromethylating Agent," Tetrahedron Letters (1991), vol. 32, pp. 7689-7690.
Coffey, D. Scott et al., "Six-Membered Ring Systems: Pyridines and Benzo Derivatives," Progress in Heterocyclic Chemistry (2001), vol. 13, pp. 238-260.
Hughes, D.L. et al., "A Mechanistic Study of the Mitsunobu Esterification Reaction," Journal of the American Chemical Society (1988), vol. 110, pp. 6487-6491.
Mills, David C.B., "ADP Receptors on Platelets," Thrombosis and Haemostasis (1996), vol. 76, pp. 835-856.
Camp, David et al., "Mechanism of the Mitsunobu Esterification Reaction. 1. The Involvement of Phosphoranes and Oxyphosphonium Salts," The Journal of Organic Chemistry (1989), vol. 54, pp. 3045-3049.
Crich, David et al., "Some Observation on the Mechanism of the Mitsunobu Reaction," The Journal of Organic Chemistry (1989), vol. 54, pp. 257-259.
Nichols, David E. et al., "1-(2,5-Dimethoxy-4-(trifluoromethyl)phenyl)-2-aminopropane: A Potent Serotonin 5-$HT_{2A/2C}$ Agonist," The Journal of Medicinal Chemistry (1994), vol. 37, pp. 4346-4357.
Bundgaard, Hans, "Bioreversible derivatives for various functional groups and chemical entities," Elsevier (1985), pp. 1-92.
Testa, Bernard et al., "Hydrolysis in Drug and Prodrug Metabolism," Wiley-VHC (2003), pp. 1-9.
Mustard, J. Fraser et al., "[1] Isolation of Human Platelets from Plasma by Centrifugation and Washing," Methods in Enzymology (1989), vol. 169, pp. 3-11.
Herbert, J.M. et al., "Inhibitory Effect of Clopidogrel on Platelet Adhesion and Intimal Proliferation After Arterial Injury in Rabbits," Arteriosclerosis, Thrombosis, and Vascular Biology (1993), vol. 13, pp. 1171-1179.
Herbert, J.M. et al., "Clopidogrel, A Novel Antiplatelet and Antithrombotic Agent," Cardiovascular Drug Reviews (1993), vol. 11, pp. 180-198.
Maffrand, J.P. et al., "ADP Plays a Key Role in Thrombogenesis in Rats," Thrombosis and Haemostasis (1988), vol. 59, pp. 225-230.
Pelletier, Jeffrey C. et al., "Mitsunobu reaction modifications allowing product isolation without chromatography: application to a small parallel library," Tetrahedron Letters (2000), vol. 41, pp. 797-800.
Folts, John D. et al., "Platelet Aggregation in Partially Obstructed Vessels and its Elimination with Aspirin," Circulation (1976), vol. 54, pp. 365-370.
Wolfe, John P. et al., "Simple, Efficient Catalyst System for the Palladium-Catalyzed Amination of Aryl Chlorides, Bromides, and Triflates," The Journal of Organic Chemistry (2000), vol. 65, pp. 1158-1174.
Kunapuli, Satya P. et al., "ADP Receptors—Targets for Developing Antithrombotic Agents," Current Pharmaceutical Design (2003), vol. 9, pp. 2303-2316.
Bundgaard, Hans, "Novel chemical approaches in prodrug design," Drugs of the Future (1991), vol. 16, pp. 443-458.
Netherton, Matthew R. et al., "Palladium-Catalyzed Cross-Coupling Reactions of Unactivated Alkyl Electrophiles with Organometallic Compounds," Topics in Organometallic Chemistry (2005), vol. 14, pp. 85-108.
Ahmad, Nadia M. et al., "Palladium in Quinoline Synthesis," Advances in Heterocyclic Chemistry (2003), vol. 84, pp. 1-30.
Peet, Norton P. et al., "Synthesis and Antiallergic Activity of Some Quinolinones and Imidazoquinolinones," Journal of Medicinal Chemistry (1985), vol. 28, pp. 298-302.
Savi, P. et al., "Identification and Biological Activity of the Active Metabolite of Clopidogrel," Journal of Thrombosis and Haemostasis (2000), vol. 84, pp. 891-896.
Andre, Patrick et al., "$P2Y_{12}$ regulates platelet adhesion/activation, thrombus growth, and thrombus stability in injured arteries," The Journal of Clinical Investigation (2003), vol. 112, pp. 398-406.
Lam, Patrick Y.S. et al., "New Aryl/Heteroaryl C-N Bond Cross-coupling Reactions via Arylboronic Acid/Cupric Acetate Arylation," Tetrahedron Letters (1998), vol. 39, pp. 2941-2944.
Chong, R.J. et al., "Synthetic Connections to the Aromatic Directed Metalation Reaction. A Modified von Niementowski Quinoline Synthesis from Anthranilamides," Tetrahedron Letters (1986), vol. 27, pp. 5323-5326.
Fleisher, David et al., "Improved oral drug delivery: solubility limitations overcome by the use of prodrugs," Advanced Drug Delivery Reviews (1996), vol. 19, pp. 115-130.
Larsen, R.D. et al., "Science of Synthesis," Georg Thieme Verlag, Stuttgart, Germany 2005 vol. 15.3, pp. 389-550.
Larsen, R.D. et al., "Science of Synthesis," Georg Thieme Verlag, Stuttgart, Germany (2005), vol. 15.4, pp. 551-660.
Humphries, R.G. et al., "Pharmacological profile of the novel $P_{2T}$-purinoceptor antagonist, FPL 67085 in vitro and in the anaesthetized rat in vivo," British Journal of Pharmacology (1995), vol. 115, pp. 1110-1116.
Kwong, Fuk Yee et al., "Copper-Catalyzed Coupling of Alkylamines and Aryl Iodides: An Efficient System Even in an Air Atmosphere," Organic Letters (2002), vol. 4, pp. 581-584.
Torii, Sigeru et al., "A Direct Approach to 2-Substituted 1,4-Dihydro-4-Oxo-Quinoline-3-Carboxylates by Palladium-Catalyzed Carbonylative Cyclization," Tetrahedron Letters (1990), vol. 31, pp. 7175-7178.
Torii, Sigeru et al., "Syntheses of Chromones and Quinolones via Pd-Catalyzed Carbonylation of o-Iodophenols and Anilines in the Presence of Acetylenes," Tetrahedron (1993), vol. 49, pp. 6773-6784.
Coltman, Stephen C.W. et al., "A New Efficient Route to 4-Oxo-1,4-dihydroquinoline-2-carboxylic Esters," Synthesis (1984), pp. 150-152.
Klapars, Artis et al., "A General and Efficient Copper Catalyst for the Amidation of Aryl Halides and the N-Arylation of Nitrogen Heterocycles," Journal of the American Chemical Society (2001), vol. 123, pp. 7727-7729.
Kang, Suk-Ku et al., "Copper-catalyzed N-Arylation of Aryl Iodides with Benzamides or Nitrogen Heterocycles in the Presence of Ethylenediamine," Synlett (2002), No. 3, pp. 427-430.
Urata, Hisao et al., "A Novel and Convenient Method for Trifluoromethylation of Organic Halides Using $CF_3SiR'_3$/KF/Cu(I) System," Tetrahedron Letters (1991), vol. 32, pp. 91-94.
Sakamoto, Takao et al., "Palladium-catalyzed cyanation of aryl and heteroaryl iodides with copper(I) cyanide," Journal of the American Chemical Society, Perkin Transactions 1 (1999), pp. 2323-2326.
Corey, E.J. et al., "Total Synthesis of the Quinonoid Alcohol Dehydrogenase Coenzyme (1) of Methylotrophic Bacteria," Journal of the American Chemical Society (1981), vol. 103, pp. 5599-5600.
Steck, Edgar A. et al., "The Synthesis of 3-Methyl-4-(1'-methyl-4'-diethylaminobutyl-amino)-quinoline and Some 6-Substituted Derivatives" Journal of the American Chemical Society (1946), vol. 68, pp. 129-132.
Qing, Feng-Ling et al., "First synthesis of ortho-trifluoromethylated aryl triflates," Journal of the Chemical Society, Perkins Transactions 1 (1997), pp. 3053-3057.
Chan, Dominic M.T. et al., "New N- and O-Arylations with Phenylboronic Acids and Cupric Acetate," Tetrahedron Letters (1998), vol. 39, pp. 2933-2936.
European Search Report dated Sep. 17, 2007.
International Search Report dated Sep. 5, 2008.

* cited by examiner

QUINOLINE-CARBOXAMIDE DERIVATIVES AS P2Y12 ANTAGONISTS

FIELD OF THE INVENTION

The present invention relates to compounds of the formula I,

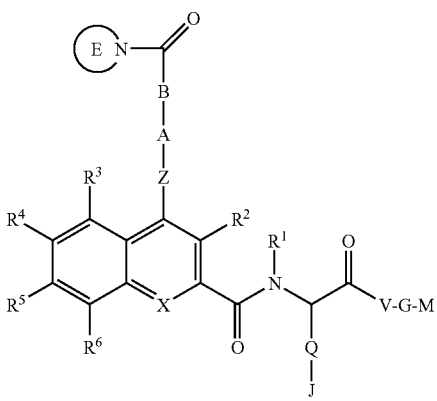

in which $R^1$; $R^2$; $R^3$; $R^4$; $R^5$; $R^6$; Z; A; B; E; X; Q; J; V; G and M have the meanings indicated below. The compounds of the formula I are valuable pharmacologically active compounds. They exhibit a strong anti-aggregating effect on platelets and thus an anti-thrombotic effect and are suitable e.g. for the therapy and prophylaxis of cardio-vascular disorders like thromboembolic diseases or restenoses. They are reversible antagonists of the platelet ADP receptor P2Y12, and can in general be applied in conditions in which an undesired activation of the platelet ADP receptor P2Y12 is present or for the cure or prevention of which an inhibition of the platelet ADP receptor P2Y12 is intended. The invention furthermore relates to processes for the preparation of compounds of the formula I, their use, in particular as active ingredients in pharmaceuticals, and pharmaceutical preparations comprising them.

BACKGROUND OF THE INVENTION

In the industrialized world thrombotic complications are one of the major causes of death. Examples of conditions associated with pathological thrombus formation include deep vein thrombosis, venous and arterial thromboembolism, thrombophlebitis, coronary and cerebral arterial thrombosis, cerebral embolism, renal embolism and pulmonary embolism, disseminated intravascular coagulation, transient ischemic attacks, strokes, acute myocardial infarction, unstable angina, chronic stable angina, peripheral vascular disease, preeclampsia/eclampsia, and thrombotic cytopenic purpura. Also during or following invasive procedures, including insertion of endovascular devices and protheses, carotid endarterectomy, angioplasty, CABG (coronary artery bypass graft) surgery, vascular graft surgery, and stent placements, thrombotic and restenotic complications could occur.

Platelet adhesion and aggregation play a critical role in these intravascular thrombotic events. Platelets can be activated by mediators released from circulating cells and damaged endothelial cells lining the vessel or by exposed subendothelial matrix molecules such as collagen, or by thrombin, which is formed in the coagulation cascade. Furthermore platelets can be activated under conditions of high shear blood flow in diseased vessels. Following activation, platelets, which normally circulate freely in the vasculature, and other cells, accumulate at the site of a vessel injury to form a thrombus and recruit more platelets to the developing thrombus. During this process, thrombi can grow to a sufficient size to partly or completely block arterial blood vessels.

In veins thrombi can also form in areas of stasis or slow blood flow. These venous thrombi can create emboli that travel through the circulatory system, as they easily detach portions of themselves. These traveling emboli can block other vessels, such as pulmonary or coronary arteries, which can result in the above-mentioned pathological outcomes such as pulmonary or coronary embolism.

In summary, for venous thrombi, morbidity and mortality arise primarily after embolization or distant blockade of vessels, whereas arterial thrombi cause serious pathological conditions by local blockade.

It was demonstrated by many studies that ADP (adenosine 5'-diphosphate) is an important mediator of platelet activation and aggregation. It therefore plays a key role in the initiation and progression of arterial thrombus formation (Maffrand, et al., Thromb. Haemostas. (1988); 59: 225-230; Herbert, et al., Arterioscl. Thromb. (1993), 13: 1171-1179).

Upon activation by various agents, such as collagen and thrombin, ADP is released from blood platelets in the vasculature, as well as from damaged blood cells, endothelium or tissues. The ADP-induced platelet aggregation is triggered by its binding to two specific G protein-coupled receptors expressed on the plasma membrane of human platelets: $P2Y_1$, and $P2Y_{12}$. ADP binding to these receptors induces inhibition of adenylyl cyclase and modulation of intracellular signaling pathways such as influx and mobilization of intracellular $Ca^{2+}$, activation of phosphoinositide-3 kinase (PI3K), shape change, secretion of other mediators, and platelet aggregation (Dangelmaier, et al. Thromb. Haemost. (2001), 85: 341-348). Activation by ADP results in the recruitment of more platelets and stabilization of existing platelet aggregates. Activation of the $P2Y_1$ receptor leads to calcium mobilization from intracellular stores, platelet shape change and initiation of aggregation.

Activation of the $P2Y_{12}$ receptor (also referred to as HORK3, P2RY12, SP1999, P2TAC, or P2YAC) by ADP, leads to inhibition of adenylyl cyclase and activation of PI3K. Activation of $P2Y_{12}$ is required for platelet secretion and stabilization of platelet aggregates (Gachet, Thromb. Haemost. (2001), 86, 222-232; Andre, et al., J. Clin. Invest., (2003), 112, 398-406). There are several reports about directly or indirectly acting synthetic inhibitors of ADP-dependent platelet aggregation, which show antithrombotic activity.

The orally active thienopyridines, ticlopidine and clopidogrel, react covalently with the $P2Y_{12}$ receptor and lead to an irreversible platelet inhibition in vivo. They also inhibit binding of radiolabeled ADP receptor agonist 2-methylthioadenosine 5'-diphosphate to platelets, and other ADP-dependent events (Savi, et al., Thromb Haemost. (2000), 84: 891-896).

Bryant et al. (WO 2002/098856 and WO2004/052366) disclose quinoline derivatives, useful as antithrombotic agents via inhibition of the platelet ADP receptor. Watanuki et al. WO2005/009971 and Koga et al. WO2006/077851 disclose quinolone derivatives and 4-quinolone-3-carboxamide derivatives as P2Y12 inhibitors However, besides being effective P2Y12 antagonists, which antagonize the effect of endogenous ADP on its platelet ADP receptor, it is desirable that such antagonists also have further advantageous properties, for instance stability in plasma and liver and selectivity versus other receptors whose agonism or antagonism is not intended. There is an ongoing need for further low molecular weight P2Y12 antagonist, which are effective and have the above advantages as well.

DESCRIPTION OF THE INVENTION

The present invention satisfies the above needs by providing novel compounds of the formula I, which exhibit better P2Y12 antagonistic activity and are favorable agents with high bioavailability.

Thus, the present invention relates to compounds of formula I,

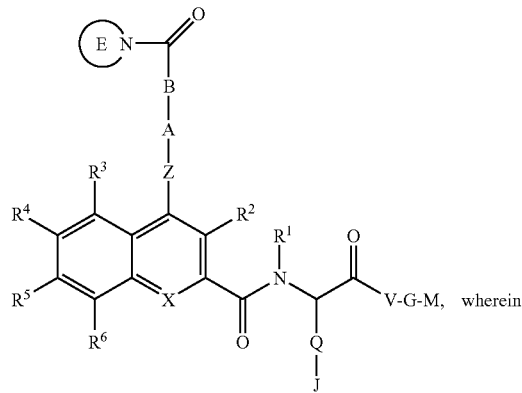

(I)

E is 3- to 10-membered heterocyclic residue, containing one nitrogen atom and up to 0, 1, 2, or 3 additional heteroatoms chosen from nitrogen, sulfur or oxygen, wherein said heterocyclic residue is monocyclic, bicyclic or a spiro-heterocycle and is bond by its nitrogen atom to the carbonyl carbon atom and wherein said heterocyclic residue is unsubstituted or mono-, di- or trisubstituted independently of one another by R7, X is selected from nitrogen atom or C—R8, Q is selected from
1) a covalent bond,
2) —($C_2$-$C_{10}$)-alkenyl-,
3) —($C_2$-$C_{10}$)-alkynyl-,
4) —($C_0$-$C_4$)-alkylene-CH(OH)—($C_0$-$C_4$)-alkylene-,
5) —($C_0$-$C_4$)-alkylene-O—($C_0$-$C_4$)-alkylene-,
6) —($C_0$-$C_4$)-alkylene-O—C(O)—N(R10)-($C_0$-$C_4$)-alkylene-,
7) —($C_0$-$C_4$)-alkylene-C(O)—($C_0$-$C_4$)-alkylene-,
8) —($C_0$-$C_4$)-alkylene-C(O)—O—($C_0$-$C_4$)-alkylene-,
9) —($C_0$-$C_4$)-alkylene-C(O)—N(R10)-,
10) —($C_0$-$C_4$)-alkylene-N(R10)-($C_0$-$C_4$)-alkylene-,
11) —($C_0$-$C_4$)-alkylene-N(R10)-C(O)—($C_0$-$C_4$)-alkylene-,
12) —($C_0$-$C_4$)-alkylene-N(R10)-C(O)—O—($C_0$-$C_4$)-alkylene-,
13) —($C_0$-$C_4$)-alkylene-N(R10)-C(O)—N(R10)-($C_0$-$C_4$)-alkylene-,
14) —($C_0$-$C_4$)-alkylene-N(R10)-$SO_2$—($C_0$-$C_4$)-alkylene-,
15) —($C_0$-$C_4$)-alkylene-N(R10)-$SO_2$—$NR^{10}$—($C_0$-$C_4$)-alkylene-,
16) —($C_0$-$C_4$)-alkylene-S—($C_0$-$C_4$)-alkylene-,
17) —($C_0$-$C_4$)-alkylene-S(O)—($C_0$-$C_4$)-alkylene-,
18) —($C_0$-$C_4$)-alkylene-$SO_2$—($C_0$-$C_4$)-alkylene-,
19) —($C_0$-$C_4$)-alkylene-$SO_2$—N(R10)-($C_0$-$C_4$)-alkylene-,
20) —($C_0$-$C_4$)-alkylene-($C_3$-$C_8$)-cycloalkyl-($C_0$-$C_4$)-alkylene-,
21) —($C_0$-$C_4$)-alkylene-phenyl-($C_6$-$C_{14}$)-aryl, or
22) —($C_0$-$C_4$)-alkylene-heterocyclyl-($C_0$-$C_4$)-alkylene-, wherein heterocyclyl is mono or bicyclic and contains 3 to 15 ring carbon atoms and wherein one or more of the ring carbon atoms are replaced by 1, 2, 3 or 4 heteroatoms chosen from nitrogen, sulfur or oxygen, and wherein said heterocyclyl is unsubstituted or mono-, di- or trisubstituted independently of one another by R14; and wherein the alkyl residues are unsubstituted or mono-, di- or trisubstituted independently of one another by halogen, —$NH_2$, —OH; or —($C_3$-$C_6$)-cycloalkyl, wherein cycloalkyl is unsubstituted or mono-, di- or trisubstituted independently of one another by halogen, —$NH_2$ or —OH;

J is
1) hydrogen atom,
2) —($C_1$-$C_6$)-alkyl, wherein alkyl is unsubstituted or mono-, di- or trisubstituted independently of one another by R13,
3) —($C_0$-$C_4$)-alkylene-O—$CH_2$—($C_1$-$C_3$)-fluoroalkylene-$CH_2$—O—($C_1$-$C_4$)-alkyl,
4) —($C_0$-$C_4$)-alkylene-C(O)—R11,
5) —($C_0$-$C_4$)-alkylene-C(O)—O—R11,
6) —($C_0$-$C_4$)-alkylene-C(O)—O—($C_1$-$C_4$)-alkylene-O—C(O)—R17, wherein —($C_1$-$C_4$)-alkylene is unsubstituted or mono-, di- or trisubstituted independently of one another by R15,
7) —($C_0$-$C_4$)-alkylene-C(O)—O—($C_1$-$C_4$)-alkylene-O—C(O)—O—R17, wherein —($C_1$-$C_4$)-alkylene is unsubstituted or mono-, di- or trisubstituted independently of one another by R15,
8) —($C_0$-$C_4$)-alkylene-C(O)—N(R11)-R13
9) —($C_0$-$C_4$)-alkylene-N(R11)-R13,
10) —($C_0$-$C_4$)-alkylene-N(R10)-$SO_2$—R10,
11) —($C_0$-$C_4$)-alkylene-S—R10,
12) —($C_0$-$C_4$)-alkylene-$SO_s$—R11, wherein s is 1 or 2,
13) —($C_0$-$C_4$)-alkylene-$SO_t$—N(R11)-R12, wherein t is 1 or 2,
14) —($C_0$-$C_4$)-alkylene-$SO_w$—N(R11)-R13, wherein w is 1 or 2,
15) —($C_0$-$C_4$)-alkylene-R22,
16) —($C_0$-$C_4$)-alkylene-($C_3$-$C_8$)-cycloalkyl, wherein cycloalkyl is unsubstituted or mono-, di- or trisubstituted independently of one another by R13,
17) —($C_0$-$C_4$)-alkylene-($C_6$-$C_{14}$)-aryl, wherein aryl is unsubstituted or mono-, di- or trisubstituted independently of one another by R13, or
18) —($C_0$-$C_4$)-alkylene-($C_3$-$C_{15}$)-heterocyclyl, wherein heterocyclyl is un-substituted or mono-, di- or trisubstituted independently of one another by R13, R1 is a hydrogen atom, —($C_1$-$C_4$)-alkyl, wherein alkyl is unsubstituted or substituted one to three times by R13; —($C_1$-$C_3$)-alkylene-C(O)—NH—R10, or —($C_1$-$C_3$)-alkylene-C(O)—O—R10, Z is
1) —($C_0$-$C_8$)-alkylene-,
2) —($C_2$-$C_{10}$)-alkenyl-,
3) —($C_2$-$C_{10}$)-alkynyl-,
4) —($C_0$-$C_4$)-alkylene-O—($C_0$-$C_4$)-alkylene-,
5) —($C_0$-$C_4$)-alkylene-O—C(O)—N(R10)-($C_0$-$C_4$)-alkylene-,
6) —($C_0$-$C_4$)-alkylene-C(O)—($C_0$-$C_4$)-alkylene-,
7) —($C_0$-$C_4$)-alkylene-N(R10)-($C_0$-$C_4$)-alkylene-, 8) —($C_0$-$C_4$)-alkylene-N(R10)-C(O)—($C_0$-$C_4$)-alkylene-,
9) —($C_0$-$C_4$)-alkylene-N(R10)-C(O)—O—($C_0$-$C_4$)-alkylene-,
10) —($C_0$-$C_4$)-alkylene-N(R10)-C(O)—N(R10)-($C_0$-$C_4$)-alkylene-,
11) —($C_0$-$C_4$)-alkylene-N(R10)-$SO_2$—($C_0$-$C_4$)-alkylene-,
12) —($C_0$-$C_4$)-alkylene-N(R10)-$SO_2$—N(R10)-($C_0$-$C_4$)-alkylene-,
13) —($C_0$-$C_4$)-alkylene-S—($C_0$-$C_4$)-alkylene-,
14) —($C_0$-$C_4$)-alkylene-S(O)—($C_0$-$C_4$)-alkylene-,
15) —($C_0$-$C_4$)-alkylene-$SO_2$—($C_0$-$C_4$)-alkylene-,
16) —($C_0$-$C_4$)-alkylene-$SO_2$—N(R10)-($C_0$-$C_4$)-alkylene-, or
17) —($C_0$-$C_4$)-alkylene-($C_3$-$C_8$)-cycloalkyl-($C_0$-$C_4$)-alkylene-, A is selected from a covalent bond, —($C_3$-$C_8$)-alkylene, —($C_3$-$C_8$)-cycloalkylene or —($C_3$-$C_{15}$)-heterocyclyl, B is
1) a covalent bond,
2) —($C_2$-$C_{10}$)-alkenyl-,
3) —($C_2$-$C_{10}$)-alkynyl-,
4) —($C_0$-$C_4$)-alkylene-CH(OH)—($C_0$-$C_4$)-alkylene-,
5) —($C_0$-$C_4$)-alkylene-O—($C_0$-$C_4$)-alkylene-,
6) —($C_0$-$C_4$)-alkylene-O—C(O)—N(R10)-($C_0$-$C_4$)-alkylene-,
7) —($C_0$-$C_4$)-alkylene-C(O)—($C_0$-$C_4$)-alkylene-,
8) —($C_0$-$C_4$)-alkylene-C(O)—O—($C_0$-$C_4$)-alkylene-,
9) —($C_0$-$C_4$)-alkylene-C(O)—N(R10)-,
10) —($C_0$-$C_4$)-alkylene-N(R10)-($C_0$-$C_4$)-alkylene-,
11) —($C_0$-$C_4$)-alkylene-N(R10)-C(O)—($C_0$-$C_4$)-alkylene-,
12) —($C_0$-$C_4$)-alkylene-N(R10)-C(O)—O—($C_0$-$C_4$)-alkylene-,
13) —($C_0$-$C_4$)-alkylene-N(R10)-C(O)—N(R10)-($C_0$-$C_4$)-alkylene-,
14) —($C_0$-$C_4$)-alkylene-N(R10)-$SO_2$—($C_0$-$C_4$)-alkylene-,
15) —($C_0$-$C_4$)-alkylene-N(R10)-$SO_2$—N(R10)-($C_0$-$C_4$)-alkylene-,
16) —($C_0$-$C_4$)-alkylene-S—($C_0$-$C_4$)-alkylene-,
17) —($C_0$-$C_4$)-alkylene-S(O)—($C_0$-$C_4$)-alkylene-,
18) —($C_0$-$C_4$)-alkylene-$SO_2$—($C_0$-$C_4$)-alkylene-,
19) —($C_0$-$C_4$)-alkylene-$SO_2$—N(R10)-($C_0$-$C_4$)-alkylene-,
20) —($C_0$-$C_4$)-alkylene-($C_3$-$C_8$)-cycloalkyl-($C_0$-$C_4$)-alkylene-, or
21) —($C_0$-$C_4$)-alkylene-heterocyclyl-($C_0$-$C_4$)-alkylene-, wherein heterocyclyl is a 3- to 7-membered cyclic residue, containing up to 1, 2, 3 or 4 heteroatoms chosen from nitrogen, sulfur or oxygen, wherein said cyclic residue is unsubstituted or mono-, di- or trisubstituted independently of one another by R14, and wherein the alkyl residues are unsubstituted or mono-, di- or trisubstituted independently of one another by halogen, —$NH_2$, —OH; or —($C_3$-$C_6$)-cycloalkyl, wherein cycloalkyl is unsubstituted or mono-, di- or trisubstituted independently of one another by halogen, —$NH_2$ or —OH;

R14 is halogen, —OH, =O, —($C_1$-$C_8$)-alkyl, —($C_1$-$C_4$)-alkoxy, —$NO_2$, —CN, —$NH_2$, —S—R18, —($C_1$-$C_4$)-alkylene-C(O)—OH, —C(O)—O—($C_1$-$C_4$)-alkyl, —($C_1$-$C_4$)-alkylene-C(O)—$NH_2$, —($C_0$-$C_8$)-alkylene-$SO_2$—($C_1$-$C_4$)-alkyl, —($C_0$-$C_8$)-alkylene-$SO_2$—($C_1$-$C_3$)-fluoroalkyl, —($C_0$-$C_8$)-alkylene-$SO_2$—N(R18)-R21, —($C_1$-$C_4$)-alkylene-C(O)—NH—($C_1$-$C_8$)-alkyl, —($C_1$-$C_4$)-alkylene-C(O)—N—[($C_1$-$C_8$)-alkyl]$_2$, —N(R18)-C(O)—NH—($C_1$-$C_8$)-alkyl, hydrogen, —N(R18)-C(O)—NH—[($C_1$-$C_8$)-alkyl]$_2$, —($C_2$-$C_{10}$)-alkenyl, or —($C_2$-$C_{10}$)-alkynyl, wherein R18 and R21 are independently from each other hydrogen atom, —($C_1$-$C_3$)-fluoroalkyl or —($C_1$-$C_6$)-alkyl, V is a monocyclic or bicyclic 3- to 15-membered heterocyclyl or —N(R1)-($C_3$-$C_{15}$)-heterocyclyl, wherein heterocyclyl is unsubstituted or mono-, di- or trisubstituted independently of one another by R14, G is
1) a covalent bond,
2) —($C_2$-$C_{10}$)-alkenyl-,
3) —($C_2$-$C_{10}$)-alkynyl-,
4) —($C_0$-$C_4$)-alkylene-CH(OH)—($C_0$-$C_4$)-alkylene-,
5) —($C_0$-$C_4$)-alkylene-O—($C_0$-$C_4$)-alkylene-,
6) —($C_0$-$C_4$)-alkylene-O—C(O)—N(R10)-($C_0$-$C_4$)-alkylene-,
7) —($C_0$-$C_4$)-alkylene-C(O)—($C_0$-$C_4$)-alkylene-,
8) —($C_0$-$C_4$)-alkylene-C(O)—O—($C_0$-$C_4$)-alkylene-,
9) —($C_0$-$C_4$)-alkylene-C(O)—N(R10)-,
10) —($C_0$-$C_4$)-alkylene-N(R10)-($C_0$-$C_4$)-alkylene-,
11) —($C_0$-$C_4$)-alkylene-N(R10)-C(O)—($C_0$-$C_4$)-alkylene-,
12) —($C_0$-$C_4$)-alkylene-N(R10)-C(O)—O—($C_0$-$C_4$)-alkylene-,
13) —($C_0$-$C_4$)-alkylene-N(R10)-C(O)—N(R10)-($C_0$-$C_4$)-alkylene-,
14) —($C_0$-$C_4$)-alkylene-N(R10)-$SO_2$—($C_0$-$C_4$)-alkylene-,
15) —($C_0$-$C_4$)-alkylene-N(R10)-$SO_2$—N(R10)-($C_0$-$C_4$)-alkylene-,
16) —($C_0$-$C_4$)-alkylene-S—($C_0$-$C_4$)-alkylene-,
17) —($C_0$-$C_4$)-alkylene-S(O)—($C_0$-$C_4$)-alkylene-,
18) —($C_0$-$C_4$)-alkylene-$SO_2$—($C_0$-$C_4$)-alkylene-,
19) —($C_0$-$C_4$)-alkylene-$SO_2$—N(R10)-($C_0$-$C_4$)-alkylene-,
20) —($C_0$-$C_4$)-alkylene-($C_3$-$C_8$)-cycloalkyl-($C_0$-$C_4$)-alkylene-, or
21) —($C_0$-$C_4$)-alkylene-heterocyclyl-($C_0$-$C_4$)-alkylene-, wherein heterocyclyl is a 3- to 7-membered cyclic residue, containing up to 1, 2, 3 or 4 heteroatoms chosen from nitrogen, sulfur or oxygen, wherein said cyclic residue is unsubstituted or mono-, di- or trisubstituted independently of one another by R14; and wherein the alkyl residues are unsubstituted or mono-, di- or trisubstituted independently of one another by halogen, —$NH_2$, —OH; or —($C_3$-$C_6$)-cycloalkyl, wherein cycloalkyl is unsubstituted or mono-, di- or trisubstituted independently of one another by halogen, —$NH_2$ or —OH;

M is
1) a hydrogen atom,
2) —($C_1$-$C_8$)-alkyl, wherein alkyl is unsubstituted or mono-, di- or trisubstituted independently of one another by R14,
3) —($C_1$-$C_8$)-alkylen-N(R10)$_2$,
4) —C(O)—O—R12,
5) —C(O)—N(R11)-R12,
6) —($C_3$-$C_8$)-cycloalkyl, wherein said cycloalkyl is unsubstituted or mono-, di- or trisubstituted independently of one another by R14, or
7) —($C_6$-$C_{14}$)-aryl, wherein aryl is unsubstituted or mono-, di- or trisubstituted independently of one another by R14,
8) a 3- to 7-membered heterocyclyl, containing 1, 2, 3 or 4 heteroatoms chosen from nitrogen, sulfur or oxygen, wherein said cyclic residue is unsubstituted or mono-, di- or trisubstituted independently of one another by R14, R2, R3, R4, R5, R6 and R8 are independently of one another selected from
1) hydrogen atom,
2) —($C_1$-$C_6$)-alkyl, wherein alkyl is unsubstituted or mono-, di- or trisubstituted independently of one another by R13,
3) —($C_0$-$C_4$)-alkylene-O—R10,
4) halogen,
5) —($C_1$-$C_3$)-fluoroalkyl,
6) —CN or
7) phenyl, wherein phenyl is unsubstituted or mono-, di- or trisubstituted independently of one another by R13, or R3 and R4, R4 and R5 or R5 and R6 are each time both —O—R10 and form together with the atoms which they are attached to a 5- or 6-membered ring, which is unsubstituted or substituted one, two, three or four times by R13, R3 and R4, R4 and R5 or R5 and R6 form together with the atoms which they are attached to a 5- or 6-membered cycloalkyl ring, which is unsubstituted or substituted one, two, three or four times by R13, R7 is
1) hydrogen atom,
2) halogen,
3) —($C_1$-$C_6$)-alkyl, wherein alkyl is unsubstituted or mono-, di- or trisubstituted independently of one another by R13,
4) =O,
5) —($C_1$-$C_3$)-fluoroalkyl,
6) —($C_0$-$C_4$)-alkylene-O—R19, wherein R19 is
   a) hydrogen atom,
   b) —($C_1$-$C_4$)-alkyl, wherein alkyl is unsubstituted or mono-, di- or trisubstituted independently of one another by R13,
   c) —($C_3$-$C_8$)-cycloalkyl, wherein alkyl is unsubstituted or mono-, di- or trisubstituted independently of one another by R13,
   d) phenyl, wherein phenyl is unsubstituted or mono-, di- or trisubstituted independently of one another by R13,
   e) —$CF_3$, or
   f) —$CHF_2$,
7) —$NO_2$,
8) —CN,
9) —($C_0$-$C_4$)-alkylene-O—$CH_2$—($C_1$-$C_3$)-fluoroalkylene-$CH_2$—O—($C_1$-$C_4$)-alkyl,
10) —($C_0$-$C_4$)-alkylene-C(O)—R11,
11) —($C_0$-$C_4$)-alkylene-C(O)—O—R11,
12) —($C_0$-$C_4$)-alkylene-C(O)—O—($C_1$-$C_4$)-alkylene-O—C(O)—R17, wherein —($C_1$-$C_4$)-alkylene is unsubstituted or mono-, di- or trisubstituted independently of one another by R15,
13) —($C_0$-$C_4$)-alkylene-C(O)—O—($C_1$-$C_4$)-alkylene-O—C(O)—O—R17, wherein —($C_1$-$C_4$)-alkylene is unsubstituted or mono-, di- or trisubstituted independently of one another by R15,
14) —($C_0$-$C_4$)-alkylene-C(O)—N(R11)-R12,
15) —($C_0$-$C_4$)-alkylene-C(O)—N(R11)-R13,
16) —($C_0$-$C_4$)-alkylene-C(O)—N[($C_0$-$C_4$)-alkylene]-R13, wherein alkyl and cycloalkyl are unsubstituted or mono-, di- or trisubstituted independently of one another by R13,
17) —($C_0$-$C_4$)-alkylene-C(O)—N[($C_0$-$C_4$)-alkylene-($C_3$-$C_8$)-cycloalkyl]-R13, wherein alkyl and cycloalkyl is unsubstituted or mono-, di- or trisubstituted independently of one another by R13,
18) —($C_0$-$C_4$)-alkylene-N(R11)-R12,
19) —($C_0$-$C_4$)-alkylene-N(R11)-R13,
20) —($C_0$-$C_4$)-alkylene-N(R10)-$SO_2$—R10,
21) —($C_0$-$C_4$)-alkylene-S—R10,
22) —($C_0$-$C_4$)-alkylene-$SO_s$—R11, wherein s is 1 or 2,
23) —($C_0$-$C_4$)-alkylene-$SO_t$—N(R11)-R12, wherein t is 1 or 2,
24) —($C_0$-$C_4$)-alkylene-$SO_w$—N(R11)-R13, wherein w is 1 or 2,
25) —($C_0$-$C_4$)-alkylene-$SO_u$—($C_0$-$C_4$)-alkylene-C(O)—O—R10, wherein u is 1 or 2,
26) —($C_0$-$C_4$)-alkylene-($C_3$-$C_8$)-cycloalkyl, wherein cycloalkyl is unsubstituted or mono-, di- or trisubstituted independently of one another by R13,
27) —($C_0$-$C_4$)-alkylene-($C_6$-$C_{14}$)-aryl, wherein aryl is unsubstituted or mono-, di- or trisubstituted independently of one another by R13, or
28) —($C_0$-$C_4$)-alkylene-($C_3$-$C_{15}$)-heterocyclyl, wherein heterocyclyl is un-substituted or mono-, di- or trisubstituted independently of one another by R13,
29) —($C_0$-$C_4$)-alkylene-O—($C_0$-$C_4$)-alkylene-($C_6$-$C_{14}$)-aryl, wherein aryl is unsubstituted or mono-, di- or trisubstituted independently of one another by R13,
30) —($C_0$-$C_4$)-alkylene-O—($C_0$-$C_4$)-alkylene-($C_3$-$C_{15}$)-heterocyclyl, wherein heterocyclyl is un-substituted or mono-, di- or trisubstituted independently of one another by R13,
31) —($C_0$-$C_4$)-alkylene-N(R13)-($C_0$-$C_4$)-alkylene-($C_6$-$C_{14}$)-aryl, wherein aryl is unsubstituted or mono-, di- or trisubstituted independently of one another by R13, or
32) —($C_0$-$C_4$)-alkylene-N(R13)-($C_0$-$C_4$)-alkylene-($C_3$-$C_{15}$)-heterocyclyl, wherein heterocyclyl is un-substituted or mono-, di- or trisubstituted independently of one another by R13, R11 and R12 are independently of one another identical or different and are
1) hydrogen atom,
2) —($C_1$-$C_6$)-alkyl, wherein alkyl is unsubstituted or mono-, di- or trisubstituted independently of one another by R13,
7) —O—R17,
4) —$SO_t$—R10, wherein t is 1 or 2,
6) —($C_1$-$C_3$)-fluoroalkyl,
3) —($C_0$-$C_6$)-alkylene-($C_3$-$C_8$)-cycloalkyl, wherein alkylene and cycloalkyl independently from one another are unsubstituted or mono-, di- or trisubstituted independently of one another by R13,
5) —($C_0$-$C_6$)-alkylene-($C_6$-$C_{14}$)-aryl, wherein alkylene and aryl independently from one another are unsubstituted or mono-, di- or trisubstituted by R13, or
8) —($C_0$-$C_6$)-alkylene-($C_3$-$C_{15}$)-heterocyclyl, wherein alkylene and heterocyclyl independently from one another are unsubstituted or mono-, di- or trisubstituted by R13, or R11 and R12 together with the nitrogen atom to which they are bonded form a 4- to 8-membered monocyclic heterocyclic ring which in addition to the nitrogen atom can contain one or two identical or different ring heteroatoms chosen from oxygen, sulfur and nitrogen; wherein said heterocyclic ring is unsubstituted or mono-, di- or trisubstituted independently of one another by R13, R13 is halogen, —$NO_2$, —CN, =O, —OH, —$CF_3$, —C(O)—O—R10, —C(O)—N(R10)-R20, —N(R10)-R20, —($C_3$-$C_8$)-cycloalkyl, —($C_2$-$C_{10}$)-alkenyl-, —($C_2$-$C_{10}$)-alkynyl-, —O—$CF_3$, —Si—$(CH_3)_3$, —($C_0$-$C_4$)-alkylene-O—R10, —N(R10)-S(O)$_u$—R10, wherein u is 1 or 2, —$SO_r$—R10, wherein r is 1 or 2, —S(O)$_v$—N(R10)-

R20, wherein v is 1 or 2, —S—R10, —C(O)—R10, —($C_1$-$C_8$)-alkyl, —($C_1$-$C_8$)-alkoxy, phenyl, phenyloxy-, —($C_1$-$C_8$)-alkoxy-phenyl, —($C_0$-$C_4$)-alkylene-C(O)—O—C(R15, R16)-O—C(O)—R17, —O—R15, —NH—C(O)—NH—R10, —($C_0$-$C_4$)-alkylene-C(O)—O—C(R15, R16)-O—C(O)—O—R17, —($C_1$-$C_3$)-fluoroalkyl, hydrogen, —NH—C(O)—O—R10, or —($C_0$-$C_4$)-alkylene-R22, R10 and R20 are independently of one another hydrogen, —($C_1$-$C_4$)-alkyl, —($C_1$-$C_4$)-alkyl-OH, —($C_0$-$C_4$)-alkylene-O—($C_1$-$C_4$)-alkyl or —($C_1$-$C_3$)-fluoroalkyl, R15 and R16 are independently of one another hydrogen atom, —($C_1$-$C_6$)-alkyl, or together with the carbon atom to which they are bonded form a —($C_3$-$C_6$)-cycloalkyl, which is unsubstituted or mono, di- or trisubstituted by R10, R17 is hydrogen atom, —($C_1$-$C_6$)-alkyl, —($C_1$-$C_6$)-alkyl-OH, —($C_1$-$C_6$)-alkylene-O—($C_1$-$C_6$)-alkyl, —($C_0$-$C_6$)-alkylene-($C_3$-$C_8$)-cycloalkyl or —($C_1$-$C_6$)-alkylene-O—($C_1$-$C_6$)-alkylene-($C_3$-$C_8$)-cycloalkyl, wherein said cycloalkyl ring is unsubstituted or substituted one, two or three times by —OH, —O—($C_1$-$C_4$)-alkyl or R10, and R22 is a residue from the following list:

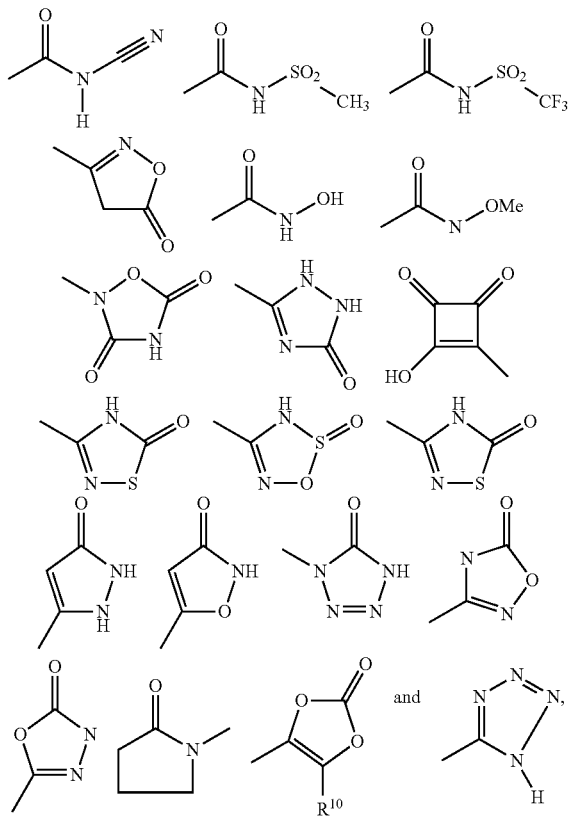

wherein Me is methyl,
in all its stereoisomeric forms and mixtures thereof in any ratio, and its physiologically tolerable salts.

2) Thus, the present invention also relates to compounds of the formula I, wherein E is a heterocyclic residue selected from aza-bicycloheptane, aza-bicyclohexane, aza-bicyclooctane, aza-spirohexane, aza-spirohexane, aza-spirooctane, aza-spiropentane, azepane, azepine, azetidine, aziridine, decahydro-quinoline, diaza-bicyclohexane, diaza-bicycloheptane, 2,5-Diaza-bicyclo[2.2.1]heptane, 1,2-diazapane, 2,7-diaza-spiro[4.5]decane, 2,8-diaza-spiro[4.5]decane, diaza-spirohexane, diaza-spirooctane, diaza-spiropentane, diaza-spiroheptane, 1,3-diazepane, 1,4-diazepane, 1,2-diazepine, 1,3-diazepine, 1,4-diazepine, dihydroazepine, 2,3-dihydro-1H-indole, 3,4-dihydro-1H-isoquinoline, 4,7-dihydro-5H-isoxazolo[5,4-c]pyridine, 6,7-dihydro-4H-isoxazolo[4,5-c]pyridine, dihydro-pyridazine, dihydro-oxazepine, 6,7-dihydro-4H-oxazolo[5,4-c]pyridine, 4,6-dihydro-1H-pyrrolo[3,4-c]pyrazol, 4,6-dihydro-4H-pyrrolo[3,4-d]thiazole, 6,7-dihydro-4H-thiazolo[5,4-c]pyridine, 4,7-dihydro-5H-thieno[2,3-c]pyridine, 5,6-Dihydro-8H-[1,2,4]triazolo[4,3-a]pyrazin, dioxazole, hexahydro-cyclopenta[c]pyrroline, hexahydro-pyridazine, hexahydro-pyrrolo[1,2-a]pyrazin, hexahydro-pyrrolo[3,4-b]pyrrol, Hexahydro-pyrrolo[1,2-a]pyrazin, imidazoline, imidazolidine, indole, isoquinoline, isothiazolidine, isothiazoline, isoxazoline, isoxazolidine, ketopiperazine, morpholine, octahydro-cyclopenta[c]pyrrole, octahydro-indole, octahydro-pyrrolo[3,4-b]pyridine, octahydro-pyrrolo[3,4-c]pyridine, 1,4-oxazepane, oxazepine, 1,2-oxa-thiepane, 1,2-oxazine, 1,3-oxazine, 1,4-oxazine, oxazolidine, piperazine, piperidine, pyrazine, pyrazoline, pyrazolidine, pyridazine, pyrrolidine, pyrrolidinone, pyrroline, tetrahydropyridine, tetrahydro-azepine, 1,2,3,4-tetrahydro-isoquinoline, 4,5,6,7-tetrahydro-isoxazolo[4,5-c]pyridine, 1,2,3,4-tetrahydropyrazine, 1,4,6,7-tetrahydro-pyrazolo[4,3-c]pyridine, 4,5,6,7-tetrahydro-1H-pyrazolo[4,3-c]pyridine, tetrahydro-pyridazine, 3,5,7,8-tetrahydro-4H-pyrido[4,3-d]pyrimidine, 4,5,6,6a-tetrahydro-3aH-pyrrolo[3,4-d]isoxazole, 1,2,3,4-tetrahydro-quinoline, 4,5,6,7-tetrahydro-thieno[2,3-c]pyridine, 1,4,6,7-tetrahydro-thiazolo[5,4-c]pyridine, 4,5,6,7-tetrahydro-thieno[3,2-c]pyridine, tetrazine, tetrazole, thiadiazine, 1,2-thiazine, 1,3-thiazine, 1,4-thiazine, 1,3-thiazole, thiazolidine, thiazoline, thietan, thiomorpholine, 1,3,8-triaza-spiro[4.5]decane, triaza-spirooctane, triazepane, 1,2,4-triazinane and 1,3,5-triazinane, wherein said heterocyclic residue is bond by its nitrogen atom to the carbonyl carbon atom and wherein said heterocyclic residue is unsubstituted or mono-, di- or trisubstituted independently of one another by R7, X is selected from nitrogen atom or C—R8, Q is selected from
1) a covalent bond,
2) —($C_0$-$C_4$)-alkylene-CH(OH)—($C_0$-$C_4$)-alkylene-,
3) —($C_0$-$C_4$)-alkylene-O—($C_0$-$C_4$)-alkylene-,
4) —($C_0$-$C_4$)-alkylene-O—C(O)—N(R10)-($C_0$-$C_4$)-alkylene-,
5) —($C_0$-$C_4$)-alkylene-C(O)—($C_0$-$C_4$)-alkylene-,
6) —($C_0$-$C_4$)-alkylene-C(O)—O—($C_0$-$C_4$)-alkylene-,
7) —($C_0$-$C_4$)-alkylene-C(O)—NR10-,
8) —($C_0$-$C_4$)-alkylene-N(R10)-($C_0$-$C_4$)-alkylene-,
9) —($C_0$-$C_4$)-alkylene-N(R10)-C(O)—($C_0$-$C_4$)-alkylene-,
10) —($C_0$-$C_4$)-alkylene-N(R10)-C(O)—O—($C_0$-$C_4$)-alkylene-,
11) —($C_0$-$C_4$)-alkylene-N(R10)-C(O)—N(R10)-($C_0$-$C_4$)-alkylene-,
12) —($C_0$-$C_4$)-alkylene-N(R10)-SO$_2$—($C_0$-$C_4$)-alkylene-,
13) —($C_0$-$C_4$)-alkylene-N(R10)-SO$_2$—NR10-($C_0$-$C_4$)-alkylene-,
14) —($C_0$-$C_4$)-alkylene-S—($C_0$-$C_4$)-alkylene-,
15) —($C_0$-$C_4$)-alkylene-SO$_2$—($C_0$-$C_4$)-alkylene-,
16) —($C_0$-$C_4$)-alkylene-($C_3$-$C_8$)-cycloalkyl-($C_0$-$C_4$)-alkylene-, or 17) —($C_0$-$C_4$)-alkylene-($C_3$-$C_{15}$)-heterocyclyl-($C_0$-$C_4$)-alkylene-, wherein heterocyclyl is selected from acridinyl, azabenzimidazolyl, aza-bicycloheptanyl, aza-bicyclohexanyl, aza-bicyclooctanyl, 8-aza-bicyclo[3.2.1]octanyl, azaspirodecanyl, aza-spiroheptanyl, aza-spirohexanyl, aza-spirooctanyl, aza-spiropentanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydro-quinolinyl, diaza-bicyclohexanyl, diaza-bicycloheptanyl, 2,5-Diaza-bicyclo[2.2.1]heptanyl, 1,2-diazapanyl, diaza-spirohexanyl, diaza-spirooctanyl, diaza-spiropentanyl, diaza-spiroheptanyl, 1,3-diazepanyl, 1,4-diazepanyl, 1,2-diazepinyl, 1,3-diazepinyl, 1,4-diazepinyl, dihydroazepinyl, 3,4-dihydro-2H-quinoline, dihydrofuro[2,3-b]-tetrahydrofuranyl, 2,3-dihydro-1H-indolyl, 3,4-dihydro-1H-isoquinolinyl, 6,7-dihydro-4H-isoxazolo[4,5-c]pyridinyl, dihydro-pyridazinyl, 4,5-dihydro-[1,3,4]oxadiazol, dihydro-oxazepinyl, 4,5-dihydrooxazolinyl, 4,6-dihydro-4H-pyrrolo[3,4-d]thiazolyl, 6,7-dihydro-4H-thiazolo[5,4-c]pyridinyl, 4,7-dihydro-5H-thieno[2,3-c]pyridinyl, 1,3-dioxanyl, dioxazolyl, dioxazinyl, 1,3-dioxolanyl, 1,3-dioxolenyl, 3,3-dioxo[1,3,4]oxathiazinyl, 6H-1,5,2-dithiazinyl, furanyl, furazanyl, hexahydro-pyridazine, hexahydro-cyclopenta[c]pyrroline, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydro-cyclopenta[c]pyrrolyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 1H-pyrrolopyridinyl, 2H-pyrrolyl, pyrrolyl, quinazolinyl, quinolinyl, 4H-quinolizinyl, quinoxalinyl, quinuclidinyl, tetrahydrofuranyl, 1,2,3,4-tetrahydroisoquinolinyl, 4,5,6,7-tetrahydro-isoxazolo[4,5-c]pyridinyl, tetrahydropyranyl, 1,2,3,4-tetrahydropyrazinyl, 4,5,6,7-tetrahydro-1H-pyrazolo[4,3-c]pyridinyl, tetrahydro-pyridazinyl, tetrahydro-pyridinyl, 4,5,6,6a-tetrahydro-3aH-pyrrolo[3,4-d]isoxazolyl, 1,2,3,4-tetrahydro-quinolinyl, 4,5,6,7-tetrahydro-thieno[2,3-c]pyridinyl, 1,4,6,7-tetrahydro-thiazolo[5,4-c]pyridinyl, 4,5,6,7-tetrahydro-thieno[3,2-c]pyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, triaza-spirooctanyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl, and xanthenyl, and wherein said —($C_3$-$C_{15}$)-heterocyclyl is unsubstituted or mono-, di- or trisubstituted independently of one another by R14; and wherein the alkyl residues are unsubstituted or mono-, di- or trisubstituted independently of one another by halogen, —$NH_2$, —OH; or —($C_3$-$C_6$)-cycloalkyl, wherein cycloalkyl is unsubstituted or mono-, di- or trisubstituted independently of one another by halogen, —$NH_2$ or —OH;

J is
1) hydrogen atom,
2) —($C_1$-$C_6$)-alkyl, wherein alkyl is unsubstituted or mono-, di- or trisubstituted independently of one another by R13,
3) —($C_0$-$C_4$)-alkylene-C(O)—R11,
4) —($C_0$-$C_4$)-alkylene-C(O)—O—R11,
5) —($C_0$-$C_4$)-alkylene-C(O)—O—($C_1$-$C_4$)-alkylene-O—C(O)—R17, wherein —($C_1$-$C_4$)-alkylene is unsubstituted or mono-, di- or trisubstituted independently of one another by R15,
6) —($C_0$-$C_4$)-alkylene-C(O)—O—($C_1$-$C_4$)-alkylene-O—C(O)—O—R17, wherein —($C_1$-$C_4$)-alkylene is unsubstituted or mono-, di- or trisubstituted independently of one another by R15,
7) —($C_0$-$C_4$)-alkylene-C(O)—N(R11)-R13
8) —($C_0$-$C_4$)-alkylene-N(R11)-R13,
9) —($C_0$-$C_4$)-alkylene-N(R10)-$SO_2$—R10,
10) —($C_0$-$C_4$)-alkylene-$SO_s$—R11, wherein s is 1 or 2,
11) —($C_0$-$C_4$)-alkylene-$SO_t$—N(R11)-R12, wherein t is 1 or 2,
12) —($C_0$-$C_4$)-alkylene-$SO_w$—N(R11)-R13, wherein w is 1 or 2,
13) —($C_0$-$C_4$)-alkylene-R22,
14) —($C_0$-$C_4$)-alkylene-($C_3$-$C_8$)-cycloalkyl, wherein cycloalkyl is unsubstituted or mono-, di- or trisubstituted independently of one another by R13,
15) —($C_0$-$C_4$)-alkylene-($C_6$-$C_{14}$)-aryl, wherein aryl is selected from phenyl, naphthyl, biphenylyl, indanyl, anthryl and fluorenyl and aryl is unsubstituted or mono-, di- or trisubstituted independently of one another by R13, or
16) —($C_0$-$C_4$)-alkylene-($C_3$-$C_{15}$)-heterocyclyl, wherein —($C_3$-$C_{15}$)-heterocyclyl is as defined above and is unsubstituted or mono-, di- or trisubstituted independently of one another by R13, R1 is a hydrogen atom, —($C_1$-$C_4$)-alkyl, wherein alkyl is unsubstituted or substituted one to three times by R13; —($C_1$-$C_3$)-alkylene-C(O)—NH—R10 or —($C_1$-$C_3$)-alkylene-C(O)—O—R10, Z is
1) —($C_0$-$C_8$)-alkylene-,
2) —($C_2$-$C_{10}$)-alkenyl-,
3) —($C_2$-$C_{10}$)-alkynyl-,
4) —($C_0$-$C_4$)-alkylene-O—($C_0$-$C_4$)-alkylene-,
5) —($C_0$-$C_4$)-alkylene-O—C(O)—N(R10)-($C_0$-$C_4$)-alkylene-,
6) —($C_0$-$C_4$)-alkylene-C(O)—($C_0$-$C_4$)-alkylene-,
7) —($C_0$-$C_4$)-alkylene-N(R10)-C(O)—($C_0$-$C_4$)-alkylene-,
8) —($C_0$-$C_4$)-alkylene-N(R10)-C(O)—O—($C_0$-$C_4$)-alkylene-,
9) —($C_0$-$C_4$)-alkylene-N(R10)-C(O)—N(R10)-($C_0$-$C_4$)-alkylene-,
10) —($C_0$-$C_4$)-alkylene-N(R10)-($C_0$-$C_4$)-alkylene-,
11) —($C_0$-$C_4$)-alkylene-S—($C_0$-$C_4$)-alkylene-,
12) —($C_0$-$C_4$)-alkylene-S(O)—($C_0$-$C_4$)-alkylene-,
13) —($C_0$-$C_4$)-alkylene-$SO_2$—($C_0$-$C_4$)-alkylene-, or
14) —($C_0$-$C_4$)-alkylene-($C_3$-$C_8$)-cycloalkyl-($C_0$-$C_4$)-alkylene-, A is a covalent bond, —$(C_3$-$C_8)$-alkylene, —$(C_3$-$C_8)$-cycloalkylene or —$(C_3$-$C_{15})$-heterocyclyl, wherein —$(C_3$-$C_{15})$-heterocyclyl is as defined above, B is
1) a covalent bond,
2) —$(C_2$-$C_{10})$-alkenyl-,
3) —$(C_2$-$C_{10})$-alkynyl-,
4) —$(C_0$-$C_4)$-alkylene-CH(OH)—$(C_0$-$C_4)$-alkylene-,
5) —$(C_0$-$C_4)$-alkylene-O—$(C_0$-$C_4)$-alkylene-,
6) —$(C_0$-$C_4)$-alkylene-O—C(O)—N(R10)-$(C_0$-$C_4)$-alkylene-,
7) —$(C_0$-$C_4)$-alkylene-C(O)—$(C_0$-$C_4)$-alkylene-,
8) —$(C_0$-$C_4)$-alkylene-C(O)—O—$(C_0$-$C_4)$-alkylene-,
9) —$(C_0$-$C_4)$-alkylene-C(O)—N(R10)-,
10) —$(C_0$-$C_4)$-alkylene-N(R10)-$(C_0$-$C_4)$-alkylene-,
11) —$(C_0$-$C_4)$-alkylene-N(R10)-C(O)—$(C_0$-$C_4)$-alkylene-,
12) —$(C_0$-$C_4)$-alkylene-N(R10)-C(O)—O—$(C_0$-$C_4)$-alkylene-,
13) —$(C_0$-$C_4)$-alkylene-N(R10)-C(O)—N(R10)-$(C_0$-$C_4)$-alkylene-,
14) —$(C_0$-$C_4)$-alkylene-N(R10)-$SO_2$—$(C_0$-$C_4)$-alkylene-,
15) —$(C_0$-$C_4)$-alkylene-N(R10)-$SO_2$—N(R10)-$(C_0$-$C_4)$-alkylene-,
16) —$(C_0$-$C_4)$-alkylene-S—$(C_0$-$C_4)$-alkylene-,
17) —$(C_0$-$C_4)$-alkylene-S(O)—$(C_0$-$C_4)$-alkylene-,
18) —$(C_0$-$C_4)$-alkylene-$SO_2$—$(C_0$-$C_4)$-alkylene-,
19) —$(C_0$-$C_4)$-alkylene-$SO_2$—N(R10)-$(C_0$-$C_4)$-alkylene-,
20) —$(C_0$-$C_4)$-alkylene-$(C_3$-$C_8)$-cycloalkyl-$(C_0$-$C_4)$-alkylene-, or
21) —$(C_0$-$C_4)$-alkylene-$(C_3$-$C_{15})$-heterocyclyl-$(C_0$-$C_4)$-alkylene-, wherein —$(C_3$-$C_{15})$-heterocyclyl is as defined above, wherein said heterocyclyl is unsubstituted or mono-, di- or trisubstituted independently of one another by R14, and wherein the alkyl residues are unsubstituted or mono-, di- or trisubstituted independently of one another by halogen, —$NH_2$, —OH; or —$(C_3$-$C_6)$-cycloalkyl, wherein cycloalkyl is unsubstituted or mono-, di- or trisubstituted independently of one another by halogen, —$NH_2$ or —OH;

R14 is halogen, —OH, =O, —$(C_1$-$C_8)$-alkyl, —$(C_1$-$C_4)$-alkoxy, —$NO_2$, —CN, —$NH_2$, —S—R18, —$(C_1$-$C_4)$-alkylene-C(O)—OH, —C(O)—O—$(C_1$-$C_4)$-alkyl, —$(C_1$-$C_4)$-alkylene-C(O)—$NH_2$, —$(C_0$-$C_8)$-alkylene-$SO_2$—$(C_1$-$C_4)$-alkyl, —$(C_0$-$C_8)$-alkylene-$SO_2$—$(C_1$-$C_3)$-fluoroalkyl, —$(C_0$-$C_8)$-alkylene-$SO_2$—N(R18)-R21, —$(C_1$-$C_4)$-alkylene-C(O)—NH—$(C_1$-$C_8)$-alkyl, —$(C_1$-$C_4)$-alkylene-C(O)—N—[$(C_1$-$C_8)$-alkyl]$_2$, —N(R18)-C(O)—NH—$(C_1$-$C_8)$-alkyl, —N(R18)-C(O)—NH—[$(C_1$-$C_8)$-alkyl]$_2$, —$(C_2$-$C_{10})$-alkenyl, or —$(C_2$-$C_{10})$-alkynyl, wherein R18 and R21 are independently from each other hydrogen atom, —$(C_1$-$C_3)$-fluoroalkyl or —$(C_1$-$C_6)$-alkyl, V is —$(C_3$-$C_{15})$-heterocyclyl or —N(R1)-$(C_3$-$C_{15})$-heterocyclyl, wherein —$(C_3$-$C_{15})$-heterocyclyl is as defined above and is unsubstituted or mono-, di- or trisubstituted independently of one another by R14, G is
1) a covalent bond,
2) —$(C_0$-$C_4)$-alkylene-CH(OH)—$(C_0$-$C_4)$-alkylene-,
3) —$(C_0$-$C_4)$-alkylene-O—$(C_0$-$C_4)$-alkylene-,
4) —$(C_0$-$C_4)$-alkylene-O—C(O)—N(R10)-$(C_0$-$C_4)$-alkylene-,
5) —$(C_0$-$C_4)$-alkylene-C(O)—$(C_0$-$C_4)$-alkylene-,
6) —$(C_0$-$C_4)$-alkylene-C(O)—O—$(C_0$-$C_4)$-alkylene-,
7) —$(C_0$-$C_4)$-alkylene-C(O)—N(R10)-,
8) —$(C_0$-$C_4)$-alkylene-N(R10)-$(C_0$-$C_4)$-alkylene-,
9) —$(C_0$-$C_4)$-alkylene-N(R10)-C(O)—$(C_0$-$C_4)$-alkylene-,
10) —$(C_0$-$C_4)$-alkylene-N(R10)-C(O)—O—$(C_0$-$C_4)$-alkylene-,
11) —$(C_0$-$C_4)$-alkylene-N(R10)-C(O)—N(R10)-$(C_0$-$C_4)$-alkylene-,
12) —$(C_0$-$C_4)$-alkylene-N(R10)-$SO_2$—$(C_0$-$C_4)$-alkylene-,
13) —$(C_0$-$C_4)$-alkylene-N(R10)-$SO_2$—N(R10)-$(C_0$-$C_4)$-alkylene-,
14) —$(C_0$-$C_4)$-alkylene-S—$(C_0$-$C_4)$-alkylene-,
15) —$(C_0$-$C_4)$-alkylene-S(O)—$(C_0$-$C_4)$-alkylene-,
16) —$(C_0$-$C_4)$-alkylene-$SO_2$—$(C_0$-$C_4)$-alkylene-,
17) —$(C_0$-$C_4)$-alkylene-$SO_2$—N(R10)-$(C_0$-$C_4)$-alkylene-, or
18) —$(C_0$-$C_4)$-alkylene-$(C_3$-$C_8)$-cycloalkyl-$(C_0$-$C_4)$-alkylene-,
and wherein the alkyl residues are unsubstituted or mono-, di- or trisubstituted independently of one another by halogen, —$NH_2$, —OH; or —$(C_3$-$C_6)$-cycloalkyl, wherein cycloalkyl is unsubstituted or mono-, di- or trisubstituted independently of one another by halogen, —$NH_2$ or —OH;

M is
1) a hydrogen atom,
2) —$(C_1$-$C_8)$-alkyl, wherein alkyl is unsubstituted or mono-, di- or trisubstituted independently of one another by R14,
3) —C(O)—N(R11)-R12,
4) —C(O)—O—R12,
5) —$(C_1$-$C_8)$-alkylen-N(R10)$_2$,
6) —$(C_6$-$C_{14})$-aryl, wherein aryl is as defined above and is unsubstituted or mono-, di- or trisubstituted independently of one another by R14,
7) —$(C_3$-$C_8)$-cycloalkyl, wherein said cycloalkyl is unsubstituted or mono-, di- or trisubstituted independently of one another by R14, or
8) a 3- to 7-membered heterocyclyl, containing 1, 2, 3 or 4 heteroatoms chosen from nitrogen, sulfur or oxygen, selected from azepine, azetidine, aziridine, azirine, 1,4-diazepane, 1,2-diazepine, 1,3-diazepine, 1,4-diazepine, diaziridine, diazirine, dihydroimidazolone, dioxazole, dioxazine, dioxole, 1,3-dioxolene, 1,3-dioxolane, furan, imidazole, imidazoline, imidazolidine, imidazolidinone, isothiazole, isothiazolidine, isothiazoline, isoxazole, isoxazoline, isoxazolidine, morpholine, 1,2-oxathiepane, 1,2-oxathiolane, 1,4-oxazepane, 1,2-oxazine, 1,3-oxazine, 1,4-oxazine, oxazolone, oxazole, [1,3,4] oxathiazinane 3,3-dioxide, oxaziridine, oxazolidinone, oxetan, oxirane, piperazine, piperidine, pyran, pyrazine, pyrazole, pyrazoline, pyrazolidine, pyridazine, pyridine, pyridinone, pyrimidine, pyrimidine-2,4-dione, pyrrole, pyrrolidine, pyrrolidinone, pyrroline, tetrahydrofuran, tetrahydropyran, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiomorpholine 1,1-dioxide thiopyran, 1,2,3-triazine, 1,2,4-triazine, 1,3,5-triazine, 1,2,3-triazole and 1,2,4-triazole, wherein said cyclic residue is unsubstituted or mono-, di- or trisubstituted independently of one another by R14, R2, R3, R4, R5, R6 and R8 are independently of one another selected from
1) hydrogen atom,
2) —$(C_1-C_6)$-alkyl, wherein alkyl is unsubstituted or mono-, di- or trisubstituted independently of one another by R13,
3) —$(C_0-C_4)$-alkylene-O—R10,
4) halogen,
5) —$(C_1-C_3)$-fluoroalkyl,
6) —CN or
7) phenyl, wherein phenyl is unsubstituted or mono-, di- or trisubstituted independently of one another by R13, or R3 and R4, R4 and R5 or R5 and R6 are each time both —O—R10 and form together with the atoms which they are attached to a 1,3-dioxole ring or 2,3-dihydro-[1,4]dioxine ring, which is unsubstituted or substituted one, two, three or four times by R13, R3 and R4, R4 and R5 or R5 and R6 form together with the atoms which they are attached to a cyclopentyl or cyclohexyl, which is unsubstituted or substituted one, two, three or four times by R13, R7 is
1) hydrogen atom,
2) halogen,
3) —$(C_1-C_6)$-alkyl, wherein alkyl is unsubstituted or mono-, di- or trisubstituted independently of one another by R13,
4) =O,
5) —$(C_1-C_3)$-fluoroalkyl,
6) —$(C_0-C_4)$-alkylene-O—R19, wherein R19 is
  a) hydrogen atom,
  b) —$(C_1-C_4)$-alkyl, wherein alkyl is unsubstituted or mono-, di- or trisubstituted independently of one another by R13,
  c) —$(C_3-C_8)$-cycloalkyl, wherein alkyl is unsubstituted or mono-, di- or trisubstituted independently of one another by R13,
  d) phenyl, wherein phenyl is unsubstituted or mono-, di- or trisubstituted independently of one another by R13,
  e) —$CF_3$, or
  f) —$CHF_2$,
7) —$NO_2$,
8) —CN,
9) —$(C_0-C_4)$-alkylene-O—$CH_2$—$(C_1-C_3)$-fluoroalkylene-$CH_2$—O—$(C_1-C_4)$-alkyl,
10) —$(C_0-C_4)$-alkylene-C(O)—R11,
11) —$(C_0-C_4)$-alkylene-C(O)—O—R11,
12) —$(C_0-C_4)$-alkylene-C(O)—O—$(C_1-C_4)$-alkylene-O—C(O)—R17, wherein —$(C_1-C_4)$-alkylene is unsubstituted or mono-, di- or trisubstituted independently of one another by R15,
13) —$(C_0-C_4)$-alkylene-C(O)—O—$(C_1-C_4)$-alkylene-O—C(O)—O—R17, wherein —$(C_1-C_4)$-alkylene is unsubstituted or mono-, di- or trisubstituted independently of one another by R15,
14) —$(C_0-C_4)$-alkylene-C(O)—N(R11)-R12,
15) —$(C_0-C_4)$-alkylene-C(O)—N(R11)-R13,
16) —$(C_0-C_4)$-alkylene-C(O)—N[$(C_0-C_4)$-alkylene]-R13, wherein alkyl and cycloalkyl are unsubstituted or mono-, di- or trisubstituted independently of one another by R13,
17) —$(C_0-C_4)$-alkylene-C(O)—N[$(C_0-C_4)$-alkylene-$(C_3-C_8)$-cycloalkyl]-R13, wherein alkyl and cycloalkyl is unsubstituted or mono-, di- or trisubstituted independently of one another by R13,
18) —$(C_0-C_4)$-alkylene-N(R11)-R12,
19) —$(C_0-C_4)$-alkylene-N(R11)-R13,
20) —$(C_0-C_4)$-alkylene-N(R10)-$SO_2$—R10,
21) —$(C_0-C_4)$-alkylene-S—R10,
22) —$(C_0-C_4)$-alkylene-$SO_s$—R11, wherein s is 1 or 2,
23) —$(C_0-C_4)$-alkylene-$SO_t$—N(R11)-R12, wherein t is 1 or 2,
24) —$(C_0-C_4)$-alkylene-$SO_w$—N(R11)-R13, wherein w is 1 or 2,
25) —$(C_0-C_4)$-alkylene-$SO_u$—$(C_0-C_4)$-alkylene-C(O)—O—R10, wherein u is 1 or 2,
26) —$(C_0-C_4)$-alkylene-$(C_3-C_8)$-cycloalkyl, wherein cycloalkyl is unsubstituted or mono-, di- or trisubstituted independently of one another by R13,
27) —$(C_0-C_4)$-alkylene-$(C_6-C_{14})$-aryl, wherein aryl is selected from phenyl, naphthyl, biphenylyl, indanyl, anthryl or fluorenyl; and wherein aryl is unsubstituted or mono-, di- or trisubstituted independently of one another by R13, or
28) —$(C_0-C_4)$-alkylene-$(C_3-C_{15})$-heterocyclyl, wherein —$(C_3-C_{15})$-heterocyclyl is as defined above and is unsubstituted or mono-, di- or trisubstituted independently of one another by R13,
29) —$(C_0-C_4)$-alkylene-O—$(C_0-C_4)$-alkylene-$(C_6-C_{14})$-aryl, wherein aryl is unsubstituted or mono-, di- or trisubstituted independently of one another by R13,
30) —$(C_0-C_4)$-alkylene-O—$(C_0-C_4)$-alkylene-$(C_3-C_{15})$-heterocyclyl, wherein —$(C_3-C_{15})$-heterocyclyl is un-substituted or mono-, di- or trisubstituted independently of one another by R13,
31) —$(C_0-C_4)$-alkylene-N(R13)-$(C_0-C_4)$-alkylene-$(C_6-C_{14})$-aryl, wherein aryl is unsubstituted or mono-, di- or trisubstituted independently of one another by R13, or
32) —$(C_0-C_4)$-alkylene-N(R13)-$(C_0-C_4)$-alkylene-$(C_3-C_{15})$-heterocyclyl, wherein —$(C_3-C_{15})$-heterocyclyl is un-substituted or mono-, di- or trisubstituted independently of one another by R13, R11 and R12 are independently of one another identical or different and are
1) hydrogen atom,
2) —$(C_1-C_6)$-alkyl, wherein alkyl is unsubstituted or mono-, di- or trisubstituted independently of one another by R13,
3) —$(C_0-C_6)$-alkylene-$(C_3-C_8)$-cycloalkyl, wherein alkylene and cycloalkyl independently from one another are unsubstituted or mono-, di- or trisubstituted independently of one another by R13,
4) —$SO_t$—R10, wherein t is 1 or 2,
5) —$(C_0-C_6)$-alkylene-$(C_6-C_{14})$-aryl, wherein aryl is as defined above and alkylene and aryl independently from one another are unsubstituted or mono-, di- or trisubstituted by R13,
6) —$(C_1-C_3)$-fluoroalkyl,
7) —O—R17, or
8) —$(C_0-C_6)$-alkylene-$(C_3-C_{15})$-heterocyclyl, wherein —$(C_3-C_{15})$-heterocyclyl is as defined above and alkylene and heterocyclyl independently from one another are unsubstituted or mono-, di- or trisubstituted by R13, or R11 and R12 together with the nitrogen atom to which they are bonded form a 4- to 8-membered monocyclic heterocyclic ring, which is selected from aza-bicycloheptane, aza-bicyclohexane, aza-spiroheptane, aza-spirohexane, aza-spirooctane, aza-spiropentane, azepane, azepine, azetidine, diaza-bicycloheptane, diaza-bicyclohexane, diaza-spiroheptane, diaza-spirohexane, diaza-spiropentane, diaza-spirooctane 1,2-diazapane, 1,3-diazapane, 1,4-diazapane, 1,2-diazepine, 1,3-diazepine, 1,4-diazepine, dihydroazepine, dihydro-oxazepine, dihydro-pyridazine, dioxazole, hexahydro-pyridazine, imidazoline, imidazolidine, isothiazolidine, isothiazoline, isoxazoline, isoxazolidine, ketopiperazine, morpholine, 1,4-oxazepane, 1,2-oxa-thiepane, oxazepine, 1,2-oxazine, 1,3-oxazine, 1,4-oxazine, piperazine, piperidine, pyrazine, pyrazoline, pyrazolidine, pyridazine, pyrrolidine, pyrrolidinone, pyrroline, tetrahydro-azepine, 1,2,3,4-tetrahydropyrazine, tetrahydropyridine, tetrazine, tetrazole, thiadiazine, 1,2-thiazine, 1,3-thiazine, 1,4-thiazine, 1,3-thiazole, thiazolidine, thiazoline, thietan, thiomorpholine, triazepane, 1,2,4-triazinane and 1,3,5-triazinane; wherein said heterocyclic ring is unsubstituted or mono-, di- or trisubstituted independently of one another by R13, R13 is halogen, —$NO_2$, —CN, =O, —OH, —$CF_3$, —C(O)—O—R10, —C(O)—N(R10)-R20, —N(R10)-R20, —($C_3$-$C_8$)-cycloalkyl, —($C_2$-$C_{10}$)-alkenyl-, —($C_2$-$C_{10}$)-alkynyl-, —O—$CF_3$, —Si—$(CH_3)_3$, —($C_0$-$C_4$)-alkylene-O—R10, —N(R10)-S(O)$_u$—R10, wherein u is 1 or 2, —$SO_r$—R10, wherein r is 1 or 2, —S(O)$_v$—N(R10)-R20, wherein v is 1 or 2, —S—R10, —C(O)—R10, —($C_1$-$C_8$)-alkyl, —($C_1$-$C_8$)-alkoxy, phenyl, phenyloxy-, —($C_1$-$C_8$)-alkoxy-phenyl, —($C_0$-$C_4$)-alkylene-C(O)—O—C(R15, R16)-O—C(O)—R17, —O—R15, —NH—C(O)—NH—R10, —($C_0$-$C_4$)-alkylene-C(O)—O—C(R15, R16)-O—C(O)—O—R17, —($C_1$-$C_3$)-fluoroalkyl, —NH—C(O)—O—R10 or —($C_0$-$C_4$)-alkylene-R22, R10 and R20 are independently of one another hydrogen, —($C_1$-$C_4$)-alkyl, —($C_1$-$C_4$)-alkyl-OH, —($C_0$-$C_4$)-alkylene-O—($C_1$-$C_4$)-alkyl or —($C_1$-$C_3$)-fluoroalkyl, R15 and R16 are independently of one another hydrogen atom, —($C_1$-$C_6$)-alkyl, or together with the carbon atom to which they are bonded form a —($C_3$-$C_6$)-cycloalkyl, which is unsubstituted or mono, di- or trisubstituted by R10, R17 is hydrogen atom, —($C_1$-$C_6$)-alkyl, —($C_1$-$C_6$)-alkyl-OH, —($C_1$-$C_6$)-alkylene-O—($C_1$-$C_6$)-alkyl, —($C_0$-$C_6$)-alkylene-($C_3$-$C_8$)-cycloalkyl or —($C_1$-$C_6$)-alkylene-O—($C_1$-$C_6$)-alkylene-($C_3$-$C_8$)-cycloalkyl, wherein said cycloalkyl ring is unsubstituted or substituted one, two or three times by —OH, —O—($C_1$-$C_4$)-alkyl or R10, and R22 is a residue from the following list:

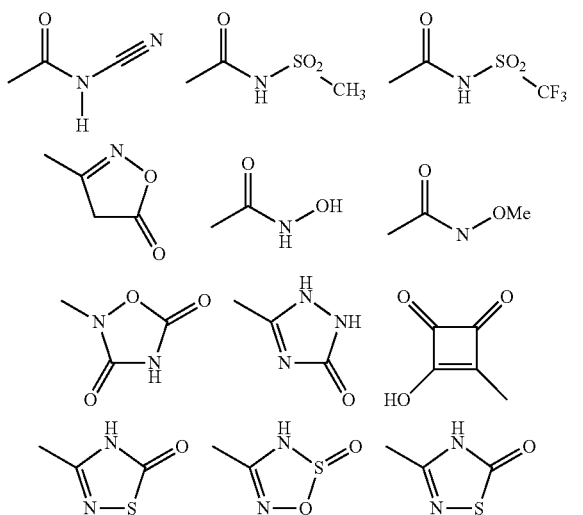

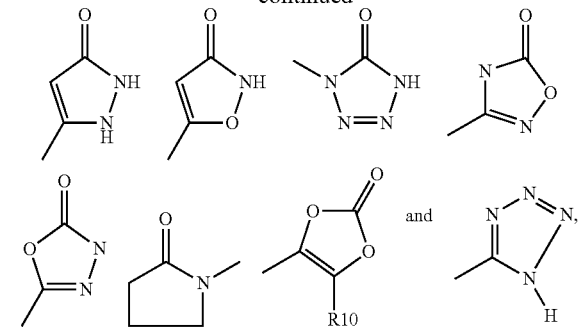

wherein Me is methyl,
in all its stereoisomeric forms and mixtures thereof in any ratio, and its physiologically tolerable salts.

3) The present invention further relates to compounds of the formula I, wherein

E is a heterocyclic residue selected from aza-bicycloheptane, aza-bicyclohexane, aza-bicyclooctane, aza-spiroheptane, aza-spirohexane, aza-spirooctane, aza-spiropentane, azepane, azepine, azetidine, aziridine, decahydro-quinoline, diaza-bicyclohexane, diaza-bicycloheptane, 2,5-Diaza-bicyclo[2.2.1]heptane, 1,2-diazapane, 2,7-diaza-spiro[4.5]decane, 2,8-diaza-spiro[4.5]decane, diaza-spirohexane, diaza-spirooctane, diaza-spiropentane, diaza-spiroheptane, 1,3-diazapane, 1,4-diazapane, 1,2-diazepine, 1,3-diazepine, 1,4-diazepine, dihydroazepine, 2,3-dihydro-1H-indole, 3,4-dihydro-1H-isoquinoline, 4,7-dihydro-5H-isoxazolo[5,4-c]pyridine, 6,7-dihydro-4H-isoxazolo[4,5-c]pyridine, dihydro-pyridazine, dihydro-oxazepine, 6,7-dihydro-4H-oxazolo[5,4-c]pyridine, 4,6-dihydro-1H-pyrrolo[3,4-c]pyrazol, 4,6-dihydro-4H-pyrrolo[3,4-d]thiazole, 6,7-dihydro-4H-thiazolo[5,4-c]pyridine, 4,7-dihydro-5H-thieno[2,3-c]pyridine, 5,6-Dihydro-8H-[1,2,4]triazolo[4,3-a]pyrazin, dioxazole, hexahydro-cyclopenta[c]pyrroline, hexahydro-pyridazine, hexahydro-pyrrolo[1,2-a]pyrazin, hexahydro-pyrrolo[3,4-b]pyrrol, Hexahydro-pyrrolo[1,2-a]pyrazin, imidazoline, imidazolidine, indole, isoquinoline, isothiazolidine, isothiazoline, isoxazoline, isoxazolidine, ketopiperazine, morpholine, octahydro-cyclopenta[c]pyrrole, octahydro-indole, octahydro-pyrrolo[3,4-b]pyridine, octahydro-pyrrolo[3,4-c]pyridine, 1,4-oxazepane, oxazepine, 1,2-oxa-thiepane, 1,2-oxazine, 1,3-oxazine, 1,4-oxazine, oxazolidine, piperazine, piperidine, pyrazine, pyrazoline, pyrazolidine, pyridazine, pyrrolidine, pyrrolidinone, pyrroline, tetrahydropyridine, tetrahydro-azepine, 1,2,3,4-tetrahydro-isoquinoline, 4,5,6,7-tetrahydro-isoxazolo[4,5-c]pyridine, 1,2,3,4-tetrahydropyrazine, 1,4,6,7-tetrahydro-pyrazolo[4,3-c]pyridine, 4,5,6,7-tetrahydro-1H-pyrazolo[4,3-c]pyridine, tetrahydro-pyridazine, 3,5,7,8-tetrahydro-4H-pyrido[4,3-d]pyrimidine, 4,5,6,6a-tetrahydro-3aH-pyrrolo[3,4-d]isoxazole, 1,2,3,4-tetrahydro-quinoline, 4,5,6,7-tetrahydro-thieno[2,3-c]pyridine, 1,4,6,7-tetrahydro-thiazolo[5,4-c]pyridine, 4,5,6,7-tetrahydro-thieno[3,2-c]pyridine, tetrazine, tetrazole, thiadiazine, 1,2-thiazine, 1,3-thiazine, 1,4-thiazine, 1,3-thiazole, thiazolidine, thiazoline, thietan, thiomorpholine, 1,3,8-triaza-spiro[4.5]decane, triaza-spirooctane, triazepane, 1,2,4-triazinane and 1,3,5-triazinane, wherein said heterocyclic residue is bond by its nitrogen atom to the carbonyl carbon atom and wherein said heterocyclic residue is unsubstituted or mono-, di- or trisubstituted independently of one another by R7, X is a nitrogen atom,
Q is
1) a covalent bond,
2) —($C_0$-$C_4$)-alkylene-CH(OH)—($C_0$-$C_4$)-alkylene-,
3) —($C_0$-$C_4$)-alkylene-O—($C_0$-$C_4$)-alkylene-,
4) —($C_0$-$C_4$)-alkylene-C(O)—($C_0$-$C_4$)-alkylene-,
5) —($C_0$-$C_4$)-alkylene-C(O)—O—($C_0$-$C_4$)-alkylene-,
6) —($C_0$-$C_4$)-alkylene-C(O)—N(R10)-,
7) —($C_0$-$C_4$)-alkylene-N(R10)-($C_0$-$C_4$)-alkylene-,
8) —($C_0$-$C_4$)-alkylene-N(R10)-C(O)—($C_0$-$C_4$)-alkylene-,
9) —($C_0$-$C_4$)-alkylene-N(R10)-C(O)—O—($C_0$-$C_4$)-alkylene-,
10) —($C_0$-$C_4$)-alkylene-N(R10)-C(O)—N(R10)-($C_0$-$C_4$)-alkylene-,
11) —($C_0$-$C_4$)-alkylene-S—($C_0$-$C_4$)-alkylene-,
12) —($C_0$-$C_4$)-alkylene-$SO_2$—($C_0$-$C_4$)-alkylene-,
13) —($C_0$-$C_4$)-alkylene-($C_3$-$C_6$)-cycloalkyl-($C_0$-$C_4$)-alkylene-, or
14) —($C_0$-$C_4$)-alkylene-($C_3$-$C_{15}$)-heterocyclyl-($C_0$-$C_4$)-alkylene-, wherein
—($C_3$-$C_{15}$)-heterocyclyl is selected from acridinyl, aza-benzimidazolyl, aza-bicycloheptanyl, aza-bicyclohexanyl, aza-bicyclooctanyl, 8-aza-bicyclo[3.2.1]octanyl, azaspirodecanyl, aza-spiroheptanyl, aza-spirohexanyl, aza-spirooctanyl, aza-spiropentanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydroquinolinyl, diaza-bicyclohexanyl, diaza-bicycloheptanyl, 2,5-Diaza-bicyclo[2.2.1]heptanyl, 1,2-diazapanyl, diaza-spirohexanyl, diaza-spirooctanyl, diaza-spiropentanyl, diaza-spiroheptanyl, 1,3-diazepanyl, 1,4-diazepanyl, 1,2-diazepinyl, 1,3-diazepinyl, 1,4-diazepinyl, dihydroazepinyl, 3,4-dihydro-2H-quinoline, dihydrofuro[2,3-b]-tetrahydrofuranyl, 2,3-dihydro-1H-indolyl, 3,4-dihydro-1H-isoquinolinyl, 6,7-dihydro-4H-isoxazolo[4,5-c]pyridinyl, dihydro-pyridazinyl, 4,5-dihydro-[1,3,4]oxadiazol, dihydro-oxazepinyl, 4,5-dihydrooxazolinyl, 4,6-dihydro-4H-pyrrolo[3,4-d]thiazolyl, 6,7-dihydro-4H-thiazolo[5,4-c]pyridinyl, 4,7-dihydro-5H-thieno[2,3-c]pyridinyl, 1,3-dioxanyl, dioxazolyl, dioxazinyl, 1,3-dioxolanyl, 1,3-dioxolenyl, 3,3-dioxo[1,3,4]oxathiazinyl, 6H-1,5,2-dithiazinyl, furanyl, furazanyl, hexahydro-pyridazine, hexahydro-cyclopenta[c]pyrroline, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydro-cyclopenta[c]pyrrolyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 1H-pyrrolopyridinyl, 2H-pyrrolyl, pyrrolyl, quinazolinyl, quinolinyl, 4H-quinolizinyl, quinoxalinyl, quinuclidinyl, tetrahydrofuranyl, 1,2,3,4-tetrahydroisoquinolinyl, 4,5,6,7-tetrahydro-isoxazolo[4,5-c]pyridinyl, tetrahydropyranyl, 1,2,3,4-tetrahydropyrazinyl, 4,5,6,7-tetrahydro-1H-pyrazolo[4,3-c]pyridinyl, tetrahydro-pyridazinyl, tetrahydro-pyridinyl, 4,5,6,6a-tetrahydro-3aH-pyrrolo[3,4-d]isoxazolyl, 1,2,3,4-tetrahydro-quinolinyl, 4,5,6,7-tetrahydro-thieno[2,3-c]pyridinyl, 1,4,6,7-tetrahydro-thiazolo[5,4-c]pyridinyl, 4,5,6,7-tetrahydro-thieno[3,2-c]pyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, triaza-spirooctanyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl, and xanthenyl, and wherein —($C_3$-$C_{15}$)-heterocyclyl is unsubstituted or mono-, di- or trisubstituted independently of one another by R14; and wherein the alkyl residues are unsubstituted or mono-, di- or trisubstituted independently of one another by halogen, —$NH_2$, —OH; or —($C_3$-$C_6$)-cycloalkyl, wherein cycloalkyl is unsubstituted or mono-, di- or trisubstituted independently of one another by halogen, —$NH_2$ or —OH;
J is
1) hydrogen atom,
2) —($C_1$-$C_6$)-alkyl, wherein alkyl is unsubstituted or mono-, di- or trisubstituted independently of one another by R13,
3) —($C_0$-$C_4$)-alkylene-C(O)—R11,
4) —($C_0$-$C_4$)-alkylene-C(O)—O—R11,
5) —($C_0$-$C_4$)-alkylene-C(O)—O—($C_1$-$C_4$)-alkylene-O—C(O)—R17, wherein —($C_1$-$C_4$)-alkylene is unsubstituted or mono-, di- or trisubstituted independently of one another by R15,
6) —($C_0$-$C_4$)-alkylene-C(O)—O—($C_1$-$C_4$)-alkylene-O—C(O)—O—R17, wherein —($C_1$-$C_4$)-alkylene is unsubstituted or mono-, di- or trisubstituted independently of one another by R15,
7) —($C_0$-$C_4$)-alkylene-C(O)—N(R11)-R13,
8) —($C_0$-$C_4$)-alkylene-N(R11)-R13,
9) —($C_0$-$C_4$)-alkylene-N(R10)-$SO_2$—R10,
10) —($C_0$-$C_4$)-alkylene-$SO_s$—R11, wherein s is 1 or 2,
11) —($C_0$-$C_4$)-alkylene-$SO_t$—N(R11)-R12, wherein t is 1 or 2,
12) —($C_0$-$C_4$)-alkylene-$SO_w$—N(R11)-R13, wherein w is 1 or 2,
13) —($C_0$-$C_4$)-alkylene-R22,
14) —($C_0$-$C_4$)-alkylene-($C_3$-$C_6$)-cycloalkyl, wherein cycloalkyl is unsubstituted or 5 mono-, di- or trisubstituted independently of one another by R13,
15) —($C_0$-$C_4$)-alkylene-($C_6$-$C_{14}$)-aryl, wherein aryl is selected from phenyl or indanyl, and aryl is unsubstituted or mono-, di- or trisubstituted independently of one another by R13, or
16) —($C_0$-$C_4$)-alkylene-($C_3$-$C_{15}$)-heterocyclyl, wherein heterocyclyl is as defined above and is unsubstituted or mono-, di- or trisubstituted independently of one another by R13,
R1 is a hydrogen atom, —($C_1$-$C_4$)-alkyl, wherein alkyl is unsubstituted or substituted one to three times by R13; —($C_1$-$C_3$)-alkylene-C(O)—NH—R10 or —($C_1$-$C_3$)-alkylene-C(O)—O—R10, Z is
1) —($C_0$-$C_8$)-alkylene-,
2) —($C_2$-$C_{10}$)-alkenyl-,
3) —($C_2$-$C_{10}$)-alkynyl-,
4) —($C_0$-$C_4$)-alkylene-O—($C_0$-$C_4$)-alkylene-,
5) —($C_0$-$C_4$)-alkylene-O—C(O)—N(R10)-($C_0$-$C_4$)-alkylene-,
6) —($C_0$-$C_4$)-alkylene-C(O)—($C_0$-$C_4$)-alkylene-,
7) —($C_0$-$C_4$)-alkylene-N(R10)-C(O)—($C_0$-$C_4$)-alkylene-,
8) —($C_0$-$C_4$)-alkylene-N(R10)-C(O)—O—($C_0$-$C_4$)-alkylene-,
9) —($C_0$-$C_4$)-alkylene-N(R10)-C(O)—N(R10)-($C_0$-$C_4$)-alkylene-,
10) —($C_0$-$C_4$)-alkylene-N(R10)-($C_0$-$C_4$)-alkylene-,
11) —($C_0$-$C_4$)-alkylene-S—($C_0$-$C_4$)-alkylene-,
12) —($C_0$-$C_4$)-alkylene-S(O)—($C_0$-$C_4$)-alkylene-,
13) —($C_0$-$C_4$)-alkylene-$SO_2$—($C_0$-$C_4$)-alkylene-, or
14) —($C_0$-$C_4$)-alkylene-($C_3$-$C_8$)-cycloalkyl-($C_0$-$C_4$)-alkylene-, A is selected from a covalent bond, —($C_3$-$C_8$)-alkylene, —($C_3$-$C_8$)-cycloalkylene or —($C_3$-$C_{15}$)-heterocyclyl, wherein —($C_3$-$C_{15}$)-heterocyclyl is as defined above, B is
1) a covalent bond,
2) —($C_2$-$C_{10}$)-alkenyl-,
3) —($C_2$-$C_{10}$)-alkynyl-,
4) —($C_0$-$C_4$)-alkylene-CH(OH)—($C_0$-$C_4$)-alkylene-,
5) —($C_0$-$C_4$)-alkylene-O—($C_0$-$C_4$)-alkylene-,
6) —($C_0$-$C_4$)-alkylene-O—C(O)—N(R10)-($C_0$-$C_4$)-alkylene-,
7) —($C_0$-$C_4$)-alkylene-C(O)—($C_0$-$C_4$)-alkylene-,
8) —($C_0$-$C_4$)-alkylene-C(O)—O—($C_0$-$C_4$)-alkylene-,
9) —($C_0$-$C_4$)-alkylene-C(O)—N(R10)-,
10) —($C_0$-$C_4$)-alkylene-N(R10)-($C_0$-$C_4$)-alkylene-,
11) —($C_0$-$C_4$)-alkylene-N(R10)-C(O)—($C_0$-$C_4$)-alkylene-,
12) —($C_0$-$C_4$)-alkylene-N(R10)-C(O)—O—($C_0$-$C_4$)-alkylene-,
13) —($C_0$-$C_4$)-alkylene-N(R10)-C(O)—N(R10)-($C_0$-$C_4$)-alkylene-,
14) —($C_0$-$C_4$)-alkylene-N(R10)-$SO_2$—($C_0$-$C_4$)-alkylene-,
15) —($C_0$-$C_4$)-alkylene-N(R10)-$SO_2$—N(R10)-($C_0$-$C_4$)-alkylene-,
16) —($C_0$-$C_4$)-alkylene-S—($C_0$-$C_4$)-alkylene-,
17) —($C_0$-$C_4$)-alkylene-S(O)—($C_0$-$C_4$)-alkylene-,
18) —($C_0$-$C_4$)-alkylene-$SO_2$—($C_0$-$C_4$)-alkylene-,
19) —($C_0$-$C_4$)-alkylene-$SO_2$—N(R10)-($C_0$-$C_4$)-alkylene-,
20) —($C_0$-$C_4$)-alkylene-($C_3$-$C_8$)-cycloalkyl-($C_0$-$C_4$)-alkylene-, or
21) —($C_0$-$C_4$)-alkylene-($C_3$-$C_{15}$)-heterocyclyl-($C_0$-$C_4$)-alkylene-, wherein heterocyclyl is as defined above, wherein —($C_3$-$C_{15}$)-heterocyclyl is unsubstituted or mono-, di- or trisubstituted independently of one another by R14, and wherein the alkyl residues are unsubstituted or mono-, di- or trisubstituted independently of one another by halogen, —$NH_2$, —OH; or —($C_3$-$C_6$)-cycloalkyl, wherein cycloalkyl is unsubstituted or mono-, di- or trisubstituted independently of one another by halogen, —$NH_2$ or —OH;

R14 is halogen, —OH, =O, —($C_1$-$C_8$)-alkyl, —($C_1$-$C_4$)-alkoxy, —$NO_2$, —CN, —$NH_2$, —S—R18, —($C_1$-$C_4$)-alkylene-C(O)—OH, —C(O)—O—($C_1$-$C_4$)-alkyl, —($C_1$-$C_4$)-alkylene-C(O)—$NH_2$, —($C_0$-$C_8$)-alkylene-$SO_2$—($C_1$-$C_4$)-alkyl, —($C_0$-$C_8$)-alkylene-$SO_2$—($C_1$-$C_3$)-fluoroalkyl, —($C_0$-$C_8$)-alkylene-$SO_2$—N(R18)-R21, —($C_1$-$C_4$)-alkylene-C(O)—NH—($C_1$-$C_8$)-alkyl, —($C_1$-$C_4$)-alkylene-C(O)—N—[($C_1$-$C_8$)-alkyl]$_2$, —N(R18)-C(O)—NH—($C_1$-$C_8$)-alkyl, —N(R18)-C(O)—NH—[($C_1$-$C_8$)-alkyl]$_2$, —($C_2$-$C_{10}$)-alkenyl, or —($C_2$-$C_{10}$)-alkynyl, wherein R18 and R21 are independently from each other hydrogen atom, —($C_1$-$C_3$)-fluoroalkyl or —($C_1$-$C_6$)-alkyl, V is —($C_3$-$C_{15}$)-heterocyclyl or —N(R1)-($C_3$-$C_{15}$)-heterocyclyl, wherein —($C_3$-$C_{15}$)-heterocyclyl is as defined above and is unsubstituted or mono-, di- or trisubstituted independeatnly of one another by R14, G is
1) a covalent bond,
2) —($C_0$-$C_4$)-alkylene-O—($C_0$-$C_4$)-alkylene-,
3) —($C_0$-$C_4$)-alkylene-O—C(O)—N(R10)-($C_0$-$C_4$)-alkylene-,
4) —($C_0$-$C_4$)-alkylene-C(O)—($C_0$-$C_4$)-alkylene-,
5) —($C_0$-$C_4$)-alkylene-C(O)—O—($C_0$-$C_4$)-alkylene-,
6) —($C_0$-$C_4$)-alkylene-C(O)—N(R10)-,
7) —($C_0$-$C_4$)-alkylene-N(R10)-($C_0$-$C_4$)-alkylene-,
8) —($C_0$-$C_4$)-alkylene-N(R10)-C(O)—($C_0$-$C_4$)-alkylene-,
9) —($C_0$-$C_4$)-alkylene-N(R10)-C(O)—O—($C_0$-$C_4$)-alkylene-,
10) —($C_0$-$C_4$)-alkylene-N(R10)-C(O)—N(R10)-($C_0$-$C_4$)-alkylene-,
11) —($C_0$-$C_4$)-alkylene-N(R10)-$SO_2$—($C_0$-$C_4$)-alkylene-,
12) —($C_0$-$C_4$)-alkylene-N(R10)-$SO_2$—N(R10)-($C_0$-$C_4$)-alkylene-,
13) —($C_0$-$C_4$)-alkylene-$SO_2$—($C_0$-$C_4$)-alkylene-, or
14) —($C_0$-$C_4$)-alkylene-$SO_2$—N(R10)-($C_0$-$C_4$)-alkylene-, and wherein the alkyl residues are unsubstituted or mono-, di- or trisubstituted independently of one another by halogen, —$NH_2$, —OH; or —($C_3$-$C_6$)-cycloalkyl, wherein cycloalkyl is unsubstituted or mono-, di- or trisubstituted independently of one another by halogen, —$NH_2$ or —OH;

M is
1) a hydrogen atom,
2) —($C_1$-$C_8$)-alkyl, wherein alkyl is unsubstituted or mono-, di- or trisubstituted independently of one another by R14,
3) —C(O)—N(R11)-R12,
4) —C(O)—O—R12,
5) —($C_1$-$C_8$)-alkylene-N(R10)$_2$,
6) —($C_6$-$C_{14}$)-aryl, wherein aryl is selected from phenyl, naphthyl, biphenylyl, indanyl, anthryl and fluorenyl and aryl is unsubstituted or mono-, di- or trisubstituted independently of one another by R14,
7) —($C_3$-$C_8$)-cycloalkyl, wherein said cycloalkyl is unsubstituted or mono-, di- or trisubstituted independently of one another by R14, or
8) a 3- to 7-membered heterocyclyl, containing 1, 2, 3 or 4 heteroatoms chosen from nitrogen, sulfur or oxygen, selected from azepine, azetidine, aziridine, azirine, 1,4-diazepane, 1,2-diazepine, 1,3-diazepine, 1,4-diazepine, diaziridine, diazirine, dihydroimidazolone, dioxazole, dioxazine, dioxole, 1,3-dioxolene, 1,3-dioxolane, furan, imidazole, imidazoline, imidazolidine, imidazolidinone, isothiazole, isothiazolidine, isothiazoline, isoxazole, isoxazoline, isoxazolidine, morpholine, 1,2-oxathiepane, 1,2-oxathiolane, 1,4-oxazepane, 1,2-oxazine, 1,3-oxazine, 1,4-oxazine, oxazolone, oxazole, [1,3,4] oxathiazinane 3,3-dioxide, oxaziridine, oxazolidinone, oxetan, oxirane, piperazine, piperidine, pyran, pyrazine, pyrazole, pyrazoline, pyrazolidine, pyridazine, pyridine, pyridinone, pyrimidine, pyrimidine-2,4-dione, pyrrole, pyrrolidine, pyrrolidinone, pyrroline, tetrahydrofuran, tetrahydropyran, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiomorpholine-1,1-dioxide, thiopyran, 1,2,3-triazine, 1,2,4-triazine, 1,3,5-triazine, 1,2,3-triazole and 1,2,4-triazole, wherein said cyclic residue is unsubstituted or mono-, di- or trisubstituted independently of one another by R14, R2, R3, R4, R5 and R6 are independently of one another selected from
1) hydrogen atom,
2) —$(C_1$-$C_6)$-alkyl, wherein alkyl is unsubstituted or mono-, di- or trisubstituted independently of one another by R13,
3) —$(C_0$-$C_4)$-alkylene-O—R10,
4) halogen,
5) —$(C_1$-$C_3)$-fluoroalkyl,
6) —CN or
7) phenyl, wherein phenyl is unsubstituted or mono-, di- or trisubstituted independently of one another by R13, or R3 and R4, R4 and R5 or R5 and R6 are each time both —O—R10 and form together with the atoms which they are attached to a 1,3-dioxole ring or 2,3-dihydro-[1,4]dioxine ring, which is unsubstituted or substituted one, two, three or four times by R13, R3 and R4, R4 and R5 or R5 and R6 form together with the atoms which they are attached to a cyclopentyl or cyclohexyl, which is unsubstituted or substituted one, two, three or four times by R13, R7 is
1) hydrogen atom,
2) halogen,
3) —$(C_1$-$C_6)$-alkyl, wherein alkyl is unsubstituted or mono-, di- or trisubstituted independently of one another by R13,
4) =O,
5) —$(C_1$-$C_3)$-fluoroalkyl,
6) —$(C_0$-$C_4)$-alkylene-O—R19, wherein R19 is
  a) hydrogen atom,
  b) —$(C_1$-$C_4)$-alkyl, wherein alkyl is unsubstituted or mono-, di- or trisubstituted independently of one another by R13,
  c) —$(C_3$-$C_8)$-cycloalkyl, wherein alkyl is unsubstituted or mono-, di- or trisubstituted independently of one another by R13,
  d) phenyl, wherein phenyl is unsubstituted or mono-, di- or trisubstituted independently of one another by R13,
  e) —$CF_3$, or
  f) —$CHF_2$,
7) —$NO_2$,
8) —CN,
9) —$(C_0$-$C_4)$-alkylene-O—$CH_2$—$(C_1$-$C_3)$-fluoroalkylene-$CH_2$—O—$(C_1$-$C_4)$-alkyl,
10) —$(C_0$-$C_4)$-alkylene-C(O)—R11,
11) —$(C_0$-$C_4)$-alkylene-C(O)—O—R11,
12) —$(C_0$-$C_4)$-alkylene-C(O)—O—$(C_1$-$C_4)$-alkylene-O—C(O)—R17, wherein —$(C_1$-$C_4)$-alkylene is unsubstituted or mono-, di- or trisubstituted independently of one another by R15,
13) —$(C_0$-$C_4)$-alkylene-C(O)—O—$(C_1$-$C_4)$-alkylene-O—C(O)—O—R17, wherein —$(C_1$-$C_4)$-alkylene is unsubstituted or mono-, di- or trisubstituted independently of one another by R15,
14) —$(C_0$-$C_4)$-alkylene-C(O)—N(R11)-R12,
15) —$(C_0$-$C_4)$-alkylene-C(O)—N(R11)-R13,
16) —$(C_0$-$C_4)$-alkylene-C(O)—N[$(C_0$-$C_4)$-alkylene]-R13, wherein alkyl and cycloalkyl are unsubstituted or mono-, di- or trisubstituted independently of one another by R13,
17) —$(C_0$-$C_4)$-alkylene-C(O)—N[$(C_0$-$C_4)$-alkylene-$(C_3$-$C_8)$-cycloalkyl]-R13, wherein alkyl and cycloalkyl is unsubstituted or mono-, di- or trisubstituted independently of one another by R13,
18) —$(C_0$-$C_4)$-alkylene-N(R11)-R12,
19) —$(C_0$-$C_4)$-alkylene-N(R11)-R13,
20) —$(C_0$-$C_4)$-alkylene-N(R10)-$SO_2$—R10,
21) —$(C_0$-$C_4)$-alkylene-S—R10,
22) —$(C_0$-$C_4)$-alkylene-$SO_s$—R11, wherein s is 1 or 2,
23) —$(C_0$-$C_4)$-alkylene-$SO_t$—N(R11)-R12, wherein t is 1 or 2,
24) —$(C_0$-$C_4)$-alkylene-$SO_w$—N(R11)-R13, wherein w is 1 or 2,
25) —$(C_0$-$C_4)$-alkylene-$SO_u$—$(C_0$-$C_4)$-alkylene-C(O)—O—R10, wherein u is 1 or 2,
26) —$(C_0$-$C_4)$-alkylene-$(C_3$-$C_8)$-cycloalkyl, wherein cycloalkyl is unsubstituted or mono-, di- or trisubstituted independently of one another by R13,
27) —$(C_0$-$C_4)$-alkylene-$(C_6$-$C_{14})$-aryl, wherein aryl is selected from phenyl, naphthyl, biphenylyl, indanyl, anthryl or fluorenyl; and wherein aryl is unsubstituted or mono-, di- or trisubstituted independently of one another by R13, or
28) —$(C_0$-$C_4)$-alkylene-$(C_3$-$C_{15})$-heterocyclyl, wherein heterocyclyl is as defined above and is unsubstituted or mono-, di- or trisubstituted independently of one another by R13,
29) —$(C_0$-$C_4)$-alkylene-O—$(C_0$-$C_4)$-alkylene-$(C_6$-$C_{14})$-aryl, wherein aryl is unsubstituted or mono-, di- or trisubstituted independently of one another by R13,
30) —$(C_0$-$C_4)$-alkylene-O—$(C_0$-$C_4)$-alkylene-$(C_3$-$C_{15})$-heterocyclyl, wherein heterocyclyl is un-substituted or mono-, di- or trisubstituted independently of one another by R13,
31) —$(C_0$-$C_4)$-alkylene-N(R13)-$(C_0$-$C_4)$-alkylene-$(C_6$-$C_{14})$-aryl, wherein aryl is unsubstituted or mono-, di- or trisubstituted independently of one another by R13, or
32) —$(C_0$-$C_4)$-alkylene-N(R13)-$(C_0$-$C_4)$-alkylene-$(C_3$-$C_{15})$-heterocyclyl, wherein heterocyclyl is un-substituted or mono-, di- or trisubstituted independently of one another by R13, R11 and R12 are independently of one another identical or different and are
1) hydrogen atom,
2) —$(C_1$-$C_6)$-alkyl, wherein alkyl is unsubstituted or mono-, di- or trisubstituted independently of one another by R13,
3) —$(C_0$-$C_6)$-alkylene-$(C_3$-$C_8)$-cycloalkyl, wherein alkylene and cycloalkyl independently from one another are unsubstituted or mono-, di- or trisubstituted independently of one another by R13,
4) —$SO_t$—R10, wherein t is 1 or 2,
5) —$(C_0$-$C_6)$-alkylene-$(C_6$-$C_{14})$-aryl, wherein aryl is as defined above and alkylene and aryl independently from one another are unsubstituted or mono-, di- or trisubstituted by R13,
6) —$(C_1$-$C_3)$-fluoroalkyl,
7) —O—R17, or
8) —$(C_0$-$C_6)$-alkylene-$(C_3$-$C_{15})$-heterocyclyl, wherein heterocyclyl is as defined above and alkylene and heterocyclyl independently from one another are unsubstituted or mono-, di- or trisubstituted by R13, or R11 and R12 together with the nitrogen atom to which they are bonded form a 4- to 8-membered monocyclic heterocyclic ring, which is selected from aza-bicycloheptane, aza-bicyclohexane, aza-spiroheptane, aza-spirohexane, aza-spirooctane, aza-spiropentane, azepane, azepine, azetidine, diaza-bicycloheptane, diaza-bicyclohexane, diaza-spiroheptane, diaza-spirohexane, diaza-spiropentane, diaza-spirooctane 1,2-diazapane, 1,3-diazepane, 1,4-diazepane, 1,2-diazepine, 1,3-diazepine, 1,4-diazepine, dihydroazepine, dihydro-oxazepine, dihydro-pyridazine, dioxazole, hexahydro-pyridazine, imidazoline, imidazolidine, isothiazolidine, isothiazoline, isoxazoline, isoxazolidine, ketopiperazine, morpholine, 1,4-oxazepane, 1,2-oxa-thiepane, oxazepine, 1,2-oxazine, 1,3-oxazine, 1,4-oxazine, piperazine, piperidine, pyrazine, pyrazoline, pyrazolidine, pyridazine, pyrrolidine, pyrrolidinone, pyrroline, tetrahydro-azepine, 1,2,3,4-tetrahydropyrazine, tetrahydropyridine, tetrazine, tetrazole, thiadiazine, 1,2-thiazine, 1,3-thiazine, 1,4-thiazine, 1,3-thiazole, thiazolidine, thiazoline, thietan, thiomorpholine, triazepane, 1,2,4-triazinane and 1,3,5-triazinane; wherein said heterocyclic ring is unsubstituted or mono-, di- or trisubstituted independently of one another by R13, R13 is halogen, —$NO_2$, —CN, =O, —OH, —$CF_3$, —C(O)—O—R10, —C(O)—N(R10)-R20, —N(R10)-R20, —($C_3$-$C_8$)-cycloalkyl, —($C_2$-$C_{10}$)-alkenyl-, —($C_2$-$C_{10}$)-alkynyl-, —O—$CF_3$, —Si—$(CH_3)_3$, —($C_0$-$C_4$)-alkylene-O—R10, —N(R10)-S(O)$_u$—R10, wherein u is 1 or 2, —$SO_r$—R10, wherein r is 1 or 2, —S(O)$_v$—N(R10)-R20, wherein v is 1 or 2, —S—R10, —C(O)—R10, —($C_1$-$C_8$)-alkyl, —($C_1$-$C_8$)-alkoxy, phenyl, phenyloxy-, —($C_1$-$C_8$)-alkoxy-phenyl, —($C_0$-$C_4$)-alkylene-C(O)—O—C(R15, R16)-O—C(O)—R17, —O—R15, —NH—C(O)—NH—R10, —($C_0$-$C_4$)-alkylene-C(O)—O—C(R15, R16)-O—C(O)—O—R17, —($C_1$-$C_3$)-fluoroalkyl, —NH—C(O)—O—R10, or —($C_0$-$C_4$)-alkylene-R22, R10 and R20 are independently of one another hydrogen, —($C_1$-$C_4$)-alkyl, —($C_1$-$C_4$)-alkyl-OH, —($C_0$-$C_4$)-alkylene-O—($C_1$-$C_4$)-alkyl or —($C_1$-$C_3$)-fluoroalkyl, R15 and R16 are independently of one another hydrogen atom or —($C_1$-$C_6$)-alkyl, or together with the carbon atom to which they are bonded form a —($C_3$-$C_6$)-cycloalkyl, which is unsubstituted or mono, di- or trisubstituted by R10, R17 is hydrogen atom, —($C_1$-$C_6$)-alkyl, —($C_1$-$C_6$)-alkyl-OH, —($C_1$-$C_6$)-alkylene-O—($C_1$-$C_6$)-alkyl, —($C_0$-$C_6$)-alkylene-($C_3$-$C_8$)-cycloalkyl or —($C_1$-$C_6$)-alkylene-O—($C_1$-$C_6$)-alkylene-($C_3$-$C_8$)-cycloalkyl, wherein said cycloalkyl ring is unsubstituted or substituted one, two or three times by —OH, —O—($C_1$-$C_4$)-alkyl or R10, and R22 is a residue from the following list:

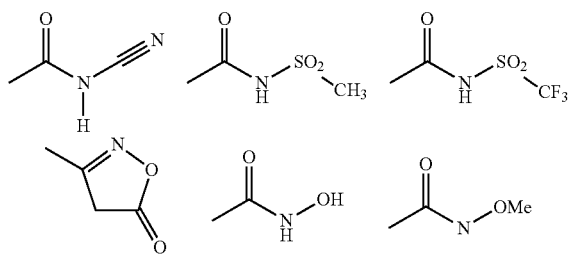

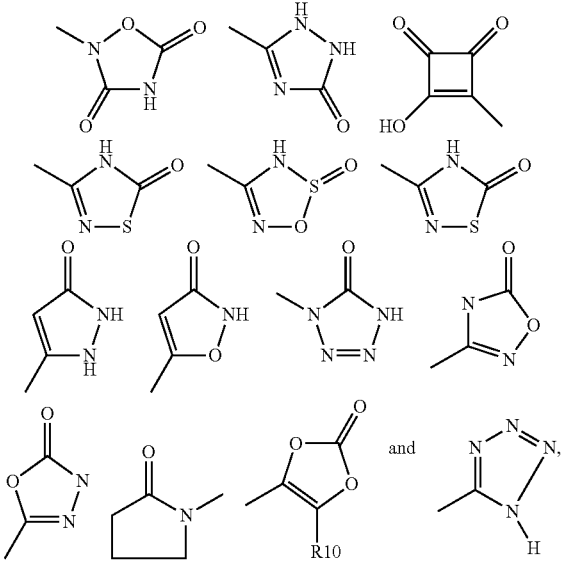

wherein Me is methyl,
in all its stereoisomeric forms and mixtures thereof in any ratio, and its physiologically tolerable salts.

4) The present invention further relates to compounds of the formula Ia,

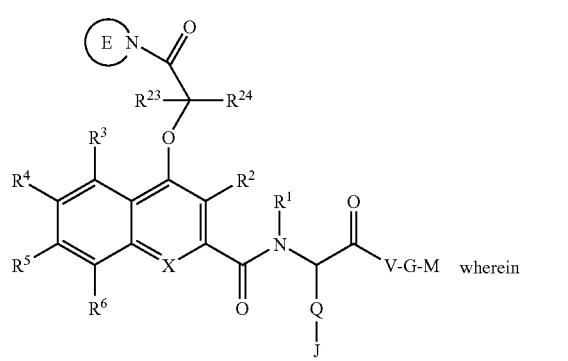

(Ia)

E is a heterocyclic residue selected from aza-bicycloheptane, aza-bicyclohexane, aza-bicyclooctane, aza-spiroheptane, aza-spirohexane, aza-spirooctane, aza-spiropentane, azepane, azepine, azetidine, aziridine, decahydro-quinoline, diaza-bicyclohexane, diaza-bicycloheptane, 2,5-Diaza-bicyclo[2.2.1]heptane, 1,2-diazapane, 2,7-diaza-spiro[4.5]decane, 2,8-diaza-spiro[4.5]decane, diaza-spirohexane, diaza-spirooctane, diaza-spiropentane, diaza-spiroheptane, 1,3-diazepane, 1,4-diazepane, 1,2-diazepine, 1,3-diazepine, 1,4-diazepine, dihydroazepine, 2,3-dihydro-1H-indole, 3,4-dihydro-1H-isoquinoline, 4,7-dihydro-5H-isoxazolo[5,4-c]pyridine, 6,7-dihydro-4H-isoxazolo[4,5-c]pyridine, dihydro-pyridazine, dihydro-oxazepine, 6,7-dihydro-4H-oxazolo[5,4-c]pyridine, 4,6-dihydro-1H-pyrrolo[3,4-c]pyrazol, 4,6-dihydro-4H-pyrrolo[3,4-d]thiazole, 6,7-dihydro-4H-thiazolo[5,4-c]pyridine, 4,7-dihydro-5H-thieno[2,3-c]pyridine, 5,6-Dihydro-8H-[1,2,4]triazolo[4,3-a]pyrazin, dioxazole, hexahydro-cyclopenta[c]pyrroline, hexahydro-pyridazine, hexahydro-pyrrolo[1,2-a]pyrazin, hexahydropyrrolo[3,4-b]pyrrol, Hexahydro-pyrrolo[1,2-a]pyrazin, imidazoline, imidazolidine, indole, isoquinoline, isothiazolidine, isothiazoline, isoxazoline, isoxazolidine, ketopiperazine, morpholine, octahydro-cyclopenta[c]pyrrole, octahydro-indole, octahydro-pyrrolo[3,4-b]pyridine, octahydro-pyrrolo[3,4-c]pyridine, 1,4-oxazepane, oxazepine, 1,2-oxa-thiepane, 1,2-oxazine, 1,3-oxazine, 1,4-oxazine, oxazolidine, piperazine, piperidine, pyrazine, pyrazoline, pyrazolidine, pyridazine, pyrrolidine, pyrrolidinone, pyrroline, tetrahydropyridine, tetrahydro-azepine, 1,2,3,4-tetrahydro-isoquinoline, 4,5,6,7-tetrahydro-isoxazolo[4,5-c]pyridine, 1,2,3,4-tetrahydropyrazine, 1,4,6,7-tetrahydro-pyrazolo[4,3-c]pyridine, 4,5,6,7-tetrahydro-1H-pyrazolo[4,3-c]pyridine, tetrahydro-pyridazine, 3,5,7,8-tetrahydro-4H-pyrido[4,3-d]pyrimidine, 4,5,6,6a-tetrahydro-3aH-pyrrolo[3,4-d]isoxazole, 1,2,3,4-tetrahydro-quinoline, 4,5,6,7-tetrahydro-thieno[2,3-c]pyridine, 1,4,6,7-tetrahydro-thiazolo[5,4-c]pyridine, 4,5,6,7-tetrahydro-thieno[3,2-c]pyridine, tetrazine, tetrazole, thiadiazine, 1,2-thiazine, 1,3-thiazine, 1,4-thiazine, 1,3-thiazole, thiazolidine, thiazoline, thietan, thiomorpholine, 1,3,8-triaza-spiro[4.5]decane, triaza-spirooctane, triazepane, 1,2,4-triazinane and 1,3,5-triazinane, wherein said heterocyclic residue is bond by its nitrogen atom to the carbonyl carbon atom and wherein said heterocyclic residue is mono-, di- or trisubstituted independently of one another by R7, Q is
1) a covalent bond,
2) —($C_0$-$C_4$)-alkylene-CH(OH)—($C_0$-$C_4$)-alkylene-,
3) —($C_0$-$C_4$)-alkylene-O—($C_0$-$C_4$)-alkylene-,
4) —($C_0$-$C_4$)-alkylene-C(O)—($C_0$-$C_4$)-alkylene-,
5) —($C_0$-$C_4$)-alkylene-C(O)—O—($C_0$-$C_4$)-alkylene-,
6) —($C_0$-$C_4$)-alkylene-C(O)—N(R10)-,
7) —($C_0$-$C_4$)-alkylene-N(R10)-($C_0$-$C_4$)-alkylene-,
8) —($C_0$-$C_4$)-alkylene-N(R10)-C(O)—($C_0$-$C_4$)-alkylene-,
9) —($C_0$-$C_4$)-alkylene-N(R10)-C(O)—O—($C_0$-$C_4$)-alkylene-,
10) —($C_0$-$C_4$)-alkylene-N(R10)-C(O)—N(R10)-($C_0$-$C_4$)-alkylene-,
11) —($C_0$-$C_4$)-alkylene-S—($C_0$-$C_4$)-alkylene-,
12) —($C_0$-$C_4$)-alkylene-$SO_2$—($C_0$-$C_4$)-alkylene-,
13) —($C_0$-$C_4$)-alkylene-($C_3$-$C_6$)-cycloalkyl-($C_0$-$C_4$)-alkylene-, or
14) —($C_0$-$C_4$)-alkylene-($C_3$-$C_{15}$)-heterocyclyl-($C_0$-$C_4$)-alkylene-, wherein —($C_3$-$C_{15}$)-heterocyclyl is selected from acridinyl, azabenzimidazolyl, aza-bicycloheptanyl, aza-bicyclohexanyl, aza-bicyclooctanyl, 8-aza-bicyclo[3.2.1]octanyl, azaspirodecanyl, aza-spiroheptanyl, aza-spirohexanyl, aza-spirooctanyl, aza-spiropentanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydro-quinolinyl, diaza-bicyclohexanyl, diaza-bicycloheptanyl, 2,5-Diaza-bicyclo[2.2.1]heptanyl, 1,2-diazapanyl, diaza-spirohexanyl, diaza-spirooctanyl, diaza-spiropentanyl, diaza-spiroheptanyl, 1,3-diazepanyl, 1,4-diazepanyl, 1,2-diazepinyl, 1,3-diazepinyl, 1,4-diazepinyl, dihydroazepinyl, 3,4-dihydro-2H-quinoline, dihydrofuro[2,3-b]-tetrahydrofuranyl, 2,3-dihydro-1H-indolyl, 3,4-dihydro-1H-isoquinolinyl, 6,7-dihydro-4H-isoxazolo[4,5-c]pyridinyl, dihydro-pyridazinyl, 4,5-dihydro-[1,3,4]oxadiazol, 4,5-dihydro-oxazolinyl, 4,5-dihydrooxazolinyl, 4,6-dihydro-4H-pyrrolo[3,4-d]thiazolyl, 6,7-dihydro-4H-thiazolo[5,4-c]pyridinyl, 4,7-dihydro-5H-thieno[2,3-c]pyridinyl, 1,3-dioxanyl, dioxazolyl, dioxazinyl, 1,3-dioxolanyl, 1,3-dioxolenyl, 3,3-dioxo[1,3,4]oxathiazinyl, 6H-1,5,2-dithiazinyl, furanyl, furazanyl, hexahydro-pyridazine, hexahydro-cyclopenta[c]pyrroline, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydro-cyclopenta[c]pyrrolyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 1H-pyrrolopyridinyl, 2H-pyrrolyl, pyrrolyl, quinazolinyl, quinolinyl, 4H-quinolizinyl, quinoxalinyl, quinuclidinyl, tetrahydrofuranyl, 1,2,3,4-tetrahydro-isoquinolinyl, 4,5,6,7-tetrahydro-isoxazolo[4,5-c]pyridinyl, tetrahydropyranyl, 1,2,3,4-tetrahydropyrazinyl, 4,5,6,7-tetrahydro-1H-pyrazolo[4,3-c]pyridinyl, tetrahydro-pyridazinyl, tetrahydro-pyridinyl, 4,5,6,6a-tetrahydro-3aH-pyrrolo[3,4-d]isoxazolyl, 1,2,3,4-tetrahydro-quinolinyl, 4,5,6,7-tetrahydro-thieno[2,3-c]pyridinyl, 1,4,6,7-tetrahydro-thiazolo[5,4-c]pyridinyl, 4,5,6,7-tetrahydro-thieno[3,2-c]pyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, triaza-spirooctanyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl, and xanthenyl, and wherein —($C_3$-$C_{15}$)-heterocyclyl is unsubstituted or mono-, di- or trisubstituted independently of one another by R14; and wherein the alkyl residues are unsubstituted or mono-, di- or trisubstituted independently of one another by halogen, —$NH_2$, —OH; or —($C_3$-$C_6$)-cycloalkyl, wherein cycloalkyl is unsubstituted or mono-, di- or trisubstituted independently of one another by halogen, —$NH_2$ or —OH;

J is
1) hydrogen atom,
2) —($C_1$-$C_6$)-alkyl, wherein alkyl is unsubstituted or mono-, di- or trisubstituted independently of one another by R13,
3) —($C_0$-$C_4$)-alkylene-C(O)—R11,
4) —($C_0$-$C_4$)-alkylene-C(O)—O—R11,
5) —($C_0$-$C_4$)-alkylene-C(O)—O—($C_1$-$C_4$)-alkylene-O—C(O)—R17, wherein —($C_1$-$C_4$)-alkylene is unsubstituted or mono-, di- or trisubstituted independently of one another by R15, 6) —($C_0$-$C_4$)-alkylene-C(O)—O—($C_1$-$C_4$)-alkylene-O—C(O)—O—R17, wherein —($C_1$-$C_4$)-alkylene is unsubstituted or mono-, di- or trisubstituted independently of one another by R15,
7) —($C_0$-$C_4$)-alkylene-C(O)—N(R11)-R13
8) —($C_0$-$C_4$)-alkylene-N(R11)-R13,
9) —($C_0$-$C_4$)-alkylene-N(R10)-$SO_2$—R10,
10) —($C_0$-$C_4$)-alkylene-$SO_s$—R11, wherein s is 1 or 2,
11) —($C_0$-$C_4$)-alkylene-$SO_t$—N(R11)-R12, wherein t is 1 or 2,
12) —($C_0$-$C_4$)-alkylene-$SO_w$—N(R11)-R13, wherein w is 1 or 2,
13) —($C_0$-$C_4$)-alkylene-R22,
14) —($C_0$-$C_4$)-alkylene-($C_3$-$C_6$)-cycloalkyl, wherein cycloalkyl is unsubstituted or mono-, di- or trisubstituted independently of one another by R13,
15) —($C_0$-$C_4$)-alkylene-($C_6$-$C_{14}$)-aryl, wherein aryl is selected from phenyl or indanyl, and aryl is unsubstituted or mono-, di- or trisubstituted independently of one another by R13, or
16) —($C_0$-$C_4$)-alkylene-($C_3$-$C_{15}$)-heterocyclyl, wherein —($C_3$-$C_{15}$)-heterocyclyl is as defined above and is unsubstituted or mono-, di- or trisubstituted independently of one another by R13, V is —($C_3$-$C_{15}$)-heterocyclyl or —N(R1)-($C_3$-$C_{15}$)-heterocyclyl, wherein —($C_3$-$C_{15}$)-heterocyclyl is as defined above and is unsubstituted or mono-, di- or trisubstituted independently of one another by R14, G is
1) a covalent bond,
2) —($C_0$-$C_4$)-alkylene-O—($C_0$-$C_4$)-alkylene-,
3) —($C_0$-$C_4$)-alkylene-O—C(O)—N(R10)-($C_0$-$C_4$)-alkylene-,
4) —($C_0$-$C_4$)-alkylene-C(O)—($C_0$-$C_4$)-alkylene-,
5) —($C_0$-$C_4$)-alkylene-C(O)—O—($C_0$-$C_4$)-alkylene-,
6) —($C_0$-$C_4$)-alkylene-C(O)—N(R10)-,
7) —($C_0$-$C_4$)-alkylene-N(R10)-($C_0$-$C_4$)-alkylene-,
8) —($C_0$-$C_4$)-alkylene-N(R10)-C(O)—($C_0$-$C_4$)-alkylene-,
9) —($C_0$-$C_4$)-alkylene-N(R10)-C(O)—O—($C_0$-$C_4$)-alkylene-,
10) —($C_0$-$C_4$)-alkylene-N(R10)-C(O)—N(R10)-($C_0$-$C_4$)-alkylene-,
11) —($C_0$-$C_4$)-alkylene-N(R10)-$SO_2$—($C_0$-$C_4$)-alkylene-,
12) —($C_0$-$C_4$)-alkylene-N(R10)-$SO_2$—N(R10)-($C_0$-$C_4$)-alkylene-,
13) —($C_0$-$C_4$)-alkylene-$SO_2$—($C_0$-$C_4$)-alkylene-, or
14) —($C_0$-$C_4$)-alkylene-$SO_2$—N(R10)-($C_0$-$C_4$)-alkylene-,
and wherein the alkyl residues are unsubstituted or mono-, di- or trisubstituted independently of one another by halogen, —$NH_2$, —OH; or —($C_3$-$C_6$)-cycloalkyl, wherein cycloalkyl is unsubstituted or mono-, di- or trisubstituted independently of one another by halogen, —$NH_2$ or —OH;

M is
1) a hydrogen atom,
2) —($C_1$-$C_8$)-alkyl, wherein alkyl is unsubstituted or mono-, di- or trisubstituted independently of one another by R14,
3) —C(O)—N(R11)-R12,
4) —C(O)—O—R12,
5) —($C_1$-$C_8$)-alkylene-N(R10)$_2$,
6) —($C_6$-$C_{14}$)-aryl, wherein aryl is selected from phenyl, naphthyl, biphenylyl, indanyl, anthryl and fluorenyl and aryl is unsubstituted or mono-, di- or trisubstituted independently of one another by R14,
7) —($C_3$-$C_6$)-cycloalkyl, wherein said cycloalkyl is unsubstituted or mono-, di- or trisubstituted independently of one another by R14, or
8) a 3- to 7-membered heterocyclyl, containing 1, 2, 3 or 4 heteroatoms chosen from nitrogen, sulfur or oxygen, selected from azepine, azetidine, aziridine, azirine, 1,4-diazepane, 1,2-diazepine, 1,3-diazepine, 1,4-diazepine, diaziridine, diazirine, dihydroimidazolone, dioxazole, dioxazine, dioxole, 1,3-dioxolene, 1,3-dioxolane, furan, imidazole, imidazoline, imidazolidine, imidazolidinone, isothiazole, isothiazolidine, isothiazoline, isoxazole, isoxazoline, isoxazolidine, morpholine, 1,2-oxathiepane, 1,2-oxathiolane, 1,4-oxazepane, 1,2-oxazine, 1,3-oxazine, 1,4-oxazine, oxazolone, oxazole, [1,3,4]oxathiazinane 3,3-dioxide, oxaziridine, oxazolidinone, oxetan, oxirane, piperazine, piperidine, pyran, pyrazine, pyrazole, pyrazoline, pyrazolidine, pyridazine, pyridine, pyridinone, pyrimidine, pyrimidine-2,4-dione, pyrrole, pyrrolidine, pyrrolidinone, pyrroline, tetrahydrofuran, tetrahydropyran, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiomorpholine 1,1-dioxide thiopyran, 1,2,3-triazine, 1,2,4-triazine, 1,3,5-triazine, 1,2,3-triazole and 1,2,4-triazole, wherein said cyclic residue is unsubstituted or mono-, di- or trisubstituted independently of one another by R14, R1 is a hydrogen atom, —($C_1$-$C_4$)-alkyl, wherein alkyl is unsubstituted or substituted one to three times by R13; —($C_1$-$C_3$)-alkylene-C(O)—NH—R10 or —($C_1$-$C_3$)-alkylene-C(O)—O—R10, R2, R3, R4, R5 and R6 are independently of one another selected from
1) hydrogen atom,
2) —($C_1$-$C_6$)-alkyl, wherein alkyl is unsubstituted or mono-, di- or trisubstituted independently of one another by R13,
3) —($C_0$-$C_4$)-alkylene-O—R10,
4) halogen,
5) —($C_1$-$C_3$)-fluoroalkyl,
6) —CN or
5) phenyl, wherein phenyl is unsubstituted or mono-, di- or trisubstituted independently of one another by R13, or R3 and R4, R4 and R5 or R5 and R6 are each time both —O—R10 and form together with the atoms which they are attached to a 1,3-dioxole ring or 2,3-dihydro-[1,4]dioxine ring, which is unsubstituted or substituted one, two, three or four times by R13, R3 and R4, R4 and R5 or R5 and R6 form together with the atoms which they are attached to a cyclopentyl or cyclohexyl, which is unsubstituted or substituted one, two, three or four times by R13, R7 is
1) hydrogen atom,
2) halogen,
3) —($C_1$-$C_6$)-alkyl, wherein alkyl is unsubstituted or mono-, di- or trisubstituted independently of one another by R13,
4) =O,
5) —($C_1$-$C_3$)-fluoroalkyl,
6) —($C_0$-$C_4$)-alkylene-O—R19, wherein R19 is
a) hydrogen atom,
b) —($C_1$-$C_4$)-alkyl, wherein alkyl is unsubstituted or mono-, di- or trisubstituted independently of one another by R13, c) —($C_3$-$C_8$)-cycloalkyl, wherein alkyl is unsubstituted or mono-, di- or trisubstituted independently of one another by R13, d) phenyl, wherein phenyl is unsubstituted or mono-, di- or trisubstituted independently of one another by R13, e) —$CF_3$, or f) —$CHF_2$,

7) —$NO_2$,

8) —CN,

9) —($C_0$-$C_4$)-alkylene-O—$CH_2$—($C_1$-$C_3$)-fluoroalkylene-$CH_2$—O—($C_1$-$C_4$)-alkyl, 10) —($C_0$-$C_4$)-alkylene-C(O)—R11, 11) —($C_0$-$C_4$)-alkylene-C(O)—O—R11, 12) —($C_0$-$C_4$)-alkylene-C(O)—O—($C_1$-$C_4$)-alkylene-O—C(O)—R17, wherein —($C_1$-$C_4$)-alkylene is unsubstituted or mono-, di- or trisubstituted independently of one another by R15, 13) —($C_0$-$C_4$)-alkylene-C(O)—O—($C_1$-$C_4$)-alkylene-O—C(O)—O—R17, wherein —($C_1$-$C_4$)-alkylene is unsubstituted or mono-, di- or trisubstituted independently of one another by R15, 14) —($C_0$-$C_4$)-alkylene-C(O)—N(R11)-R12, 15) —($C_0$-$C_4$)-alkylene-C(O)—N(R11)-R13, 16) —($C_0$-$C_4$)-alkylene-C(O)—N[($C_0$-$C_4$)-alkylene]-R13, wherein alkyl and cycloalkyl are unsubstituted or mono-, di- or trisubstituted independently of one another by R13, 17) —($C_0$-$C_4$)-alkylene-C(O)—N[($C_0$-$C_4$)-alkylene-($C_3$-$C_8$)-cycloalkyl]-R13, wherein alkyl and cycloalkyl is unsubstituted or mono-, di- or trisubstituted independently of one another by R13, 18) —($C_0$-$C_4$)-alkylene-N(R11)-R12, 19) —($C_0$-$C_4$)-alkylene-N(R11)-R13, 20) —($C_0$-$C_4$)-alkylene-N(R10)-$SO_2$—R10, 21) —($C_0$-$C_4$)-alkylene-S—R10, 22) —($C_0$-$C_4$)-alkylene-$SO_s$—R11, wherein s is 1 or 2, 23) —($C_0$-$C_4$)-alkylene-$SO_t$—N(R11)-R12, wherein t is 1 or 2, 24) —($C_0$-$C_4$)-alkylene-$SO_w$—N(R11)-R13, wherein w is 1 or 2, 25) —($C_0$-$C_4$)-alkylene-$SO_u$—($C_0$-$C_4$)-alkylene-C(O)—O—R10, wherein u is 1 or 2, 26) —($C_0$-$C_4$)-alkylene-($C_3$-$C_6$)-cycloalkyl, wherein cycloalkyl is unsubstituted or mono-, di- or trisubstituted independently of one another by R13, 27) —($C_0$-$C_4$)-alkylene-($C_6$-$C_{14}$)-aryl, wherein aryl is selected from phenyl, naphthyl, biphenylyl, indanyl, anthryl or fluorenyl; and wherein aryl is unsubstituted or mono-, di- or trisubstituted independently of one another by R13, 28) —($C_0$-$C_4$)-alkylene-($C_3$-$C_{15}$)-heterocyclyl, wherein heterocyclyl is as defined above and is unsubstituted or mono-, di- or trisubstituted independently of one another by R13, 29) —($C_0$-$C_4$)-alkylene-O—($C_0$-$C_4$)-alkylene-($C_6$-$C_{14}$)-aryl, wherein aryl is unsubstituted or mono-, di- or trisubstituted independently of one another by R13, 30) —($C_0$-$C_4$)-alkylene-O—($C_0$-$C_4$)-alkylene-($C_3$-$C_{15}$)-heterocyclyl, wherein heterocyclyl is un-substituted or mono-, di- or trisubstituted independently of one another by R13, 31) —($C_0$-$C_4$)-alkylene-N(R13)-($C_0$-$C_4$)-alkylene-($C_6$-$C_{14}$)-aryl, wherein aryl is unsubstituted or mono-, di- or trisubstituted independently of one another by R13, or 32) —($C_0$-$C_4$)-alkylene-N(R13)-($C_0$-$C_4$)-alkylene-($C_3$-$C_{15}$)-heterocyclyl, wherein heterocyclyl is un-substituted or mono-, di- or trisubstituted independently of one another by R13, R11 and R12 are independently of one another identical or different and are 1) hydrogen atom, 2) —($C_1$-$C_6$)-alkyl, wherein alkyl is unsubstituted or mono-, di- or trisubstituted independently of one another by R13, 3) —($C_0$-$C_6$)-alkylene-($C_3$-$C_8$)-cycloalkyl, wherein alkylene and cycloalkyl independently from one another are unsubstituted or mono-, di- or trisubstituted independently of one another by R13, 4) —$SO_t$—R10, wherein t is 1 or 2, 5) —($C_0$-$C_6$)-alkylene-($C_6$-$C_{14}$)-aryl, wherein aryl is as defined above and alkylene and aryl independently from one another are unsubstituted or mono-, di- or trisubstituted by R13, 6) —($C_1$-$C_3$)-fluoroalkyl, 7) —O—R17, or 8) —($C_0$-$C_6$)-alkylene-($C_3$-$C_{15}$)-heterocyclyl, wherein —($C_3$-$C_{15}$)-heterocyclyl is as defined above and alkylene and heterocyclyl independently from one another are unsubstituted or mono-, di- or trisubstituted by R13, or R11 and R12 together with the nitrogen atom to which they are bonded form a 4- to 8-membered monocyclic heterocyclic ring, which is selected from aza-bicycloheptane, aza-bicyclohexane, aza-spiroheptane, aza-spirohexane, aza-spirooctane, aza-spiropentane, azepane, azepine, azetidine, diaza-bicycloheptane, diaza-bicyclohexane, diaza-spiroheptane, diaza-spirohexane, diaza-spiropentane, diaza-spirooctane 1,2-diazapane, 1,3-diazepane, 1,4-diazepane, 1,2-diazepine, 1,3-diazepine, 1,4-diazepine, dihydroazepine, dihydro-oxazepine, dihydro-pyridazine, dioxazole, hexahydro-pyridazine, imidazoline, imidazolidine, isothiazolidine, isothiazoline, isoxazoline, isoxazolidine, ketopiperazine, morpholine, 1,4-oxazepane, 1,2-oxa-thiepane, oxazepine, 1,2-oxazine, 1,3-oxazine, 1,4-oxazine, piperazine, piperidine, pyrazine, pyrazoline, pyrazolidine, pyridazine, pyrrolidine, pyrrolidinone, pyrroline, tetrahydro-azepine, 1,2,3,4-tetrahydropyrazine, tetrahydropyridine, tetrazine, tetrazole, thiadiazine, 1,2-thiazine, 1,3-thiazine, 1,4-thiazine, 1,3-thiazole, thiazolidine, thiazoline, thietan, thiomorpholine, triazepane, 1,2,4-triazinane and 1,3,5-triazinane; wherein said heterocyclic ring is unsubstituted or mono-, di- or trisubstituted independently of one another by R13, R13 is halogen, —$NO_2$, —CN, =O, —OH, —$CF_3$, —C(O)—O—R10, —C(O)—N(R10)-R20, —N(R10)-R20, —($C_3$-$C_8$)-cycloalkyl, —($C_2$-$C_{10}$)-alkenyl-, —($C_2$-$C_{10}$)-alkynyl-, —O—$CF_3$, —Si—$(CH_3)_3$, —($C_0$-$C_4$)-alkylene-O—R10, —N(R10)-S(O)$_u$—R10, wherein u is 1 or 2, —$SO_r$—R10, wherein r is 1 or 2, —$S(O)_v$—N(R10)-R20, wherein v is 1 or 2, —S—R10, —C(O)—R10, —($C_1$-$C_8$)-alkyl, —($C_1$-$C_8$)-alkoxy, phenyl, phenyloxy-, —($C_1$-$C_8$)-alkoxy-phenyl, —($C_0$-$C_4$)-alkylene-C(O)—O—C(R15, R16)-O—C(O)—R17, —O—R15, —NH—C(O)—NH—R10, —($C_0$-$C_4$)-alkylene-C(O)—O—C(R15, R16)-O—C(O)—O—R17, —($C_1$-$C_3$)-fluoroalkyl, hydrogen, —NH—C(O)—O—R10, or —($C_0$-$C_4$)-alkylene-R22, R10 and R20 are independently of one another hydrogen, —($C_1$-$C_4$)-alkyl, —($C_1$-$C_4$)-alkyl-OH, —($C_0$-$C_4$)-alkylene-O—($C_1$-$C_4$)-alkyl or —($C_1$-$C_3$)-fluoroalkyl, R14 is halogen, —OH, =O, —($C_1$-$C_4$)-alkyl, —($C_1$-$C_4$)-alkoxy, —$NO_2$, —CN, —$NH_2$, —S—R18, —($C_1$-$C_4$)- alkylene-C(O)—OH, —C(O)—O—(C$_1$-C$_4$)-alkyl, —(C$_1$-C$_4$)-alkylene-C(O)—NH$_2$, —(C$_0$-C$_8$)-alkylene-SO$_2$—(C$_1$-C$_4$)-alkyl, —(C$_0$-C$_8$)-alkylene-SO$_2$—(C$_1$-C$_3$)-fluoroalkyl, —(C$_0$-C$_8$)-alkylene-SO$_2$—N(R18)-R21, —(C$_1$-C$_4$)-alkylene-C(O)—NH—(C$_1$-C$_8$)-alkyl, —(C$_1$-C$_4$)-alkylene-C(O)—N—[(C$_1$-C$_8$)-alkyl]$_2$, —N(R18)-C(O)—NH—(C$_1$-C$_8$)-alkyl, hydrogen, —N(R18)-C(O)—NH—[(C$_1$-C$_8$)-alkyl]$_2$, —(C$_2$-C$_{10}$)-alkenyl, or —(C$_2$-C$_{10}$)-alkynyl, wherein R18 and R21 are independently from each other hydrogen atom, —(C$_1$-C$_3$)-fluoroalkyl or —(C$_1$-C$_6$)-alkyl, R15 and R16 are independently of one another hydrogen atom or —(C$_1$-C$_6$)-alkyl, or together with the carbon atom to which they are bonded form a —(C$_3$-C$_6$)-cycloalkyl, which is unsubstituted or mono, di- or trisubstituted by R10, R17 is hydrogen atom, —(C$_1$-C$_6$)-alkyl, —(C$_1$-C$_6$)-alkyl-OH, —(C$_1$-C$_6$)-alkylene-O—(C$_1$-C$_6$)-alkyl, —(C$_0$-C$_6$)-alkylene-(C$_3$-C$_8$)-cycloalkyl or —(C$_1$-C$_6$)-alkylene-O—(C$_1$-C$_6$)-alkylene-(C$_3$-C$_8$)-cycloalkyl, wherein each cycloalkyl ring is unsubstituted or substituted one, two or three times by —OH, —O—(C$_1$-C$_4$)-alkyl or R10, and R22 is a residue from the following list:

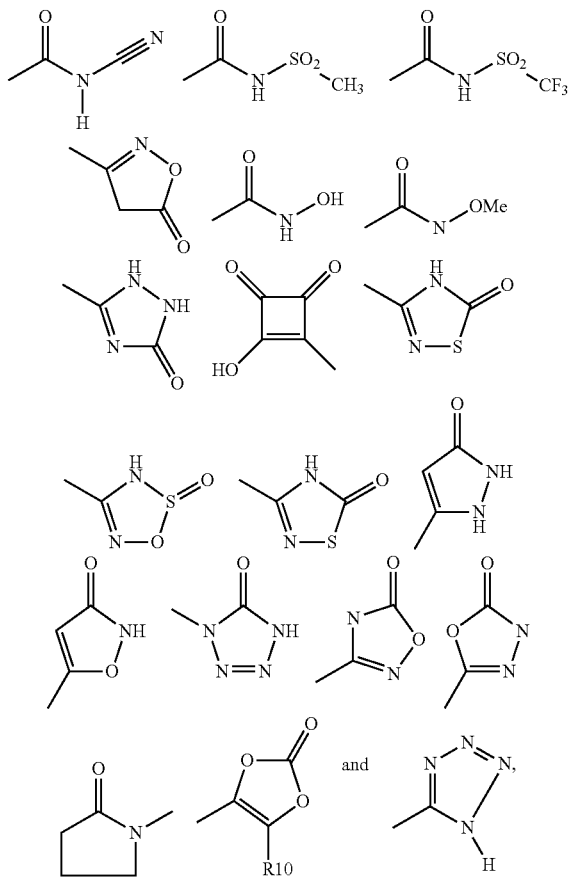

wherein Me is methyl,

R23 and R24 are independently of one another selected from hydrogen atom or methyl, in all its stereoisomeric forms and mixtures thereof in any ratio, and its physiologically tolerable salts.

5) The present invention also relates to compounds of the formula Ia, wherein

E is a heterocyclic residue selected from aza-bicyclohexane, aza-bicyclooctane, azetidine, aziridine, decahydro-quinoline, 2,5-diaza-bicyclo[2.2.1]heptane, 1,4-diazepane, 2,7-diaza-spiro[4.5]decane, 2,8-diaza-spiro[4.5]decane, 2,3-dihydro-1H-indole, 4,7-dihydro-5H-isoxazolo[5,4-c]pyridine, 6,7-dihydro-4H-oxazolo[5,4-c]pyridine, 4,6-dihydro-1H-pyrrolo[3,4-c]pyrazol, 4,6-dihydro-4H-pyrrolo[3,4-d]thiazole, 5,6-Dihydro-8H-[1,2,4]triazolo[4,3-a]pyrazin, hexahydro-pyrrolo[1,2-a]pyrazin, hexahydro-pyrrolo[3,4-b]pyrrol, hexahydro-pyrrolo[1,2-a]pyrazin, imidazolidine, morpholine, indole, octahydro-cyclopenta[c]pyrrole, octahydro-indole, octahydro-pyrrolo[3,4-b]pyridine, octahydro-pyrrolo[3,4-c]pyridine, oxazolidine, piperazine, piperidine, pyrazolidine, pyrrolidine, 1,4,6,7-tetrahydro-pyrazolo[4,3-c]pyridine, 1,2,3,4-tetrahydro-isoquinoline, 4,5,6,7-tetrahydro-isoxazolo[4,5-c]pyridine, 4,5,6,7-tetrahydro-1H-pyrazolo[4,3-c]pyridine, 3,5,7,8-tetrahydro-4H-pyrido[4,3-d]pyrimidine, 4,5,6,6a-tetrahydro-3aH-pyrrolo[3,4-d]isoxazole, 1,2,3,4-tetrahydro-quinoline, 4,5,6,7-tetrahydro-thieno[2,3-c]pyridine, 4,5,6,7-tetrahydro-thieno[3,2-c]pyridine, 4,5,6,7-tetrahydro-thiazolo[5,4-c]pyridine, 1,3,8-triaza-spiro[4.5]decane or triaza-spirooctane, wherein said heterocyclic residue is mono-, di- or trisubstituted independently of one another by R7, Q is
1) a covalent bond,
2) —(C$_0$-C$_4$)-alkylene-CH(OH)—,
3) —(C$_0$-C$_4$)-alkylene-C(O)—N(R10)-,
4) —(C$_1$-C$_3$)-alkylene-C(O)—O—,
5) —(C$_1$-C$_3$)-alkylene-O— or
6) —(C$_1$-C$_3$)-alkylene-S(O)$_2$—, J is
1) hydrogen atom,
2) —(C$_1$-C$_6$)-alkyl,
3) —(C$_0$-C$_4$)-alkylene-C(O)—R11,
4) —(C$_0$-C$_4$)-alkylene-C(O)—O—R11,
5) —(C$_0$-C$_4$)-alkylene-N(R11)-R13,
6) —(C$_0$-C$_2$)-alkylene-(C$_3$-C$_6$)-cycloalkyl,
7) —(C$_0$-C$_2$)-alkylene-(C$_6$-C$_{14}$)-aryl, wherein aryl is selected from phenyl or indanyl, or
8) —(C$_0$-C$_4$)-alkylene-(C$_3$-C$_{15}$)-heterocyclyl, wherein —(C$_3$-C$_{15}$)-heterocyclyl is azetidinyl, benzimidazolyl, 2,3-dihydro-1H-indolyl, 4,5-dihydro-[1,3,4]oxadiazolyl, 3,4-dihydro-2H-quinolinyl, 1,3-dioxanyl, 1,3-dioxolanyl, isoxazolyl, furanyl, morpholinyl, oxadiazolyl, oxazolidinyl, oxetanyl, piperidinyl, pyridyl, pyrimidinyl, pyrrolidinyl, tetrahydrofuranyl, tetrahydropyranyl, tetrazolyl, thiazolyl or thiophenyl, wherein heterocyclyl is unsubstituted or mono- or di-substituted independently of one another by R13, V is azetidinyl, aminoazetidinyl, piperazinyl, piperidinyl or pyrrolidinyl, G and M together form a —C(O)—(C$_0$-C$_4$)-alkyl, —C(O)—O—(C$_2$-C$_6$)-alkyl or —N(R10) —C(O)—O—(C$_2$-C$_6$)-alkyl, or G is a direct bond and M is a phenyl residue, which is unsubstituted or substituted by Cl, F or Br, R1 is a hydrogen atom, methyl or ethyl, R2, R3, R4, R5 and R6 are independently of one another selected from hydrogen atom, Cl, F, Br, —CN, —O—CH$_3$, —O—CH$_2$—CH$_3$, methyl, ethyl, propyl or butyl, or R3 and R4, R4 and R5 or R5 and R6 form together with the atoms which they are attached to a cyclohexyl ring, R7 is
1) a hydrogen atom,
2) halogen,
3) —$(C_1-C_6)$-alkyl, wherein alkyl is unsubstituted or mono-, di- or trisubstituted independently of one another by R13,
4) =O,
5) —$(C_1-C_3)$-fluoroalkyl,
6) —$(C_0-C_4)$-alkylene-O—R19, wherein R19 is
  a) hydrogen atom,
  b) —$(C_1-C_4)$-alkyl, wherein alkyl is unsubstituted or mono-, di- or trisubstituted independently of one another by R13,
  c) phenyl, wherein phenyl is unsubstituted or mono-, di- or trisubstituted independently of one another by R13,
  d) —$CF_3$, or
  e) —$CHF_2$,
7) —$NO_2$,
8) —CN,
9) —$(C_0-C_4)$-alkylene-O—$CH_2$—$(C_1-C_3)$-fluoroalkylene-$CH_2$—O—$(C_1-C_4)$-alkyl,
10) —$(C_0-C_4)$-alkylene-C(O)—R11,
11) —$(C_0-C_4)$-alkylene-C(O)—O—R11,
12) —$(C_0-C_4)$-alkylene-C(O)—O—$(C_1-C_4)$-alkylene-O—C(O)—R17, wherein —$(C_1-C_4)$-alkylene is unsubstituted or mono-, di- or trisubstituted independently of one another by R15,
13) —$(C_0-C_4)$-alkylene-C(O)—O—$(C_1-C_4)$-alkylene-O—C(O)—O—R17, wherein —$(C_1-C_4)$-alkylene is unsubstituted or mono-, di- or trisubstituted independently of one another by R15,
14) —$(C_0-C_4)$-alkylene-C(O)—N(R11)-R12,
15) —$(C_0-C_4)$-alkylene-C(O)—N(R11)-R13,
16) —$(C_0-C_4)$-alkylene-C(O)—N[$(C_0-C_4)$-alkylene]-R13, wherein alkyl and cycloalkyl are unsubstituted or mono-, di- or trisubstituted independently of one another by R13,
17) —$(C_0-C_4)$-alkylene-C(O)—N[$(C_0-C_4)$-alkylene-$(C_3-C_8)$-cycloalkyl]-R13, wherein alkyl and cycloalkyl is unsubstituted or mono-, di- or trisubstituted independently of one another by R13,
18) —$(C_0-C_4)$-alkylene-N(R11)-R12,
19) —$(C_0-C_4)$-alkylene-N(R11)-R13,
20) —$(C_0-C_4)$-alkylene-N(R10)-$SO_2$—R10,
21) —$(C_0-C_4)$-alkylene-S—R10,
22) —$(C_0-C_4)$-alkylene-$SO_s$—R11, wherein s is 1 or 2,
23) —$(C_0-C_4)$-alkylene-$SO_t$—N(R11)-R12, wherein t is 1 or 2,
24) —$(C_0-C_4)$-alkylene-$SO_w$—N(R11)-R13, wherein w is 1 or 2,
25) —$(C_0-C_4)$-alkylene-$SO_u$—$(C_0-C_4)$-alkylene-C(O)—O—R10, wherein u is 1 or 2,
26) —$(C_0-C_4)$-alkylene-$(C_3-C_6)$-cycloalkyl, wherein cycloalkyl is unsubstituted or mono-, di- or trisubstituted independently of one another by R13,
27) —$(C_0-C_4)$-alkylene-$(C_6-C_{14})$-aryl, wherein aryl is selected from phenyl, naphthyl, biphenylyl, indanyl, anthryl or fluorenyl; and wherein aryl is unsubstituted or mono-, di- or trisubstituted independently of one another by R13,
28) —$(C_0-C_4)$-alkylene-$(C_3-C_{15})$-heterocyclyl, wherein —$(C_3-C_{15})$-heterocyclyl is selected from the group consisting of azetidinyl, benzimidazolyl, 2,3-dihydro-1H-indolyl, 4,5-dihydro-[1,3,4]oxadiazolyl, 3,4-dihydro-2H-quinolinyl, 1,3-dioxanyl, 1,3-dioxolanyl, furanyl, morpholinyl, oxadiazolyl, oxazolidinyl, oxetanyl, piperidinyl, pyridyl, pyrimidinyl, pyrrolidinyl, tetrahydrofuranyl, tetrahydropyranyl, tetrazolyl, thiazolyl or thiophenyl, and is unsubstituted or mono-, di- or trisubstituted independently of one another by R13,
29) —$(C_0-C_4)$-alkylene-O—$(C_0-C_4)$-alkylene-$(C_6-C_{14})$-aryl, wherein aryl is as defined above and is unsubstituted or mono-, di- or trisubstituted independently of one another by R13,
30) —$(C_0-C_4)$-alkylene-O—$(C_0-C_4)$-alkylene-$(C_3-C_{15})$-heterocyclyl, wherein —$(C_3-C_{15})$-heterocyclyl is as defined above and is un-substituted or mono-, di- or trisubstituted independently of one another by R13,
31) —$(C_0-C_4)$-alkylene-N(R13)-$(C_0-C_4)$-alkylene-$(C_6-C_{14})$-aryl, wherein aryl is as defined above and is unsubstituted or mono-, di- or trisubstituted independently of one another by R13, or
32) —$(C_0-C_4)$-alkylene-N(R13)-$(C_0-C_4)$-alkylene-$(C_3-C_{15})$-heterocyclyl, wherein —$(C_3-C_{15})$-heterocyclyl is as defined above and is un-substituted or mono-, di- or trisubstituted independently of one another by R13, R10 is hydrogen atom or —$(C_1-C_4)$-alkyl, R11 and R12 are independently of one another identical or different and are
1) hydrogen atom,
2) —$(C_1-C_4)$-alkyl, wherein alkyl is unsubstituted or mono- or di-substituted independently of one another by R13,
3) —$(C_1-C_3)$-fluoroalkyl,
4) —$(C_0-C_4)$-alkylene-$(C_3-C_6)$-cycloalkyl, wherein cycloalkyl is unsubstituted or mono- or di-substituted independently of one another by R13,
5) —$(C_0-C_4)$-alkylene-$(C_3-C_{15})$-heterocyclyl, wherein —$(C_3-C_{15})$-heterocyclyl is azetidinyl, benzimidazolyl, 2,3-dihydro-1H-indolyl, 4,5-dihydro-[1,3,4]oxadiazolyl, 3,4-dihydro-2H-quinolinyl, 1,3-dioxanyl, 1,3-dioxolanyl, furanyl, morpholinyl, oxadiazolyl, oxazolidinyl, oxetanyl, piperidinyl, pyridyl, pyrimidinyl, pyrrolidinyl, tetrahydrofuranyl, tetrahydropyranyl, tetrazolyl, thiazolyl or thiophenyl, or R11 and R12 together with the nitrogen atom to which they are bonded form a 4- to 8-membered monocyclic heterocyclic ring selected from azetidine, piperidine, pyrrolidine or morpholine, R13 is F, Cl, Br, —CN, =O, —OH, —$CF_3$, —C(O)—O—R10, —$(C_3-C_6)$-cycloalkyl, —$(C_0-C_4)$-alkylene-O—R10, —C(O)—R10, —$(C_1-C_4)$-alkyl or phenyl, R15 is hydrogen atom or —$(C_1-C_6)$-alkyl, R17 is hydrogen atom or —$(C_1-C_6)$-alkyl, R23 and R24 are independently of one another selected from hydrogen atom or methyl, in all its stereoisomeric forms and mixtures thereof in any ratio, and its physiologically tolerable salts.

6) The present invention also relates to compounds of the formula Ia, wherein

E is a heterocyclic residue selected from aza-bicyclohexane, aza-bicyclooctane, azetidine, aziridine, decahydro-quinoline, 2,5-diaza-bicyclo[2.2.1]heptane, 1,4-diazepane, 2,7-diaza-spiro[4.5]decane, 2,8-diaza-spiro[4.5]decane, 2,3-dihydro-1H-indole, 4,7-dihydro-5H-isoxazolo[5,4-c]pyridine, 6,7-dihydro-4H-oxazolo[5,4-c]pyridine, 4,6-dihydro-1H-pyrrolo[3,4-c]pyrazol, 4,6-dihydro-4H-pyrrolo[3,4-d]thiazole, 5,6-Dihydro-8H-[1,2,4]triazolo[4,3-a]pyrazin, hexahydro-pyrrolo[1,2-a]pyrazin, hexahydro-pyrrolo[3,4-b]pyrrol, Hexahydro-pyrrolo[1,2-a]pyrazin, imidazolidine, morpholine, indole, octahydro-cyclopenta[c]pyrrole, octahydro-indole, octahydro-pyrrolo[3,4-b]pyridine, octahydro-pyrrolo[3,4-c]pyridine, oxazolidine, piperazine, piperidine, pyrazolidine, pyrrolidine, 1,4,6,7-tetrahydro-pyrazolo[4,3-c]pyridine, 1,2,3,4-tetrahydro-isoquinoline, 4,5,6,7-tetrahydro-isoxazolo[4,5-c]pyridine, 4,5,6,7-tetrahydro-1H-pyrazolo[4,3-c]pyridine, 3,5,7,8-tetrahydro-4H-pyrido[4,3-d]pyrimidine, 4,5,6,6a-tetrahydro-3aH-pyrrolo[3,4-d]isoxazole, 1,2,3,4-tetrahydro-quinoline, 4,5,6,7-tetrahydro-thieno[2,3-c]pyridine, 4,5,6,7-tetrahydro-thieno[3,2-c]pyridine, 4,5,6,7-tetrahydro-thiazolo[5,4-c]pyridine, 1,3,8-triaza-spiro[4.5]decane or triaza-spirooctane, wherein said heterocyclic residue is mono-, di- or trisubstituted independently of one another by R7, Q is
1) a covalent bond,
2) —$(C_0-C_4)$-alkylene-CH(OH)—,
3) —$(C_0-C_4)$-alkylene-C(O)—N(R10)-,
4) —$(C_1-C_3)$-alkylene-C(O)—O—,
5) —$(C_1-C_3)$-alkylene-O— or
6) —$(C_1-C_3)$-alkylene-S(O)$_2$—, J is
1) hydrogen atom,
2) —$(C_1-C_6)$-alkyl,
3) —$(C_0-C_4)$-alkylene-C(O)—R11,
4) —$(C_0-C_4)$-alkylene-C(O)—O—R11,
5) —$(C_0-C_4)$-alkylene-N(R11)-R13,
6) —$(C_0-C_2)$-alkylene-$(C_3-C_6)$-cycloalkyl,
7) —$(C_0-C_2)$-alkylene-phenyl or
8) —$(C_0-C_4)$-alkylene-$(C_3-C_{15})$-heterocyclyl, wherein —$(C_3-C_{15})$-heterocyclyl is azetidinyl, benzimidazolyl, 2,3-dihydro-1H-indolyl, 4,5-dihydro-[1,3,4]oxadiazolyl, 3,4-dihydro-2H-quinolinyl, 1,3-dioxanyl, 1,3-dioxolanyl, indanyl, isoxazolyl, furanyl, morpholinyl, oxadiazolyl, oxazolidinyl, oxetanyl, piperidinyl, pyridyl, pyrimidinyl, pyrrolidinyl, tetrahydrofuranyl, tetrahydropyranyl, tetrazolyl, thiazolyl or thiophenyl, wherein heterocyclyl is unsubstituted or mono- or di-substituted independently of one another by R13, V is a piperazinyl, piperidinyl, azetidinyl or aminoazetidinyl,
G and M together form a —C(O)—$(C_0-C_4)$-alkyl, —C(O)—O—$(C_2-C_4)$-alkyl or —N(R10)-C(O)—O—$(C_2-C_4)$-alkyl, or
G is a direct bond and M is a phenyl residue, which is unsubstituted or substituted by Cl, F or Br,
R1 is a hydrogen atom, methyl or ethyl,
R2, R3, R4, R5 and R6 are independently of one another selected from hydrogen atom, Cl, F, Br, —CN, —O—$CH_3$, —O—$CH_2$—$CH_3$, methyl, ethyl, propyl or butyl, or
R3 and R4, R4 and R5 or R5 and R6 form together with the atoms which they are attached to a cyclohexyl ring,
R7 is
1) hydrogen atom,
2) Cl, F or Br,
3) —$(C_1-C_4)$-alkyl,
4) =O,
5) —$(C_1-C_3)$-fluoroalkyl,
6) —$(C_0-C_2)$-alkylene-OH,
7) —$(C_0-C_2)$-alkylene-O—$(C_1-C_4)$-alkyl,
8) —$(C_0-C_2)$-alkylene-O—$CF_3$,
9) —CN,
10) —C(O)—R11,
11) —$(C_0-C_2)$-alkylene-C(O)—O—R11,
12) —$(C_0-C_2)$-alkylene-C(O)—N(R11)-R12,
13) —N(R11)-R12,
14) —N(R11)-R13,
15) —$SO_2$—$(C_1-C_4)$-alkyl,
16) —$(C_0-C_4)$-alkyl-$(C_3-C_6)$-cycloalkyl,
17) phenyl,
18) —$(C_0-C_4)$-alkylene-$(C_3-C_{15})$-heterocyclyl, wherein —$(C_3-C_{15})$-heterocyclyl is azetidinyl, benzimidazolyl, 2,3-dihydro-1H-indolyl, 4,5-dihydro-[1,3,4]oxadiazolyl, 3,4-dihydro-2H-quinolinyl, 1,3-dioxanyl, 1,3-dioxolanyl, furanyl, morpholinyl, oxadiazolyl, oxazolidinyl, oxetanyl, piperidinyl, pyridyl, pyrimidinyl, pyrrolidinyl, tetrahydrofuranyl, tetrahydropyranyl, tetrazolyl, thiazolyl or thiophenyl, or
19) —O-phenyl, wherein phenyl is unsubstituted or mono- or di-substituted independently of one another by R13, R10 is hydrogen atom or —$(C_1-C_4)$-alkyl,
R11 and R12 are independently of one another identical or different and are
1) hydrogen atom,
2) —$(C_1-C_4)$-alkyl, wherein alkyl is unsubstituted or mono- or di-substituted independently of one another by R13,
3) —$(C_1-C_3)$-fluoroalkyl,
4) —$(C_0-C_4)$-alkylene-$(C_3-C_6)$-cycloalkyl, wherein cycloalkyl is unsubstituted or mono- or di-substituted independently of one another by R13,
5) phenyl or
6) —$(C_0-C_4)$-alkylene-$(C_3-C_{15})$-heterocyclyl, wherein —$(C_3-C_{15})$-heterocyclyl is azetidinyl, benzimidazolyl, 2,3-dihydro-1H-indolyl, 4,5-dihydro-[1,3,4]oxadiazolyl, 3,4-dihydro-2H-quinolinyl, 1,3-dioxanyl, 1,3-dioxolanyl, furanyl, morpholinyl, oxadiazolyl, oxazolidinyl, oxetanyl, piperidinyl, pyridyl, pyrimidinyl, pyrrolidinyl, tetrahydrofuranyl, tetrahydropyranyl, tetrazolyl, thiazolyl or thiophenyl, R13 is F, Cl, Br, —CN, =O, —OH, —$CF_3$, —C(O)—O—R10, —$(C_3-C_6)$-cycloalkyl, —$(C_0-C_4)$-alkylene-O—R10, —C(O)—R10, —$(C_1-C_4)$-alkyl or phenyl,
R23 and R24 are independently of one another selected from hydrogen atom or methyl,
in all its stereoisomeric forms and mixtures thereof in any ratio, and its physiologically tolerable salts.

As used herein, the term alkyl is a hydrocarbon residue, which can be linear, e.g. straight-chain, or branched. Examples of "—$(C_1-C_8)$-alkyl" or "—$(C_1-C_8)$-alkylene" are alkyl residues containing 1, 2, 3, 4, 5, 6, 7 or 8 carbon atoms are methyl, methylene, ethyl, ethylene, propyl, propylene, butyl, butylene, pentyl, pentylene, hexyl, hexylene, heptyl or octyl, the n-isomers of all these residues, isopropyl, isobutyl, 1-methylbutyl, isopentyl, neopentyl, 2,2-dimethylbutyl, 2-methylpentyl, 3-methylpentyl, isohexyl, secondary-butyl, tertiary-butyl, tertiary-pentyl, secondary-butyl. The terms "—$(C_0-C_8)$-alkyl" or "—$(C_0-C_8)$-alkylene" are each hydrocarbon residues containing 1, 2, 3, 4, 5, 6, 7 or 8 carbon atoms. The terms "—$C_0$-alkyl" or "—$C_0$-alkylene" are understood as meaning each a covalent bond.

The terms "—$(C_2-C_{10})$-alkenyl" or "—$(C_2-C_{10})$-alkenylene" are understood as meaning alkyl residues containing 2, 3, 4, 5, 6, 7, 8, 9 or 10 carbon atoms are, wherein said alkyl residues depending on the chain length contain 1, 2 or 3 double bonds. Examples of such residues are residues such as vinyl, 1-propenyl, 2-propenyl (=allyl), 2-butenyl, 3-butenyl, 2-methyl-2-butenyl, 3-methyl-2-butenyl, 5-hexenyl or 1,3-pentadienyl.

The terms "—$(C_2-C_{10})$-alkynyl" or "—$(C_2-C_{10})$-alkynylene" are understood as meaning alkyl residues containing 2, 3, 4, 5, 6, 7, 8, 9 or 10 carbon atoms are, wherein said alkyl residues depending on the chain length contain 1, 2 or 3 triple bonds, such as ethynyl, 1-propynyl, 2-propynyl (=propargyl) or 2-butynyl.

The term "—$(C_3-C_8)$-cycloalkyl" is understood as meaning cycloalkyl residues containing 3, 4, 5, 6, 7 or 8 ring carbon atoms like cyclopropyl, cyclobutyl, cyclopentyl, cyclohexyl, cycloheptyl, bicycle[2.2.1]heptyl or cyclooctyl.

The terms "6- to 14-membered aryl" or "—($C_6$-$C_{14}$)-aryl" are understood as meaning a mono- or bicyclic-aromatic hydrocarbon radicals containing from 6 to 14 carbon atoms in the ring. Examples are phenyl, naphthyl, for example 1-naphthyl and 2-naphthyl, biphenylyl, for example 2-biphenylyl, 3-biphenylyl and 4-biphenylyl, indanyl, anthryl or fluorenyl. Biphenylyl radicals, naphthyl radicals and, in particular, phenyl radicals are preferred aryl radicals.

The term "a 3- to 7-membered cyclic residue, containing up to 1, 2, 3 or 4 heteroatoms" refer to structures of heterocycles which can be derived from compounds such as azepine, azetidine, aziridine, azirine, 1,4 diazepane, 1,2-diazepine, 1,3-diazepine, 1,4-diazepine, diaziridine, diazirine, dihydroimidazolone, dioxazole, dioxazine, dioxole, 1,3-dioxolene, 1,3-dioxolane, furan, imidazole, imidazoline, imidazolidine, imidazolidinone, isothiazole, isothiazolidine, isothiazoline, isoxazole, isoxazoline, isoxazolidine, morpholine, 1,2-oxa-thiepane, 1,2-oxathiolane, 1,4-oxazepane, 1,2-oxazine, 1,3-oxazine, 1,4-oxazine, oxazolone, oxazole, [1,3,4]oxathiazinane 3,3-dioxide, oxaziridine, oxazolidinone, oxetan, oxirane, piperazine, piperidine, pyran, pyrazine, pyrazole, pyrazoline, pyrazolidine, pyridazine, pyridine, pyridinone, pyrimidine, pyrimidine-2,4-dione, pyrrole, pyrrolidine, pyrrolidinone, pyrroline, tetrahydrofuran, tetrahydropyran, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiomorpholine 1,1-dioxide thiopyran, 1,2,3-triazine, 1,2,4-triazine, 1,3,5-triazine, 1,2,3-triazole or 1,2,4-triazole.

The terms "mono- or bicyclic 3- to 15-membered heterocyclyl" or "—($C_3$-$C_{15}$)-heterocyclyl" refers to heterocycles wherein one or more of the 3 to 15 ring carbon atoms are replaced by heteroatoms such as nitrogen, oxygen or sulfur such as acridinyl, azabenzimidazolyl, aza-bicycloheptanyl, aza-bicyclohexanyl, aza-bicyclooctanyl, 8-aza-bicyclo[3.2.1]octanyl, azaspirodecanyl, aza-spiroheptanyl, aza-spirohexanyl, aza-spirooctanyl, aza-spiropentanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydro-quinolinyl, diaza-bicyclohexanyl, diaza-bicycloheptanyl, 2,5-Diaza-bicyclo[2.2.1]heptanyl, 1,2-diazapanyl, diaza-spirohexanyl, diaza-spirooctanyl, diaza-spiropentanyl, diaza-spiroheptanyl, 1,3-diazepanyl, 1,4-diazepanyl, 1,2-diazepinyl, 1,3-diazepinyl, 1,4-diazepinyl, dihydroazepinyl, 3,4-dihydro-2H-quinoline, dihydrofuro[2,3-b]-tetrahydrofuranyl, 2,3-dihydro-1H-indolyl, 3,4-dihydro-1H-isoquinolinyl, 6,7-dihydro-4H-isoxazolo[4,5-c]pyridinyl, dihydro-pyridazinyl, 4,5-dihydro-[1,3,4]oxadiazol, dihydro-oxazepinyl, 4,5-dihydrooxazolinyl, 4,6-dihydro-4H-pyrrolo[3,4-d]thiazolyl, 6,7-dihydro-4H-thiazolo[5,4-c]pyridinyl, 4,7-dihydro-5H-thieno[2,3-c]pyridinyl, 1,3-dioxanyl, dioxazolyl, dioxazinyl, 1,3-dioxolanyl, 1,3-dioxolenyl, 3,3-dioxo[1,3,4]oxathiazinyl, 6H-1,5,2-dithiazinyl, furanyl, furazanyl, hexahydro-pyridazinyl, hexahydro-cyclopenta[c]pyrroline, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydro-cyclopenta[c]pyrrolyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 1H-pyrrolopyridinyl, 2H-pyrrolyl, pyrrolyl, quinazolinyl, quinolinyl, 4H-quinolizinyl, quinoxalinyl, quinuclidinyl, tetrahydrofuranyl, 1,2,3,4-tetrahydro-isoquinolinyl, 4,5,6,7-tetrahydro-isoxazolo[4,5-c]pyridinyl, tetrahydropyranyl, 1,2,3,4-tetrahydropyrazinyl, 4,5,6,7-tetrahydro-1H-pyrazolo[4,3-c]pyridinyl, tetrahydro-pyridazinyl, tetrahydro-pyridinyl, 4,5,6,6a-tetrahydro-3aH-pyrrolo[3,4-d]isoxazolyl, 1,2,3,4-tetrahydro-quinolinyl, 4,5,6,7-tetrahydro-thieno[2,3-c]pyridinyl, 1,4,6,7-tetrahydro-thiazolo[5,4-c]pyridinyl, 4,5,6,7-tetrahydro-thieno[3,2-c]pyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, triaza-spirooctanyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl, and xanthenyl.

The term "E is 3- to 10-membered heterocyclic residue, containing one nitrogen atom and up to 0, 1, 2, or 3 additional heteroatoms chosen from nitrogen, sulfur or oxygen, wherein said heterocyclic residue is monocyclic, bicyclic or a spiroheterocycle" refers to structures of heterocycles which are residues selected from compounds such as aza-bicycloheptane, aza-bicyclohexane, aza-bicyclooctane, aza-spiroheptane, aza-spirohexane, aza-spirooctane, aza-spiropentane, azepane, azepine, azetidine, aziridine, decahydro-quinoline, diaza-bicyclohexane, diaza-bicycloheptane, 2,5-Diaza-bicyclo[2.2.1]heptane, 1,2-diazapane, 2,7-diaza-spiro[4.5]decane, 2,8-diaza-spiro[4.5]decane, diaza-spirohexane, diazaspirooctane, diaza-spiropentane, diaza-spiroheptane, 1,3-diazepane, 1,4-diazepane, 1,2-diazepine, 1,3-diazepine, 1,4-diazepine, dihydroazepine, 2,3-dihydro-1H-indole, 3,4-dihydro-1H-isoquinoline, 4,7-dihydro-5H-isoxazolo[5,4-c]pyridine, 6,7-dihydro-4H-isoxazolo[4,5-c]pyridine, dihydropyridazine, dihydro-oxazepine, 6,7-dihydro-4H-oxazolo[5,4-c]pyridine, 4,6-dihydro-1H-pyrrolo[3,4-c]pyrazol, 4,6-dihydro-4H-pyrrolo[3,4-d]thiazole, 6,7-dihydro-4H-thiazolo[5,4-c]pyridine, 4,7-dihydro-5H-thieno[2,3-c]pyridine, 5,6-Dihydro-8H-[1,2,4]triazolo[4,3-a]pyrazin, dioxazole, hexahydro-cyclopenta[c]pyrroline, hexahydropyridazine, hexahydro-pyrrolo[1,2-a]pyrazin, hexahydropyrrolo[3,4-b]pyrrol, Hexahydro-pyrrolo[1,2-a]pyrazin, imidazoline, imidazolidine, indole, isoquinoline, isothiazolidine, isothiazoline, isoxazoline, isoxazolidine, ketopiperazine, morpholine, octahydro-cyclopenta[c]pyrrole, octahydro-indole, octahydro-pyrrolo[3,4-b]pyridine, octahydro-pyrrolo[3,4-c]pyridine, 1,4-oxazepane, oxazepine, 1,2-oxa-thiepane, 1,2-oxazine, 1,3-oxazine, 1,4-oxazine, oxazolidine, piperazine, piperidine, pyrazine, pyrazoline, pyrazolidine, pyridazine, pyrrolidine, pyrrolidinone, pyrroline, tetrahydropyridine, tetrahydro-azepine, 1,2,3,4-tetrahydro-isoquinoline, 4,5,6,7-tetrahydro-isoxazolo[4,5-c]pyridine, 1,2,3,4-tetrahydropyrazine, 1,4,6,7-tetrahydropyrazolo[4,3-c]pyridine, 4,5,6,7-tetrahydro-1H-pyrazolo[4,3-c]pyridine, tetrahydro-pyridazine, 3,5,7,8-tetrahydro-4H- pyrido[4,3-d]pyrimidine, 4,5,6,6a-tetrahydro-3aH-pyrrolo[3,4-d]isoxazole, 1,2,3,4-tetrahydro-quinoline, 4,5,6,7-tetrahydro-thieno[2,3-c]pyridine, 1,4,6,7-tetrahydro-thiazolo[5,4-c]pyridine, 4,5,6,7-tetrahydro-thieno[3,2-c]pyridine, tetrazine, tetrazole, thiadiazine, 1,2-thiazine, 1,3-thiazine, 1,4-thiazine, 1,3-thiazole, thiazolidine, thiaoline, thietan, thiomorpholine, 1,3,8-triaza-spiro[4.5]decane, triaza-spirooctane, triazepane, 1,2,4-triazinane and 1,3,5-triazinane.

The term "R11 and R12 together with the nitrogen atom to which they are bonded can form a 4- to 8-membered monocyclic heterocyclic ring which in addition to the nitrogen atom can contain one or two identical or different ring heteroatoms chosen from oxygen, sulfur and nitrogen" refer to structures of heterocycles which are residues selected from compounds such as aza-bicycloheptane, aza-bicyclohexane, aza-spiroheptane, aza-spirohexane, aza-spirooctane, aza-spiropentane, azepane, azepine, azetidine, diaza-bicycloheptane, diaza-bicyclohexane, diaza-spiroheptane, diaza-spirohexane, diaza-spiropentane, diaza-spirooctane 1,2-diazapane, 1,3-diazepane, 1,4-diazepane, 1,2-diazepine, 1,3-diazepine, 1,4-diazepine, dihydroazepine, dihydrooxazepine, dihydro-pyridazine, dioxazole, hexahydropyridazine, imidazoline, imidazolidine, isothiazolidine, isothiazoline, isoxazoline, isoxazolidine, ketopiperazine, morpholine, 1,4-oxazepane, 1,2-oxa-thiepane, oxazepine, 1,2-oxazine, 1,3-oxazine, 1,4-oxazine, piperazine, piperidine, pyrazine, pyrazoline, pyrazolidine, pyridazine, pyrrolidine, pyrrolidinone, pyrroline, tetrahydro-azepine, 1,2,3,4-tetrahydropyrazine, tetrahydropyridine, tetrazine, tetrazole, thiadiazine, 1,2-thiazine, 1,3-thiazine, 1,4-thiazine, 1,3-thiazole, thiazolidine, thiazoline, thietan, thiomorpholine, triazepane, 1,2,4-triazinane and 1,3,5-triazinane.

The term "—($C_1$-$C_3$)-fluoroalkyl" is a partial or totally fluorinated alkyl-residue consisting of 1 to 3 carbon atoms, which can be derived from residues such as —$CF_3$, —$CHF_2$, —$CH_2F$, —$CHF$—$CF_3$, —$CHF$—$CHF_2$, —$CHF$—$CH_2F$, —$CH_2$—$CF_3$, —$CH_2$—$CHF_2$, —$CH_2$—$CH_2F$, —$CF_2$—$CF_3$, —$CF_2$—$CHF_2$, —$CF_2$—$CH_2F$, —$CH_2$—$CHF$—$CF_3$, —$CH_2$—$CHF$—$CHF_2$, —$CH_2$—$CHF$—$CH_2F$, —$CH_2$—$CH_2$—$CF_3$, —$CH_2$—$CH_2$—$CHF_2$, —$CH_2$—$CH_2$—$CH_2F$, —$CH_2$—$CF_2$—$CF_3$, —$CH_2$—$CF_2$—$CHF_2$, —$CH_2$—$CF_2$—$CH_2F$, —$CHF$—$CHF$—$CF_3$, —$CHF$—$CHF$—$CHF_2$, —$CHF$—$CHF$—$CH_2F$, —$CHF$—$CH_2$—$CF_3$, —$CHF$—$CH_2$—$CHF_2$, —$CHF$—$CH_2$—$CH_2F$, —$CHF$—$CF_2$—$CF_3$, —$CHF$—$CF_2$—$CHF_2$, —$CHF$—$CF_2$—$CH_2F$, —$CF_2$—$CHF$—$CF_3$, —$CF_2$—$CHF$—$CHF_2$, —$CF_2$—$CHF$—$CH_2F$, —$CF_2$—$CH_2$—$CF_3$, —$CF_2$—$CH_2$—$CHF_2$, —$CF_2$—$CH_2$—$CH_2F$, —$CF_2$—$CF_2$—$CF_3$, —$CF_2$—$CF_2$—$CHF_2$ or —$CF_2$—$CF_2$—$CH_2F$.

The term "—($C_1$-$C_3$)-fluoroalkylene" is a partial or totally fluorinated alkylene-residue, residue consisting of 1 to 3 carbon atoms, which can be derived from residues such as —$CF_2$—, —$CHF$—, —$CHF$—$CHF_2$—, —$CHF$—$CHF$—, —$CH_2$—$CF_2$—, —$CH_2$—$CHF$—, —$CF_2$—$CF_2$—, —$CF_2$—$CHF$—, —$CH_2$—$CHF$—$CF_2$—, —$CH_2$—$CHF$—$CHF$—, —$CH_2$—$CH_2$—$CF_2$—, —$CH_2$—$CH_2$—$CHF$, —$CH_2$—$CF_2$—$CF_2$—, —$CH_2$—$CF_2$—$CHF$—, —$CHF$—$CHF$—$CF_2$—, —$CHF$—$CHF$—$CHF$—, —$CHF$—$CH_2$—$CF_2$—, —$CHF$—$CH_2$—$CHF$—, —$CHF$—$CF_2$—$CF_2$—, —$CHF$—$CF_2$—$CHF$—, —$CF_2$—$CHF$—$CF_2$—, —$CF_2$—$CHF$—$CHF$—, —$CF_2$—$CH_2$—$CF_2$—, —$CF_2$—$CH_2$—$CHF$—, —$CF_2$—$CF_2$—$CF_2$—, or —$CF_2$—$CF_2$—$CHF$.

The term "R3 and R4, R4 and R5 or R5 and R6 form together with the atoms which they are attached to a 5- or 6-membered cycloalkyl ring" refers to residues such as cyclopentyl and cyclohexyl.

The term "R3 and R4, R4 and R5 or R5 and R6 are each time both —O—R10 and form together with the atoms which they are attached to a 5- or 6-membered ring" refers to structures such as 1,3-dioxole ring and 2,3-dihydro-[1,4]dioxine ring.

The term "oxo-residue" or "=O" refers to residues such as carbonyl (—C(O)—) or nitroso (—N=O).

The term "Z-A-B together with the carbonyl carbon atom form a residue selected from —O—$CH_2$—C(O)—, —O—CH($CH_3$)—C(O)— or —O—C($CH_3$)$_2$—C(O)—, wherein said residue is bond via oxygen atom to quinoline residue and by the carbonyl carbon atom to the nitrogen atom of E" refers to the following substructure of formula I:

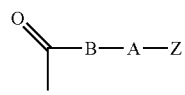

The term —O—$CH_2$—C(O)— is a residue with the following structural formula:

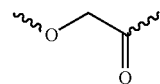

wherein the oxygen atom has a covalent bond with the quinoline residue and the carbonyl carbon atom has a covalent bond with the nitrogen atom of the residue E.

The term —O—CH($CH_3$)—C(O)— is a residue with the following structural formula:

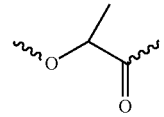

wherein the oxygen atom has a covalent bond with the quinoline residue and the carbonyl carbon atom has a covalent bond with the nitrogen atom of the residue E.

The term —O—C($CH_3$)$_2$—C(O)— is a residue with the following structural formula:

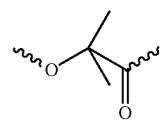

wherein the oxygen atom has a covalent bond with the quinoline residue and the carbonyl carbon atom has a covalent bond with the nitrogen atom of the residue E. Halogen is fluorine, chlorine, bromine or iodine.

Optically active carbon atoms present in the compounds of the formula I can independently of each other have R configuration or S configuration. The compounds of the formula I can be present in the form of pure enantiomers or pure diastereomers or in the form of mixtures of enantiomers and/or diastereomers, for example in the form of racemates. The present invention relates to pure enantiomers and mixtures of enantiomers as well as to pure diastereomers and mixtures of diastereomers. The invention comprises mixtures of two or of more than two stereoisomers of the formula I, and it comprises all ratios of the stereoisomers in the mixtures. In case the compounds of the formula I can be present as E isomers or Z isomers (or cis isomers or trans isomers) the invention relates both to pure E isomers and pure Z isomers and to E/Z mixtures in all ratios. The invention also comprises all tautomeric forms of the compounds of the formula I.

Diastereomers, including E/Z isomers, can be separated into the individual isomers, for example, by chromatography. Racemates can be separated into the two enantiomers by customary methods, for example by chromatography on chiral phases or by resolution, for example by crystallization of diastereomeric salts obtained with optically active acids or bases. Stereochemically uniform compounds of the formula I can also be obtained by employing stereochemically uniform starting materials or by using stereoselective reactions.

Physiologically tolerable salts of the compounds of formula I are nontoxic salts that are physiologically acceptable, in particular pharmaceutically utilizable salts. Such salts of compounds of the formula I containing acidic groups, for example a carboxyl group COOH, are for example alkali metal salts or alkaline earth metal salts such as sodium salts, potassium salts, magnesium salts and calcium salts, and also salts with physiologically tolerable quaternary ammonium ions such as tetramethylammonium or tetraethylammonium, and acid addition salts with ammonia and physiologically tolerable organic amines, such as methylamine, dimethylamine, trimethylamine, ethylamine, triethylamine, ethanolamine or tris-(2-hydroxyethyl)amine. Basic groups contained in the compounds of the formula I, for example amino groups or guanidino groups, form acid addition salts, for example with inorganic acids such as hydrochloric acid, hydrobromic acid, sulfuric acid, nitric acid or phosphoric acid, or with organic carboxylic acids and sulfonic acids such as formic acid, acetic acid, oxalic acid, citric acid, lactic acid, malic acid, succinic acid, malonic acid, benzoic acid, maleic acid, fumaric acid, tartaric acid, methanesulfonic acid or p-toluenesulfonic acid. Compounds of the formula I, which simultaneously contain a basic group and an acidic group, for example a guanidino group and a carboxyl group, can also be present as zwitterions (betaines) which are likewise included in the present invention.

Salts of compounds of the formula I can be obtained by customary methods known to those skilled in the art, for example by combining a compound of the formula I with an inorganic or organic acid or base in a solvent or dispersant, or from other salts by cation exchange or anion exchange. The present invention also includes all salts of the compounds of the formula I which, because of low physiological tolerability, are not directly suitable for use in pharmaceuticals but are suitable, for example, as intermediates for carrying out further chemical modifications of the compounds of the formula I or as starting materials for the preparation of physiologically tolerable salts.

The present invention furthermore includes all solvates of compounds of the formula I, for example hydrates or adducts with alcohols.

The invention also includes derivatives and modifications of the compounds of the formula I, for example prodrugs, protected forms and other physiologically tolerable derivatives, as well as active metabolites of the compounds of the formula I. The invention relates in particular to prodrugs and protected forms of the compounds of the formula I, which can be converted into compounds of the formula I under physiological conditions. Suitable prodrugs for the compounds of the formula I, i.e. chemically modified derivatives of the compounds of the formula I having properties which are improved in a desired manner, for example with respect to solubility, bioavailability or duration of action, are known to those skilled in the art. More detailed information relating to prodrugs is found in standard literature like, for example, Design of Prodrugs, H. Bundgaard (ed.), Elsevier, 1985; Fleisher et al., Advanced Drug Delivery Reviews 19 (1996) 115-130; or H. Bundgaard, Drugs of the Future 16 (1991) 443; or Hydrolysis in Drug and Prodrug Metabolism, B. Testa, J. M. Mayer, Wiley-VCH, 2003, which are all incorporated herein by reference. Suitable prodrugs for the compounds of the formula I are especially acyl prodrugs and carbamate prodrugs of acylatable nitrogen-containing groups such as amino groups and the guanidino group and also ester prodrugs and amide prodrugs of carboxylic acid groups which may be present in compounds of the formula I. In the acyl prodrugs and carbamate prodrugs one or more, for example one or two, hydrogen atoms on nitrogen atoms in such groups are replaced with an acyl group or a carbamate, preferably a —$(C_1-C_6)$-alkyloxycarbonyl group. Suitable acyl groups and carbamate groups for acyl prodrugs and carbamate prodrugs are, for example, the groups $R^{p1}$—CO— and $R^{p2}$O—CO—, in which $R^{p1}$ is hydrogen, $(C_1-C_{18})$-alkyl, $(C_3-C_8)$-cycloalkyl, $(C_3-C_8)$-cycloalkyl-$(C_1-C_4)$-alkyl-, $(C_6-C_{14})$-aryl, het-, $(C_6-C_{14})$-aryl-$(C_1-C_4)$-alkyl- or het-$(C_1-C_4)$-alkyl- and in which $R^{p1}$ has the meanings indicated for $R^{p1}$ with the exception of hydrogen.

Also with respect to all preferred compounds of the formula I all their stereoisomeric forms and mixtures thereof in any ratio and their physiologically acceptable salts explicitly are a subject of the present invention, as well as are their prodrugs. Similarly, also in all preferred compounds of the formula I, all residues that are present more than one time in the molecule are independent of each other and can be identical or different.

In general, compounds of the formula I can be prepared, for example in the course of a convergent synthesis, by linking two or more fragments which can be derived retrosynthetically from the formula I. More specifically, suitably substituted starting quinoline derivatives are employed as building blocks in the preparation of the compounds of formula I. If not commercially available, such quinoline derivatives can be prepared according to the well-known standard procedures for the formation of the quinoline ring system. By choosing suitable precursor molecules, these quinoline syntheses allow the introduction of a variety of substituents into the various positions of the quinoline system, which can be chemically modified in order to finally arrive at the molecule of the formula I having the desired substituent pattern. As one of the comprehensive reviews in which numerous details and literature references on the chemistry of quinoline and on synthetic procedures for their preparation can be found R. D. Larsen, D. Cai in Houben-Weyl, "Science of Synthesis", Georg Thieme Verlag, Stuttgart, Germany 2005, Vol. 15.3, 389-550; R. D. Larsen in Houben-Weyl, "Science of Synthesis", Georg Thieme Verlag, Stuttgart, Germany 2005, Vol. 15.4, 551-660; E. Reimann in Houben-Weyl, "Methoden der organischen Chemie", Georg Thieme Verlag, Stuttgart, Germany 1991, Vol. E7a, 290-492, Hetarene II; N. M Ahmad, J. J. Li, Adv. Heterocycl. Chem. 2003, 84 1-30; S. D. Coffey, S. A. May, A. M. Ratz, Prog. Heterocycl. Chem. 2001, 13, 238-260.

If starting quinoline derivatives are not commercially available and have to be synthesized this can be done, for example, according to the well-known quinoline syntheses mentioned above. In the following, procedures of particular interest for the embodiment of this invention are listed and referenced briefly. These are, however, standard procedures comprehensively discussed in the literature, and are well known to one skilled in the art. Although not always shown explicitly, in certain cases positional isomers will occur during the synthesis of the below mentioned reactions. Nevertheless such mixtures of positional isomers, can be separated by modern separation techniques like, for example, preparative HPLC.

1) N. P. Peet et al. J. Med. Chem. (1985), 28, 298.

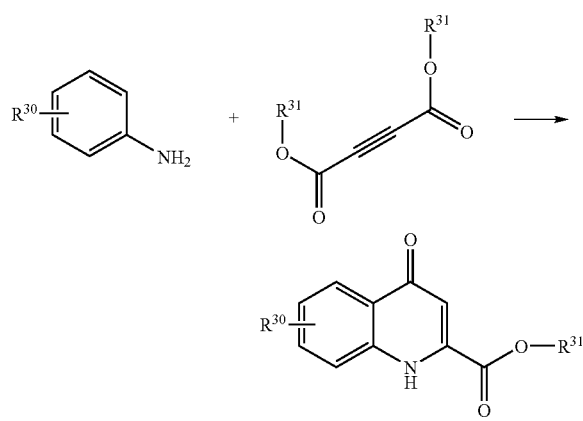

2) E. J. Corey et al., J. Am. Chem. Soc. (1981), 103, 5599.

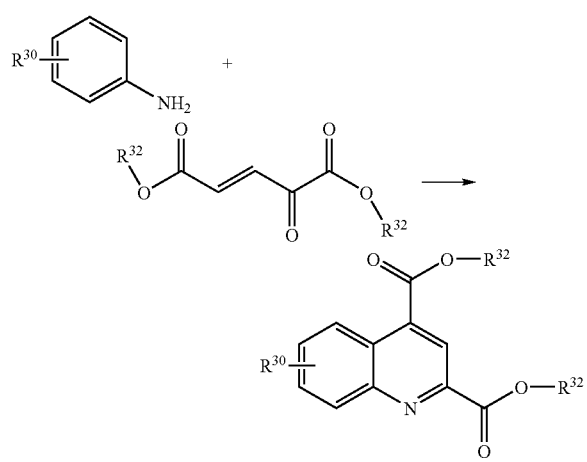

3) A. E. Senear et al., J. Am. Chem. Soc. (1946), 68, 2695.

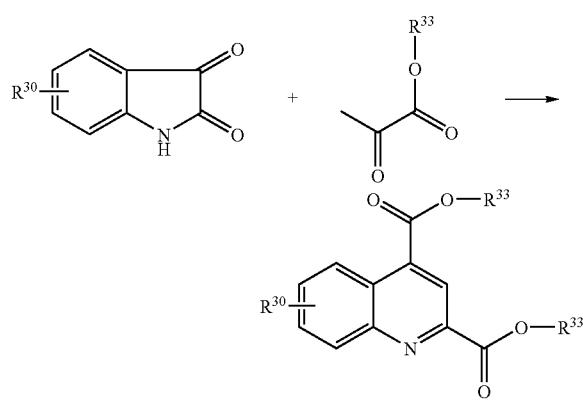

4) E. A. Steck et al., J. Am. Chem. Soc. (1946), 68, 129.

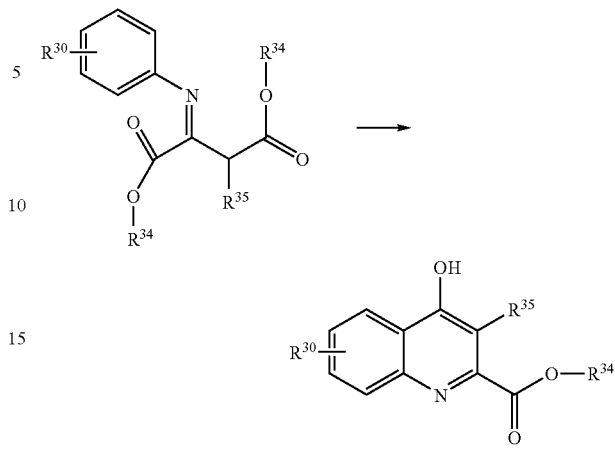

5) a) Limpach, Ber. Dtsch. Chem. Ges. (1931), 64, 969.
b) A. R. Surrey et al. J. Am. Chem. Soc. (1946), 68, 113.

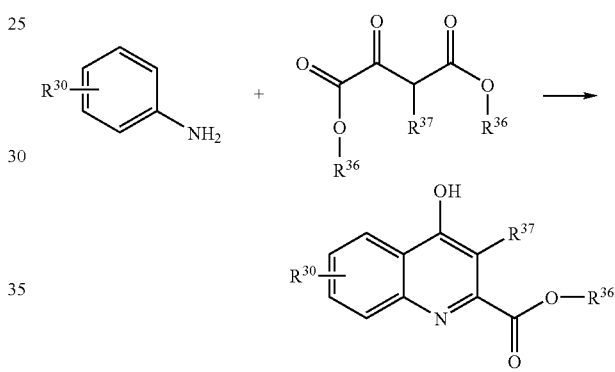

6) S. C. W. Coltman, et al., Synthesis (1984), 150.

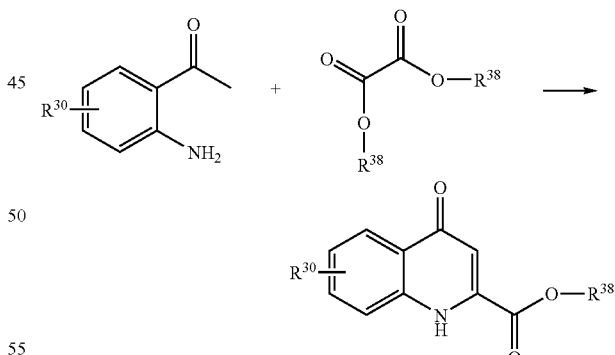

7) J. R. Chong et al., Tetrahedron Lett. (1986), 27, 5323.

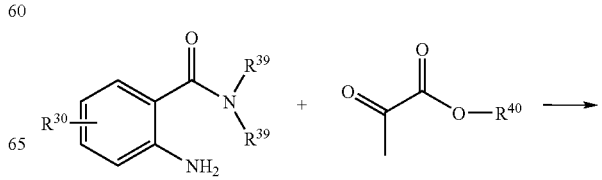

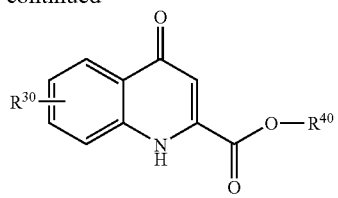

8) S. Torri et al. Tetrahedron Lett. (1990), 31, 7175.

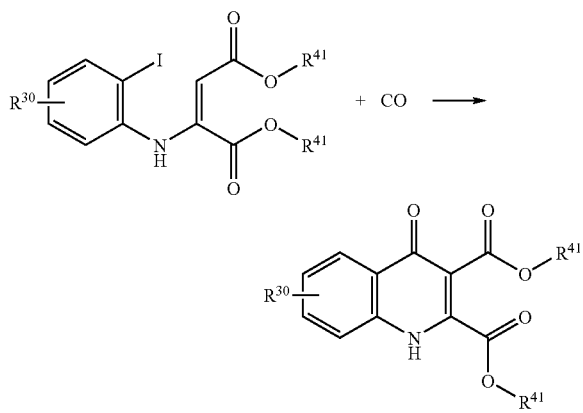

9) S. Torri et al., Tetrahedron (1993), 34, 6773.

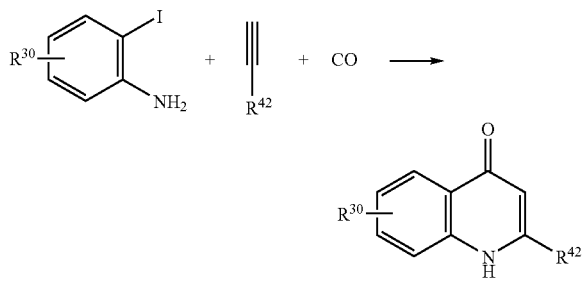

Depending on the substituents in the starting materials, in certain quinoline syntheses mixtures of positional isomers may be obtained, which, however, can be separated by modern separation techniques like, for example, preparative HPLC.

Further, in order to obtain the desired substituents at the quinoline ring system in the formula I, the functional groups introduced into the ring system during the quinoline synthesis can be chemically modified. Especially the substituents present on the quinoline ring system can be modified by a variety of reactions and thus the desired residues $R^{30}$ can be obtained. For example, a quinoline carrying a hydrogen atom in the 3-position can also be obtained by saponification and subsequent decarboxylation of quinoline carrying an ester group in the relevant position. Carboxylic acid groups and acetic acid groups in the 2-position, the 3-position, 4-position, 5-position, 6-position, 7-position and the 8-position can be converted into their homologues by standard reactions for chain elongation of carboxylic acids. Halogen atoms can be introduced, for example according to well-known procedures described in the literature. The fluorination of quinolines can be carried out using a variety of reagents, including, for example N-fluoro-2,4,6-trimethylpyridinium triflate. The chlorination, bromination, or iodination of quinolines can be accomplished by the reaction of the elemental halogens or by, for example the use of NCS, NBS or NIS and many other reagents well known to those skilled in the art. Depending on the reaction conditions, reagent, stoichiometry and substitution pattern the halogen is introduced in the 2-position and/or 3-position and/or 4-position and/or 5-position and/or 6-position and/or 7-position and/or 8-position. By selective halogen/metal exchange or metalation by selective hydrogen/metal exchange and subsequent reaction with a wide range of electrophiles various substituents can be introduced at the heterocyclic nucleus using procedures well-known to those skilled in the art. Among others the corresponding quinolinones can be useful precursors for the introduction of halogen atoms. For example a 1H-quinolin-4-one can be converted to 4-chloro-quinoline by using for example phosphorous oxychloride. The 4-bromo-quinolines can be obtained from 1H-quinolin-4-one by similar standard procedures using phosphorous oxybromide, phosphorous tribromide or phosphorous pentabromide.

Halogens, hydroxy groups (via the triflate or nonaflate) or primary amines (via the diazonium salt) or after interconversion to the corresponding stannane, or boronic acid—present in the quinoline structure can be converted into a variety of other functional groups like for example—CN, —$CF_3$, —$C_2F_5$, ethers, acids, amides, amines, alkyl- or aryl-groups mediated by means of transition metals, such as palladium or nickel catalysts or copper salts and reagents for example referred to below (F. Diederich, P. Stang, Metal-catalyzed Cross-coupling Reactions, Wiley-VCH, 1998; or M. Beller, C. Bolm, Transition Metals for Organic Synthesis, Wiley-VCH, 1998; J. Tsuji, Palladium Reagents and Catalysts, Wiley, 1996; J. Hartwig, Angew. Chem. 1998, 110, 2154; B. Yang, S. Buchwald, J. Organomet. Chem. 1999, 576, 125; T. Sakamoto, K. Ohsawa, J. Chem. Soc. Perkin Trans I, 1999, 2323; D. Nichols, S. Frescas, D. Marona-Lewicka, X. Huang, B. Roth, G. Gudelsky, J. Nash, J. Med. Chem, 1994, 37, 4347; P. Lam, C. Clark, S. Saubern, J. Adams, M. Winters, D. Chan, A. Combs, Tetrahedron Lett., 1998, 39, 2941; D. Chan, K. Monaco, R. Wang, M. Winters, Tetrahedron Lett. 1998, 39, 2933; V. Farina, V. Krishnamurthy, W. Scott, The Stille Reaction, Wiley, 1994; F. Qing et al. J. Chem. Soc. Perkin Trans. 11997, 3053; S. Buchwald et al. J. Am. Chem. Soc. 2001, 123, 7727; S. Kang et al. Synlett 2002, 3, 427; S. Buchwald et al. Organic Lett. 2002, 4, 581; T. Fuchikami et al. Tetrahedron Lett. 1991, 32, 91; Q. Chen et al. Tetrahedron Lett. 1991, 32, 7689; M. R. Netherton, G. C. Fu, Topics in Organometallic Chemistry 2005, 14, 85-108; A. F. Littke, G. F. Fu, Angew. Chem. Int. Ed. 2002, 41, 4176-4211; A. R. Muci, S. L. Buchwald, Topics in Current Chemistry 2002, 219, 131-209.

For example, nitro groups can be reduced to amino groups with various reducing agents, such as sulfides, dithionites, complex hydrides or by catalytic hydrogenation. A reduction of a nitro group may also be carried out at a later stage of the synthesis of a compound of the formula I, and a reduction of a nitro group to an amino group may also occur simultaneously with a reaction performed on another functional group, for example when reacting a group like a cyano group with hydrogen sulfide or when hydrogenating a group. In order to introduce the residues $R^{30}$, amino groups can then be modified according to standard procedures for alkylation, for example by reaction with (substituted) alkyl halogenides or by reductive amination of carbonyl compounds, according to standard procedures for acylation, for example by reaction with activated carboxylic acid derivatives such as acid chlorides, anhydrides, activated esters or others or by reaction with carboxylic acids in the presence of an activating agent, or according to standard procedures for sulfonylation, for example by reaction with sulfonyl chlorides.

Ester groups present in the quinoline nucleus can be hydrolyzed to the corresponding carboxylic acids, which after activation can then be reacted with amines or alcohols under standard conditions. Furthermore these ester or acid groups can be reduced to the corresponding alcohols by many standard procedures. Ether groups present at the quinoline, for example benzyloxy groups or other easily cleavable ether groups, can be cleaved to give hydroxy groups which then can be reacted with a variety of agents, for example etherification agents or activating agents allowing replacement of the hydroxy group by other groups. Sulfur-containing groups can be reacted analogously.

During the course of the synthesis in order to modify the groups $R^{43}$ or $R^{45}$ attached to the quinoline ring system by application of parallel synthesis methodology, beside a variety of reactions, palladium, nickel or copper catalysis can be extremely useful. Such reactions are described for example in F. Diederich, P. Stang, Metal-catalyzed Cross-coupling Reactions, Wiley-VCH, 1998; or M. Beller, C. Bolm, Transition Metals for Organic Synthesis, Wiley-VCH, 1998; J. Tsuji, Palladium Reagents and Catalysts, Wiley, 1996; J. Hartwig, Angew. Chem. 1998, 110, 2154; B. Yang, S. Buchwald, J. Organomet. Chem. 1999, 576, 125; P. Lam, C. Clark, S. Saubern, J. Adams, M. Winters, D. Chan, A. Combs, Tetrahedron Lett. 1998, 39, 2941; D. Chan, K. Monaco, R. Wang, M. Winters, Tetrahedron Lett. 1998, 39, 2933; J. Wolfe, H. Tomori, J. Sadight, J. Yin, S. Buchwald, J. Org. Chem. 2000, 65, 1158; V. Farina, V. Krishnamurthy, W. Scott, The Stille Reaction, Wiley, 1994; S. Buchwald et al., J. Am. Chem Soc. 2001, 123, 7727; S. Kang et al., Synlett 2002, 3, 427; S. Buchwald et al., Org. Lett. 2002, 4, 581.

The previously-mentioned reactions for the conversion of functional groups are furthermore, in general, extensively described in textbooks of organic chemistry like M. Smith, J. March, March's Advanced Organic Chemistry, Wiley-VCH, 2001 and in treatises like Houben-Weyl, "Methoden der Organischen Chemie" (Methods of Organic Chemistry), Georg Thieme Verlag, Stuttgart, Germany, or "Organic Reactions", John Wiley & Sons, New York, or R. C. Larock, "Comprehensive Organic Transformations", Wiley-VCH, $2^{nd}$ ed (1999), B. Trost, I. Fleming (eds.) Comprehensive Organic Synthesis, Pergamon, 1991; A. Katritzky, C. Rees, E. Scriven Comprehensive Heterocyclic Chemistry II, Elsevier Science, 1996) in which details on the reactions and primary source literature can be found. Due to the fact that in the present case the functional groups are attached to a quinoline ring it may in certain cases become necessary to specifically adapt reaction conditions or to choose specific reagents from a variety of reagents that can in principle be employed in a conversion reaction, or otherwise to take specific measures for achieving a desired conversion, for example to use protection group techniques. However, finding suitable reaction variants and reaction conditions in such cases does not cause any problems for one skilled in the art.

The structural elements present in the residues at the 4-position of the quinoline ring in the compounds of the formula I and in the $COR^{45}$ group present in the 2-position of the quinoline ring can be introduced into the starting quinoline derivative using the methods outlined above by consecutive reaction steps using parallel synthesis methodologies like those outlined below using procedures which per se are well known to one skilled in the art.

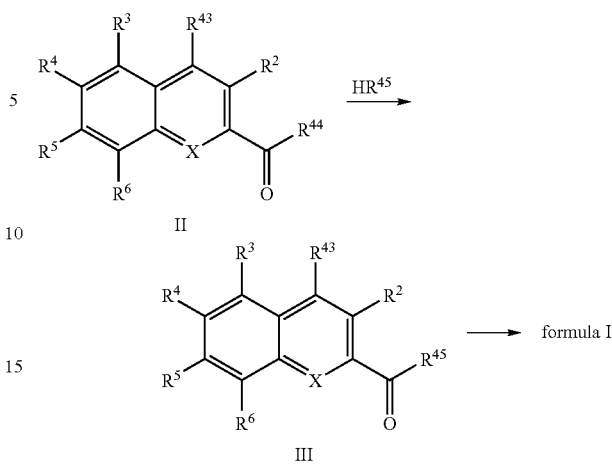

The residues $R^{45}$ can be introduced in compounds of the formula II, for example, by condensing a corresponding carboxylic acid of the formula II with a compound of the formula $HR^{45}$, whereby $HR^{45}$ is an amine of the formula IV, to give a compound of the formula III.

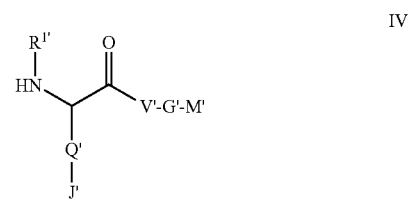

The compound of the formula III thus obtained can already contain the desired final groups, i.e. the groups $R^{45}$ and $R^{43}$ can be the groups of the formulae V and VI, respectively, as defined in formula I, or optionally in the compound of the formula III thus obtained the residue $R^{45}$ or the residues $R^{45}$ and $R^{43}$ are subsequently converted into the residues of the formulae V and VI, respectively, to give the desired compound of the formula I.

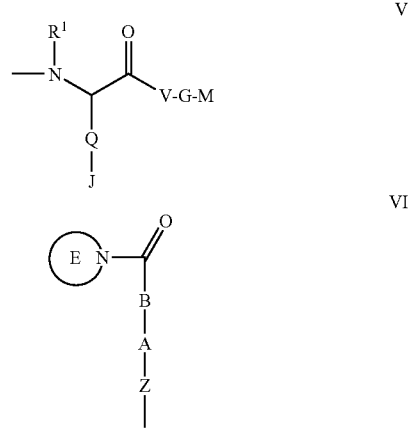

Thus, the residues $R^{45}$ and the residues V', G', Q', J' and M' contained in formula IV can have the denotations of residues of the formula V, respectively, given above or in addition in the residues of the formula IV functional groups can also be present in the form of groups that can subsequently be transformed into the final groups of the formula V, i.e. functional groups can be present in the form of precursor groups or of derivatives, for example in protected form. In the course of the preparation of the compounds of the formula I it can generally be advantageous or necessary to introduce functional groups which reduce or prevent undesired reactions or side reactions in the respective synthesis steps, in the form of precursor groups which are later converted into the desired functional groups, or to temporarily block functional groups by a protective group strategy suited to the synthesis problem. Such strategies are well known to those skilled in the art (see, for example, Greene and Wuts, Protective Groups in Organic Synthesis, Wiley, 1991, or P. Kocienski, Protecting Groups, Thieme 1994). Examples of precursor groups are cyano groups and nitro groups. The cyano group can, in a later step, be transformed into carboxylic acid derivatives or by reduction into aminomethyl groups, Nitro groups may be transformed by reduction like catalytic hydrogenation into amino groups. Protective groups can also have the meaning of a solid phase, and cleavage from the solid phase stands for the removal of the protective group. The use of such techniques is known to those skilled in the art (Burgess K (Ed.) Solid Phase Organic Synthesis, New York, Wiley, 2000). For example, a phenolic hydroxy group can be attached to a trityl-polystyrene resin, which serves as a protecting group, and the molecule is cleaved from this resin by treatment with TFA or other acids at a later stage of the synthesis.

The residue $R^{43}$ in the compounds of the formulae II and III can denote the group of formula VI as defined above which finally is to be present in the desired target molecule of the formula I, or it can denote a group which can subsequently be transformed into the group of formula VI, for example a precursor group or a derivative of the group of formula VI in which functional groups are present in protected form, or $R^{43}$ can denote a hydrogen, a oxygen atom, or a nitrogen, or a sulfur atom or a protective group masking the aforementioned atoms of the quinoline ring. Similarly, the residues $R^{30}$ have the corresponding definitions of $R^2$, $R^3$, $R^4$, $R^5$ or $R^6$ in formula I as defined above, however, for the synthesis of the compounds of the formula I these residues, too, can in principle be present in the form of precursor groups or in protected form at the stage of the condensation of a compound of the formula II with a compound of the formula $HR^{45}$ giving a compound of the formula III.

The residue $R^{44}$ in the compounds of the formula II which can be identical or different, can be, for example, hydroxy or $(C_1-C_4)$-alkoxy, i.e., the groups $COR^{44}$ present in the compounds of the formula II can be, for example, the free carboxylic acids or esters thereof like alkyl esters as can be the groups $COR^{45}$ in the compounds of the formula III. The groups $COR^{44}$ can also be any other activated derivative of a carboxylic acid which allows amide formation with a compound of the formula $HR^{45}$. The group $COR^{44}$ can be, for example, an acid chloride, an activated ester like a substituted phenyl ester or thioester, an azolide like an imidazolide, an azide or a mixed anhydride, for example a mixed anhydride with a carbonic acid ester or with a sulfonic acid. These derivatives can all be prepared from the carboxylic acid by standard procedures and can be reacted with an amine of the formula $HR^{45}$ under standard conditions. A carboxylic acid group COOH representing $COR^{44}$ in a compound of the formula II can be obtained, for example by standard hydrolysis procedures, from an ester group introduced into the quinoline system during a quinoline synthesis.

Compounds of the formula I in which a group $COR^{45}$ is an amide group can be prepared from amines and compounds of the formula II in which $COR^{44}$ is a carboxylic acid group or an ester or thioester thereof by common amination reactions. Especially for the preparation of amides the compounds of the formula II in which $COR^{44}$ is a carboxylic acid group can be condensed under standard conditions with compounds of the formula $HR^{45}$ which are amines by means of common coupling reagents used in peptide synthesis. Such coupling reagents are, for example, carbodiimides like dicyclohexylcarbodiimide (DCC) or diisopropylcarbodiimide, carbonyldiazoles like carbonyldiimidazole (CD) and similar reagents, propylphosphonic anhydride, O-((cyano-(ethoxycarbonyl)-methylene)amino)-N,N,N',N'-tetramethyluronium tetrafluoroborate (TOTU), diethylphosphoryl cyanide (DEPC) or bis-(2-oxo-3-oxazolidinyl)-phosphoryl chloride (BOP-Cl) and many others. O-(benzotriazol-1-yl)-1,1,3,3-tetramethyluronium hexafluorophosphate (HBTU), O-(7-azabenzotriazol-1-yl)-1,1,3,3-tetramethyluronium hexafluorophosphate (HATU), bromo-tris-pyrrolidino-phosphonium hexafluorophosphate (Pybrop).

The activation of the carboxylic acid function may also favourably be carried out, for example, by conversion of the carboxylic acid group into the pentafluorophenyl ester using dicyclohexylcarbodiimide and pentafluorophenol or by using reagents like pentafluorophenyl trifluoroacetate, tert-butyl pentafluorophenyl carbonate, bis(pentafluorophenyl)carbonate, 2,3,4,5,6-pentafluorophenyl 4-methylbenzenesulfonate, pentafluorophenol-tetramethyluronium hexafluorophosphate, octafluoroacetophenone. The activation of the carboxylic function by conversion to other phenylesters like for example 4-nitro-phenyl esters or 2-nitro-phenyl esters can be also effective. The activation and the subsequent reaction with a group of the formula IX are usually carried out in the presence of an inert solvent or diluent, for example DCM, chloroform, THF, diethyl ether, n-heptane, n-hexane, n-pentane, cyclohexane, diisopropyl ether, methyl tBu ether, acetonitrile, DMF, DMA, NMP, DMSO, dioxane, toluene, benzene, ethyl acetate or a mixture of these solvents, if appropriate with addition of a base such as, for example, potassium tert-butoxide or tributylamine or triethylamine or diisopropylethylamine or N-ethylmorpholine.

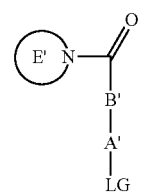

VII

If the residue of the formula VI present in a quinoline of the formula I or the residue $R^{43}$ present in a quinoline of the formula II or formula III, or a residue in which functional groups within the residue of the formula VI or $R^{43}$ are present in protected form or in the form of a precursor group, have not already been introduced during a preceding step, for example during a synthesis of the quinoline nucleus, these residues can, for example, be introduced into the 4-position of the quinoline system by standard alkylation procedures well-known to one skilled in the art.

The starting quinoline derivative that is to be employed in such a reaction carries oxygen, nitrogen, or sulfur atom in the 4-position. Alkylation of the aforementioned atom can, for example, be performed under standard conditions, preferably in the presence of a base like $K_2CO_3$, $Cs_2CO_3$, NaH or KO$^t$Bu, using an alkylating compound of the formula VII or of the formula $R^{43}$-LG, wherein the atom in the group A' of the formula VII or in the group $R^{43}$ bonded to the group LG in this case is an aliphatic carbon atom of an alkyl moiety and LG is a leaving group, for example halogen like chlorine, bromine or iodine, or a sulfonyloxy group like tosyloxy, mesyloxy or trifluormethylsulfonyloxy. These standard procedures are for example described in treatises like M. Smith, J. March, March's Advanced Organic Chemistry, Wiley-VCH, 2001; Houben-Weyl, "Methoden der Organischen Chemie" (Methods of Organic Chemistry), Georg Thieme Verlag, Stuttgart, Germany, or "Organic Reactions", John Wiley & Sons, New York, or R. C. Larock, "Comprehensive Organic Transformations", Wiley-VCH, 2$^{nd}$ ed (1999), B. Trost, I. Fleming (eds.) Comprehensive Organic Synthesis, Pergamon, 1991. LG may, for example, also be a hydroxy group which, in order to achieve the alkylation reaction, is activated under the well-known conditions of the Mitsunobu procedure (O. Mitsunobu, Synthesis 1981, 1) or by further modified procedures (A. Tunoori, D. Dutta, G. Gunda, Tetrahedron Lett. 39 (1998) 8751; J. Pelletier, S. Kincaid, Tetrahedron Lett. 41 (2000) 797; D. L. Hughes, R. A. Reamer, J. J. Bergan, E. J. J. Grabowski, J. Am. Chem. Soc. 110 (1998) 6487; D. J. Camp, I. D. Jenkins, J. Org. Chem. 54 (1989) 3045; D. Crich, H. Dyker, R. J. Harris, J. Org. Chem. 54 (1989) 257) of even greater use.

The residue of the formula VI present in a quinoline of the formula I or the residue $R^{43}$ present in a quinoline of the formula II, or a residue in which functional groups within the residue of the formula VI or $R^{43}$ are present in protected form or in the form of a precursor group, can be for example introduced into the 4-position of the quinoline system by conventional literature procedures for the amination, etherification or thioetherification of quinolines well-known to those skilled in the art. The appropriately substituted quinoline useful for these reactions carries a leaving group in the 4-position of the quinoline like for example halogen, triflate, nonaflate, tosylate, azide, or a diazonium salt. Preferably the reaction is carried out in the presence of a base like $K_2CO_3$, $Cs_2CO_3$, NaH or KO$^t$Bu. The desired transformation can also be accomplished with halogens, hydroxy groups (via the triflate or nonaflate) or primary amines (via the diazonium salt) or after interconversion to the corresponding stannane, or boronic acid—present in the 4-position of quinoline structure can be converted into a variety of other functional groups like for example —CN, —CF$_3$, —C$_2$F$_5$, ethers, acids, amides, amines, alkyl- or aryl-groups mediated by means of transition metals, such as palladium or nickel catalysts or copper salts and reagents for example referred to below (F. Diederich, P. Stang, Metal-catalyzed Cross-coupling Reactions, Wiley-VCH, 1998; or M. Beller, C. Bolm, Transition Metals for Organic Synthesis, Wiley-VCH, 1998; J. Tsuji, Palladium Reagents and Catalysts, Wiley, 1996; J. Hartwig, Angew. Chem. 1998, 110, 2154; B. Yang, S. Buchwald, J. Organomet. Chem. 1999, 576, 125; T. Sakamoto, K. Ohsawa, J. Chem. Soc. Perkin Trans I, 1999, 2323; D. Nichols, S. Frescas, D. Marona-Lewicka, X. Huang, B. Roth, G. Gudelsky, J. Nash, J. Med. Chem, 1994, 37, 4347; P. Lam, C. Clark, S. Saubern, J. Adams, M. Winters, D. Chan, A. Combs, Tetrahedron Lett., 1998, 39, 2941; D. Chan, K. Monaco, R. Wang, M. Winters, Tetrahedron Lett. 1998, 39, 2933; V. Farina, V. Krishnamurthy, W. Scott, The Stille Reaction, Wiley, 1994; F. Qing et al. J. Chem. Soc. Perkin Trans. I 1997, 3053; S. Buchwald et al. J. Am. Chem. Soc. 2001, 123, 7727; S. Kang et al. Synlett 2002, 3, 427; S. Buchwald et al. Organic Lett. 2002, 4, 581; T. Fuchikami et al. Tetrahedron Lett. 1991, 32, 91; Q. Chen et al. Tetrahedron Lett. 1991, 32, 7689; M. R. Netherton, G. C. Fu, Topics in Organometallic Chemistry 2005, 14, 85-108.). A. F. Littke, G. F. Fu, Angew. Chem. Int. Ed. 2002, 41, 4176-4211; A. R. Muci, S. L. Buchwald, Topics in Current Chemistry 2002, 219, 131-209.

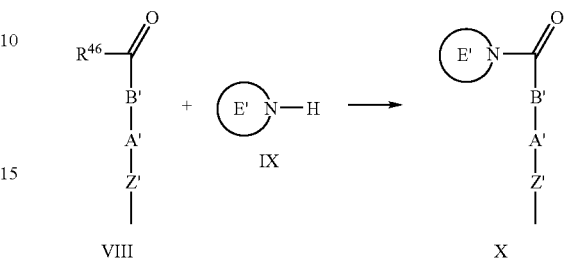

The residues $R^{46}$ in the compounds of the formula VIII which can be identical or different, can be, for example, hydroxy or (C$_1$-C$_4$)-alkoxy, i.e., the groups COR$^{46}$ present in the residues of the formula VIII can be, for example, the free carboxylic acid group or esters thereof like alkyl esters. The groups COR$^{46}$ can also be any other activated derivative of a carboxylic acid group which allows amide bond formation with a compound of the formula IX. The group COR$^{46}$ can be, for example, an acyl chloride, an activated ester like a substituted phenyl ester, an azolide like an imidazolide, an acyl azide or a mixed anhydride, for example a mixed anhydride with a carbonic acid ester or with a sulfonic acid. These derivatives can all be prepared from the carboxylic acid group by standard procedures and can be reacted with an amine of the formula IX under standard conditions. Such coupling reagents are, for example, carbodiimides like dicyclohexylcarbodiimide (DCC) or diisopropylcarbodiimide, carbonyldiazoles like carbonyldiimidazole (CD) and similar reagents, propylphosphonic anhydride, O-((cyano-(ethoxycarbonyl)-methylene)amino)-N,N,N',N'-tetramethyluronium tetrafluoroborate (TOTU), diethylphosphoryl cyanide (DEPC) or bis-(2-oxo-3-oxazolidinyl)-phosphoryl chloride (BOP-Cl) and many others. O-(benzotriazol-1-yl)-1,1,3,3-tetramethyluronium hexafluorophosphate (HBTU), O-(7-azabenzotriazol-1-yl)-1,1,3,3-tetramethyluronium hexafluorophosphate (HATU), bromo-tris-pyrrolidino-phosphonium hexafluorophosphate (Pybrop). The activation of the carboxylic acid function may also favourably be carried, for example, by conversion of the carboxylic acid group into the pentafluorophenyl ester using dicyclohexylcarbodiimide and pentafluorophenol or by using reagents like pentafluorophenyl trifluoroacetate, tert-butyl pentafluorophenyl carbonate, bis (pentafluorophenyl)carbonate, 2,3,4,5,6-pentafluorophenyl 4-methylbenzenesulfonate, pentafluorophenol-tetramethyluronium hexafluorophosphate, octafluoroacetophenone. The activation of the carboxylic function by conversion to other phenylesters like for example 4-nitro-phenyl esters or 2-nitrophenyl esters can be also effective. The activation and the subsequent reaction with the compound of the formula IX are usually carried in the presence of an inert solvent or diluent, for example DCM, chloroform, THF, diethyl ether, n-heptane, n-hexane, n-pentane, cyclohexane, diisopropyl ether, methyl tBu ether, acetonitrile, DMF, DMA, NMP, DMSO, dioxane, toluene, benzene, ethyl acetate or a mixture of these solvents, if appropriate with addition of a base such as, for example, potassium tert-butoxide or tributylamine or triethylamine or diisopropylethylamine or N-ethylmorpholine. A carboxylic acid group —COOH representing COR⁴⁶ in a residue of the formula VIII can be obtained, for example, from an ester group introduced into the quinoline system during a quinoline synthesis by standard deprotection procedures like hydrolysis or hydrogenation. For the formation of an amide bond with residues of the formula VIII in which COR⁴⁶ is a carboxylic acid group can be condensed under standard conditions with compounds of the formula IX which are amines by means of common coupling reagents used in peptide synthesis.

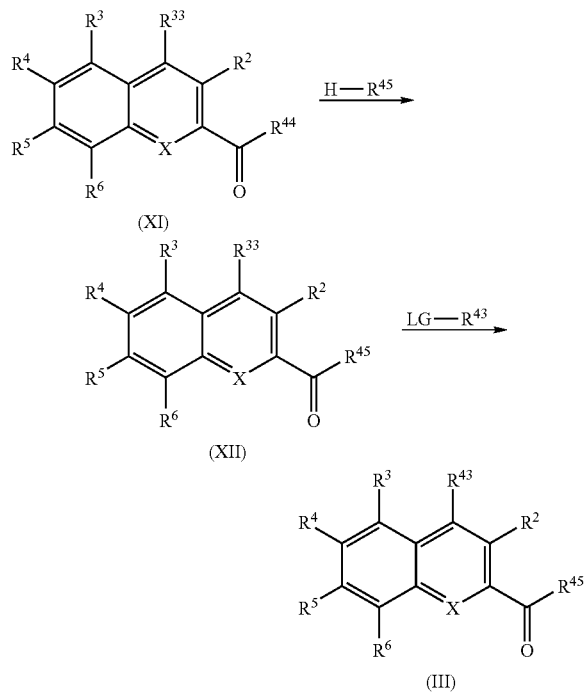

The residues of the formulae VII, VIII, IX and X thus obtained can already contain the desired final groups, i.e. the groups E', Z', A', B', V', G' and M' can be the groups of the formulae V and VI as defined in the formula I, or optionally in the compound of the formula III thus obtained subsequently the residue or the residues R⁴⁵ and R⁴³ are converted into the residues of the formulae V and VI, respectively, to give the desired compound of the formula I. Thus, the residues of the formulae VII, VIII, IX and X contained therein can have the denotations of residues of the formulae V and VI, respectively, given above or in addition in the residues of the formulae VII, VIII, IX and X can also be present in the form of groups that can subsequently be transformed into the final groups of the formulae V and VI, i.e. functional groups can be present in the form of precursor groups or of derivatives, for example in protected form. In the course of the preparation of the compounds of the formula I it can generally be advantageous or necessary to introduce functional groups which reduce or prevent undesired reactions or side reactions in the respective synthesis step, in the form of precursor groups which are later converted into the desired functional groups, or to temporarily block functional groups by a protective group strategy suited to the synthesis problem. Such strategies are well known to those skilled in the art (see, for example, Greene and Wuts, Protective Groups in Organic Synthesis, Wiley, 1991, or P. Kocienski, Protecting Groups, Thieme 1994). Protective groups can also have the meaning of a solid phase, and cleavage from the solid phase stands for the removal of the protective group. The use of such techniques is known to those skilled in the art (Burgess K (Ed.) Solid Phase Organic Synthesis, New York, Wiley, 2000).

During the above-mentioned transformations positional isomers may occur, nevertheless these mixtures of positional isomers can be separated by modern separation techniques like, for example, preparative HPLC.

The compounds of the present invention are platelet ADP P2Y12 receptor antagonists, which antagonize the platelet aggregating effect of the activation of the platelet ADP P2Y12 receptors. In particular, they are highly active antagonists of the P2Y12 receptor. They are specific platelet ADP receptor antagonists inasmuch as they do not substantially inhibit or promote the activity of other receptors whose activation or inhibition is not desired. The activity of the compounds of the formula I can be determined, for example, in the assays described below or in other in vitro, ex vivo or in vivo assays known to those skilled in the art. For example, the ability of the compounds to bind to the P2Y12 receptor may be measured by methods similar to those described in Gachet, C. et al., Br. J. Haemotol. (1995), 91, 434-444 and Mills, D. C., Thromb. Haemost (1996), 76, 835-856, and by the assay described below. With respect to P2Y12 binding affinity, a preferred embodiment of the invention comprises compounds which have an IC50<1 mM for P2Y12 binding affinity as determined in the assay described, and which preferably do not substantially influence the activity of other receptors involved in platelet aggregation and fibrinolysis whose inhibition or activation is not desired (using the same concentration of the antagonist). The ability of the compounds to inhibit ADP-induced aggregation of platelets may be measured by methods similar to those described in R. G. Humphries et al., Br. J. Pharm. (1995), Vol. 115, pp. 1110-1116 and J. F. Mustard et al. Methods in Enzymology, Vol. 169, p. 3 and by the method described below. The ability of the compounds to inhibit thrombus formation in vivo or ex vivo may be measured by methods similar to those described in J. M. Herbert et al., Cardiovasc. Drug Rev. (1993), 11, 180-198 or J. D. Folts et al., Circulation (1976), 54, 365. The results of these assays clearly demonstrate that the compounds of the invention are functional antagonists of the platelet adenosine diphosphate receptor and are therefore useful for inhibiting platelet aggregation and thrombus formation.

As platelet ADP P2Y12 receptor antagonists the compounds of the formula I and/or their physiologically tolerable salts and/or their prodrugs are generally suitable for the therapy and prophylaxis of conditions in which the activity of platelet ADP P2Y12 receptor plays a role or has an undesired extent, or which can favorably be influenced by inhibiting P2Y12 receptor or decreasing the activity, or for the prevention, alleviation or cure of which an inhibition of platelet ADP P2Y12 receptor or a decrease in the activity is desired by the physician. As inhibition of the platelet ADP P2Y12 receptor influences platelet activation, platelet aggregation and platelet degranulation and promote platelet disaggregation, the compounds of the formula I and/or their physiologically tolerable salts and/or their prodrugs are generally suitable for reducing blood thrombus formation, or for the therapy and prophylaxis of conditions in which the activity of the platelet aggregation and thus blood coagulation system plays a role or has an undesired extent, or which can favorably be influenced by reducing thrombus formation, or for the prevention, alleviation or cure of which a decreased activity of the platelet aggregation system is desired by the physician. A specific subject of the present invention thus are the reduction or inhibition of unwanted thrombus formation, in particular in an individual, by administering an effective amount of a compound of the formula I and/or a physiologically tolerable salt and/or a prodrug thereof, as well as pharmaceutical preparations thereof.

The present invention also relates to the compounds of the formula I and/or their physiologically tolerable salts and/or their prodrugs for use as pharmaceuticals (or medicaments), to the use of the compounds of the formula I and/or their physiologically tolerable salts and/or their prodrugs for the production of pharmaceuticals for inhibition of the P2Y12 receptor or for influencing platelet activation, platelet aggregation and platelet degranulation and promote platelet disaggregation, inflammatory response or for the therapy or prophylaxis of the diseases mentioned above or below, for example for the production of pharmaceuticals for the therapy and prophylaxis of cardiovascular disorders, thromboembolic diseases or restenosis. The invention also relates to the use of the compounds of the formula I and/or their physiologically tolerable salts and/or their prodrugs for the inhibition of P2Y12 receptor or for influencing platelet activation, platelet aggregation and platelet degranulation and promote platelet disaggregation or for the therapy or prophylaxis of the diseases mentioned above or below, for example for use in the therapy and prophylaxis of cardiovascular disorders, thromboembolic diseases or restenoses, and to methods of treatment aiming at such purposes including methods for said therapies and prophylaxis. The present invention also relates to pharmaceutical preparations (or pharmaceutical compositions) which contain an effective amount of at least one compound of the formula I and/or its physiologically tolerable salts and/or its prodrugs in addition to a customary pharmaceutically acceptable carrier, i.e. one or more pharmaceutically acceptable carrier substances or excipients and/or auxiliary substances or additives.

The invention also relates to the treatment of disease states such as abnormal thrombus formation, acute myocardial infarction, unstable angina, thromboembolism, acute vessel closure associated with thrombolytic therapy or percutaneous transluminal coronary angioplasty (PTCA), transient ischemic attacks, stroke, intermittent claudication or bypass grafting of the coronary or peripheral arteries, vessel luminal narrowing, restenosis post coronary or venous angioplasty, maintenance of vascular access patency in long-term hemodialysis patients, pathologic thrombus formation occurring in the veins of the lower extremities following abdominal, knee or hip surgery, pathologic thrombus formation occurring in the veins of the lower extremities following abdominal, knee and hip surgery, a risk of pulmonary thromboembolism, or disseminated systemic intravascular coagulatopathy occurring in vascular systems during septic shock, certain viral infections or cancer.

The compounds of the present invention can also be used to reduce an inflammatory response. Examples of specific disorders for the treatment or prophylaxis of which the compounds of the formula I can be used are coronary heart disease, myocardial infarction, angina pectoris, vascular restenosis, for example restenosis following angioplasty like PTCA, adult respiratory distress syndrome, multi-organ failure and disseminated intravascular clotting disorder. Examples of related complications associated with surgery are thromboses like deep vein and proximal vein thrombosis, which can occur following surgery.

The compounds of the formula I and their physiologically tolerable salts and their prodrugs can be administered to animals, preferably to mammals, and in particular to humans as pharmaceuticals for therapy or prophylaxis. They can be administered on their own, or in mixtures with one another or in the form of pharmaceutical preparations, which permit enteral or parenteral administration.

The pharmaceuticals can be administered orally, for example in the form of pills, tablets, lacquered tablets, coated tablets, granules, hard and soft gelatine capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the invention are prepared in a manner known per se and familiar to one skilled in the art, pharmaceutically acceptable inert inorganic and/or organic carriers being used in addition to the compound(s) of the formula I and/or its (their) physiologically tolerable salts and/or its (their) prodrugs. For the production of pills, tablets, coated tablets and hard gelatine capsules it is possible to use, for example, lactose, cornstarch or derivatives thereof, talc, stearic acid or its salts, etc. Carriers for soft gelatine capsules and suppositories are, for example, fats, waxes, semisolid and liquid polyols, natural or hardened oils, etc. Suitable carriers for the production of solutions, for example injection solutions, or of emulsions or syrups are, for example, water, saline, alcohols, glycerol, polyols, sucrose, invert sugar, glucose, vegetable oils, etc. Suitable carriers for microcapsules, implants or rods are, for example, copolymers of glycolic acid and lactic acid. The pharmaceutical preparations normally contain about 0.5% to 90% by weight of the compounds of the formula I and/or their physiologically tolerable salts and/or their prodrugs. The amount of the active ingredient of the formula I and/or its physiologically tolerable salts and/or its prodrugs in the pharmaceutical preparations normally is from about 0.5 mg to about 1000 mg, preferably from about 1 mg to about 500 mg.

In addition to the active ingredients of the formula I and/or their physiologically acceptable salts and/or prodrugs and to carrier substances, the pharmaceutical preparations can contain additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formula I, and/or their physiologically tolerable salts and/or their prodrugs. In case a pharmaceutical preparation contains two or more compounds of the formula I, the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of the formula I allows a great deal of control over the biological and physico-chemical properties of the compounds and thus allows the selection of such desired compounds. Furthermore, in addition to at least one compound of the formula I and/or a physiologically tolerable salt and/or its prodrug, the pharmaceutical preparations can also contain one or more other therapeutically or prophylactically active ingredients.

When using the compounds of the formula I the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from 0.01 mg/kg to 100 mg/kg, preferably from 0.1 mg/kg to 50 mg/kg, in particular from 0.1 mg/kg to 10 mg/kg, (in each case in mg per kg of body weight). The daily dose can be divided, in particular in the case of the administration of relatively large amounts, into several, for example 2, 3 or 4, part administrations. As usual, depending on individual behaviour it may be necessary to deviate upwards or downwards from the daily dose indicated.

The compounds of the present invention can be administered alone or in combination with one or more additional therapeutic agents. These other agents include, but are not limited to, anticoagulant or coagulation inhibitory agents, other antiplatelet or platelet inhibitory agents, or thrombolytic or fibrinolytic agents.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

Examples of suitable anti-arrhythmic agents for use in combination with the present compounds include: Class I agents (such as propafenone); Class II agents (such as carvadiol and propranolol); Class HI agents (such as sotalol, dofetilide, amiodarone, azimilide, and ibutilide); Class IV agents (such as ditiazem and verapamil); K+ channel openers such as IAch inhibitors, and IκUR inhibitors (e.g., compounds such as those disclosed in WO01/40231).

Examples of suitable antihypertensive agents for use in combination with the compounds of the present invention include: alpha adrenergic blockers; beta adrenergic blockers; calcium channel blockers (e.g. diltiazem, verapamil, nifedipine, amlodipine, and mybefradil); diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone); renin inhibitors; angiotensin-converting enzyme (ACE) inhibitors (e.g., captopril, zofenopril, fosinopril, enalapril, ceranopril, cilazopril, delapril, pentopril, quinapril, ramipril, lisinopril); angiotensin AT-I receptor antagonists (e.g., losartan, irbesartan, valsartan); ET-A receptor antagonists (e.g., sitaxsentan, atrsentan, and compounds disclosed in U.S. Pat. Nos. 5,612,359 and 6,043,265); Dual ET-A/AT-I antagonist (e.g., compounds disclosed in WO 00/01389); neutral endopeptidase (NEP) inhibitors; vasopepsidase inhibitors (dual NEP-ACE inhibitors) (e.g., omapatrilat, gemopatrilat, and nitrates); and β-blockers (e.g., propanolol, nadolol, or carvedilol).

Examples of other suitable anti-platelet agents for use in combination with the compounds of the present invention, include, but are not limited to, the various known non-steroidal anti-inflammatory drugs (NSAIDS) such as acetaminophen, aspirin, codeine, diclofenac, droxicam, fentaynl, ibuprofen, indomethacin, ketorolac-, mefenamate, morphine, naproxen, phenacetin, piroxicam, sufentanyl, sulfinpyrazone, sulindac, and pharmaceutically acceptable salts or prodrugs thereof. Of the NSAIDS, aspirin (acetylsalicyclic acid or ASA) and piroxicam are preferred. Other suitable platelet inhibitory agents include glycoprotein IIb/IIIa blockers (e.g., abciximab, eptifibatide, tirofiban, integrelin), thromboxane-A2-receptor antagonists (e.g., ifetroban), thromboxane-A2-synthetase inhibitors, phosphodiesterase-111 (PDE-III) inhibitors (e.g., dipyridamole, cilostazol), and PDE V inhibitors (such as sildenafil), protease-activated receptor 1 (PAR-I) antagonists (e.g., SCH-530348, SCH-203099, SCH-529153, and SCH-205831), and pharmaceutically acceptable salts or prodrugs thereof.

Examples of suitable anticoagulants for use in combination with the compounds of the present invention include warfarin and heparin (either unfractionated heparin such as enoxaparin and dalteparin or any commercially available low molecular weight heparin, for example LOVENOX™), synthetic pentasaccharide, direct acting thrombin inhibitors including hirudin and argatroban, factor VIIa inhibitors, factor IXa inhibitors, factor Xa inhibitors (e.g., Arixtra™, apixaban, rivaroxaban, LY-517717, DU-176b, DX-9065a, and those disclosed in WO 98/57951, WO 03/026652, WO 01/047919, and WO 00/076970), factor XIa inhibitors, and inhibitors of activated TAFI and PAI-I known in the art. The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the secretion of platelet granule contents including serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, dabigatran, AZD-0837, and those disclosed in WO 98/37075 and WO 02/044145, and pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, thrombin inhibitors, inhibitors of factors EKa, Xa, and XIa, PAI-I inhibitors (i.e., inactivators of tissue plasminogen activator inhibitors), inhibitors of activated TAFI, alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable calcium channel blockers (L-type or T-type) for use in combination with the compounds of the present invention include diltiazem, verapamil, nifedipine, amlodipine and mybefradil.

Examples of suitable cardiac glycosides for use in combination with the compounds of the present invention include digitalis and ouabain. Examples of suitable diuretics for use in combination with the compounds of the present invention include: chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, and spironolactone. Examples of suitable mineralocorticoid receptor antagonists for use in combination with the compounds of the present invention include sprionolactone and eplirinone.

Examples of suitable cholesterol/lipid lowering agents and lipid profile therapies for use in combination with the compounds of the present invention include: HMG-CoA reductase inhibitors (e.g., pravastatin lovastatin, atorvastatin, simvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; nicotonic acid; fenofibric acid derivatives (e.g., gemfibrozil, clofibrat, fenofibrate and benzafibrate); probucol; choesterol absorption inhibitors; and cholesterol ester transfer protein inhibitors (e.g., CP-529414). Examples of suitable anti-diabetic agents for use in combination with the compounds of the present invention include: biguanides (e.g. metformin); glucosidase inhibitors (e.g. acarbose); insulins (including insulin secretagogues or insulin sensitizers); meglitinides (e.g. repaglinide); sulfonylureas (e.g., glimepiride, glyburide and glipizide); biguanide/glyburide combinations (e.g., glucovance), thiozolidinediones (e.g. troglitazone, rosiglitazone, and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagon-like peptide-1 (GLP-I), and dipeptidyl peptidase IV (DPP4) inhibitors.

Examples of suitable anti-depressant agents for use in combination with the compounds of the present invention include nefazodone and sertraline. Examples of suitable anti-inflammatory agents for use in combination with the compounds of the present invention include: prednisone; dexamethasone; enbrel; protein tyrosine kinase (PTK) inhibitors; cyclooxygenase inhibitors (including NSAIDs, and COX-I and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene. Examples of suitable hormone replacement therapies for use in combination with the compounds of the present invention include estrogen (e.g., conjugated estrogens) and estradiol.

Examples of suitable anti-obesity agents for use in combination with the compounds of the present invention include orlistat, aP2 inhibitors (such as those disclosed in WO00/59506), and cannabinoid receptor CBI antagonists (e.g., rimonabant, AVE-1625, SR-147778, and CP-945598).

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epithilones, cisplatin, and carboplatin.

Examples of suitable anti-ulcer and gastroesophageal reflux disease agents for use in combination with the compounds of the present invention include famotidine, ranitidine, and omeprazole.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each. A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

The compounds of the present invention are also useful as standard or reference compounds, for example as a quality standard or control, in tests or assays involving the inhibition of platelet ADP receptor. Such compounds may be provided in a commercial kit, for example, for use in pharmaceutical research involving platelet ADP receptor. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

A compound of the formula I can also advantageously be used as an antiaggregant outside an individual. For example, an effective amount of a compound of the invention can be contacted with a freshly drawn blood sample to prevent aggregation of the blood sample. Further, a compound of the formula I or its salts can be used for diagnostic purposes, for example in in vitro diagnoses, and as an auxiliary in biochemical investigations. For example, a compound of the formula I can be used in an assay to identify the presence of the P2Y12 receptor or to isolate the P2Y12 receptor containing tissue in a substantially purified form. A compound of the invention can be labelled with, for example, a radioisotope, and the labelled compound bound to the P2Y12 receptor is then detected using a routine method useful for detecting the particular label. Thus, a compound of the formula I or a salt thereof can be used as a probe to detect the location or amount of P2Y12 receptors activity in vivo, in vitro or ex vivo.

Furthermore, the compounds of the formula I can be used as synthesis intermediates for the preparation of other compounds, in particular of other pharmaceutical active ingredients, which are obtainable from the compounds of the formula I, for example by introduction of substituents or modification of functional groups.

The general synthetic sequences for preparing the compounds useful in the present invention are outlined in the examples given below. Both an explanation of, and the actual procedure for, the various aspects of the present invention are described where appropriate. The following examples are intended to be merely illustrative of the present invention, and not limiting thereof in either scope or spirit. Those with skill in the art will readily understand that known variations of the conditions and processes described in the examples can be used to synthesize the compounds of the present invention.

It is understood that changes that do not substantially affect the activity of the various embodiments of this invention are included within the invention disclosed herein. Thus, the following examples are intended to illustrate but not limit the present invention.

EXAMPLES

When in the final step of the synthesis of a compound an acid such as trifluoroacetic acid or acetic acid was used, for example when trifluoroacetic acid was employed to an acid-labile protecting group (eg. a tBu group) or when a compound was purified by chromatography using an eluent which contained such an acid, in some cases, depending on the work-up procedure, for example the details of a freeze-drying process, the compound was obtained partially or completely in the form of a salt of the acid used, for example in the form of the acetic acid salt, formic acid salt or trifluoroacetic acid salt or hydrochloric acid salt. Likewise starting materials or intermediates bearing a basic center like for example a basic nitrogen were either obtained and used as free base or in salt form like, for example, a trifluoroacetic acid salt, a hydrobromic acid salt, sulfuric acid salt, or a hydrochloric acid salt.

| Abbreviations used: | |
|---|---|
| tert-Butyl | tBu |
| 2,2'-bis(diphenylphoshino-1,1'-binaphthyl | Binap |
| Bis-(oxo-3-oxazolidinyl)-phosphoryl chloride | BOP-Cl |
| Dibenzylidenacetone | dba |
| Dichloromethane | DCM |
| Dicyclohexyl-carbodiimide | DCC |
| Diethylphosphoryl cyanide | DEPC |
| Diisopropylethyl amine | DIPEA |
| 4-Dimethyaminopyridine | DMAP |
| N,N-Dimethylformamide | DMF |
| Dimethylsulfoxide | DMSO |
| 1,1'-Bis(diphenylphosphino)ferrocene | DPPF |
| O-(7-Azabenzotriazol-1-yl)-N,N,N',N'-Tetramethyluronium-hexafluorophosphate | HATU |
| 1-(3-Dimethylaminopropyl)-3-ethylcarbodiimide hydrochloride | EDC |
| 1-Hydroxy-7-azabenzotriazole | HOAT |
| 1-Hydroxybenzotriazole | HOBT |
| N-Bromosuccinimide | NBS |
| N-Chlorosuccinimide | NCS |
| N-Iodosuccinimide | NIS |
| N-Ethylmorpholine | NEM |
| Methanol | MeOH |
| Room temperature 20° C. to 25° C. | RT |
| Saturated | sat. |
| Tetrahydrofuran | THF |
| Trifluoroacetic acid | TFA |
| O-((Ethoxycarbonyl)cyanomethyleneamino)-N,N,N',N'-tetramethyluronium tetrafluoroborate | TOTU |

Example 1

4-[(S)-4-Carboxy-2-({4-[2-(4-hydroxy-2-methoxy-carbonyl-pyrrolidin-1-yl)-2-oxo-ethoxy]-7-methyl-quinoline-2-carbonyl}-amino)-butyryl]-piperazine-1-carboxylic acid ethyl ester (i) 4-Hydroxy-7-methyl-quinoline-2-carboxylic acid ethyl ester To a solution of 15.5 g of m-Tolylamine in 130 ml of methanol, 24.6 g of but-2-ynedioic acid diethyl ester was added drop-wise over 30 min at 0° C. and stirred for 3 h at RT. Then, the solvents were removed under reduced pressure and the residue was dissolved in 70 ml of Dowtherm® and heated to 250° C. for 2 h. Then, the reaction mixture was allowed to cool to RT and 300 ml of n-heptane was added to precipitate the crude product, which was collected by filtration. The title compound was purified by chromatography on silica gel eluting with a gradient of n-heptane/ethyl acetate. The fractions containing the product were combined and the solvent evaporated under reduced pressure. Yield: 9.7 g.

As a second fraction the regioisomeric product 4-Hydroxy-5-methyl-quinoline-2-carboxylic acid ethyl ester was isolated. Yield: 8.6 g.

(ii) 4-Hydroxy-7-methyl-quinoline-2-carboxylic acid

To a solution of 9.7 g of 4-Hydroxy-7-methyl-quinoline-2-carboxylic acid ethyl ester in 200 ml of THF, 84 ml of a 1M aqueous sodium hydroxide solution was added and stirred for 16 h at RT. The reaction mixture was acidified with 1M hydrochloric acid to pH 1 to precipitate the product, which was then collected by filtration. The residue was co-distilled additional two times with toluene. After drying under reduced pressure the product was pure enough for the next reaction step. Yield: 7.7 g.

(iii) 4-((S)-2-Benzyloxycarbonylamino-4-tert-butoxycarbonyl-butyryl)-piperazine-1-carboxylic acid ethyl ester To a solution of 15 g of (S)-2-Benzyloxycarbonylamino-pentanedioic acid 5-tert-butyl ester, 20.4 g of NEM and 14.5 g of TOTU in 75 ml of DMF, 7.4 g of Piperazine-1-carboxylic acid ethyl ester was added at RT and stirred for 16 h. The reaction mixture was then diluted with saturated aqueous sodium hydrogen carbonate solution and then extracted with 300 ml of ethyl acetate. The organic phase was washed with diluted saturated aqueous sodium hydrogen carbonate solution and dried over $MgSO_4$. The solvents were removed under reduced pressure. The crude product was purified by chromatography on silica gel eluting with n-heptane/ethyl acetate (1/1). The fractions containing the product were combined and the solvent evaporated under reduced pressure. Yield: 20.6 g.

(iv) 4-((S)-2-Amino-4-tert-butoxycarbonyl-butyryl)-piperazine-1-carboxylic acid ethyl ester A solution of 20.6 g of 4-((S)-2-Benzyloxycarbonylamino-4-tert-butoxycarbonyl-butyryl)-piperazine-1-carboxylic acid ethyl ester in 200 ml of ethanol was purged with argon. Then, 2 g of Pd/C (5-10%) was added and the mixture stirred under a hydrogen atmosphere (4 bar). After 16 h the reaction mixture was filtered through a pad of celite and the solvents were removed under reduced pressure. After drying under reduced pressure the product was pure enough for the next reaction step. Yield: 14.4 g.

(v) 4-{(S)-4-tert-Butoxycarbonyl-2-[(4-hydroxy-7-methyl-quinoline-2-carbonyl)-amino]-butyryl}-piperazine-1-carboxylic acid ethyl ester To a solution of 4 g of 4-Hydroxy-7-methyl-quinoline-2-carboxylic acid and 6.7 g of 4-((S)-2-Amino-4-tert-butoxy-carbonyl-butyryl)-piperazine-1-carboxylic acid ethyl ester in 40 ml of DMF, 3 g of HOBT and 3.7 g of EDC was added and the reaction mixture was stirred for 2 h at RT. Then, the reaction mixture was diluted with water and extracted with DCM. The organic phase was dried over MgSO$_4$ and the solvents were removed under reduced pressure. The crude product was purified by chromatography on silica gel eluting with a gradient of n-heptane/ethyl acetate. The fractions containing the product were combined and the solvent evaporated under reduced pressure. Yield: 9.4 g.

(iiv) 4-[(S)-4-tert-Butoxycarbonyl-2-({4-[2-(4-hydroxy-2-methoxycarbonyl-pyrrolidin-1-yl)-2-oxoethoxy]-7-methyl-quinoline-2-carbonyl}-amino)-butyryl]-piperazine-1-carboxylic acid ethyl ester To a solution of 100 mg 4-{(S)-4-Carboxy-2-[(4-hydroxy-7-methyl-quinoline-2-carbonyl)-amino]-butyryl}-piperazine-1-carboxylic acid ethyl ester and 100 mg of 1-(2-Bromo-acetyl)-4-hydroxy-pyrrolidine-2-carboxylic acid methyl ester in 2 ml of DMF, 122 mg of cesium carbonate was added. The reaction mixture was heated to 80° C. for 5 h, then cooled to RT and diluted with water. After filtration through a chem Elut® cartridge by eluting with ethyl acetate the solvents were removed under reduced pressure. The isolated crude product was pure enough for the next reaction step.

(vi) 4-[(S)-4-Carboxy-2-({4-[2-(4-hydroxy-2-methoxycarbonyl-pyrrolidin-1-yl)-2-oxo-ethoxy]-7-methyl-quinoline-2-carbonyl}-amino)-butyryl]-piperazine-1-carboxylic acid ethyl ester To a solution of 4-[(S)-4-tert-Butoxycarbonyl-2-({4-[2-(4-hydroxy-2-methoxycarbonyl-pyrrolidin-1-yl)-2-oxo-ethoxy]-7-methyl-quinoline-2-carbonyl}-amino)-butyryl]-piperazine-1-carboxylic acid ethyl ester from the preceding reaction step (v) in 5 ml of DCM 1 ml of TFA was added at RT. After 3 h, 20 ml of toluene was added and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. Yield: 13 mg MS (ES+): m/e=658.

Example 2

4-[(S)-4-Carboxy-2-({7-methyl-4-[2-oxo-2-(2-oxo-pyrrolidin-1-yl)-ethoxy]-quinoline-2-carbonyl}-amino)-butyryl]-piperazine-1-carboxylic acid ethyl ester (i) 4-[(S)-4-tert-Butoxycarbonyl-2-({7-methyl-4-[2-oxo-2-(2-oxo-pyrrolidin-1-yl)-ethoxy]-quinoline-2-carbonyl}-amino)-butyryl]-piperazine-1-carboxylic acid ethyl ester To a solution of 200 mg of 4-{(S)-4-Carboxy-2-[(4-hydroxy-7-methyl-quinoline-2-carbonyl)-amino]-butyryl}-piperazine-1-carboxylic acid ethyl ester in 2.5 ml of DMF, 184 mg of cesium carbonate and 91 mg of 1-(2-Chloro-acetyl)-pyrrolidin-2-one was added and the reaction mixture was stirred for 3 days at RT. Then, the reaction mixture was diluted with water and filtered through a chem Elut® cartridge by eluting with ethyl acetate. The solvents were removed under reduced pressure and the isolated crude product was pure enough for the next reaction step.

(ii) 4-[(S)-4-Carboxy-2-({7-methyl-4-[2-oxo-2-(2-oxo-pyrrolidin-1-yl)-ethoxy]-quinoline-2-carbonyl}-amino)-butyryl]-piperazine-1-carboxylic acid ethyl ester To a solution of 4-[(S)-4-tert-Butoxycarbonyl-2-({7-methyl-4-[2-oxo-2-(2-oxo-pyrrolidin-1-yl)-ethoxy]-quinoline-2-carbonyl}-amino)-butyryl]-piperazine-1-carboxylic acid ethyl ester from the preceding reaction step (i) in 5 ml of DCM, 0.2 ml of TFA was added at RT. After 5 h, 20 ml of toluene was added and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. Yield: 108 mg MS (ES+): m/e=598.

Example 3

4-[(S)-4-Carboxy-2-({4-[2-((S)-2-cyclopropylcarbamoyl-pyrrolidin-1-yl)-2-oxo-ethoxy]-7-methyl-quinoline-2-carbonyl}-amino)-butyryl]-piperazine-1-carboxylic acid ethyl ester (i) (S)-2-Cyclopropylcarbamoyl-pyrrolidine-1-carboxylic acid tert-butyl ester To a solution of 10 g of (S)-Pyrrolidine-1,2-dicarboxylic acid 1-tert-butyl ester in 953 ml of DMF, 9.2 g of HOBT, 11.5 g of EDC, 3.4 g of cyclopropylamine and 13.8 g of DIPEA was added and the reaction mixture was stirred for 16 h at RT. Then, the reaction mixture was diluted with saturated aqueous sodium hydrogen carbonate solution and extracted with ethyl acetate. The organic phase was washed with saturated aqueous sodium hydrogen carbonate solution and water and dried over MgSO$_4$. The solvents were removed under reduced pressure and the crude product was pure enough for the next reaction step.

(ii) (S)-Pyrrolidine-2-carboxylic acid cyclopropylamide hydrochloride

The crude (S)-2-Cyclopropylcarbamoyl-pyrrolidine-1-carboxylic acid tert-butyl ester from the preceding reaction step was dissolved in 20 ml of saturated ethanolic hydrochloric acid and stirred for 2 h. Then, the reaction mixture was diluted with 200 ml of toluene and the solvents were removed under reduced pressure. The residue was co-distilled additional 3 times with toluene and then, triturated with ether. The obtained crystalline white solid was filtered and dried. Yield: 8.2 g.

(iii) 4-{(S)-2-[(4-Benzyloxycarbonylmethoxy-7-methyl-quinoline-2-carbonyl)-amino]-4-tert-butoxycarbonyl-butyryl}-piperazine-1-carboxylic acid ethyl ester To a solution of 5 g of 4-{(S)-4-tert-Butoxycarbonyl-2-[(4-hydroxy-7-methyl-quinoline-2-carbonyl)-amino]-butyryl}-piperazine-1-carboxylic acid ethyl ester (prepared analogously as in example 1) in 150 ml of DMF, 3.3 g of cesium carbonate and 2.4 g of Bromo-acetic acid benzyl ester was added and stirred for 2 h. Then, the reaction mixture was diluted with water and extracted with ethyl acetate (3×150 ml). The combined organic phases were dried over MgSO$_4$

(iv) 4-{(S)-4-tert-Butoxycarbonyl-2-[(4-carboxymethoxy-7-methyl-quinoline-2-carbonyl)-amino]-butyryl}-piperazine-1-carboxylic acid ethyl ester A solution of 5.4 g of 4-{(S)-2-[(4-Benzyloxycarbonyl-methoxy-7-methyl-quinoline-2-carbonyl)-amino]-4-tert-butoxycarbonyl-butyryl}-piperazine-1-carboxylic acid ethyl ester in 30 ml of ethyl acetate was purged with argon. Then, 2 g of Pd/C (5-10%) was added and the mixture stirred under a hydrogen atmosphere (3 bar). After 16 h reaction the mixture was filtered through a pad of celite and the solvents were removed under reduced pressure. After drying under reduced pressure the product was pure enough for the next reaction step. Yield: 4.5 g.

(v) 4-[(S)-4-tert-Butoxycarbonyl-2-({4-[2-((S)-2-cyclopropylcarbamoyl-pyrrolidin-1-yl)-2-oxo-ethoxy]-7-methyl-quinoline-2-carbonyl}-amino)-butyryl]-piperazine-1-carboxylic acid ethyl ester To a solution of 1 g of 4-{(S)-4-tert-Butoxycarbonyl-2-[(4-carboxymethoxy-7-methyl-quinoline-2-carbonyl)-amino]-butyryl}-piperazine-1-carboxylic acid ethyl ester in 12 ml of DMF, 392 mg of EDC, 376 mg of pentafluorophenol and 392 mg of NEM was added and the reaction mixture was warmed to 50° C. for 2 h. Then, after cooling to RT, 334 mg of (S)-Pyrrolidine-2-carboxylic acid cyclopropylamide hydrochloride and 201 mg of NEM in 5 ml of DMF was added. After 1 h the reaction mixture was diluted with water and extracted with DCM (3×50 ml). The combined organic phases were dried over $MgSO_4$ and the solvents were removed under reduced pressure. The crude product was pure enough for the next reaction step. Yield: 1.2 g.

(vi) 4-[(S)-4-Carboxy-2-({4-[2-((S)-2-cyclopropyl-carbamoyl-pyrrolidin-1-yl)-2-oxo-ethoxy]-7-methyl-quinoline-2-carbonyl}-amino)-butyryl]-piperazine-1-carboxylic acid ethyl ester To a solution of 184 mg of 4-[(S)-4-tert-Butoxycarbonyl-2-({4-[2-((S)-2-cyclopropylcarbamoyl-pyrrolidin-1-yl)-2-oxo-ethoxy]-7-methyl-quinoline-2-carbonyl}-amino)-butyryl]-piperazine-1-carboxylic acid ethyl ester in 2 ml of DCM, 0.2 ml of TFA was added at RT. After 4 h 20 ml of toluene was added and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. Yield: 104 mg MS (ES+): m/e=667.

Example 4

4-[(S)-4-Carboxy-2-({7-methyl-4-[2-oxo-2-(3-oxo-piperazin-1-yl)-ethoxy]-quinoline-2-carbonyl}-amino)-butyryl]-piperazine-1-carboxylic acid ethyl ester The title compound was prepared by adapting the procedures described in example 3 with the difference that Piperazin-2-one was used instead of (S)-Pyrrolidine-2-carboxylic acid cyclopropylamide hydrochloride. MS (ES$^+$): m/e=613.

Example 5

4-[(S)-4-Carboxy-2-({4-[2-(3-carboxy-azetidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that Azetidine-3-carboxylic acid was used instead of (S)-Pyrrolidine-2-carboxylic acid cyclopropylamide hydrochloride. MS (ES$^+$): m/e=614.

Example 6

4-[(S)-4-Carboxy-2-({4-[2-((2S,3S)-2-carboxy-3-hydroxy-pyrrolidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that (2S,3S)-3-Hydroxy-pyrrolidine-2-carboxylic acid was used instead of (S)-Pyrrolidine-2-carboxylic acid cyclopropylamide hydrochloride. MS (ES$^+$): m/e=644.

Example 7

4-[(S)-4-Carboxy-2-({4-[2-((2S,4R)-2-ethoxycarbonyl-4-hydroxy-pyrrolidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that (2S,4R)-4-Hydroxy-pyrrolidine-2-carboxylic acid ethyl ester was used instead of (S)-Pyrrolidine-2-carboxylic acid cyclopropylamide hydrochloride. MS (ES$^+$): m/e=672.

Example 8

4-[(S)-4-Carboxy-2-({4-[2-((R)-3-hydroxy-pyrrolidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that (R)-Pyrrolidin-3-ol was used instead of (S)-Pyrrolidine-2-carboxylic acid cyclopropylamide hydrochloride. MS (ES$^+$): m/e=600.

Example 9

4-[(S)-4-Carboxy-2-({4-[2-((S)-3-hydroxy-pyrrolidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that (S)-Pyrrolidin-3-ol was used instead of (S)-Pyrrolidine-2-carboxylic acid cyclopropylamide hydrochloride. MS (ES$^+$): m/e=600.

Example 10

4-[(S)-4-Carboxy-2-({4-[2-(4-hydroxy-piperidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that Piperidin-4-ol was used instead of (S)-Pyrrolidine-2-carboxylic acid cyclopropylamide hydrochloride. MS (ES$^+$): m/e=614.

Example 11

4-[(S)-4-Carboxy-2-({4-[2-((S)-2-ethoxycarbonyl-pyrrolidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that (S)-Pyrrolidine-2-carboxylic acid ethyl ester was used instead of (5)-Pyrrolidine-2-carboxylic acid cyclopropylamide hydrochloride. MS (ES$^+$): m/e=656.

Example 12

4-[(S)-4-Carboxy-2-({4-[2-((2R,4R)-2-carboxy-4-hydroxy-pyrrolidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that (2R,4R)-4-Hydroxy-pyrrolidine-2-carboxylic acid was used instead of (S)-Pyrrolidine-2-carboxylic acid cyclopropylamide hydrochloride. MS (ES$^+$): m/e=644.

Example 13

4-[(S)-4-Carboxy-2-({4-[2-(3-hydroxy-azetidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that Azetidin-3-ol was used instead of (S)-Pyrrolidine-2-carboxylic acid cyclopropylamide hydrochloride. MS (ES$^+$): m/e=586.

Example 14

4-[(S)-4-Carboxy-2-({4-[2-((S)-2-methoxycarbonyl-pyrrolidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that (S)-Pyrrolidine-2-carboxylic acid methyl ester was used instead of (S)-Pyrrolidine-2-carboxylic acid cyclopropylamide hydrochloride. MS (ES$^+$): m/e=642.

Example 15

4-[(S)-4-Carboxy-2-({4-[2-((S)-2-carboxy-azetidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that (5)-Azetidine-2-carboxylic acid was used instead of (5)-Pyrrolidine-2-carboxylic acid cyclopropylamide hydrochloride. MS (ES$^+$): m/e=614.

Example 16

4-[(S)-4-Ethoxycarbonyl-2-({7-methyl-4-[2-oxo-2-(2-oxo-pyrrolidin-1-yl)-ethoxy]-quinoline-2-carbonyl}-amino)-butyryl]-piperazine-1-carboxylic acid ethyl ester To 10 ml of a saturated ethanolic solution of hydrochloric acid 100 mg of 4-[(S)-4-Carboxy-2-({7-methyl-4-[2-oxo-2-(2-oxo-pyrrolidin-1-yl)-ethoxy]-quinoline-2-carbonyl}-amino)-butyryl]-piperazine-1-carboxylic acid ethyl ester was added and the mixture was stirred for 1 h. Then, 30 ml of toluene was added and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. Yield: 47 mg MS (ES$^+$): m/e=626.

Example 17

4-[(S)-4-Carboxy-2-({4-[2-((S)-2-carboxy-pyrrolidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that (S)-Pyrrolidine-2-carboxylic acid was used instead of (S)-Pyrrolidine-2-carboxylic acid cyclopropylamide hydrochloride. MS (ES$^+$): m/e=628.

Example 18

4-[(S)-4-Carboxy-2-({4-[2-(3-methanesulfonyl-pyrrolidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that 3-Methanesulfonyl-pyrrolidine was used instead of (S)-Pyrrolidine-2-carboxylic acid cyclopropylamide hydrochloride. MS (ES$^+$): m/e=662.

Example 19

4-[(S)-4-Carboxy-2-({4-[2-(3-carboxy-pyrrolidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that Pyrrolidine-3-carboxylic acid was used instead of (S)-Pyrrolidine-2-carboxylic acid cyclopropylamide hydrochloride. MS (ES$^+$): m/e=628.

Example 20

4-[(S)-4-Carboxy-2-({4-[2-((3S,4S)-3,4-dihydroxy-pyrrolidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that (3S,4S)-Pyrrolidine-3,4-diol was used instead of (S)-Pyrrolidine-2-carboxylic acid cyclopropylamide hydrochloride. MS (ES$^+$): m/e=616.

Example 21

4-[(S)-4-Carboxy-2-({7-methyl-4-[2-oxo-2-(2-oxo-oxazolidin-3-yl)-ethoxy]-quinoline-2-carbonyl}-amino)-butyryl]-piperazine-1-carboxylic acid ethyl ester The title compound was prepared by adapting the procedures described in example 3 with the difference that Oxazolidin-2-one was used instead of (S)-Pyrrolidine-2-carboxylic acid cyclopropylamide hydrochloride. MS (ES$^+$): m/e=600.

Example 22

4-[(S)-4-Carboxy-2-({4-[2-(3-cyclopropylcarbamoyl-azetidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that Azetidine-3-carboxylic acid cyclopropylamide was used instead of (S)-Pyrrolidine-2-carboxylic acid cyclopropylamide hydrochloride. MS (ES$^+$): m/e=653.

Example 23

4-[(S)-4-Carboxy-2-({4-[2-((R)-2-cyclopropylcarbamoyl-azetidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that (R)-Azetidine-2-carboxylic acid cyclopropylamide was used instead of (S)-Pyrrolidine-2-carboxylic acid cyclopropylamide hydrochloride. MS (ES$^+$): m/e=653.

Example 24

4-[(S)-2-({4-[2-((S)-2-Cyclopropylcarbamoyl-pyrrolidin-1-yl)-2-oxo-ethoxy]-7-methyl-quinoline-2-carbonyl}-amino)-4-ethoxycarbonyl-butyryl]-piperazine-1-carboxylic acid ethyl ester To 15 ml of a saturated solution of hydrochloric acid in ethanol 100 mg of 4-[(S)-4-Carboxy-2-({4-[2-((S)-2-cyclopropylcarbamoyl-pyrrolidin-1-yl)-2-oxo-ethoxy]-7-methyl-quinoline-2-carbonyl}-amino)-butyryl]piperazine-1-carboxylic acid ethyl ester was added and the mixture was stirred for 1 h. Then, 30 ml of toluene was added and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. Yield: 72 mg MS (ES$^+$): m/e=695.

Example 25

4-[(S)-4-Carboxy-2-({4-[2-((S)-2-ethylcarbamoyl-pyrrolidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that (S)-Pyrrolidine-2-carboxylic acid ethylamide was used instead of (S)-Pyrrolidine-2-carboxylic acid cyclopropylamide hydrochloride. MS (ES$^+$): m/e=655.

Example 26

4-[(S)-4-Carboxy-2-({4-[2-((S)-2-cyclopropylcarbamoyl-pyrrolidin-1-yl)-1,1-dimethyl-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that 2-Bromo-2-methyl-propionic acid benzyl ester was used instead of Bromo-acetic acid benzyl ester. MS (ES$^+$): m/e=695.

Example 27

4-[(S)-4-Carboxy-2-({4-[2-((S)-2-dimethylcarbamoyl-pyrrolidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that (S)-Pyrrolidine-2-carboxylic acid dimethylamide was used instead of (S)-Pyrrolidine-2-carboxylic acid cyclopropylamide hydrochloride. MS (ES$^+$): m/e=655.

Example 28

4-[(S)-2-({4-[2-((S)-2-Carbamoyl-pyrrolidin-1-yl)-2-oxo-ethoxy]-7-methyl-quinoline-2-carbonyl}-amino)-4-carboxy-butyryl]-piperazine-1-carboxylic acid ethyl ester The title compound was prepared by adapting the procedures described in example 3 with the difference that (S)-Pyrrolidine-2-carboxylic acid amide was used instead of (S)-Pyrrolidine-2-carboxylic acid cyclopropylamide hydrochloride. MS (ES$^+$): m/e=627.

Example 29

4-[(S)-4-Carboxy-2-({4-[2-((S)-3-cyclopropylcarbamoyl-pyrrolidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that (S)-

Pyrrolidine-3-carboxylic acid cyclopropylamide was used instead of (S)-Pyrrolidine-2-carboxylic acid cyclopropylamide hydrochloride. MS (ES$^+$): m/e=667.

Example 30

4-[(S)-4-Carboxy-2-({4-[2-((R)-3-cyclopropylcarbamoyl-pyrrolidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that (R)-Pyrrolidine-3-carboxylic acid cyclopropylamide was used instead of (S)-Pyrrolidine-2-carboxylic acid cyclopropylamide hydrochloride. MS (ES$^+$): m/e=667.

Example 31

4-[(S)-4-Carboxy-2-({4-[2-((S)-2-hydroxymethyl-pyrrolidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that (S)-1-Pyrrolidin-2-yl-methanol was used instead of (S)-Pyrrolidine-2-carboxylic acid cyclopropylamide hydrochloride. MS (ES$^+$): m/e=614.

Example 32

4-{(S)-4-Carboxy-2-[(7-methyl-4-{2-oxo-2-[(S)-2-(2,2,2-trifluoro-ethylcarbamoyl)-pyrrolidin-1-yl]-ethoxy}-quinoline-2-carbonyl)-amino]-butyryl}-piperazine-1-carboxylic acid ethyl ester The title compound was prepared by adapting the procedures described in example 3 with the difference that (S)-Pyrrolidine-2-carboxylic acid (2,2,2-trifluoro-ethyl)-amide was used instead of (S)-Pyrrolidine-2-carboxylic acid cyclopropylamide hydrochloride. MS (ES$^+$): m/e=709.

Example 33

4-[(S)-4-Carboxy-2-({4-[2-(4-methoxy-piperidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that 4-Methoxy-piperidine was used instead of (S)-Pyrrolidine-2-carboxylic acid cyclopropylamide hydrochloride. MS (ES$^+$): m/e=628.

Example 34

4-[(S)-4-Carboxy-2-({7-methyl-4-[2-oxo-2-(3-oxo-pyrazolidin-1-yl)-ethoxy]-quinoline-2-carbonyl}-amino)-butyryl]-piperazine-1-carboxylic acid ethyl ester The title compound was prepared by adapting the procedures described in example 3 with the difference that Pyrazolidin-3-one was used instead of (S)-Pyrrolidine-2-carboxylic acid cyclopropylamide hydrochloride. MS (ES$^+$): m/e=599.

Example 35

4-[(S)-4-Carboxy-2-({4-[2-(2-hydroxymethyl-morpholin-4-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that Morpholin-2-yl-methanol was used instead of (S)-Pyrrolidine-2-carboxylic acid cyclopropylamide hydrochloride. MS (ES$^+$): m/e=630.

Example 36

4-[(S)-4-Carboxy-2-({7-methyl-4-[2-oxo-2-((1S,5R)-3-oxo-8-aza-bicyclo[3.2.1]oct-8-yl)-ethoxy]-quinoline-2-carbonyl}-amino)-butyryl]-piperazine-1-carboxylic acid ethyl ester The title compound was prepared by adapting the procedures described in example 3 with the difference that (1S,5R)-8-Aza-bicyclo[3.2.1]octan-3-one was used instead of (S)-Pyrrolidine-2-carboxylic acid cyclopropylamide hydrochloride. MS (ES$^+$): m/e=638.

Example 37

4-[(S)-4-Carboxy-2-({7-methyl-4-[2-oxo-2-(5-oxo-[1,4]diazepan-1-yl)-ethoxy]-quinoline-2-carbonyl}-amino)-butyryl]-piperazine-1-carboxylic acid ethyl ester The title compound was prepared by adapting the procedures described in example 3 with the difference that [1,4]Diazepan-5-one was used instead of (S)-Pyrrolidine-2-carboxylic acid cyclopropylamide hydrochloride. MS (ES$^+$): m/e=627.

Example 38

4-[(S)-4-Carboxy-2-({4-[2-(4-ethoxycarbonyl-piperidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that Piperidine-4-carboxylic acid ethyl ester was used instead of (S)-Pyrrolidine-2-carboxylic acid cyclopropylamide hydrochloride. MS (ES$^+$): m/e=670.

Example 39

4-[(S)-4-Carboxy-2-({4-[2-(4-ethoxy-piperidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that 4-Ethoxy-piperidine was used instead of (S)-Pyrrolidine-2-carboxylic acid cyclopropylamide hydrochloride. MS (ES+): m/e=642.

Example 40

4-((S)-4-Carboxy-2-{[7-methyl-4-(2-morpholin-4-yl-2-oxo-ethoxy)-quinoline-2-carbonyl]-amino}-butyryl)-piperazine-1-carboxylic acid ethyl ester The title compound was prepared by adapting the procedures described in example 3 with the difference that Morpholine was used instead of (S)-Pyrrolidine-2-carboxylic acid cyclopropylamide hydrochloride. MS (ES+): m/e=600.

Example 41

4-[(S)-4-Carboxy-2-({4-[2-(3-hydroxy-piperidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that Piperidin-3-ol was used instead of (S)-Pyrrolidine-2-carboxylic acid cyclopropylamide hydrochloride. MS (ES+): m/e=614.

Example 42

4-[(S)-4-Carboxy-2-({4-[2-(4-carboxy-piperidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that Piperidine-4-carboxylic acid was used instead of (S)-Pyrrolidine-2-carboxylic acid cyclopropylamide hydrochloride. MS (ES+): m/e=642.

Example 43

4-[(S)-4-Carboxy-2-({4-[2-((R)-3-hydroxy-piperidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that (R)-Piperidin-3-ol was used instead of (S)-Pyrrolidine-2-carboxylic acid cyclopropylamide hydrochloride. MS (ES+): m/e=614.

Example 44

4-[(S)-4-Carboxy-2-({4-[2-(2,2-dimethyl-3-oxo-piperazin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that 3,3-Dimethyl-piperazin-2-one was used instead of (S)-Pyrrolidine-2-carboxylic acid cyclopropylamide hydrochloride. MS (ES+): m/e=641.

Example 45

4-[(S)-4-Carboxy-2-({4-[2-((S)-2-carboxy-piperidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that (S)-Piperidine-2-carboxylic acid was used instead of (S)-Pyrrolidine-2-carboxylic acid cyclopropylamide hydrochloride. MS (ES+): m/e=642.

Example 46

4-[(S)-4-Carboxy-2-({4-[2-((R)-2-carboxy-piperidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that (R)-Piperidine-2-carboxylic acid was used instead of (S)-Pyrrolidine-2-carboxylic acid cyclopropylamide hydrochloride. MS (ES+): m/e=642.

Example 47

4-[(S)-4-Carboxy-2-({4-[2-((S)-2-methoxymethyl-pyrrolidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that (S)-2-Methoxymethyl-pyrrolidine was used instead of (S)-Pyrrolidine-2-carboxylic acid cyclopropylamide hydrochloride. MS (ES+): m/e=628.

Example 48

4-[(S)-4-Carboxy-2-({4-[2-(4-cyclopropylcarbamoyl-piperidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that Piperidine-4-carboxylic acid cyclopropylamide was used instead of (S)-Pyrrolidine-2-carboxylic acid cyclopropylamide hydrochloride. MS (ES+): m/e=681.

Example 49

4-[(S)-4-Carboxy-2-({4-[2-((R)-2-cyclopropylcarbamoyl-piperidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that (R)-Piperidine-2-carboxylic acid cyclopropylamide was used instead of (S)-Pyrrolidine-2-carboxylic acid cyclopropylamide hydrochloride. MS (ES⁺): m/e=681.

Example 50

4-[(S)-4-Carboxy-2-({4-[2-((S)-3-hydroxymethyl-pyrrolidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that (S)-1-Pyrrolidin-3-yl-methanol was used instead of (S)-Pyrrolidine-2-carboxylic acid cyclopropylamide hydrochloride. MS (ES⁺): m/e=614.

Example 51

4-[(S)-4-Carboxy-2-({4-[2-((R)-3-hydroxymethyl-pyrrolidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that (R)-1-Pyrrolidin-3-yl-methanol was used instead of (S)-Pyrrolidine-2-carboxylic acid cyclopropylamide hydrochloride. MS (ES⁺): m/e=614.

Example 52

4-[(S)-4-Carboxy-2-({4-[2-(2-carboxy-4,4-difluoro-pyrrolidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that 4,4-Difluoro-pyrrolidine-2-carboxylic acid was used instead of (S)-Pyrrolidine-2-carboxylic acid cyclopropylamide hydrochloride. MS (ES⁺): m/e=664.

Example 53

4-[(S)-4-Carboxy-2-({7-methyl-4-[2-oxo-2-(3-oxo-pyrrolidin-1-yl)-ethoxy]-quinoline-2-carbonyl}-amino)-butyryl]-piperazine-1-carboxylic acid ethyl ester The title compound was prepared by adapting the procedures described in example 3 with the difference that Pyrrolidin-3-one was used instead of (S)-Pyrrolidine-2-carboxylic acid cyclopropylamide hydrochloride. MS (ES⁺): m/e=598.

Example 54

4-[(S)-4-Carboxy-2-({4-[2-((S)-2-cyclopropylcarbamoyl-piperidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that (S)-Piperidine-2-carboxylic acid cyclopropylamide was used instead of (S)-Pyrrolidine-2-carboxylic acid cyclopropylamide hydrochloride. MS (ES⁺): m/e=681.

Example 55

4-[(S)-4-Carboxy-2-({4-[2-(3-cyclopropylcarbamoyl-piperidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that Piperidine-3-carboxylic acid cyclopropylamide was used instead of (S)-Pyrrolidine-2-carboxylic acid cyclopropylamide hydrochloride. MS (ES⁺): m/e=681.

Example 56

4-[(S)-4-Carboxy-2-({4-[2-((S)-2-cyclopropylcarbamoyl-pyrrolidin-1-yl)-2-oxo-ethoxy]-5,7-dimethyl-quinoline-2-carbonyl}-amino)-butyryl]-piperazine-1-carboxylic acid ethyl ester (i) (S)-1-(2-Bromo-acetyl)-pyrrolidine-2-carboxylic acid cyclopropylamide To a solution of 1.2 g of bromo-acetyl bromide in 30 ml of DCM a solution of 1 g of (S)-Pyrrolidine-2-carboxylic acid cyclopropylamide hydrochloride, 0.6 g of triethylamine and 7 mg of DMAP in 10 ml of DCM was added drop-wise at 0° C. After 1 h the reaction mixture was diluted with ethyl acetate and the solids were filtered off. The organic phase was evaporated under reduced pressure and the residue was filtered over silica gel eluting with ethyl acetate/heptane (8/2). After evaporation of the solvent the obtained product was pure enough for the subsequent reaction step. Yield: 1.3 g.

(ii) 4-[(S)-4-Carboxy-2-({4-[2-((S)-2-cyclopropylcarbamoyl-pyrrolidin-1-yl)-2-oxo-ethoxy]-5,7-dimethyl-quinoline-2-carbonyl}-amino)-butyryl]-piperazine-1-carboxylic acid ethyl ester To a solution of 100 mg of (S)-1-(2-Bromo-acetyl)-pyrrolidine-2-carboxylic acid cyclopropylamide and 98 mg of 4-{(S)-4-tert-Butoxycarbonyl-2-[(4-hydroxy-5,7-dimethyl-quinoline-2-carbonyl)-amino]-butyryl}-piperazine-1-carboxylic acid ethyl ester [prepared by adapting the procedures described in example 3 using 4-Hydroxy-5,7-dimethyl-quinoline-2-carboxylic acid] in 2 ml of DMF, 118 mg of cesium carbonate was added and the reaction mixture was heated to 80° C. for 5 h. Then, the reaction mixture was diluted with water and filtered through a chem Elut® cartridge by eluting with ethyl acetate. The solvents were removed under reduced pressure and the residue was dissolved in 1 ml of DCM and 0.2 ml of TFA. After 16 h at RT 10 ml of toluene was added and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. Yield: 10 mg MS (ES+): m/e=681.

Example 57

4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester

(i) (S)-2-Cyclobutylcarbamoyl-pyrrolidine-1-carboxylic acid tert-butyl ester To a solution of 1.5 g of (S)-Pyrrolidine-1,2-dicarboxylic acid 1-tert-butyl ester in 30 ml of DMF, 948 mg of HOAT, 1.3 g of EDC and 495 mg of cyclobutylamine was added and the reaction mixture was stirred for 16 h at RT. Then, water was added and the reaction mixture was extracted with DCM. The organic phase was dried over $MgSO_4$ and the solvents were removed under reduced pressure. The crude product was pure enough for the next reaction step.

(ii) (S)-Pyrrolidine-2-carboxylic acid cyclobutylamide

The crude (S)-2-Cyclobutylcarbamoyl-pyrrolidine-1-carboxylic acid tert-butyl ester from the preceding reaction step was dissolved in 10 ml of DCM and 5 ml of TFA and stirred for 3 h. Then, the reaction mixture was diluted with 70 ml of toluene and the solvents were removed under reduced pressure. The residue was co-distilled additional three times with toluene. The product was obtained as its trifluoroacetate. Yield: 2 g.

(iii) 4-{(S)-2-[(4-Benzyloxycarbonylmethoxy-7-methyl-quinoline-2-carbonyl)-amino]-4-tert-butoxycarbonyl-butyryl}-piperazine-1-carboxylic acid ethyl ester To a solution of 26.4 g of 4-{(S)-4-tert-Butoxycarbonyl-2-[(4-hydroxy-7-methyl-quinoline-2-carbonyl)-amino]-butyryl}-piperazine-1-carboxylic acid ethyl ester (prepared analogously as in example 1) in 150 ml of DMF, 18 g of cesium carbonate and 12.7 g of Bromo-acetic acid benzyl ester was added and stirred for 16 h. Then, the reaction mixture was diluted with water and extracted with ethyl acetate (3×300 ml). The combined organic phases were dried over $MgSO_4$ and the solvents were removed under reduced pressure. The crude product was purified by chromatography on silica gel eluting with a gradient of n-heptane/ethyl acetate. The fractions containing the product were combined and the solvent evaporated under reduced pressure. Yield: 23.6 g.

(iv) 4-{(S)-4-tert-Butoxycarbonyl-2-[(4-carboxymethoxy-7-methyl-quinoline-2-carbonyl)-amino]-butyryl}-piperazine-1-carboxylic acid ethyl ester A solution of 23.6 g of 4-{(S)-2-[(4-Benzyloxycarbonylmethoxy-7-methyl-quinoline-2-carbonyl)-amino]-4-tert-butoxycarbonyl-butyryl}-piperazine-1-carboxylic acid ethyl ester in 200 ml of ethyl acetate was purged with argon. Then, 2.4 g of Pd/C (5-10%) was added and the mixture stirred under a hydrogen atmosphere (3 bar). After 16 h the reaction mixture was filtered through a pad of celite and the solvents were removed under reduced pressure. After drying under reduced pressure the product was pure enough for the next reaction step. Yield: 19.8 g.

(v) 4-[(S)-4-tert-Butoxycarbonyl-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester To a solution of 3.5 g of 4-{(S)-4-tert-Butoxycarbonyl-2-[(4-carboxymethoxy-7-methyl-quinoline-2-carbonyl)-amino]-butyryl}-piperazine-1-carboxylic acid ethyl ester in 30 ml of DMF, 1.1 g of EDC, 1.1 g of pentafluorophenol and 1.8 g of NEM was added and the reaction mixture was warmed to 40° C. for 4 h. Then, after cooling to RT 2.6 g of (S)-Pyrrolidine-2-carboxylic acid cyclobutylamide trifluoroacetate and 1 g of NEM in 10 ml of DMF was added. After 4 h the reaction mixture was diluted with water and extracted with DCM (3×150 ml). The combined organic phases were dried over $MgSO_4$ and the solvents were removed under reduced pressure. The crude product was purified by chromatography on silica gel eluting with a gradient of n-heptane/ethyl acetate. The fractions containing the product were combined and the solvent evaporated under reduced pressure. Yield: 1.8 g.

(vi) 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester To a solution of 1.3 g of 4-[(S)-4-tert-Butoxycarbonyl-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester in 10 ml of DCM, 2.1 ml of TFA was added at RT. After 16 h 20 ml of toluene was added and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. Yield: 2.1 g MS (ES+): m/e=681.

Example 58

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-ethoxycarbonyl-butyryl]-piperazine-1-carboxylic acid ethyl ester To 100 ml of a saturated solution of hydrochloric acid in ethanol 2.5 g of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester was added and the mixture was stirred for 3 h. Then, 30 ml of toluene was added and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid. The product was dissolved in DCM and washed with saturated aqueous sodium hydrogen carbonate solution and water. The organic phase dried over $MgSO_4$. The solvents were removed under reduced pressure to yield the product as a white solid. Yield: 1.2 g MS (ES+): m/e=709.

Alternatively the product was prepared by the following procedure:

To 100 ml of a saturated solution of hydrochloric acid in ethanol 5 g of 4-[(S)-4-tert-Butoxycarbonyl-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester was added and the mixture was stirred for 2 h. Then, 30 ml of toluene was added and the solvents were removed under reduced pressure. The residue was filtered through a plug of silica gel eluting with a gradient of n-heptane/ethyl acetate. The fractions containing the product were combined and the solvent evaporated under reduced pressure. The residue was purified by re-crystallisation from n-heptane/ethyl acetate and dried under reduced pressure. Yield: 3.8 g MS (ES$^+$): m/e=709.

Example 59

4-[(S)-4-Carboxy-2-({4-[2-((S)-2-cyclopropylcarbamoyl-pyrrolidin-1-yl)-2-oxo-ethoxy]-6-fluoro-7-methyl-quinoline-2-carbonyl}-amino)-butyryl]-piperazine-1-carboxylic acid ethyl ester The title compound was prepared by adapting the procedures described in example 56 with the difference that 4-{(S)-4-tert-Butoxycarbonyl-2-[(6-fluoro-4-hydroxy-7-methyl-quinoline-2-carbonyl)-amino]-butyryl}-piperazine-1-carboxylic acid ethyl ester was used instead of 4-{(S)-4-tert-Butoxycarbonyl-2-[(4-hydroxy-5,7-dimethyl-quinoline-2-carbonyl)-amino]-butyryl}-piperazine-1-carboxylic acid ethyl ester. MS (ES$^+$): m/e=685.

Example 60

4-[(S)-4-Carboxy-2-({4-[2-((R)-2-ethoxycarbonyl-pyrrolidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that (R)-Pyrrolidine-2-carboxylic acid ethyl ester was used instead of (5)-Pyrrolidine-2-carboxylic acid cyclopropylamide hydrochloride. MS (ES$^+$): m/e=656.

Example 61

4-[(S)-2-({4-[2-((R)-2-Carbamoyl-pyrrolidin-1-yl)-2-oxo-ethoxy]-7-methyl-quinoline-2-carbonyl}-amino)-4-carboxy-butyryl]-piperazine-1-carboxylic acid ethyl ester The title compound was prepared by adapting the procedures described in example 3 with the difference that (R)-Pyrrolidine-2-carboxylic acid amide was used instead of (S)-Pyrrolidine-2-carboxylic acid cyclopropylamide hydrochloride. MS (ES$^+$): m/e=627.

Example 62

4-[(S)-4-Carboxy-2-({4-[2-((S)-2-carboxy-2-methyl-pyrrolidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that (S)-2-Methyl-pyrrolidine-2-carboxylic acid was used instead of (S)-Pyrrolidine-2-carboxylic acid cyclopropylamide hydrochloride. MS (ES$^+$): m/e=642.

Example 63

4-{(S)-4-Carboxy-2-[(4-{2-[(S)-2-(cyclopropylmethyl-carbamoyl)-pyrrolidin-1-yl]-2-oxo-ethoxy}-7-methyl-quinoline-2-carbonyl)-amino]-butyryl}-piperazine-1-carboxylic acid ethyl ester The title compound was prepared by adapting the procedures described in example 3 with the difference that (S)-Pyrrolidine-2-carboxylic acid cyclopropylmethyl-amide was used instead of (S)-Pyrrolidine-2-carboxylic acid cyclopropylamide hydrochloride. MS (ES$^+$): m/e=681.

Example 64

4-[(S)-4-Carboxy-2-({4-[2-((S)-2-isopropylcarbamoyl-pyrrolidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that (S)-Pyrrolidine-2-carboxylic acid isopropylamide was used instead of (S)-Pyrrolidine-2-carboxylic acid cyclopropylamide hydrochloride. MS (ES$^+$): m/e=669.

Example 65

4-{(S)-4-Carboxy-2-[(4-{2-[(S)-2-(2,2-difluoro-ethylcarbamoyl)-pyrrolidin-1-yl]-2-oxo-ethoxy}-7-methyl-quinoline-2-carbonyl)-amino]-butyryl}-piperazine-1-carboxylic acid ethyl ester The title compound was prepared by adapting the procedures described in example 3 with the difference that (S)-Pyrrolidine-2-carboxylic acid (2,2-difluoro-ethyl)-amide was used instead of (S)-Pyrrolidine-2-carboxylic acid cyclopropylamide hydrochloride. MS (ES$^+$): m/e=691.

Example 66

4-{(S)-4-Carboxy-2-[(4-{2-[(S)-2-(2-fluoro-ethylcarbamoyl)-pyrrolidin-1-yl]-2-oxo-ethoxy}-7-methyl-quinoline-2-carbonyl)-amino]-butyryl}-piperazine-1-carboxylic acid ethyl ester The title compound was prepared by adapting the procedures described in example 3 with the difference that (S)-Pyrrolidine-2-carboxylic acid (2-fluoro-ethyl)-amide was used instead of (S)-Pyrrolidine-2-carboxylic acid cyclopropylamide hydrochloride. MS (ES$^+$): m/e=673.

Example 67

4-[(S)-4-Carboxy-2-({4-[2-((R)-2-cyclopropylcarbamoyl-pyrrolidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that (R)-Pyrrolidine-2-carboxylic acid cyclopropylamide was used

Example 68

4-[(S)-4-Carboxy-2-({4-[2-(4,4-dimethyl-oxazolidin-3-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that 4,4-Dimethyl-oxazolidine was used instead of (S)-Pyrrolidine-2-carboxylic acid cyclopropylamide hydrochloride. MS (ES$^+$): m/e=614.

Example 69

4-[(S)-4-Ethoxycarbonyl-2-({4-[2-(4-hydroxy-piperidin-1-yl)-2-oxo-ethoxy]-7-methyl-quinoline-2-carbonyl}-amino)-butyryl]-piperazine-1-carboxylic acid ethyl ester To 10 ml of a saturated solution of hydrochloric acid in ethanol 178 mg of 4-[(S)-4-tert-Butoxycarbonyl-2-({4-[2-(4-hydroxy-piperidin-1-yl)-2-oxo-ethoxy]-7-methyl-quinoline-2-carbonyl}-amino)-butyryl]-piperazine-1-carboxylic acid ethyl ester was added and the mixture was stirred for 2 h. Then, 30 ml of toluene was added and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. Yield: 105 mg MS (ES$^+$): m/e=642.

Example 70

4-[(S)-4-Carboxy-2-({7-methyl-4-[2-oxo-2-((S)-2-propylcarbamoyl-pyrrolidin-1-yl)-ethoxy]-quinoline-2-carbonyl}-amino)-butyryl]-piperazine-1-carboxylic acid ethyl ester The title compound was prepared by adapting the procedures described in example 3 with the difference that (S)-Pyrrolidine-2-carboxylic acid propylamide was used instead of (S)-Pyrrolidine-2-carboxylic acid cyclopropylamide hydrochloride. MS (ES$^+$): m/e=669.

Example 71

4-[(S)-4-Carboxy-2-({4-[2-(4-hydroxy-2-methoxycarbonyl-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 1 with the difference that 4-Hydroxy-quinoline-2-carboxylic acid was used instead of 4-Hydroxy-7-methyl-quinoline-2-carboxylic acid. MS (ES$^+$): m/e=644.

Example 72

4-[(S)-4-Carboxy-2-({4-[2-oxo-2-(2-oxo-pyrrolidin-1-yl)-ethoxy]-quinoline-2-carbonyl}-amino)-butyryl]-piperazine-1-carboxylic acid ethyl ester The title compound was prepared by adapting the procedures described in example 2 with the difference that 4-Hydroxy-quinoline-2-carboxylic acid was used instead of 4-Hydroxy-7-methyl-quinoline-2-carboxylic acid. MS (ES$^+$): m/e=584.

Example 73

4-[(S)-4-Carboxy-2-({4-[2-((S)-2-cyclopropylcarbamoyl-pyrrolidin-1-yl)-2-oxo-ethoxy]-quinoline-2-carbonyl}-amino)-butyryl]-piperazine-1-carboxylic acid ethyl ester (i) (S)-2-Cyclopropylcarbamoyl-pyrrolidine-1-carboxylic acid tert-butyl ester To a solution of 10 g of (S)-Pyrrolidine-1,2-dicarboxylic acid 1-tert-butyl ester in 953 ml of DMF, 9.2 g of HOBT, 11.5 g of EDC, 3.4 g of cyclopropylamine and 13.8 g of DIPEA was added and the reaction mixture was stirred for 16 h at RT. Then, the reaction mixture was diluted with saturated aqueous sodium hydrogen carbonate solution and extracted with ethyl acetate. The organic phase was washed with saturated aqueous sodium hydrogen carbonate solution and water and dried over MgSO$_4$. The solvents were removed under reduced pressure and the crude product was pure enough for the next reaction step.

(ii) (S)-Pyrrolidine-2-carboxylic acid cyclopropylamide hydrochloride

The crude (S)-2-Cyclopropylcarbamoyl-pyrrolidine-1-carboxylic acid tert-butyl ester from the preceding reaction step was dissolved in 20 ml of saturated ethanolic hydrochloric acid and stirred for 2 h. Then, the reaction mixture was diluted with 200 ml of toluene and the solvents were removed under reduced pressure. The residue was co-distilled additional 3 times with toluene and then, triturated with ether. The obtained crystalline white solid was filtered and dried. Yield: 8.2 g.

(iii) 4-{(S)-4-tert-Butoxycarbonyl-2-[(4-hydroxy-quinoline-2-carbonyl)-amino]-butyryl}-piperazine-1-carboxylic acid ethyl ester To a solution of 2.7 g 4-Hydroxy-quinoline-2-carboxylic acid and 5 g of 4-((S)-2-Amino-4-tert-butoxycarbonyl-butyryl)-piperazine-1-carboxylic acid ethyl ester in 25 ml of DMF, 2.2 g of HOBT and 2.8 g of EDC was added and the reaction mixture was stirred for 3 h at RT. Then, the reaction mixture was diluted with water and extracted with DCM. The organic phase was dried over MgSO$_4$ and the solvents were removed under reduced pressure. The crude product was purified by re-crystallisation from n-heptane/ethyl acetate and dried under reduced pressure. Yield: 7.2 g.

(iv) 4-{(S)-2-[(4-Benzyloxycarbonylmethoxy-quinoline-2-carbonyl)-amino]-4-tert-butoxycarbonyl-butyryl}-piperazine-1-carboxylic acid ethyl ester To a solution of 6.2 g of 4-{(S)-4-tert-Butoxycarbonyl-2-[(4-hydroxy-quinoline-2-carbonyl)-amino]-butyryl}-piperazine-1-carboxylic acid ethyl ester 80 ml of DMF, 4.3 g of cesium carbonate and 2.5 g of Bromo-acetic acid benzyl ester was added and stirred for 2 h. Then, the reaction mixture was diluted with water and extracted with ethyl acetate (3×150 ml). The combined organic phases were dried over MgSO$_4$ and the solvents were removed under reduced pressure. The crude product was purified by chromatography on silica gel eluting with a gradient of n-heptane/ethyl acetate. The fractions containing the product were combined and the solvent evaporated under reduced pressure. Yield: 4.4 g.

(v) 4-{(S)-4-tert-Butoxycarbonyl-2-[(4-carboxymethoxy-quinoline-2-carbonyl)-amino]-butyryl}-piperazine-1-carboxylic acid ethyl ester A solution of 4.4 g of 4-{(S)-2-[(4-Benzyloxycarbonylmethoxy-quinoline-2-carbonyl)-amino]-4-tert-butoxycarbonyl-butyryl}-piperazine-1-carboxylic acid ethyl ester in 30 ml of ethyl acetate was purged with argon. Then, 2 g of Pd/C (5-10%) was added and the mixture stirred under a hydrogen atmosphere (3 bar). After 16 h reaction the mixture was filtered through a pad of celite and the solvents were removed under reduced pressure. After drying under reduced pressure the product was pure enough for the next reaction step. Yield: 3.9 g.

(vi) 4-[(S)-4-tert-Butoxycarbonyl-2-({4-[2-((S)-2-cyclopropylcarbamoyl-pyrrolidin-1-yl)-2-oxo-ethoxy]-quinoline-2-carbonyl}-amino)-butyryl]-piperazine-1-carboxylic acid ethyl ester To a solution of 2.2 g of 4-{(S)-4-tert-Butoxycarbonyl-2-[(4-carboxymethoxy-quinoline-2-carbonyl)-amino]-butyryl}-piperazine-1-carboxylic acid ethyl ester in 30 ml of DMF, 883 mg of EDC, 848 mg of pentafluorophenol and 885 mg of NEM was added and the reaction mixture was stirred for 2 h at RT. Then, 732 mg of (S)-Pyrrolidine-2-carboxylic acid cyclopropylamide hydrochloride and 442 mg of NEM in 5 ml of DMF was added. After 2 h the reaction mixture was diluted with water and extracted with DCM (3×50 ml). The combined organic phases were dried over MgSO$_4$ and the solvents were removed under reduced pressure. The crude product was pure enough for the next reaction step. Yield: 2.9 g.

(vii) 4-[(S)-4-Carboxy-2-({4-[2-((S)-2-cyclopropylcarbamoyl-pyrrolidin-1-yl)-2-oxo-ethoxy]-quinoline-2-carbonyl}-amino)-butyryl]piperazine-1-carboxylic acid ethyl ester To a solution of 80 mg of 4-[(S)-4-tert-Butoxycarbonyl-2-({4-[2-((S)-2-cyclopropylcarbamoyl-pyrrolidin-1-yl)-2-oxo-ethoxy]-quinoline-2-carbonyl}-amino)-butyryl]-piperazine-1-carboxylic acid ethyl ester in 2 ml of DCM, 0.1 ml of TFA was added at RT. After 4 h 20 ml of toluene was added and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. Yield: 41 mg MS (ES+): m/e=653.

Example 74

4-[(S)-4-Carboxy-2-({4-[2-((R)-3-hydroxy-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference (R)-Pyrrolidin-3-ol was used instead of (S)-Pyrrolidine-2-carboxylic acid cyclopropylamide hydrochloride. MS (ES$^+$): m/e=586.

Example 75

4-[(S)-4-Carboxy-2-({4-[2-((2S,4R)-2-ethoxycarbonyl-4-hydroxy-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (2S, 4R)-4-Hydroxy-pyrrolidine-2-carboxylic acid ethyl ester was used instead of (S)-Pyrrolidine-2-carboxylic acid cyclopropylamide hydrochloride. MS (ES$^+$): m/e=658.

Example 76

4-[(S)-4-Carboxy-2-({4-[2-((S)-2-carboxy-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (S)-Pyrrolidine-2-carboxylic acid was used instead of (S)-Pyrrolidine-2-carboxylic acid cyclopropylamide hydrochloride. MS (ES$^+$): m/e=614.

Example 77

4-[(S)-4-Carboxy-2-({4-[2-((2S,4R)-2-carboxy-4-hydroxy-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (2S, 4R)-4-Hydroxy-pyrrolidine-2-carboxylic acid was used instead of (S)-Pyrrolidine-2-carboxylic acid cyclopropylamide hydrochloride. MS (ES$^+$): m/e=630.

Example 78

4-[(S)-4-Carboxy-2-({4-[2-((2S,3S)-2-carboxy-3-hydroxy-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (2S, 3S)-3-Hydroxy-pyrrolidine-2-carboxylic acid was used instead of (S)-Pyrrolidine-2-carboxylic acid cyclopropylamide hydrochloride. MS (ES$^+$): m/e=630.

Example 79

4-[(S)-4-Carboxy-2-({4-[2-((S)-2-carboxy-azetidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (S)-Azetidine-2-carboxylic acid was used instead of (S)-Pyrrolidine-2-carboxylic acid cyclopropylamide hydrochloride. MS (ES$^+$): m/e=600.

Example 80

4-[(S)-4-Carboxy-2-({4-[2-(2,4-dioxo-1,3,8-triaza-spiro[4.5]dec-8-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 1,3,8-Triaza-spiro[4.5]decane-2,4-dione was used instead of (S)-Pyrrolidine-2-carboxylic acid cyclopropylamide hydrochloride. MS (ES$^+$): m/e=668.

Example 81

4-[(S)-2-({4-[2-(3-Acetylamino-pyrrolidin-1-yl)-2-oxo-ethoxy]-quinoline-2-carbonyl}-amino)-4-carboxy-butyryl]-piperazine-1-carboxylic acid ethyl ester The title compound was prepared by adapting the procedures described in example 73 with the difference that N-Pyrrolidin-3-yl-acetamide was used instead of (S)-Pyrrolidine-2-carboxylic acid cyclopropylamide hydrochloride. MS (ES$^+$): m/e=627.

Example 82

4-(2-{2-[(S)-3-Carboxy-1-(4-ethoxycarbonyl-piperazine-1-carbonyl)-propylcarbamoyl]-quinolin-4-yloxy}-acetyl)-piperazine-1-carboxylic acid ethyl ester The title compound was prepared by adapting the procedures described in example 73 with the difference that Piperazine-1-carboxylic acid ethyl ester was used instead of (5)-Pyrrolidine-2-carboxylic acid cyclopropylamide hydrochloride. MS (ES$^+$): m/e=657.

Example 83

4-[(S)-4-Carboxy-2-({4-[2-(4-ethyl-piperazin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 1-Ethyl-piperazine was used instead of (S)-Pyrrolidine-2-carboxylic acid cyclopropylamide hydrochloride. MS (ES$^+$): m/e=613.

Example 84

4-[(S)-4-Carboxy-2-({4-[2-((2S,4S)-2-carboxy-4-hydroxy-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (2S,4S)-4-Hydroxy-pyrrolidine-2-carboxylic acid was used instead of (S)-Pyrrolidine-2-carboxylic acid cyclopropylamide hydrochloride. MS (ES$^+$): m/e=630.

Example 85

4-[(S)-4-Carboxy-2-({4-[2-(3-methanesulfonyl-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 3-Methanesulfonyl-pyrrolidine was used instead of (S)-Pyrrolidine-2-carboxylic acid cyclopropylamide hydrochloride. MS (ES$^+$): m/e=648.

Example 86

4-[(S)-4-Carboxy-2-({4-[2-oxo-2-(3-oxo-piperazin-1-yl)-ethoxy]-quinoline-2-carbonyl}-amino)-butyryl]-piperazine-1-carboxylic acid ethyl ester The title compound was prepared by adapting the procedures described in example 73 with the difference that Piperazin-2-one was used instead of (S)-Pyrrolidine-2-carboxylic acid cyclopropylamide hydrochloride. MS (ES$^+$): m/e=599.

Example 87

4-{(S)-4-Carboxy-2-[(4-{2-[4-(2-hydroxy-ethyl)-piperazin-1-yl]-2-oxo-ethoxy}-quinoline-2-carbonyl)-amino]-butyryl}-piperazine-1-carboxylic acid ethyl ester The title compound was prepared by adapting the procedures described in example 73 with the difference that 2-Piperazin-1-yl-ethanol was used instead of (S)-Pyrrolidine-2-carboxylic acid cyclopropylamide hydrochloride. MS (ES$^+$): m/e=629.

Example 88

4-[(S)-2-({4-[2-(4-Acetyl-piperazin-1-yl)-2-oxo-ethoxy]-quinoline-2-carbonyl}-amino)-4-carboxy-butyryl]-piperazine-1-carboxylic acid ethyl ester The title compound was prepared by adapting the procedures described in example 73 with the difference that 1-Piperazin-1-yl-ethanone was used instead of (S)-Pyrrolidine-2-carboxylic acid cyclopropylamide hydrochloride. MS (ES$^+$): m/e=627.

Example 89

4-[(S)-4-Carboxy-2-({4-[2-((2R,4R)-2-carboxy-4-hydroxy-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (2R,4R)-4-Hydroxy-pyrrolidine-2-carboxylic acid was used instead of (S)-Pyrrolidine-2-carboxylic acid cyclopropylamide hydrochloride. MS (ES+): m/e=630.

Example 90

4-[(S)-2-({4-[2-(3-Amino-azetidin-1-yl)-2-oxo-ethoxy]-quinoline-2-carbonyl}-amino)-4-carboxy-butyryl]-piperazine-1-carboxylic acid ethyl ester The title compound was prepared by adapting the procedures described in example 73 with the difference that Azetidin-3-ylamine was used instead of (S)-Pyrrolidine-2-carboxylic acid cyclopropylamide hydrochloride. MS (ES+): m/e=571.

Example 91

4-[(S)-4-Carboxy-2-({4-[2-(3-hydroxy-azetidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that Azetidin-3-ol was used instead of (S)-Pyrrolidine-2-carboxylic acid cyclopropylamide hydrochloride. MS (ES+): m/e=572.

Example 92

4-[(S)-4-Carboxy-2-({4-[2-((2S,4R)-4-hydroxy-2-methoxycarbonyl-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (2S,4R)-4-Hydroxy-pyrrolidine-2-carboxylic acid methyl ester was used instead of (S)-Pyrrolidine-2-carboxylic acid cyclopropylamide hydrochloride. MS (ES+): m/e=644.

Example 93

4-[(S)-4-Carboxy-2-({4-[2-(3-carboxy-azetidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that Azetidine-3-carboxylic acid was used instead of (S)-Pyrrolidine-2-carboxylic acid cyclopropylamide hydrochloride. MS (ES+): m/e=600.

Example 94

3-(2-{2-[(S)-3-Carboxy-1-(4-ethoxycarbonyl-piperazine-1-carbonyl)-propylcarbamoyl]-quinolin-4-yloxy}-acetyl)-3-aza-bicyclo[3.1.0]hexane-6-carboxylic acid ethyl ester The title compound was prepared by adapting the procedures described in example 73 with the difference that 3-Aza-bicyclo[3.1.0]hexane-6-carboxylic acid ethyl ester was used instead of (S)-Pyrrolidine-2-carboxylic acid cyclopropylamide hydrochloride. MS (ES+): m/e=654.

Example 95

4-[(S)-4-Carboxy-2-({4-[2-((S)-2-ethoxycarbonyl-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (S)-Pyrrolidine-2-carboxylic acid ethyl ester was used instead of (S)-Pyrrolidine-2-carboxylic acid cyclopropylamide hydrochloride. MS (ES+): m/e=642.

Example 96

4-[(S)-4-Carboxy-2-({4-[2-(4-carboxymethyl-piperazin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that Piperazin-1-yl-acetic acid was used instead of (S)-Pyrrolidine-2-carboxylic acid cyclopropylamide hydrochloride. MS (ES+): m/e=643.

Example 97

4-[(S)-4-Carboxy-2-({4-[2-((S)-2-methoxycarbonyl-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (S)-Pyrrolidine-2-carboxylic acid methyl ester was used instead of (S)-Pyrrolidine-2-carboxylic acid cyclopropylamide hydrochloride. MS (ES+): m/e=628.

Example 98

4-[(S)-4-Carboxy-2-({4-[2-(3-methoxycarbonyl-methanesulfonyl-azetidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (Azetidine-3-sulfonyl)-acetic acid methyl ester was used instead of (S)-Pyrrolidine-2-carboxylic acid cyclopropylamide hydrochloride. MS (ES+): m/e=692.

Example 99

4-[(S)-4-Carboxy-2-({4-[2-((3R,4R)-3,4-dihydroxy-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (3R,4R)-Pyrrolidine-3,4-diol was used instead of (S)-Pyrrolidine-2-carboxylic acid cyclopropylamide hydrochloride. MS (ES+): m/e=602.

Example 100

4-[(S)-4-Carboxy-2-({4-[2-((3S,4S)-3,4-dihydroxy-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (3S,4S)-Pyrrolidine-3,4-diol was used instead of (S)-Pyrrolidine-2-carboxylic acid cyclopropylamide hydrochloride. MS (ES$^+$): m/e=602.

Example 101

4-[(S)-4-Carboxy-2-({4-[2-((S)-3-hydroxy-2-oxo-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (S)-3-Hydroxy-pyrrolidin-2-one was used instead of (S)-Pyrrolidine-2-carboxylic acid cyclopropylamide hydrochloride. MS (ES$^+$): m/e=600.

Example 102

4-[(S)-4-Carboxy-2-({4-[2-(4-hydroxy-piperidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that Piperidin-4-ol was used instead of (S)-Pyrrolidine-2-carboxylic acid cyclopropylamide hydrochloride. MS (ES$^+$): m/e=600.

Example 103

4-[(S)-4-Carboxy-2-({4-[2-(3-carboxy-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that Pyrrolidine-3-carboxylic acid was used instead of (S)-Pyrrolidine-2-carboxylic acid cyclopropylamide hydrochloride. MS (ES$^+$): m/e=614.

Example 104

4-[(S)-4-Carboxy-2-({4-[2-((S)-3-hydroxy-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (S)-Pyrrolidin-3-ol was used instead of (S)-Pyrrolidine-2-carboxylic acid cyclopropylamide hydrochloride. MS (ES$^+$): m/e=586.

Example 105

4-[(S)-4-Carboxy-2-({4-[2-((2S,4S)-4-hydroxy-2-methoxycarbonyl-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (2S,4S)-4-Hydroxy-pyrrolidine-2-carboxylic acid methyl ester was used instead of (S)-Pyrrolidine-2-carboxylic acid cyclopropylamide hydrochloride. MS (ES$^+$): m/e=644.

Example 106

4-[(S)-4-Ethoxycarbonyl-2-({4-[2-oxo-2-(2-oxo-pyrrolidin-1-yl)-ethoxy]-quinoline-2-carbonyl}-amino)-butyryl]-piperazine-1-carboxylic acid ethyl ester To 10 ml of a saturated solution of hydrochloric acid in ethanol 100 mg of 4-[(S)-4-Carboxy-2-({4-[2-oxo-2-(2-oxo-pyrrolidin-1-yl)-ethoxy]-quinoline-2-carbonyl}-amino)-butyryl]-piperazine-1-carboxylic acid ethyl ester was added and the mixture was stirred for 1 h. Then, 30 ml of toluene was added and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. Yield: 38 mg MS (ES$^+$): m/e=612.

Example 107

4-[(S)-2-({4-[2-((S)-2-Cyclopropylcarbamoyl-pyrrolidin-1-yl)-2-oxo-ethoxy]-quinoline-2-carbonyl}-amino)-4-ethoxycarbonyl-butyryl]-piperazine-1-carboxylic acid ethyl ester To 150 ml of a saturated solution of hydrochloric acid in ethanol 4.1 g of 4-[(S)-4-tert-Butoxycarbonyl-2-({4-[2-((S)-2-cyclopropylcarbamoyl-pyrrolidin-1-yl)-2-oxo-ethoxy]-quinoline-2-carbonyl}-amino)-butyryl]-piperazine-1-carboxylic acid ethyl ester was added and the mixture was stirred for 1 h. Then, 200 ml of toluene was added and the solvents were removed under reduced pressure. The residue was co-distilled twice with toluene and then purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. Yield: 1 g MS (ES$^+$): m/e=681.

Example 108

4-[(S)-4-Carboxy-2-({4-[2-((S)-2-dimethylcarbamoyl-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (S)-Pyrrolidine-2-carboxylic acid dimethylamide was used instead of (S)-Pyrrolidine-2-carboxylic acid cyclopropylamide hydrochloride. MS (ES$^+$): m/e=641.

Example 109

4-[(S)-4-Carboxy-2-({4-[2-((S)-2-ethylcarbamoyl-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (S)-Pyrrolidine-2-carboxylic acid ethylamide was used instead of (S)-Pyrrolidine-2-carboxylic acid cyclopropylamide hydrochloride. MS (ES+): m/e=641.

Example 110

4-[(S)-2-({4-[2-((S)-2-Carbamoyl-pyrrolidin-1-yl)-2-oxo-ethoxy]-quinoline-2-carbonyl}-amino)-4-carboxy-butyryl]-piperazine-1-carboxylic acid ethyl ester The title compound was prepared by adapting the procedures described in example 73 with the difference that (S)-Pyrrolidine-2-carboxylic acid amide was used instead of (S)-Pyrrolidine-2-carboxylic acid cyclopropylamide hydrochloride. MS (ES+): m/e=613.

Example 111

4-[(S)-4-Carboxy-2-({4-[2-(3-cyclopropylcarbamoyl-azetidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that Azetidine-3-carboxylic acid cyclopropylamide was used instead of (S)-Pyrrolidine-2-carboxylic acid cyclopropylamide hydrochloride. MS (ES+): m/e=639.

Example 112

4-[(S)-4-Carboxy-2-({4-[2-((S)-3-cyclopropylcarbamoyl-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (S)-Pyrrolidine-3-carboxylic acid cyclopropylamide was used instead of (S)-Pyrrolidine-2-carboxylic acid cyclopropylamide hydrochloride. MS (ES+): m/e=653.

Example 113

4-[(S)-4-Carboxy-2-({4-[2-((R)-3-cyclopropylcarbamoyl-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (R)-Pyrrolidine-3-carboxylic acid cyclopropylamide was used instead of (S)-Pyrrolidine-2-carboxylic acid cyclopropylamide hydrochloride. MS (ES+): m/e=653.

Example 114

4-{(S)-4-Carboxy-2-[(4-{2-[(S)-2-(2,2-difluoro-ethylcarbamoyl)-pyrrolidin-1-yl]-2-oxo-ethoxy}-quinoline-2-carbonyl)-amino]-butyryl}-piperazine-1-carboxylic acid ethyl ester The title compound was prepared by adapting the procedures described in example 73 with the difference that (5)-Pyrrolidine-2-carboxylic acid (2,2-difluoro-ethyl)-amide was used instead of (S)-Pyrrolidine-2-carboxylic acid cyclopropylamide hydrochloride. MS (ES+): m/e=677.

Example 115

4-{(S)-4-Carboxy-2-[(4-{2-[(S)-2-(2-fluoro-ethylcarbamoyl)-pyrrolidin-1-yl]-2-oxo-ethoxy}-quinoline-2-carbonyl)-amino]-butyryl}-piperazine-1-carboxylic acid ethyl ester The title compound was prepared by adapting the procedures described in example 73 with the difference that (S)-Pyrrolidine-2-carboxylic acid (2-fluoro-ethyl)-amide was used instead of (S)-Pyrrolidine-2-carboxylic acid cyclopropylamide hydrochloride. MS (ES+): m/e=659.

Example 116

4-[(S)-4-Carboxy-2-({4-[2-oxo-2-((1S,5R)-3-oxo-8-aza-bicyclo[3.2.1]oct-8-yl)-ethoxy]-quinoline-2-carbonyl}-amino)-butyryl]-piperazine-1-carboxylic acid ethyl ester The title compound was prepared by adapting the procedures described in example 73 with the difference that (1S,5R)-8-Aza-bicyclo[3.2.1]octan-3-one was used instead of (S)-Pyrrolidine-2-carboxylic acid cyclopropylamide hydrochloride. MS (ES+): m/e=624.

Example 117

4-[(S)-4-Carboxy-2-({4-[2-(2-hydroxymethyl-morpholin-4-yl)-2-oxo-ethoxy]-quinoline-2-carbonyl}-amino)-butyryl]piperazine-1-carboxylic acid ethyl ester The title compound was prepared by adapting the procedures described in example 73 with the difference that Morpholin-2-yl-methanol was used instead of (S)-Pyrrolidine-2-carboxylic acid cyclopropylamide hydrochloride. MS (ES+): m/e=616.

Example 118

4-[(S)-4-Carboxy-2-({4-[2-((R)-3-hydroxy-piperidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (R)-Piperidin-3-ol was used instead of (S)-Pyrrolidine-2-carboxylic acid cyclopropylamide hydrochloride. MS (ES+): m/e=600.

Example 119

4-[(S)-4-Carboxy-2-({4-[2-oxo-2-(3-oxo-pyrazolidin-1-yl)-ethoxy]-quinoline-2-carbonyl}-amino)-butyryl]-piperazine-1-carboxylic acid ethyl ester The title compound was prepared by adapting the procedures described in example 73 with the difference that Pyrazolidin-3-one was used instead of (S)-Pyrrolidine-2-carboxylic acid cyclopropylamide hydrochloride. MS (ES$^+$): m/e=585.

Example 120

4-[(S)-4-Carboxy-2-({4-[2-(4-methoxy-piperidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 4-Methoxy-piperidine was used instead of (S)-Pyrrolidine-2-carboxylic acid cyclopropylamide hydrochloride. MS (ES$^+$): m/e=614.

Example 121

4-{(S)-4-Carboxy-2-[(4-{2-oxo-2-[(S)-2-(2,2,2-trifluoro-ethylcarbamoyl)-pyrrolidin-1-yl]-ethoxy}-quinoline-2-carbonyl)-amino]-butyryl}-piperazine-1-carboxylic acid ethyl ester The title compound was prepared by adapting the procedures described in example 73 with the difference that (S)-Pyrrolidine-2-carboxylic acid (2,2,2-trifluoro-ethyl)-amide was used instead of (S)-Pyrrolidine-2-carboxylic acid cyclopropylamide hydrochloride. MS (ES$^+$): m/e=695.

Example 122

4-[(S)-4-Carboxy-2-({4-[2-((S)-2-hydroxymethyl-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (S)-1-Pyrrolidin-2-yl-methanol was used instead of (S)-Pyrrolidine-2-carboxylic acid cyclopropylamide hydrochloride. MS (ES$^+$): m/e=600.

Example 123

4-[(S)-4-Carboxy-2-({4-[2-(4-cyclopropylcarbamoyl-piperidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that Piperidine-4-carboxylic acid cyclopropylamide was used instead of (S)-Pyrrolidine-2-carboxylic acid cyclopropylamide hydrochloride. MS (ES$^+$): m/e=667.

Example 124

4-[(S)-4-Carboxy-2-({4-[2-((S)-2-cyclopropylcarbamoyl-piperidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (S)-Piperidine-2-carboxylic acid cyclopropylamide was used instead of (S)-Pyrrolidine-2-carboxylic acid cyclopropylamide hydrochloride. MS (ES$^+$): m/e=667.

Example 125

4-[(S)-4-Carboxy-2-({4-[2-((S)-3-hydroxymethyl-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (S)-1-Pyrrolidin-3-yl-methanol was used instead of (S)-Pyrrolidine-2-carboxylic acid cyclopropylamide hydrochloride. MS (ES$^+$): m/e=600.

Example 126

4-[(S)-4-Carboxy-2-({4-[2-((R)-3-hydroxymethyl-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (R)-1-Pyrrolidin-3-yl-methanol was used instead of (S)-Pyrrolidine-2-carboxylic acid cyclopropylamide hydrochloride. MS (ES$^+$): m/e=600.

Example 127

4-((S)-4-Carboxy-2-{[4-(2-morpholin-4-yl-2-oxo-ethoxy)-quinoline-2-carbonyl]-amino}-butyryl)-piperazine-1-carboxylic acid ethyl ester The title compound was prepared by adapting the procedures described in example 73 with the difference that Morpholine was used instead of (S)-Pyrrolidine-2-carboxylic acid cyclopropylamide hydrochloride. MS (ES$^+$): m/e=586.

Example 128

4-[(S)-4-Carboxy-2-({4-[2-(4-ethoxy-piperidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 4-Ethoxy-piperidine was used instead of (S)-Pyrrolidine-2-carboxylic acid cyclopropylamide hydrochloride. MS (ES$^+$): m/e=628.

Example 129

4-[(S)-4-Carboxy-2-({4-[2-(4-carboxy-piperidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that Piperidine-4-carboxylic acid was used instead of (S)-Pyrrolidine-2-carboxylic acid cyclopropylamide hydrochloride. MS (ES$^+$): m/e=628.

Example 130

4-[(S)-4-Carboxy-2-({4-[2-(4-ethoxycarbonyl-piperidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that Piperidine-4-carboxylic acid ethyl ester was used instead of (S)-Pyrrolidine-2-carboxylic acid cyclopropylamide hydrochloride. MS (ES$^+$): m/e=656.

Example 131

4-[(S)-4-Carboxy-2-({4-[2-oxo-2-(5-oxo-[1,4]diazepan-1-yl)-ethoxy]-quinoline-2-carbonyl}-amino)-butyryl]-piperazine-1-carboxylic acid ethyl ester The title compound was prepared by adapting the procedures described in example 73 with the difference that [1,4]Diazepan-5-one was used instead of (S)-Pyrrolidine-2-carboxylic acid cyclopropylamide hydrochloride. MS (ES$^+$): m/e=613.

Example 132

4-[(S)-4-Carboxy-2-({4-[2-(3-cyclopropylcarbamoyl-piperidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that Piperidine-3-carboxylic acid cyclopropylamide was used instead of (S)-Pyrrolidine-2-carboxylic acid cyclopropylamide hydrochloride. MS (ES$^+$): m/e=667.

Example 133

4-[(S)-4-Carboxy-2-({4-[2-((R)-2-cyclopropylcarbamoyl-piperidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (R)-Piperidine-2-carboxylic acid cyclopropylamide was used instead of (S)-Pyrrolidine-2-carboxylic acid cyclopropylamide hydrochloride. MS (ES$^+$): m/e=667.

Example 134

4-[(S)-4-Carboxy-2-({4-[2-oxo-2-(3-oxo-pyrrolidin-1-yl)-ethoxy]-quinoline-2-carbonyl}-amino)-butyryl]-piperazine-1-carboxylic acid ethyl ester The title compound was prepared by adapting the procedures described in example 73 with the difference that Pyrrolidin-3-one was used instead of (S)-Pyrrolidine-2-carboxylic acid cyclopropylamide hydrochloride. MS (ES$^+$): m/e=584.

Example 135

4-[(S)-4-Carboxy-2-({4-[2-(2-carboxy-4,4-difluoro-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 4,4-Difluoro-pyrrolidine-2-carboxylic acid was used instead of (S)-Pyrrolidine-2-carboxylic acid cyclopropylamide hydrochloride. MS (ES$^+$): m/e=650.

Example 136

4-[(S)-4-Carboxy-2-({4-[2-(3-hydroxy-piperidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that Piperidin-3-ol was used instead of (S)-Pyrrolidine-2-carboxylic acid cyclopropylamide hydrochloride. MS (ES$^+$): m/e=600.

Example 137

4-[(S)-4-Carboxy-2-({4-[2-((S)-2-carboxy-piperidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (S)-Piperidine-2-carboxylic acid was used instead of (S)-Pyrrolidine-2-carboxylic acid cyclopropylamide hydrochloride. MS (ES$^+$): m/e=628.

Example 138

4-[(S)-4-Carboxy-2-({4-[2-((R)-2-carboxy-piperidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (R)-Piperidine-2-carboxylic acid was used instead of (S)-Pyrrolidine-2-carboxylic acid cyclopropylamide hydrochloride. MS (ES$^+$): m/e=628.

Example 139

4-[(S)-4-Carboxy-2-({4-[2-((S)-2-methoxymethyl-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (S)-2-Methoxymethyl-pyrrolidine was used instead of (S)-Pyrrolidine-2-carboxylic acid cyclopropylamide hydrochloride. MS (ES$^+$): m/e=614.

Example 140

4-[(S)-4-Carboxy-2-({6-chloro-4-[2-((S)-2-cyclopropylcarbamoyl-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 56 with the difference that 4-{(S)-4-tert-Butoxycarbonyl-2-[(6-chloro-4-hydroxy-quinoline-2-carbonyl)-amino]-butyryl}-piperazine-1-carboxylic acid ethyl ester was used instead of 4-{(S)-4-tert-Butoxycarbonyl-2-[(4-hydroxy-5,7-dimethyl-quinoline-2-carbonyl)-amino]-butyryl}-piperazine-1-carboxylic acid ethyl ester. MS (ES$^+$): m/e=687.

Example 141

4-[(S)-4-Carboxy-2-({4-[2-((S)-2-cyclopropylcarbamoyl-pyrrolidin-1-yl)-2-oxo-ethoxy]-6-methyl-quinoline-2-carbonyl}-amino)-butyryl]-piperazine-1-carboxylic acid ethyl ester The title compound was prepared by adapting the procedures described in example 56 with the difference that 4-{(S)-4-tert-Butoxycarbonyl-2-[(4-hydroxy-6-methyl-quinoline-2-carbonyl)-amino]-butyryl}-piperazine-1-carboxylic acid ethyl ester was used instead of 4-{(S)-4-tert-Butoxycarbonyl-2-[(4-hydroxy-5,7-dimethyl-quinoline-2-carbonyl)-amino]-butyryl}-piperazine-1-carboxylic acid ethyl ester. MS (ES$^+$): m/e=667.

Example 142

4-[(S)-4-Carboxy-2-({4-[2-((S)-2-cyclopropylcarbamoyl-pyrrolidin-1-yl)-2-oxo-ethoxy]-5-methyl-quinoline-2-carbonyl}-amino)-butyryl]-piperazine-1-carboxylic acid ethyl ester The title compound was prepared by adapting the procedures described in example 56 with the difference that 4-{(S)-4-tert-Butoxycarbonyl-2-[(4-hydroxy-5-methyl-quinoline-2-carbonyl)-amino]-butyryl}-piperazine-1-carboxylic acid ethyl ester was used instead of 4-{(S)-4-tert-Butoxycarbonyl-2-[(4-hydroxy-5,7-dimethyl-quinoline-2-carbonyl)-amino]-butyryl}-piperazine-1-carboxylic acid ethyl ester. MS (ES$^+$): m/e=667.

Example 143

4-[(S)-4-Carboxy-2-({4-[2-((S)-2-cyclobutylcarbamoyl-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (S)-Pyrrolidine-2-carboxylic acid cyclobutylamide was used instead of (S)-Pyrrolidine-2-carboxylic acid cyclopropylamide hydrochloride. MS (ES$^+$): m/e=667.

Example 144

4-[(S)-4-Carboxy-2-({4-[2-((R)-2-ethoxycarbonyl-pyrrolidin-1-yl)-2-oxo-ethoxy]-quinoline-2-carbonyl}-amino)-butyryl]piperazine-1-carboxylic acid ethyl ester The title compound was prepared by adapting the procedures described in example 73 with the difference that (R)-Pyrrolidine-2-carboxylic acid ethyl ester was used instead of (S)-Pyrrolidine-2-carboxylic acid cyclopropylamide hydrochloride. MS (ES$^+$): m/e=642.

Example 145

4-[(S)-2-({4-[2-((R)-2-Carbamoyl-pyrrolidin-1-yl)-2-oxo-ethoxy]-quinoline-2-carbonyl}-amino)-4-carboxy-butyryl]-piperazine-1-carboxylic acid ethyl ester The title compound was prepared by adapting the procedures described in example 73 with the difference that (R)-Pyrrolidine-2-carboxylic acid amide was used instead of (S)-Pyrrolidine-2-carboxylic acid cyclopropylamide hydrochloride. MS (ES$^+$): m/e=613.

Example 146

4-[(S)-4-Carboxy-2-({4-[2-((S)-2-carboxy-2-methyl-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (S)-2-Methyl-pyrrolidine-2-carboxylic acid was used instead of (S)-Pyrrolidine-2-carboxylic acid cyclopropylamide hydrochloride. MS (ES$^+$): m/e=628.

Example 147

4-{(S)-4-Carboxy-2-[(4-{2-[(S)-2-(cyclopropylmethyl-carbamoyl)-pyrrolidin-1-yl]-2-oxo-ethoxyl}-quinoline-2-carbonyl)-amino]-butyryl}-piperazine-1-carboxylic acid ethyl ester The title compound was prepared by adapting the procedures described in example 73 with the difference that (S)-Pyrrolidine-2-carboxylic acid cyclopropylmethyl-amide was used instead of (S)-Pyrrolidine-2-carboxylic acid cyclopropylamide hydrochloride. MS (ES$^+$): m/e=667.

Example 148

4-[(S)-4-Carboxy-2-({4-[2-((S)-2-isopropylcarbamoyl-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (S)-Pyrrolidine-2-carboxylic acid isopropylamide was used instead of (S)-Pyrrolidine-2-carboxylic acid cyclopropylamide hydrochloride. MS (ES$^+$): m/e=655.

Example 149

4-[(S)-4-Carboxy-2-({4-[2-((R)-2-cyclopropylcarbamoyl-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (R)-Pyrrolidine-2-carboxylic acid cyclopropylamide was used instead of (S)-Pyrrolidine-2-carboxylic acid cyclopropylamide hydrochloride. MS (ES+): m/e=653.

Example 150

4-[(S)-4-Carboxy-2-({4-[2-(4,4-dimethyl-oxazolidin-3-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 4,4-Dimethyl-oxazolidine was used instead of (S)-Pyrrolidine-2-carboxylic acid cyclopropylamide hydrochloride. MS (ES+): m/e=600.

Example 151

4-[(S)-4-Carboxy-2-({4-[2-oxo-2-((S)-2-propylcarbamoyl-pyrrolidin-1-yl)-ethoxy]-quinoline-2-carbonyl}-amino)-butyryl]-piperazine-1-carboxylic acid ethyl ester The title compound was prepared by adapting the procedures described in example 73 with the difference that (S)-Pyrrolidine-2-carboxylic acid propylamide was used instead of (S)-Pyrrolidine-2-carboxylic acid cyclopropylamide hydrochloride. MS (ES+): m/e=655.

Example 152

4-[(S)-4-Carboxy-2-({4-[2-((R)-2-hydroxymethyl-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (R)-1-Pyrrolidin-2-yl-methanol was used instead of (S)-Pyrrolidine-2-carboxylic acid cyclopropylamide hydrochloride. MS (ES+): m/e=600.

Example 153

4-((S)-4-Carboxy-2-{[4-(3-carboxy-azetidine-1-carbonyl)-quinoline-2-carbonyl]-amino}-butyryl)-piperazine-1-carboxylic acid ethyl ester (i) 2-Furan-2-yl-quinoline-4-carboxylic acid ethyl ester To 40 ml of a saturated solution of hydrochloric acid in ethanol 2 g of 2-Furan-2-yl-quinoline-4-carboxylic acid was added and the mixture was heated to reflux for 3 h. Then, after cooling to RT, 30 ml of toluene was added and the solvents were removed under reduced pressure. The obtained crude product was pure enough for the next reaction step. Yield: 2.5 g.

(ii) Quinoline-2,4-dicarboxylic acid 4-ethyl ester

To a vigorously stirred of 8 g of sodium periodate and 20 mg of ruthenium trichloride in 37 ml of tetrachloro-methane, 37 ml of acteonitrile and 54 ml of water 2.5 g of 2-Furan-2-yl-quinoline-4-carboxylic acid ethyl ester was added at RT. Then, after 4 h additional 8 g of sodium periodate and 10 mg of ruthenium trichloride was added and the reaction mixture was stirred for an additional hour. Then, the reaction mixture was diluted with water and extracted with DCM (3×150 ml). The combined organic phases were dried over MgSO4 and the solvents were removed under reduced pressure. The crude product was used in the next reaction step without further purification. Yield: 2.0 g.

(iii) 2-[(S)-3-tert-Butoxycarbonyl-1-(4-ethoxycarbonyl-piperazine-1-carbonyl)-propylcarbamoyl]-quinoline-4-carboxylic acid ethyl ester To a solution of 2 g of Quinoline-2,4-dicarboxylic acid 4-ethyl ester and 2.8 g of 4-((S)-2-Amino-4-tert-butoxycarbonyl-butyryl)-piperazine-1-carboxylic acid ethyl ester in 21 ml of DMF, 1.3 g of HOBT and 1.6 g of EDC was added and the reaction mixture was stirred for 16 h at RT. Then, the reaction mixture was diluted with water and extracted with DCM. The organic phase was dried over MgSO4 and the solvents were removed under reduced pressure. The crude product was purified by chromatography on silica gel eluting with a gradient of n-heptane/ethyl acetate. The fractions containing the product were combined and the solvent evaporated under reduced pressure. Yield: 1.1 g.

(iv) 2-[(S)-3-tert-Butoxycarbonyl-1-(4-ethoxycarbonyl-piperazine-1-carbonyl)-propylcarbamoyl]-quinoline-4-carboxylic acid To a solution of 1.1 g of 2-[(S)-3-tert-Butoxycarbonyl-1-(4-ethoxycarbonyl-piperazine-1-carbonyl)-propylcarbamoyl]-quinoline-4-carboxylic acid ethyl ester in 10 ml of THF, 2 ml of a 1 M aqueous NaOH solution was added. After stirring for 5 h at RT additional 1 ml of a 1 M aqueous NaOH solution was added and allowed to stir upon completion of the reaction. Then, the reaction was acidified to pH 1 with diluted aqueous hydrochloric acid and extracted with DCM (3×100 ml). The combined organic phases were dried over MgSO4 and the solvents were removed under reduced pressure. The crude product was used in the next reaction step without further purification. Yield: 1.0 g.

(v) 4-((S)-4-tert-Butoxycarbonyl-2-{[4-(3-carboxy-azetidine-1-carbonyl)-quinoline-2-carbonyl]-amino}-butyryl)-piperazine-1-carboxylic acid ethyl ester To a solution of 80 mg of 2-[(S)-3-tert-Butoxycarbonyl-1-(4-ethoxycarbonyl-piperazine-1-carbonyl)-propylcarbamoyl]-quinoline-4-carboxylic acid 68 mg of NEM and 53 mg of TOTU in 2 ml of DMF, 30 mg of Azetidine-3-carboxylic acid was added at RT and stirred for 16 h. Then, the reaction mixture was diluted with water and filtered through a chem Elut® cartridge by eluting with DCM. The solvents were removed and the residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. Yield: 8 mg.

(vi) 4-((S)-4-Carboxy-2-{[4-(3-carboxy-azetidine-1-carbonyl)-quinoline-2-carbonyl]-amino}-butyryl)-piperazine-1-carboxylic acid ethyl ester To a solution of 8 mg of 4-((S)-4-tert-Butoxycarbonyl-2-{[4-(3-carboxy-azetidine-1-carbonyl)-quinoline-2-carbonyl]-amino}-butyryl)-piperazine-1-carboxylic acid ethyl ester in 1 ml of DCM, 0.4 ml of TFA was added at RT. After 16 h 10 ml of toluene was added and the solvents were removed under reduced pressure. The residue was dissolved

Example 154

4-((S)-2-{[4-(Azetidine-1-carbonyl)-quinoline-2-carbonyl]-amino}-4-carboxy-butyryl)-piperazine-1-carboxylic acid ethyl ester The title compound was prepared by adapting the procedures described in example 153 with the difference that Azetidine was used instead of Azetidine-3-carboxylic acid. MS (ES$^+$): m/e=526.

Example 155

4-((S)-4-Carboxy-2-{[4-(morpholine-4-carbonyl)-quinoline-2-carbonyl]-amino}-butyryl)-piperazine-1-carboxylic acid ethyl ester The title compound was prepared by adapting the procedures described in example 153 with the difference that Morpholine was used instead of Azetidine-3-carboxylic acid. MS (ES$^+$): m/e=556.

Example 156

4-((S)-4-Carboxy-2-{[4-((S)-2-carboxy-azetidine-1-carbonyl)-quinoline-2-carbonyl]-amino}-butyryl)-piperazine-1-carboxylic acid ethyl ester The title compound was prepared by adapting the procedures described in example 153 with the difference that (S)-Azetidine-2-carboxylic acid was used instead of Azetidine-3-carboxylic acid. MS (ES$^+$): m/e=570.

Example 157

4-((S)-4-Carboxy-2-{[4-(2-carboxy-pyrrolidine-1-carbonyl)-quinoline-2-carbonyl]-amino}-butyryl)-piperazine-1-carboxylic acid ethyl ester The title compound was prepared by adapting the procedures described in example 153 with the difference that Pyrrolidine-2-carboxylic acid was used instead of Azetidine-3-carboxylic acid. MS (ES$^+$): m/e=584.

Example 158

4-((S)-4-Carboxy-2-{[4-(3-hydroxy-azetidine-1-carbonyl)-quinoline-2-carbonyl]-amino}-butyryl)-piperazine-1-carboxylic acid ethyl ester The title compound was prepared by adapting the procedures described in example 153 with the difference that Azetidin-3-ol was used instead of Azetidine-3-carboxylic acid. MS (ES$^+$): m/e=542.

Example 159

4-((S)-4-Carboxy-2-{[4-(2-methoxycarbonyl-aziridine-1-carbonyl)-quinoline-2-carbonyl]-amino}-butyryl)-piperazine-1-carboxylic acid ethyl ester The title compound was prepared by adapting the procedures described in example 153 with the difference that Aziridine-2-carboxylic acid methyl ester was used instead of Azetidine-3-carboxylic acid. MS (ES$^+$): m/e=570.

Example 160

4-[(S)-4-Carboxy-2-({4-[2-(2-carboxy-4-hydroxy-pyrrolidin-1-yl)-2-oxo-ethoxy]-quinoline-2-carbonyl}-amino)-butyryl]-piperazine-1-carboxylic acid ethyl ester To a solution of 40 mg of 4-[(S)-4-Carboxy-2-({4-[2-(4-hydroxy-2-methoxycarbonyl-pyrrolidin-1-yl)-2-oxo-ethoxy]-quinoline-2-carbonyl}-amino)-butyryl]-piperazine-1-carboxylic acid ethyl ester in 1 ml of THF/MeOH (3/1), 4 mg of lithium hydroxide was added at 0° C. and stirred for 1 h. Then, the reaction mixture was neutralized with amberlite IR-120. After filtration the solvents were removed under reduced pressure and the residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. Yield: 10 mg MS (ES$^+$): m/e=630.

Example 161

4-[(S)-4-Carboxy-2-({7-fluoro-4-[2-(4-hydroxy-piperidin-1-yl)-2-oxo-ethoxy]-quinoline-2-carbonyl}-amino)-butyryl]-piperazine-1-carboxylic acid ethyl ester The title compound was prepared by adapting the procedures described in example 3 with the difference that Piperidin-4-ol and 7-Fluoro-4-hydroxy-quinoline-2-carboxylic acid was used instead of (S)-Pyrrolidine-2-carboxylic acid cyclopropylamide hydrochloride and 4-Hydroxy-7-methyl-quinoline-2-carboxylic acid. MS (ES$^+$): m/e=618.

Example 162

4-[(S)-4-Carboxy-2-({4-[2-((S)-2-cyclobutylcarbamoyl-pyrrolidin-1-yl)-2-oxo-ethoxy]-8-fluoro-quinoline-2-carbonyl}-amino)-butyryl]-piperazine-1-carboxylic acid ethyl ester The title compound was prepared by adapting the procedures described in example 3 with the difference that (S)-Pyrrolidine-2-carboxylic acid cyclobutylamide and 8-Fluoro-4-hydroxy-quinoline-2-carboxylic acid was used instead of (S)-Pyrrolidine-2-carboxylic acid cyclopropylamide hydrochloride and 4-Hydroxy-7-methyl-quinoline-2-carboxylic acid. MS (ES$^+$): m/e=685.

Example 163

4-[(S)-4-Carboxy-2-({4-[2-((S)-2-cyclobutylcarbamoyl-pyrrolidin-1-yl)-2-oxo-ethoxy]-7-fluoro-quinoline-2-carbonyl}-amino)-butyryl]-piperazine-1-carboxylic acid ethyl ester The title compound was prepared by adapting the procedures described in example 3 with the difference that (S)-Pyrrolidine-2-carboxylic acid cyclobutylamide and 7-Fluoro-4-hydroxy-quinoline-2-carboxylic acid was used instead of (S)-Pyrrolidine-2-carboxylic acid cyclopropyla-

Example 164

4-[(S)-4-Carboxy-2-({4-[2-((S)-2-ethylcarbamoyl-pyrrolidin-1-yl)-2-oxo-ethoxy]-7-fluoro-quinoline-2-carbonyl}-amino)-butyryl]-piperazine-1-carboxylic acid ethyl ester The title compound was prepared by adapting the procedures described in example 3 with the difference that (S)-Pyrrolidine-2-carboxylic acid ethylamide and 7-Fluoro-4-hydroxy-quinoline-2-carboxylic acid was used instead of (S)-Pyrrolidine-2-carboxylic acid cyclopropylamide hydrochloride and 4-Hydroxy-7-methyl-quinoline-2-carboxylic acid. MS (ES$^+$): m/e=685.

Example 165

4-[(S)-4-Carboxy-2-({4-[2-((S)-2-cyclobutylcarbamoyl-azetidin-1-yl)-2-oxo-ethoxy]-7-fluoro-quinoline-2-carbonyl}-amino)-butyryl]-piperazine-1-carboxylic acid ethyl ester The title compound was prepared by adapting the procedures described in example 3 with the difference that (S)-Azetidine-2-carboxylic acid cyclobutylamide and 7-Fluoro-4-hydroxy-quinoline-2-carboxylic acid was used instead of (S)-Pyrrolidine-2-carboxylic acid cyclopropylamide hydrochloride and 4-Hydroxy-7-methyl-quinoline-2-carboxylic acid. MS (ES$^+$): m/e=671.

Example 166

4-[(S)-4-Carboxy-2-({4-[2-((S)-2-cyclopropylcarbamoyl-pyrrolidin-1-yl)-2-oxo-ethoxy]-7-fluoro-quinoline-2-carbonyl}-amino)-butyryl]-piperazine-1-carboxylic acid ethyl ester The title compound was prepared by adapting the procedures described in example 3 with the difference and 7-Fluoro-4-hydroxy-quinoline-2-carboxylic acid was used instead 4-Hydroxy-7-methyl-quinoline-2-carboxylic acid. MS (ES$^+$): m/e=671.

Example 167

4-[(S)-4-Carboxy-2-({4-[2-((S)-2-cyclobutylcarbamoyl-azetidin-1-yl)-2-oxo-ethoxy]-8-fluoro-quinoline-2-carbonyl}-amino)-butyryl]-piperazine-1-carboxylic acid ethyl ester The title compound was prepared by adapting the procedures described in example 3 with the difference that (S)-Azetidine-2-carboxylic acid cyclobutylamide and 8-Fluoro-4-hydroxy-quinoline-2-carboxylic acid was used instead of (S)-Pyrrolidine-2-carboxylic acid cyclopropylamide hydrochloride and 4-Hydroxy-7-methyl-quinoline-2-carboxylic acid. MS (ES$^+$): m/e=671.

Example 168

4-[(S)-4-Carboxy-2-({4-[2-((S)-2-ethylcarbamoyl-pyrrolidin-1-yl)-2-oxo-ethoxy]-8-fluoro-quinoline-2-carbonyl}-amino)-butyryl]-piperazine-1-carboxylic acid ethyl ester The title compound was prepared by adapting the procedures described in example 3 with the difference that (S)-Pyrrolidine-2-carboxylic acid ethylamide and 8-Fluoro-4-hydroxy-quinoline-2-carboxylic acid was used instead of (S)-Pyrrolidine-2-carboxylic acid cyclopropylamide hydrochloride and 4-Hydroxy-7-methyl-quinoline-2-carboxylic acid. MS (ES$^+$): m/e=659.

Example 169

4-[(S)-4-Carboxy-2-({4-[2-((S)-2-cyclopropylcarbamoyl-pyrrolidin-1-yl)-2-oxo-ethoxy]-8-fluoro-quinoline-2-carbonyl}-amino)-butyryl]-piperazine-1-carboxylic acid ethyl ester The title compound was prepared by adapting the procedures described in example 3 with the difference that 8-Fluoro-4-hydroxy-quinoline-2-carboxylic acid was used instead of 4-Hydroxy-7-methyl-quinoline-2-carboxylic acid. MS (ES$^+$): m/e=671.

Example 170

4-[(S)-4-Carboxy-2-({8-fluoro-4-[2-(4-hydroxy-piperidin-1-yl)-2-oxo-ethoxy]-quinoline-2-carbonyl}-amino)-butyryl]-piperazine-1-carboxylic acid ethyl ester The title compound was prepared by adapting the procedures described in example 3 with the difference that Piperidin-4-ol and 8-Fluoro-4-hydroxy-quinoline-2-carboxylic acid was used instead of (S)-Pyrrolidine-2-carboxylic acid cyclopropylamide hydrochloride and 4-Hydroxy-7-methyl-quinoline-2-carboxylic acid. MS (ES$^+$): m/e=618.

Example 171

4-[(S)-4-Carboxy-2-({6-fluoro-4-[2-(4-hydroxy-piperidin-1-yl)-2-oxo-ethoxy]-quinoline-2-carbonyl}-amino)-butyryl]-piperazine-1-carboxylic acid ethyl ester The title compound was prepared by adapting the procedures described in example 3 with the difference that Piperidin-4-ol and 6-Fluoro-4-hydroxy-quinoline-2-carboxylic acid was used instead of (S)-Pyrrolidine-2-carboxylic acid cyclopropylamide hydrochloride and 4-Hydroxy-7-methyl-quinoline-2-carboxylic acid. MS (ES$^+$): m/e=618.

Example 172

4-[(S)-4-Carboxy-2-({4-[2-((S)-2-ethylcarbamoyl-pyrrolidin-1-yl)-2-oxo-ethoxy]-6-fluoro-quinoline-2-carbonyl}-amino)-butyryl]-piperazine-1-carboxylic acid ethyl ester The title compound was prepared by adapting the procedures described in example 3 with the difference that (S)-Pyrrolidine-2-carboxylic acid ethylamide and 6-Fluoro-4-hydroxy-quinoline-2-carboxylic acid was used instead of (S)-Pyrrolidine-2-carboxylic acid cyclopropylamide

Example 173

4-[(S)-4-Carboxy-2-({4-[2-((S)-2-cyclopropylcarbamoyl-pyrrolidin-1-yl)-2-oxo-ethoxy]-5-fluoro-quinoline-2-carbonyl}-amino)-butyryl]-piperazine-1-carboxylic acid ethyl ester The title compound was prepared by adapting the procedures described in example 3 with the difference that 5-Fluoro-4-hydroxy-quinoline-2-carboxylic acid was used instead of 4-Hydroxy-7-methyl-quinoline-2-carboxylic acid. MS (ES$^+$): m/e=671.

Example 174

4-[(S)-4-Carboxy-2-({4-[2-((S)-2-cyclobutylcarbamoyl-pyrrolidin-1-yl)-2-oxo-ethoxy]-5-fluoro-quinoline-2-carbonyl}-amino)-butyryl]-piperazine-1-carboxylic acid ethyl ester The title compound was prepared by adapting the procedures described in example 3 with the difference that (S)-Pyrrolidine-2-carboxylic acid cyclobutylamide and 5-Fluoro-4-hydroxy-quinoline-2-carboxylic acid was used instead of (S)-Pyrrolidine-2-carboxylic acid cyclopropylamide hydrochloride and 4-Hydroxy-7-methyl-quinoline-2-carboxylic acid. MS (ES$^+$): m/e=685.

Example 175

4-[(S)-4-Carboxy-2-({4-[2-((S)-2-cyclopropylcarbamoyl-pyrrolidin-1-yl)-2-oxo-ethoxy]-6-fluoro-quinoline-2-carbonyl}-amino)-butyryl]-piperazine-1-carboxylic acid ethyl ester The title compound was prepared by adapting the procedures described in example 3 with the difference that 6-Fluoro-4-hydroxy-quinoline-2-carboxylic acid was used instead of 4-Hydroxy-7-methyl-quinoline-2-carboxylic acid. MS (ES$^+$): m/e=671.

Example 176

4-[(S)-4-Carboxy-2-({4-[2-((S)-2-cyclobutylcarbamoyl-pyrrolidin-1-yl)-2-oxo-ethoxy]-6-fluoro-quinoline-2-carbonyl}-amino)-butyryl]-piperazine-1-carboxylic acid ethyl ester The title compound was prepared by adapting the procedures described in example 3 with the difference that (S)-Pyrrolidine-2-carboxylic acid cyclobutylamide and 6-Fluoro-4-hydroxy-quinoline-2-carboxylic acid was used instead of (S)-Pyrrolidine-2-carboxylic acid cyclopropylamide hydrochloride and 4-Hydroxy-7-methyl-quinoline-2-carboxylic acid. MS (ES$^+$): m/e=685.

Example 177

4-[(S)-4-Carboxy-2-({4-[2-((S)-2-cyclobutylcarbamoyl-azetidin-1-yl)-2-oxo-ethoxy]-6-fluoro-quinoline-2-carbonyl}-amino)-butyryl]-piperazine-1-carboxylic acid ethyl ester The title compound was prepared by adapting the procedures described in example 3 with the difference that (S)-Azetidine-2-carboxylic acid cyclobutylamide and 6-Fluoro-4-hydroxy-quinoline-2-carboxylic acid was used instead of (S)-Pyrrolidine-2-carboxylic acid cyclopropylamide hydrochloride and 4-Hydroxy-7-methyl-quinoline-2-carboxylic acid. MS (ES$^+$): m/e=671.

Example 178

4-[(S)-4-Carboxy-2-({5-fluoro-4-[2-(4-hydroxy-piperidin-1-yl)-2-oxo-ethoxy]-quinoline-2-carbonyl}-amino)-butyryl]-piperazine-1-carboxylic acid ethyl ester The title compound was prepared by adapting the procedures described in example 3 with the difference that Piperidin-4-ol and 5-Fluoro-4-hydroxy-quinoline-2-carboxylic acid was used instead of (S)-Pyrrolidine-2-carboxylic acid cyclopropylamide hydrochloride and 4-Hydroxy-7-methyl-quinoline-2-carboxylic acid. MS (ES$^+$): m/e=618.

Example 179

4-[(S)-4-Carboxy-2-({4-[2-((S)-2-ethylcarbamoyl-pyrrolidin-1-yl)-2-oxo-ethoxy]-5-fluoro-quinoline-2-carbonyl}-amino)-butyryl]-piperazine-1-carboxylic acid ethyl ester The title compound was prepared by adapting the procedures described in example 3 with the difference that (S)-Pyrrolidine-2-carboxylic acid ethylamide and 5-Fluoro-4-hydroxy-quinoline-2-carboxylic acid was used instead of (S)-Pyrrolidine-2-carboxylic acid cyclopropylamide hydrochloride and 4-Hydroxy-7-methyl-quinoline-2-carboxylic acid. MS (ES$^+$): m/e=659.

Example 180

4-[(S)-4-Carboxy-2-({4-[2-((S)-2-cyclobutylcarbamoyl-azetidin-1-yl)-2-oxo-ethoxy]-5-fluoro-quinoline-2-carbonyl}-amino)-butyryl]-piperazine-1-carboxylic acid ethyl ester The title compound was prepared by adapting the procedures described in example 3 with the difference that (S)-Azetidine-2-carboxylic acid cyclobutylamide and 5-Fluoro-4-hydroxy-quinoline-2-carboxylic acid was used instead of (S)-Pyrrolidine-2-carboxylic acid cyclopropylamide hydrochloride and 4-Hydroxy-7-methyl-quinoline-2-carboxylic acid. MS (ES$^+$): m/e=671.

Example 181

4-{(S)-2-[(4-{2-[(S)-2-(Azetidine-1-carbonyl)-pyrrolidin-1-yl]-2-oxo-ethoxy}-7-methyl-quinoline-2-carbonyl)-amino]-4-carboxy-butyryl}-piperazine-1-carboxylic acid ethyl ester The title compound was prepared by adapting the procedures described in example 3 with the difference that Azetidin-1-yl-(S)-pyrrolidin-2-yl-methanone was used instead of (S)-Pyrrolidine-2-carboxylic acid cyclopropylamide hydrochloride. MS (ES$^+$): m/e=667.

Example 182

4-{(S)-4-Carboxy-2-[(7-methyl-4-{2-oxo-2-[(S)-2-(pyrrolidine-1-carbonyl)-pyrrolidin-1-yl]ethoxyl}-quinoline-2-carbonyl)-amino]butyryl}-piperazine-1-carboxylic acid ethyl ester The title compound was prepared by adapting the procedures described in example 3 with the difference that (S)-Pyrrolidin-2-yl-pyrrolidin-1-yl-methanone was used instead of (S)-Pyrrolidine-2-carboxylic acid cyclopropylamide. MS (ES+): m/e=681.

Example 182

4-{(S)-4-Carboxy-2-[(7-methyl-4-{2-oxo-2-[(S)-2-(piperidine-1-carbonyl)-pyrrolidin-1-yl]-ethoxyl}-quinoline-2-carbonyl)-amino]-butyryl}-piperazine-1-carboxylic acid ethyl ester The title compound was prepared by adapting the procedures described in example 3 with the difference that Piperidin-1-yl-(S)-pyrrolidin-2-yl-methanone was used instead of (S)-Pyrrolidine-2-carboxylic acid cyclopropylamide. MS (ES+): m/e=695.

Example 183

4-[(S)-4-Carboxy-2-({4-[2-((S)-2-cyclopentylcarbamoyl-pyrrolidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that (S)-Pyrrolidine-2-carboxylic acid cyclopentylamide was used instead of (S)-Pyrrolidine-2-carboxylic acid cyclopropylamide. MS (ES+): m/e=695.

Example 184

4-[(S)-4-Carboxy-2-({4-[2-((S)-2-cyclopropylcarbamoyl-pyrrolidin-1-yl)-2-oxo-ethoxy]-7,8,9,10-tetrahydro-benzo[h]quinoline-2-carbonyl}-amino)-butyryl]-piperazine-1-carboxylic acid ethyl ester The title compound was prepared by adapting the procedures described in example 56 with the difference that 4-{(S)-4-tert-Butoxycarbonyl-2-[(4-hydroxy-7,8,9,10-tetrahydro-benzo[h]quinoline-2-carbonyl)-amino]-butyryl}-piperazine-1-carboxylic acid ethyl ester was used instead of 4-{(S)-4-tert-Butoxycarbonyl-2-[(4-hydroxy-5,7-dimethyl-quinoline-2-carbonyl)-amino]-butyryl}-piperazine-1-carboxylic acid ethyl ester. MS (ES+): m/e=707.

Example 185

4-[(S)-3-Carboxy-2-({4-[(S)-2-((S)-2-cyclopentylcarbamoyl-pyrrolidin-1-yl)-1-methyl-2-oxo-ethoxy]-7-methyl-quinoline-2-carbonyl}-amino)-propionyl]-piperazine-1-carboxylic acid ethyl ester (i) 4-((S)-2-{[4-((S)-1-Benzyloxycarbonyl-ethoxy)-7-methyl-quinoline-2-carbonyl]-amino}-3-tert-butoxycarbonyl-propionyl)-piperazine-1-carboxylic acid ethyl ester To a solution of 1 g of 4-{(S)-3-tert-Butoxycarbonyl-2-[(4-hydroxy-7-methyl-quinoline-2-carbonyl)-amino]-propionyl}-piperazine-1-carboxylic acid ethyl ester and 350 mg of (R)-2-Hydroxy-propionic acid benzyl ester in 20 ml of THF, 764 mg of Triphenyl-phosphane and 507 mg of Diethyl azodicarboxylate was added and stirred for 2 h. Then, the reaction mixture was diluted with water and extracted with ethyl acetate. The organic phase was dried over MgSO$_4$ and the solvents were removed under reduced pressure. The crude product was purified by chromatography on silica gel eluting with a gradient of n-heptane/ethyl acetate. The fractions containing the product were combined and the solvent evaporated under reduced pressure. Yield: 1.3 g.

(ii) 4-((S)-3-tert-Butoxycarbonyl-2-{[4-((S)-1-carboxy-ethoxy)-7-methyl-quinoline-2-carbonyl]-amino}-propionyl)-piperazine-1-carboxylic acid ethyl ester A solution of 1.3 g of 4-((S)-2-{[4-((S)-1-Benzyloxycarbonyl-ethoxy)-7-methyl-quinoline-2-carbonyl]-amino}-3-tert-butoxycarbonyl-propionyl)-piperazine-1-carboxylic acid ethyl ester in 20 ml of ethyl acetate was purged with argon. Then, 200 mg of Pd/C (5-10%) was added and the mixture was stirred under a hydrogen atmosphere (3 bar). After 16 h the reaction mixture was filtered through a pad of celite and the solvents were removed under reduced pressure. After drying under reduced pressure the product was pure enough for the next reaction step. Yield: 1.2 g.

(iii) 4-[(S)-3-tert-Butoxycarbonyl-2-({4-[(S)-2-((S)-2-cyclopentylcarbamoyl-pyrrolidin-1-yl)-1-methyl-2-oxo-ethoxy]-7-methyl-quinoline-2-carbonyl}-amino)-propionyl]-piperazine-1-carboxylic acid ethyl ester To a solution of 146 mg of 4-((S)-3-tert-Butoxycarbonyl-2-{[4-((S)-1-carboxy-ethoxy)-7-methyl-quinoline-2-carbonyl]-amino}-propionyl)-piperazine-1-carboxylic acid ethyl ester in 1 ml of DMF, 52 mg of EDC, 34 mg of pentafluorophenol and 24 mg of NEM was added and the reaction mixture was stirred for 2 h. Then, 62 mg of (S)-Pyrrolidine-2-carboxylic acid cyclopentylamide trifluoroacetate and 20 mg of NEM in 2 ml of DMF was added. After 1 h the reaction mixture was diluted with water. After filtration through a chem Elut® cartridge by eluting with ethyl acetate the solvents were removed under reduced pressure. The isolated crude product was pure enough for the next reaction step.

(iv) 4-[(S)-3-Carboxy-2-({4-[(S)-2-((S)-2-cyclopentylcarbamoyl-pyrrolidin-1-yl)-1-methyl-2-oxo-ethoxy]-7-methyl-quinoline-2-carbonyl}-amino)-propionyl]-piperazine-1-carboxylic acid ethyl ester To a solution of the 4-[(S)-3-tert-Butoxycarbonyl-2-({4-[(S)-2-((S)-2-cyclopentylcarbamoyl-pyrrolidin-1-yl)-1-methyl-2-oxo-ethoxy]-7-methyl-quinoline-2-carbonyl}-amino)-propionyl]-piperazine-1-carboxylic acid ethyl ester obtained by the preceding reaction step in 1 ml of DCM, 2 ml of TFA was added at RT. After 1 h 20 ml of toluene was added and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. Yield: 5 mg MS (ES+): m/e=695.

Example 186

4-[(S)-3-Carboxy-2-({4-[(S)-2-((S)-2-cyclopentyl-carbamoyl-azetidin-1-yl)-1-methyl-2-oxo-ethoxy]-7-methyl-quinoline-2-carbonyl}-amino)-propionyl]-piperazine-1-carboxylic acid ethyl ester The title compound was prepared by adapting the procedures described in example 185 with the difference that (S)-Azetidine-2-carboxylic acid cyclopentylamide was used instead of (S)-Pyrrolidine-2-carboxylic acid cyclopentylamide. MS (ES$^+$): m/e=681.

Example 187

4-[(S)-3-Carboxy-2-({4-[(S)-2-((S)-2-cyclopropyl-carbamoyl-pyrrolidin-1-yl)-1-methyl-2-oxo-ethoxy]-7-methyl-quinoline-2-carbonyl}-amino)-propionyl]-piperazine-1-carboxylic acid ethyl ester The title compound was prepared by adapting the procedures described in example 185 with the difference that (S)-Pyrrolidine-2-carboxylic acid cyclopropylamide was used instead of (S)-Pyrrolidine-2-carboxylic acid cyclopentylamide. MS (ES$^+$): m/e=667.

Example 188

4-[(S)-3-Carboxy-2-({4-[(S)-2-((S)-2-ethylcarbamoyl-pyrrolidin-1-yl)-1-methyl-2-oxo-ethoxy]-7-methyl-quinoline-2-carbonyl}-amino)-propionyl]-piperazine-1-carboxylic acid ethyl ester The title compound was prepared by adapting the procedures described in example 185 with the difference that (S)-Pyrrolidine-2-carboxylic acid ethylamide was used instead of (S)-Pyrrolidine-2-carboxylic acid cyclopentylamide. MS (ES$^+$): m/e=655.

Example 189

4-[(S)-3-Carboxy-2-({4-[(S)-2-(4-hydroxy-piperidin-1-yl)-1-methyl-2-oxo-ethoxy]-7-methyl-quinoline-2-carbonyl}-amino)-propionyl]-piperazine-1-carboxylic acid ethyl ester The title compound was prepared by adapting the procedures described in example 185 with the difference that Piperidin-4-ol was used instead of (S)-Pyrrolidine-2-carboxylic acid cyclopentylamide. MS (ES$^+$): m/e=614.

Example 190

4-[(S)-3-Carboxy-2-({4-[(S)-2-((S)-2-hydroxymethyl-pyrrolidin-1-yl)-1-methyl-2-oxo-ethoxy]-7-methyl-quinoline-2-carbonyl}-amino)-propionyl]-piperazine-1-carboxylic acid ethyl ester The title compound was prepared by adapting the procedures described in example 185 with the difference that (S)-1-Pyrrolidin-2-yl-methanol was used instead of (S)-Pyrrolidine-2-carboxylic acid cyclopentylamide. MS (ES$^+$): m/e=614.

Example 191

4-[(S)-3-Carboxy-2-({4-[(S)-2-((S)-3-hydroxymethyl-pyrrolidin-1-yl)-1-methyl-2-oxo-ethoxy]-7-methyl-quinoline-2-carbonyl}-amino)-propionyl]-piperazine-1-carboxylic acid ethyl ester The title compound was prepared by adapting the procedures described in example 185 with the difference that (S)-1-Pyrrolidin-3-yl-methanol was used instead of (S)-Pyrrolidine-2-carboxylic acid cyclopentylamide. MS (ES$^+$): m/e=614.

Example 192

4-[(S)-3-Carboxy-2-({4-[(S)-2-((S)-2-cyclobutylcarbamoyl-azetidin-1-yl)-1-methyl-2-oxo-ethoxy]-7-methyl-quinoline-2-carbonyl}-amino)-propionyl]-piperazine-1-carboxylic acid ethyl ester The title compound was prepared by adapting the procedures described in example 185 with the difference that (S)-Azetidine-2-carboxylic acid cyclobutylamide was used instead of (S)-Pyrrolidine-2-carboxylic acid cyclopentylamide. MS (ES$^+$): m/e=667.

Example 193

4-[(S)-3-Carboxy-2-({4-[(S)-2-((S)-2-isopropylcarbamoyl-pyrrolidin-1-yl)-1-methyl-2-oxo-ethoxy]-7-methyl-quinoline-2-carbonyl}-amino)-propionyl]-piperazine-1-carboxylic acid ethyl ester The title compound was prepared by adapting the procedures described in example 185 with the difference that (S)-Pyrrolidine-2-carboxylic acid isopropylamide was used instead of (S)-Pyrrolidine-2-carboxylic acid cyclopentylamide. MS (ES$^+$): m/e=669.

Example 194

4-[(S)-4-Carboxy-2-({4-[2-((S)-2-cyclopentylcarbamoyl-azetidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that (S)-Azetidine-2-carboxylic acid cyclopentylamide was used instead of (S)-Pyrrolidine-2-carboxylic acid cyclopropylamide hydrochloride. MS (ES$^+$): m/e=681.

Example 195

4-[(S)-4-Carboxy-2-({4-[2-((S)-2-ethylcarbamoyl-pyrrolidin-1-yl)-2-oxo-ethoxy]-6,7-difluoro-quinoline-2-carbonyl}-amino)-butyryl]-piperazine-1-carboxylic acid ethyl ester The title compound was prepared by adapting the procedures described in example 3 with the difference that (S)-Pyrrolidine-2-carboxylic acid ethylamide and 6,7-Difluoro-4-hydroxy-quinoline-2-carboxylic acid was used instead of (S)-Pyrrolidine-2-carboxylic acid cyclopropylamide hydrochloride and 4-Hydroxy-7-methyl-quinoline-2-carboxylic acid. MS (ES$^+$): m/e=677.

Example 196

4-[(S)-4-Carboxy-2-({4-[2-((S)-2-cyclobutylcarbamoyl-pyrrolidin-1-yl)-2-oxo-ethoxy]-6,7-difluoro-quinoline-2-carbonyl}-amino)-butyryl]-piperazine-1-carboxylic acid ethyl ester The title compound was prepared by adapting the procedures described in example 3 with the difference that (S)-Pyrrolidine-2-carboxylic acid cyclobutylamide and 6,7-Difluoro-4-hydroxy-quinoline-2-carboxylic acid was used instead of (S)-Pyrrolidine-2-carboxylic acid cyclopropylamide hydrochloride and 4-Hydroxy-7-methyl-quinoline-2-carboxylic acid. MS (ES+): m/e=703.

Example 197

4-[(S)-3-Carboxy-2-({4-[2-((S)-2-ethylcarbamoyl-pyrrolidin-1-yl)-2-oxo-ethoxy]-7-methyl-quinoline-2-carbonyl}-amino)-propionyl]-piperazine-1-carboxylic acid ethyl ester (i) 4-((S)-2-Benzyloxycarbonylamino-3-tert-butoxycarbonyl-propionyl)-piperazine-1-carboxylic acid ethyl ester To a solution of 25 g of (S)-2-Benzyloxycarbonylaminosuccinic acid 4-tert-butyl ester, 35.6 g of NEM and 25.3 g of TOTU in 125 ml of DMF, 12.9 g of Piperazine-1-carboxylic acid ethyl ester was added at RT and stirred for 3 h. The reaction mixture was diluted saturated aqueous sodium hydrogen carbonate solution and extracted with 400 ml of ethyl acetate. The organic phase was washed with diluted saturated aqueous sodium hydrogen carbonate solution and dried over $MgSO_4$ and the solvents were removed under reduced pressure. The crude product was purified by chromatography on silica gel eluting with n-heptane/ethyl acetate (1/1). The fractions containing the product were combined and the solvent evaporated under reduced pressure. Yield: 35.4 g.

(ii) 4-((S)-2-Amino-3-tert-butoxycarbonyl-propionyl)-piperazine-1-carboxylic acid ethyl ester A solution of 20.6 g of 4-((S)-2-Benzyloxycarbonylamino-3-tert-butoxycarbonyl-propionyl)-piperazine-1-carboxylic acid ethyl ester in 200 ml of ethanol was purged with argon. Then, 3.5 g of Pd/C (5-10%) was added and the mixture stirred under a hydrogen atmosphere (4 bar). After 16 h the reaction mixture was filtered through a pad of celite and the solvents were removed under reduced pressure. After drying under reduced pressure the product was pure enough for the next reaction step. Yield: 24.5 g.

(iii) 4-{(S)-3-tert-Butoxycarbonyl-2-[(4-hydroxy-7-methyl-quinoline-2-carbonyl)-amino]-propionyl}-piperazine-1-carboxylic acid ethyl ester To a solution of 4 g of 4-Hydroxy-7-methyl-quinoline-2-carboxylic acid and 6.4 g of 4-((S)-2-Amino-3-tert-butoxycarbonyl-propionyl)-piperazine-1-carboxylic acid ethyl ester in 37 ml of DMF, 3.0 g of HOBT and 3.7 g of EDC was added and the reaction mixture was stirred for 2 h at RT. Then, the reaction mixture was diluted with water and extracted with ethyl acetate. The organic phase was dried over $MgSO_4$ and the solvents were removed under reduced pressure. The crude product was purified by crystallization from ethyl acetate/heptane. Yield: 5.4 g.

(iv) 4-{(S)-2-[(4-Benzyloxycarbonylmethoxy-7-methyl-quinoline-2-carbonyl)-amino]-3-tert-butoxycarbonyl-propionyl}-piperazine-1-carboxylic acid ethyl ester To a solution of 3 g of 4-{(S)-3-tert-Butoxycarbonyl-2-[(4-hydroxy-7-methyl-quinoline-2-carbonyl)-amino]-propionyl}-piperazine-1-carboxylic acid ethyl ester and 1.5 g of Bromo-acetic acid benzyl ester in 38 ml of DMF, 2 g of cesium carbonate was added. The reaction mixture was stirred for 4 h at RT, diluted with water and extracted with ethyl acetate. The organic phase was dried over $MgSO_4$ and the solvents were removed under reduced pressure. The crude product was purified by chromatography on silica gel eluting with a gradient of n-heptane/ethyl acetate. The fractions containing the product were combined and the solvent evaporated under reduced pressure. Yield: 2.8 g.

(v) 4-{(S)-3-tert-Butoxycarbonyl-2-[(4-carboxymethoxy-7-methyl-quinoline-2-carbonyl)-amino]-propionyl}-piperazine-1-carboxylic acid ethyl ester A solution of 2.8 g of 4-{(S)-2-[(4-Benzyloxycarbonylmethoxy-7-methyl-quinoline-2-carbonyl)-amino]-3-tert-butoxycarbonyl-propionyl}-piperazine-1-carboxylic acid ethyl ester in 30 ml of ethyl acetate was purged with argon. Then, 280 mg of Pd/C (5-10%) was added and the mixture stirred under a hydrogen atmosphere (3 bar). After 4 h the reaction mixture was filtered through a pad of celite and the solvents were removed under reduced pressure. After drying under reduced pressure the product was pure enough for the next reaction step. Yield: 2.2 g.

(vi) 4-[(S)-3-tert-Butoxycarbonyl-2-({4-[2-((S)-2-ethylcarbamoyl-pyrrolidin-1-yl)-2-oxo-ethoxy]-7-methyl-quinoline-2-carbonyl}-amino)-propionyl]-piperazine-1-carboxylic acid ethyl ester To a solution of 80 mg of 4-{(S)-3-tert-Butoxycarbonyl-2-[(4-carboxymethoxy-7-methyl-quinoline-2-carbonyl)-amino]-propionyl}-piperazine-1-carboxylic acid ethyl ester in 8 ml of DMF, 33 mg of EDC, 32 mg of pentafluorophenol and 24 mg of NEM was added and the reaction mixture was stirred for 2 h. Then, 39 mg of (S)-Pyrrolidine-2-carboxylic acid ethylamide trifluoroacetate and 20 mg of NEM in 5 ml of DMF was added. After 1 h the reaction mixture was diluted with water. After filtration through a chem Elut® cartridge by eluting with ethyl acetate the solvents were removed under reduced pressure. The isolated crude product was pure enough for the next reaction step.

(vii) 4-[(S)-3-Carboxy-2-({4-[2-((S)-2-ethylcarbamoyl-pyrrolidin-1-yl)-2-oxo-ethoxy]-7-methyl-quinoline-2-carbonyl}-amino)-propionyl]-piperazine-1-carboxylic acid ethyl ester To a solution of 184 mg of 4-[(S)-3-tert-Butoxycarbonyl-2-({4-[2-((S)-2-ethylcarbamoyl-pyrrolidin-1-yl)-2-oxo-ethoxy]-7-methyl-quinoline-2-carbonyl}-amino)-propionyl]-piperazine-1-carboxylic acid ethyl ester in 1 ml of DCM, 2 ml of TFA was added at RT. After 1 h 20 ml of toluene was added and the solvents were removed under reduced pressure.

The residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. Yield: 19 mg MS (ES+): m/e=641.

Example 198

4-[(S)-3-Carboxy-2-({4-[2-((S)-2-isopropylcarbamoyl-pyrrolidin-1-yl)-2-oxo-ethoxy]-7-methyl-quinoline-2-carbonyl}-amino)-propionyl]-piperazine-1-carboxylic acid ethyl ester The title compound was prepared by adapting the procedures described in example 197 with the difference that (S)-Pyrrolidine-2-carboxylic acid isopropylamide was used instead of (S)-Pyrrolidine-2-carboxylic acid ethylamide. MS (ES+): m/e=655.

Example 199

4-[(S)-3-Carboxy-2-({4-[2-((S)-2-cyclopentylcarbamoyl-pyrrolidin-1-yl)-2-oxo-ethoxy]-7-methyl-quinoline-2-carbonyl}-amino)-propionyl]-piperazine-1-carboxylic acid ethyl ester The title compound was prepared by adapting the procedures described in example 197 with the difference that (S)-Pyrrolidine-2-carboxylic acid cyclopentylamide was used instead of (S)-Pyrrolidine-2-carboxylic acid ethylamide. MS (ES+): m/e=681.

Example 200

4-{(S)-3-Carboxy-2-[(4-{2-[(S)-2-(cyclopropylmethyl-carbamoyl)-pyrrolidin-1-yl]-2-oxo-ethoxy}-7-methyl-quinoline-2-carbonyl)-amino]-propionyl}-piperazine-1-carboxylic acid ethyl ester The title compound was prepared by adapting the procedures described in example 197 with the difference that (S)-Pyrrolidine-2-carboxylic acid cyclopropylmethyl-amide was used instead of (S)-Pyrrolidine-2-carboxylic acid ethylamide. MS (ES+): m/e=667.

Example 201

4-[(S)-3-Carboxy-2-({4-[2-((S)-2-cyclopentylcarbamoyl-azetidin-1-yl)-2-oxo-ethoxy]-7-methyl-quinoline-2-carbonyl}-amino)-propionyl]-piperazine-1-carboxylic acid ethyl ester The title compound was prepared by adapting the procedures described in example 197 with the difference that (S)-Azetidine-2-carboxylic acid cyclopentylamide was used instead of (S)-Pyrrolidine-2-carboxylic acid ethylamide. MS (ES+): m/e=667.

Example 202

4-[(S)-3-Carboxy-2-({4-[2-((S)-2-cyclopentylcarbamoyl-azetidin-1-yl)-2-oxo-ethoxy]-quinoline-2-carbonyl}-amino)-propionyl]-piperazine-1-carboxylic acid ethyl ester The title compound was prepared by adapting the procedures described in example 197 with the difference that (S)-Azetidine-2-carboxylic acid cyclopentylamide and 4-Hydroxy-quinoline-2-carboxylic acid was used instead of (S)-Pyrrolidine-2-carboxylic acid ethylamide and 4-Hydroxy-7-methyl-quinoline-2-carboxylic acid. MS (ES+): m/e=653.

Example 203

4-[(S)-3-Carboxy-2-({4-[2-((S)-2-cyclopropylcarbamoyl-pyrrolidin-1-yl)-2-oxo-ethoxy]-7-methyl-quinoline-2-carbonyl}-amino)-propionyl]-piperazine-1-carboxylic acid ethyl ester The title compound was prepared by adapting the procedures described in example 197 with the difference that 4-{(S)-3-tert-Butoxycarbonyl-2-[(4-hydroxy-7-methyl-quinoline-2-carbonyl)-amino]-propionyl}-piperazine-1-carboxylic acid ethyl ester was used instead of 4-{(S)-4-tert-Butoxycarbonyl-2-[(4-hydroxy-5,7-dimethyl-quinoline-2-carbonyl)-amino]-butyryl}-piperazine-1-carboxylic acid ethyl ester. MS (ES+): m/e=653.

Example 204

4-[(S)-3-Carboxy-2-({7-methyl-4-[2-oxo-2-((S)-2-propylcarbamoyl-pyrrolidin-1-yl)-ethoxy]-quinoline-2-carbonyl}-amino)-propionyl]-piperazine-1-carboxylic acid ethyl ester The title compound was prepared by adapting the procedures described in example 197 with the difference that (S)-Pyrrolidine-2-carboxylic acid propylamide was used instead of (S)-Pyrrolidine-2-carboxylic acid ethylamide. MS (ES+): m/e=655.

Example 205

4-[(S)-3-Carboxy-2-({4-[2-((S)-2-cyclopentylcarbamoyl-pyrrolidin-1-yl)-2-oxo-ethoxy]-quinoline-2-carbonyl}-amino)-propionyl]-piperazine-1-carboxylic acid ethyl ester The title compound was prepared by adapting the procedures described in example 197 with the difference that (S)-Pyrrolidine-2-carboxylic acid cyclopentylamide and 4-Hydroxy-quinoline-2-carboxylic acid was used instead of (S)-Pyrrolidine-2-carboxylic acid ethylamide and 4-Hydroxy-7-methyl-quinoline-2-carboxylic acid. MS (ES+): m/e=667.

Example 206

4-[(S)-4-Carboxy-2-({4-[2-((S)-2-ethylcarbamoyl-pyrrolidin-1-yl)-2-oxo-ethoxy]-7-methoxy-quinoline-2-carbonyl}-amino)-butyryl]-piperazine-1-carboxylic acid ethyl ester The title compound was prepared by adapting the procedures described in example 3 with the difference that (S)-Pyrrolidine-2-carboxylic acid ethylamide and 4-Hydroxy-7-methoxy-quinoline-2-carboxylic acid was used instead of (S)-Pyrrolidine-2-carboxylic acid cyclopropylamide hydrochloride and 4-Hydroxy-7-methyl-quinoline-2-carboxylic acid. MS (ES+): m/e=657.

Example 207

4-[(S)-4-Carboxy-2-({4-[2-((S)-2-cyclobutylcarbamoyl-pyrrolidin-1-yl)-2-oxo-ethoxy]-7-methoxy-quinoline-2-carbonyl}-amino)-butyryl]-piperazine-1-carboxylic acid ethyl ester The title compound was prepared by adapting the procedures described in example 3 with the difference that (S)-Pyrrolidine-2-carboxylic acid cyclobutylamide and 4-Hydroxy-7-methoxy-quinoline-2-carboxylic acid was used instead of (S)-Pyrrolidine-2-carboxylic acid cyclopropylamide hydrochloride and 4-Hydroxy-7-methyl-quinoline-2-carboxylic acid. MS (ES$^+$): m/e=697.

Example 208

4-[(S)-4-Carboxy-2-({7-ethyl-4-[2-((S)-2-ethylcarbamoyl-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 3 with the difference that (S)-Pyrrolidine-2-carboxylic acid ethylamide and 7-Ethyl-4-hydroxy-quinoline-2-carboxylic acid was used instead of (S)-Pyrrolidine-2-carboxylic acid cyclopropylamide hydrochloride and 4-Hydroxy-7-methyl-quinoline-2-carboxylic acid. MS (ES$^+$): m/e=669.

Example 209

4-[(S)-4-Carboxy-2-({4-[2-((S)-2-cyclobutylcarbamoyl-pyrrolidin-1-yl)-2-oxo-ethoxy]-7-ethyl-quinoline-2-carbonyl}-amino)-butyryl]-piperazine-1-carboxylic acid ethyl ester The title compound was prepared by adapting the procedures described in example 3 with the difference that (S)-Pyrrolidine-2-carboxylic acid cyclobutylamide and 7-Ethyl-4-hydroxy-quinoline-2-carboxylic acid was used instead of (S)-Pyrrolidine-2-carboxylic acid cyclopropylamide hydrochloride and 4-Hydroxy-7-methyl-quinoline-2-carboxylic acid. MS (ES$^+$): m/e=695.

Example 210

4-[(S)-4-Carboxy-2-({4-[2-((S)-2-cyclopropylcarbamoyl-pyrrolidin-1-yl)-2-oxo-ethoxy]-7-ethyl-quinoline-2-carbonyl}-amino)-butyryl]-piperazine-1-carboxylic acid ethyl ester The title compound was prepared by adapting the procedures described in example 3 with the difference that 7-Ethyl-4-hydroxy-quinoline-2-carboxylic acid was used instead of 4-Hydroxy-7-methyl-quinoline-2-carboxylic acid. MS (ES$^+$): m/e=681.

Example 211

4-[(S)-4-Carboxy-2-({4-[2-((S)-2-ethylcarbamoyl-pyrrolidin-1-yl)-2-oxo-ethoxy]-6-fluoro-5-methyl-quinoline-2-carbonyl}-amino)-butyryl]-piperazine-1-carboxylic acid ethyl ester The title compound was prepared by adapting the procedures described in example 3 with the difference that (S)-Pyrrolidine-2-carboxylic acid ethylamide and 6-Fluoro-4-hydroxy-5-methyl-quinoline-2-carboxylic acid was used instead of (S)-Pyrrolidine-2-carboxylic acid cyclopropylamide hydrochloride and 4-Hydroxy-7-methyl-quinoline-2-carboxylic acid. MS (ES$^+$): m/e=673.

Example 212

4-[(S)-4-Carboxy-2-({4-[2-((S)-2-cyclobutylcarbamoyl-pyrrolidin-1-yl)-2-oxo-ethoxy]-6-fluoro-5-methyl-quinoline-2-carbonyl}-amino)-butyryl]-piperazine-1-carboxylic acid ethyl ester The title compound was prepared by adapting the procedures described in example 3 with the difference that (S)-Pyrrolidine-2-carboxylic acid cyclobutylamide and 6-Fluoro-4-hydroxy-5-methyl-quinoline-2-carboxylic acid was used instead of (S)-Pyrrolidine-2-carboxylic acid cyclopropylamide hydrochloride and 4-Hydroxy-7-methyl-quinoline-2-carboxylic acid. MS (ES$^+$): m/e=699.

Example 213

4-[(S)-4-Carboxy-2-({4-[2-((S)-2-cyclopropylcarbamoyl-pyrrolidin-1-yl)-2-oxo-ethoxy]-6-ethoxy-quinoline-2-carbonyl}-amino)-butyryl]-piperazine-1-carboxylic acid ethyl ester The title compound was prepared by adapting the procedures described in example 3 with the difference that 6-Ethoxy-4-hydroxy-quinoline-2-carboxylic acid was used instead of 4-Hydroxy-7-methyl-quinoline-2-carboxylic acid. MS (ES$^+$): m/e=697.

Example 214

4-[(S)-4-Carboxy-2-({6-ethoxy-4-[2-((S)-2-ethylcarbamoyl-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 3 with the difference that (S)-Pyrrolidine-2-carboxylic acid ethylamide and 6-Ethoxy-4-hydroxy-quinoline-2-carboxylic acid was used instead of (S)-Pyrrolidine-2-carboxylic acid cyclopropylamide hydrochloride and 4-Hydroxy-7-methyl-quinoline-2-carboxylic acid. MS (ES$^+$): m/e=685.

Example 215

4-[(S)-4-Carboxy-2-({4-[2-((S)-2-cyclobutylcarbamoyl-pyrrolidin-1-yl)-2-oxo-ethoxy]-6-ethoxy-quinoline-2-carbonyl}-amino)-butyryl]-piperazine-1-carboxylic acid ethyl ester The title compound was prepared by adapting the procedures described in example 3 with the difference that (S)-Pyrrolidine-2-carboxylic acid cyclobutylamide and 6-Ethoxy-4-hydroxy-quinoline-2-carboxylic acid was used instead of (S)-Pyrrolidine-2-carboxylic acid cyclopropylamide hydrochloride and 4-Hydroxy-7-methyl-quinoline-2-carboxylic acid. MS (ES$^+$): m/e=711.

Example 216

4-[(S)-4-Carbamoyl-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester To 10 ml of a saturated solution of ammonia in methanol (7M) 43 mg of 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-ethoxycarbonyl-butyryl]-piperazine-1-carboxylic acid ethyl ester and 10 mg of sodium cyanide was added and the reaction was stirred at 40° C. for two days. Then, 20 ml of toluene was added and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. Yield: 12 mg MS (ES$^+$): m/e=680.

Example 217

4-{(S)-4-Carboxy-2-[(6-fluoro-7-methyl-4-{2-oxo-2-[(S)-2-(pyrrolidine-1-carbonyl)-pyrrolidin-1-yl]-ethoxy}-quinoline-2-carbonyl)-amino]-butyryl}-piperazine-1-carboxylic acid ethyl ester The title compound was prepared by adapting the procedures described in example 3 with the difference that (5)-pyrrolidin-2-yl-pyrrolidin-1-yl-methanone and 6-Fluoro-4-hydroxy-7-methyl-quinoline-2-carboxylic acid was used instead of (S)-Pyrrolidine-2-carboxylic acid cyclopropylamide hydrochloride and 4-Hydroxy-7-methyl-quinoline-2-carboxylic acid. MS (ES$^+$): m/e=699.

Example 218

4-[(S)-4-Carboxy-2-({4-[2-((S)-2-ethylcarbamoyl-pyrrolidin-1-yl)-2-oxo-ethoxy]-6-fluoro-7-methyl-quinoline-2-carbonyl}-amino)-butyryl]-piperazine-1-carboxylic acid ethyl ester The title compound was prepared by adapting the procedures described in example 3 with the difference that (S)-Pyrrolidine-2-carboxylic acid ethylamide and 6-Fluoro-4-hydroxy-7-methyl-quinoline-2-carboxylic acid was used instead of (S)-Pyrrolidine-2-carboxylic acid cyclopropylamide hydrochloride and 4-Hydroxy-7-methyl-quinoline-2-carboxylic acid. MS (ES$^+$): m/e=673.

Example 219

4-[(S)-4-Carboxy-2-({4-[2-((S)-2-cyclobutylcarbamoyl-pyrrolidin-1-yl)-2-oxo-ethoxy]-6-fluoro-7-methyl-quinoline-2-carbonyl}-amino)-butyryl]-piperazine-1-carboxylic acid ethyl ester The title compound was prepared by adapting the procedures described in example 3 with the difference that (S)-Pyrrolidine-2-carboxylic acid cyclobutylamide and 6-Fluoro-4-hydroxy-7-methyl-quinoline-2-carboxylic acid was used instead of (S)-Pyrrolidine-2-carboxylic acid cyclopropylamide hydrochloride and 4-Hydroxy-7-methyl-quinoline-2-carboxylic acid. MS (ES$^+$): m/e=699.

Example 220

4-{(S)-4-Carboxy-2-[(7-fluoro-4-{2-oxo-2-[(S)-2-(pyrrolidine-1-carbonyl)-pyrrolidin-1-yl]-ethoxy}-quinoline-2-carbonyl)-amino]-butyryl}-piperazine-1-carboxylic acid ethyl ester The title compound was prepared by adapting the procedures described in example 3 with the difference that (S)-pyrrolidin-2-yl-pyrrolidin-1-yl-methanone and 7-Fluoro-4-hydroxy-quinoline-2-carboxylic acid was used instead of (S)-Pyrrolidine-2-carboxylic acid cyclopropylamide hydrochloride and 4-Hydroxy-7-methyl-quinoline-2-carboxylic acid. MS (ES$^+$): m/e=685.

Example 221

4-[(S)-4-Carboxy-2-({7-fluoro-4-[2-oxo-2-((S)-2-propylcarbamoyl-pyrrolidin-1-yl)-ethoxy]-quinoline-2-carbonyl}-amino)-butyryl]-piperazine-1-carboxylic acid ethyl ester The title compound was prepared by adapting the procedures described in example 3 with the difference that (S)-Pyrrolidine-2-carboxylic acid propylamide and 7-Fluoro-4-hydroxy-quinoline-2-carboxylic acid was used instead of (S)-Pyrrolidine-2-carboxylic acid cyclopropylamide hydrochloride and 4-Hydroxy-7-methyl-quinoline-2-carboxylic acid. MS (ES$^+$): m/e=673.

Example 222

4-[(S)-4-Ethoxycarbonyl-2-({7-fluoro-4-[2-oxo-2-((S)-2-propylcarbamoyl-pyrrolidin-1-yl)-ethoxy]-quinoline-2-carbonyl}-amino)-butyryl]-piperazine-1-carboxylic acid ethyl ester To a solution of 31 mg of 4-[(S)-4-Carboxy-2-({7-fluoro-4-[2-oxo-2-((S)-2-propylcarbamoyl-pyrrolidin-1-yl)-ethoxy]-quinoline-2-carbonyl}-amino)-butyryl]-piperazine-1-carboxylic acid ethyl ester in 0.2 ml of ethanol, 1 ml of a saturated solution of hydrochloric acid in ethanol was added and the mixture was stirred for 16 h at RT. Then, 5 ml of toluene was added and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. Yield: 10 mg MS (ES$^+$): m/e=701.

Example 223

4-[(S)-4-Ethoxycarbonyl-2-({4-[2-((S)-2-ethylcarbamoyl-pyrrolidin-1-yl)-2-oxo-ethoxy]-7-fluoro-quinoline-2-carbonyl}-amino)-butyryl]-piperazine-1-carboxylic acid ethyl ester The title compound was prepared by adapting the procedure described in example 222 with the difference that 4-[(S)-4-Carboxy-2-({4-[2-((S)-2-ethylcarbamoyl-pyrrolidin-1-yl)-2-oxo-ethoxy]-7-fluoro-quinoline-2-carbonyl}-amino)-butyryl]-piperazine-1-carboxylic acid ethyl ester was used instead of 4-[(S)-4-Carboxy-2-({7-fluoro-4-[2-oxo-2-((S)-2-propylcarbamoyl-pyrrolidin-1-yl)-ethoxy]-quinoline-2-carbonyl}-amino)-butyryl]-piperazine-1-carboxylic acid ethyl ester. MS (ES$^+$): m/e=687.

Example 224

4-[(S)-2-({4-[2-((S)-2-Cyclobutylcarbamoyl-pyrrolidin-1-yl)-2-oxo-ethoxy]-7-fluoro-quinoline-2-carbonyl}-amino)-4-ethoxycarbonyl-butyryl]-piperazine-1-carboxylic acid ethyl ester The title compound was prepared by adapting the procedure described in example 222 with the difference that 4-[(S)-4-Carboxy-2-({4-[2-((S)-2-cyclobutylcarbamoyl-pyrrolidin-1-yl)-2-oxo-ethoxy]-7-fluoro-quinoline-2-carbonyl}-amino)-butyryl]-piperazine-1-carboxylic acid ethyl ester was used instead of 4-[(S)-4-Carboxy-2-({7-fluoro-4-[2-oxo-2-((S)-2-propylcarbamoyl-pyrrolidin-1-yl)-ethoxy]-quinoline-2-carbonyl}-amino)-butyryl]-piperazine-1-carboxylic acid ethyl ester. MS (ES$^+$): m/e=713.

Example 225

4-{(S)-4-Carboxy-2-[(4-{2-[(S)-2-(ethyl-methyl-carbamoyl)-pyrrolidin-1-yl]-2-oxo-ethoxy}-7-methyl-quinoline-2-carbonyl)-amino]-butyryl}-piperazine-1-carboxylic acid ethyl ester The title compound was prepared by adapting the procedures described in example 3 with the difference that (S)-Pyrrolidine-2-carboxylic acid ethyl-methyl-amide was used instead of (S)-Pyrrolidine-2-carboxylic acid cyclopropylamide hydrochloride. MS (ES$^+$): m/e=669.

Example 226

4-[(S)-3-Carboxy-2-({4-[(R)-2-((S)-2-cyclobutylcarbamoyl-pyrrolidin-1-yl)-1-methyl-2-oxo-ethoxy]-7-methyl-quinoline-2-carbonyl}-amino)-propionyl]-piperazine-1-carboxylic acid ethyl ester

(i) 4-((S)-2-{[4-((R)-1-Benzyloxycarbonyl-ethoxy)-7-methyl-quinoline-2-carbonyl]-amino}-3-carboxy-propionyl)-piperazine-1-carboxylic acid ethyl ester To a solution of 1 g of 4-{(S)-3-tert-Butoxycarbonyl-2-[(4-hydroxy-7-methyl-quinoline-2-carbonyl)-amino]-propionyl}-piperazine-1-carboxylic acid ethyl ester and 350 mg of (S)-2-Hydroxy-propionic acid benzyl ester in 20 ml of THF, 764 mg of Triphenyl-phosphane and 507 mg of Diethyl azodicarboxylate was added and stirred for 2 h. Then, the reaction mixture was diluted with water and extracted with ethyl acetate. The organic phase was dried over MgSO$_4$ and the solvents were removed under reduced pressure. The crude product was purified by chromatography on silica gel eluting with a gradient of n-heptane/ethyl acetate. The fractions containing the product were combined and the solvent evaporated under reduced pressure. Yield: 1.0 g.

(ii) 4-((S)-3-tert-Butoxycarbonyl-2-{[4-((R)-1-carboxy-ethoxy)-7-methyl-quinoline-2-carbonyl]-amino}-propionyl)-piperazine-1-carboxylic acid ethyl ester A solution of 1.3 g of 4-((S)-2-{[4-((R)-1-Benzyloxycarbonyl-ethoxy)-7-methyl-quinoline-2-carbonyl]-amino}-3-carboxy-propionyl)-piperazine-1-carboxylic acid ethyl ester in 20 ml of ethyl acetate was purged with argon. Then, 120 mg of Pd/C (5-10%) was added and the mixture stirred under a hydrogen atmosphere (3 bar). After 16 h the reaction mixture was filtered through a pad of celite and the solvents were removed under reduced pressure. After drying under reduced pressure the product was pure enough for the next reaction step. Yield: 850 mg.

(iii) (S)-2-Cyclobutylcarbamoyl-pyrrolidine-1-carboxylic acid tert-butyl ester To a solution of 1.5 g of (S)-Pyrrolidine-1,2-dicarboxylic acid 1-tert-butyl ester in 30 ml of DMF 948 mg of HOAT, 1.3 g of EDC and 495 mg of cyclobutylamine was added and the reaction mixture was stirred for 16 h at RT. Then, water was added and the reaction mixture was extracted with DCM. The organic phase was dried over MgSO$_4$ and the solvents were removed under reduced pressure. The crude product was pure enough for the next reaction step.

(iv) (S)-Pyrrolidine-2-carboxylic acid cyclobutylamide

The crude (S)-2-Cyclobutylcarbamoyl-pyrrolidine-1-carboxylic acid tert-butyl ester from the preceding reaction step was dissolved in 10 ml of DCM and 5 ml of TFA and stirred for 3 h. Then, the reaction mixture was diluted with 70 ml of toluene and the solvents were removed under reduced pressure. The residue was co-distilled additional 3 times with toluene. The product was obtained as its trifluoroacetate. Yield: 2 g.

(iii) 4-[(S)-3-tert-Butoxycarbonyl-2-({4-[(R)-2-((S)-2-cyclobutylcarbamoyl-pyrrolidin-1-yl)-1-methyl-2-oxo-ethoxy]-7-methyl-quinoline-2-carbonyl}-amino)-propionyl]-piperazine-1-carboxylic acid ethyl ester To a solution of 121 mg of 4-((S)-3-tert-Butoxycarbonyl-2-{[4-((R)-1-carboxy-ethoxy)-7-methyl-quinoline-2-carbonyl]-amino}-propionyl)-piperazine-1-carboxylic acid ethyl ester in 1 ml of DCM, 43 mg of EDC, 43 mg of pentafluorophenol and 27 mg of NEM was added and the reaction mixture was stirred for 2 h. Then, 67 mg of (S)-Pyrrolidine-2-carboxylic acid cyclobutylamide trifluoroacetate and 20 mg of NEM in 2 ml of DCM was added. After 1 h the reaction mixture was diluted with water. After filtration through a chem Elut® cartridge by eluting with ethyl acetate the solvents were removed under reduced pressure. The isolated crude product was pure enough for the next reaction step.

(iv) 4-[(S)-3-Carboxy-2-({4-[(R)-2-((S)-2-cyclobutylcarbamoyl-pyrrolidin-1-yl)-1-methyl-2-oxo-ethoxy]-7-methyl-quinoline-2-carbonyl}-amino)-propionyl]-piperazine-1-carboxylic acid ethyl ester To a solution of the 4-[(S)-3-tert-Butoxycarbonyl-2-({4-[(R)-2-((S)-2-cyclobutylcarbamoyl-pyrrolidin-1-yl)-1-methyl-2-oxo-ethoxy]-7-methyl-quinoline-2-carbonyl}-amino)-propionyl]-piperazine-1-carboxylic acid ethyl ester obtained by the preceding reaction step in 1 ml of DCM, 2 ml of TFA was added at RT. After 1 h, 20 ml of toluene was added and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. Yield: 39 mg MS (ES+): m/e=681.

Example 227

4-{(S)-3-Carboxy-2-[(7-methyl-4-{(R)-1-methyl-2-oxo-2-[(S)-2-(pyrrolidine-1-carbonyl)-pyrrolidin-1-yl]-ethoxy}-quinoline-2-carbonyl)-amino]-propionyl}-piperazine-1-carboxylic acid ethyl ester The title compound was prepared by adapting the procedures described in example 226 with the difference that (S)-Pyrrolidin-2-yl-pyrrolidin-1-yl-methanone was used instead of (S)-Pyrrolidine-2-carboxylic acid cyclobutylamide. MS (ES+): m/e=681.

Example 228

4-[(S)-3-Carboxy-2-({7-methyl-4-[(R)-1-methyl-2-oxo-2-((S)-2-propylcarbamoyl-pyrrolidin-1-yl)-ethoxy]-quinoline-2-carbonyl}-amino)-propionyl]-piperazine-1-carboxylic acid ethyl ester The title compound was prepared by adapting the procedures described in example 226 with the difference that (S)-Pyrrolidine-2-carboxylic acid propylamide was used instead of (S)-Pyrrolidine-2-carboxylic acid cyclobutylamide. MS (ES+): m/e=669.

Example 229

4-[(S)-3-Carboxy-2-({4-[(R)-2-((S)-2-cyclopropylcarbamoyl-pyrrolidin-1-yl)-1-methyl-2-oxo-ethoxy]-7-methyl-quinoline-2-carbonyl}-amino)-propionyl]-piperazine-1-carboxylic acid ethyl ester The title compound was prepared by adapting the procedures described in example 226 with the difference that (S)-Pyrrolidine-2-carboxylic acid cyclopropylamide was used instead of (S)-Pyrrolidine-2-carboxylic acid cyclobutylamide. MS (ES+): m/e=667.

Example 230

4-[(S)-3-Carboxy-2-({4-[(R)-2-((S)-2-cyclobutylcarbamoyl-azetidin-1-yl)-1-methyl-2-oxo-ethoxy]-7-methyl-quinoline-2-carbonyl}-amino)-propionyl]-piperazine-1-carboxylic acid ethyl ester The title compound was prepared by adapting the procedures described in example 226 with the difference that (S)-Azetidine-2-carboxylic acid cyclobutylamide was used instead of (S)-Pyrrolidine-2-carboxylic acid cyclobutylamide. MS (ES+): m/e=667.

Example 231

4-[(S)-3-Carboxy-2-({4-[(R)-2-((S)-3-hydroxymethyl-pyrrolidin-1-yl)-1-methyl-2-oxo-ethoxy]-7-methyl-quinoline-2-carbonyl}-amino)-propionyl]-piperazine-1-carboxylic acid ethyl ester The title compound was prepared by adapting the procedures described in example 226 with the difference that (S)-1-Pyrrolidin-3-yl-methanol was used instead of (S)-Pyrrolidine-2-carboxylic acid cyclobutylamide. MS (ES+): m/e=614.

Example 232

4-[(S)-4-Ethoxycarbonyl-2-({4-[2-((S)-2-ethylcarbamoyl-pyrrolidin-1-yl)-2-oxo-ethoxy]-6-fluoro-7-methyl-quinoline-2-carbonyl}-amino)-butyryl]-piperazine-1-carboxylic acid ethyl ester The title compound was prepared by adapting the procedure described in example 222 with the difference that 4-[(S)-4-Carboxy-2-({4-[2-((S)-2-ethylcarbamoyl-pyrrolidin-1-yl)-2-oxo-ethoxy]-6-fluoro-7-methyl-quinoline-2-carbonyl}-amino)-butyryl]-piperazine-1-carboxylic acid ethyl ester was used instead of 4-[(S)-4-Carboxy-2-({7-fluoro-4-[2-oxo-2-((S)-2-propylcarbamoyl-pyrrolidin-1-yl)-ethoxy]-quinoline-2-carbonyl}-amino)-butyryl]-piperazine-1-carboxylic acid ethyl ester. MS (ES+): m/e=701.

Example 233

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-ethylcarbamoyl-butyryl]-piperazine-1-carboxylic acid ethyl ester To 11 mg of DMAP and 17 mg of EDC a solution of 50 mg of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester in 2 ml of DCM was added. Then, 24 mg of ethylamine was added and the reaction mixture was stirred for 16 h at RT. The solvents were removed under reduced pressure and the residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. Yield: 6 mg MS (ES+): m/e=708.

Example 234

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-dimethylcarbamoyl-butyryl]-piperazine-1-carboxylic acid ethyl ester The title compound was prepared by adapting the procedures described in example 233 with the difference that dimethyl-amine was used instead of ethylamine. MS (ES+): m/e=708.

Example 235

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-methylcarbamoyl-butyryl]-piperazine-1-carboxylic acid ethyl ester The title compound was prepared by adapting the procedures described in example 233 with the difference that methylamine was used instead of ethylamine. MS (ES+): m/e=694.

Example 236

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-cyclopropylcarbamoyl-butyryl]-piperazine-1-carboxylic acid ethyl ester The title compound was prepared by adapting the procedures described in example 233 with the difference that Cyclopropylamine was used instead of ethylamine. MS (ES$^+$): m/e=720.

Example 237

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-methoxycarbonyl-butyryl]-piperazine-1-carboxylic acid ethyl ester To 11 mg of DMAP and 17 mg of EDC a solution of 50 mg of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester in 2 ml of DCM was added. Then, 12 mg of methanol was added and the reaction mixture was stirred for 16 h at RT. The solvents were removed under reduced pressure and the residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. Yield: 18 mg MS (ES+): m/e=695.

Alternatively 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-methoxycarbonyl-butyryl]-piperazine-1-carboxylic acid ethyl ester was obtained by the following procedure.

To 10 ml of a saturated solution of hydrochloric acid in methanol 700 mg of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester was added and the mixture was stirred for 16 h. Then, 30 ml of toluene was added and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid. This solid was dissolved in 8 ml of a water/acetonitrile mixture, 2 ml of a 1 M aqueous hydrochloric acid was added and the solution was again lyophilized to yield the product as its hydrochloride. Yield: 389 mg MS (ES$^+$): m/e=695.

Example 238

4-[(S)-4-Butoxycarbonyl-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester To 165 mg of DMAP and 260 mg of EDC a solution of 900 mg of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester in 6 ml of DCM was added. Then, 420 mg of Butan-1-ol was added and the reaction mixture was stirred for 16 h at RT. The solvents were removed under reduced pressure and the residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. This solid was dissolved in 8 ml of a water/actonitrile mixture, 2 ml of a 1 M aqueous hydrochloric acid was added and the solution was again lyophilized to yield the product as its hydrochloride. Yield: 571 mg MS (ES+): m/e=737.

Example 239

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-pentyloxycarbonyl-butyryl]-piperazine-1-carboxylic acid ethyl ester The title compound was prepared by adapting the procedures described in example 237 with the difference that Pentan-1-ol was used instead of methanol. MS (ES$^+$): m/e=751.

Example 240

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-isopropoxycarbonyl-butyryl]-piperazine-1-carboxylic acid ethyl ester To 10 ml of a saturated solution of hydrochloric acid in 2-propanol 400 mg of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester was added and the mixture was stirred for 16 h. Then, 30 ml of toluene was added and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid. This solid was dissolved in 8 ml of a water/acetonitrile mixture, 2 ml of a 1 M aqueous hydrochloric acid was added and the solution was again lyophilized to yield the product as its hydrochloride. Yield: 371 mg MS (ES$^+$): m/e=723.

Example 241

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(1-ethyl-propoxycarbonyl)-butyryl]-piperazine-1-carboxylic acid ethyl ester The title compound was prepared by adapting the procedures described in example 237 with the difference that Pentan-3-ol was used instead of methanol. MS (ES$^+$): m/e=751.

Example 242

4-[(S)-4-Cyclobutoxycarbonyl-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 237 with the difference that Cyclobutanol was used instead of methanol. MS (ES$^+$): m/e=735.

Example 243

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-cyclopentyloxycarbonyl-butyryl]-piperazine-1-carboxylic acid ethyl ester The title compound was prepared by adapting the procedures described in example 237 with the difference that cyclopentanol was used instead of methanol. MS (ES$^+$): m/e=749.

Example 244

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-cyclopropylmethoxycarbonyl-butyryl]-piperazine-1-carboxylic acid ethyl ester To 165 mg of DMAP and 260 mg of EDC a solution of 900 mg of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester in 6 ml of DCM was added. Then, 408 mg of Cyclopropyl-methanol was added and the reaction mixture was stirred for 16 h at RT. The solvents were removed under reduced pressure and the residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. This solid was dissolved in 8 ml of a water/actonitrile mixture, 2 ml of a 1 M aqueous hydrochloric acid was added and the solution was again lyophilized to yield the product as its hydrochloride. Yield: 507 mg MS (ES+): m/e=735.

Example 245

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(indan-5-yloxycarbonyl)-butyryl]-piperazine-1-carboxylic acid ethyl ester To 92 mg of DMAP and 144 mg of EDC a solution of 500 mg of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester in 6 ml of DCM was added. Then, 422 mg of Indan-5-ol was added and the reaction mixture was stirred for 16 h at RT. The solvents were removed under reduced pressure and the residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. This solid was dissolved in 8 ml of a water/actonitrile mixture, 2 ml of a 1 M aqueous hydrochloric acid was added and the solution was again lyophilized to yield the product as its hydrochloride. Yield: 296 mg MS (ES+): m/e=797.

Example 246

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-cyclopentylmethoxycarbonyl-butyryl]-piperazine-1-carboxylic acid ethyl ester To 161 mg of DMAP and 253 mg of EDC a solution of 750 mg of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester in 6 ml of DCM was added. Then, 552 mg of Cyclopentyl-methanol was added and the reaction mixture was stirred for 16 h at RT. The solvents were removed under reduced pressure and the residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. This solid was dissolved in 8 ml of a water/actonitrile mixture, 2 ml of a 1 M aqueous hydrochloric acid was added and the solution was again lyophilized to yield the product as its hydrochloride. Yield: 570 mg MS (ES+): m/e=763.

Example 247

4-[(S)-2-({4-[2-((S)-2-Cyclopropylcarbamoyl-pyrrolidin-1-yl)-2-oxo-ethoxy]-7-fluoro-quinoline-2-carbonyl}-amino)-4-ethoxycarbonyl-butyryl]-piperazine-1-carboxylic acid ethyl ester The title compound was prepared by adapting the procedure described in example 222 with the difference that 4-[(S)-4-Carboxy-2-({4-[2-((S)-2-cyclopropylcarbamoyl-pyrrolidin-1-yl)-2-oxo-ethoxy]-7-fluoro-quinoline-2-carbonyl}-amino)-butyryl]-piperazine-1-carboxylic acid ethyl ester was used instead of 4-[(S)-4-Carboxy-2-({7-fluoro-4-[2-oxo-2-((S)-2-propylcarbamoyl-pyrrolidin-1-yl)-ethoxy]-quinoline-2-carbonyl}-amino)-butyryl]-piperazine-1-carboxylic acid ethyl ester. MS (ES$^+$): m/e=699.

Example 248

4-{(S)-4-Ethoxycarbonyl-2-[(7-fluoro-4-{2-oxo-2-[(S)-2-(pyrrolidine-1-carbonyl)-pyrrolidin-1-yl]-ethoxy}-quinoline-2-carbonyl)-amino]-butyryl}-piperazine-1-carboxylic acid ethyl ester The title compound was prepared by adapting the procedure described in example 222 with the difference that 4-{(S)-4-Carboxy-2-[(7-fluoro-4-{2-oxo-2-[(S)-2-(pyrrolidine-1-carbonyl)-pyrrolidin-1-yl]-ethoxy}-quinoline-2-carbonyl)-amino]-butyryl}-piperazine-1-carboxylic acid ethyl ester was used instead of 4-[(S)-4-Carboxy-2-({7-fluoro-4-[2-oxo-2-((S)-2-propylcarbamoyl-pyrrolidin-1-yl)-ethoxy]-quinoline-2-carbonyl}-amino)-butyryl]-piperazine-1-carboxylic acid ethyl ester. MS (ES$^+$): m/e=713.

Example 249

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(2-morpholin-4-yl-ethoxycarbonyl)-butyryl]-piperazine-1-carboxylic acid ethyl ester The title compound was prepared by adapting the procedures described in example 237 with the difference that 2-Morpholin-4-yl-ethanol was used instead of methanol. MS (ES$^+$): m/e=794.

Example 250

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(1-morpholin-4-ylmethyl-propoxycarbonyl)-butyryl]-piperazine-1-carboxylic acid ethyl ester The title compound was prepared by adapting the procedures described in example 237 with the difference that 1-Morpholin-4-yl-butan-2-ol was used instead of methanol. MS (ES+): m/e=822.

Example 251

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-cyclohexyloxycarbonyl-butyryl]-piperazine-1-carboxylic acid ethyl ester The title compound was prepared by adapting the procedures described in example 237 with the difference that Cyclohexanol was used instead of methanol. MS (ES+): m/e=763.

Example 252

4-[(S)-4-Benzyloxycarbonyl-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester To 161 mg of DMAP and 253 mg of EDC a solution of 750 mg of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester in 6 ml of DCM was added. Then, 596 mg of Phenyl-methanol was added and the reaction mixture was stirred for 16 h at RT. The solvents were removed under reduced pressure and the residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. This solid was dissolved in 8 ml of a water/actonitrile mixture, 2 ml of a 1 M aqueous hydrochloric acid was added and the solution was again lyophilized to yield the product as its hydrochloride. Yield: 555 mg MS (ES+): m/e=771.

Example 253

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-isobutoxycarbonyl-butyryl]-piperazine-1-carboxylic acid ethyl ester The title compound was prepared by adapting the procedures described in example 237 with the difference that 2-Methyl-propan-1-ol was used instead of methanol. MS (ES+): m/e=737.

Example 254

4-[(S)-2-({4-[2-((S)-2-Cyclopropylcarbamoyl-pyrrolidin-1-yl)-2-oxo-ethoxy]-6-fluoro-7-methyl-quinoline-2-carbonyl}-amino)-4-ethoxycarbonyl-butyryl]-piperazine-1-carboxylic acid ethyl ester The title compound was prepared by adapting the procedure described in example 222 with the difference that 4-[(S)-4-Carboxy-2-({4-[2-((S)-2-cyclopropylcarbamoyl-pyrrolidin-1-yl)-2-oxo-ethoxy]-6-fluoro-7-methyl-quinoline-2-carbonyl}-amino)-butyryl]-piperazine-1-carboxylic acid ethyl ester was used instead of 4-[(S)-4-Carboxy-2-({7-fluoro-4-[2-oxo-2-((S)-2-propylcarbamoyl-pyrrolidin-1-yl)-ethoxy]-quinoline-2-carbonyl}-amino)-butyryl]-piperazine-1-carboxylic acid ethyl ester. MS (ES+): m/e=713.

Example 255

4-[(S)-2-({4-[2-((S)-2-Cyclobutylcarbamoyl-pyrrolidin-1-yl)-2-oxo-ethoxy]-6-fluoro-7-methyl-quinoline-2-carbonyl}-amino)-4-ethoxycarbonyl-butyryl]-piperazine-1-carboxylic acid ethyl ester The title compound was prepared by adapting the procedure described in example 222 with the difference that 4-[(S)-4-Carboxy-2-({4-[2-((S)-2-cyclobutylcarbamoyl-pyrrolidin-1-yl)-2-oxo-ethoxy]-6-fluoro-7-methyl-quinoline-2-carbonyl}-amino)-butyryl]-piperazine-1-carboxylic acid ethyl ester was used instead of 4-[(S)-4-Carboxy-2-({7-fluoro-4-[2-oxo-2-((S)-2-propylcarbamoyl-pyrrolidin-1-yl)-ethoxy]-quinoline-2-carbonyl}-amino)-butyryl]-piperazine-1-carboxylic acid ethyl ester. MS (ES+): m/e=727.

Example 256

4-{(S)-4-Ethoxycarbonyl-2-[(6-fluoro-7-methyl-4-{2-oxo-2-[(S)-2-(pyrrolidine-1-carbonyl)-pyrrolidin-1-yl]-ethoxy}-quinoline-2-carbonyl)-amino]-butyryl}-piperazine-1-carboxylic acid ethyl ester The title compound was prepared by adapting the procedure described in example 222 with the difference that 4-{(S)-4-Carboxy-2-[(6-fluoro-7-methyl-4-{2-oxo-2-[(S)-2-(pyrrolidine-1-carbonyl)-pyrrolidin-1-yl]-ethoxy}-quinoline-2-carbonyl)-amino]-butyryl}-piperazine-1-carboxylic acid ethyl ester was used instead of 4-[(S)-4-Carboxy-2-({7-fluoro-4-[2-oxo-2-((S)-2-propylcarbamoyl-pyrrolidin-1-yl)-ethoxy]-quinoline-2-carbonyl}-amino)-butyryl]-piperazine-1-carboxylic acid ethyl ester. MS (ES+): m/e=727.

Example 257

4-{(S)-4-Ethoxycarbonyl-2-[(7-methyl-4-{2-oxo-2-[(S)-2-(pyrrolidine-1-carbonyl)-pyrrolidin-1-yl]-ethoxy}-quinoline-2-carbonyl)-amino]-butyryl}-piperazine-1-carboxylic acid ethyl ester The title compound was prepared by adapting the procedure described in example 222 with the difference that 4-{(S)-4-Carboxy-2-[(7-methyl-4-{2-oxo-2-[(S)-2-(pyrrolidine-1-carbonyl)-pyrrolidin-1-yl]-ethoxy}-quinoline-2-carbonyl)-amino]-butyryl}-piperazine-1-carboxylic acid ethyl ester was used instead of 4-[(S)-4-Carboxy-2-({7-fluoro-4-[2-oxo-2-((S)-2-propylcarbamoyl-pyrrolidin-1-yl)-ethoxy]-quinoline-2-carbonyl}-amino)-butyryl]-piperazine-1-carboxylic acid ethyl ester. MS (ES+): m/e=709.

Example 258

4-[(S)-3-Carboxy-2-({4-[2-((S)-2-cyclobutylcarbamoyl-pyrrolidin-1-yl)-2-oxo-ethoxy]-5-fluoro-quinoline-2-carbonyl}-amino)-propionyl]-piperazine-1-carboxylic acid ethyl ester The title compound was prepared by adapting the procedures described in example 197 with the difference that 5-Fluoro-4-hydroxy-quinoline-2-carboxylic acid and (S)-Pyrrolidine-2-carboxylic acid cyclobutylamide was used instead of 4-Hydroxy-7-methyl-quinoline-2-carboxylic acid and (S)-Pyrrolidine-2-carboxylic acid ethylamide. MS (ES$^+$): m/e=671.

Example 259

4-[(S)-3-Carboxy-2-({5-fluoro-4-[2-oxo-2-((S)-2-propylcarbamoyl-pyrrolidin-1-yl)-ethoxy]-quinoline-2-carbonyl}-amino)-propionyl]-piperazine-1-carboxylic acid ethyl ester The title compound was prepared by adapting the procedures described in example 197 with the difference that 5-Fluoro-4-hydroxy-quinoline-2-carboxylic acid and (S)-Pyrrolidine-2-carboxylic acid propylamide was used instead of 4-Hydroxy-7-methyl-quinoline-2-carboxylic acid and (S)-Pyrrolidine-2-carboxylic acid ethylamide. MS (ES$^+$): m/e=659.

Example 260

4-[(S)-4-Carboxy-2-({5-fluoro-7-methyl-4-[2-oxo-2-((S)-2-propylcarbamoyl-pyrrolidin-1-yl)-ethoxy]-quinoline-2-carbonyl}-amino)-butyryl]-piperazine-1-carboxylic acid ethyl ester The title compound was prepared by adapting the procedures described in example 3 with the difference that (S)-Pyrrolidine-2-carboxylic acid propylamide and 5-Fluoro-4-hydroxy-7-methyl-quinoline-2-carboxylic acid was used instead of (S)-Pyrrolidine-2-carboxylic acid cyclopropylamide hydrochloride and 4-Hydroxy-7-methyl-quinoline-2-carboxylic acid. MS (ES$^+$): m/e=687.

Example 261

4-{(S)-4-Carboxy-2-[(5-fluoro-7-methyl-4-{2-oxo-2-[(S)-2-(pyrrolidine-1-carbonyl)-pyrrolidin-1-yl]-ethoxy}-quinoline-2-carbonyl)-amino]-butyryl}-piperazine-1-carboxylic acid ethyl ester The title compound was prepared by adapting the procedures described in example 3 with the difference that (S)-Pyrrolidin-2-yl-pyrrolidin-1-yl-methanone and 5-Fluoro-4-hydroxy-7-methyl-quinoline-2-carboxylic acid was used instead of (S)-Pyrrolidine-2-carboxylic acid cyclopropylamide hydrochloride and 4-Hydroxy-7-methyl-quinoline-2-carboxylic acid. MS (ES$^+$): m/e=699.

Example 262

4-[(S)-4-Carboxy-2-({4-[2-((S)-2-cyclobutylcarbamoyl-pyrrolidin-1-yl)-2-oxo-ethoxy]-5-fluoro-7-methyl-quinoline-2-carbonyl}-amino)-butyryl]-piperazine-1-carboxylic acid ethyl ester The title compound was prepared by adapting the procedures described in example 3 with the difference that (S)-Pyrrolidine-2-carboxylic acid cyclobutylamide and 5-Fluoro-4-hydroxy-7-methyl-quinoline-2-carboxylic acid was used instead of (S)-Pyrrolidine-2-carboxylic acid cyclopropylamide hydrochloride and 4-Hydroxy-7-methyl-quinoline-2-carboxylic acid. MS (ES$^+$): m/e=699.

Example 263

4-{(S)-3-Carboxy-2-[(7-methyl-4-{2-oxo-2-[(S)-2-(pyrrolidine-1-carbonyl)-pyrrolidin-1-yl]-ethoxy}-quinoline-2-carbonyl)-amino]-propionyl}-piperazine-1-carboxylic acid ethyl ester The title compound was prepared by adapting the procedures described in example 197 with the difference that (S)-Pyrrolidin-2-yl-pyrrolidin-1-yl-methanone was used instead of (S)-Pyrrolidine-2-carboxylic acid ethylamide. MS (ES$^+$): m/e=667.

Example 264

4-[(S)-2-({4-[2-((S)-2-Cyclopentylcarbamoyl-pyrrolidin-1-yl)-2-oxo-ethoxy]-7-methyl-quinoline-2-carbonyl}-amino)-4-ethoxycarbonyl-butyryl]-piperazine-1-carboxylic acid ethyl ester The title compound was prepared by adapting the procedure described in example 222 with the difference that 4-[(S)-4-Carboxy-2-({4-[2-((S)-2-cyclopentylcarbamoyl-pyrrolidin-1-yl)-2-oxo-ethoxy]-7-methyl-quinoline-2-carbonyl}-amino)-butyryl]-piperazine-1-carboxylic acid ethyl ester was used instead of 4-[(S)-4-Carboxy-2-({7-fluoro-4-[2-oxo-2-((S)-2-propylcarbamoyl-pyrrolidin-1-yl)-ethoxy]-quinoline-2-carbonyl}-amino)-butyryl]-piperazine-1-carboxylic acid ethyl ester. MS (ES$^+$): m/e=723.

Example 265

4-[(S)-3-Carboxy-2-({4-[2-((S)-2-cyclobutylcarbamoyl-pyrrolidin-1-yl)-2-oxo-ethoxy]-7-fluoro-quinoline-2-carbonyl}-amino)-propionyl]-piperazine-1-carboxylic acid ethyl ester The title compound was prepared by adapting the procedures described in example 197 with the difference that 7-Fluoro-4-hydroxy-quinoline-2-carboxylic acid and (S)-Pyrrolidine-2-carboxylic acid cyclobutylamide was used instead of 4-Hydroxy-7-methyl-quinoline-2-carboxylic acid and (S)-Pyrrolidine-2-carboxylic acid ethylamide. MS (ES$^+$): m/e=671.

Example 266

4-[(S)-3-Carboxy-2-({5-fluoro-7-methyl-4-[2-oxo-2-((S)-2-propylcarbamoyl-pyrrolidin-1-yl)-ethoxy]-quinoline-2-carbonyl}-amino)-propionyl]-piperazine-1-carboxylic acid ethyl ester The title compound was prepared by adapting the procedures described in example 197 with the difference that 5-Fluoro-4-hydroxy-7-methyl-quinoline-2-carboxylic acid and (S)-Pyrrolidine-2-carboxylic acid propylamide was used instead of 4-Hydroxy-7-methyl-quinoline-2-carboxylic acid and (S)-Pyrrolidine-2-carboxylic acid ethylamide. MS (ES$^+$): m/e=673.

Example 267

4-{(S)-3-Carboxy-2-[(5-fluoro-7-methyl-4-{2-oxo-2-[(S)-2-(pyrrolidine-1-carbonyl)-pyrrolidin-1-yl]-ethoxy}-quinoline-2-carbonyl)-amino]-propionyl}-piperazine-1-carboxylic acid ethyl ester The title compound was prepared by adapting the procedures described in example 197 with the difference that (S)-

Pyrrolidin-2-yl-pyrrolidin-1-yl-methanone and 5-Fluoro-4-hydroxy-7-methyl-quinoline-2-carboxylic acid was used instead of (S)-Pyrrolidine-2-carboxylic acid ethylamide and 4-Hydroxy-7-methyl-quinoline-2-carboxylic acid. MS (ES+): m/e=685.

Example 268

4-[(S)-3-Carboxy-2-({4-[2-((S)-2-cyclobutylcarbamoyl-pyrrolidin-1-yl)-2-oxo-ethoxy]-5-fluoro-7-methyl-quinoline-2-carbonyl}-amino)-propionyl]-piperazine-1-carboxylic acid ethyl ester The title compound was prepared by adapting the procedures described in example 197 with the difference that 5-Fluoro-4-hydroxy-7-methyl-quinoline-2-carboxylic acid and (5)-Pyrrolidine-2-carboxylic acid cyclobutylamide was used instead of 4-Hydroxy-7-methyl-quinoline-2-carboxylic acid and (S)-Pyrrolidine-2-carboxylic acid ethylamide. MS (ES+): m/e=685.

Example 269

4-{(S)-3-Carboxy-2-[(5-fluoro-4-{2-oxo-2-[(S)-2-(pyrrolidine-1-carbonyl)-pyrrolidin-1-yl]-ethoxy}-quinoline-2-carbonyl)-amino]-propionyl}-piperazine-1-carboxylic acid ethyl ester The title compound was prepared by adapting the procedures described in example 197 with the difference that 5-Fluoro-4-hydroxy-quinoline-2-carboxylic acid and (S)-Pyrrolidin-2-yl-pyrrolidin-1-yl-methanone was used instead of 4-Hydroxy-7-methyl-quinoline-2-carboxylic acid and (S)-Pyrrolidine-2-carboxylic acid ethylamide. MS (ES+): m/e=671.

Example 270

4-[(S)-3-Carboxy-2-({4-[2-((S)-2-cyclobutylcarbamoyl-pyrrolidin-1-yl)-2-oxo-ethoxy]-6-fluoro-7-methyl-quinoline-2-carbonyl}-amino)-propionyl]-piperazine-1-carboxylic acid ethyl ester The title compound was prepared by adapting the procedures described in example 197 with the difference that 6-Fluoro-4-hydroxy-7-methyl-quinoline-2-carboxylic acid and (S)-Pyrrolidine-2-carboxylic acid cyclobutylamide was used instead of 4-Hydroxy-7-methyl-quinoline-2-carboxylic acid and (S)-Pyrrolidine-2-carboxylic acid ethylamide. MS (ES+): m/e=685.

Example 271

4-{(S)-4-Ethoxycarbonyl-2-[(5-fluoro-7-methyl-4-{2-oxo-2-[(S)-2-(pyrrolidine-1-carbonyl)-pyrrolidin-1-yl]-ethoxy}-quinoline-2-carbonyl)-amino]-butyryl}-piperazine-1-carboxylic acid ethyl ester The title compound was prepared by adapting the procedure described in example 222 with the difference that 4-{(S)-4-Carboxy-2-[(5-fluoro-7-methyl-4-{2-oxo-2-[(S)-2-(pyrrolidine-1-carbonyl)-pyrrolidin-1-yl]-ethoxy}-quinoline-2-carbonyl)-amino]-butyryl}-piperazine-1-carboxylic acid ethyl ester was used instead of 4-[(S)-4-Carboxy-2-({7-fluoro-4-[2-oxo-2-((S)-2-propylcarbamoyl-pyrrolidin-1-yl)-ethoxy]-quinoline-2-carbonyl}-amino)-butyryl]-piperazine-1-carboxylic acid ethyl ester. MS (ES+): m/e=727.

Example 272

4-[(S)-2-({4-[2-((S)-2-Cyclobutylcarbamoyl-pyrrolidin-1-yl)-2-oxo-ethoxy]-5-fluoro-7-methyl-quinoline-2-carbonyl}-amino)-4-ethoxycarbonyl-butyryl]-piperazine-1-carboxylic acid ethyl ester The title compound was prepared by adapting the procedure described in example 222 with the difference that 4-[(S)-4-Carboxy-2-({4-[2-((S)-2-cyclobutylcarbamoyl-pyrrolidin-1-yl)-2-oxo-ethoxy]-5-fluoro-7-methyl-quinoline-2-carbonyl}-amino)-butyryl]-piperazine-1-carboxylic acid ethyl ester was used instead of 4-[(S)-4-Carboxy-2-({7-fluoro-4-[2-oxo-2-((S)-2-propylcarbamoyl-pyrrolidin-1-yl)-ethoxy]-quinoline-2-carbonyl}-amino)-butyryl]-piperazine-1-carboxylic acid ethyl ester. MS (ES+): m/e=727.

Example 273

4-{(S)-3-Carboxy-2-[(4-{2-[(S)-2-(ethyl-methyl-carbamoyl)-pyrrolidin-1-yl]-2-oxo-ethoxy}-7-methyl-quinoline-2-carbonyl)-amino]-propionyl}-piperazine-1-carboxylic acid ethyl ester The title compound was prepared by adapting the procedures described in example 197 with the difference that (S)-Pyrrolidine-2-carboxylic acid ethyl-methyl-amide was used instead of (S)-Pyrrolidine-2-carboxylic acid ethylamide. MS (ES+): m/e=655.

Example 274

4-[(S)-4-Carboxy-2-({4-[(R)-2-((S)-2-cyclobutylcarbamoyl-pyrrolidin-1-yl)-1-methyl-2-oxo-ethoxy]-7-methyl-quinoline-2-carbonyl}-amino)-butyryl]-piperazine-1-carboxylic acid ethyl ester (i) 4-((S)-2-{[4-((R)-1-Benzyloxycarbonyl-ethoxy)-7-methyl-quinoline-2-carbonyl]-amino}-4-tert-butoxycarbonyl-butyryl)-piperazine-1-carboxylic acid ethyl ester To a solution of 1 g of 4-{(S)-4-tert-Butoxycarbonyl-2-[(4-hydroxy-7-methyl-quinoline-2-carbonyl)-amino]-butyryl}-piperazine-1-carboxylic acid ethyl ester and 341 mg of (S)-2-Hydroxy-propionic acid benzyl ester in 15 ml of THF, 744 mg of Triphenyl-phosphane and 494 mg of Diethyl azodicarboxylate was added and stirred for 2 h. Then, the reaction mixture was diluted with water and extracted with ethyl acetate. The organic phase was dried over MgSO$_4$ and the solvents were removed under reduced pressure. The crude product was purified by chromatography on silica gel eluting with a gradient of n-heptane/ethyl acetate. The fractions containing the product were combined and the solvent evaporated under reduced pressure. Yield: 1.0 g.

(ii) 4-((S)-4-tert-Butoxycarbonyl-2-{[4-((R)-1-carboxy-ethoxy)-7-methyl-quinoline-2-carbonyl]-amino}-butyryl)-piperazine-1-carboxylic acid ethyl ester A solution of 1.4 g of 4-((S)-2-{[4-((R)-1-Benzyloxycarbonyl-ethoxy)-7-methyl-quinoline-2-carbonyl]-amino}-4-tert-butoxycarbonyl-butyryl)-piperazine-1-carboxylic acid ethyl ester in 20 ml of ethyl acetate was purged with argon. Then, 140 mg of Pd/C (5-10%) was added and the mixture stirred under a hydrogen atmosphere (3 bar). After 16 h the reaction mixture was filtered through a pad of celite and the solvents were removed under reduced pressure. After drying under reduced pressure the product was pure enough for the next reaction step. Yield: 1.2 g.

(iii) (S)-2-Cyclobutylcarbamoyl-pyrrolidine-1-carboxylic acid tert-butyl ester

To a solution of 1.5 g of (S)-Pyrrolidine-1,2-dicarboxylic acid 1-tert-butyl ester in 30 ml of DMF 948 mg of HOAT, 1.3 g of EDC and 495 mg of cyclobutylamine was added and the reaction mixture was stirred for 16 h at RT. Then, water was added and the reaction mixture was extracted with DCM. The organic phase was dried over $MgSO_4$ and the solvents were removed under reduced pressure. The crude product was pure enough for the next reaction step.

(iv) (S)-Pyrrolidine-2-carboxylic acid cyclobutylamide

The crude (S)-2-Cyclobutylcarbamoyl-pyrrolidine-1-carboxylic acid tert-butyl ester from the preceding reaction step was dissolved in 10 ml of DCM and 5 ml of TFA and stirred for 3 h. Then, the reaction mixture was diluted with 70 ml of toluene and the solvents were removed under reduced pressure. The residue was co-distilled additional 3 times with toluene. The product was obtained as its trifluoroacetate. Yield: 2 g.

(v) 4-[(S)-4-tert-Butoxycarbonyl-2-({4-[(R)-2-((S)-2-cyclobutylcarbamoyl-pyrrolidin-1-yl)-1-methyl-2-oxo-ethoxy]-7-methyl-quinoline-2-carbonyl}-amino)-butyryl]-piperazine-1-carboxylic acid ethyl ester To a solution of 250 mg of 4-((S)-4-tert-Butoxycarbonyl-2-{[4-((R)-1-carboxy-ethoxy)-7-methyl-quinoline-2-carbonyl]-amino}-butyryl)-piperazine-1-carboxylic acid ethyl ester in 2.5 ml of DCM, 96 mg of EDC, 92 mg of pentafluorophenol was added and the reaction mixture was stirred for 2 h. Then, 117 mg of (S)-Pyrrolidine-2-carboxylic acid cyclobutylamide trifluoroacetate and 192 mg of NEM in 2 ml of DCM was added. After 2 h the reaction mixture was diluted with water. After filtration through a chem Elut® cartridge by eluting with ethyl acetate the solvents were removed under reduced pressure. The isolated crude product was pure enough for the next reaction step.

(vi) 4-[(S)-4-Carboxy-2-({4-[(R)-2-((S)-2-cyclobutylcarbamoyl-pyrrolidin-1-yl)-1-methyl-2-oxo-ethoxy]-7-methyl-quinoline-2-carbonyl}-amino)-butyryl]-piperazine-1-carboxylic acid ethyl ester To a solution of the 4-((S)-4-tert-Butoxycarbonyl-2-{[4-((R)-1-carboxy-ethoxy)-7-methyl-quinoline-2-carbonyl]-amino}-butyryl)-piperazine-1-carboxylic acid ethyl ester obtained by the preceding reaction step in 1.4 ml of DCM, 0.1 ml of TFA was added at RT. After 2 h, 20 ml of toluene was added and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. Yield: 17 mg MS (ES+): m/e=695.

Example 275

4-[(S)-4-Ethoxycarbonyl-2-({5-fluoro-7-methyl-4-[2-oxo-2-((S)-2-propylcarbamoyl-pyrrolidin-1-yl)-ethoxy]-quinoline-2-carbonyl}-amino)-butyryl]-piperazine-1-carboxylic acid ethyl ester The title compound was prepared by adapting the procedure described in example 222 with the difference that 4-[(S)-4-Carboxy-2-({5-fluoro-7-methyl-4-[2-oxo-2-((S)-2-propylcarbamoyl-pyrrolidin-1-yl)-ethoxy]-quinoline-2-carbonyl}-amino)-butyryl]-piperazine-1-carboxylic acid ethyl ester was used instead of 4-[(S)-4-Carboxy-2-({7-fluoro-4-[2-oxo-2-((S)-2-propylcarbamoyl-pyrrolidin-1-yl)-ethoxy]-quinoline-2-carbonyl}-amino)-butyryl]-piperazine-1-carboxylic acid ethyl ester. MS (ES+): m/e=715.

Example 276

4-{(S)-3-Carboxy-2-[(6-fluoro-7-methyl-4-{2-oxo-2-[(S)-2-(pyrrolidine-1-carbonyl)-pyrrolidin-1-yl]-ethoxy}-quinoline-2-carbonyl)-amino]-propionyl}-piperazine-1-carboxylic acid ethyl ester The title compound was prepared by adapting the procedures described in example 197 with the difference that 6-Fluoro-4-hydroxy-7-methyl-quinoline-2-carboxylic acid and (S)-Pyrrolidin-2-yl-pyrrolidin-1-yl-methanone was used instead of 4-Hydroxy-7-methyl-quinoline-2-carboxylic acid and (S)-Pyrrolidine-2-carboxylic acid ethylamide. MS (ES+): m/e=685.

Example 277

4-[(S)-3-Carboxy-2-({4-[2-((S)-2-ethylcarbamoyl-pyrrolidin-1-yl)-2-oxo-ethoxy]-7-fluoro-quinoline-2-carbonyl}-amino)-propionyl]-piperazine-1-carboxylic acid ethyl ester The title compound was prepared by adapting the procedures described in example 197 with the difference that 7-Fluoro-4-hydroxy-quinoline-2-carboxylic acid was used instead of 4-Hydroxy-7-methyl-quinoline-2-carboxylic acid. MS (ES+): m/e=645.

Example 278

4-[(S)-3-Carboxy-2-({7-fluoro-4-[2-oxo-2-((S)-2-propylcarbamoyl-pyrrolidin-1-yl)-ethoxy]-quinoline-2-carbonyl}-amino)-propionyl]-piperazine-1-carboxylic acid ethyl ester The title compound was prepared by adapting the procedures described in example 197 with the difference that 7-Fluoro-4-hydroxy-quinoline-2-carboxylic acid and (S)-Pyrrolidine-2-carboxylic acid propylamide was used instead of 4-Hydroxy-7-methyl-quinoline-2-carboxylic acid and (S)-Pyrrolidine-2-carboxylic acid ethylamide. MS (ES+): m/e=659.

Example 279

4-[(S)-3-Carboxy-2-({4-[2-((S)-2-cyclopropylcarbamoyl-pyrrolidin-1-yl)-2-oxo-ethoxy]-7-fluoro-quinoline-2-carbonyl}-amino)-propionyl]-piperazine-1-carboxylic acid ethyl ester

The title compound was prepared by adapting the procedures described in example 197 with the difference that 7-Fluoro-4-hydroxy-quinoline-2-carboxylic acid and (S)-Pyrrolidine-2-carboxylic acid cyclopropylamide was used instead of 4-Hydroxy-7-methyl-quinoline-2-carboxylic acid and (S)-Pyrrolidine-2-carboxylic acid ethylamide. MS (ES+): m/e=657.

Example 280

4-[(S)-4-Carboxy-2-({4-[2-((S)-2-cyclopropylcarbamoyl-pyrrolidin-1-yl)-2-oxo-ethoxy]-naphthalene-2-carbonyl}-amino)-butyryl]-piperazine-1-carboxylic acid ethyl ester

(i) 2-Benzylidene-malonic acid diethyl ester

To a solution of 12.8 g sodium ethylate in 140 ml of ethanol, 10.0 g of benzaldehyde and 17.4 g of Malonic acid diethyl ester dissolved in 35 ml ethanol was added drop-wise over 1 h at 50° C. Then, the reaction mixture was heated to reflux for 12 h. After cooling to RT half of the solvent was evaporated under reduced pressure and diluted with 200 ml of water. The remaining reaction mixture was acidified to pH 1 by addition of concentrated hydrochloric acid and then extracted with ethyl acetate. The organic phase was dried over MgSO$_4$ and the solvents were removed under reduced pressure. The crude product was pure enough for the next reaction step.

(ii) 4-Acetoxy-naphthalene-2-carboxylic acid ethyl ester

To a solution of 24 g of 2-Benzylidene-malonic acid diethyl ester in 60 ml of acetic acid anhydride, 7.5 g sodium acetate was added and the reaction mixture was heated to reflux for 5 h. After cooling to RT the reaction mixture was diluted with water and extracted with ethyl acetate. The combined organic phases were washed three times with saturated aqueous sodium hydrogen carbonate solution. The organic phase was dried over MgSO$_4$ and the solvents were removed under reduced pressure. The crude product was pure enough for the next reaction step.

(iii) 4-Hydroxy-naphthalene-2-carboxylic acid

To a solution of 18.5 g of 4-Acetoxy-naphthalene-2-carboxylic acid ethyl ester in 100 ml ethanol/water (9:1), 240 ml of a 1M NaOH was added and stirred for 2 days at RT. Then, the reaction mixture was acidified to pH 2 with diluted hydrochloric acid to precipitate the product. The product was then collected by filtration and dried reduced pressure. Yield: 13.7 g.

(iv) 4-{(S)-4-tert-Butoxycarbonyl-2-[(4-hydroxy-naphthalene-2-carbonyl)-amino]-butyryl}-piperazine-1-carboxylic acid ethyl ester To a solution of 630 mg of 4-Hydroxy-naphthalene-2-carboxylic acid and 1.1 g of 4-((S)-2-Amino-4-tert-butoxycarbonyl-butyryl)-piperazine-1-carboxylic acid ethyl ester in 3 ml of DMF, 512 mg of HOBT and 641 mg of EDC was added and the reaction mixture was stirred for 4 h at RT. Then, the reaction mixture was diluted with water and extracted with DCM. The organic phase was dried over MgSO$_4$ and the solvents were removed under reduced pressure. The crude product was purified by chromatography on silica gel eluting with n-heptane/ethyl acetate (1/2). The fractions containing the product were combined and the solvent evaporated under reduced pressure. Yield: 246 mg.

(v) 4-[(S)-4-Carboxy-2-({4-[2-((S)-2-cyclopropyl-carbamoyl-pyrrolidin-1-yl)-2-oxo-ethoxy]-naphthalene-2-carbonyl}-amino)-butyryl]-piperazine-1-carboxylic acid ethyl ester To a solution of 100 mg of (S)-1-(2-Bromo-acetyl)-pyrrolidine-2-carboxylic acid cyclopropylamide and 93 mg of 4-{(S)-4-tert-Butoxycarbonyl-2-[(4-hydroxy-naphthalene-2-carbonyl)-amino]-butyryl}-piperazine-1-carboxylic acid ethyl ester in 2 ml of DMF, 118 mg of cesium carbonate was added and the reaction mixture was heated to 80° C. for 5 h. Then, the reaction mixture was diluted with water and filtered through a chem Elut® cartridge by eluting with ethyl acetate. The solvents were removed under reduced pressure and the residue was dissolved in 1 ml of DCM and 0.2 ml of TFA. After 16 h at RT 10 ml of toluene was added and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid. Yield: 40 mg MS (ES+): m/e=652.

Example 281

4-{(S)-4-Carboxy-2-[(6,7-dimethyl-4-{2-oxo-2-[(S)-2-(pyrrolidine-1-carbonyl)-pyrrolidin-1-yl]-ethoxy}-quinoline-2-carbonyl)-amino]-butyryl}-piperazine-1-carboxylic acid ethyl ester

The title compound was prepared by adapting the procedures described in example 3 with the difference that (S)-Pyrrolidin-2-yl-pyrrolidin-1-yl-methanone and 4-Hydroxy-6,7-dimethyl-quinoline-2-carboxylic acid was used instead of (S)-Pyrrolidine-2-carboxylic acid cyclopropylamide hydrochloride and 4-Hydroxy-7-methyl-quinoline-2-carboxylic acid. MS (ES+): m/e=695.

Example 282

4-{(S)-4-Ethoxycarbonyl-2-[(7-methyl-4-{2-oxo-2-[(S)-2-(2,2,2-trifluoro-ethylcarbamoyl)-pyrrolidin-1-yl]-ethoxy}-quinoline-2-carbonyl)-amino]-butyryl}-piperazine-1-carboxylic acid ethyl ester

The title compound was prepared by adapting the procedure described in example 107 with the difference that 4-{(S)-4-tert-Butoxycarbonyl-2-[(7-methyl-4-{2-oxo-2-[(S)-2-(2,2,2-trifluoro-ethylcarbamoyl)-pyrrolidin-1-yl]-ethoxy}-quinoline-2-carbonyl)-amino]-butyryl}-piperazine-1-carboxylic acid ethyl ester was used instead of 4-[(S)-4-tert-Butoxycarbonyl-2-({4-[2-((S)-2-cyclopropylcarbamoyl-pyrrolidin-1-yl)-2-oxo-ethoxy]-quinoline-2-carbonyl}-amino)-butyryl]-piperazine-1-carboxylic acid ethyl ester. MS (ES+): m/e=737.

Example 283

4-{(S)-2-[(4-{2-[(S)-2-(Cyclopropylmethyl-carbamoyl)-pyrrolidin-1-yl]-2-oxo-ethoxy}-7-methyl-quinoline-2-carbonyl)-amino]-4-ethoxycarbonyl-butyryl}-piperazine-1-carboxylic acid ethyl ester The title compound was prepared by adapting the procedure described in example 107 with the difference that 4-{(S)-4-tert-Butoxycarbonyl-2-[(4-{2-[(S)-2-(cyclopropylmethyl-carbamoyl)-pyrrolidin-1-yl]-2-oxo-ethoxy}-7-methyl-quinoline-2-carbonyl)-amino]-butyryl}-piperazine-1-carboxylic acid ethyl ester was used instead of 4-[(S)-4-tert-Butoxycarbonyl-2-({4-[2-((S)-2-cyclopropylcarbamoyl-pyrrolidin-1-yl)-2-oxo-ethoxy]-quinoline-2-carbonyl}-amino)-butyryl]-piperazine-1-carboxylic acid ethyl ester. MS (ES+): m/e=709.

Example 284

4-[(S)-4-Ethoxycarbonyl-2-({7-methyl-4-[2-oxo-2-((S)-2-propylcarbamoyl-pyrrolidin-1-yl)-ethoxy]-quinoline-2-carbonyl}-amino)-butyryl]-piperazine-1-carboxylic acid ethyl ester The title compound was prepared by adapting the procedure described in example 107 with the difference that 4-[(S)-4-tert-Butoxycarbonyl-2-({7-methyl-4-[2-oxo-2-((S)-2-propylcarbamoyl-pyrrolidin-1-yl)-ethoxy]-quinoline-2-carbonyl}-amino)-butyryl]-piperazine-1-carboxylic acid ethyl ester was used instead of 4-[(S)-4-tert-Butoxycarbonyl-2-({4-[2-((S)-2-cyclopropylcarbamoyl-pyrrolidin-1-yl)-2-oxo-ethoxy]-quinoline-2-carbonyl}-amino)-butyryl]-piperazine-1-carboxylic acid ethyl ester. MS (ES+): m/e=725.

Example 285

4-[(S)-4-Carboxy-2-({6,7-dimethyl-4-[2-oxo-2-((S)-2-propylcarbamoyl-pyrrolidin-1-yl)-ethoxy]-quinoline-2-carbonyl}-amino)-butyryl]-piperazine-1-carboxylic acid ethyl ester The title compound was prepared by adapting the procedures described in example 3 with the difference that (S)-Pyrrolidine-2-carboxylic acid propylamide and 4-Hydroxy-6,7-dimethyl-quinoline-2-carboxylic acid was used instead of (S)-Pyrrolidine-2-carboxylic acid cyclopropylamide hydrochloride and 4-Hydroxy-7-methyl-quinoline-2-carboxylic acid. MS (ES$^+$): m/e=683.

Example 286

4-[(S)-2-({4-[2-((S)-2-Cyclobutylcarbamoyl-pyrrolidin-1-yl)-2-oxo-ethoxy]-5-fluoro-quinoline-2-carbonyl}-amino)-4-ethoxycarbonyl-butyryl]-piperazine-1-carboxylic acid ethyl ester The title compound was prepared by adapting the procedure described in example 107 with the difference that 4-[(S)-4-tert-Butoxycarbonyl-2-({4-[2-((S)-2-cyclobutylcarbamoyl-pyrrolidin-1-yl)-2-oxo-ethoxy]-5-fluoro-quinoline-2-carbonyl}-amino)-butyryl]-piperazine-1-carboxylic acid ethyl ester was used instead of 4-[(S)-4-tert-Butoxycarbonyl-2-({4-[2-((S)-2-cyclopropylcarbamoyl-pyrrolidin-1-yl)-2-oxo-ethoxy]-quinoline-2-carbonyl}-amino)-butyryl]-piperazine-1-carboxylic acid ethyl ester. MS (ES+): m/e=713.

Example 287

4-[(S)-2-({4-[2-((S)-2-Cyclobutylcarbamoyl-pyrrolidin-1-yl)-2-oxo-ethoxy]-6-fluoro-quinoline-2-carbonyl}-amino)-4-ethoxycarbonyl-butyryl]-piperazine-1-carboxylic acid ethyl ester The title compound was prepared by adapting the procedure described in example 107 with the difference that 4-[(S)-4-tert-Butoxycarbonyl-2-({4-[2-((S)-2-cyclobutylcarbamoyl-pyrrolidin-1-yl)-2-oxo-ethoxy]-6-fluoro-quinoline-2-carbonyl}-amino)-butyryl]-piperazine-1-carboxylic acid ethyl ester was used instead of 4-[(S)-4-tert-Butoxycarbonyl-2-({4-[2-((S)-2-cyclopropylcarbamoyl-pyrrolidin-1-yl)-2-oxo-ethoxy]-quinoline-2-carbonyl}-amino)-butyryl]-piperazine-1-carboxylic acid ethyl ester. MS (ES+): m/e=713.

Example 288

4-{(S)-4-Carboxy-2-[(5,6-difluoro-4-{2-oxo-2-[(S)-2-(pyrrolidine-1-carbonyl)-pyrrolidin-1-yl]-ethoxy}-quinoline-2-carbonyl)-amino]-butyryl}-piperazine-1-carboxylic acid ethyl ester The title compound was prepared by adapting the procedures described in example 3 with the difference that (S)-Pyrrolidine-2-carboxylic acid propylamide and 5,6-Difluoro-4-hydroxy-quinoline-2-carboxylic acid was used instead of (S)-Pyrrolidine-2-carboxylic acid cyclopropylamide hydrochloride and 4-Hydroxy-7-methyl-quinoline-2-carboxylic acid. MS (ES$^+$): m/e=703.

Example 289

4-[(S)-4-Carboxy-2-({4-[2-((S)-2-cyclobutylcarbamoyl-pyrrolidin-1-yl)-2-oxo-ethoxy]-5,6-difluoro-quinoline-2-carbonyl}-amino)-butyryl]-piperazine-1-carboxylic acid ethyl ester The title compound was prepared by adapting the procedures described in example 3 with the difference that (S)-Pyrrolidine-2-carboxylic acid cyclobutylamide and 5,6-Difluoro-4-hydroxy-quinoline-2-carboxylic acid was used instead of (S)-Pyrrolidine-2-carboxylic acid cyclopropylamide hydrochloride and 4-Hydroxy-7-methyl-quinoline-2-carboxylic acid. MS (ES$^+$): m/e=703.

Example 290

4-[(S)-4-Carboxy-2-({5,6-difluoro-4-[2-oxo-2-((S)-2-propylcarbamoyl-pyrrolidin-1-yl)-ethoxy]-quinoline-2-carbonyl}-amino)-butyryl]-piperazine-1-carboxylic acid ethyl ester The title compound was prepared by adapting the procedures described in example 3 with the difference that (S)-Pyrrolidine-2-carboxylic acid propylamide and 5,6-Difluoro-4-hydroxy-quinoline-2-carboxylic acid was used instead of (S)-Pyrrolidine-2-carboxylic acid cyclopropylamide hydrochloride and 4-Hydroxy-7-methyl-quinoline-2-carboxylic acid. MS (ES$^+$): m/e=691.

Example 291

4-[(S)-4-Carboxy-2-({4-[2-((S)-2-cyclobutylcarbamoyl-pyrrolidin-1-yl)-2-oxo-ethoxy]-6,7-dimethyl-quinoline-2-carbonyl}-amino)-butyryl]-piperazine-1-carboxylic acid ethyl ester The title compound was prepared by adapting the procedures described in example 3 with the difference that (S)-

Pyrrolidine-2-carboxylic acid cyclobutylamide and 4-Hydroxy-6,7-dimethyl-quinoline-2-carboxylic acid was used instead of (S)-Pyrrolidine-2-carboxylic acid cyclopropylamide hydrochloride and 4-Hydroxy-7-methyl-quinoline-2-carboxylic acid. MS (ES$^+$): m/e=695.

Example 292

4-[(S)-2-({4-[2-((S)-2-Cyclobutylcarbamoyl-pyrrolidin-1-yl)-2-oxo-ethoxy]-6-fluoro-5-methyl-quinoline-2-carbonyl}-amino)-4-ethoxycarbonyl-butyryl]-piperazine-1-carboxylic acid ethyl ester The title compound was prepared by adapting the procedure described in example 107 with the difference that 4-[(S)-4-tert-Butoxycarbonyl-2-({4-[2-((S)-2-cyclobutylcarbamoyl-pyrrolidin-1-yl)-2-oxo-ethoxy]-6-fluoro-5-methyl-quinoline-2-carbonyl}-amino)-butyryl]-piperazine-1-carboxylic acid ethyl ester was used instead of 4-[(S)-4-tert-Butoxycarbonyl-2-({4-[2-((S)-2-cyclopropylcarbamoyl-pyrrolidin-1-yl)-2-oxo-ethoxy]-quinoline-2-carbonyl}-amino)-butyryl]-piperazine-1-carboxylic acid ethyl ester. MS (ES+): m/e=727.

Example 293

4-[(S)-2-({4-[(R)-2-((S)-2-Cyclobutylcarbamoyl-pyrrolidin-1-yl)-1-methyl-2-oxo-ethoxy]-7-methyl-quinoline-2-carbonyl}-amino)-4-ethoxycarbonyl-butyryl]-piperazine-1-carboxylic acid ethyl ester To 3 ml of a saturated solution of hydrochloric acid in ethanol 150 mg of 4-[(S)-4-tert-Butoxycarbonyl-2-({4-[(R)-2-((S)-2-cyclobutylcarbamoyl-pyrrolidin-1-yl)-1-methyl-2-oxo-ethoxy]-7-methyl-quinoline-2-carbonyl}-amino)-butyryl]-piperazine-1-carboxylic acid ethyl ester was added and the mixture was stirred for 2 h. Then, 20 ml of toluene was added and the solvents were removed under reduced pressure. The residue was co-distilled twice with toluene and then purified by preparative HPLC (C18 reverse phase column, elution with a water/MeCN gradient with 0.1% TFA). The fractions containing the product were evaporated and lyophilized to yield a white solid. This solid was dissolved in 8 ml of a water/actonitrile mixture, 2 ml of a 1 M aqueous hydrochloric acid was added and the solution was again lyophilized to yield the product as its hydrochloride. Yield: 135 mg MS (ES$^+$): m/e=723.

Example 294

4-[(S)-4-Carboxy-2-({4-[(R)-2-((S)-2-cyclopentyl-carbamoyl-pyrrolidin-1-yl)-1-methyl-2-oxo-ethoxy]-7-methyl-quinoline-2-carbonyl}-amino)-butyryl]-piperazine-1-carboxylic acid ethyl ester The title compound was prepared by adapting the procedures described in example 274 with the difference that (S)-Pyrrolidine-2-carboxylic acid cyclopentylamide was used instead of (S)-Pyrrolidine-2-carboxylic acid cyclobutylamide. MS (ES$^+$): m/e=709.

Example 295

4-[(S)-2-({4-[(R)-2-((S)-2-Cyclopentylcarbamoyl-pyrrolidin-1-yl)-1-methyl-2-oxo-ethoxy]-7-methyl-quinoline-2-carbonyl}-amino)-4-ethoxycarbonyl-butyryl]-piperazine-1-carboxylic acid ethyl ester The title compound was prepared by adapting the procedure described in example 107 with the difference that 4-[(S)-4-tert-Butoxycarbonyl-2-({4-[(R)-2-((S)-2-cyclopentylcarbamoyl-pyrrolidin-1-yl)-1-methyl-2-oxo-ethoxy]-7-methyl-quinoline-2-carbonyl}-amino)-butyryl]-piperazine-1-carboxylic acid ethyl ester was used instead of 4-[(S)-4-tert-Butoxycarbonyl-2-({4-[2-((S)-2-cyclopropylcarbamoyl-pyrrolidin-1-yl)-2-oxo-ethoxy]-quinoline-2-carbonyl}-amino)-butyryl]-piperazine-1-carboxylic acid ethyl ester. MS (ES+): m/e=737.

Example 296

4-{(S)-4-Carboxy-2-[(7-methyl-4-{(R)-1-methyl-2-oxo-2-[(S)-2-(piperidine-1-carbonyl)-pyrrolidin-1-yl]-ethoxy}-quinoline-2-carbonyl)-amino]-butyryl}-piperazine-1-carboxylic acid ethyl ester The title compound was prepared by adapting the procedures described in example 274 with the difference that Piperidin-1-yl-(S)-pyrrolidin-2-yl-methanone was used instead of (S)-Pyrrolidine-2-carboxylic acid cyclobutylamide. MS (ES$^+$): m/e=709.

Example 297

4-{(S)-4-Ethoxycarbonyl-2-[(7-methyl-4-{(R)-1-methyl-2-oxo-2-[(S)-2-(piperidine-1-carbonyl)-pyrrolidin-1-yl]-ethoxy}-quinoline-2-carbonyl)-amino]-butyryl}-piperazine-1-carboxylic acid ethyl ester The title compound was prepared by adapting the procedure described in example 107 with the difference that 4-{(S)-4-tert-Butoxycarbonyl-2-[(7-methyl-4-{(R)-1-methyl-2-oxo-2-[(S)-2-(piperidine-1-carbonyl)-pyrrolidin-1-yl]-ethoxy}-quinoline-2-carbonyl)-amino]-butyryl}-piperazine-1-carboxylic acid ethyl ester was used instead of 4-[(S)-4-tert-Butoxycarbonyl-2-({4-[2-((S)-2-cyclopropylcarbamoyl-pyrrolidin-1-yl)-2-oxo-ethoxy]-quinoline-2-carbonyl}-amino)-butyryl]-piperazine-1-carboxylic acid ethyl ester. MS (ES+): m/e=737.

Example 298

4-[(S)-4-Carboxy-2-({7-methyl-4-[(R)-1-methyl-2-oxo-2-((S)-2-propylcarbamoyl-pyrrolidin-1-yl)-ethoxy]-quinoline-2-carbonyl}-amino)-butyryl]-piperazine-1-carboxylic acid ethyl ester The title compound was prepared by adapting the procedures described in example 274 with the difference that Piperidin-1-yl-(S)-pyrrolidin-2-yl-methanone was used instead of (S)-Pyrrolidine-2-carboxylic acid propylamide. MS (ES$^+$): m/e=683.

Example 299

4-[(S)-4-Ethoxycarbonyl-2-({7-methyl-4-[(R)-1-methyl-2-oxo-2-((S)-2-propylcarbamoyl-pyrrolidin-1-yl)-ethoxy]-quinoline-2-carbonyl}-amino)-butyryl]-piperazine-1-carboxylic acid ethyl ester The title compound was prepared by adapting the procedure described in example 107 with the difference that 4-[(S)-4-tert-Butoxycarbonyl-2-({7-methyl-4-[(R)-1-methyl-2-oxo-2-((S)-2-propylcarbamoyl-pyrrolidin-1-yl)-ethoxy]-quinoline-2-carbonyl}-amino)-butyryl]-piperazine-1-carboxylic acid ethyl ester was used instead of 4-[(S)-4-tert-Butoxycarbonyl-2-({4-[2-((S)-2-cyclopropylcarbamoyl-pyrrolidin-1-yl)-2-oxo-ethoxy]-quinoline-2-carbonyl}-amino)-butyryl]-piperazine-1-carboxylic acid ethyl ester. MS (ES+): m/e=711.

Example 300

4-{(S)-4-Carboxy-2-[(4-{(R)-2-[(S)-2-(cyclopropyl-methyl-carbamoyl)-pyrrolidin-1-yl]-1-methyl-2-oxo-ethoxy}-7-methyl-quinoline-2-carbonyl)-amino]-butyryl}-piperazine-1-carboxylic acid ethyl ester The title compound was prepared by adapting the procedures described in example 274 with the difference that (S)-Pyrrolidine-2-carboxylic acid cyclopropylmethyl-amide was used instead of (S)-Pyrrolidine-2-carboxylic acid propylamide. MS (ES$^+$): m/e=695.

Example 301

4-{(S)-2-[(4-{(R)-2-[(S)-2-(Cyclopropylmethyl-carbamoyl)-pyrrolidin-1-yl]-1-methyl-2-oxo-ethoxy}-7-methyl-quinoline-2-carbonyl)-amino]-4-ethoxycarbonyl-butyryl}-piperazine-1-carboxylic acid ethyl ester The title compound was prepared by adapting the procedure described in example 107 with the difference that 4-{(S)-4-tert-Butoxycarbonyl-2-[(4-{(R)-2-[(S)-2-(cyclopropylmethyl-carbamoyl)-pyrrolidin-1-yl]-1-methyl-2-oxo-ethoxy}-7-methyl-quinoline-2-carbonyl)-amino]-butyryl}-piperazine-1-carboxylic acid ethyl ester was used instead of 4-[(S)-4-tert-Butoxycarbonyl-2-({4-[2-((S)-2-cyclopropyl-carbamoyl-pyrrolidin-1-yl)-2-oxo-ethoxy]-quinoline-2-carbonyl}-amino)-butyryl]-piperazine-1-carboxylic acid ethyl ester. MS (ES+): m/e=723.

Example 302

4-{(S)-4-Carboxy-2-[(4-{2-[(S)-2-(4,4-difluoro-piperidine-1-carbonyl)-pyrrolidin-1-yl]-2-oxo-ethoxy}-7-methyl-quinoline-2-carbonyl)-amino]-butyryl}-piperazine-1-carboxylic acid ethyl ester The title compound was prepared by adapting the procedures described in example 57 with the difference that and (4,4-Difluoro-piperidin-1-yl)-(S)-pyrrolidin-2-yl-methanone was used instead of (S)-Pyrrolidine-2-carboxylic acid cyclobutylamide. MS (ES$^+$): m/e=731.

Example 303

4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid butyl ester

(i) Piperazine-1,4-dicarboxylic acid butyl ester tert-butyl ester

To a solution of 15 g of Piperazine-1-carboxylic acid tert-butyl ester in 200 ml of DCM, 18 g of triethylamine was added and the mixture was cooled to 0° C. Then, 12.1 g of butyl chloroformate was slowly added. After the addition was completed the reaction mixture was allowed to warm to RT and to stir for 16 h. Then, 200 ml of DCM was added and the organic phase was washed two times with 0.1 M aqueous hydrochloric acid followed by saturated aqueous sodium hydrogen carbonate solution. The organic phase was dried over MgSO$_4$ and the solvents were removed under reduced pressure. The crude product was pure enough for the next reaction step. Yield: 21.9 g.

(ii) Piperazine-1-carboxylic acid butyl ester

To a solution of 21.9 g of Piperazine-1,4-dicarboxylic acid butyl ester tert-butyl ester from the preceding reaction step (i) in 20 ml of DCM, 30 ml of TFA was slowly added at RT. After 16 h, 200 ml of toluene was added and the solvents were removed under reduced pressure. The isolated crude product was obtained as its trifluoroacetate salt and was pure enough for the next reaction step. Yield: 23 g.

(iii) 4-((S)-2-Benzyloxycarbonylamino-4-tert-butoxycarbonyl-butyryl)-piperazine-1-carboxylic acid butyl ester To a solution of 22.4 g of (S)-2-Benzyloxycarbonylamino-pentanedioic acid 5-tert-butyl ester, 30.7 g of NEM and 21.8 g of TOTU in 75 ml of DMF, 20 g of Piperazine-1-carboxylic acid butyl ester trifluoroacetate was added at RT and stirred for 16 h. The reaction mixture was then diluted with saturated aqueous sodium hydrogen carbonate solution and then extracted with 300 ml of ethyl acetate. The organic phase was washed with diluted saturated aqueous sodium hydrogen carbonate solution and dried over MgSO$_4$. The solvents were removed under reduced pressure. The crude product was purified by chromatography on silica gel eluting with n-heptane/ethyl acetate (1/1). The fractions containing the product were combined and the solvent evaporated under reduced pressure. Yield: 33.4 g.

(iv) 4-((S)-2-Amino-4-tert-butoxycarbonyl-butyryl)-piperazine-1-carboxylic acid butyl ester A solution of 33.4 g of 4-((S)-2-Benzyloxycarbonylamino-4-tert-butoxycarbonyl-butyryl)-piperazine-1-carboxylic acid ethyl ester in 130 ml of ethanol was purged with argon. Then, 3.3 g of Pd/C (5-10%) was added and the mixture stirred under a hydrogen atmosphere (3 bar). After 6 h the reaction mixture was filtered through a pad of celite and the solvents were removed under reduced pressure. After drying under reduced pressure the product was pure enough for the next reaction step. Yield: 17.3 g.

(v) 4-tert-Butoxycarbonylmethoxy-7-methyl-quinoline-2-carboxylic acid ethyl ester To a solution of 3.0 g of 4-Hydroxy-7-methyl-quinoline-2-carboxylic acid ethyl ester in 20 ml of DMF, 3.0 g of potassium carbonate and 3.8 g of Bromo-acetic acid tert-butyl ester was added and stirred for 16 h. Then, the reaction mixture was diluted with water and extracted with ethyl acetate (3×150 ml). The combined organic phases were dried over MgSO$_4$ and the solvents were removed under reduced pressure. The crude product was pure enough for the next reaction step. Yield: 4.9 g.

(vi) 4-Carboxymethoxy-7-methyl-quinoline-2-carboxylic acid ethyl ester

To a solution of 4.9 g of -tert-Butoxycarbonylmethoxy-7-methyl-quinoline-2-carboxylic acid ethyl ester from the preceding reaction step (v) in 50 ml of DCM 1.5 ml of TFA was added at RT. After 16 h, 20 ml of toluene was added and the solvents were removed under reduced pressure. The residue was co-distilled additional two times with toluene. After drying under reduced pressure the product was pure enough for the next reaction step. Yield: 3.8 g.

(vii) 4-[2-((S)-2-Cyclobutylcarbamoyl-pyrrolidin-1-yl)-2-oxo-ethoxy]-7-methyl-quinoline-2-carboxylic acid ethyl ester To a solution of 2 g of 4-Carboxymethoxy-7-methyl-quinoline-2-carboxylic acid ethyl ester in 30 ml of DCM, 3.6 g of EDC, 3.4 g of pentafluorophenol, 2.2 g of NEM was added and the reaction mixture was stirred at RT for 2 h. Then, 5.3 g of (S)-Pyrrolidine-2-carboxylic acid cyclobutylamide trifluoroacetate and 2.1 g of NEM in 10 ml of DCM was added. After 16 h the reaction mixture was diluted with water and extracted with DCM (3×150 ml). The combined organic phases were dried over $MgSO_4$ and the solvents were removed under reduced pressure. The crude product was purified by chromatography on silica gel eluting with a gradient of n-heptane/ethyl acetate. The fractions containing the product were combined and the solvent evaporated under reduced pressure. Yield: 2.5 g.

(viii) 4-[2-((S)-2-Cyclobutylcarbamoyl-pyrrolidin-1-yl)-2-oxo-ethoxy]-7-methyl-quinoline-2-carboxylic acid To a solution of 2.5 g 4-[2-((S)-2-Cyclobutylcarbamoyl-pyrrolidin-1-yl)-2-oxo-ethoxy]-7-methyl-quinoline-2-carboxylic acid ethyl ester in 20 ml of THF, 5.7 ml of a 1M aqueous sodium hydroxide solution was added and stirred for 16 h at RT. The reaction mixture was acidified with 1M hydrochloric acid to pH 3 and the solvents were evaporated under reduced pressure. The residue was dissolved in a mixture of methanol/DCM and the solids were filtered off. The filtrate was evaporated under reduced pressure to yield the product which was pure enough for the next reaction step. Yield: 2.0 g.

(iix) 4-[(S)-4-tert-Butoxycarbonyl-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid butyl ester To a solution of 500 mg of 4-[2-((S)-2-Cyclobutylcarbamoyl-pyrrolidin-1-yl)-2-oxo-ethoxy]-7-methyl-quinoline-2-carboxylic acid and 451 mg of 4-((S)-2-Amino-4-tert-butoxycarbonyl-butyryl)piperazine-1-carboxylic acid butyl ester in 5 ml of DMF, 186 mg of HOBT and 232 mg of EDC was added and the reaction mixture was stirred for 4 h at RT. Then, the reaction mixture was diluted with water and filtered through a chem Elut® cartridge by eluting with ethyl acetate. The solvents were removed under reduced pressure and the isolated crude product was pure enough for the next reaction step. Yield: 930 mg.

(ix) 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid butyl ester To a solution of 50 mg of 4-[(S)-4-tert-Butoxycarbonyl-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid butyl ester from the preceding reaction step (viii) in 2 ml of DCM 0.2 ml of TFA was added at RT. After 5 h, 20 ml of toluene was added and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. Yield: 6 mg MS (ES+): m/e=709.

Example 304

4-[(S)-2-({4-[2-((S)-2-Cyclobutylcarbamoyl-pyrrolidin-1-yl)-2-oxo-ethoxy]-quinoline-2-carbonyl}-amino)-4-hydroxy-butyryl]-piperazine-1-carboxylic acid ethyl ester

(i) 4-((S)-4-Benzyloxy-2-tert-butoxycarbonylamino-butyryl)-piperazine-1-carboxylic acid ethyl ester To a solution of 220 mg of (S)-4-Benzyloxy-2-tert-butoxycarbonylamino-butyric acid, 327 mg of NEM and 233 mg of TOTU in 1.6 ml of DMF, 112 mg of Piperazine-1-carboxylic acid ethyl ester was added at RT and stirred for 16 h. The reaction mixture was diluted saturated aqueous sodium hydrogen carbonate solution. After filtration through a chem Elut® cartridge by eluting with ethyl acetate the solvents were removed under reduced pressure. The isolated crude product was pure enough for the next reaction step.

(ii) 4-((S)-2-Amino-4-benzyloxy-butyryl)-piperazine-1-carboxylic acid ethyl ester To a solution of 325 mg of 4-((S)-4-Benzyloxy-2-tert-butoxycarbonylamino-butyryl)-piperazine-1-carboxylic acid ethyl ester from the preceding reaction step (i) in 1.2 ml of DCM 0.6 ml of TFA was added at RT. After 16 h, 20 ml of toluene was added and the solvents were removed under reduced pressure. The isolated crude product was obtained as its trifluoroacetate salt and was pure enough for the next reaction step. Yield: 389 mg.

(iii) 4-Benzyloxycarbonylmethoxy-quinoline-2-carboxylic acid ethyl ester

To a solution of 10 g of 4-Hydroxy-quinoline-2-carboxylic acid ethyl ester in 300 ml of DMF, 10 g of potassium carbonate and 15.2 g of Bromo-acetic acid benzyl ester was added and stirred for 16 h. Then, the reaction mixture was diluted with water and extracted with ethyl acetate (3×150 ml). The combined organic phases were dried over $MgSO_4$ and the solvents were removed under reduced pressure. The crude product was purified by chromatography on silica gel eluting with n-heptane/ethyl acetate (2/8). The fractions containing the product were combined and the solvent evaporated under reduced pressure. Yield: 10.2 g.

(iv) 4-Carboxymethoxy-quinoline-2-carboxylic acid ethyl ester

A solution of 10.2 g of 4-Benzyloxycarbonylmethoxy-quinoline-2-carboxylic acid ethyl ester in 200 ml of ethyl acetate was purged with argon. Then, 2 g of Pd/C (5-10%) was added and the mixture stirred under a hydrogen atmosphere (4 bar). After 16 h the reaction mixture was filtered through a pad of celite washing with isopropanol, followed by acetonitrile and then DMF. The solvents were removed under reduced pressure. After drying under reduced pressure the product was pure enough for the next reaction step. Yield: 8.7 g.

(v) 4-[2-((S)-2-Cyclobutylcarbamoyl-pyrrolidin-1-yl)-2-oxo-ethoxy]-quinoline-2-carboxylic acid ethyl ester To a solution of 2 g of 4-Carboxymethoxy-quinoline-2-carboxylic acid ethyl ester in 20 ml of DMF, 2.8 g of EDC, 2.7 g of pentafluorophenol was added and the reaction mixture was stirred at RT for 2 h. Then, 3.1 g of (S)-Pyrrolidine-2-carboxylic acid cyclobutylamide trifluoroacetate and 1.7 g of NEM in 10 ml of DMF was added. After 16 h the reaction mixture was diluted with water and extracted with DCM (3×150 ml). The combined organic phases were dried over $MgSO_4$ and the solvents were removed under reduced pressure. The crude product was purified by chromatography on silica gel eluting with a gradient of n-heptane/ethyl acetate. The fractions containing the product were combined and the solvent evaporated under reduced pressure. Yield: 1.4 g.

(vi) 4-[2-((S)-2-Cyclobutylcarbamoyl-pyrrolidin-1-yl)-2-oxo-ethoxy]-quinoline-2-carboxylic acid To a solution of 1.4 g 4-[2-((S)-2-Cyclobutylcarbamoyl-pyrrolidin-1-yl)-2-oxo-ethoxy]-quinoline-2-carboxylic acid ethyl ester in 20 ml of THF, 3.3 ml of a 1M aqueous sodium hydroxide solution was added and stirred for 16 h at RT. The reaction mixture was acidified with 1M hydrochloric acid to pH 1 to precipitate the product, which was then collected by filtration. The residue was co-distilled additional two times with toluene. After drying under reduced pressure the product was pure enough for the next reaction step. Yield: 945 mg.

(vii) 4-[(S)-4-Benzyloxy-2-({4-[2-((S)-2-cyclobutylcarbamoyl-pyrrolidin-1-yl)-2-oxo-ethoxy]-quinoline-2-carbonyl}-amino)-butyryl]-piperazine-1-carboxylic acid ethyl ester To a solution of 200 mg of 4-[2-((S)-2-Cyclobutylcarbamoyl-pyrrolidin-1-yl)-2-oxo-ethoxy]-quinoline-2-carboxylic acid and 233 mg of 4-((S)-2-Amino-4-benzyloxy-butyryl)-piperazine-1-carboxylic acid ethyl ester trifluoroacetate in 4 ml of DMF, 77 mg of HOBT, 97 mg of EDC and 1 ml NEM was added and the reaction mixture was stirred for 16 h at RT. Then, the reaction mixture was diluted with water and filtered through a chem Elut® cartridge by eluting with ethyl acetate. The solvents were removed under reduced pressure and the residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. Yield: 448 mg MS (ES+): m/e=729.

(viii) 4-[(S)-2-({4-[2-((S)-2-Cyclobutylcarbamoyl-pyrrolidin-1-yl)-2-oxo-ethoxyl]-quinoline-2-carbonyl}-amino)-4-hydroxy-butyryl]-piperazine-1-carboxylic acid ethyl ester A solution of 580 mg of 4-[(S)-4-Benzyloxy-2-({4-[2-((S)-2-cyclobutylcarbamoyl-pyrrolidin-1-yl)-2-oxo-ethoxy]-quinoline-2-carbonyl}-amino)-butyryl]-piperazine-1-carboxylic acid ethyl ester and 0.1 ml of acetic acid in 20 ml of ethanol was purged with argon. Then, 200 mg of Pd/C (5-10%) was added and the mixture was stirred under a hydrogen atmosphere (5 bar). After 16 h the reaction mixture was filtered through a pad of celite and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. Yield: 206 mg MS (ES+): m/e=639.

Example 305

4-[(S)-2-({4-[2-((S)-2-Cyclobutylcarbamoyl-pyrrolidin-1-yl)-2-oxo-ethoxy]-quinoline-2-carbonyl}-amino)-4-hydroxy-butyryl]-piperazine-1-carboxylic acid butyl ester

(i) 4-((S)-4-Benzyloxy-2-tert-butoxycarbonylaminobutyryl)-piperazine-1-carboxylic acid butyl ester To a solution of 5 g of (S)-4-Benzyloxy-2-tert-butoxycarbonylamino-butyric acid, 7.4 g of NEM and 5.3 g of TOTU in 35 ml of DMF, 4.8 g of Piperazine-1-carboxylic acid butyl ester trifluoroacetate was added at RT and stirred for 16 h. The reaction mixture was diluted saturated aqueous sodium hydrogen carbonate solution and extracted with 250 ml of ethyl acetate. The organic phase was dried over $MgSO_4$ and the solvents were removed under reduced pressure. The crude product was purified by chromatography on silica gel eluting with a gradient of n-heptane/ethyl acetate. The fractions containing the product were combined and the solvent evaporated under reduced pressure. Yield: 6.3 g.

(ii) 4-((S)-2-Amino-4-benzyloxy-butyryl)-piperazine-1-carboxylic acid butyl ester To a solution of 6.3 g of 4-((S)-4-Benzyloxy-2-tert-butoxycarbonylamino-butyryl)-piperazine-1-carboxylic acid butyl ester from the preceding reaction step (i) in 24 ml of DCM 5 ml of TFA was added at RT. After 5 h, 100 ml of toluene was added and the solvents were removed under reduced pressure. The residue was co-distilled with toluene additional two times and then dissolved in DCM and washed with water. The organic phase was dried over $MgSO_4$ and the solvents were removed under reduced pressure. The isolated crude product was obtained as its trifluoroacetate salt and was pure enough for the next reaction step. Yield: 6.1 g.

(iii) 4-{(S)-4-Benzyloxy-2-[(4-hydroxy-quinoline-2-carbonyl)-amino]-butyryl}-piperazine-1-carboxylic acid butyl ester To a solution of 1 g of 4-Hydroxy-quinoline-2-carboxylic acid and 2.6 g of 4-((S)-2-Amino-4-benzyloxy-butyryl)-piperazine-1-carboxylic acid butyl ester trifluoroacetate in 12 ml of DMF, 0.8 g of HOBT, 1.0 g of EDC and 1.2 g of NEM was added and the reaction mixture was stirred for 16 h at RT. Then, the reaction mixture was diluted with water and extracted with ethyl acetate. The organic phase was dried over $MgSO_4$ and the solvents were removed under reduced pressure. The crude product was precipitated from a mixture of n-heptane and ethyl acetate. The precipitated product was collected by filtration and dried under reduced pressure. The isolated product was pure enough for the next reaction step. Yield: 900 mg.

(iv) 4-{(S)-4-Benzyloxy-2-[(4-tert-butoxycarbonylmethoxy-quinoline-2-carbonyl)-amino]-butyryl}-piperazine-1-carboxylic acid butyl ester To a solution of 900 mg 4-{(S)-4-Benzyloxy-2-[(4-hydroxy-quinoline-2-carbonyl)-amino]-butyryl}-piperazine-1- carboxylic acid butyl ester in 6.7 ml of DMF, 587 mg of cesium carbonate and 351 mg of Bromo-acetic acid tert-butyl ester was added and the reaction mixture was stirred for 5 h at RT. Then, the reaction mixture was diluted with water and extracted with ethyl acetate. The organic phase was dried over MgSO$_4$ and the solvents were removed under reduced pressure. The isolated crude product was pure enough for the next reaction step. Yield: 1.1 g.

(v) 4-{(S)-4-Benzyloxy-2-[(4-carboxymethoxy-quinoline-2-carbonyl)-amino]-butyryl}-piperazine-1-carboxylic acid butyl ester To a solution 1.1 g of 4-{(S)-4-Benzyloxy-2-[(4-tert-butoxycarbonylmethoxy-quinoline-2-carbonyl)-amino]-butyryl}-piperazine-1-carboxylic acid butyl ester from the preceding reaction step (iv) in 5 ml of DCM, 0.5 ml of TFA was added at RT. After 16 h, 20 ml of toluene was added and the solvents were removed under reduced pressure. The residue was dissolved in 100 ml of DCM and washed with water. The organic phase was dried over MgSO$_4$ and the solvents were removed under reduced pressure. The isolated crude product was obtained as its trifluoroacetate salt and was pure enough for the next reaction step. Yield: 990 mg.

(vi) 4-[(S)-4-Benzyloxy-2-({4-[2-((S)-2-cyclobutyl-carbamoyl-pyrrolidin-1-yl)-2-oxo-ethoxy]-quinoline-2-carbonyl}-amino)-butyryl]-piperazine-1-carboxylic acid butyl ester To a solution of 990 mg of 4-{(S)-4-Benzyloxy-2-[(4-carboxymethoxy-quinoline-2-carbonyl)-amino]-butyryl}-piperazine-1-carboxylic acid butyl ester in 5 ml of DCM, 631 mg of EDC, 19 mg of NEM and 607 mg of pentafluorophenol was added and the reaction mixture was stirred at RT for 2 h. Then, 480 mg of (S)-Pyrrolidine-2-carboxylic acid cyclobutylamide trifluoroacetate and 380 mg of NEM in 2 ml of DCM was added. After 3 h the reaction mixture was diluted with water and extracted with DCM (3×150 ml). The combined organic phases were dried over MgSO$_4$ and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. Yield: 270 mg.

(vii) 4-[(S)-2-({4-[2-((S)-2-Cyclobutylcarbamoyl-pyrrolidin-1-yl)-2-oxo-ethoxy]-quinoline-2-carbonyl}-amino)-4-hydroxy-butyryl]-piperazine-1-carboxylic acid butyl ester A solution of 270 mg of 4-[(S)-4-Benzyloxy-2-({4-[2-((S)-2-cyclobutylcarbamoyl-pyrrolidin-1-yl)-2-oxo-ethoxy]-quinoline-2-carbonyl}-amino)-butyryl]-piperazine-1-carboxylic acid butyl ester and 0.1 ml of acetic acid in 10 ml of ethanol was purged with argon. Then, 100 mg of Pd/C (5-10%) was added and the mixture was stirred under a hydrogen atmosphere (5 bar). After 16 h the reaction mixture was filtered through a pad of celite and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. Yield: 76 mg MS (ES+): m/e=667.

Example 306

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-hydroxy-butyryl]-piperazine-1-carboxylic acid ethyl ester (i) 4-{(S)-4-Benzyloxy-2-[(4-hydroxy-7-methyl-quinoline-2-carbonyl)-amino]-butyryl}-piperazine-1-carboxylic acid ethyl ester To a solution of 1 g of 4-Hydroxy-7-methyl-quinoline-2-carboxylic acid and 1.7 g of 4-((S)-2-Amino-4-benzyloxy-butyryl)-piperazine-1-carboxylic acid ethyl ester trifluoroacetate in 15 ml of DMF, 566 mg of NEM, 753 mg of HOBT and 943 mg of EDC was added and the reaction mixture was stirred for 16 h at RT. Then, the reaction mixture was diluted with water and extracted with ethyl acetate. The organic phase was dried over MgSO$_4$ and the solvents were removed under reduced pressure. The crude product was precipitated from a mixture of n-heptane and ethyl acetate. The precipitated product was collected by filtration and dried under reduced pressure. The isolated product was pure enough for the next reaction step. Yield: 1.8 g.

(ii) 4-{(S)-4-Benzyloxy-2-[(4-tert-butoxycarbonylmethoxy-7-methyl-quinoline-2-carbonyl)-amino]-butyryl}-piperazine-1-carboxylic acid ethyl ester To a solution of 1.8 g of 4-{(S)-4-Benzyloxy-2-[(4-hydroxy-7-methyl-quinoline-2-carbonyl)-amino]-butyryl}-piperazine-1-carboxylic acid ethyl ester in 20 ml of DMF, 1.2 g of cesium carbonate and 723 mg of Bromo-acetic acid tert-butyl ester was added and the reaction mixture was stirred for 2 h at RT. Then, the reaction mixture was diluted with water and extracted with ethyl acetate. The organic phase was dried over MgSO$_4$ and the solvents were removed under reduced pressure. The crude product was purified by chromatography on silica gel eluting with a gradient of n-heptane/ethyl acetate. The fractions containing the product were combined and the solvent evaporated under reduced pressure. Yield: 1.3 g.

(iii) 4-{(S)-4-Benzyloxy-2-[(4-carboxymethoxy-7-methyl-quinoline-2-carbonyl)-amino]-butyryl}-piperazine-1-carboxylic acid ethyl ester To a solution of 4-{(S)-4-Benzyloxy-2-[(4-tert-butoxycarbonylmethoxy-7-methyl-quinoline-2-carbonyl)-amino]-butyryl}-piperazine-1-carboxylic acid ethyl ester from the preceding reaction step (ii) in 10 ml of DCM 1.5 ml of TFA was added at RT. After 3 h, 20 ml of toluene was added and the solvents were removed under reduced pressure. Then, the reaction mixture was diluted with water and extracted with ethyl acetate. The organic phase was dried over MgSO$_4$ and the solvents were removed under reduced pressure. The product was obtained as its trifluoroacetate salt. Yield: 1.2 g.

(iv) 4-[(S)-4-Benzyloxy-2-({4-[2-((S)-2-cyclobutyl-carbamoyl-pyrrolidin-1-yl)-2-oxo-ethoxy]-7-methyl-quinoline-2-carbonyl}-amino)-butyryl]-piperazine-1-carboxylic acid ethyl ester To a solution of 1.2 g of 4-{(S)-4-Benzyloxy-2-[(4-carboxymethoxy-7-methyl-quinoline-2-carbonyl)-amino]-butyryl}-piperazine-1-carboxylic acid ethyl ester in 10 ml of DCM, 465 mg of EDC, 447 mg of pentafluorophenol and 466 mg of NEM was added and the reaction mixture was stirred for 2 h at RT. Then, 1.1 g of (S)-Pyrrolidine-2-carboxylic acid cyclobutylamide trifluoroacetate and 466 mg of NEM in 4 ml of DCM was added. After 16 h the reaction mixture was diluted with water and extracted with DCM (3×150 ml). The combined organic phases were dried over MgSO$_4$ and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. Yield: 2.5 g.

(v) 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-hydroxy-butyryl]-piperazine-1-carboxylic acid ethyl ester A solution of 600 mg of 4-[(S)-4-Benzyloxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester and 0.1 ml of acetic acid in 20 ml of ethanol was purged with argon. Then, 200 mg of Pd/C (5-10%) was added and the mixture was stirred under a hydrogen atmosphere (5 bar). After 16 h the reaction mixture was filtered through a pad of celite and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid. This solid was dissolved in 5 ml of a water/actonitrile mixture, 2 ml of a 1 M aqueous hydrochloric acid was added and the solution was again lyophilized to yield the product as its hydrochloride. Yield: 441 mg MS (ES+): m/e=653.

Example 307

4-[(S)-2-({4-[2-((S)-2-Cyclobutylcarbamoyl-pyrrolidin-1-yl)-2-oxo-ethoxy]-7-fluoro-quinoline-2-carbonyl}-amino)-4-ethoxycarbonyl-butyryl]-piperazine-1-carboxylic acid ethyl ester The title compound was prepared by adapting the procedure described in example 107 with the difference that 4-[(S)-4-tert-Butoxycarbonyl-2-({4-[2-((S)-2-cyclobutylcarbamoyl-pyrrolidin-1-yl)-2-oxo-ethoxy]-7-fluoro-quinoline-2-carbonyl}-amino)-butyryl]-piperazine-1-carboxylic acid ethyl ester was used instead of 4-[(S)-4-tert-Butoxycarbonyl-2-({4-[2-((S)-2-cyclopropylcarbamoyl-pyrrolidin-1-yl)-2-oxo-ethoxy]-quinoline-2-carbonyl}-amino)-butyryl]-piperazine-1-carboxylic acid ethyl ester. MS (ES+): m/e=713.

Example 308

4-{(S)-4-Carboxy-2-[(4-{2-[(S)-2-(cyclobutylmethyl-carbamoyl)-pyrrolidin-1-yl]-2-oxo-ethoxy}-7-methyl-quinoline-2-carbonyl)-amino]-butyryl}-piperazine-1-carboxylic acid ethyl ester The title compound was prepared by adapting the procedures described in example 57 with the difference that and (S)-Pyrrolidine-2-carboxylic acid cyclobutylmethyl-amide was used instead of (S)-Pyrrolidine-2-carboxylic acid cyclobutylamide. MS (ES$^+$): m/e=695.

Example 309

4-[(S)-4-Carboxy-2-({4-[2-(3,3-difluoro-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 3,3-Difluoro-pyrrolidine was used instead of (S)-Pyrrolidine-2-carboxylic acid cyclopropylamide hydrochloride. MS (ES$^+$): m/e=606.

Example 310

4-[(S)-2-({4-[2-(2-Butyl-pyrrolidin-1-yl)-2-oxo-ethoxy]-quinoline-2-carbonyl}-amino)-4-carboxy-butyryl]-piperazine-1-carboxylic acid ethyl ester The title compound was prepared by adapting the procedures described in example 73 with the difference that 2-Butyl-pyrrolidine was used instead of (S)-Pyrrolidine-2-carboxylic acid cyclopropylamide hydrochloride. MS (ES$^+$): m/e=626.

Example 311

4-[(S)-4-Carboxy-2-({4-[2-(4-cyclohexyl-3-oxo-piperazin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 1-Cyclohexyl-piperazin-2-one was used instead of (S)-Pyrrolidine-2-carboxylic acid cyclopropylamide hydrochloride. MS (ES$^+$): m/e=681.

Example 312

4-[(S)-4-Carboxy-2-({4-[2-(2-methyl-3-oxo-piperazin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 3-Methyl-piperazin-2-one was used instead of (S)-Pyrrolidine-2-carboxylic acid cyclopropylamide hydrochloride. MS (ES$^+$): m/e=613.

Example 313

4-{(S)-4-Carboxy-2-[(4-{2-oxo-2-[4-(2-oxo-pyrrolidin-1-yl)-piperidin-1-yl]-ethoxy}-quinoline-2-carbonyl)-amino]-butyryl}-piperazine-1-carboxylic acid ethyl ester The title compound was prepared by adapting the procedures described in example 73 with the difference that 1-Piperidin-4-yl-pyrrolidin-2-one was used instead of (S)-Pyrrolidine-2-carboxylic acid cyclopropylamide hydrochloride. MS (ES$^+$): m/e=667.

Example 314

4-[(S)-4-Carboxy-2-({4-[2-oxo-2-(3-oxo-4-phenyl-piperazin-1-yl)-ethoxy]-quinoline-2-carbonyl}-amino)-butyryl]-piperazine-1-carboxylic acid ethyl ester The title compound was prepared by adapting the procedures described in example 73 with the difference that 1-Phenyl-piperazin-2-one was used instead of (S)-Pyrrolidine-2-carboxylic acid cyclopropylamide hydrochloride. MS (ES$^+$): m/e=675.

Example 315

4-[(S)-4-Carboxy-2-({4-[2-(4-isobutoxy-piperidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 4-Isobutoxy-piperidine was used instead of (S)-Pyrrolidine-2-carboxylic acid cyclopropylamide hydrochloride. MS (ES$^+$): m/e=656.

Example 316

4-[(S)-4-Carboxy-2-({4-[2-(4-isopropoxy-piperidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 4-Isopropoxy-piperidine was used instead of (S)-Pyrrolidine-2-carboxylic acid cyclopropylamide hydrochloride. MS (ES$^+$): m/e=642.

Example 317

4-[(S)-4-Carboxy-2-({4-[2-(2-furan-2-yl-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 2-Furan-2-yl-pyrrolidine was used instead of (S)-Pyrrolidine-2-carboxylic acid cyclopropylamide hydrochloride. MS (ES$^+$): m/e=636.

Example 318

4-[(S)-4-Carboxy-2-({4-[2-((R)-2-cyano-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (R)-Pyrrolidine-2-carbonitrile was used instead of (S)-Pyrrolidine-2-carboxylic acid cyclopropylamide hydrochloride. MS (ES$^+$): m/e=595.

Example 319

4-{(S)-4-Carboxy-2-[(4-{2-[4-(2-morpholin-4-yl-2-oxo-ethyl)-piperazin-1-yl]-2-oxo-ethoxy}-quinoline-2-carbonyl)-amino]-butyryl}-piperazine-1-carboxylic acid ethyl ester The title compound was prepared by adapting the procedures described in example 73 with the difference that 1-Morpholin-4-yl-2-piperazin-1-yl-ethanone was used instead of (S)-Pyrrolidine-2-carboxylic acid cyclopropylamide hydrochloride. MS (ES$^+$): m/e=712.

Example 320

4-[(S)-4-Carboxy-2-({4-[2-((2S,4R)-4-hydroxy-2-methoxycarbonyl-piperidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (2S,4R)-4-Hydroxy-piperidine-2-carboxylic acid methyl ester was used instead of (S)-Pyrrolidine-2-carboxylic acid cyclopropylamide hydrochloride. MS (ES$^+$): m/e=658.

Example 321

4-{(S)-4-Carboxy-2-[(4-{2-[2-(5-methyl-furan-2-yl)-pyrrolidin-1-yl]-2-oxo-ethoxy}-quinoline-2-carbonyl)-amino]-butyryl}-piperazine-1-carboxylic acid ethyl ester The title compound was prepared by adapting the procedures described in example 73 with the difference that 2-(5-Methyl-furan-2-yl)-pyrrolidine was used instead of (S)-Pyrrolidine-2-carboxylic acid cyclopropylamide hydrochloride. MS (ES$^+$): m/e=650.

Example 322

4-[(S)-4-Carboxy-2-({4-[2-(2-methoxymethyl-piperidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 2-Methoxymethyl-piperidine was used instead of (S)-Pyrrolidine-2-carboxylic acid cyclopropylamide hydrochloride. MS (ES$^+$): m/e=628.

Example 323

4-[(S)-4-Carboxy-2-({4-[2-(4-morpholin-4-yl-piperidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 4-Piperidin-4-yl-morpholine was used instead of (S)-Pyrrolidine-2-carboxylic acid cyclopropylamide hydrochloride. MS (ES$^+$): m/e=669.

Example 324

4-[(S)-4-Carboxy-2-({4-[2-(4-isopropyl-piperazin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 1-Isopropyl-piperazine was used instead of (S)-Pyrrolidine-2-carboxylic acid cyclopropylamide hydrochloride. MS (ES$^+$): m/e=627.

Example 325

4-[(S)-4-Carboxy-2-({4-[2-(2-ethoxymethyl-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 2-Ethoxymethyl-pyrrolidine was used instead of (S)-Pyrrolidine-2-carboxylic acid cyclopropylamide hydrochloride. MS (ES$^+$): m/e=628.

Example 326

4-[(S)-4-Carboxy-2-({4-[2-(4-cyclopropanecarbonyl-piperazin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that Cyclopropyl-piperazin-1-yl-methanone was used instead of (S)-Pyrrolidine-2-carboxylic acid cyclopropylamide hydrochloride. MS (ES$^+$): m/e=653.

Example 327

4-((S)-4-Carboxy-2-{[4-(2-oxo-2-piperazin-1-yl-ethoxy)-quinoline-2-carbonyl]-amino}-butyryl)-piperazine-1-carboxylic acid ethyl ester The title compound was prepared by adapting the procedures described in example 73 with the difference that Piperazine-1-carboxylic acid tert-butyl ester was used instead of (S)-Pyrrolidine-2-carboxylic acid cyclopropylamide hydrochloride. MS (ES$^+$): m/e=585.

Example 328

4-[(S)-4-Carboxy-2-({4-[2-(4-ethanesulfonyl-piperazin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 1-Ethanesulfonyl-piperazine was used instead of (S)-Pyrrolidine-2-carboxylic acid cyclopropylamide hydrochloride. MS (ES$^+$): m/e=677.

Example 329

4-[(S)-4-Carboxy-2-({4-[2-oxo-2-((S)-2-trifluoromethyl-pyrrolidin-1-yl)-ethoxy]-quinoline-2-carbonyl}-amino)-butyryl]-piperazine-1-carboxylic acid ethyl ester The title compound was prepared by adapting the procedures described in example 73 with the difference that (S)-2-Trifluoromethyl-pyrrolidine was used instead of (S)-Pyrrolidine-2-carboxylic acid cyclopropylamide hydrochloride. MS (ES$^+$): m/e=638.

Example 330

4-{(S)-4-Carboxy-2-[(4-{2-oxo-2-[2-(tetrahydro-furan-2-yl)-piperidin-1-yl]-ethoxy}-quinoline-2-carbonyl)-amino]-butyryl}-piperazine-1-carboxylic acid ethyl ester The title compound was prepared by adapting the procedures described in example 73 with the difference that 2-(Tetrahydro-furan-2-yl)-piperidine was used instead of (S)-Pyrrolidine-2-carboxylic acid cyclopropylamide hydrochloride. MS (ES$^+$): m/e=654.

Example 331

4-[(S)-4-Carboxy-2-({4-[2-(2-morpholin-4-ylmethyl-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 4-Pyrrolidin-2-ylmethyl-morpholine was used instead of (S)-Pyrrolidine-2-carboxylic acid cyclopropylamide hydrochloride. MS (ES$^+$): m/e=669.

Example 332

4-[(S)-4-Carboxy-2-({4-[2-(2,2-dimethyl-3-oxo-piperazin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 3,3-Dimethyl-piperazin-2-one was used instead of (S)-Pyrrolidine-2-carboxylic acid cyclopropylamide hydrochloride. MS (ES$^+$): m/e=627.

Example 333

4-[(S)-4-Carboxy-2-({4-[2-(2-methylsulfanylmethyl-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 2-Methylsulfanylmethyl-pyrrolidine was used instead of (S)-Pyrrolidine-2-carboxylic acid cyclopropylamide hydrochloride. MS (ES$^+$): m/e=630.

Example 334

4-[(S)-4-Carboxy-2-({4-[2-oxo-2-(2-phenyl-pyrrolidin-1-yl)-ethoxy]-quinoline-2-carbonyl}-amino)-butyryl]-piperazine-1-carboxylic acid ethyl ester The title compound was prepared by adapting the procedures described in example 73 with the difference that 2-Phenyl-pyrrolidine was used instead of (S)-Pyrrolidine-2-carboxylic acid cyclopropylamide hydrochloride. MS (ES$^+$): m/e=646.

Example 335

4-[(S)-4-Carboxy-2-({4-[2-oxo-2-(2-thiazol-2-yl-pyrrolidin-1-yl)-ethoxy]-quinoline-2-carbonyl}-amino)-butyryl]-piperazine-1-carboxylic acid ethyl ester The title compound was prepared by adapting the procedures described in example 73 with the difference that 2-Pyrrolidin-2-yl-thiazole was used instead of (S)-Pyrrolidine-2-carboxylic acid cyclopropylamide hydrochloride. MS (ES$^+$): m/e=653.

Example 336

4-[(S)-4-Carboxy-2-({4-[2-(2-cyclopentyl-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 2-Cyclopentyl-pyrrolidine was used instead of (5)-Pyrrolidine-2-carboxylic acid cyclopropylamide hydrochloride. MS (ES$^+$): m/e=638.

Example 337

4-[(S)-4-Carboxy-2-({4-[2-(3-methoxy-3a,4,6,6a-tetrahydro-pyrrolo[3,4-d]isoxazol-5-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 3-Methoxy-4,5,6,6a-tetrahydro-3aH-pyrrolo[3,4-d]isoxazole was used instead of (S)-Pyrrolidine-2-carboxylic acid cyclopropylamide hydrochloride. MS (ES$^+$): m/e=641.

Example 338

4-[(S)-4-Carboxy-2-({4-[2-(4,4-difluoro-piperidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 4,4-Difluoro-piperidine was used instead of (S)-Pyrrolidine-2-carboxylic acid cyclopropylamide hydrochloride. MS (ES$^+$): m/e=620.

Example 339

4-[(S)-4-Carboxy-2-({4-[2-((S)-2-cyano-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (S)-Pyrrolidine-2-carbonitrile was used instead of (S)-Pyrrolidine-2-carboxylic acid cyclopropylamide hydrochloride. MS (ES$^+$): m/e=595.

Example 340

4-[(S)-4-Carboxy-2-({4-[2-oxo-2-(3-trifluoromethyl-pyrrolidin-1-yl)-ethoxy]-quinoline-2-carbonyl}-amino)-butyryl]-piperazine-1-carboxylic acid ethyl ester The title compound was prepared by adapting the procedures described in example 73 with the difference that 3-Trifluoromethyl-pyrrolidine was used instead of (S)-Pyrrolidine-2-carboxylic acid cyclopropylamide hydrochloride. MS (ES$^+$): m/e=638.

Example 341

4-[(S)-4-Carboxy-2-({4-[2-oxo-2-(4-oxo-hexahydro-cyclopenta[c]pyrrol-2-yl)-ethoxy]-quinoline-2-carbonyl}-amino)-butyryl]-piperazine-1-carboxylic acid ethyl ester The title compound was prepared by adapting the procedures described in example 73 with the difference that Hexahydro-cyclopenta[c]pyrrol-4-one was used instead of (S)-Pyrrolidine-2-carboxylic acid cyclopropylamide hydrochloride. MS (ES$^+$): m/e=624.

Example 342

4-[(S)-4-Carboxy-2-({4-[2-oxo-2-(4-oxo-imidazolidin-1-yl)-ethoxy]-quinoline-2-carbonyl}-amino)-butyryl]-piperazine-1-carboxylic acid ethyl ester The title compound was prepared by adapting the procedures described in example 73 with the difference that Imidazolidin-4-one was used instead of (S)-Pyrrolidine-2-carboxylic acid cyclopropylamide hydrochloride. MS (ES$^+$): m/e=585.

Example 343

(S)-4-({4-[2-((S)-2-Cyclobutylcarbamoyl-pyrrolidin-1-yl)-2-oxo-ethoxy]-quinoline-2-carbonyl}-amino)-5-[4-(3-methoxy-phenyl)-piperazin-1-yl]-5-oxo-pentanoic acid (i) (S)-4-Benzyloxycarbonylamino-5-[4-(3-methoxy-phenyl)-piperazin-1-yl]-5-oxo-pentanoic acid tert-butyl ester To a solution of 2 g of (S)-2-Benzyloxycarbonylamino-pentanedioic acid 5-tert-butyl ester 2.7 g of NEM and 1.9 g of TOTU in 10 ml of DMF, 1.1 g of 1-(3-Methoxy-phenyl)-piperazine was added at RT and stirred for 16 h. The reaction mixture was diluted with 150 ml of ethyl and subsequently extracted with aqueous LiCl (4% w/w), 0.1 M HCl and aqueous NaHCO$_3$. The organic layer was dried over MgSO$_4$ and the solvent was removed under reduced pressure. The crude product thus obtained was pure enough for the further manipulations. Yield: 4 g.

(ii) (S)-4-Amino-5-[4-(3-methoxy-phenyl)-piperazin-1-yl]-5-oxo-pentanoic acid tert-butyl ester A solution of 4 g of (S)-4-Benzyloxycarbonylamino-5-[4-(3-methoxy-phenyl)-piperazin-1-yl]-5-oxo-pentanoic acid tert-butyl ester in 60 ml of ethanol was purged with argon. Then, 0.7 g of Pd/C (5-10%) was added and the mixture stirred under a hydrogen atmosphere (3 bar). After 16 h the reaction mixture was filtered through a pad of celite and the solvents were removed under reduced pressure. After drying under reduced pressure the product was pure enough for the next reaction step. Yield: 2.9 g.

(iii) (S)-4-({4-[2-((S)-2-Cyclobutylcarbamoyl-pyrrolidin-1-yl)-2-oxo-ethoxy]-quinoline-2-carbonyl}-amino)-5-[4-(3-methoxy-phenyl)-piperazin-1-yl]-5-oxo-pentanoic acid To a solution of 70 mg of 4-[2-((S)-2-Cyclobutylcarbamoyl-pyrrolidin-1-yl)-2-oxo-ethoxy]-quinoline-2-carboxylic acid and 66 mg (S)-4-Amino-5-[4-(3-methoxy-phenyl)-piperazin-1-yl]-5-oxo-pentanoic acid tert-butyl ester in 2 ml of DMF, 27 mg of HOBT, 27 mg of EDC and 0.5 ml NEM was added and the reaction mixture was stirred for 16 h at RT. Then, the reaction mixture was diluted with water and filtered through a chem Elut® cartridge by eluting with ethyl acetate. The solvents were removed under reduced pressure and the residue was dissolved in 1 ml of DCM and 0.6 ml of TFA. After 16 h at RT 10 ml of toluene was added and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. Yield: 65 mg MS (ES+): m/e=701.

Example 344

4-[(S)-5-Carboxy-2-({4-[2-((S)-2-cyclobutylcarbamoyl-pyrrolidin-1-yl)-2-oxo-ethoxy]-quinoline-2-carbonyl}-amino)-pentanoyl]-piperazine-1-carboxylic acid ethyl ester (i) 4-((S)-2-Benzyloxycarbonylamino-5-tert-butoxycarbonyl-pentanoyl)-piperazine-1-carboxylic acid ethyl ester To a solution of 2 g of (S)-2-Benzyloxycarbonylamino-hexanedioic acid 6-tert-butyl ester dicyclohexyl-ammonium salt, 1.7 g of NEM and 1.2 g of TOTU in 6 ml of DMF, 0.62 g of Piperazine-1-carboxylic acid ethyl ester was added at RT and stirred for 16 h. The reaction mixture was diluted saturated aqueous sodium hydrogen carbonate solution and extracted with 150 ml of ethyl acetate. The organic phase was dried over $MgSO_4$ and the solvents were removed under reduced pressure. The crude product was purified by chromatography on silica gel eluting with a gradient of n-heptane/ethyl acetate. The fractions containing the product were combined and the solvent evaporated under reduced pressure. Yield: 2.2 g.

(ii) 4-((S)-2-Amino-5-tert-butoxycarbonyl-pentanoyl)-piperazine-1-carboxylic acid ethyl ester A solution of 2.3 g of 4-((S)-2-Benzyloxycarbonylamino-5-tert-butoxycarbonyl-pentanoyl)-piperazine-1-carboxylic acid ethyl ester in 50 ml of ethanol was purged with argon. Then, 50 mg of Pd/C (5-10%) was added and the mixture stirred under a hydrogen atmosphere (3 bar). After 4 h the reaction mixture was filtered through a pad of celite and the solvents were removed under reduced pressure. After drying under reduced pressure the product was pure enough for the next reaction step. Yield: 1.7 g.

(iii) 4-[(S)-5-Carboxy-2-({4-[2-((S)-2-cyclobutylcarbamoyl-pyrrolidin-1-yl)-2-oxo-ethoxy]-quinoline-2-carbonyl}-amino)-pentanoyl]-piperazine-1-carboxylic acid ethyl ester To a solution of 70 mg of 4-[2-((S)-2-Cyclobutylcarbamoyl-pyrrolidin-1-yl)-2-oxo-ethoxy]-quinoline-2-carboxylic acid and 63 mg of 4-((S)-2-Amino-5-tert-butoxycarbonyl-pentanoyl)-piperazine-1-carboxylic acid ethyl ester in 2 ml of DMF, 27 mg of HOBT, 27 mg of EDC and 0.5 ml NEM was added and the reaction mixture was stirred for 16 h at RT. Then, the reaction mixture was diluted with water and filtered through a chem Elut® cartridge by eluting with ethyl acetate. The solvents were removed under reduced pressure and the residue was dissolved in 1 ml of DCM and 0.6 ml of TFA. After 16 h at RT 10 ml of toluene was added and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. Yield: 33 mg MS (ES+): m/e=681.

Example 345

4-[(S)-2-({4-[2-((S)-2-Cyclobutylcarbamoyl-pyrrolidin-1-yl)-2-oxo-ethoxy]-quinoline-2-carbonyl}-amino)-4-methanesulfonyl-butyryl]-piperazine-1-carboxylic acid ethyl ester (i) 4-((S)-2-tert-Butoxycarbonylamino-4-methanesulfonyl-butyryl)-piperazine-1-carboxylic acid ethyl ester To a solution of 2 g of (S)-2-tert-Butoxycarbonylamino-4-methanesulfonyl-butyric acid, 3.2 g of NEM and 2.3 g of TOTU in 10 ml of DMF, 1.2 g of Piperazine-1-carboxylic acid ethyl ester was added at RT and stirred for 2 h. The reaction mixture was diluted saturated aqueous sodium hydrogen carbonate solution and extracted with 400 ml of ethyl acetate. The organic phase was washed with diluted saturated aqueous sodium hydrogen carbonate solution and dried over $MgSO_4$ and the solvents were removed under reduced pressure. The crude product was purified by chromatography on silica gel eluting with a gradient of n-heptane/ethyl acetate. The fractions containing the product were combined and the solvent evaporated under reduced pressure. Yield: 1.9 g.

(ii) 4-((S)-2-Amino-4-methanesulfonyl-butyryl)-piperazine-1-carboxylic acid ethyl ester To 1.9 g of 4-((S)-2-tert-Butoxycarbonylamino-4-methanesulfonyl-butyryl)-piperazine-1-carboxylic acid ethyl ester, 20 ml of methanolic hydrochloric acid was added at RT and stirred for 3 h. Then, 100 ml of toluene was added and the solvents were removed under reduced pressure. The product was obtained as its hydrochloric acid salt. Yield: 1.9 g.

(iii) 4-[(S)-2-({4-[2-((S)-2-Cyclobutylcarbamoyl-pyrrolidin-1-yl)-2-oxo-ethoxy]-quinoline-2-carbonyl}-amino)-4-methanesulfonyl-butyryl]-piperazine-1-carboxylic acid ethyl ester To a solution of 70 mg of 4-[2-((S)-2-Cyclobutylcarbamoyl-pyrrolidin-1-yl)-2-oxo-ethoxy]-quinoline-2-carboxylic acid and 57 mg of 4-((S)-2-Amino-4-methanesulfonyl-butyryl)-piperazine-1-carboxylic acid ethyl ester in 2 ml of DMF, 27 mg of HOBT, 27 mg of EDC and 0.5 ml NEM was added and the reaction mixture was stirred for 16 h at RT. Then, the reaction mixture was diluted with water and filtered through a chem Elut® cartridge by eluting with ethyl acetate. The solvents were removed under reduced pressure and the residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. Yield: 120 mg MS (ES+): m/e=701.

Example 346

4-[(S)-4-Carboxy-2-({4-[2-((S)-2-methyl-3-oxo-piperazin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (S)-3-Methyl-piperazin-2-one was used instead of (S)-Pyrrolidine-2-carboxylic acid cyclopropylamide hydrochloride. MS (ES$^+$): m/e=613.

Example 347

4-[(S)-4-Carboxy-2-({4-[2-oxo-2-(2-pyridin-3-yl-pyrrolidin-1-yl)-ethoxy]-quinoline-2-carbonyl}-amino)-butyryl]-piperazine-1-carboxylic acid ethyl ester The title compound was prepared by adapting the procedures described in example 73 with the difference that 3-Pyrrolidin-2-yl-pyridine was used instead of (S)-Pyrrolidine-2-carboxylic acid cyclopropylamide hydrochloride. MS (ES$^+$): m/e=647.

Example 348

4-((S)-4-Carboxy-2-{[4-((1S,4S)-2-2,5-diaza-bicyclo[2.2.1]hept-2-yl-2-oxo-ethoxy)-quinoline-2-carbonyl]-amino}-butyryl)-piperazine-1-carboxylic acid ethyl ester The title compound was prepared by adapting the procedures described in example 73 with the difference that (1S,4S)-2,5-Diaza-bicyclo[2.2.1]heptane-2-carboxylic acid tert-butyl ester was used instead of (S)-Pyrrolidine-2-carboxylic acid cyclopropylamide hydrochloride. MS (ES$^+$): m/e=597.

Example 349

4-[(S)-2-({4-[2-((S)-3-Amino-pyrrolidin-1-yl)-2-oxo-ethoxy]-quinoline-2-carbonyl}-amino)-4-carboxy-butyryl]-piperazine-1-carboxylic acid ethyl ester The title compound was prepared by adapting the procedures described in example 73 with the difference that (S)-Pyrrolidin-3-yl-carbamic acid tert-butyl ester was used instead of (S)-Pyrrolidine-2-carboxylic acid cyclopropylamide hydrochloride. MS (ES$^+$): m/e=585.

Example 350

4-{(S)-4-Carboxy-2-[(4-{2-[2-(1-methyl-piperidin-2-yl)-pyrrolidin-1-yl]-2-oxo-ethoxy}-quinoline-2-carbonyl)-amino]-butyryl}-piperazine-1-carboxylic acid ethyl ester The title compound was prepared by adapting the procedures described in example 73 with the difference that 1-Methyl-2-pyrrolidin-2-yl-piperidine was used instead of (S)-Pyrrolidine-2-carboxylic acid cyclopropylamide hydrochloride. MS (ES$^+$): m/e=667.

Example 351

4-[(S)-4-Carboxy-2-({4-[2-oxo-2-(3-pyridin-4-yl-pyrrolidin-1-yl)-ethoxy]-quinoline-2-carbonyl}-amino)-butyryl]-piperazine-1-carboxylic acid ethyl ester The title compound was prepared by adapting the procedures described in example 73 with the difference that 4-Pyrrolidin-3-yl-pyridine was used instead of (S)-Pyrrolidine-2-carboxylic acid cyclopropylamide hydrochloride. MS (ES$^+$): m/e=647.

Example 352

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-ethoxycarbonyl-butyryl]-piperazine-1-carboxylic acid butyl ester To 5 ml of a saturated solution of hydrochloric acid in ethanol 200 mg of 4-[(S)-4-tert-Butoxycarbonyl-2-({4-[2-((S)-2-cyclobutylcarbamoyl-pyrrolidin-1-yl)-2-oxo-ethoxy]-7-methyl-quinoline-2-carbonyl}-amino)-butyryl]piperazine-1-carboxylic acid butyl ester was added and the mixture was stirred for 16 h. Then, 30 ml of toluene was added and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid. This solid was dissolved in 5 ml of a water/actonitrile mixture, 1 ml of a 1 M aqueous hydrochloric acid was added and the solution was again lyophilized to yield the product as its hydrochloride. Yield: 167 mg MS (ES$^+$): m/e=737.

Example 353

4-[(S)-4-Carboxy-2-({4-[2-((R)-2-methoxymethyl-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (R)-2-Methoxymethyl-pyrrolidine was used instead of (S)-Pyrrolidine-2-carboxylic acid cyclopropylamide hydrochloride. MS (ES$^+$): m/e=614.

Example 354

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-hydroxy-butyryl]-piperazine-1-carboxylic acid butyl ester

(i) 4-((S)-4-Benzyloxy-2-tert-butoxycarbonylamino-butyryl)-piperazine-1-carboxylic acid butyl ester To a solution of 5 g of (S)-4-Benzyloxy-2-tert-butoxycarbonylamino-butyric acid, 7.4 g of NEM and 5.3 g of TOTU in 35 ml of DMF, 4.8 g of Piperazine-1-carboxylic acid butyl ester trifluoroacetate was added at RT and stirred for 16 h. The reaction mixture was diluted saturated aqueous sodium hydrogen carbonate solution and extracted with 250 ml of ethyl acetate. The organic phase was dried over $MgSO_4$ and the solvents were removed under reduced pressure. The crude product was purified by chromatography on silica gel eluting with a gradient of n-heptane/ethyl acetate. The fractions containing the product were combined and the solvent evaporated under reduced pressure. Yield: 6.3 g.

(ii) 4-((S)-2-Amino-4-benzyloxy-butyryl)-piperazine-1-carboxylic acid butyl ester To a solution of 6.3 g of 4-((S)-4-Benzyloxy-2-tert-butoxycarbonylamino-butyryl)-piperazine-1-carboxylic acid butyl ester from the preceding reaction step (i) in 24 ml of DCM 5 ml of TFA was added at RT. After 5 h, 100 ml of toluene was added and the solvents were removed under reduced pressure. The residue was co-distilled with toluene additional two times and then dissolved in DCM and washed with water. The organic phase was dried over $MgSO_4$ and the solvents were removed under reduced pressure. The isolated crude product was obtained as its trifluoroacetate salt and was pure enough for the next reaction step. Yield: 6.1 g.

(iii) 4-{(S)-4-Benzyloxy-2-[(4-hydroxy-7-methyl-quinoline-2-carbonyl)-amino]-butyryl}-piperazine-1-carboxylic acid butyl ester To a solution of 1 g of 4-Hydroxy-7-methyl-quinoline-2-carboxylic acid and 1.8 g of 4-((S)-2-Amino-4-benzyloxy-butyryl)-piperazine-1-carboxylic acid butyl ester trifluoroacetate in 12 ml of DMF, 566 mg of NEM, 1.1 g of HOBT and 1.4 g of EDC was added and the reaction mixture was stirred for 16 h at RT. Then, the reaction mixture was diluted with water and extracted with ethyl acetate. The organic phase was dried over $MgSO_4$ and the solvents were removed under reduced pressure. The crude product was purified by chromatography on silica gel eluting with a gradient of n-heptane/ethyl acetate. The fractions containing the product were combined and the solvent evaporated under reduced pressure. Yield: 650 mg.

(iv) 4-{(S)-4-Benzyloxy-2-[(4-tert-butoxycarbonylmethoxy-7-methyl-quinoline-2-carbonyl)-amino]-butyryl}-piperazine-1-carboxylic acid butyl ester To a solution of 650 mg of 4-{(S)-4-Benzyloxy-2-[(4-hydroxy-7-methyl-quinoline-2-carbonyl)-amino]-butyryl}-piperazine-1-carboxylic acid butyl ester in 7.7 ml of DMF, 414 mg of cesium carbonate and 248 mg of Bromo-acetic acid tert-butyl ester was added and the reaction mixture was stirred for 2 h at RT. Then, the reaction mixture was diluted with water and extracted with ethyl acetate. The organic phase was dried over $MgSO_4$ and the solvents were removed under reduced pressure. The crude product was purified by chromatography on silica gel eluting with a gradient of n-heptane/ethyl acetate. The fractions containing the product were combined and the solvent evaporated under reduced pressure. Yield: 590 mg.

(v) 4-{(S)-4-Benzyloxy-2-[(4-carboxymethoxy-7-methyl-quinoline-2-carbonyl)-amino]-butyryl}-piperazine-1-carboxylic acid butyl ester To a solution of 4-{(S)-4-Benzyloxy-2-[(4-tert-butoxycarbonylmethoxy-7-methyl-quinoline-2-carbonyl)-amino]-butyryl}-piperazine-1-carboxylic acid butyl ester from the preceding reaction step (iv) in 10 ml of DCM 0.5 ml of TFA was added at RT. After 3 h, 20 ml of toluene was added and the solvents were removed under reduced pressure. Then, the reaction mixture was diluted with water and extracted with ethyl acetate. The organic phase was dried over $MgSO_4$ and the solvents were removed under reduced pressure. The product was obtained as its trifluoroacetate salt. Yield: 850 mg.

(vi) 4-[(S)-4-Benzyloxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid butyl ester To a solution of 850 mg of 4-{(S)-4-Benzyloxy-2-[(4-carboxymethoxy-7-methyl-quinoline-2-carbonyl)-amino]-butyryl}-piperazine-1-carboxylic acid butyl ester in 10 ml of DCM, 524 mg of EDC and 504 mg of pentafluorophenol was added and the reaction mixture was stirred for 2 h at RT. Then, 772 mg of (S)-Pyrrolidine-2-carboxylic acid cyclobutylamide trifluoroacetate and 315 mg of NEM in 2 ml of DCM was added. After 16 h the reaction mixture was diluted with water and filtered through a chem Elut® cartridge by eluting with ethyl acetate. Then, the solvents were removed under reduced pressure and the residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. Yield: 80 mg.

(vii) 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-hydroxy-butyryl]-piperazine-1-carboxylic acid ethyl ester A solution of 600 mg of 4-[(S)-4-Benzyloxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester and 0.1 ml of acetic acid in 5 ml of ethanol was purged with argon. Then, 100 mg of Pd/C (5-10%) was added and the mixture was stirred under a hydrogen atmosphere (5 bar). After 16 h the reaction mixture was filtered through a pad of celite and the solvents were removed under reduced pressure. The residue was co-distilled twice with toluene and then purified by preparative HPLC (C18 reverse phase column, elution with a water/MeCN gradient with 0.1% TFA). The fractions containing the product were evaporated and lyophilized to yield a white solid. This solid was dissolved in 8 ml of a water/actonitrile mixture, 1 ml of a 1 M aqueous hydrochloric acid was added and the solution was again lyophilized to yield the product as its hydrochloride. Yield: 55 mg MS (ES+): m/e=681.

Example 355

4-[(S)-4-Carboxy-2-({4-[(R)-2-((S)-2-carboxy-pyrrolidin-1-yl)-1-methyl-2-oxo-ethoxy]-7-methyl-quinoline-2-carbonyl}-amino)-butyryl]-piperazine-1-carboxylic acid ethyl ester The title compound was prepared by adapting the procedures described in example 274 with the difference that (S)-Pyrrolidine-2-carboxylic acid was used instead of (S)-Pyrrolidine-2-carboxylic acid cyclobutylamide. MS (ES$^+$): m/e=642.

Example 356

4-[(S)-4-Carboxy-2-({7-methyl-4-[(R)-1-methyl-2-oxo-2-(2-phenyl-pyrrolidin-1-yl)-ethoxy]-quinoline-2-carbonyl}-amino)-butyryl]-piperazine-1-carboxylic acid ethyl ester The title compound was prepared by adapting the procedures described in example 274 with the difference that 2-Phenyl-pyrrolidine was used instead of (S)-Pyrrolidine-2-carboxylic acid cyclobutylamide. MS (ES$^+$): m/e=674.

Example 357

4-[(S)-4-Carboxy-2-({4-[2-oxo-2-(2-o-tolyl-pyrrolidin-1-yl)-ethoxy]-quinoline-2-carbonyl}-amino)-butyryl]-piperazine-1-carboxylic acid ethyl ester The title compound was prepared by adapting the procedures described in example 73 with the difference that 2-o-Tolyl-pyrrolidine was used instead of (S)-Pyrrolidine-2-carboxylic acid cyclopropylamide hydrochloride. MS (ES$^+$): m/e=660.

Example 358

4-[(S)-4-Carboxy-2-({4-[2-oxo-2-(3-phenyl-pyrrolidin-1-yl)-ethoxy]-quinoline-2-carbonyl}-amino)-butyryl]-piperazine-1-carboxylic acid ethyl ester The title compound was prepared by adapting the procedures described in example 73 with the difference that 3-Phenyl-pyrrolidine was used instead of (S)-Pyrrolidine-2-carboxylic acid cyclopropylamide hydrochloride. MS (ES$^+$): m/e=646.

Example 359

4-[(S)-4-Carboxy-2-({4-[2-(2-hydroxymethyl-2,3-dihydro-indol-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (2,3-Dihydro-1H-indol-2-yl)-methanol was used instead of (S)-Pyrrolidine-2-carboxylic acid cyclopropylamide hydrochloride. MS (ES$^+$): m/e=648.

Example 360

4-[(S)-2-({4-[2-(5-Acetyl-2,3-dihydro-indol-1-yl)-2-oxo-ethoxy]-quinoline-2-carbonyl}-amino)-4-carboxy-butyryl]-piperazine-1-carboxylic acid ethyl ester The title compound was prepared by adapting the procedures described in example 73 with the difference that 1-(2,3-Dihydro-1H-indol-5-yl)-ethanone was used instead of (S)-Pyrrolidine-2-carboxylic acid cyclopropylamide hydrochloride. MS (ES$^+$): m/e=660.

Example 361

(S)-1-(2-{2-[(S)-3-Carboxy-1-(4-ethoxycarbonyl-piperazine-1-carbonyl)-propylcarbamoyl]-quinolin-4-yloxy}-acetyl)-2,3-dihydro-1H-indole-2-carboxylic acid The title compound was prepared by adapting the procedures described in example 73 with the difference that (S)-2,3-Dihydro-1H-indole-2-carboxylic acid was used instead of (S)-Pyrrolidine-2-carboxylic acid cyclopropylamide hydrochloride. MS (ES$^+$): m/e=662.

Example 362

4-[(S)-4-Carboxy-2-({4-[2-(2-methyl-2,3-dihydro-indol-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 2-Methyl-2,3-dihydro-1H-indole was used instead of (S)-Pyrrolidine-2-carboxylic acid cyclopropylamide hydrochloride. MS (ES$^+$): m/e=632.

Example 363

4-[(S)-4-Carboxy-2-({4-[2-(2,3-dihydro-indol-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 2,3-Dihydro-1H-indole was used instead of (S)-Pyrrolidine-2-carboxylic acid cyclopropylamide hydrochloride. MS (ES$^+$): m/e=618.

Example 364

4-[(S)-4-Carboxy-2-({4-[2-((S)-3-hydroxymethyl-3,4-dihydro-1H-isoquinolin-2-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (S)-1-(1,2,3,4-Tetrahydro-isoquinolin-3-yl)-methanol was used instead of (S)-Pyrrolidine-2-carboxylic acid cyclopropylamide hydrochloride. MS (ES+): m/e=662.

Example 365

4-[(S)-4-Carboxy-2-({4-[2-(3,4-dihydro-1H-isoquinolin-2-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 1,2,3,4-Tetrahydro-isoquinoline was used instead of (S)-Pyrrolidine-2-carboxylic acid cyclopropylamide hydrochloride. MS (ES+): m/e=632.

Example 366

4-[(S)-4-Carboxy-2-({4-[2-(6-methoxy-3,4-dihydro-2H-quinolin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 6-Methoxy-1,2,3,4-tetrahydro-quinoline was used instead of (5)-Pyrrolidine-2-carboxylic acid cyclopropylamide hydrochloride. MS (ES+): m/e=662.

Example 367

4-[(S)-4-Carboxy-2-({4-[2-(3,4-dihydro-2H-quinolin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 1,2,3,4-Tetrahydro-quinoline was used instead of (S)-Pyrrolidine-2-carboxylic acid cyclopropylamide hydrochloride. MS (ES+): m/e=632.

Example 368

4-{(S)-4-Carboxy-2-[(4-{2-[2-(4-fluoro-phenyl)-pyrrolidin-1-yl]-2-oxo-ethoxy}-quinoline-2-carbonyl)-amino]-butyryl}-piperazine-1-carboxylic acid ethyl ester The title compound was prepared by adapting the procedures described in example 73 with the difference that 2-(4-Fluoro-phenyl)-pyrrolidine was used instead of (S)-Pyrrolidine-2-carboxylic acid cyclopropylamide hydrochloride. MS (ES+): m/e=664.

Example 369

4-{(S)-4-Carboxy-2-[(4-{2-[2-(2-chloro-phenyl)-pyrrolidin-1-yl]-2-oxo-ethoxy}-quinoline-2-carbonyl)-amino]-butyryl}-piperazine-1-carboxylic acid ethyl ester The title compound was prepared by adapting the procedures described in example 73 with the difference that 2-(2-Chloro-phenyl)-pyrrolidine was used instead of (S)-Pyrrolidine-2-carboxylic acid cyclopropylamide hydrochloride. MS (ES+): m/e=680, chloro pattern.

Example 370

4-[(S)-4-Carboxy-2-({4-[2-(4-methyl-3-oxo-piperazin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 1-Methyl-piperazin-2-one was used instead of (S)-Pyrrolidine-2-carboxylic acid cyclopropylamide hydrochloride. MS (ES+): m/e=613.

Example 371

4-[(S)-4-Carboxy-2-({4-[2-(5-methyl-3-oxo-pyrazolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 5-Methyl-pyrazolidin-3-one was used instead of (S)-Pyrrolidine-2-carboxylic acid cyclopropylamide hydrochloride. MS (ES+): m/e=599.

Example 372

4-[(S)-4-Carboxy-2-({4-[2-oxo-2-(2-pyridin-4-yl-pyrrolidin-1-yl)-ethoxy]-quinoline-2-carbonyl}-amino)-butyryl]-piperazine-1-carboxylic acid ethyl ester The title compound was prepared by adapting the procedures described in example 73 with the difference that 4-Pyrrolidin-2-yl-pyridine was used instead of (S)-Pyrrolidine-2-carboxylic acid cyclopropylamide hydrochloride. MS (ES+): m/e=647.

Example 373

4-[(S)-4-Carboxy-2-({4-[2-(2-methyl-4,6-dihydro-pyrrolo[3,4-d]thiazol-5-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 2-Methyl-5,6-dihydro-4H-pyrrolo[3,4-d]thiazole was used instead of (5)-Pyrrolidine-2-carboxylic acid cyclopropylamide hydrochloride. MS (ES+): m/e=639.

Example 374

4-[(S)-4-Carboxy-2-({4-[2-oxo-2-(3-pyridin-2-yl-pyrrolidin-1-yl)-ethoxy]-quinoline-2-carbonyl}-amino)-butyryl]-piperazine-1-carboxylic acid ethyl ester The title compound was prepared by adapting the procedures described in example 73 with the difference that 2-Pyrrolidin-3-yl-pyridine was used instead of (S)-Pyrrolidine-2-carboxylic acid cyclopropylamide hydrochloride. MS (ES+): m/e=647.

Example 375

4-[(S)-4-Carboxy-2-({4-[2-oxo-2-((R)-2-phenylaminomethyl-pyrrolidin-1-yl)-ethoxy]-quinoline-2-carbonyl}-amino)-butyryl]-piperazine-1-carboxylic acid ethyl ester The title compound was prepared by adapting the procedures described in example 73 with the difference that Phenyl-(R)-1-pyrrolidin-2-ylmethyl-amine was used instead of (S)-Pyrrolidine-2-carboxylic acid cyclopropylamide hydrochloride. MS (ES$^+$): m/e=675.

Example 376

4-[(S)-2-({4-[2-(2-Benzyloxymethyl-pyrrolidin-1-yl)-2-oxo-ethoxy]-quinoline-2-carbonyl}-amino)-4-carboxy-butyryl]-piperazine-1-carboxylic acid ethyl ester The title compound was prepared by adapting the procedures described in example 73 with the difference that 2-Benzyloxymethyl-pyrrolidine was used instead of (S)-Pyrrolidine-2-carboxylic acid cyclopropylamide hydrochloride. MS (ES$^+$): m/e=690.

Example 377

4-[(S)-4-Carboxy-2-({4-[2-(4,7-dihydro-5H-thieno[2,3-c]pyridin-6-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 4,5,6,7-Tetrahydro-thieno[2,3-c]pyridine was used instead of (S)-Pyrrolidine-2-carboxylic acid cyclopropylamide hydrochloride. MS (ES$^+$): m/e=638.

Example 378

4-[(S)-4-Carboxy-2-({4-[2-(4-methyl-6,7-dihydro-4H-thieno[3,2-c]pyridin-5-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 4-Methyl-4,5,6,7-tetrahydro-thieno[3,2-c]pyridine was used instead of (S)-Pyrrolidine-2-carboxylic acid cyclopropylamide hydrochloride. MS (ES$^+$): m/e=652.

Example 379

4-[(S)-4-Carboxy-2-({4-[2-oxo-2-(3-phenyl-6,7-dihydro-4H-isoxazolo[4,5-c]pyridin-5-yl)-ethoxy]-quinoline-2-carbonyl}-amino)-butyryl]-piperazine-1-carboxylic acid ethyl ester The title compound was prepared by adapting the procedures described in example 73 with the difference that 3-Phenyl-4,5,6,7-tetrahydro-isoxazolo[4,5-c]pyridine was used instead of (S)-Pyrrolidine-2-carboxylic acid cyclopropylamide hydrochloride. MS (ES$^+$): m/e=699.

Example 380

4-[(S)-2-({4-[2-(3-Benzyloxy-pyrrolidin-1-yl)-2-oxo-ethoxy]-quinoline-2-carbonyl}-amino)-4-carboxy-butyryl]-piperazine-1-carboxylic acid ethyl ester The title compound was prepared by adapting the procedures described in example 73 with the difference that 3-Benzyloxy-pyrrolidine was used instead of (S)-Pyrrolidine-2-carboxylic acid cyclopropylamide hydrochloride. MS (ES$^+$): m/e=676.

Example 381

4-[(S)-4-Carboxy-2-({4-[2-oxo-2-(3-trifluoromethyl-1,4,6,7-tetrahydro-pyrazolo[4,3-c]pyridin-5-yl)-ethoxy]-quinoline-2-carbonyl}-amino)-butyryl]-piperazine-1-carboxylic acid ethyl ester The title compound was prepared by adapting the procedures described in example 73 with the difference that 3-Trifluoromethyl-4,5,6,7-tetrahydro-1H-pyrazolo[4,3-c]pyridine was used instead of (S)-Pyrrolidine-2-carboxylic acid cyclopropylamide hydrochloride. MS (ES$^+$): m/e=690.

Example 382

4-[(S)-4-Carboxy-2-({4-[2-(2-isopropyl-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 2-Isopropyl-pyrrolidine was used instead of (S)-Pyrrolidine-2-carboxylic acid cyclopropylamide hydrochloride. MS (ES$^+$): m/e=612.

Example 383

4-[(S)-4-Carboxy-2-({4-[2-oxo-2-(2-m-tolyl-pyrrolidin-1-yl)-ethoxy]-quinoline-2-carbonyl}-amino)-butyryl]-piperazine-1-carboxylic acid ethyl ester The title compound was prepared by adapting the procedures described in example 73 with the difference that 2-m-Tolyl-pyrrolidine was used instead of (S)-Pyrrolidine-2-carboxylic acid cyclopropylamide hydrochloride. MS (ES$^+$): m/e=660.

Example 384

4-[(S)-4-Carboxy-2-({4-[2-oxo-2-((R)-3-phenyl-pyrrolidin-1-yl)-ethoxy]-quinoline-2-carbonyl}-amino)-butyryl]-piperazine-1-carboxylic acid ethyl ester The title compound was prepared by adapting the procedures described in example 73 with the difference that (R)-3-Phenyl-pyrrolidine was used instead of (S)-Pyrrolidine-2-carboxylic acid cyclopropylamide hydrochloride. MS (ES$^+$): m/e=646.

Example 385

4-[(S)-4-Carboxy-2-({4-[2-(2-isopropyl-4-methyl-3-oxo-piperazin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 3-Isopropyl-1-methyl-piperazin-2-one was used instead of (S)-Pyrrolidine-2-carboxylic acid cyclopropylamide hydrochloride. MS (ES$^+$): m/e=655.

Example 386

4-[(S)-4-Carboxy-2-({4-[2-(2-ethyl-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 2-Ethyl-pyrrolidine was used instead of (S)-Pyrrolidine-2-carboxylic acid cyclopropylamide hydrochloride. MS (ES$^+$): m/e=598.

Example 387

4-[(S)-4-Carboxy-2-({4-[2-oxo-2-(2-pyridin-2-yl-pyrrolidin-1-yl)-ethoxy]-quinoline-2-carbonyl}-amino)-butyryl]-piperazine-1-carboxylic acid ethyl ester The title compound was prepared by adapting the procedures described in example 73 with the difference that 2-Pyrrolidin-2-yl-pyridine was used instead of (S)-Pyrrolidine-2-carboxylic acid cyclopropylamide hydrochloride. MS (ES$^+$): m/e=647.

Example 388

4-[(S)-2-({4-[2-(2-tert-Butyl-pyrrolidin-1-yl)-2-oxo-ethoxy]-quinoline-2-carbonyl}-amino)-4-carboxy-butyryl]-piperazine-1-carboxylic acid ethyl ester The title compound was prepared by adapting the procedures described in example 73 with the difference that 2-tert-Butyl-pyrrolidine was used instead of (S)-Pyrrolidine-2-carboxylic acid cyclopropylamide hydrochloride. MS (ES$^+$): m/e=626.

Example 389

4-{(S)-2-[(4-{2-[2-(1H-Benzoimidazol-2-yl)-pyrrolidin-1-yl]-2-oxo-ethoxy}-quinoline-2-carbonyl)-amino]-4-carboxy-butyryl}-piperazine-1-carboxylic acid ethyl ester The title compound was prepared by adapting the procedures described in example 73 with the difference that 2-Pyrrolidin-2-yl-1H-benzoimidazole was used instead of (S)-Pyrrolidine-2-carboxylic acid cyclopropylamide hydrochloride. MS (ES$^+$): m/e=686.

Example 390

4-[(S)-4-Carboxy-2-({4-[2-oxo-2-(3-phenylamino-pyrrolidin-1-yl)-ethoxy]-quinoline-2-carbonyl}-amino)-butyryl]-piperazine-1-carboxylic acid ethyl ester The title compound was prepared by adapting the procedures described in example 73 with the difference that Phenyl-pyrrolidin-3-yl-amine was used instead of (S)-Pyrrolidine-2-carboxylic acid cyclopropylamide hydrochloride. MS (ES$^+$): m/e=661.

Example 391

4-((S)-2-{[4-(2-[1,3']Bipyrrolidinyl-1'-yl-2-oxo-ethoxy)-quinoline-2-carbonyl]-amino}-4-carboxy-butyryl)-piperazine-1-carboxylic acid ethyl ester The title compound was prepared by adapting the procedures described in example 73 with the difference that [1,3']Bipyrrolidinyl was used instead of (S)-Pyrrolidine-2-carboxylic acid cyclopropylamide hydrochloride. MS (ES$^+$): m/e=639.

Example 392

4-{(S)-4-Carboxy-2-[(4-{2-oxo-2-[(S)-2-(1H-tetrazol-5-ylmethyl)-pyrrolidin-1-yl]-ethoxy}-quinoline-2-carbonyl)-amino]-butyryl}-piperazine-1-carboxylic acid ethyl ester The title compound was prepared by adapting the procedures described in example 73 with the difference that 5-(S)-1-Pyrrolidin-2-ylmethyl-1H-tetrazole was used instead of (S)-Pyrrolidine-2-carboxylic acid cyclopropylamide hydrochloride. MS (ES$^+$): m/e=652.

Example 393

4-[(S)-4-Carboxy-2-({4-[2-oxo-2-(3-o-tolyloxy-pyrrolidin-1-yl)-ethoxy]-quinoline-2-carbonyl}-amino)-butyryl]-piperazine-1-carboxylic acid ethyl ester The title compound was prepared by adapting the procedures described in example 73 with the difference that 3-o-Tolyloxy-pyrrolidine was used instead of (S)-Pyrrolidine-2-carboxylic acid cyclopropylamide hydrochloride. MS (ES$^+$): m/e=676.

Example 394

4-[(S)-4-Carboxy-2-({4-[2-(2-methyl-6,7-dihydro-4H-thiazolo[5,4-c]pyridin-5-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 2-Methyl-4,5,6,7-tetrahydro-thiazolo[5,4-c]pyridine was used instead of (S)-Pyrrolidine-2-carboxylic acid cyclopropylamide hydrochloride. MS (ES$^+$): m/e=653.

Example 395

4-[(S)-2-({4-[2-(2-Butyl-4-methyl-3-oxo-piperazin-1-yl)-2-oxo-ethoxy]-quinoline-2-carbonyl}-amino)-4-carboxy-butyryl]-piperazine-1-carboxylic acid ethyl ester The title compound was prepared by adapting the procedures described in example 73 with the difference that 3-Butyl-1-methyl-piperazin-2-one was used instead of (S)-Pyrrolidine-2-carboxylic acid cyclopropylamide hydrochloride. MS (ES$^+$): m/e=669.

Example 396

4-{(S)-4-Carboxy-2-[(4-{2-[2-(3-methoxy-phenyl)-pyrrolidin-1-yl]-2-oxo-ethoxy}-quinoline-2-carbonyl)-amino]-butyryl}-piperazine-1-carboxylic acid ethyl ester The title compound was prepared by adapting the procedures described in example 73 with the difference that 2-(3-Methoxy-phenyl)-pyrrolidine was used instead of (S)-Pyrrolidine-2-carboxylic acid cyclopropylamide hydrochloride. MS (ES$^+$): m/e=676.

Example 397

4-[(S)-4-Carboxy-2-({4-[2-(6-methyl-octahydro-pyrrolo[3,4-b]pyridin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 6-Methyl-octahydro-pyrrolo[3,4-b]pyridine was used instead of (S)-Pyrrolidine-2-carboxylic acid cyclopropylamide hydrochloride. MS (ES$^+$): m/e=639.

Example 398

4-{(S)-4-Carboxy-2-[(4-{2-[2-(2-methoxy-phenyl)-pyrrolidin-1-yl]-2-oxo-ethoxy}-quinoline-2-carbonyl)-amino]-butyryl}-piperazine-1-carboxylic acid ethyl ester The title compound was prepared by adapting the procedures described in example 73 with the difference that 2-(2-Methoxy-phenyl)-pyrrolidine was used instead of (S)-Pyrrolidine-2-carboxylic acid cyclopropylamide hydrochloride. MS (ES$^+$): m/e=676.

Example 399

4-[(S)-4-Carboxy-2-({4-[2-(3-diethylamino-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that Diethyl-pyrrolidin-3-yl-amine was used instead of (S)-Pyrrolidine-2-carboxylic acid cyclopropylamide hydrochloride. MS (ES$^+$): m/e=641.

Example 400

4-[(S)-4-Carboxy-2-({4-[2-oxo-2-(3-o-tolyloxy-pyrrolidin-1-yl)-ethoxy]-quinoline-2-carbonyl}-amino)-butyryl]-piperazine-1-carboxylic acid ethyl ester The title compound was prepared by adapting the procedures described in example 73 with the difference that 3-o-Tolyloxy-pyrrolidine was used instead of (S)-Pyrrolidine-2-carboxylic acid cyclopropylamide hydrochloride. MS (ES$^+$): m/e=676.

Example 401

4-{(S)-4-Carboxy-2-[(4-{2-[(S)-2-(cyclobutyl-methyl-carbamoyl)-pyrrolidin-1-yl]-2-oxo-ethoxy}-7-methyl-quinoline-2-carbonyl)-amino]-butyryl}-piperazine-1-carboxylic acid ethyl ester The title compound was prepared by adapting the procedures described in example 57 with the difference that (S)-Pyrrolidine-2-carboxylic acid cyclobutyl-methyl-amide was used instead of (S)-Pyrrolidine-2-carboxylic acid cyclobutylamide. MS (ES$^+$): m/e=695.

Example 402

4-{(S)-2-[(4-{2-[(S)-2-(Cyclobutyl-methyl-carbamoyl)-pyrrolidin-1-yl]-2-oxo-ethoxy}-7-methyl-quinoline-2-carbonyl)-amino]-4-ethoxycarbonyl-butyryl}-piperazine-1-carboxylic acid ethyl ester The title compound was prepared by adapting the procedures described in example 58 with the difference that (S)-Pyrrolidine-2-carboxylic acid cyclobutyl-methyl-amide was used instead of (S)-Pyrrolidine-2-carboxylic acid cyclobutylamide. MS (ES$^+$): m/e=723.

Example 403

4-[(S)-4-Carboxy-2-({4-[2-oxo-2-((R)-2-phenyl-pyrrolidin-1-yl)-ethoxy]-quinoline-2-carbonyl}-amino)-butyryl]-piperazine-1-carboxylic acid ethyl ester The title compound was prepared by adapting the procedures described in example 73 with the difference that (R)-2-Phenyl-pyrrolidine was used instead of (S)-Pyrrolidine-2-carboxylic acid cyclopropylamide hydrochloride. MS (ES$^+$): m/e=646.

Example 404

4-[(S)-4-Carboxy-2-({4-[2-oxo-2-((S)-2-phenyl-pyrrolidin-1-yl)-ethoxy]-quinoline-2-carbonyl}-amino)-butyryl]-piperazine-1-carboxylic acid ethyl ester The title compound was prepared by adapting the procedures described in example 73 with the difference that (S)-2-Phenyl-pyrrolidine was used instead of (S)-Pyrrolidine-2-carboxylic acid cyclopropylamide hydrochloride. MS (ES$^+$): m/e=646.

Example 405

4-{(S)-4-Carboxy-2-[(4-{2-[2-(2-fluoro-phenyl)-pyrrolidin-1-yl]-2-oxo-ethoxy}-quinoline-2-carbonyl)-amino]-butyryl}-piperazine-1-carboxylic acid ethyl ester The title compound was prepared by adapting the procedures described in example 73 with the difference that 2-(2-Fluoro-phenyl)-pyrrolidine was used instead of (S)-Pyrrolidine-2-carboxylic acid cyclopropylamide hydrochloride. MS (ES$^+$): m/e=664.

Example 406

4-{(S)-4-Carboxy-2-[(4-{2-[3-(2-fluoro-phenyl)-pyrrolidin-1-yl]-2-oxo-ethoxy}-quinoline-2-carbonyl)-amino]-butyryl}-piperazine-1-carboxylic acid ethyl ester The title compound was prepared by adapting the procedures described in example 73 with the difference that 3-(2-Fluoro-phenyl)-pyrrolidine was used instead of (S)-Pyrrolidine-2-carboxylic acid cyclopropylamide hydrochloride. MS (ES$^+$): m/e=664.

Example 407

4-{(S)-4-Carboxy-2-[(4-{2-[2-(2,4-dimethoxy-phenyl)-pyrrolidin-1-yl]-2-oxo-ethoxy}-quinoline-2-carbonyl)-amino]-butyryl}-piperazine-1-carboxylic acid ethyl ester The title compound was prepared by adapting the procedures described in example 73 with the difference that 2-(2,4-Dimethoxy-phenyl)-pyrrolidine was used instead of (S)-Pyrrolidine-2-carboxylic acid cyclopropylamide hydrochloride. MS (ES$^+$): m/e=706.

Example 408

4-[(S)-4-Carboxy-2-({4-[2-((2S,5R)-2-carboxy-5-phenyl-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (2S,5R)-5-Phenyl-pyrrolidine-2-carboxylic acid was used instead of (S)-Pyrrolidine-2-carboxylic acid cyclopropylamide hydrochloride. MS (ES$^+$): m/e=690.

Example 409

4-[(S)-4-Carboxy-2-({4-[2-oxo-2-(2-p-tolyl-pyrrolidin-1-yl)-ethoxy]-quinoline-2-carbonyl}-amino)-butyryl]-piperazine-1-carboxylic acid ethyl ester The title compound was prepared by adapting the procedures described in example 73 with the difference that 2-p-Tolyl-pyrrolidine was used instead of (S)-Pyrrolidine-2-carboxylic acid cyclopropylamide hydrochloride. MS (ES$^+$): m/e=660.

Example 410

4-{(S)-4-Carboxy-2-[(4-{2-[2-(3,4-difluoro-phenyl)-pyrrolidin-1-yl]-2-oxo-ethoxy}-quinoline-2-carbonyl)-amino]-butyryl}-piperazine-1-carboxylic acid ethyl ester The title compound was prepared by adapting the procedures described in example 73 with the difference that 2-(3,4-Difluoro-phenyl)-pyrrolidine was used instead of (S)-Pyrrolidine-2-carboxylic acid cyclopropylamide hydrochloride. MS (ES$^+$): m/e=682.

Example 411

4-{(S)-4-Carboxy-2-[(4-{2-[2-(3,4-dimethoxy-phenyl)-pyrrolidin-1-yl]-2-oxo-ethoxy}-quinoline-2-carbonyl)-amino]-butyryl}-piperazine-1-carboxylic acid ethyl ester The title compound was prepared by adapting the procedures described in example 73 with the difference that 2-(3,4-Dimethoxy-phenyl)-pyrrolidine was used instead of (S)-Pyrrolidine-2-carboxylic acid cyclopropylamide hydrochloride. MS (ES$^+$): m/e=706.

Example 412

4-[(S)-4-Carboxy-2-({4-[2-(2-ethyl-3-oxo-piperazin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 3-Ethyl-piperazin-2-one was used instead of (S)-Pyrrolidine-2-carboxylic acid cyclopropylamide hydrochloride. MS (ES$^+$): m/e=627.

Example 413

4-{(S)-4-Carboxy-2-[(4-{2-oxo-2-[3-(2-oxo-pyrrolidin-1-ylmethyl)-piperidin-1-yl]-ethoxy}-quinoline-2-carbonyl)-amino]-butyryl}-piperazine-1-carboxylic acid ethyl ester The title compound was prepared by adapting the procedures described in example 73 with the difference that 1-Piperidin-3-ylmethyl-pyrrolidin-2-one was used instead of (5)-Pyrrolidine-2-carboxylic acid cyclopropylamide hydrochloride. MS (ES$^+$): m/e=681.

Example 414

4-[(S)-4-Carboxy-2-({4-[2-oxo-2-(2-thiophen-2-yl-pyrrolidin-1-yl)-ethoxy]-quinoline-2-carbonyl}-amino)-butyryl]-piperazine-1-carboxylic acid ethyl ester The title compound was prepared by adapting the procedures described in example 73 with the difference that 2-Thiophen-2-yl-pyrrolidine was used instead of (S)-Pyrrolidine-2-carboxylic acid cyclopropylamide hydrochloride. MS (ES$^+$): m/e=652.

Example 415

4-[(S)-4-Carboxy-2-({4-[2-oxo-2-(2-pyrimidin-4-yl-pyrrolidin-1-yl)-ethoxy]-quinoline-2-carbonyl}-amino)-butyryl]-piperazine-1-carboxylic acid ethyl ester The title compound was prepared by adapting the procedures described in example 73 with the difference that 4-Pyrrolidin-2-yl-pyrimidine was used instead of (S)-Pyrrolidine-2-carboxylic acid cyclopropylamide hydrochloride. MS (ES$^+$): m/e=648.

Example 416

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-cyclohexylmethoxycarbonyl-butyryl]-piperazine-1-carboxylic acid ethyl ester The title compound was prepared by adapting the procedures described in example 237 with the difference that Cyclohexyl-methanol was used instead of methanol. MS (ES$^+$): m/e=777.

Example 417

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-cyclobutylmethoxycarbonyl-butyryl]-piperazine-1-carboxylic acid ethyl ester The title compound was prepared by adapting the procedures described in example 237 with the difference that Cyclobutyl-methanol was used instead of methanol. MS (ES$^+$): m/e=749.

Example 418

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-propoxycarbonyl-butyryl]-piperazine-1-carboxylic acid ethyl ester The title compound was prepared by adapting the procedures described in example 237 with the difference that Propan-1-ol was used instead of methanol. MS (ES$^+$): m/e=737.

Example 419

4-[(S)-4-Cyclobutoxycarbonyl-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 237 with the difference that Cyclobutanol was used instead of methanol. MS (ES$^+$): m/e=735.

Example 420

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-cyclopentylmethoxycarbonyl-butyryl]-piperazine-1-carboxylic acid butyl ester The title compound was prepared by adapting the procedures described in example 246 with the difference that 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid butyl ester was used instead of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester. MS (ES$^+$): m/e=791.

Example 421

4-[(S)-4-Carboxy-2-({4-[2-oxo-2-(4-oxo-3,5,7,8-tetrahydro-4H-pyrido[4,3-d]pyrimidin-6-yl)-ethoxy]-quinoline-2-carbonyl}-amino)-butyryl]-piperazine-1-carboxylic acid ethyl ester The title compound was prepared by adapting the procedures described in example 73 with the difference that 5,6,7,8-Tetrahydro-3H-pyrido[4,3-d]pyrimidin-4-one was used instead of (S)-Pyrrolidine-2-carboxylic acid cyclopropylamide hydrochloride. MS (ES$^+$): m/e=650.

Example 422

4-{(S)-4-Carboxy-2-[(4-{2-[2-(3-chloro-phenyl)-pyrrolidin-1-yl]-2-oxo-ethoxy}-quinoline-2-carbonyl)-amino]-butyryl}-piperazine-1-carboxylic acid ethyl ester The title compound was prepared by adapting the procedures described in example 73 with the difference that 2-(3-Chloro-phenyl)-pyrrolidine was used instead of (S)-Pyrrolidine-2-carboxylic acid cyclopropylamide hydrochloride. MS (ES$^+$): m/e=681, chloro pattern.

Example 423

4-{(S)-4-Carboxy-2-[(4-{2-[2-(2,4-difluoro-phenyl)-pyrrolidin-1-yl]-2-oxo-ethoxy}-quinoline-2-carbonyl)-amino]-butyryl}-piperazine-1-carboxylic acid ethyl ester The title compound was prepared by adapting the procedures described in example 73 with the difference that 2-(2,4-Difluoro-phenyl)-pyrrolidine was used instead of (S)-Pyrrolidine-2-carboxylic acid cyclopropylamide hydrochloride. MS (ES$^+$): m/e=682.

Example 424

3-[(S)-4-Carboxy-2-({4-[2-((S)-2-cyclobutylcarbamoyl-pyrrolidin-1-yl)-2-oxo-ethoxy]-quinoline-2-carbonyl}-amino)-butyrylamino]-azetidine-1-carboxylic acid butyl ester (i)
3-Benzyloxycarbonylamino-azetidine-1-carboxylic acid butyl ester To a solution of 2 g of Azetidin-3-yl-carbamic acid benzyl ester trifluoroacetate (prepared by standard protection and deprotection procedures from 3-Amino-azetidine-1-carboxylic acid tert-butyl ester) in 10 ml of DCM, 1.9 g of triethylamine was added and the mixture was cooled to 0° C. Then, 938 mg of butyl chloroformate was slowly added. After the addition was completed the reaction mixture was allowed to warm to RT and to stir for 1 h. Then, 200 ml of DCM was added and the organic phase was washed two times with 0.1 M aqueous hydrochloric acid and the with saturated aqueous sodium hydrogen carbonate solution. The organic phase was dried over MgSO$_4$ and the solvents were removed under reduced pressure. The crude product was purified by chromatography on silica gel eluting with a gradient of n-heptane/ethyl acetate. The fractions containing the product were combined and the solvent evaporated under reduced pressure. Yield: 1.4 g.

(ii) 3-Amino-azetidine-1-carboxylic acid butyl ester

To a solution of 1.4 g 3-Benzyloxycarbonylamino-azetidine-1-carboxylic acid butyl ester in 50 ml ethyl acetate were added 150 mg Pd/C (10%) and the suspension stirred under an atmosphere of hydrogen (1 bar) for 5 h. The reaction mixture was filtrated over a plug of Celite®, washed with ethyl acetate and concentrated. Yield: 740 mg colorless solid (iii) (S)-2-[(4-Hydroxy-quinoline-2-carbonyl)-amino]-pentanedioic acid 5-tert-butyl ester 1-methyl ester To a solution of 5 g 4-Hydroxy-quinoline-2-carboxylic acid and 5 g of (S)-2-Amino-pentanedioic acid 5-tert-butyl ester 1-methyl ester hydrochloride in 50 ml of DMF, 4.0 g of HOBT, 5.1 g of EDC and 6 g of NEM was added and the reaction mixture was stirred for 16 h at RT. Then, the reaction mixture was diluted with water and extracted with DCM. The organic phase was dried over MgSO$_4$ and the solvents were removed under reduced pressure. The crude product was purified by re-crystallisation from ethyl acetate and dried under reduced pressure. Yield: 6.5 g.

(iv) (S)-2-[(4-Benzyloxycarbonylmethoxy-quinoline-2-carbonyl)-amino]-pentanedioic acid 5-tert-butyl ester 1-methyl ester To a solution of 6.5 g of (S)-2-[(4-Hydroxy-quinoline-2-carbonyl)-amino]-pentanedioic acid 5-tert-butyl ester 1-methyl ester 50 ml of DMF, 6.5 g of cesium carbonate and 4.2 g of Bromo-acetic acid benzyl ester was added and stirred for 16 h. Then, the reaction mixture was diluted with water and extracted with DCM (3×150 ml). The combined organic phases were dried over MgSO$_4$ and the solvents were removed under reduced pressure. The crude product was used in the next reaction step. Yield: 8.9 g.

(v) (S)-2-[(4-Carboxymethoxy-quinoline-2-carbonyl)-amino]-pentanedioic acid 5-tert-butyl ester 1-methyl ester A solution of 8.9 g of (S)-2-[(4-Benzyloxycarbonylmethoxy-quinoline-2-carbonyl)-amino]-pentanedioic acid 5-tert-butyl ester 1-methyl ester in 150 ml of ethanol was purged with argon. Then, 1 g of Pd/C (5-10%) was added and the mixture stirred under a hydrogen atmosphere (4 bar). After 16 h reaction the mixture was filtered through a pad of celite and the solvents were removed under reduced pressure. After drying under reduced pressure the product was pure enough for the next reaction step. Yield: 5.2 g.

(vi) (S)-2-({4-[2-((S)-2-Cyclobutylcarbamoyl-pyrrolidin-1-yl)-2-oxo-ethoxy]-quinoline-2-carbonyl}-amino)pentanedioic acid 5-tert-butyl ester 1-methyl ester To a solution of 4 g of (S)-2-[(4-Carboxymethoxy-quinoline-2-carbonyl)-amino]-pentanedioic acid 5-tert-butyl ester 1-methyl ester in 30 ml of DCM, 3.4 g of EDC and 3.2 g of pentafluorophenol was added and the reaction mixture was stirred for 2 h at RT. Then, 5 g of (S)-Pyrrolidine-2-carboxylic acid cyclopropylamide trifluoroacetate salt and 2 g of NEM in 10 ml of DCM was added. After 3 h the reaction mixture was diluted with water and extracted with DCM (3×150 ml). The combined organic phases were dried over MgSO$_4$ and the solvents were removed under reduced pressure. The crude product was purified by chromatography on silica gel eluting with a gradient of n-heptane/ethyl acetate. The fractions containing the product were combined and the solvent evaporated under reduced pressure. Yield: 1.8 g.

(vii) (S)-2-({4-[2-((S)-2-Cyclobutylcarbamoyl-pyrrolidin-1-yl)-2-oxo-ethoxy]-quinoline-2-carbonyl}-amino)-pentanedioic acid 5-tert-butyl ester To a solution of 1.8 g of 4(S)-2-({4-[2-((S)-2-Cyclobutylcarbamoyl-pyrrolidin-1-yl)-2-oxo-ethoxy]-quinoline-2-carbonyl}-amino)-pentanedioic acid 5-tert-butyl ester 1-methyl ester in 45 ml of THF, 4.5 ml of a 1M NaOH was added and stirred for 6 h at RT. Then, the reaction mixture was acidified to pH 2 with hydrochloric acid (1M), concentrated and extracted with DCM (3×150 ml). The combined organic phases were dried over MgSO$_4$ and the solvents were removed under reduced pressure. The product was used in the next reaction step without further purification. Yield: 1.4 g.

(viii) 3-[(S)-4-Carboxy-2-({4-[2-((S)-2-cyclobutylcarbamoyl-pyrrolidin-1-yl)-2-oxo-ethoxy]-quinoline-2-carbonyl}-amino)-butyrylamino]-azetidine-1-carboxylic acid butyl ester To a solution of 80 mg of (S)-2-({4-[2-((S)-2-Cyclobutylcarbamoyl-pyrrolidin-1-yl)-2-oxo-ethoxy]-quinoline-2-carbonyl}-amino)-pentanedioic acid 5-tert-butyl ester 23 mg 3-Amino-azetidine-1-carboxylic acid butyl ester in 1 ml of DMF, 21 mg of HOBT, 26 mg of EDC and 31 mg NEM was added and the reaction mixture was stirred for 16 h at RT. Then, the reaction mixture was diluted with water and filtered through a chem Elut® cartridge by eluting with ethyl acetate. The solvents were removed under reduced pressure and the residue was dissolved in 1 ml of DCM and 0.6 ml of TFA. After 16 h at RT 10 ml of toluene was added and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. Yield: 45 mg MS (ES+): m/e=681.

Example 425

(S)-5-(4-Benzoyl-piperidin-1-yl)-4-({4-[2-((S)-2-cyclobutylcarbamoyl-pyrrolidin-1-yl)-2-oxo-ethoxy]-quinoline-2-carbonyl}-amino)-5-oxo-pentanoic acid The title compound was prepared by adapting the procedures described in example 424 with the difference that Phenyl-piperidin-4-yl-methanone was used instead of 3-Amino-azetidine-1-carboxylic acid butyl ester. MS (ES$^+$): m/e=698.

Example 426

(S)-5-[4-(3-Chloro-benzoyl)-piperidin-1-yl]-4-({4-[2-((S)-2-cyclobutylcarbamoyl-pyrrolidin-1-yl)-2-oxo-ethoxy]-quinoline-2-carbonyl}-amino)-5-oxo-pentanoic acid The title compound was prepared by adapting the procedures described in example 424 with the difference that (3-Chloro-phenyl)-piperidin-4-yl-methanone was used instead of 3-Amino-azetidine-1-carboxylic acid butyl ester. MS (ES+): m/e=733, chloro pattern.

Example 427

(S)-5-(4-Benzoyl-piperazin-1-yl)-4-({4-[2-((S)-2-cyclobutylcarbamoyl-pyrrolidin-1-yl)-2-oxo-ethoxy]-quinoline-2-carbonyl}-amino)-5-oxo-pentanoic acid The title compound was prepared by adapting the procedures described in example 424 with the difference that Phenyl-piperazin-1-yl-methanone was used instead of 3-Amino-azetidine-1-carboxylic acid butyl ester. MS (ES+): m/e=699.

Example 428

4-[(S)-4-Carboxy-2-({4-[2-((2S,4R)-4-fluoro-2-methoxycarbonyl-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (2S,4R)-4-Fluoro-pyrrolidine-2-carboxylic acid methyl ester was used instead of (S)-Pyrrolidine-2-carboxylic acid cyclopropylamide hydrochloride. MS (ES+): m/e=646.

Example 429

4-[(S)-4-Carboxy-2-({4-[2-(hexahydro-pyrrolo[3,4-b]pyrrol-5-yl)-2-oxo-ethoxy]-quinoline-2-carbonyl}-amino)-butyryl]-piperazine-1-carboxylic acid ethyl ester The title compound was prepared by adapting the procedures described in example 73 with the difference that Hexahydro-pyrrolo[3,4-b]pyrrole-1-carboxylic acid tert-butyl ester was used instead of (S)-Pyrrolidine-2-carboxylic acid cyclopropylamide hydrochloride. MS (ES+): m/e=611.

Example 430

4-{(S)-2-[(4-{2-[2-(5-Bromo-pyridin-3-yl)-pyrrolidin-1-yl]-2-oxo-ethoxy}-quinoline-2-carbonyl)-amino]-4-carboxy-butyryl}-piperazine-1-carboxylic acid ethyl ester The title compound was prepared by adapting the procedures described in example 73 with the difference that 3-Bromo-5-pyrrolidin-2-yl-pyridine was used instead of (S)-Pyrrolidine-2-carboxylic acid cyclopropylamide hydrochloride. MS (ES+): m/e=726.

Example 431

(S)-5-(3-Butoxycarbonylamino-azetidin-1-yl)-4-({4-[2-((S)-2-cyclobutylcarbamoyl-pyrrolidin-1-yl)-2-oxo-ethoxy]-quinoline-2-carbonyl}-amino)-5-oxo-pentanoic acid (i)
3-tert-Butoxycarbonylamino-azetidine-1-carboxylic acid butyl ester To a solution of 686 mg of Azetidin-3-yl-carbamic acid tert-butyl ester in 10 ml of DCM, 403 mg of triethylamine was added and the mixture was cooled to 0° C. Then, 598 mg of butyl chloroformate was slowly added. After the addition was completed the reaction mixture was allowed to warm to RT and to stir for 2 h. Then, 200 ml of DCM was added and the organic phase was washed two times with 0.1M aqueous hydrochloric acid and the with saturated aqueous sodium hydrogen carbonate solution. The organic phase was dried over MgSO$_4$ and the solvents were removed under reduced pressure. The crude product was purified by chromatography on silica gel eluting with a gradient of n-heptane/ethyl acetate. The fractions containing the product were combined and the solvent evaporated under reduced pressure. Yield: 910 mg.

(ii) 3-Amino-azetidine-1-carboxylic acid butyl ester

To a solution of 910 mg of 3-tert-Butoxycarbonylamino-azetidine-1-carboxylic acid butyl ester from the preceding reaction step (i) in 18 ml of DCM, 2.4 ml of TFA was slowly added at RT. After 4 h, 200 ml of toluene was added and the solvents were removed under reduced pressure. The isolated crude product was obtained as its trifluoroacetate salt and was pure enough for the next reaction step. Yield: 1.1 g.

(iii) (S)-5-(3-Butoxycarbonylamino-azetidin-1-yl)-4-({4-[2-((S)-2-cyclobutylcarbamoyl-pyrrolidin-1-yl)-2-oxo-ethoxy]-quinoline-2-carbonyl}-amino)-5-oxo-pentanoic acid The title compound was prepared by adapting the procedures described in example 424 with the difference that Azetidin-3-yl-carbamic acid butyl ester was used instead of 3-Amino-azetidine-1-carboxylic acid butyl ester. MS (ES+): m/e=681.

Example 432

4-{(S)-4-Carboxy-2-[(4-{2-[2-(3,4-dimethyl-phenyl)-pyrrolidin-1-yl]-2-oxo-ethoxy}-quinoline-2-carbonyl)-amino]-butyryl}-piperazine-1-carboxylic acid ethyl ester The title compound was prepared by adapting the procedures described in example 73 with the difference that 2-(3,4-Dimethyl-phenyl)-pyrrolidine was used instead of (S)-Pyrrolidine-2-carboxylic acid cyclopropylamide hydrochloride. MS (ES+): m/e=674.

Example 433

4-{(S)-4-Carboxy-2-[(4-{2-[2-(3,5-dimethyl-phenyl)-pyrrolidin-1-yl]-2-oxo-ethoxy}-quinoline-2-carbonyl)-amino]-butyryl}-piperazine-1-carboxylic acid ethyl ester The title compound was prepared by adapting the procedures described in example 73 with the difference that 2-(3,5-Dimethyl-phenyl)-pyrrolidine was used instead of (S)-Pyrrolidine-2-carboxylic acid cyclopropylamide hydrochloride. MS (ES+): m/e=674.

Example 434

4-{(S)-4-Carboxy-2-[(4-{2-[2-(2,4-dimethyl-phenyl)-pyrrolidin-1-yl]-2-oxo-ethoxy}-quinoline-2-carbonyl)-amino]-butyryl}-piperazine-1-carboxylic acid ethyl ester The title compound was prepared by adapting the procedures described in example 73 with the difference that 2-(2, 4-Dimethyl-phenyl)-pyrrolidine was used instead of (S)-Pyrrolidine-2-carboxylic acid cyclopropylamide hydrochloride. MS (ES+): m/e=674.

Example 435

4-[2-({4-[2-((S)-2-Cyclobutylcarbamoyl-pyrrolidin-1-yl)-2-oxo-ethoxy]-7-methyl-quinoline-2-carbonyl}-amino)-acetyl]-piperazine-1-carboxylic acid butyl ester (i) 4-(2-Benzyloxycarbonylamino-acetyl)-piperazine-1-carboxylic acid butyl ester To a solution of 5.62 g Z-Gly-OH (Benzyloxycarbonylamino-acetic acid) in 100 ml DMF were added 13.7 ml N-ethylmorpholine, 8.8 g TOTU and 5.0 g Piperazine-1-carboxylic acid butyl ester. After stirring for 12 h, aqueous NaHCO$_3$ was added and the reaction mixture was diluted with ethyl acetate and washed with aqueous LiCl (4%) and 0.1 M HCl. The crude product obtained after evaporation of the solvent was purified by flash chromatography on silica using an ethyl acetate/heptane gradient. Yield: 6.34 g (ii) 4-(2-Amino-acetyl)-piperazine-1-carboxylic acid butyl ester To a solution of 6.34 g 4-(2-Benzyloxycarbonylamino-acetyl)-piperazine-1-carboxylic acid butyl ester in 120 ml ethanol were added 200 mg Pd/C (10%) and the suspension stirred under an atmosphere of hydrogen (3 bar) for 12 h. The reaction mixture was filtrated over a plug of Celite®, washed with ethanol and concentrated. Yield: 4.47 g colorless solid.

(iii) 4-[2-((S)-2-Cyclobutylcarbamoyl-pyrrolidin-1-yl)-2-oxo-ethoxy]-7-methyl-quinoline-2-carboxylic acid ethyl ester To a solution of 2 g of 4-Carboxymethoxy-7-methyl-quinoline-2-carboxylic acid ethyl ester in 30 ml of DCM, 3.6 g of EDC, 3.4 g of pentafluorophenol, 2.2 g of NEM was added and the reaction mixture was stirred at RT for 2 h. Then, 5.3 g of (S)-Pyrrolidine-2-carboxylic acid cyclobutylamide trifluoroacetate and 2.1 g of NEM in 10 ml of DCM was added. After 16 h the reaction mixture was diluted with water and extracted with DCM (3×150 ml). The combined organic phases were dried over MgSO$_4$ and the solvents were removed under reduced pressure. The crude product was purified by chromatography on silica gel eluting with a gradient of n-heptane/ethyl acetate. The fractions containing the product were combined and the solvent evaporated under reduced pressure. Yield: 2.5 g.

(iv) 4-[2-((S)-2-Cyclobutylcarbamoyl-pyrrolidin-1-yl)-2-oxo-ethoxy]-7-methyl-quinoline-2-carboxylic acid To a solution of 2.5 g 4-[2-((S)-2-Cyclobutylcarbamoyl-pyrrolidin-1-yl)-2-oxo-ethoxy]-7-methyl-quinoline-2-carboxylic acid ethyl ester in 20 ml of THF, 5.7 ml of a 1M aqueous sodium hydroxide solution was added and stirred for 16 h at RT. The reaction mixture was acidified with 1M hydrochloric acid to pH 3 and the solvents were evaporated under reduced pressure. The residue was dissolved in a mixture of methanol/DCM and the solids were filtered off. The filtrate was evaporated under reduced pressure to yield the product which was pure enough for the next reaction step. Yield: 2.0 g.

(v) 4-[2-({4-[2-((S)-2-Cyclobutylcarbamoyl-pyrrolidin-1-yl)-2-oxo-ethoxy]-7-methyl-quinoline-2-carbonyl}-amino)acetyl]-piperazine-1-carboxylic acid butyl ester To a solution of 1.0 g 4-[2-((S)-2-Cyclobutylcarbamoyl-pyrrolidin-1-yl)-2-oxo-ethoxy]-7-methyl-quinoline-2-carboxylic acid and 709 mg 4-(2-Amino-acetyl)-piperazine-1-carboxylic acid butyl ester in 10 ml DMF were added 1.2 ml NEM, 559 mg EDC and 446 mg HOBt and the mixture stirred for 16 h. The reaction mixture was concentrated then diluted with water and filtered through a chem Elut® cartridge by eluting DCM. The crude product obtained after evaporation of the solvent was purified by preparative HPLC (C18 reverse phase column, elution with a water/MeCN gradient with 0.1% TFA). The fractions containing the product were lyophilized to yield the pure product as its trifluoroacetate salt. The latter one was dissolved in DCM, extracted once with each saturated aqueous NaHCO$_3$ and brine, followed by evaporation of the solvent to give the title compound. Yield: 472 mg MS(ES+): m/e=637.

Alternatively 4-[2-({4-[2-((S)-2-Cyclobutylcarbamoyl-pyrrolidin-1-yl)-2-oxo-ethoxy]-7-methyl-quinoline-2-carbonyl}-amino)-acetyl]-piperazine-1-carboxylic acid butyl ester was obtained by the following procedure.

(i) 4-{2-[(4-Hydroxy-7-methyl-quinoline-2-carbonyl)-amino]-acetyl}-piperazine-1-carboxylic acid butyl ester To a solution of 4.0 g of 4-Hydroxy-7-methyl-quinoline-2-carboxylic acid and 7 g of 4-(2-Amino-acetyl)-piperazine-1-carboxylic acid butyl ester in 40 ml of DMF, 3.3 g of HOBT and 4.1 g of EDC was added and the reaction mixture was stirred for 4 h at RT. Then, the reaction mixture was diluted with water and extracted with DCM. The combined organic phases were dried over MgSO$_4$ and the solvents were removed under reduced pressure. The isolated crude product was used in the next reaction step. Yield: 4.5 g.

(ii) 4-{2-[(4-Benzyloxycarbonyl methoxy-7-methyl-quinoline-2-carbonyl)-amino]-acetyl}-piperazine-1-carboxylic acid butyl ester To a solution of 4.5 g 4-{2-[(4-Hydroxy-7-methyl-quinoline-2-carbonyl)-amino]-acetyl}-piperazine-1-carboxylic acid butyl ester in 30 ml of DMF, 3.7 g of cesium carbonate and 2.6 g of Bromo-acetic acid benzyl ester were added and the reaction mixture was stirred for 16 h at RT. Then, the reaction mixture was diluted with water and extracted with ethyl acetate. The organic phase was dried over MgSO$_4$ and the solvents were removed under reduced pressure. The isolated crude product was purified by re-crystallising from ethyl acetate/heptane. Yield: 5 g.

(iii) 4-{2-[(4-Carboxymethoxy-7-methyl-quinoline-2-carbonyl)-amino]-acetyl}-piperazine-1-carboxylic acid butyl ester To a solution of 5 g 4-{2-[(4-Benzyloxycarbonylmethoxy-7-methyl-quinoline-2-carbonyl)-amino]-acetyl}-piperazine-1-carboxylic acid butyl ester in 50 ml ethanol and 150 ml DMF were added under argon 732 mg Pd/C (10%) and the suspension was stirred under an atmosphere of hydrogen (5 bar) for 4 h. The suspension was filtered over a plug of Celite® and washed with ethanol and DMF. The crude product was obtained after evaporation of the solvent. Yield: 4.1 g.

(iv) 4-[2-({4-[2-((S)-2-Cyclobutylcarbamoyl-pyrrolidin-1-yl)-2-oxo-ethoxy]-7-methyl-quinoline-2-carbonyl}-amino)-acetyl]-piperazine-1-carboxylic acid butyl ester To a solution of 100 mg of 4-{2-[(4-Carboxymethoxy-7-methyl-quinoline-2-carbonyl)-amino]-acetyl}-piperazine-1-carboxylic acid butyl ester in 3 ml of DMF, 47 mg of EDC, 45 mg of pentafluorophenol was added and the reaction mixture was stirred for 2 h. Then, 62 mg of (S)-Pyrrolidine-2-carboxylic acid cyclobutylamide hydrochloride and 70 mg of NEM in 3 ml of DMF was added. After 1 h the reaction mixture was diluted with water. After filtration through a chem Elut® cartridge by eluting with DCM the solvents were removed under reduced pressure. The residue was purified by preparative HPLC (C18 reverse phase column, elution with a water/MeCN gradient with 0.1% TFA). The fractions containing the product were lyophilized to yield the pure product as its trifluoroacetate salt. Yield: 85 mg MS(ES+): m/e=637.

Example 436

4-{(S)-4-Carboxy-2-[(4-{2-[2-(2,5-dimethyl-phenyl)-pyrrolidin-1-yl]-2-oxo-ethoxy}-quinoline-2-carbonyl)-amino]-butyryl}-piperazine-1-carboxylic acid ethyl ester The title compound was prepared by adapting the procedures described in example 73 with the difference that 2-(2,5-Dimethyl-phenyl)-pyrrolidine was used instead of (S)-Pyrrolidine-2-carboxylic acid cyclopropylamide hydrochloride. MS (ES$^+$): m/e=674.

Example 437

4-[(S)-4-Carboxy-2-({4-[2-(3-hydroxy-4,7-dihydro-5H-isoxazolo[5,4-c]pyridin-6-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 4,5,6,7-Tetrahydro-isoxazolo[5,4-c]pyridin-3-ol was used instead of (S)-Pyrrolidine-2-carboxylic acid cyclopropylamide hydrochloride. MS (ES$^+$): m/e=639.

Example 438

4-[(S)-4-Carboxy-2-({4-[2-oxo-2-(2-trifluoromethoxymethyl-pyrrolidin-1-yl)-ethoxy]-quinoline-2-carbonyl}-amino)-butyryl]-piperazine-1-carboxylic acid ethyl ester The title compound was prepared by adapting the procedures described in example 73 with the difference that 2-Trifluoromethoxymethyl-pyrrolidine was used instead of (S)-Pyrrolidine-2-carboxylic acid cyclopropylamide hydrochloride. MS (ES$^+$): m/e=668.

Example 439

4-[(S)-4-Carboxy-2-({4-[2-(3-methoxy-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 3-Methoxy-pyrrolidine was used instead of (S)-Pyrrolidine-2-carboxylic acid cyclopropylamide hydrochloride. MS (ES$^+$): m/e=600.

Example 440

4-[(S)-4-Carboxy-2-({4-[2-((2S,4S)-4-fluoro-2-methoxycarbonyl-pyrrolidin-1-yl)-2-oxo-ethoxy]-quinoline-2-carbonyl}-amino)-butyryl]-piperazine-1-carboxylic acid ethyl ester The title compound was prepared by adapting the procedures described in example 73 with the difference that (2S,4S)-4-Fluoro-pyrrolidine-2-carboxylic acid methyl ester was used instead of (S)-Pyrrolidine-2-carboxylic acid cyclopropylamide hydrochloride. MS (ES$^+$): m/e=646.

Example 441

4-[(S)-4-Carboxy-2-({4-[2-(4,6-dihydro-1H-pyrrolo[3,4-c]pyrazol-5-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 1,4,5,6-Tetrahydro-pyrrolo[3,4-c]pyrazole was used instead of (S)-Pyrrolidine-2-carboxylic acid cyclopropylamide hydrochloride. MS (ES$^+$): m/e=608.

Example 442

4-{(S)-4-Carboxy-2-[(4-{2-[(S)-2-(5-methyl-pyridin-3-yl)-pyrrolidin-1-yl]-2-oxo-ethoxy}-quinoline-2-carbonyl)-amino]-butyryl}-piperazine-1-carboxylic acid ethyl ester The title compound was prepared by adapting the procedures described in example 73 with the difference that 3-Methyl-5-(S)-pyrrolidin-2-yl-pyridine was used instead of (S)-Pyrrolidine-2-carboxylic acid cyclopropylamide hydrochloride. MS (ES$^+$): m/e=661.

Example 443

4-[(S)-2-({4-[2-((S)-2-Cyclobutylcarbamoyl-pyrrolidin-1-yl)-2-oxo-ethoxy]-7-methyl-quinoline-2-carbonyl}-amino)-5-hydroxy-pentanoyl]-piperazine-1-carboxylic acid butyl ester (i) (S)-2-tert-Butoxycarbonylamino-5-hydroxy-pentanoic acid benzyl ester To a solution of 7.0 g Boc-Glu-OBn in 100 ml THF were added dropwise under Argon at −10° C. 2.9 ml N-ethylmorpholine and 3.0 ml isobutyl chloroformate. The reaction mixture was stirred for 10 minutes before 2.4 g sodium borohydride were added. Methanol (400 ml) was added slowly over a period of 70 minutes at this temperature. It was stirred for additional 30 minutes at RT before being neutralized with 1 N HCl. The mixture was concentrated, dissolved in ethyl acetate and washed with 1 N HCl and brine. The crude product obtained after evaporation of the solvent was purified by flash chromatography on silica using an ethyl acetate/heptane gradient. Yield: 5.3 g.

(ii) (S)-2-tert-Butoxycarbonylamino-5-(tert-butyl-diphenyl-silanyloxy)-pentanoic acid benzyl ester (S)-2-tert-Butoxycarbonylamino-5-hydroxy-pentanoic acid benzyl ester (2.5 g) was dissolved in 50 ml DMF and treated with 2.0 ml tert-butyldiphenylchlorosilane, 1.2 ml triethylamine and 95 mg DMAP. After stirring for 12 h equivalent portions of the reagents were added and the mixture stirred for additional 12 h. The mixture was concentrated, the residue was dissolved in ethyl acetate and washed with aqueous LiCl (4%), 0.1 M HCl and saturated aqueous NaHCO$_3$. The crude product obtained after evaporation of the solvent was purified by flash chromatography on silica using an ethyl acetate/heptane gradient. Yield: 2.0 g.

(iii) (S)-2-tert-Butoxycarbonylamino-5-(tert-butyl-diphenyl-silanyloxy)-pentanoic acid To a solution of 1.92 g (S)-2-tert-Butoxycarbonylamino-5-(tert-butyl-diphenyl-silanyloxy)-pentanoic acid benzyl ester in 40 ml ethyl acetate were added under argon 0.2 g Pd/C (10%) and the suspension was stirred under an atmosphere of hydrogen (3 bar) for 16 h. The suspension was filtered over a plug of Celite® and washed with ethyl acetate. The crude product was obtained after evaporation of the solvent. Yield: 1.61 g colorless oil.

(iv) 4-[(S)-2-tert-Butoxycarbonylamino-5-(tert-butyl-diphenyl-silanyloxy)-pentanoyl]-piperazine-1-carboxylic acid butyl ester To a solution of 1.61 g (S)-2-tert-Butoxycarbonylamino-5-(tert-butyl-diphenyl-silanyloxy)-pentanoic acid in 8 ml DMF were added 1.02 g piperazine-1-carboxylic acid butyl ester hydrotrifluoroacetate, 1.7 ml N-ethylmorpholine and 1.1 g TOTU. After stirring for 12 h the solution was diluted with ethyl acetate and subsequently washed with aqueous LiCl (4%), 0.1 M HCl and saturated aqueous NaHCO$_3$. The crude product obtained after evaporation of the solvent was used without further purification. Yield: 1.80 g.

(v) 4-[(S)-2-Amino-5-(tert-butyl-diphenyl-silanyloxy)-pentanoyl]-piperazine-1-carboxylic acid butyl ester hydrochloride To a solution of 900 mg 4-[(S)-2-tert-Butoxycarbonylamino-5-(tert-butyl-diphenyl-silanyloxy)-pentanoyl]-piperazine-1-carboxylic acid butyl ester in 5 ml dioxane were added 5 ml HCl in dioxane (4 M). After 2.5 h conversion was complete and the reaction mixture was neutralized with basic ion exchange resin III (Merck), filtered and concentrated. Yield: 760 mg.

(vi) 4-[(S)-5-(tert-Butyl-diphenyl-silanyloxy)-2-({4-[2-((S)-2-cyclobutylcarbamoyl-pyrrolidin-1-yl)-2-oxo-ethoxy]-7-methyl-quinoline-2-carbonyl}-amino)-pentanoyl]-piperazine-1-carboxylic acid butyl ester To a solution of 385 mg 4-[2-((S)-2-Cyclobutylcarbamoyl-pyrrolidin-1-yl)-2-oxo-ethoxy]-7-methyl-quinoline-2-carboxylic acid in 10 ml DMF were added 215 mg HOBt, 270 mg EDC and 0.4 ml DIPEA. After 20 minutes 506 mg 4-[(S)-2-Amino-5-(tert-butyl-diphenyl-silanyloxy)-pentanoyl]-piperazine-1-carboxylic acid butyl ester hydrochloride were added and the mixture stirred for 12 h. The reaction mixture was concentrated, diluted with ethyl acetate and washed with aqueous LiCl (4%), 0.1 M HCl and saturated aqueous NaHCO$_3$. The crude product thus obtained was pure enough for the following transformation. Yield: 850 mg.

(vii) 4-[(S)-2-({4-[2-((S)-2-Cyclobutylcarbamoyl-pyrrolidin-1-yl)-2-oxo-ethoxy]-7-methyl-quinoline-2-carbonyl}-amino)-5-hydroxy-pentanoyl]-piperazine-1-carboxylic acid butyl ester To a solution of 700 mg 4-[(S)-5-(tert-Butyl-diphenyl-silanyloxy)-2-({4-[2-((S)-2-cyclobutylcarbamoyl-pyrrolidin-1-yl)-2-oxo-ethoxy]-7-methyl-quinoline-2-carbonyl}-amino)-pentanoyl]-piperazine-1-carboxylic acid butyl ester in 70 ml THF were added 1.5 ml of TBAF (1 M in THF) and the mixture stirred at RT for 12 h. It was concentrated, the residue was dissolved in DCM and washed with water (3×). The solvent was removed under reduced pressure and the residue purified by preparative HPLC (C18 reverse phase column, elution with a water/MeCN gradient with 0.1% TFA). The fractions containing the product were lyophilized to yield the pure product as its trifluoroacetate salt. Yield: 28 mg MS(ES+): m/e=695.

Example 444

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(2-cyclopentyl-ethoxycarbonyl)-butyryl]-piperazine-1-carboxylic acid ethyl ester The title compound was prepared by adapting the procedures described in example 237 with the difference that 2-Cyclopentyl-ethanol was used instead of methanol. MS (ES$^+$): m/e=777.

Example 445

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(tetrahydro-furan-3-ylmethoxycarbonyl)-butyryl]-piperazine-1-carboxylic acid ethyl ester The title compound was prepared by adapting the procedures described in example 237 with the difference that (Tetrahydro-furan-3-yl)-methanol was used instead of methanol. MS (ES$^+$): m/e=765.

Example 446

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(3-methyl-oxetan-3-ylmethoxycarbonyl)-butyryl]-piperazine-1-carboxylic acid ethyl ester The title compound was prepared by adapting the procedures described in example 237 with the difference that (3-Methyl-oxetan-3-yl)-methanol was used instead of methanol. MS (ES$^+$): m/e=765.

Example 447

4-[(S)-4-((1R,4S)-1-Bicyclo[2.2.1]hept-2-yl-methoxycarbonyl)-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 237 with the difference that (1R, 4S)-1-Bicyclo[2.2.1]hept-2-yl-methanol was used instead of methanol. MS (ES$^+$): m/e=789.

Example 448

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(3-ethyl-oxetan-3-ylmethoxycarbonyl)-butyryl]-piperazine-1-carboxylic acid ethyl ester The title compound was prepared by adapting the procedures described in example 237 with the difference that (3-Ethyl-oxetan-3-yl)-methanol was used instead of methanol. MS (ES$^+$): m/e=779.

Example 449

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(tetrahydro-pyran-2-ylmethoxycarbonyl)-butyryl]-piperazine-1-carboxylic acid ethyl ester The title compound was prepared by adapting the procedures described in example 237 with the difference that (Tetrahydro-pyran-2-yl)-methanol was used instead of methanol. MS (ES$^+$): m/e=779.

Example 450

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(5-ethyl-[1,3]dioxan-5-ylmethoxycarbonyl)-butyryl]-piperazine-1-carboxylic acid ethyl The title compound was prepared by adapting the procedures described in example 237 with the difference that (5-Ethyl-[1,3]dioxan-5-yl)methanol was used instead of methanol. MS (ES$^+$): m/e=809.

Example 451

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(2-oxo-[1,3]dioxolan-4-ylmethoxycarbonyl)-butyryl]-piperazine-1-carboxylic acid ethyl ester The title compound was prepared by adapting the procedures described in example 237 with the difference that 4-Hydroxymethyl-[1,3]dioxolan-2-one was used instead of methanol. MS (ES$^+$): m/e=781.

Example 452

4-{(S)-2-({4-[2-((S)-2-Cyclobutylcarbamoyl-pyrrolidin-1-yl)-2-oxo-ethoxy]-7-methyl-quinoline-2-carbonyl}-amino)-4-[2-(2-hydroxy-ethylamino)-ethoxycarbonyl]-butyryl}-piperazine-1-carboxylic acid ethyl ester The title compound was prepared by adapting the procedures described in example 237 with the difference that 2-(2-Hydroxy-ethylamino)-ethanol was used instead of methanol. MS (ES$^+$): m/e=768.

Example 453

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(3-methoxy-butoxycarbonyl)-butyryl]-piperazine-1-carboxylic acid ethyl ester The title compound was prepared by adapting the procedures described in example 237 with the difference that 3-Methoxy-butan-1-ol was used instead of methanol. MS (ES$^+$): m/e=767.

Example 454

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(tetrahydro-furan-2-ylmethoxycarbonyl)-butyryl]-piperazine-1-carboxylic acid ethyl ester The title compound was prepared by adapting the procedures described in example 237 with the difference that (Tetrahydro-furan-2-yl)-methanol was used instead of methanol. MS (ES$^+$): m/e=765.

Example 455

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(3-dimethylamino-2,2-dimethyl-propoxycarbonyl)-butyryl]-piperazine-1-carboxylic acid ethyl ester The title compound was prepared by adapting the procedures described in example 237 with the difference that 3-Dimethylamino-2,2-dimethyl-propan-1-ol was used instead of methanol. MS (ES$^+$): m/e=794.

Example 456

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(2-dimethylamino-2-methyl-propoxycarbonyl)-butyryl]-piperazine-1-carboxylic acid ethyl ester The title compound was prepared by adapting the procedures described in example 237 with the difference that 2-Dimethylamino-2-methyl-propan-1-ol was used instead of methanol. MS (ES$^+$): m/e=780.

Example 457

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(2-morpholin-4-yl-ethoxycarbonyl)-butyryl]-piperazine-1-carboxylic acid ethyl ester The title compound was prepared by adapting the procedures described in example 237 with the difference that 2-Morpholin-4-yl-ethanol was used instead of methanol. MS (ES$^+$): m/e=794.

Example 458

4-[(S)-4-Carboxy-2-({4-[2-(4,6-dihydro-1H-pyrrolo[3,4-c]pyrazol-5-yl)-2-oxo-ethoxy]-7-methyl-quinoline-2-carbonyl}-amino)-butyryl]-piperazine-1-carboxylic acid butyl ester The title compound was prepared by adapting the procedures described in example 303 with the difference that 1,4,5,6-Tetrahydro-pyrrolo[3,4-c]pyrazole was used instead of (S)-Pyrrolidine-2-carboxylic acid cyclobutylamide. MS (ES$^+$): m/e=650.

Example 459

4-{(S)-4-Carboxy-2-[(4-{2-[2-(3,4-difluoro-phenyl)-pyrrolidin-1-yl]-2-oxo-ethoxy}-7-methyl-quinoline-2-carbonyl)-amino]-butyryl}-piperazine-1-carboxylic acid butyl ester The title compound was prepared by adapting the procedures described in example 303 with the difference that 2-(3,4-Difluoro-phenyl)-pyrrolidine was used instead of (S)-Pyrrolidine-2-carboxylic acid cyclobutylamide. MS (ES$^+$): m/e=724.

Example 460

4-[(S)-4-Carboxy-2-({4-[2-((S)-2-cyano-pyrrolidin-1-yl)-2-oxo-ethoxy]-7-methyl-quinoline-2-carbonyl}-amino)-butyryl]-piperazine-1-carboxylic acid butyl ester The title compound was prepared by adapting the procedures described in example 303 with the difference that (S)-Pyrrolidine-2-carbonitrile was used instead of (S)-Pyrrolidine-2-carboxylic acid cyclobutylamide. MS (ES$^+$): m/e=637.

Example 461

4-{(S)-4-Carboxy-2-[(4-{2-[2-(2,4-difluoro-phenyl)-pyrrolidin-1-yl]-2-oxo-ethoxy}-7-methyl-quinoline-2-carbonyl)-amino]-butyryl}-piperazine-1-carboxylic acid butyl ester The title compound was prepared by adapting the procedures described in example 303 with the difference that 2-(2,4-Difluoro-phenyl)-pyrrolidine was used instead of (S)-Pyrrolidine-2-carboxylic acid cyclobutylamide. MS (ES$^+$): m/e=724.

Example 462

4-[(S)-4-Carboxy-2-({4-[2-(2-furan-2-yl-pyrrolidin-1-yl)-2-oxo-ethoxy]-7-methyl-quinoline-2-carbonyl}-amino)-butyryl]-piperazine-1-carboxylic acid butyl ester The title compound was prepared by adapting the procedures described in example 303 with the difference that 2-Furan-2-yl-pyrrolidine was used instead of (S)-Pyrrolidine-2-carboxylic acid cyclobutylamide. MS (ES$^+$): m/e=678.

Example 463

4-[(S)-4-Carboxy-2-({7-methyl-4-[2-oxo-2-(4-oxo-3,5,7,8-tetrahydro-4H-pyrido[4,3-d]pyrimidin-6-yl)-ethoxy]-quinoline-2-carbonyl}-amino)-butyryl]-piperazine-1-carboxylic acid butyl ester The title compound was prepared by adapting the procedures described in example 303 with the difference that 5,6,7,8-Tetrahydro-3H-pyrido[4,3-d]pyrimidin-4-one was used instead of (S)-Pyrrolidine-2-carboxylic acid cyclobutylamide. MS (ES$^+$): m/e=692.

Example 464

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(1-methyl-2-morpholin-4-yl-ethoxycarbonyl)-butyryl]-piperazine-1-carboxylic acid ethyl ester The title compound was prepared by adapting the procedures described in example 237 with the difference that 1-Morpholin-4-yl-propan-2-ol was used instead of methanol. MS (ES$^+$): m/e=808.

Example 465

4-[(S)-2-({4-[(R)-2-((S)-2-Cyclobutylcarbamoyl-pyrrolidin-1-yl)-1-methyl-2-oxo-ethoxy]-7-methyl-quinoline-2-carbonyl}-amino)-4-cyclopentylmethoxycarbonyl-butyryl]-piperazine-1-carboxylic acid ethyl ester The title compound was prepared by adapting the procedures described in example 246 with the difference that 4-[(S)-4-Carboxy-2-({4-[(R)-2-((S)-2-cyclobutylcarbamoyl-pyrrolidin-1-yl)-1-methyl-2-oxo-ethoxy]-7-methyl-quinoline-2-carbonyl}-amino)-butyryl]-piperazine-1-carboxylic acid ethyl ester was used instead of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester. MS (ES$^+$): m/e=777.

Example 466

4-[(S)-4-Carboxy-2-({7-methyl-4-[2-oxo-2-(2-oxo-oxazolidin-3-yl)-ethoxy]-quinoline-2-carbonyl}-amino)-butyryl]-piperazine-1-carboxylic acid butyl ester The title compound was prepared by adapting the procedures described in example 303 with the difference that Oxazolidin-2-one was used instead of (S)-Pyrrolidine-2-carboxylic acid cyclobutylamide. MS (ES$^+$): m/e=628.

Example 467

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(3-methoxy-propoxycarbonyl)-butyryl]-piperazine-1-carboxylic acid ethyl ester The title compound was prepared by adapting the procedures described in example 237 with the difference that 3-Methoxy-propan-1-ol was used instead of methanol. MS (ES$^+$): m/e=753.

Example 468

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(2-ethoxy-ethoxycarbonyl)-butyryl]-piperazine-1-carboxylic acid ethyl ester To a solution of 19 mg of DMAP, 30 mg of EDC and 103 mg of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester in 2 ml of DCM, 94 mg of 2-Ethoxy-ethanol was added and the reaction mixture was stirred for 16 h at RT. The solvents were removed under reduced pressure and the residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. Yield: 45 mg MS (ES+): m/e=753.

Example 469

4-[(S)-4-Carboxy-2-({7-methyl-4-[2-oxo-2-(2-o-tolyl-pyrrolidin-1-yl)-ethoxy]-quinoline-2-carbonyl}-amino)-butyryl]-piperazine-1-carboxylic acid butyl ester The title compound was prepared by adapting the procedures described in example 303 with the difference that 2-o-Tolyl-pyrrolidine was used instead of (5)-Pyrrolidine-2-carboxylic acid cyclobutylamide. MS (ES$^+$): m/e=702.

Example 470

4-[(S)-4-Carboxy-2-({4-[2-((S)-2-hydroxymethyl-pyrrolidin-1-yl)-2-oxo-ethoxy]-7-methyl-quinoline-2-carbonyl}-amino)-butyryl]-piperazine-1-carboxylic acid butyl ester The title compound was prepared by adapting the procedures described in example 303 with the difference that (S)-1-Pyrrolidin-2-yl-methanol was used instead of (S)-Pyrrolidine-2-carboxylic acid cyclobutylamide. MS (ES$^+$): m/e=642.

Example 471

4-[(S)-4-Carboxy-2-({4-[2-(3,3-difluoro-pyrrolidin-1-yl)-2-oxo-ethoxy]-7-methyl-quinoline-2-carbonyl}-amino)-butyryl]-piperazine-1-carboxylic acid butyl ester The title compound was prepared by adapting the procedures described in example 303 with the difference that 3,3-Difluoro-pyrrolidine was used instead of (S)-Pyrrolidine-2-carboxylic acid cyclobutylamide. MS (ES$^+$): m/e=648.

Example 472

4-[(S)-4-Carboxy-2-({4-[2-(3-hydroxy-azetidin-1-yl)-2-oxo-ethoxy]-7-methyl-quinoline-2-carbonyl}-amino)-butyryl]-piperazine-1-carboxylic acid butyl ester The title compound was prepared by adapting the procedures described in example 303 with the difference that Azetidin-3-ol was used instead of (S)-Pyrrolidine-2-carboxylic acid cyclobutylamide. MS (ES$^+$): m/e=614.

Example 473

4-[(S)-4-Carboxy-2-({7-methyl-4-[2-(4-methyl-3-oxo-piperazin-1-yl)-2-oxo-ethoxy]-quinoline-2-carbonyl}-amino)-butyryl]-piperazine-1-carboxylic acid butyl ester The title compound was prepared by adapting the procedures described in example 303 with the difference that 1-Methyl-piperazin-2-one was used instead of (S)-Pyrrolidine-2-carboxylic acid cyclobutylamide. MS (ES$^+$): m/e=655.

Example 474

4-[(S)-4-Carboxy-2-({4-[2-(4-hydroxy-piperidin-1-yl)-2-oxo-ethoxy]-7-methyl-quinoline-2-carbonyl}-amino)-butyryl]-piperazine-1-carboxylic acid butyl ester The title compound was prepared by adapting the procedures described in example 303 with the difference that Piperidin-4-ol was used instead of (S)-Pyrrolidine-2-carboxylic acid cyclobutylamide. MS (ES$^+$): m/e=642.

Example 475

4-[(S)-4-Carboxy-2-({7-methyl-4-[2-(5-methyl-3-oxo-pyrazolidin-1-yl)-2-oxo-ethoxy]-quinoline-2-carbonyl}-amino)-butyryl]-piperazine-1-carboxylic acid butyl ester The title compound was prepared by adapting the procedures described in example 303 with the difference that 5-Methyl-pyrazolidin-3-one was used instead of (S)-Pyrrolidine-2-carboxylic acid cyclobutylamide. MS (ES$^+$): m/e=641.

Example 476

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(2-dimethylamino-ethoxycarbonyl)-butyryl]-piperazine-1-carboxylic acid ethyl ester The title compound was prepared by adapting the procedures described in example 237 with the difference that 2-Dimethylamino-ethanol was used instead of methanol. MS (ES$^+$): m/e=752.

Example 477

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(2-isopropoxy-ethoxycarbonyl)-butyryl]-piperazine-1-carboxylic acid ethyl ester The title compound was prepared by adapting the procedures described in example 237 with the difference that 2-Isopropoxy-ethanol was used instead of methanol. MS (ES$^+$): m/e=767.

Example 478

4-[(S)-4-Carboxy-2-({4-[2-((R)-3-hydroxy-pyrrolidin-1-yl)-2-oxo-ethoxy]-7-methyl-quinoline-2-carbonyl}-amino)-butyryl]-piperazine-1-carboxylic acid butyl ester The title compound was prepared by adapting the procedures described in example 303 with the difference that (R)-Pyrrolidin-3-ol was used instead of (S)-Pyrrolidine-2-carboxylic acid cyclobutylamide. MS (ES$^+$): m/e=628.

Example 479

4-{(S)-4-Carboxy-2-[(7-methyl-4-{2-[(S)-2-(5-methyl-pyridin-3-yl)-pyrrolidin-1-yl]-2-oxo-ethoxy}-quinoline-2-carbonyl)-amino]-butyryl}-piperazine-1-carboxylic acid butyl ester The title compound was prepared by adapting the procedures described in example 303 with the difference that 3-Methyl-5-(S)-pyrrolidin-2-yl-pyridine was used instead of (S)-Pyrrolidine-2-carboxylic acid cyclobutylamide. MS (ES$^+$): m/e=703.

Example 480

4-[(S)-4-Carboxy-2-({4-[2-((S)-3-hydroxy-pyrrolidin-1-yl)-2-oxo-ethoxy]-7-methyl-quinoline-2-carbonyl}-amino)-butyryl]-piperazine-1-carboxylic acid butyl ester The title compound was prepared by adapting the procedures described in example 303 with the difference that (S)-Pyrrolidin-3-ol was used instead of (S)-Pyrrolidine-2-carboxylic acid cyclobutylamide. MS (ES$^+$): m/e=628.

Example 481

4-[(S)-4-Carboxy-2-({7-methyl-4-[2-oxo-2-((S)-2-phenyl-pyrrolidin-1-yl)-ethoxy]-quinoline-2-carbonyl}-amino)-butyryl]-piperazine-1-carboxylic acid butyl ester The title compound was prepared by adapting the procedures described in example 303 with the difference that (S)-2-Phenyl-pyrrolidine was used instead of (S)-Pyrrolidine-2-carboxylic acid cyclobutylamide. MS (ES$^+$): m/e=688.

Example 482

4-[(S)-4-Carboxy-2-({4-[2-((S)-2-methoxymethyl-pyrrolidin-1-yl)-2-oxo-ethoxy]-7-methyl-quinoline-2-carbonyl}-amino)-butyryl]-piperazine-1-carboxylic acid butyl ester The title compound was prepared by adapting the procedures described in example 303 with the difference that (S)-2-Methoxymethyl-pyrrolidine was used instead of (S)-Pyrrolidine-2-carboxylic acid cyclobutylamide. MS (ES$^+$): m/e=656.

Example 483

4-((S)-4-Carboxy-2-{[7-methyl-4-(2-oxo-2-piperazin-1-yl-ethoxy)-quinoline-2-carbonyl]-amino}-butyryl)-piperazine-1-carboxylic acid butyl ester The title compound was prepared by adapting the procedures described in example 303 with the difference that Piperazine was used instead of (S)-Pyrrolidine-2-carboxylic acid cyclobutylamide. MS (ES$^+$): m/e=627.

Example 484

4-{(S)-2-({4-[2-((S)-2-Cyclobutylcarbamoyl-pyrrolidin-1-yl)-2-oxo-ethoxy]-7-methyl-quinoline-2-carbonyl}-amino)-4-[2-(2-oxo-oxazolidin-3-yl)-ethoxycarbonyl]-butyryl}-piperazine-1-carboxylic acid ethyl ester The title compound was prepared by adapting the procedures described in example 237 with the difference that 3-(2-Hydroxy-ethyl)-oxazolidin-2-one was used instead of methanol. MS (ES$^+$): m/e=794.

Example 485

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(5-methyl-[1,3]dioxan-5-yl-methoxycarbonyl)-butyryl]-piperazine-1-carboxylic acid ethyl ester The title compound was prepared by adapting the procedures described in example 237 with the difference that (5-Methyl-[1,3]dioxan-5-yl)methanol was used instead of methanol. MS (ES$^+$): m/e=795.

Example 486

4-[(S)-4-Carboxy-2-({4-[2-(3-methoxy-pyrrolidin-1-yl)-2-oxo-ethoxy]-7-methyl-quinoline-2-carbonyl}-amino)-butyryl]-piperazine-1-carboxylic acid butyl ester The title compound was prepared by adapting the procedures described in example 303 with the difference that 3-Methoxy-pyrrolidine was used instead of (S)-Pyrrolidine-2-carboxylic acid cyclobutylamide. MS (ES$^+$): m/e=642.

Example 487

4-[(S)-4-Carboxy-2-({7-methyl-4-[2-oxo-2-(3-oxo-pyrazolidin-1-yl)-ethoxy]-quinoline-2-carbonyl}-amino)-butyryl]-piperazine-1-carboxylic acid butyl ester The title compound was prepared by adapting the procedures described in example 303 with the difference that Pyrazolidin-3-one was used instead of (S)-Pyrrolidine-2-carboxylic acid cyclobutylamide. MS (ES+): m/e=627.

Example 488

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-methoxycarbonyl-butyryl]-piperazine-1-carboxylic acid butyl ester The title compound was prepared by adapting the procedures described in example 237 with the difference that 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid butyl ester was used instead of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester. MS (ES+): m/e=723.

Example 489

4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid propyl ester The title compound was prepared by adapting the procedures described in example 303 with the difference that Piperazine-1-carboxylic acid propyl ester was used instead of Piperazine-1-carboxylic acid butyl ester. MS (ES+): m/e=695.

Example 490

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-methoxycarbonyl-butyryl]-piperazine-1-carboxylic acid propyl ester The title compound was prepared by adapting the procedures described in example 237 with the difference that 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid propyl ester was used instead of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester. MS (ES+): m/e=709.

Example 491

4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid cyclobutyl ester (i) Piperazine-1,4-dicarboxylic acid benzyl ester cyclobutyl ester To a solution of 2.6 g triphosgene and 1.7 ml cyclobutanol in 40 ml dichloromethane were added 6.2 ml triethylamine dropwise at 0° C. After 30 minutes 4.4 ml benzyl 1-piperazinecarboxylate and 3.2 ml triethylamine were added at 0° C. The reaction mixture was allowed to warm to RT for 16 h. Excess triphosgene was destroyed by adding a solution of 2 g NaOH in 200 ml water and stirring for 2 h. The layers were separated, the organic layer dried over MgSO$_4$ and concentrated. The crude product thus obtained was purified by chromatography on silica using heptane/ethyl acetate 4/1 to 2/1 as eluent. Yield: 5.9 g.

(ii) Piperazine-1-carboxylic acid cyclobutyl ester

A suspension of 5.90 g Piperazine-1,4-dicarboxylic acid benzyl ester cyclobutyl ester and 0.25 g Pd/C (10%) in 50 ml ethyl acetate was stirred under an atmosphere of hydrogen (3 bar) for 12 h. The mixture was filtrated over a plug of Celite, washed with ethyl acetate and the combined wash solutions concentrated to give the title compound as colourless oil. Yield: 3.3 g.

(iii) 4-((S)-2-Benzyloxycarbonylamino-4-tert-butoxycarbonyl-butyryl)-piperazine-1-carboxylic acid cyclobutyl ester To a solution of 6.0 g (S)-2-Benzyloxycarbonylamino-pentanedioic acid 5-tert-butyl ester in 50 ml DMF were added 3.3 g piperazine-1-carboxylic acid cyclobutyl ester, 9.1 ml N-ethylmorpholine and 5.9 g TOTU. After stirring for 12 h the solution was diluted with ethyl acetate and subsequently washed with aqueous LiCl (4%) and saturated aqueous NaHCO$_3$. The crude product obtained after evaporation of the solvent was used without further purification. Yield: 11.1 g.

(iv) 4-((S)-2-Amino-4-tert-butoxycarbonyl-butyryl)-piperazine-1-carboxylic acid cyclobutyl ester To a solution of 11.1 g 4-((S)-2-Benzyloxycarbonylamino-4-tert-butoxycarbonyl-butyryl)-piperazine-1-carboxylic acid cyclobutyl ester in 80 ml ethyl acetate were added 0.6 g Pd/C (10%) and the suspension stirred under an atmosphere of hydrogen (3 bar) for 12 h. The reaction mixture was filtrated over a plug of Celite, washed with ethanol and concentrated to give the crude product which was used in the subsequent reaction. Yield: 7.2 g.

(v) 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid cyclobutyl ester The title compound was prepared by adapting the procedures described in example 303 with the difference that 4-((S)-2-Amino-4-tert-butoxycarbonyl-butyryl)-piperazine-1-carboxylic acid cyclobutyl ester was used instead of 4-((S)-2-Amino-4-tert-butoxycarbonyl-butyryl)-piperazine-1-carboxylic acid butyl ester. MS (ES+): m/e=707.

Example 492

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-methoxycarbonyl-butyryl]-piperazine-1-carboxylic acid cyclobutyl ester The title compound was prepared by adapting the procedures described in example 237 with the difference that 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid cyclobutyl ester was used instead of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester. MS (ES+): m/e=721.

Example 493

4-{(S)-4-Carboxy-2-[(4-{2-[2-(3-fluoro-phenyl)-pyrrolidin-1-yl]-2-oxo-ethoxy}-quinoline-2-carbonyl)-amino]-butyryl}-piperazine-1-carboxylic acid ethyl ester The title compound was prepared by adapting the procedures described in example 73 with the difference that 2-(3-Fluoro-phenyl)-pyrrolidine was used instead of (S)-Pyrrolidine-2-carboxylic acid cyclopropylamide hydrochloride. MS (ES$^+$): m/e=664.

Example 494

4-[(S)-4-Carboxy-2-({4-[2-oxo-2-(2-oxo-[1,4']bipiperidinyl-1'-yl)-ethoxy]-quinoline-2-carbonyl}-amino)-butyryl]-piperazine-1-carboxylic acid ethyl ester The title compound was prepared by adapting the procedures described in example 73 with the difference that [1,4'] Bipiperidinyl-2-one was used instead of (S)-Pyrrolidine-2-carboxylic acid cyclopropylamide hydrochloride. MS (ES$^+$): m/e=681.

Example 495

4-[(S)-4-Carboxy-2-({4-[2-(2-methyl-6,7-dihydro-4H-oxazolo[5,4-c]pyridin-5-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 2-Methyl-4,5,6,7-tetrahydro-oxazolo[5,4-c]pyridine was used instead of (S)-Pyrrolidine-2-carboxylic acid cyclopropylamide hydrochloride. MS (ES$^+$): m/e=637.

Example 496

4-[(S)-4-Carboxy-2-({4-[2-oxo-2-((S)-2-phenylcarbamoyl-pyrrolidin-1-yl)-ethoxy]-quinoline-2-carbonyl}-amino)-butyryl]-piperazine-1-carboxylic acid ethyl ester The title compound was prepared by adapting the procedures described in example 73 with the difference that (S)-Pyrrolidine-2-carboxylic acid phenylamide was used instead of (S)-Pyrrolidine-2-carboxylic acid cyclopropylamide hydrochloride. MS (ES$^+$): m/e=689.

Example 497

4-[(S)-4-Carboxy-2-({4-[2-(1-methyl-4,6-dihydro-1H-pyrrolo[3,4-c]pyrazol-5-yl)-2-oxo-ethoxy]-quinoline-2-carbonyl}-amino)-butyryl]-piperazine-1-carboxylic acid ethyl ester The title compound was prepared by adapting the procedures described in example 73 with the difference that 1-Methyl-1,4,5,6-tetrahydro-pyrrolo[3,4-c]pyrazole was used instead of (S)-Pyrrolidine-2-carboxylic acid cyclopropylamide hydrochloride. MS (ES$^+$): m/e=622.

Example 498

4-{(S)-2-({4-[2-((S)-2-Cyclobutylcarbamoyl-pyrrolidin-1-yl)-2-oxo-ethoxy]-7-methyl-quinoline-2-carbonyl}-amino)-4-[2-(tetrahydro-pyran-4-yl)-ethoxycarbonyl]-butyryl}-piperazine-1-carboxylic acid ethyl ester The title compound was prepared by adapting the procedures described in example 237 with the difference that 2-(Tetrahydro-pyran-4-yl)-ethanol was used instead of methanol. MS (ES$^+$): m/e=793.

Example 499

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(3-hydroxy-3-methyl-butoxycarbonyl)-butyryl]-piperazine-1-carboxylic acid ethyl ester The title compound was prepared by adapting the procedures described in example 237 with the difference that 3-Methyl-butane-1,3-diol was used instead of methanol. MS (ES$^+$): m/e=767.

Example 500

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(tetrahydro-pyran-3-ylmethoxycarbonyl)-butyryl]-piperazine-1-carboxylic acid ethyl ester The title compound was prepared by adapting the procedures described in example 237 with the difference that (Tetrahydro-pyran-3-yl)-methanol was used instead of methanol. MS (ES$^+$): m/e=779.

Example 501

4-[(S)-4-Carboxy-2-({7-methyl-4-[2-oxo-2-(3-oxo-piperazin-1-yl)-ethoxy]-quinoline-2-carbonyl}-amino)-butyryl]-piperazine-1-carboxylic acid butyl ester The title compound was prepared by adapting the procedures described in example 303 with the difference that Piperazin-2-one was used instead of (S)-Pyrrolidine-2-carboxylic acid cyclobutylamide. MS (ES$^+$): m/e=641.

Example 502

4-{(S)-4-Carboxy-2-[(4-{2-[2-(4-fluoro-phenyl)-pyrrolidin-1-yl]-2-oxo-ethoxy}-7-methyl-quinoline-2-carbonyl)-amino]-butyryl}-piperazine-1-carboxylic acid butyl ester The title compound was prepared by adapting the procedures described in example 303 with the difference that 2-(4-Fluoro-phenyl)-pyrrolidine was used instead of (S)-Pyrrolidine-2-carboxylic acid cyclobutylamide. MS (ES$^+$): m/e=706.

Example 503

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(tetrahydro-pyran-4-ylmethoxycarbonyl)-butyryl]-piperazine-1-carboxylic acid ethyl ester The title compound was prepared by adapting the procedures described in example 237 with the difference that (Tetrahydro-pyran-4-yl)-methanol was used instead of methanol. MS (ES$^+$): m/e=779.

Example 504

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(2-hydroxy-2-methyl-butoxycarbonyl)-butyryl]-piperazine-1-carboxylic acid ethyl ester The title compound was prepared by adapting the procedures described in example 237 with the difference that 2-Methyl-butane-1,2-diol was used instead of methanol. MS (ES$^+$): m/e=767.

Example 505

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(2-methyl-oxetan-2-ylmethoxycarbonyl)-butyryl]-piperazine-1-carboxylic acid ethyl ester The title compound was prepared by adapting the procedures described in example 237 with the difference that (2-Methyl-oxetan-2-yl)-methanol was used instead of methanol. MS (ES$^+$): m/e=765.

Example 506

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(3-ethyl-oxetan-3-ylmethoxycarbonyl)-butyryl]-piperazine-1-carboxylic acid butyl ester To a solution of 125 mg of DMAP, 196 mg of EDC and 700 mg of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid butyl ester in 10 ml of DCM, 494 mg of (3-Ethyl-oxetan-3-yl)-methanol was added and the reaction mixture was stirred for 16 h at RT. The solvents were removed under reduced pressure and the residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. The product was dissolved in DCM and washed with saturated aqueous sodium hydrogen carbonate solution and water. The organic phase dried over MgSO$_4$. The solvents were removed under reduced pressure. The residue was dissolved in water/acetonitrile and lyophilized to yield the product as a white solid. Yield: 301 mg MS (ES+): m/e=807.

Example 507

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(tetrahydro-pyran-2-ylmethoxycarbonyl)-butyryl]-piperazine-1-carboxylic acid butyl ester The title compound was prepared by adapting the procedures described in example 506 with the difference that (Tetrahydro-pyran-2-yl)-methanol was used instead of (3-Ethyl-oxetan-3-yl)-methanol. MS (ES$^+$): m/e=807.

Example 508

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(tetrahydro-furan-3-ylmethoxycarbonyl)-butyryl]-piperazine-1-carboxylic acid butyl ester The title compound was prepared by adapting the procedures described in example 506 with the difference that (Tetrahydro-furan-3-yl)-methanol was used instead of (3-Ethyl-oxetan-3-yl)-methanol. MS (ES$^+$): m/e=793.

Example 509

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(tetrahydro-furan-2-ylmethoxycarbonyl)-butyryl]-piperazine-1-carboxylic acid butyl ester The title compound was prepared by adapting the procedures described in example 506 with the difference that (Tetrahydro-furan-2-yl)-methanol was used instead of (3-Ethyl-oxetan-3-yl)-methanol. MS (ES$^+$): m/e=793.

Example 510

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(2-ethoxy-ethoxycarbonyl)-butyryl]-piperazine-1-carboxylic acid butyl ester To a solution of 125 mg of DMAP, 196 mg of EDC and 700 mg of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid butyl ester in 10 ml of DCM, 383 mg of 2-Ethoxy-ethanol was added and the reaction mixture was stirred for 16 h at RT. The solvents were removed under reduced pressure and the residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. The product was dissolved in DCM and washed with saturated aqueous sodium hydrogen carbonate solution and water. The organic phase dried over MgSO$_4$. The solvents were removed under reduced pressure. The residue was dissolved in water/acetonitrile and lyophilized to yield the product as a white solid. Yield: 146 mg MS (ES+): m/e=781.

Example 511

4-[(S)-4-Carboxy-2-({4-[2-((S)-2-cyclobutylcarbamoyl-pyrrolidin-1-yl)-2-oxo-ethoxy]-7-methyl-naphthalene-2-carbonyl}-amino)-butyryl]-piperazine-1-carboxylic acid butyl ester

(i) 2-[1-m-Tolyl-meth-(E)-ylidene]-succinic acid diethyl ester

To a solution of 22.6 g sodium ethylate in 440 ml of ethanol, 20 g of 3-Methyl-benzaldehyde and 31 g of Malonic acid diethyl ester dissolved in 100 ml ethanol was added drop-wise over 1.5 h at 50° C. Then, the reaction mixture was heated to reflux for 12 h. After cooling to RT half of the solvent was evaporated under reduced pressure and diluted with 200 ml of water. The remaining reaction mixture was acidified to pH 1 by addition of concentrated hydrochloric acid and then extracted with ethyl acetate. The organic phase was dried over $MgSO_4$ and the solvents were removed under reduced pressure. The crude product was pure enough for the next reaction step.

(ii) 4-Acetoxy-7-methyl-naphthalene-2-carboxylic acid ethyl ester

To a solution of 2 g of 2-[1-m-Tolyl-meth-(E)-ylidene]-succinic acid diethyl ester in 10 ml of acetic acid anhydride, 594 mg sodium acetate was added and the reaction mixture was heated to reflux for 5 h. After cooling to RT the reaction mixture was diluted with water and extracted with ethyl acetate. The combined organic phases were washed three times with saturated aqueous sodium hydrogen carbonate solution. The organic phase was dried over $MgSO_4$ and the solvents were removed under reduced pressure. The crude product was purified by chromatography on silica gel eluting with n-heptane/ethyl acetate (1/1). The fractions containing the product were combined and the solvent evaporated under reduced pressure. Yield: 860 mg.

(iii) 4-Hydroxy-7-methyl-naphthalene-2-carboxylic acid

To a solution of 860 mg of 4-Acetoxy-7-methyl-naphthalene-2-carboxylic acid ethyl ester in 3 ml ethanol/water (9:1), 12.6 ml of a 1M NaOH was added and stirred for 5 h at RT. Then, the reaction mixture was acidified to pH 2 with diluted hydrochloric acid to precipitate the product. The product was then collected by filtration and dried under reduced pressure. Yield: 550 mg.

(iv) 4-{(S)-4-tert-Butoxycarbonyl-2-[(4-hydroxy-7-methyl-naphthalene-2-carbonyl)-amino]-butyryl}-piperazine-1-carboxylic acid butyl ester To a solution of 550 mg of 4-Hydroxy-7-methyl-naphthalene-2-carboxylic acid and 1.0 g of 4-((S)-2-Amino-4-tert-butoxycarbonyl-butyryl)-piperazine-1-carboxylic acid butyl ester in 8.3 ml of DMF, 458 mg of HOBT and 573 mg of EDC was added and the reaction mixture was stirred for 16 h at RT. Then, the reaction mixture was diluted with water and extracted with ethyl acetate. The organic phase was dried over $MgSO_4$ and the solvents were removed under reduced pressure. The crude product was purified by chromatography on silica gel eluting with n-heptane/ethyl acetate (1/1). The fractions containing the product were combined and the solvent evaporated under reduced pressure. Yield: 1.0 g.

(v) 4-{(S)-2-[(4-Benzyloxycarbonylmethoxy-7-methyl-naphthalene-2-carbonyl)-amino]-4-tert-butoxycarbonyl-butyryl}-piperazine-1-carboxylic acid butyl ester To a solution of 1.0 g 4-{(S)-4-tert-Butoxycarbonyl-2-[(4-hydroxy-7-methyl-naphthalene-2-carbonyl)-amino]-butyryl}-piperazine-1-carboxylic acid butyl ester in 12 ml of DMF, 645 mg of cesium carbonate and 447 mg of Bromoacetic acid benzyl ester were added and the reaction mixture was stirred for 2 h at RT. Then, the reaction mixture was diluted with water and extracted with ethyl acetate. The organic phase was dried over $MgSO_4$ and the solvents were removed under reduced pressure. The isolated crude product was pure enough for the next reaction step. Yield: 710 mg.

(vi) 4-{(S)-4-tert-Butoxycarbonyl-2-[(4-carboxymethoxy-7-methyl-naphthalene-2-carbonyl)-amino]-butyryl}-piperazine-1-carboxylic acid butyl ester To a solution of 710 mg 4-{(S)-2-[(4-Benzyloxycarbonylmethoxy-7-methyl-naphthalene-2-carbonyl)-amino]-4-tert-butoxycarbonyl-butyryl}-piperazine-1-carboxylic acid butyl ester in 15 ml ethyl acetate were added 200 mg Pd/C (10%) and the suspension stirred under an atmosphere of hydrogen (3 bar) for 1 h. Then the reaction mixture was filtrated over a plug of Celite®, washed with ethyl acetate and concentrated. Yield: 670 mg colorless oil.

(vii) 4-[(S)-4-tert-Butoxycarbonyl-2-({4-[2-((S)-2-cyclobutylcarbamoyl-pyrrolidin-1-yl)-2-oxo-ethoxy]-7-methyl-naphthalene-2-carbonyl}-amino)-butyryl]-piperazine-1-carboxylic acid butyl ester To a solution of 670 mg of 4-{(S)-4-tert-Butoxycarbonyl-2-[(4-carboxymethoxy-7-methyl-naphthalene-2-carbonyl)-amino]-butyryl}-piperazine-1-carboxylic acid butyl ester in 10 ml of DCM, 418 mg of EDC, 402 mg of pentafluorophenol was added and the reaction mixture was stirred for 2 h. Then, 329 mg of (S)-Pyrrolidine-2-carboxylic acid cyclobutylamide hydrochloride and 251 mg of NEM in 1.5 ml of DCM was added. After 16 h the reaction mixture was diluted with water. After filtration through a chem Elut® cartridge by eluting with ethyl acetate the solvents were removed under reduced pressure. The crude product obtained after evaporation of the solvent was purified by flash chromatography on silica using an ethyl acetate/heptane gradient. Yield: 1.5 g

(viii) 4-[(S)-4-Carboxy-2-({4-[2-((S)-2-cyclobutylcarbamoyl-pyrrolidin-1-yl)-2-oxo-ethoxy]-7-methyl-naphthalene-2-carbonyl}-amino)-butyryl]-piperazine-1-carboxylic acid butyl ester To a solution of 1.5 g 4-[(S)-4-tert-Butoxycarbonyl-2-({4-[2-((S)-2-cyclobutylcarbamoyl-pyrrolidin-1-yl)-2-oxo-ethoxy]-7-methyl-naphthalene-2-carbonyl}-amino)-butyryl]-piperazine-1-carboxylic acid butyl ester in 10 ml dichloromethane were added 1.1 g TFA. After 3 h stirring at RT the solvents were removed and the residue was codistilled twice with toluene. The crude product was purified by preparative HPLC (C18 reverse phase column, elution with a water/MeCN gradient with 0.1% TFA). Yield: 970 mg MS (ES$^+$): m/e=708.

Example 512

4-[(S)-2-({4-[2-((S)-2-Cyclobutylcarbamoyl-pyrrolidin-1-yl)-2-oxo-ethoxy]-7-methyl-naphthalene-2-carbonyl}-amino)-4-methoxycarbonyl-butyryl]-piperazine-1-carboxylic acid butyl ester The title compound was prepared by adapting the procedures described in example 237 with the difference that 4-[(S)-4-Carboxy-2-({4-[2-((S)-2-cyclobutylcarbamoyl-pyrrolidin-1-yl)-2-oxo-ethoxy]-7-methyl-naphthalene-2-carbonyl}-amino)-butyryl]-piperazine-1-carboxylic acid butyl ester was used instead of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester. MS (ES$^+$): m/e=722.

Example 513

4-[(S)-2-({4-[2-((S)-2-Cyclobutylcarbamoyl-pyrrolidin-1-yl)-2-oxo-ethoxy]-7-methyl-naphthalene-2-carbonyl}-amino)-4-ethoxycarbonyl-butyryl]-piperazine-1-carboxylic acid butyl ester The title compound was prepared by adapting the procedures described in example 58 with the difference that 4-[(S)-4-Carboxy-2-({4-[2-((S)-2-cyclobutylcarbamoyl-pyrrolidin-1-yl)-2-oxo-ethoxy]-7-methyl-naphthalene-2-carbonyl}-amino)-butyryl]-piperazine-1-carboxylic acid butyl ester was used instead of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester. MS (ES$^+$): m/e=736.

Example 514

4-[(S)-3-Cyclobutyl-2-({4-[2-((S)-2-cyclobutylcarbamoyl-pyrrolidin-1-yl)-2-oxo-ethoxy]-7-methyl-quinoline-2-carbonyl}-amino)-propionyl]-piperazine-1-carboxylic acid butyl ester The title compound was prepared by adapting the procedures described in example 435 with the difference that 4-((S)-2-Amino-3-cyclobutyl-propionyl)-piperazine-1-carboxylic acid butyl ester was used instead of 4-(2-Amino-acetyl)-piperazine-1-carboxylic acid butyl ester. MS (ES$^+$): m/e=705.

Example 515

4-[(S)-2-({4-[2-((S)-2-Cyclobutylcarbamoyl-pyrrolidin-1-yl)-2-oxo-ethoxy]-7-methyl-quinoline-2-carbonyl}-amino)-butyryl]-piperazine-1-carboxylic acid butyl ester The title compound was prepared by adapting the procedures described in example 435 with the difference that 4-((S)-2-Amino-butyryl)-piperazine-1-carboxylic acid butyl ester was used instead of 4-(2-Amino-acetyl)-piperazine-1-carboxylic acid butyl ester. MS (ES$^+$): m/e=665.

Example 516

4-[(S)-2-({4-[2-((S)-2-Cyclobutylcarbamoyl-pyrrolidin-1-yl)-2-oxo-ethoxy]-7-methyl-quinoline-2-carbonyl}-amino)-3-cyclopropyl-propionyl]-piperazine-1-carboxylic acid butyl ester The title compound was prepared by adapting the procedures described in example 435 with the difference that 4-((S)-2-Amino-3-cyclopropyl-propionyl)-piperazine-1-carboxylic acid butyl ester was used instead of 4-(2-Amino-acetyl)-piperazine-1-carboxylic acid butyl ester. MS (ES$^+$): m/e=691.

Example 517

4-[(S)-2-({4-[2-((S)-2-Cyclobutylcarbamoyl-pyrrolidin-1-yl)-2-oxo-ethoxy]-7-methyl-quinoline-2-carbonyl}-amino)-3-methoxy-propionyl]-piperazine-1-carboxylic acid butyl ester The title compound was prepared by adapting the procedures described in example 435 with the difference that 4-((S)-2-Amino-3-methoxy-propionyl)-piperazine-1-carboxylic acid butyl ester was used instead of 4-(2-Amino-acetyl)-piperazine-1-carboxylic acid butyl ester. MS (ES$^+$): m/e=681.

Example 518

4-[(S)-2-({4-[2-((S)-2-Cyclobutylcarbamoyl-pyrrolidin-1-yl)-2-oxo-ethoxy]-7-methyl-naphthalene-2-carbonyl}-amino)-4-cyclopentylmethoxycarbonyl-butyryl]-piperazine-1-carboxylic acid butyl ester The title compound was prepared by adapting the procedures described in example 246 with the difference that 4-[(S)-4-Carboxy-2-({4-[2-((S)-2-cyclobutylcarbamoyl-pyrrolidin-1-yl)-2-oxo-ethoxy]-7-methyl-naphthalene-2-carbonyl}-amino)-butyryl]-piperazine-1-carboxylic acid butyl ester was used instead of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester. MS (ES$^+$): m/e=708.

Example 519

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-cyclopentylmethoxycarbonyl-butyryl]-piperazine-1-carboxylic acid cyclopropylmethyl ester The title compound was prepared by adapting the procedures described in example 246 with the difference that 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid cyclopropylmethyl ester was used instead of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester. MS (ES$^+$): m/e=789.

Example 520

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-cyclopentylmethoxycarbonyl-butyryl]-piperazine-1-carboxylic acid cyclobutyl ester The title compound was prepared by adapting the procedures described in example 246 with the difference that 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid cyclobutyl ester was used instead of 4-[(S)-4-Carboxy-2-({4-

[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester. MS (ES$^+$): m/e=789.

Example 521

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-methoxy-butyryl]-piperazine-1-carboxylic acid butyl ester The title compound was prepared by adapting the procedures described in example 435 with the difference that 4-((S)-2-Amino-4-methoxy-butyryl)-piperazine-1-carboxylic acid butyl ester was used instead of 4-(2-Amino-acetyl)-piperazine-1-carboxylic acid butyl ester. MS (ES$^+$): m/e=695.

Example 522

4-[(S)-2-({4-[2-((S)-2-Cyclobutylcarbamoyl-pyrrolidin-1-yl)-2-oxo-ethoxy]-7-methyl-quinoline-2-carbonyl}-amino)-2-cyclopropyl-acetyl]-piperazine-1-carboxylic acid butyl ester The title compound was prepared by adapting the procedures described in example 435 with the difference that 4-((S)-2-Amino-2-cyclopropyl-acetyl)-piperazine-1-carboxylic acid butyl ester was used instead of 4-(2-Amino-acetyl)-piperazine-1-carboxylic acid butyl ester. MS (ES$^+$): m/e=677.

Example 523

4-[(2S,3R)-2-({4-[2-((S)-2-Cyclobutylcarbamoyl-pyrrolidin-1-yl)-2-oxo-ethoxy]-7-methyl-quinoline-2-carbonyl}-amino)-3-methyl-pentanoyl]-piperazine-1-carboxylic acid butyl ester The title compound was prepared by adapting the procedures described in example 435 with the difference that 4-((2S,3R)-2-Amino-3-methyl-pentanoyl)-piperazine-1-carboxylic acid butyl ester was used instead of 4-(2-Amino-acetyl)-piperazine-1-carboxylic acid butyl ester. MS (ES$^+$): m/e=693.

Example 524

4-[(S)-2-({4-[2-((S)-2-Cyclobutylcarbamoyl-pyrrolidin-1-yl)-2-oxo-ethoxy]-7-methyl-quinoline-2-carbonyl}-amino)-3-hydroxy-3-methyl-butyryl]-piperazine-1-carboxylic acid butyl ester The title compound was prepared by adapting the procedures described in example 435 with the difference that 4-((S)-2-Amino-3-hydroxy-3-methyl-butyryl)-piperazine-1-carboxylic acid butyl ester was used instead of 4-(2-Amino-acetyl)-piperazine-1-carboxylic acid butyl ester. MS (ES$^+$): m/e=695.

Example 525

4-[(S)-2-({4-[2-((S)-2-Cyclobutylcarbamoyl-pyrrolidin-1-yl)-2-oxo-ethoxy]-7-methyl-quinoline-2-carbonyl}-amino)-3-ethoxy-propionyl]-piperazine-1-carboxylic acid butyl ester The title compound was prepared by adapting the procedures described in example 435 with the difference that 4-((S)-2-Amino-3-ethoxy-propionyl)-piperazine-1-carboxylic acid butyl ester was used instead of 4-(2-Amino-acetyl)-piperazine-1-carboxylic acid butyl ester. MS (ES$^+$): m/e=695.

Example 526

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-hydroxy-butyryl]-piperazine-1-carboxylic acid cyclopropylmethyl ester (i) Piperazine-1,4-dicarboxylic acid tert-butyl ester cyclopropylmethyl ester To a solution of 3.3 g triphosgene and 2 g Cyclopropyl-methanol in 40 ml dichloromethane were added 9.1 ml DIPEA dropwise at 0° C. After 1 h, 5.1 g Piperazine-1-carboxylic acid tert-butyl ester and 4.5 ml DIPEA in 7 ml were added at 0° C. The reaction mixture was allowed to warm to RT and stirred for 16 h. Excess triphosgene was destroyed by adding a solution of 2 g NaOH in 120 ml water and stirring for 2 h. The layers were separated and the aqueous layer was extracted with DCM. The combined organic layers were washed with 1M aqueous hydrochloric acid, dried over MgSO$_4$ and concentrated. The crude product thus obtained was purified was used in the next reaction step. Yield: 7.9 g.

(ii) Piperazine-1-carboxylic acid cyclopropylmethyl ester

To a solution of 7.9 g Piperazine-1,4-dicarboxylic acid tert-butyl ester cyclobutyl ester in 20 ml dichloromethane 10 ml of TFA were added. After 16 h stirring at RT the solvents were removed and the residue was codistilled twice with toluene. The product was obtained as its trifluoroacetate salt. Yield: 11.7 g.

(iii) 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-hydroxy-butyryl]-piperazine-1-carboxylic acid cyclopropylmethyl ester The title compound was prepared by adapting the procedures described in example 354 with the difference that Piperazine-1-carboxylic acid cyclopropylmethyl ester was used instead of Piperazine-1-carboxylic acid butyl ester. MS (ES$^+$): m/e=679.

Example 527

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-hydroxy-butyryl]-piperazine-1-carboxylic acid cyclobutyl ester (i) Piperazine-1,4-dicarboxylic acid benzyl ester cyclobutyl ester To a solution of 2.6 g triphosgene and 1.7 ml cyclobutanol in 40 ml dichloromethane were added 6.2 ml triethylamine dropwise at 0° C. After 30 minutes 4.4 ml benzyl 1-piperazinecarboxylate and 3.2 ml triethylamine were added at 0° C. The reaction mixture was allowed to warm to RT for 16 h. Excess triphosgene was destroyed by adding a solution of 2 g NaOH in 200 ml water and stirring for 2 h. The layers were separated, the organic layer dried over MgSO$_4$ and concentrated. The crude product thus obtained was purified by chromatography on silica using heptane/ethyl acetate 4/1 to 2/1 as eluent. Yield: 5.9 g.

(ii) Piperazine-1-carboxylic acid cyclobutyl ester

A suspension of 5.90 g Piperazine-1,4-dicarboxylic acid benzyl ester cyclobutyl ester and 0.25 g Pd/C (10%) in 50 ml ethyl acetate was stirred under an atmosphere of hydrogen (3 bar) for 12 h. The mixture was filtrated over a plug of Celite, washed with ethyl acetate and the combined wash solutions concentrated to give the title compound as colourless oil. Yield: 3.3 g.

(iii) 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-hydroxy-butyryl]-piperazine-1-carboxylic acid cyclobutyl ester The title compound was prepared by adapting the procedures described in example 354 with the difference that Piperazine-1-carboxylic acid cyclobutyl ester was used instead of Piperazine-1-carboxylic acid butyl ester. MS (ES$^+$): m/e=679.

Example 528

4-[(S)-2-({4-[2-((S)-2-Cyclobutylcarbamoyl-pyrrolidin-1-yl)-2-oxo-ethoxy]-7-methyl-quinoline-2-carbonyl}-amino)-3-hydroxy-propionyl]-piperazine-1-carboxylic acid butyl ester The title compound was prepared by adapting the procedures described in example 435 with the difference that 4-((S)-2-Amino-3-hydroxy-propionyl)-piperazine-1-carboxylic acid butyl ester was used instead of 4-(2-Amino-acetyl)-piperazine-1-carboxylic acid butyl ester. MS (ES$^+$): m/e=667.

Example 529

4-[(S)-2-({4-[2-((S)-2-Cyclobutylcarbamoyl-pyrrolidin-1-yl)-2-oxo-ethoxy]-7-methyl-quinoline-2-carbonyl}-amino)-propionyl]-piperazine-1-carboxylic acid butyl ester The title compound was prepared by adapting the procedures described in example 435 with the difference that 4-((S)-2-Amino-propionyl)-piperazine-1-carboxylic acid butyl ester was used instead of 4-(2-Amino-acetyl)-piperazine-1-carboxylic acid butyl ester. MS (ES$^+$): m/e=651.

Example 530

4-[(2S,3R)-2-({4-[2-((S)-2-Cyclobutylcarbamoyl-pyrrolidin-1-yl)-2-oxo-ethoxy]-7-methyl-quinoline-2-carbonyl}-amino)-3-methoxy-butyryl]-piperazine-1-carboxylic acid butyl ester The title compound was prepared by adapting the procedures described in example 435 with the difference that 4-((2S,3R)-2-Amino-3-methoxy-butyryl)piperazine-1-carboxylic acid butyl ester was used instead of 4-(2-Amino-acetyl)-piperazine-1-carboxylic acid butyl ester. MS (ES$^+$): m/e=695.

Example 531

4-[(S)-2-({4-[2-((S)-2-Cyclobutylcarbamoyl-pyrrolidin-1-yl)-2-oxo-ethoxy]-quinoline-2-carbonyl}-amino)-4-cyclopentylmethoxycarbonyl-butyryl]-piperazine-1-carboxylic acid butyl ester The title compound was prepared by adapting the procedures described in example 246 with the difference that 4-[(S)-4-Carboxy-2-({4-[2-((S)-2-cyclobutylcarbamoyl-pyrrolidin-1-yl)-2-oxo-ethoxy]-quinoline-2-carbonyl}-amino)-butyryl]-piperazine-1-carboxylic acid butyl ester was used instead of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester. MS (ES$^+$): m/e=777.

Example 532

4-[2-({4-[2-((S)-2-Cyclobutylcarbamoyl-pyrrolidin-1-yl)-2-oxo-ethoxy]-7-methyl-quinoline-2-carbonyl}-amino)-2-(tetrahydro-furan-3-yl)-acetyl]-piperazine-1-carboxylic acid butyl ester The title compound was prepared by adapting the procedures described in example 435 with the difference that 4-[2-Amino-2-(tetrahydro-furan-3-yl)-acetyl]-piperazine-1-carboxylic acid butyl ester was used instead of 4-(2-Amino-acetyl)piperazine-1-carboxylic acid butyl ester. MS (ES$^+$): m/e=707.

Example 533

4-[2-({4-[2-((S)-2-Cyclobutylcarbamoyl-pyrrolidin-1-yl)-2-oxo-ethoxy]-7-methyl-quinoline-2-carbonyl}-amino)-2-(tetrahydro-pyran-4-yl)-acetyl]-piperazine-1-carboxylic acid butyl ester The title compound was prepared by adapting the procedures described in example 435 with the difference that 4-[2-Amino-2-(tetrahydro-pyran-4-yl)-acetyl]-piperazine-1-carboxylic acid butyl ester was used instead of 4-(2-Amino-acetyl)piperazine-1-carboxylic acid butyl ester. MS (ES$^+$): m/e=721.

Example 534

4-[(S)-2-({4-[(R)-2-((S)-2-Cyclobutylcarbamoyl-pyrrolidin-1-yl)-1-methyl-2-oxo-ethoxy]-7-methyl-quinoline-2-carbonyl}-amino)-4-hydroxy-butyryl]-piperazine-1-carboxylic acid butyl ester (i) 4-Hydroxy-7-methyl-quinoline-2-carboxylic acid methyl ester 4-Hydroxy-7-methyl-quinoline-2-carboxylic acid (1.00 g) was suspended in 20 ml HCl (4 M in MeOH) and stirred until LCMS indicated complete conversion to the methyl ester. The reaction mixture was concentrated and the residue obtained codistilled twice with toluene to give the crude product as hydrochloride salt. Yield: 1.24 g (ii) 4-((R)-1-Benzyloxycarbonyl-ethoxy)-7-methyl-quinoline-2-carboxylic acid methyl ester To a solution of 1.00 g 4-Hydroxy-7-methyl-quinoline-2-carboxylic acid methyl ester hydrochloride and 0.83 g benzyl-L-lactate in 30 ml THF were added 1.81 g triphenylphosphine and 1.20 g diethylazodicarboxylate. After 2 h LCMS indicated complete conversion and water was added to the reaction mixture which was subsequently extracted with ethyl acetate. The residue obtained after evaporation of the solvent was purified by flash chromatography on silica using an ethyl acetate/heptane gradient. Yield: 1.80 g (iii) 4-((R)-1-Carboxy-ethoxy)-7-methyl-quinoline-2-carboxylic acid To a solution of 1.80 g 4-((R)-1-Benzyloxycarbonyl-ethoxy)-7-methyl-quinoline-2-carboxylic acid methyl ester in 15 ml ethanol were added 200 mg Pd/C (10%) and the suspension stirred under an atmosphere of hydrogen (5 bar) for 18 h. Then, the reaction mixture was filtrated over a plug of Celite®, washed with ethanol and concentrated. Yield: 1.30 g colorless oil (iv) 4-[(R)-2-((S)-2-Cyclobutylcarbamoyl-pyrrolidin-1-yl)-1-methyl-2-oxo-ethoxy]-7-methyl-quinoline-2-carboxylic acid methyl ester To a solution of 1.30 g 4-((R)-1-Carboxy-ethoxy)-7-methyl-quinoline-2-carboxylic acid in 10 ml DCM, 1.24 g pentafluorophenol and 1.29 g EDC were added. The mixture was stirred under exclusion of moisture until LCMS indicated complete conversion to the corresponding pentafluorophenolester. (S)-Pyrrolidine-2-carboxylic acid cyclobutylamide hydrochloride (1.10 g) was mixed with 1.1 ml N-ethylmorpholine and 5 ml DCM and this mixture added dropwise to the solution of the pentafluorophenolester. After 12 h the reaction mixture was diluted with water and extracted with DCM. The crude product obtained after evaporation of the solvent was purified by flash chromatography on silica eluting with ethyl acetate/heptane gradient. Yield: 1.40 g.

(v) 4-[(R)-2-((S)-2-Cyclobutylcarbamoyl-pyrrolidin-1-yl)-1-methyl-2-oxo-ethoxy]-7-methyl-quinoline-2-carboxylic acid To a solution of 6.30 g 4-[(R)-2-((S)-2-Cyclobutylcarbamoyl-pyrrolidin-1-yl)-1-methyl-2-oxo-ethoxy]-7-methyl-quinoline-2-carboxylic acid methyl ester in 14 ml THF were added 14.3 ml aqueous NaOH (1 M) and the reaction mixture was stirred for 4 h at RT. The reaction mixture was acidified with 15 ml 1 M HCl, concentrated to a volume of 25 ml and extracted with DCM to give the crude product after evaporation of the solvent. Yield: 5.00 g.

(vi) 4-((S)-4-Benzyloxy-2-tert-butoxycarbonylamino-butyryl)-piperazine-1-carboxylic acid butyl ester To a solution of 5 g of (S)-4-Benzyloxy-2-tert-butoxycarbonylamino-butyric acid, 7.4 g of NEM and 5.3 g of TOTU in 35 ml of DMF, 4.8 g of Piperazine-1-carboxylic acid butyl ester trifluoroacetate was added at RT and stirred for 16 h. The reaction mixture was diluted saturated aqueous sodium hydrogen carbonate solution and extracted with 250 ml of ethyl acetate. The organic phase was dried over MgSO$_4$ and the solvents were removed under reduced pressure. The crude product was purified by chromatography on silica gel eluting with a gradient of n-heptane/ethyl acetate. The fractions containing the product were combined and the solvent evaporated under reduced pressure. Yield: 6.3 g.

(vii) 4-((S)-2-Amino-4-benzyloxy-butyryl)-piperazine-1-carboxylic acid butyl ester To a solution of 6.3 g of 4-((S)-4-Benzyloxy-2-tert-butoxycarbonylamino-butyryl)-piperazine-1-carboxylic acid butyl ester from the preceding reaction step (vi) in 24 ml of DCM 5 ml of TFA was added at RT. After 5 h, 100 ml of toluene was added and the solvents were removed under reduced pressure. The residue was co-distilled with toluene additional two times and then dissolved in DCM and washed with water. The organic phase was dried over MgSO$_4$ and the solvents were removed under reduced pressure. The isolated crude product was obtained as its trifluoroacetate salt and was pure enough for the next reaction step. Yield: 6.1 g.

(viii) 4-[(S)-4-Benzyloxy-2-({4-[(R)-2-((S)-2-cyclobutylcarbamoyl-pyrrolidin-1-yl)-1-methyl-2-oxo-ethoxy]-7-methyl-quinoline-2-carbonyl}-amino)-butyryl]-piperazine-1-carboxylic acid butyl ester To a solution of 1.0 g 4-[(R)-2-((S)-2-Cyclobutylcarbamoyl-pyrrolidin-1-yl)-1-methyl-2-oxo-ethoxy]-7-methyl-quinoline-2-carboxylic acid in 30 ml DMF were added 1.2 g DIPEA, 319 mg HOAt and 450 mg EDC. After 5 minutes 1.1 g 4-((S)-2-Amino-4-benzyloxy-butyryl)-piperazine-1-carboxylic acid butyl ester hydrotrifluoroacetate were added and the mixture stirred for 16 h. The mixture was concentrated, diluted with DCM and washed with aqueous LiCl (4%), saturated aqueous NaHCO$_3$ and brine. The crude product was used in the next reaction step. Yield: 2.8 g.

(ix) 4-[(S)-2-({4-[(R)-2-((S)-2-Cyclobutylcarbamoyl-pyrrolidin-1-yl)-1-methyl-2-oxo-ethoxy]-7-methyl-quinoline-2-carbonyl}-amino)-4-hydroxy-butyryl]-piperazine-1-carboxylic acid butyl ester A solution of 1.1 g of 4-[(S)-4-Benzyloxy-2-({4-[(R)-2-((S)-2-cyclobutylcarbamoyl-pyrrolidin-1-yl)-1-methyl-2-oxo-ethoxy]-7-methyl-quinoline-2-carbonyl}-amino)-butyryl]-piperazine-1-carboxylic acid butyl ester in 20 ml of ethanol was purged with argon. Then, 500 mg of Pd/C (5-10%) was added and the mixture was stirred under a hydrogen atmosphere (4.5 bar). After 16 h the reaction mixture was filtered through a pad of celite and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid. The product was dissolved in DCM and washed with saturated aqueous sodium hydrogen carbonate solution and water. The organic phase dried over MgSO$_4$. The solvents were removed under reduced pressure. The residue was dissolved in water/acetonitrile and lyophilized to yield the product as a white solid. Yield: 500 mg MS (ES+): m/e=695.

Example 535

4-[(S)-2-({4-[2-((S)-2-Cyclobutylcarbamoyl-pyrrolidin-1-yl)-2-oxo-ethoxy]-7-methyl-quinoline-2-carbonyl}-amino)-5-cyclopentylmethoxycarbonyl-pentanoyl]-piperazine-1-carboxylic acid ethyl ester The title compound was prepared by adapting the procedures described in example 246 with the difference that 4-[(S)-5-Carboxy-2-({4-[2-((S)-2-cyclobutylcarbamoyl-pyrrolidin-1-yl)-2-oxo-ethoxy]-7-methyl-quinoline-2-carbonyl}-amino)-pentanoyl]-piperazine-1-carboxylic acid

Example 536

4-[(S)-2-[(4-{2-[(S)-2-(Cyclobutyl-methyl-carbamoyl)-pyrrolidin-1-yl]-2-oxo-ethoxy}-7-methyl-quinoline-2-carbonyl)-amino]-4-(2-ethoxy-ethoxycarbonyl)-butyryl]-piperazine-1-carboxylic acid butyl ester The title compound was prepared by adapting the procedures described in example 510 with the difference that 4-{(S)-4-Carboxy-2-[(4-{2-[(S)-2-(cyclobutyl-methyl-carbamoyl)-pyrrolidin-1-yl]-2-oxo-ethoxy}-7-methyl-quinoline-2-carbonyl)-amino]-butyryl}-piperazine-1-carboxylic acid butyl ester was used instead of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid butyl ester. MS (ES$^+$): m/e=795.

Example 537

4-[(S)-4-Cyclopentylmethoxycarbonyl-2-({4-[2-((S)-2-cyclopropylcarbamoyl-pyrrolidin-1-yl)-2-oxo-ethoxy]-7-methyl-quinoline-2-carbonyl}-amino)-butyryl]-piperazine-1-carboxylic acid butyl ester The title compound was prepared by adapting the procedures described in example 246 with the difference that 4-[(S)-4-Carboxy-2-({4-[2-((S)-2-cyclopropylcarbamoyl-pyrrolidin-1-yl)-2-oxo-ethoxy]-7-methyl-quinoline-2-carbonyl}-amino)-butyryl]-piperazine-1-carboxylic acid butyl ester was used instead of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester. MS (ES$^+$): m/e=777.

Example 538

4-[(S)-2-[(4-{2-[(S)-2-(Cyclobutylmethyl-carbamoyl)-pyrrolidin-1-yl]-2-oxo-ethoxy}-7-methyl-quinoline-2-carbonyl)-amino]-4-(2-ethoxy-ethoxycarbonyl)-butyryl]-piperazine-1-carboxylic acid butyl ester The title compound was prepared by adapting the procedures described in example 510 with the difference that 4-{(S)-4-Carboxy-2-[(4-{2-[(S)-2-(cyclobutylmethyl-carbamoyl)-pyrrolidin-1-yl]-2-oxo-ethoxy}-7-methyl-quinoline-2-carbonyl)-amino]-butyryl}-piperazine-1-carboxylic acid butyl ester was used instead of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid butyl ester. MS (ES$^+$): m/e=795.

Example 539

4-{(S)-2-[(4-{2-[(S)-2-(Cyclobutylmethyl-carbamoyl)-pyrrolidin-1-yl]-2-oxo-ethoxy}-7-methyl-quinoline-2-carbonyl)-amino]-4-cyclopentylmethoxycarbonyl-butyryl}-piperazine-1-carboxylic acid butyl ester The title compound was prepared by adapting the procedures described in example 246 with the difference that 4-{(S)-4-Carboxy-2-[(4-{2-[(S)-2-(cyclobutylmethyl-carbamoyl)-pyrrolidin-1-yl]-2-oxo-ethoxy}-7-methyl-quinoline-2-carbonyl)-amino]-butyryl}-piperazine-1-carboxylic acid butyl ester was used instead of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester. MS (ES$^+$): m/e=805.

Example 540

4-[(S)-4-(2-Ethoxy-ethoxycarbonyl)-2-({4-[2-((S)-2-methoxymethyl-pyrrolidin-1-yl)-2-oxo-ethoxy]-7-methyl-quinoline-2-carbonyl}-amino)-butyryl]-piperazine-1-carboxylic acid butyl ester The title compound was prepared by adapting the procedures described in example 510 with the difference that 4-[(S)-4-Carboxy-2-({4-[2-((S)-2-methoxymethyl-pyrrolidin-1-yl)-2-oxo-ethoxy]-7-methyl-quinoline-2-carbonyl}-amino)-butyryl]-piperazine-1-carboxylic acid butyl ester was used instead of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid butyl ester. MS (ES$^+$): m/e=728.

Example 541

4-[(S)-4-Cyclopentylmethoxycarbonyl-2-({4-[2-((R)-3-hydroxy-pyrrolidin-1-yl)-2-oxo-ethoxy]-7-methyl-quinoline-2-carbonyl}-amino)-butyryl]-piperazine-1-carboxylic acid butyl ester The title compound was prepared by adapting the procedures described in example 246 with the difference that 4-[(S)-4-Carboxy-2-({4-[2-((R)-3-hydroxy-pyrrolidin-1-yl)-2-oxo-ethoxy]-7-methyl-quinoline-2-carbonyl}-amino)-butyryl]-piperazine-1-carboxylic acid butyl ester was used instead of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester. MS (ES$^+$): m/e=710.

Example 542

4-[(S)-4-(2-Ethoxy-ethoxycarbonyl)-2-({4-[2-((R)-3-hydroxy-pyrrolidin-1-yl)-2-oxo-ethoxy]-7-methyl-quinoline-2-carbonyl}-amino)-butyryl]-piperazine-1-carboxylic acid butyl ester The title compound was prepared by adapting the procedures described in example 510 with the difference that 4-[(S)-4-Carboxy-2-({4-[2-((R)-3-hydroxy-pyrrolidin-1-yl)-2-oxo-ethoxy]-7-methyl-quinoline-2-carbonyl}-amino)-butyryl]-piperazine-1-carboxylic acid butyl ester was used instead of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid butyl ester. MS (ES$^+$): m/e=700.

Example 543

4-[(S)-4-Cyclopentylmethoxycarbonyl-2-({4-[2-(3,3-difluoro-pyrrolidin-1-yl)-2-oxo-ethoxy]-7-methyl-quinoline-2-carbonyl}-amino)-butyryl]-piperazine-1-carboxylic acid butyl ester The title compound was prepared by adapting the procedures described in example 246 with the difference that 4-[(S)-4-Carboxy-2-({4-[2-(3,3-difluoro-pyrrolidin-1-yl)-2-oxo-ethoxy]-7-methyl-quinoline-2-carbonyl}-amino)-butyryl]-piperazine-1-carboxylic acid butyl ester was used instead of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester. MS (ES$^+$): m/e=730.

Example 544

4-[(S)-2-({4-[2-(3,3-Difluoro-pyrrolidin-1-yl)-2-oxo-ethoxy]-7-methyl-quinoline-2-carbonyl}-amino)-4-(2-ethoxy-ethoxycarbonyl)-butyryl]-piperazine-1-carboxylic acid butyl ester The title compound was prepared by adapting the procedures described in example 510 with the difference that 4-[(S)-4-Carboxy-2-({4-[2-(3,3-difluoro-pyrrolidin-1-yl)-2-oxo-ethoxy]-7-methyl-quinoline-2-carbonyl}-amino)-butyryl]-piperazine-1-carboxylic acid butyl ester was used instead of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid butyl ester. MS (ES$^+$): m/e=720.

Example 545

4-[(2S,3S)-2-({4-[2-((S)-2-Cyclobutylcarbamoyl-pyrrolidin-1-yl)-2-oxo-ethoxy]-7-methyl-quinoline-2-carbonyl}-amino)-3-methyl-pentanoyl]-piperazine-1-carboxylic acid butyl ester The title compound was prepared by adapting the procedures described in example 435 with the difference that 4-((2S,3S)-2-Amino-3-methyl-pentanoyl)-piperazine-1-carboxylic acid butyl ester was used instead of 4-(2-Aminoacetyl)-piperazine-1-carboxylic acid butyl ester. MS (ES$^+$): m/e=693.

Example 546

4-[(S)-2-({6-[2-((S)-2-Cyclobutylcarbamoyl-pyrrolidin-1-yl)-2-oxo-ethoxy]-2,3-dihydro-1H-9-aza-cyclopenta[a]naphthalene-8-carbonyl}-amino)-4-cyclopentylmethoxycarbonyl-butyryl]-piperazine-1-carboxylic ethyl ester The title compound was prepared by adapting the procedures described in example 246 with the difference that 4-[(S)-4-Carboxy-2-({6-[2-((S)-2-cyclobutylcarbamoyl-pyrrolidin-1-yl)-2-oxo-ethoxy]-2,3-dihydro-1H-9-aza-cyclopenta[a]naphthalene-8-carbonyl}-amino)-butyryl]-piperazine-1-carboxylic acid ethyl ester was used instead of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester. MS (ES$^+$): m/e=789.

Example 547

4-[(S)-2-({4-[2-((S)-2-Cyclopropylcarbamoyl-pyrrolidin-1-yl)-2-oxo-ethoxy]-7-methyl-quinoline-2-carbonyl}-amino)-4-(2-ethoxy-ethoxycarbonyl)-butyryl]-piperazine-1-carboxylic acid butyl ester The title compound was prepared by adapting the procedures described in example 510 with the difference that 4-[(S)-4-Carboxy-2-({4-[2-((S)-2-cyclopropylcarbamoyl-pyrrolidin-1-yl)-2-oxo-ethoxy]-7-methyl-quinoline-2-carbonyl}-amino)-butyryl]-piperazine-1-carboxylic acid butyl ester was used instead of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid butyl ester. MS (ES$^+$): m/e=767.

Example 548

4-[(S)-4-Cyclopentylmethoxycarbonyl-2-({4-[2-((S)-2-methoxymethyl-pyrrolidin-1-yl)-2-oxo-ethoxy]-7-methyl-quinoline-2-carbonyl}-amino)-butyryl]-piperazine-1-carboxylic acid butyl ester The title compound was prepared by adapting the procedures described in example 246 with the difference that 4-[(S)-4-Carboxy-2-({4-[2-((S)-2-methoxymethyl-pyrrolidin-1-yl)-2-oxo-ethoxy]-7-methyl-quinoline-2-carbonyl}-amino)-butyryl]-piperazine-1-carboxylic acid butyl ester was used instead of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester. MS (ES$^+$): m/e=738.

Example 549

4-[(S)-4-Cyclopentylmethoxycarbonyl-2-({7-methyl-4-[2-oxo-2-((S)-2-phenyl-pyrrolidin-1-yl)-ethoxy]-quinoline-2-carbonyl}-amino)-butyryl]-piperazine-1-carboxylic acid butyl ester The title compound was prepared by adapting the procedures described in example 246 with the difference that 4-[(S)-4-Carboxy-2-({7-methyl-4-[2-oxo-2-((S)-2-phenyl-pyrrolidin-1-yl)-ethoxy]-quinoline-2-carbonyl}-amino)-butyryl]-piperazine-1-carboxylic acid butyl ester was used instead of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester. MS (ES$^+$): m/e=770.

Example 550

4-[(S)-4-(2-Ethoxy-ethoxycarbonyl)-2-({7-methyl-4-[2-oxo-2-((S)-2-phenyl-pyrrolidin-1-yl)-ethoxy]-quinoline-2-carbonyl}-amino)-butyryl]-piperazine-1-carboxylic acid butyl ester The title compound was prepared by adapting the procedures described in example 510 with the difference that 4-[(S)-4-Carboxy-2-({7-methyl-4-[2-oxo-2-((S)-2-phenyl-pyrrolidin-1-yl)-ethoxy]-quinoline-2-carbonyl}-amino)-butyryl]-piperazine-1-carboxylic acid butyl ester was used instead of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid butyl ester. MS (ES$^+$): m/e=760.

Example 551

4-{(S)-2-[(4-{2-[(S)-2-(Cyclobutyl-methyl-carbamoyl)-pyrrolidin-1-yl]-2-oxo-ethoxy}-7-methyl-quinoline-2-carbonyl)-amino]-4-cyclopentylmethoxycarbonyl-butyryl}-piperazine-1-carboxylic acid butyl ester The title compound was prepared by adapting the procedures described in example 246 with the difference that 4-{(S)-4-Carboxy-2-[(4-{2-[(S)-2-(cyclobutyl-methyl-carbamoyl)-pyrrolidin-1-yl]-2-oxo-ethoxy}-7-methyl-quinoline-2-carbonyl)-amino]-butyryl}-piperazine-1-carboxylic acid butyl ester was used instead of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester. MS (ES$^+$): m/e=805.

Example 552

4-[2-({7-Methyl-4-[2-oxo-2-(3-oxo-piperazin-1-yl)-ethoxy]-quinoline-2-carbonyl}-amino)acetyl]-piperazine-1-carboxylic acid butyl ester The title compound was prepared by adapting the procedures described in example 435 with the difference that Piperazin-2-one was used instead of (S)-Pyrrolidine-2-carboxylic acid cyclobutylamide. MS (ES$^+$): m/e=569.

Example 553

4-[2-({4-[2-(4,4-Difluoro-piperidin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that 4,4-Difluoro-piperidine was used instead of (S)-Pyrrolidine-2-carboxylic acid cyclobutylamide. MS (ES$^+$): m/e=590.

Example 554

4-[2-({4-[2-(3,3-Difluoro-pyrrolidin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that 3,3-Difluoro-pyrrolidine was used instead of (S)-Pyrrolidine-2-carboxylic acid cyclobutylamide. MS (ES$^+$): m/e=576.

Example 555

4-[2-({4-[2-(4-Cyclopropylmethyl-piperazin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that 1-Cyclopropylmethyl-piperazine was used instead of (S)-Pyrrolidine-2-carboxylic acid cyclobutylamide. MS (ES$^+$): m/e=609.

Example 556

4-[2-({4-[2-((R)-3-Hydroxy-pyrrolidin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that (R)-Pyrrolidin-3-ol was used instead of (S)-Pyrrolidine-2-carboxylic acid cyclobutylamide. MS (ES$^+$): m/e=556.

Example 557

4-[2-({4-[2-(4-Isobutyl-piperazin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that 1-Isobutyl-piperazine was used instead of (S)-Pyrrolidine-2-carboxylic acid cyclobutylamide. MS (ES$^+$): m/e=611.

Example 558

4-{2-[(7-Methyl-4-{2-[(S)-2-(5-methyl-pyridin-3-yl)-pyrrolidin-1-yl]-2-oxo-ethoxy}-quinoline-2-carbonyl)-amino]-acetyl}-piperazine-1-carboxylic acid butyl ester The title compound was prepared by adapting the procedures described in example 435 with the difference that 3-Methyl-5-(S)-pyrrolidin-2-yl-pyridine was used instead of (S)-Pyrrolidine-2-carboxylic acid cyclobutylamide. MS (ES$^+$): m/e=631.

Example 559

4-{2-[(4-{2-[2-(4-Fluoro-phenyl)-pyrrolidin-1-yl]-2-oxo-ethoxy}-7-methyl-quinoline-2-carbonyl)-amino]-acetyl}-piperazine-1-carboxylic acid butyl ester The title compound was prepared by adapting the procedures described in example 435 with the difference that 2-(4-Fluoro-phenyl)-pyrrolidine was used instead of (S)-Pyrrolidine-2-carboxylic acid cyclobutylamide. MS (ES$^+$): m/e=634.

Example 560

4-[2-({4-[2-(3-Hydroxy-azetidin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that Azetidin-3-ol was used instead of (S)-Pyrrolidine-2-carboxylic acid cyclobutylamide. MS (ES$^+$): m/e=542.

Example 561

4-{2-[(4-{2-[2-(3,4-Difluoro-phenyl)-pyrrolidin-1-yl]-2-oxo-ethoxy}-7-methyl-quinoline-2-carbonyl)-amino]-acetyl}-piperazine-1-carboxylic acid butyl ester The title compound was prepared by adapting the procedures described in example 435 with the difference that 2-(3, 4-Difluoro-phenyl)-pyrrolidine was used instead of (S)-Pyrrolidine-2-carboxylic acid cyclobutylamide. MS (ES+): m/e=652.

Example 562

4-{2-[(4-{2-[2-(2,4-Difluoro-phenyl)-pyrrolidin-1-yl]-2-oxo-ethoxy}-7-methyl-quinoline-2-carbonyl)-amino]-acetyl}-piperazine-1-carboxylic acid butyl ester The title compound was prepared by adapting the procedures described in example 435 with the difference that 2-(2,4-Difluoro-phenyl)-pyrrolidine was used instead of (S)-Pyrrolidine-2-carboxylic acid cyclobutylamide. MS (ES+): m/e=652.

Example 563

4-[2-({4-[2-((S)-2-Ethoxycarbonyl-pyrrolidin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that (S)-Pyrrolidine-2-carboxylic acid ethyl ester was used instead of (S)-Pyrrolidine-2-carboxylic acid cyclobutylamide. MS (ES+): m/e=612.

Example 564

4-[2-({4-[2-(3,3-Difluoro-piperidin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that 3,3-Difluoro-piperidine was used instead of (S)-Pyrrolidine-2-carboxylic acid cyclobutylamide. MS (ES+): m/e=590.

Example 565

4-[2-({4-[2-((S)-2-Cyano-pyrrolidin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that (S)-Pyrrolidine-2-carbonitrile was used instead of (S)-Pyrrolidine-2-carboxylic acid cyclobutylamide. MS (ES+): m/e=565.

Example 566

4-[2-({4-[2-(Hexahydro-pyrrolo[1,2-a]pyrazin-2-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that Octahydro-pyrrolo[1,2-a]pyrazine was used instead of (S)-Pyrrolidine-2-carboxylic acid cyclobutylamide. MS (ES+): m/e=595.

Example 567

4-[2-({7-Methyl-4-[2-oxo-2-(4-oxo-3,5,7,8-tetrahydro-4H-pyrido[4,3-d]pyrimidin-6-yl)-ethoxy]-quinoline-2-carbonyl}-amino)-acetyl]-piperazine-1-carboxylic acid butyl ester The title compound was prepared by adapting the procedures described in example 435 with the difference that 5,6,7,8-Tetrahydro-3H-pyrido[4,3-d]pyrimidin-4-one was used instead of (S)-Pyrrolidine-2-carboxylic acid cyclobutylamide. MS (ES+): m/e=620.

Example 568

4-[2-({7-Methyl-4-[2-(4-methyl-piperazin-1-yl)-2-oxo-ethoxy]-quinoline-2-carbonyl}-amino)-acetyl]-piperazine-1-carboxylic acid butyl ester The title compound was prepared by adapting the procedures described in example 435 with the difference that 1-Methyl-piperazine was used instead of (S)-Pyrrolidine-2-carboxylic acid cyclobutylamide. MS (ES+): m/e=569.

Example 569

4-[2-({4-[2-((R)-2-Hydroxymethyl-pyrrolidin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that (R)-1-Pyrrolidin-2-yl-methanol was used instead of (S)-Pyrrolidine-2-carboxylic acid cyclobutylamide. MS (ES+): m/e=570.

Example 570

4-[2-({7-Methyl-4-[2-(4-methoxycarbonyl-piperazin-1-yl)-2-oxo-ethoxy]-quinoline-2-carbonyl}-amino)-acetyl]-piperazine-1-carboxylic acid butyl ester The title compound was prepared by adapting the procedures described in example 435 with the difference that Piperazine-1-carboxylic acid methyl ester was used instead of (S)-Pyrrolidine-2-carboxylic acid cyclobutylamide. MS (ES+): m/e=613.

Example 571

4-[2-({4-[2-((S)-3-Hydroxy-pyrrolidin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that (S)-Pyrrolidin-3-ol was used instead of (S)-Pyrrolidine-2-carboxylic acid cyclobutylamide. MS (ES+): m/e=556.

Example 572

4-{2-[(4-{2-[4-(2-Methoxy-ethyl)-piperazin-1-yl]-2-oxo-ethoxy}-7-methyl-quinoline-2-carbonyl)-amino]-acetyl}-piperazine-1-carboxylic acid butyl ester The title compound was prepared by adapting the procedures described in example 435 with the difference that 1-(2-

Methoxy-ethyl)-piperazine was used instead of (S)-Pyrrolidine-2-carboxylic acid cyclobutylamide. MS (ES$^+$): m/e=613.

Example 573

4-[2-({4-[2-(4,6-Dihydro-1H-pyrrolo[3,4-c]pyrazol-5-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that 1,4,5,6-Tetrahydro-pyrrolo[3,4-c]pyrazole was used instead of (S)-Pyrrolidine-2-carboxylic acid cyclobutylamide. MS (ES$^+$): m/e=578.

Example 574

4-[2-({7-Methyl-4-[2-oxo-2-(3-oxo-pyrazolidin-1-yl)-ethoxy]-quinoline-2-carbonyl}-amino)-acetyl]-piperazine-1-carboxylic acid butyl ester The title compound was prepared by adapting the procedures described in example 435 with the difference that Pyrazolidin-3-one was used instead of (S)-Pyrrolidine-2-carboxylic acid cyclobutylamide. MS (ES$^+$): m/e=555.

Example 575

4-[2-({7-Methyl-4-[2-(4-methyl-3-oxo-piperazin-1-yl)-2-oxo-ethoxy]-quinoline-2-carbonyl}-amino)-acetyl]-piperazine-1-carboxylic acid butyl ester The title compound was prepared by adapting the procedures described in example 435 with the difference that 1-Methyl-piperazin-2-one was used instead of (S)-Pyrrolidine-2-carboxylic acid cyclobutylamide. MS (ES$^+$): m/e=583.

Example 576

4-[(S)-2-({4-[2-((S)-2-Cyclobutylcarbamoyl-4,4-difluoro-pyrrolidin-1-yl)-2-oxo-ethoxy]-7-methyl-quinoline-2-carbonyl}-amino)-4-(2-ethoxy-ethoxy-carbonyl)-butyryl]-piperazine-1-carboxylic acid butyl ester The title compound was prepared by adapting the procedures described in example 510 with the difference that 4-[(S)-4-Carboxy-2-({4-[2-((S)-2-cyclobutylcarbamoyl-4,4-difluoro-pyrrolidin-1-yl)-2-oxo-ethoxy]-7-methyl-quinoline-2-carbonyl}-amino)-butyryl]-piperazine-1-carboxylic acid butyl ester was used instead of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid butyl ester. MS (ES$^+$): m/e=817.

Example 577

4-{2-[(7-Methyl-4-{2-oxo-2-[(S)-2-(pyrrolidine-1-carbonyl)-pyrrolidin-1-yl]-ethoxy}-quinoline-2-carbonyl)-amino]-acetyl}-piperazine-1-carboxylic acid butyl ester The title compound was prepared by adapting the procedures described in example 435 with the difference that (S)-Pyrrolidin-2-yl-pyrrolidin-1-yl-methanone was used instead of (S)-Pyrrolidine-2-carboxylic acid cyclobutylamide. MS (ES$^+$): m/e=637.

Example 578

4-{2-[(7-Methyl-4-{2-oxo-2-[4-(2,2,2-trifluoro-ethyl)-piperazin-1-yl]-ethoxy}-quinoline-2-carbonyl)-amino]-acetyl}-piperazine-1-carboxylic acid butyl ester The title compound was prepared by adapting the procedures described in example 435 with the difference that 1-(2,2,2-Trifluoro-ethyl)-piperazine was used instead of (S)-Pyrrolidine-2-carboxylic acid cyclobutylamide. MS (ES$^+$): m/e=637.

Example 579

4-[2-({4-[2-((S)-2-Carboxy-pyrrolidin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that (S)-Pyrrolidine-2-carboxylic acid was used instead of (S)-Pyrrolidine-2-carboxylic acid cyclobutylamide. MS (ES$^+$): m/e=584.

Example 580

4-[2-({4-[2-(4-Cyclopropyl-piperazin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that 1-Cyclopropyl-piperazine was used instead of (S)-Pyrrolidine-2-carboxylic acid cyclobutylamide. MS (ES$^+$): m/e=595.

Example 581

4-{2-[(4-{2-[4-(2-Hydroxy-ethyl)-piperazin-1-yl]-2-oxo-ethoxy}-7-methyl-quinoline-2-carbonyl)-amino]-acetyl}-piperazine-1-carboxylic acid butyl ester The title compound was prepared by adapting the procedures described in example 435 with the difference that 2-Piperazin-1-yl-ethanol was used instead of (S)-Pyrrolidine-2-carboxylic acid cyclobutylamide. MS (ES$^+$): m/e=599.

Example 582

4-[2-({7-Methyl-4-[2-oxo-2-((S)-2-phenylcarbamoyl-pyrrolidin-1-yl)-ethoxy]-quinoline-2-carbonyl}-amino)-acetyl]-piperazine-1-carboxylic acid butyl ester The title compound was prepared by adapting the procedures described in example 435 with the difference that (S)-Pyrrolidine-2-carboxylic acid phenylamide was used instead of (S)-Pyrrolidine-2-carboxylic acid cyclobutylamide. MS (ES$^+$): m/e=659.

Example 583

4-[2-({4-[2-((S)-2-Cyclopropylcarbamoyl-pyrrolidin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that (S)-Pyrrolidine-2-carboxylic acid cyclopropylamide was used instead of (S)-Pyrrolidine-2-carboxylic acid cyclobutylamide. MS (ES$^+$): m/e=623.

Example 584

4-[2-({4-[2-(3-Methoxy-pyrrolidin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that 3-Methoxy-pyrrolidine was used instead of (S)-Pyrrolidine-2-carboxylic acid cyclobutylamide. MS (ES$^+$): m/e=570.

Example 585

4-[2-({4-[2-((S)-3-tert-Butoxycarbonylamino-pyrrolidin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that (S)-Pyrrolidin-3-yl-carbamic acid tert-butyl ester was used instead of (S)-Pyrrolidine-2-carboxylic acid cyclobutylamide. MS (ES$^+$): m/e=655.

Example 586

4-[2-({7-Methyl-4-[2-(4-ethoxycarbonyl-piperazin-1-yl)-2-oxo-ethoxy]-quinoline-2-carbonyl}-amino)-acetyl]-piperazine-1-carboxylic acid butyl ester The title compound was prepared by adapting the procedures described in example 435 with the difference that Piperazine-1-carboxylic acid ethyl ester was used instead of (S)-Pyrrolidine-2-carboxylic acid cyclobutylamide. MS (ES$^+$): m/e=627.

Example 587

4-[2-({4-[2-(4-Hydroxy-piperidin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that Piperidin-4-ol was used instead of (S)-Pyrrolidine-2-carboxylic acid cyclobutylamide. MS (ES$^+$): m/e=570.

Example 588

4-[2-({4-[2-(4-Ethyl-piperazin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that 1-Ethyl-piperazine was used instead of (S)-Pyrrolidine-2-carboxylic acid cyclobutylamide. MS (ES$^+$): m/e=583.

Example 589

4-(2-{[7-Methyl-4-(2-oxo-2-piperazin-1-yl-ethoxy)-quinoline-2-carbonyl]-amino}-acetyl)-piperazine-1-carboxylic acid butyl ester The title compound was prepared by adapting the procedures described in example 435 with the difference that Piperazine was used instead of (S)-Pyrrolidine-2-carboxylic acid cyclobutylamide. MS (ES$^+$): m/e=555.

Example 590

4-[2-({7-Methyl-4-[2-oxo-2-((S)-2-propylcarbamoyl-pyrrolidin-1-yl)-ethoxy]-quinoline-2-carbonyl}-amino)acetyl]-piperazine-1-carboxylic acid butyl ester The title compound was prepared by adapting the procedures described in example 435 with the difference that (S)-Pyrrolidine-2-carboxylic acid propylamide was used instead of (S)-Pyrrolidine-2-carboxylic acid cyclobutylamide. MS (ES$^+$): m/e=625.

Example 591

4-{2-[(4-{2-[(S)-2-(Cyclopropylmethyl-carbamoyl)-pyrrolidin-1-yl]-2-oxo-ethoxy}-7-methyl-quinoline-2-carbonyl)-amino]-acetyl}-piperazine-1-carboxylic acid butyl ester The title compound was prepared by adapting the procedures described in example 435 with the difference that (S)-Pyrrolidine-2-carboxylic acid cyclopropylmethyl-amide was used instead of (S)-Pyrrolidine-2-carboxylic acid cyclobutylamide. MS (ES$^+$): m/e=637.

Example 592

4-{2-[(7-Methyl-4-{2-oxo-2-[(S)-2-(piperidine-1-carbonyl)-pyrrolidin-1-yl]-ethoxy}-quinoline-2-carbonyl)-amino]-acetyl}-piperazine-1-carboxylic acid butyl ester The title compound was prepared by adapting the procedures described in example 435 with the difference that Piperidin-1-yl-(S)-pyrrolidin-2-yl-methanone was used instead of (S)-Pyrrolidine-2-carboxylic acid cyclobutylamide. MS (ES$^+$): m/e=651.

Example 593

4-{2-[(4-{2-[(S)-2-(4,4-Difluoro-piperidine-1-carbonyl)-pyrrolidin-1-yl]-2-oxo-ethoxy}-7-methyl-quinoline-2-carbonyl)-amino]-acetyl}-piperazine-1-carboxylic acid butyl ester The title compound was prepared by adapting the procedures described in example 435 with the difference that (4,4-Difluoro-piperidin-1-yl)-(S)-pyrrolidin-2-yl-methanone was used instead of (S)-Pyrrolidine-2-carboxylic acid cyclobutylamide. MS (ES$^+$): m/e=687.

Example 594

4-[2-({4-[2-((S)-2-Cyclopentylcarbamoyl-pyrrolidin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that (S)-Pyrrolidine-2-carboxylic acid cyclopentylamide was used instead of (S)-Pyrrolidine-2-carboxylic acid cyclobutylamide. MS (ES+): m/e=651.

Example 595

4-[2-({4-[2-(2-Furan-2-yl-pyrrolidin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that 2-Furan-2-yl-pyrrolidine was used instead of (S)-Pyrrolidine-2-carboxylic acid cyclobutylamide. MS (ES+): m/e=606.

Example 596

4-[2-({7-Methyl-4-[2-oxo-2-(3-oxo-pyrrolidin-1-yl)-ethoxy]-quinoline-2-carbonyl}-amino)-acetyl]-piperazine-1-carboxylic acid butyl ester The title compound was prepared by adapting the procedures described in example 435 with the difference that Pyrrolidin-3-one was used instead of (S)-Pyrrolidine-2-carboxylic acid cyclobutylamide. MS (ES+): m/e=554.

Example 597

4-[2-({7-Methyl-4-[2-oxo-2-((S)-2-phenyl-pyrrolidin-1-yl)-ethoxy]-quinoline-2-carbonyl}-amino)-acetyl]-piperazine-1-carboxylic acid butyl ester The title compound was prepared by adapting the procedures described in example 435 with the difference that (S)-2-Phenyl-pyrrolidine was used instead of (S)-Pyrrolidine-2-carboxylic acid cyclobutylamide. MS (ES+): m/e=616.

Example 598

4-[2-({4-[2-((S)-2-Methoxymethyl-pyrrolidin-1-yl)-2-oxo-ethoxy]-7-methyl-quinoline-2-carbonyl}-amino)acetyl]-piperazine-1-carboxylic acid butyl ester The title compound was prepared by adapting the procedures described in example 435 with the difference that (S)-2-Methoxymethyl-pyrrolidine was used instead of (S)-Pyrrolidine-2-carboxylic acid cyclobutylamide. MS (ES+): m/e=584.

Example 599

4-{2-[(7-Methyl-4-{2-oxo-2-[(S)-2-(pyridin-2-ylcarbamoyl)-pyrrolidin-1-yl]-ethoxy}-quinoline-2-carbonyl)-amino]-acetyl}-piperazine-1-carboxylic acid butyl ester The title compound was prepared by adapting the procedures described in example 435 with the difference that (S)-Pyrrolidine-2-carboxylic acid pyridin-2-ylamide was used instead of (S)-Pyrrolidine-2-carboxylic acid cyclobutylamide. MS (ES+): m/e=660.

Example 600

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(2H-tetrazol-5-yl)-butyryl]-piperazine-1-carboxylic acid butyl ester

(i) (S)-4-Benzylcarbamoyl-2-tert-butoxycarbonylamino-butyric acid benzyl ester To a solution of 10.00 g (S)-2-tert-butoxycarbonylaminopentanedioic acid 1-benzyl ester in 80 ml DMF were added 5.85 g EDC, 4.67 g HOBt, 10.8 ml DIPEA and 3.2 ml benzylamine at 0° C. After stirring for 12 h the reaction mixture was concentrated, the residue was dissolved in dichloromethane and subsequently extracted with aqueous LiCl (4%), 0.1 M HCl and saturated aqueous NaHCO$_3$. The crude product obtained after evaporation of the solvent was purified by flash chromatography on silica using ethyl acetate/heptane 1:1 as eluent. Yield: 11.2 g colorless amorphous solid.

(ii) (S)-4-(4-Benzyl-2H-tetrazol-5-yl)-2-tert-butoxycarbonylamino-butyric acid benzyl ester To a suspension of 5.92 g (S)-4-benzylcarbamoyl-2-tert-butoxycarbonylamino-butyric acid benzyl ester and 9.10 g triphenylphosphine in 120 ml acetonitrile were added dropwise at 0° C. 7.1 ml diisopropylazodicarboxylate and after 2 minutes 4.8 ml trimethylsilylazide over a period of 20 minutes. After 30 minutes the mixture was allowed to warm to RT and stirred for 12 h. The mixture was cooled to 0° C. and 4.8 ml aqueous sodium nitrite (2.9 M) were added, after 30 minutes a solution of 7.6 g ceric ammonium nitrate in 15 ml water was added and stirred for another 20 minutes. After this time the mixture was poured into ice and extracted twice with dichloromethane.

The crude product thus obtained after evaporation of the solvent was purified by flash chromatography on silica eluting with ethyl acetate/heptane 1:3 to 1:2. Yield: 4.63 g colorless needles.

iii) (S)-2-tert-Butoxycarbonylamino-4-(2H-tetrazol-5-yl)-butyric acid

To a solution of 4.63 g (S)-4-(4-benzyl-2H-tetrazol-5-yl)-2-tert-butoxycarbonylamino-butyric acid benzyl ester in 400 ml ethyl acetate were added 800 mg Pd(OH)$_2$/C (10%) and the suspension stirred under an atmosphere of hydrogen (4 bar) for 12 h. The reaction mixture was filtrated over a plug of Celite® and washed with ethyl acetate. Yield: 2.84 g colorless solid.

(iv) 4-[(S)-2-tert-Butoxycarbonylamino-4-(2H-tetrazol-5-yl)-butyryl]-piperazine-1-carboxylic acid butyl ester To a solution of 500 mg (S)-2-tert-butoxycarbonylamino-4-(2H-tetrazol-5-yl)-butyric acid in 20 ml DMF were added 701 mg HATU, 457 µl DIPEA and 343 mg 1-butoxycarbonyl-piperazine. After 3 h the solution was concentrated, the residue obtained diluted with DCM and subsequently washed with aqueous LiCl (4%) and 0.1 M HCl. The organic layer was dried over $MgSO_4$ and concentrated. Yield: 730 mg.

(v) 4-[(S)-2-Amino-4-(2H-tetrazol-5-yl)-butyryl]-piperazine-1-carboxylic acid butyl ester hydrotrifluoroacetate To a solution of 730 mg 4-[(S)-2-tert-butoxycarbonylamino-4-(2H-tetrazol-5-yl)-butyryl]-piperazine-1-carboxylic acid butyl ester in 10 ml dichloromethane were added 1.2 ml TFA. After 12 h stirring at RT the solvents were removed and the residue was codistilled twice with toluene. Yield: 900 mg.

(vi) 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(2H-tetrazol-5-yl)-butyryl]-piperazine-1-carboxylic acid butyl ester To a solution of 600 mg 4-[2-((S)-2-Cyclobutylcarbamoyl-pyrrolidin-1-yl)-2-oxo-ethoxy]-7-methyl-quinoline-2-carboxylic acid in 60 ml DMF were added 279 µl DIPEA, 294 mg EDC and 234 mg HOBt. After 5 minutes 661 mg 4-[(S)-2-amino-4-(2H-tetrazol-5-yl)-butyryl]-piperazine-1-carboxylic acid butyl ester hydrotrifluoroacetate were added and the mixture stirred for 48 h.

The reaction mixture was concentrated, the residue obtained diluted with DCM and subsequently washed with aqueous LiCl (4%) and 0.1 M HCl. The crude product obtained after evaporation of the solvent was purified by preparative HPLC (C18 reverse phase column, elution with a water/MeCN gradient with 0.1% TFA). The fractions containing the product were lyophilized to yield the pure product as its trifluoroacetate salt. Yield: 491 mg MS(ES+): m/e=733.

Example 601

4-[2-({4-[2-((2S,5S)-2,5-Bis-cyclobutylcarbamoyl-pyrrolidin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that (2S,5S)-Pyrrolidine-2,5-dicarboxylic acid bis-cyclobutylamide was used instead of (S)-Pyrrolidine-2-carboxylic acid cyclobutylamide. MS (ES+): m/e=734.

Example 602

4-{(S)-4-Carboxy-2-[(4-{2-[(S)-2-(2,2-difluoro-cyclopropylcarbamoyl)-pyrrolidin-1-yl]-2-oxo-ethoxy}-7-methyl-quinoline-2-carbonyl)-amino]-butyryl}-piperazine-1-carboxylic acid butyl ester The title compound was prepared by adapting the procedures described in example 303 with the difference that (S)-Pyrrolidine-2-carboxylic acid (2,2-difluoro-cyclopropyl)-amide was used instead of (S)-Pyrrolidine-2-carboxylic acid cyclobutylamide MS (ES+): m/e=731.

Example 603

4-{2-[(4-{2-[(S)-2-(2,2-Difluoro-cyclopropylcarbamoyl)-pyrrolidin-1-yl]-2-oxo-ethoxy}-7-methyl-quinoline-2-carbonyl)-amino]-acetyl}-piperazine-1-carboxylic acid butyl ester The title compound was prepared by adapting the procedures described in example 435 with the difference that (S)-Pyrrolidine-2-carboxylic acid (2,2-difluoro-cyclopropyl)-amide was used instead of (S)-Pyrrolidine-2-carboxylic acid cyclobutylamide. MS (ES+): m/e=659.

Example 604

4-[2-({4-[2-(5,6-Dihydro-8H-[1,2,4]triazolo[4,3-a]pyrazin-7-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that 5,6,7,8-Tetrahydro-[1,2,4]triazolo[4,3-a]pyrazine was used instead of (S)-Pyrrolidine-2-carboxylic acid cyclobutylamide. MS (ES+): m/e=593.

Example 605

4-[2-({7-Methyl-4-[2-oxo-2-(2-o-tolyl-pyrrolidin-1-yl)-ethoxy]-quinoline-2-carbonyl}-amino)-acetyl]-piperazine-1-carboxylic acid butyl ester The title compound was prepared by adapting the procedures described in example 435 with the difference that 2-o-Tolyl-pyrrolidine was used instead of (5)-Pyrrolidine-2-carboxylic acid cyclobutylamide. MS (ES+): m/e=630.

Example 606

4-{2-[(4-{2-[(S)-2-(Ethyl-methyl-carbamoyl)-pyrrolidin-1-yl]-2-oxo-ethoxy}-7-methyl-quinoline-2-carbonyl)-amino]-acetyl}-piperazine-1-carboxylic acid butyl ester The title compound was prepared by adapting the procedures described in example 435 with the difference that (S)-Pyrrolidine-2-carboxylic acid ethyl-methyl-amide was used instead of (S)-Pyrrolidine-2-carboxylic acid cyclobutylamide. MS (ES+): m/e=625.

Example 607

4-[(S)-2-({4-[2-((S)-2-Cyclobutylcarbamoyl-4,4-difluoro-pyrrolidin-1-yl)-2-oxo-ethoxy]-7-methyl-quinoline-2-carbonyl}-amino)-4-cyclopentyl-methoxycarbonyl-butyryl]-piperazine-1-carboxylic acid butyl ester The title compound was prepared by adapting the procedures described in example 246 with the difference that 4-[(S)-4-Carboxy-2-({4-[2-((S)-2-cyclobutylcarbamoyl-4,4-difluoro-pyrrolidin-1-yl)-2-oxo-ethoxy]-7-methyl-quinoline-2-carbonyl}-amino)-butyryl]-piperazine-1-carboxylic acid butyl ester was used instead of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester. MS (ES+): m/e=827.

Example 608

4-[2-({4-[2-((S)-3-Amino-pyrrolidin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that (S)-

Pyrrolidin-3-yl-carbamic acid tert-butyl ester was used instead of (S)-Pyrrolidine-2-carboxylic acid cyclobutylamide followed by cleavage of the Boc protecting group with TFA under standard conditions. MS (ES$^+$): m/e=555.

Example 609

4-[2-({4-[2-((S)-2-Cyclobutylcarbamoyl-pyrrolidin-1-yl)-2-oxo-ethoxy]-7-methyl-quinoline-2-carbonyl}-amino)-acetyl]-piperazine-1-carboxylic acid cyclobutyl ester (i) Piperazine-1,4-dicarboxylic acid benzyl ester cyclobutyl ester To a solution of 2.6 g triphosgene and 1.7 ml cyclobutanol in 40 ml dichloromethane were added 6.2 ml triethylamine dropwise at 0° C. After 30 minutes 4.4 ml benzyl 1-piperazinecarboxylate and 3.2 ml triethylamine were added at 0° C. The reaction mixture was allowed to warm to RT for 16 h. Excess triphosgene was destroyed by adding a solution of 2 g NaOH in 200 ml water and stirring for 2 h. The layers were separated, the organic layer dried over MgSO$_4$ and concentrated. The crude product thus obtained was purified by chromatography on silica using heptane/ethyl acetate 4/1 to 2/1 as eluent. Yield: 5.9 g.

(ii) Piperazine-1-carboxylic acid cyclobutyl ester

A suspension of 5.90 g Piperazine-1,4-dicarboxylic acid benzyl ester cyclobutyl ester and 0.25 g Pd/C (10%) in 50 ml ethyl acetate was stirred under an atmosphere of hydrogen (3 bar) for 12 h. The mixture was filtrated over a plug of Celite, washed with ethyl acetate and the combined wash solutions concentrated to give the title compound as colourless oil. Yield: 3.3 g.

(iii) 4-[2-({4-[2-((S)-2-Cyclobutylcarbamoyl-pyrrolidin-1-yl)-2-oxo-ethoxy]-7-methyl-quinoline-2-carbonyl}-amino)-acetyl]-piperazine-1-carboxylic acid cyclobutyl ester The title compound was prepared by adapting the procedures described in example 435 with the difference that Piperazine-1-carboxylic acid cyclobutyl ester was used instead of Piperazine-1-carboxylic acid butyl ester. MS (ES$^+$): m/e=635.

Example 610

4-[2-({4-[2-((S)-2-Cyclobutylcarbamoyl-pyrrolidin-1-yl)-2-oxo-ethoxy]-7-methyl-quinoline-2-carbonyl}-amino)-acetyl]-piperazine-1-carboxylic acid cyclopropylmethyl ester (i) Piperazine-1,4-dicarboxylic acid tert-butyl ester cyclopropylmethyl ester To a solution of 3.3 g triphosgene and 2 g Cyclopropylmethanol in 40 ml dichloromethane were added 9.1 ml DIPEA dropwise at 0° C. After 1 h, 5.1 g Piperazine-1-carboxylic acid tert-butyl ester and 4.5 ml DIPEA in 7 ml were added at 0° C. The reaction mixture was allowed to warm to RT and stirred for 16 h. Excess triphosgene was destroyed by adding a solution of 2 g NaOH in 120 ml water and stirring for 2 h. The layers were separated and the aqueous layer was extracted with DCM. The combined organic layers were washed with 1M aqueous hydrochloric acid, dried over MgSO$_4$ and concentrated. The crude product thus obtained was purified was used in the next reaction step. Yield: 7.9 g.

(ii) Piperazine-1-carboxylic acid cyclopropylmethyl ester

To a solution of 7.9 g Piperazine-1,4-dicarboxylic acid tert-butyl ester cyclobutyl ester in 20 ml dichloromethane, 10 ml TFA were added. After 16 h stirring at RT the solvents were removed and the residue was codistilled twice with toluene. The product was obtained as its trifluoroacetate salt. Yield: 11.7 g.

(iii) 4-[2-({4-[2-((S)-2-Cyclobutylcarbamoyl-pyrrolidin-1-yl)-2-oxo-ethoxy]-7-methyl-quinoline-2-carbonyl}-amino)-acetyl]-piperazine-1-carboxylic acid cyclopropylmethyl ester The title compound was prepared by adapting the procedures described in example 435 with the difference that Piperazine-1-carboxylic acid cyclopropylmethyl ester was used instead of Piperazine-1-carboxylic acid butyl ester. MS (ES$^+$): m/e=635.

Example 611

4-[(S)-2-({4-[2-((S)-2-Cyclobutylcarbamoyl-pyrrolidin-1-yl)-2-oxo-ethoxy]-7-methoxy-quinoline-2-carbonyl}-amino)-4-cyclopentylmethoxycarbonyl-butyryl]-piperazine-1-carboxylic acid butyl ester The title compound was prepared by adapting the procedures described in example 246 with the difference that 4-[(S)-4-Carboxy-2-({4-[2-((S)-2-cyclobutylcarbamoyl-pyrrolidin-1-yl)-2-oxo-ethoxy]-7-methoxy-quinoline-2-carbonyl}-amino)-butyryl]-piperazine-1-carboxylic acid butyl ester was used instead of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester. MS (ES$^+$): m/e=807.

Example 612

4-[(R)-2-({4-[2-((S)-2-Cyclobutylcarbamoyl-pyrrolidin-1-yl)-2-oxo-ethoxy]-7-methyl-quinoline-2-carbonyl}-amino)-3-fluoro-propionyl]-piperazine-1-carboxylic acid ethyl ester (i) 4-((R)-2-tert-Butoxycarbonylamino-3-fluoro-propionyl)-piperazine-1-carboxylic acid ethyl ester To a solution of 150 mg (R)-2-tert-Butoxycarbonylamino-3-fluoro-propionic acid were added 0.18 ml N-ethylmorpholine, 237 mg TOTU and 115 mg 1-ethoxycarbonylpiperazine. After stirring for 12 h the reaction mixture was diluted with ethyl acetate and washed with aqueous LiCl (4%), 0.1 M HCl, saturated aqueous NaHCO$_3$ and brine. The crude product obtained was used without further purification. Yield: 160 mg.

(ii) 4-((R)-2-Amino-3-fluoro-propionyl)-piperazine-1-carboxylic acid ethyl ester hydrotrifluoroacetate To a solution of 160 mg 4-((R)-2-tert-Butoxycarbonylamino-3-fluoro-propionyl)-piperazine-1-carboxylic acid ethyl ester in 5 ml dichloromethane was added 1.0 ml TFA. After 12 h stirring at RT the solvents were removed and the residue was codistilled twice with toluene. Yield: 216 mg.

(iii) 4-[(R)-2-({4-[2-((S)-2-Cyclobutylcarbamoyl-pyrrolidin-1-yl)-2-oxo-ethoxy]-7-methyl-quinoline-2-carbonyl}-amino)-3-fluoro-propionyl]-piperazine-1-carboxylic acid ethyl ester To a solution of 82 mg 4-[2-((S)-2-Cyclobutylcarbamoyl-pyrrolidin-1-yl)-2-oxo-ethoxy]-7-methyl-quinoline-2-carboxylic acid in 2 ml DMF were added 102 µl DIPEA and 76 mg HATU. After 5 minutes 72 mg 4-((R)-2-Amino-3-fluoro-propionyl)piperazine-1-carboxylic acid ethyl ester hydrotrifluoroacetate were added and the mixture stirred for 3 h before 2 ml of saturated aqueous NaHCO$_3$ were added. The mixture was loaded on a chem Elute® cartridge and the crude product eluted with DCM. Further purification was performed by preparative HPLC (C18 reverse phase column, elution with a water/MeCN gradient with 0.1% TFA). The fractions containing the product were lyophilized to yield the pure product as its trifluoroacetate salt. Yield: 52 mg MS(ES+): m/e=641.

Example 613

4-[(R)-2-({4-[2-((S)-2-Cyclobutylcarbamoyl-pyrrolidin-1-yl)-2-oxo-ethoxy]-7-methyl-quinoline-2-carbonyl}-amino)-3-fluoro-propionyl]-piperazine-1-carboxylic acid butyl ester (i) 4-((R)-2-tert-Butoxycarbonylamino-3-fluoro-propionyl)-piperazine-1-carboxylic acid butyl ester To a solution of 150 mg (R)-2-tert-Butoxycarbonylamino-3-fluoro-propionic acid were added 0.18 ml N-ethylmorpholine, 237 mg TOTU and 115 mg 1-butoxycarbonylpiperazine. After stirring for 12 h the reaction mixture was diluted with ethyl acetate and washed with aqueous LiCl (4%), 0.1 M HCl, saturated aqueous NaHCO$_3$ and brine. The crude product obtained was used without further purification. Yield: 230 mg.

(ii) 4-((R)-2-Amino-3-fluoro-propionyl)piperazine-1-carboxylic acid butyl ester hydrotrifluoroacetate To a solution of 230 mg 4-((R)-2-tert-Butoxycarbonylamino-3-fluoro-propionyl)-piperazine-1-carboxylic acid butyl ester in 5 ml dichloromethane was added 1.0 ml TFA. After 12 h stirring at RT the solvents were removed and the residue was codistilled twice with toluene. Yield: 307 mg.

(iii) 4-[(R)-2-({4-[2-((S)-2-Cyclobutylcarbamoyl-pyrrolidin-1-yl)-2-oxo-ethoxy]-7-methyl-quinoline-2-carbonyl}-amino)-3-fluoro-propionyl]-piperazine-1-carboxylic acid butyl ester To a solution of 108 mg 4-[2-((S)-2-Cyclobutylcarbamoyl-pyrrolidin-1-yl)-2-oxo-ethoxy]-7-methyl-quinoline-2-carboxylic acid in 2.5 ml DMF were added 134 µl DIPEA and 97 mg HATU. After 5 minutes 102 mg 4-((R)-2-Amino-3-fluoro-propionyl)piperazine-1-carboxylic acid butyl ester hydrotrifluoroacetate were added and the mixture stirred for 3 h before 2 ml of saturated aqueous NaHCO$_3$ were added. The mixture was loaded on a chem Elute® cartridge and the crude product eluted with DCM. Further purification was performed by preparative HPLC (C18 reverse phase column, elution with a water/MeCN gradient with 0.1% TFA). The fractions containing the product were lyophilized to yield the pure product. Yield: 76 mg MS(ES+): m/e=669.

Example 614

4-[2-({4-[2-((S)-2-Cyclobutylcarbamoyl-pyrrolidin-1-yl)-2-oxo-ethoxy]-7-methoxy-quinoline-2-carbonyl}-amino)-acetyl]-piperazine-1-carboxylic acid butyl ester The title compound was prepared by adapting the procedures described in example 435 with the difference that 4-Hydroxy-7-methoxy-quinoline-2-carboxylic acid ethyl ester was used instead of 4-Hydroxy-7-methyl-quinoline-2-carboxylic acid ethyl ester. MS (ES+): m/e=653.

Example 615

3-(2-{2-[2-(4-Butoxycarbonyl-piperazin-1-yl)-2-oxo-ethylcarbamoyl]-7-methyl-quinolin-4-yloxyl}-acetyl)-3-aza-bicyclo[3.1.0]hexane-6-carboxylic acid ethyl ester The title compound was prepared by adapting the procedures described in example 435 with the difference that 3-Aza-bicyclo[3.1.0]hexane-6-carboxylic acid ethyl ester was used instead of (S)-Pyrrolidine-2-carboxylic acid cyclobutylamide. MS (ES+): m/e=624.

Example 616

4-[2-({7-Methyl-4-[2-oxo-2-(2-trifluoromethoxymethyl-pyrrolidin-1-yl)-ethoxy]-quinoline-2-carbonyl}-amino)-acetyl]-piperazine-1-carboxylic acid butyl ester The title compound was prepared by adapting the procedures described in example 435 with the difference that 2-Trifluoromethoxymethyl-pyrrolidine was used instead of (S)-Pyrrolidine-2-carboxylic acid cyclobutylamide. MS (ES+): m/e=638.

Example 617

4-[2-({4-[2-(2,4-Dioxo-1,3,8-triaza-spiro[4.5]dec-8-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that 1,3,8-Triaza-spiro[4.5]decane-2,4-dione was used instead of (S)-Pyrrolidine-2-carboxylic acid cyclobutylamide. MS (ES+): m/e=638.

Example 618

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(5-oxo-4,5-dihydro-[1,3,4]oxadiazol-2-yl)-butyryl]-piperazine-1-carboxylic acid ethyl ester (i) 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-hydrazinocarbonyl-butyryl]-piperazine-1-carboxylic acid ethyl ester To a solution of 100 mg of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester, 48 mg of TOTU and 67 mg of NEM in 2 ml of DCM, 10 mg of hydrazine hydrate was added and the reaction mixture was stirred for 16 h at RT. Then, the reaction mixture was diluted with water and extracted with DCM. The combined organic phases were dried over $MgSO_4$ and the solvents were removed under reduced pressure. The crude product was used for the next reaction step. Yield: 101 mg.

(ii) 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(5-oxo-4,5-dihydro-[1,3,4]oxadiazol-2-yl)-butyryl]-piperazine-1-carboxylic acid ethyl ester To a solution of 101 mg of 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-hydrazinocarbonyl-butyryl]-piperazine-1-carboxylic acid ethyl ester in 2 ml THF, 129 mg of triphosgene was added and the mixture was stirred of 16 h at RT. Then, 2 ml of saturated aqueous $NaHCO_3$ were added. The mixture was loaded on a chem Elute® cartridge and the crude product eluted with DCM. Further purification was performed by preparative HPLC (C18 reverse phase column, elution with a water/MeCN gradient with 0.1% TFA). The fractions containing the product were lyophilized to yield the pure product as its trifluoroacetate salt. Yield: 12 mg MS(ES+): m/e=721.

Example 619

4-[2-({4-[2-(3-Hydroxy-4,7-dihydro-5H-isoxazolo[5,4-c]pyridin-6-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that 4,5,6,7-Tetrahydro-isoxazolo[5,4-c]pyridin-3-ol was used instead of (S)-Pyrrolidine-2-carboxylic acid cyclobutylamide. MS (ES+): m/e=609.

Example 620

4-{2-[(4-{2-[2-(1H-Benzoimidazol-2-yl)-pyrrolidin-1-yl]-2-oxo-ethoxy}-7-methyl-quinoline-2-carbonyl)-amino]-acetyl}-piperazine-1-carboxylic acid butyl ester The title compound was prepared by adapting the procedures described in example 435 with the difference that 2-Pyrrolidin-2-yl-1H-benzoimidazole was used instead of (S)-Pyrrolidine-2-carboxylic acid cyclobutylamide. MS (ES+): m/e=656.

Example 621

4-[2-({4-[(R)-2-((S)-2-Cyclobutylcarbamoyl-pyrrolidin-1-yl)-1-methyl-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that 4-[(R)-2-((S)-2-Cyclobutylcarbamoyl-pyrrolidin-1-yl)-1-methyl-2-oxo-ethoxy]-7-methyl-quinoline-2-carboxylic acid was used instead of 4-[2-((S)-2-Cyclobutylcarbamoyl-pyrrolidin-1-yl)-2-oxo-ethoxy]-7-methyl-quinoline-2-carboxylic acid. MS (ES+): m/e=651.

Example 622

4-[(S)-2-({4-[2-((S)-2-Cyclobutylcarbamoyl-pyrrolidin-1-yl)-2-oxo-ethoxy]-7-methyl-quinoline-2-carbonyl}-amino)-4,4-difluoro-butyryl]-piperazine-1-carboxylic acid ethyl ester (i)
(S)-2-Benzyloxycarbonylamino-4,4-difluoro-butyric acid To a solution of 250 mg (S)-2-Benzyloxycarbonylamino-4,4-difluoro-butyric acid methyl ester in 2 ml THF was added a solution of 21 mg LiOH in 0.5 ml water at 0° C. After 2 h the mixture was brought to pH 4 by using Amberlite IR-120 ion exchange resin. The reaction mixture was filtered and concentrated and the crude product obtained used in the next step without further purification. Yield: 229 mg (ii) 4-((S)-2-Benzyloxycarbonylamino-4,4-difluoro-butyryl)-piperazine-1-carboxylic acid ethyl ester To a solution of 114 mg (S)-2-Benzyloxycarbonylamino-4,4-difluoro-butyric acid were added 0.11 ml N-ethylmorpholine, 138 mg TOTU and 66 mg 1-ethoxycarbonylpiperazine. After stirring for 12 h the reaction mixture was diluted with ethyl acetate and washed with aqueous LiCl (4%), 0.1 M HCl, saturated aqueous $NaHCO_3$ and brine. The crude product obtained was used without further purification. Yield: 168 mg (iii) 4-((S)-2-Amino-4,4-difluoro-butyryl)piperazine-1-carboxylic acid ethyl ester To a solution of 168 mg 4-((S)-2-Benzyloxycarbonylamino-4,4-difluoro-butyryl)-piperazine-1-carboxylic acid ethyl ester in 15 ml ethyl acetate were added 100 mg Pd/C (10%) and the suspension stirred under an atmosphere of hydrogen (1 bar) for 1 h. The reaction mixture was filtrated over a plug of Celite®, washed with ethyl acetate and concentrated. Yield: 100 mg colorless oil (iv) 4-[(S)-2-({4-[2-((S)-2-Cyclobutylcarbamoyl-pyrrolidin-1-yl)-2-oxo-ethoxy]-7-methyl-quinoline-2-carbonyl}-amino)-4,4-difluoro-butyryl]-piperazine-1-carboxylic acid ethyl ester To a solution of 147 mg 4-[2-((S)-2-Cyclobutylcarbamoyl-pyrrolidin-1-yl)-2-oxo-ethoxy]-7-methyl-quinoline-2-carboxylic acid in 3 ml DMF were added 122 µl DIPEA and 136 mg HATU. After 5 minutes 100 mg 4-((S)-2-Amino-4,4-difluoro-butyryl)piperazine-1-carboxylic acid ethyl ester were added and the mixture stirred for 12 h before 2 ml of saturated aqueous $NaHCO_3$ were added. The mixture was loaded on a chem Elute® cartridge and the crude product eluted with DCM. Further purification was performed by preparative HPLC (C18 reverse phase column, elution with a water/MeCN gradient with 0.1% TFA). The fractions containing the product were lyophilized to yield the pure product as its trifluoroacetate salt. Yield: 115 mg MS(ES+): m/e=673.

Example 623

4-[(S)-2-({4-[2-((S)-2-Cyclobutylcarbamoyl-pyrrolidin-1-yl)-2-oxo-ethoxy]-7-methyl-quinoline-2-carbonyl}-amino)-4,4-difluoro-butyryl]-piperazine-1-carboxylic acid butyl ester (i) 4-((S)-2-Benzyloxycarbonylamino-4,4-difluoro-butyryl)-piperazine-1-carboxylic acid butyl ester To a solution of 114 mg (S)-2-Benzyloxycarbonylamino-4,4-difluoro-butyric acid were added 0.11 ml N-ethylmorpholine, 138 mg TOTU and 78 mg 1-butoxycarbonylpiperazine. After stirring for 12 h the reaction mixture was diluted with ethyl acetate and washed with aqueous LiCl (4%), 0.1 M HCl, saturated aqueous $NaHCO_3$ and brine. The crude product obtained was used without further purification. Yield: 150 mg (ii) 4-((S)-2-Amino-4,4-difluoro-butyryl)piperazine-1-carboxylic acid butyl ester To a solution of 168 mg 4-((S)-2-Benzyloxycarbonylamino-4,4-difluoro-butyryl)-piperazine-1-carboxylic acid butyl ester in 15 ml ethyl acetate were added 100 mg Pd/C (10%) and the suspension stirred under an atmosphere of hydrogen (1 bar) for 1 h. The reaction mixture was filtrated over a plug of Celite®, washed with ethyl acetate and concentrated. Yield: 97 mg colorless oil (iii) 4-[(S)-2-({4-[2-((S)-2-Cyclobutylcarbamoyl-pyrrolidin-1-yl)-2-oxo-ethoxy]-7-methyl-quinoline-2-carbonyl}-amino)-4,4-difluoro-butyryl]-piperazine-1-carboxylic acid butyl ester To a solution of 130 mg 4-[2-((S)-2-Cyclobutylcarbamoyl-pyrrolidin-1-yl)-2-oxo-ethoxy]-7-methyl-quinoline-2-carboxylic acid in 3 ml DMF were added 108 µl DIPEA and 120 mg HATU. After 5 minutes 97 mg 4-((S)-2-Amino-4,4-difluoro-butyryl)piperazine-1-carboxylic acid butyl ester were added and the mixture stirred for 12 h before 2 ml of saturated aqueous $NaHCO_3$ were added. The mixture was loaded on a chem Elute® cartridge and the crude product eluted with DCM. Further purification was performed by preparative HPLC (C18 reverse phase column, elution with a water/MeCN gradient with 0.1% TFA). The fractions containing the product were lyophilized to yield the pure product as its trifluoroacetate salt. Yield: 45 mg MS(ES+): m/e=701.

Example 624

4-{2-[(7-Methyl-4-{2-[(S)-2-(morpholine-4-carbonyl)-pyrrolidin-1-yl]-2-oxo-ethoxy}-quinoline-2-carbonyl)-amino]-acetyl}-piperazine-1-carboxylic acid butyl ester The title compound was prepared by adapting the procedures described in example 435 with the difference that Morpholin-4-yl-(S)-pyrrolidin-2-yl-methanone was used instead of (S)-Pyrrolidine-2-carboxylic acid cyclobutylamide. MS (ES$^+$): m/e=653.

Example 625

4-[2-({4-[2-((S)-2-Cyclobutylcarbamoyl-pyrrolidin-1-yl)-2-oxo-ethoxy]-7-methyl-quinoline-2-carbonyl}-methyl-amino)-acetyl]-piperazine-1-carboxylic acid butyl ester (i) 4-[2-(Benzyloxycarbonyl-methyl-amino)-acetyl]-piperazine-1-carboxylic acid butyl ester To a solution of 500 mg Z-Sar-OH in 15 ml DMF were added 1.1 ml N-ethylmorpholine, 735 mg TOTU and 417 mg 1-butoxycarbonylpiperazine. After stirring for 12 h, aqueous $NaHCO_3$ was added and the reaction mixture was diluted with ethyl acetate and washed with aqueous LiCl (4%) and 0.1 M HCl. The crude product obtained after evaporation of the solvent was used without further purification. Yield: 746 mg.

(ii) 4-(2-Methylamino-acetyl)piperazine-1-carboxylic acid butyl ester

To a solution of 746 mg 4-[2-(Benzyloxycarbonyl-methyl-amino)-acetyl]-piperazine-1-carboxylic acid butyl ester in 10 ml ethanol were added 100 mg Pd/C (10%) and the suspension stirred under an atmosphere of hydrogen (3 bar) for 12 h. The reaction mixture was filtrated over a plug of Celite®, washed with ethanol and concentrated. Yield: 570 mg colorless oil (iii) 4-[2-({4-[2-((S)-2-Cyclobutylcarbamoyl-pyrrolidin-1-yl)-2-oxo-ethoxy]-7-methyl-quinoline-2-carbonyl}-methyl-amino)-acetyl]-piperazine-1-carboxylic acid butyl ester To a solution of 65 mg 4-[2-((S)-2-Cyclobutylcarbamoyl-pyrrolidin-1-yl)-2-oxo-ethoxy]-7-methyl-quinoline-2-carboxylic acid in 5 ml DMF were added 108 µl DIPEA and 60 mg HATU. After 5 minutes 41 mg 4-(2-Methylamino-acetyl)piperazine-1-carboxylic acid butyl ester were added and the mixture stirred for 48 h. The mixture was concentrated and the crude product thus obtained purified by preparative HPLC (C18 reverse phase column, elution with a water/MeCN gradient with 0.1% TFA). The fractions containing the product were lyophilized to yield the pure product as its trifluoroacetate salt. Yield: 35 mg MS(ES+): m/e=651.

Example 626

4-[2-({7-Methyl-4-[2-oxo-2-(6-oxo-hexahydro-pyrrolo[1,2-a]pyrazin-2-yl)-ethoxy]-quinoline-2-carbonyl}-amino)-acetyl]-piperazine-1-carboxylic acid butyl ester The title compound was prepared by adapting the procedures described in example 435 with the difference that Hexahydro-pyrrolo[1,2-a]pyrazin-6-one was used instead of (S)-Pyrrolidine-2-carboxylic acid cyclobutylamide. MS (ES$^+$): m/e=609.

Example 627

4-[2-({4-[2-(2,4-Dioxo-1,3,7-triaza-spiro[4.5]dec-7-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that 1,3,

Example 628

4-[2-({7-Methyl-4-[2-oxo-2-(3-trifluoromethyl-4,6-dihydro-1H-pyrrolo[3,4-c]pyrazol-5-yl)-ethoxy]-quinoline-2-carbonyl}-amino)-acetyl]-piperazine-1-carboxylic acid butyl ester The title compound was prepared by adapting the procedures described in example 435 with the difference that 3-Trifluoromethyl-1,4,5,6-tetrahydro-pyrrolo[3,4-c]pyrazole was used instead of (S)-Pyrrolidine-2-carboxylic acid cyclobutylamide. MS (ES$^+$): m/e=646.

Example 629

4-[2-({4-[2-((R)-3-Dimethylamino-pyrrolidin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that Dimethyl-(R)-pyrrolidin-3-yl-amine was used instead of (S)-Pyrrolidine-2-carboxylic acid cyclobutylamide. MS (ES$^+$): m/e=583.

Example 630

4-[2-({7-Methyl-4-[2-oxo-2-((S)-2-trifluoromethyl-pyrrolidin-1-yl)-ethoxy]-quinoline-2-carbonyl}-amino)-acetyl]-piperazine-1-carboxylic acid butyl ester The title compound was prepared by adapting the procedures described in example 435 with the difference that (S)-2-Trifluoromethyl-pyrrolidine was used instead of (S)-Pyrrolidine-2-carboxylic acid cyclobutylamide. MS (ES$^+$): m/e=608.

Example 631

4-[2-({4-[2-((R)-3-Acetylamino-pyrrolidin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that (R)—N-Pyrrolidin-3-yl-acetamide was used instead of (S)-Pyrrolidine-2-carboxylic acid cyclobutylamide. MS (ES$^+$): m/e=597.

Example 632

4-[2-({7-Methyl-4-[2-oxo-2-(2-trifluoromethyl-pyrrolidin-1-yl)-ethoxy]-quinoline-2-carbonyl}-amino)-acetyl]-piperazine-1-carboxylic acid butyl ester The title compound was prepared by adapting the procedures described in example 435 with the difference that 2-Trifluoromethyl-pyrrolidine was used instead of (S)-Pyrrolidine-2-carboxylic acid cyclobutylamide. MS (ES$^+$): m/e=608.

Example 633

4-[2-({4-[2-((S)-3-Dimethylamino-pyrrolidin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that Dimethyl-(S)-pyrrolidin-3-yl-amine was used instead of (S)-Pyrrolidine-2-carboxylic acid cyclobutylamide. MS (ES$^+$): m/e=583.

Example 634

4-(2-{[4-((R)-2-Hexahydro-pyrrolo[1,2-a]pyrazin-2-yl-2-oxo-ethoxy)-7-methyl-quinoline-2-carbonyl]-amino}-acetyl)-piperazine-1-carboxylic acid butyl ester The title compound was prepared by adapting the procedures described in example 435 with the difference that (R)-Octahydro-pyrrolo[1,2-a]pyrazine was used instead of (S)-Pyrrolidine-2-carboxylic acid cyclobutylamide. MS (ES$^+$): m/e=595.

Example 635

4-{2-[(4-{2-[2-(1H-Indol-2-yl)-pyrrolidin-1-yl]-2-oxo-ethoxy}-7-methyl-quinoline-2-carbonyl)-amino]-acetyl}-piperazine-1-carboxylic acid butyl ester The title compound was prepared by adapting the procedures described in example 435 with the difference that 2-Pyrrolidin-2-yl-1H-indole was used instead of (S)-Pyrrolidine-2-carboxylic acid cyclobutylamide. MS (ES$^+$): m/e=655.

Example 636

4-{2-[(7-Methyl-4-{2-[2-(3-methyl-[1,2,4]oxadiazol-5-yl)-pyrrolidin-1-yl]-2-oxo-ethoxy}-quinoline-2-carbonyl)-amino]-acetyl}-piperazine-1-carboxylic acid butyl ester The title compound was prepared by adapting the procedures described in example 435 with the difference that 3-Methyl-5-pyrrolidin-2-yl-[1,2,4]oxadiazole was used instead of (S)-Pyrrolidine-2-carboxylic acid cyclobutylamide. MS (ES$^+$): m/e=622.

Example 637

4-[2-({4-[2-((2S,4S)-2-Cyano-4-fluoro-pyrrolidin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that (2S, 4S)-4-Fluoro-pyrrolidine-2-carbonitrile was used instead of (S)-Pyrrolidine-2-carboxylic acid cyclobutylamide. MS (ES$^+$): m/e=583.

Example 638

(2S,3aR,7aR)-1-(2-{2-[2-(4-Butoxycarbonyl-piperazin-1-yl)-2-oxo-ethylcarbamoyl]-7-methyl-quinolin-4-yloxy}-acetyl)-octahydro-indole-2-carboxylic acid The title compound was prepared by adapting the procedures described in example 435 with the difference that (2S,3aR,7aR)-Octahydro-indole-2-carboxylic acid was used instead of (S)-Pyrrolidine-2-carboxylic acid cyclobutylamide. MS (ES$^+$): m/e=638.

Example 639

4-[2-({7-Methyl-4-[2-oxo-2-(3-trifluoromethyl-pyrrolidin-1-yl)-ethoxy]-quinoline-2-carbonyl}-amino)-acetyl]-piperazine-1-carboxylic acid butyl ester The title compound was prepared by adapting the procedures described in example 435 with the difference that 3-Trifluoromethyl-pyrrolidine was used instead of (5)-Pyrrolidine-2-carboxylic acid cyclobutylamide. MS (ES$^+$): m/e=608.

Example 640

4-[2-({7-Methyl-4-[2-oxo-2-((R)-2-trifluoromethyl-pyrrolidin-1-yl)-ethoxy]-quinoline-2-carbonyl}-amino)acetyl]-piperazine-1-carboxylic acid butyl ester The title compound was prepared by adapting the procedures described in example 435 with the difference that (R)-2-Trifluoromethyl-pyrrolidine was used instead of (S)-Pyrrolidine-2-carboxylic acid cyclobutylamide. MS (ES$^+$): m/e=608.

Example 641

4-[2-({4-[2-((2S,5R)-2-Carboxy-5-phenyl-pyrrolidin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that (2S,5R)-5-Phenyl-pyrrolidine-2-carboxylic acid was used instead of (S)-Pyrrolidine-2-carboxylic acid cyclobutylamide. MS (ES$^+$): m/e=660.

Example 642

4-[2-({7-Methyl-4-[2-(2-methyl-6,7-dihydro-4H-oxazolo[5,4-c]pyridin-5-yl)-2-oxo-ethoxy]-quinoline-2-carbonyl}-amino)-acetyl]-piperazine-1-carboxylic acid butyl ester The title compound was prepared by adapting the procedures described in example 435 with the difference that 2-Methyl-4,5,6,7-tetrahydro-oxazolo[5,4-c]pyridine was used instead of (S)-Pyrrolidine-2-carboxylic acid cyclobutylamide. MS (ES$^+$): m/e=607.

Example 643

4-[2-({4-[2-(3-Methanesulfonyl-pyrrolidin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that 3-Methanesulfonyl-pyrrolidine was used instead of (S)-Pyrrolidine-2-carboxylic acid cyclobutylamide. MS (ES$^+$): m/e=618.

Example 644

4-[2-({4-[2-(3-Ethoxy-piperidin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that 3-Ethoxy-piperidine was used instead of (S)-Pyrrolidine-2-carboxylic acid cyclobutylamide. MS (ES$^+$): m/e=598.

Example 645

4-[2-({7-Methyl-4-[2-oxo-2-(1-oxo-2,8-diaza-spiro[4.5]dec-8-yl)-ethoxy]-quinoline-2-carbonyl}-amino)-acetyl]-piperazine-1-carboxylic acid butyl ester The title compound was prepared by adapting the procedures described in example 435 with the difference that 2,8-Diaza-spiro[4.5]decan-1-one was used instead of (S)-Pyrrolidine-2-carboxylic acid cyclobutylamide. MS (ES$^+$): m/e=623.

Example 646

4-[(S)-2-({4-[(R)-2-((S)-2-Cyclobutylcarbamoyl-pyrrolidin-1-yl)-1-methyl-2-oxo-ethoxy]-7-methyl-quinoline-2-carbonyl}-amino)-4-hydroxy-butyryl]-piperazine-1-carboxylic acid ethyl ester The title compound was prepared by adapting the procedures described in example 534 with the difference that Piperazine-1-carboxylic acid ethyl ester was used instead of Piperazine-1-carboxylic acid butyl ester. MS (ES$^+$): m/e=667.

Example 647

4-[2-({7-Methyl-4-[2-(1-methyl-4,6-dihydro-1H-pyrrolo[3,4-c]pyrazol-5-yl)-2-oxo-ethoxy]-quinoline-2-carbonyl}-amino)-acetyl]-piperazine-1-carboxylic acid butyl ester The title compound was prepared by adapting the procedures described in example 435 with the difference that 1-Methyl-1,4,5,6-tetrahydro-pyrrolo[3,4-c]pyrazole was used instead of (S)-Pyrrolidine-2-carboxylic acid cyclobutylamide. MS (ES$^+$): m/e=592.

Example 648

4-[2-({4-[2-((1R,4R)-5-Ethyl-2,5-diaza-bicyclo[2.2.1]hept-2-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that (1R, 4R)-2-Ethyl-2,5-diaza-bicyclo[2.2.1]heptane was used instead of (S)-Pyrrolidine-2-carboxylic acid cyclobutylamide. MS (ES$^+$): m/e=595.

Example 649

4-[2-({4-[2-((R)-3-tert-Butoxycarbonylamino-pyrrolidin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that (R)-Pyrrolidin-3-yl-carbamic acid tert-butyl ester was used instead of (S)-Pyrrolidine-2-carboxylic acid cyclobutylamide. MS (ES$^+$): m/e=655.

Example 650

4-[2-({4-[2-(4-Cyanomethyl-piperazin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that Piperazin-1-yl-acetonitrile was used instead of (S)-Pyrrolidine-2-carboxylic acid cyclobutylamide. MS (ES$^+$): m/e=594.

Example 651

4-{2-[(4-{2-[3-(Acetyl-methyl-amino)-pyrrolidin-1-yl]-2-oxo-ethoxy}-7-methyl-quinoline-2-carbonyl)-amino]-acetyl}-piperazine-1-carboxylic acid butyl ester The title compound was prepared by adapting the procedures described in example 435 with the difference that N-Methyl-N-pyrrolidin-3-yl-acetamide was used instead of (S)-Pyrrolidine-2-carboxylic acid cyclobutylamide. MS (ES$^+$): m/e=611.

Example 652

4-{2-[(7-Methyl-4-{2-[2-(6-methyl-pyridin-2-yl)-pyrrolidin-1-yl]-2-oxo-ethoxy}-quinoline-2-carbonyl)-amino]-acetyl}-piperazine-1-carboxylic acid butyl ester The title compound was prepared by adapting the procedures described in example 435 with the difference that 2-Methyl-6-pyrrolidin-2-yl-pyridine was used instead of (S)-Pyrrolidine-2-carboxylic acid cyclobutylamide. MS (ES$^+$): m/e=631.

Example 653

4-{2-[(7-Methyl-4-{2-oxo-2-[4-(pyrrolidine-1-carbonyl)-piperazin-1-yl]-ethoxy}-quinoline-2-carbonyl)-amino]-acetyl}-piperazine-1-carboxylic acid butyl ester The title compound was prepared by adapting the procedures described in example 435 with the difference that Piperazin-1-yl-pyrrolidin-1-yl-methanone was used instead of (S)-Pyrrolidine-2-carboxylic acid cyclobutylamide. MS (ES$^+$): m/e=652.

Example 654

4-[2-({4-[2-(3-Methoxy-piperidin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that 3-Methoxy-piperidine was used instead of (S)-Pyrrolidine-2-carboxylic acid cyclobutylamide. MS (ES$^+$): m/e=584.

Example 655

4-[2-({4-[2-(4-Methoxy-piperidin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that 4-Methoxy-piperidine was used instead of (S)-Pyrrolidine-2-carboxylic acid cyclobutylamide. MS (ES$^+$): m/e=584.

Example 656

4-[2-({4-[2-(4-Acetylamino-piperidin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that N-Piperidin-4-yl-acetamide was used instead of (S)-Pyrrolidine-2-carboxylic acid cyclobutylamide. MS (ES$^+$): m/e=611.

Example 657

4-[2-({4-[2-((S)-3-Acetylamino-pyrrolidin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that (S)—N-Pyrrolidin-3-yl-acetamide was used instead of (S)-Pyrrolidine-2-carboxylic acid cyclobutylamide. MS (ES$^+$): m/e=597.

Example 658

4-[2-({7-Methyl-4-[2-(1-methyl-3-trifluoromethyl-1,4,6,7-tetrahydro-pyrazolo[4,3-c]pyridin-5-yl)-2-oxo-ethoxy]-quinoline-2-carbonyl}-amino)-acetyl]-piperazine-1-carboxylic acid butyl ester The title compound was prepared by adapting the procedures described in example 435 with the difference that 1-Methyl-3-trifluoromethyl-4,5,6,7-tetrahydro-1H-pyrazolo[4,3-c]pyridine was used instead of (S)-Pyrrolidine-2-carboxylic acid cyclobutylamide. MS (ES+): m/e=674.

Example 659

4-[2-({4-[2-((S)-2-Cyclobutylcarbamoyl-pyrrolidin-1-yl)-2-oxo-ethoxy]-6,7-dimethyl-quinoline-2-carbonyl}-amino)-acetyl]-piperazine-1-carboxylic acid butyl ester (i) 4-{2-[(4-Hydroxy-6,7-dimethyl-quinoline-2-carbonyl)-amino]-acetyl}-piperazine-1-carboxylic acid butyl ester To a solution of 100 mg of 4-Hydroxy-6,7-dimethyl-quinoline-2-carboxylic acid and 164 mg of 4-(2-Amino-acetyl)-piperazine-1-carboxylic acid butyl ester in 1 ml of DMF, 70 mg of HOBT and 88 mg of EDC was added and the reaction mixture was stirred for 4 h at RT. Then, the reaction mixture was diluted with water and filtered through a chem Elut® cartridge by eluting with ethyl acetate. The solvents were removed under reduced pressure and the isolated crude product was pure enough for the next reaction step. Yield: 250 mg.

(ii) 4-{2-[(4-Benzyloxycarbonylmethoxy-6,7-dimethyl-quinoline-2-carbonyl)-amino]-acetyl}-piperazine-1-carboxylic acid butyl ester To a solution of 250 mg 4-{2-[(4-Hydroxy-6,7-dimethyl-quinoline-2-carbonyl)-amino]-acetyl}-piperazine-1-carboxylic acid butyl ester in 1.5 ml of DMF, 202 mg of cesium carbonate and 142 mg of Bromo-acetic acid benzyl ester were added and the reaction mixture was stirred for 12 h at RT. Then, the reaction mixture was diluted with water and extracted with ethyl acetate. The organic phase was dried over MgSO$_4$ and the solvents were removed under reduced pressure. The isolated crude product was pure enough for the next reaction step. Yield: 290 mg.

(iii) 4-{2-[(4-Carboxymethoxy-6,7-dimethyl-quinoline-2-carbonyl)-amino]-acetyl}-piperazine-1-carboxylic acid butyl ester To a solution of 290 mg 4-{2-[(4-Benzyloxycarbonyl-methoxy-6,7-dimethyl-quinoline-2-carbonyl)-amino]-acetyl}-piperazine-1-carboxylic acid butyl ester in 10 ml ethanol were added under argon 50 mg Pd/C (10%) and the suspension was stirred under an atmosphere of hydrogen (5 bar) for 16 h. The suspension was filtered over a plug of Celite® and washed with ethanol and DMF. The crude product was obtained after evaporation of the solvent. Yield: 270 mg.

(iv) 4-[2-({4-[2-((S)-2-Cyclobutylcarbamoyl-pyrrolidin-1-yl)-2-oxo-ethoxy]-6,7-dimethyl-quinoline-2-carbonyl}-amino)-acetyl]-piperazine-1-carboxylic acid butyl ester To a solution of 270 mg of 4-{2-[(4-Carboxymethoxy-6,7-dimethyl-quinoline-2-carbonyl)-amino]-acetyl}-piperazine-1-carboxylic acid butyl ester in 5 ml of DCM, 124 mg of EDC, 119 mg of pentafluorophenol was added and the reaction mixture was stirred for 2 h. Then, 221 mg of (S)-Pyrrolidine-2-carboxylic acid cyclobutylamide hydrochloride and 248 mg of NEM in 1 ml of DCM was added. After 16 h the reaction mixture was diluted with water. After filtration through a chem Elut® cartridge by eluting with DCM the solvents were removed under reduced pressure. The residue was purified by preparative HPLC (C18 reverse phase column, elution with a water/MeCN gradient with 0.1% TFA). The fractions containing the product were lyophilized to yield the pure product as its trifluoroacetate salt. Yield: 7.7 mg MS(ES+): m/e=651.

Example 660

4-{2-[(7-Methyl-4-{2-oxo-2-[4-(pyrrolidine-1-carbonyl)-piperidin-1-yl]-ethoxy}-quinoline-2-carbonyl)-amino]-acetyl}-piperazine-1-carboxylic acid butyl ester The title compound was prepared by adapting the procedures described in example 435 with the difference that 2-Methyl-octahydro-pyrrolo[3,4-c]pyridine was used instead of (S)-Pyrrolidine-2-carboxylic acid cyclobutylamide. MS (ES+): m/e=609.

Example 661

4-{2-[(7-Methyl-4-{2-oxo-2-[4-(pyrrolidine-1-carbonyl)-piperidin-1-yl]-ethoxy}-quinoline-2-carbonyl)-amino]-acetyl}-piperazine-1-carboxylic acid butyl ester The title compound was prepared by adapting the procedures described in example 435 with the difference that Piperidin-4-yl-pyrrolidin-1-yl-methanone was used instead of (S)-Pyrrolidine-2-carboxylic acid cyclobutylamide. MS (ES+): m/e=651.

Example 662

4-[2-({4-[2-((2S,4R)-2-Ethoxycarbonyl-4-hydroxy-pyrrolidin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that (2S,4R)-4-Hydroxy-pyrrolidine-2-carboxylic acid ethyl ester was used instead of (S)-Pyrrolidine-2-carboxylic acid cyclobutylamide. MS (ES+): m/e=628.

Example 663

4-{2-[(7-Methyl-4-{2-[(S)-2-(4-methyl-piperidine-1-carbonyl)-pyrrolidin-1-yl]-2-oxo-ethoxy}-quinoline-2-carbonyl)-amino]-acetyl}-piperazine-1-carboxylic acid butyl ester The title compound was prepared by adapting the procedures described in example 435 with the difference that (4-Methyl-piperidin-1-yl)-(S)-pyrrolidin-2-yl-methanone was used instead of (S)-Pyrrolidine-2-carboxylic acid cyclobutylamide. MS (ES+): m/e=665.

Example 664

4-[2-({4-[2-((S)-2-Cyclobutylcarbamoyl-pyrrolidin-1-yl)-2-oxo-ethoxy]-7-methyl-quinoline-2-carbonyl}-methyl-amino)-acetyl]-piperazine-1-carboxylic acid ethyl ester (i) 4-[2-(Benzyloxycarbonyl-methyl-amino)-acetyl]-piperazine-1-carboxylic acid ethyl ester To a solution of 500 mg Z-Sar-OH in 15 ml DMF were added 1.1 ml N-ethylmorpholine, 735 mg TOTU and 354 mg 1-ethoxycarbonylpiperazine. After stirring for 12 h, aqueous NaHCO₃ was added and the reaction mixture was diluted with ethyl acetate and washed with aqueous LiCl (4%) and 0.1 M HCl. The crude product obtained after evaporation of the solvent was used without further purification. Yield: 830 mg.

(ii)
4-(2-Methylamino-acetyl)-piperazine-1-carboxylic acid ethyl ester

To a solution of 830 mg 4-[2-(Benzyloxycarbonyl-methyl-amino)-acetyl]-piperazine-1-carboxylic acid ethyl ester in 30 ml ethanol were added 100 mg Pd/C (10%) and the suspension stirred under an atmosphere of hydrogen (3 bar) for 12 h. The reaction mixture was filtrated over a plug of Celite®, washed with ethanol and concentrated. Yield: 490 mg colorless oil.

(iii) 4-[2-({4-[2-((S)-2-Cyclobutylcarbamoyl-pyrrolidin-1-yl)-2-oxo-ethoxy]-7-methyl-quinoline-2-carbonyl}-methyl-amino)-acetyl]-piperazine-1-carboxylic acid ethyl ester To a solution of 65 mg 4-[2-((S)-2-Cyclobutylcarbamoyl-pyrrolidin-1-yl)-2-oxo-ethoxy]-7-methyl-quinoline-2-carboxylic acid in 5 ml DMF were added 67 µl DIPEA and 60 mg HATU. After 5 minutes 36 mg 4-(2-Methylamino-acetyl) piperazine-1-carboxylic acid ethyl ester were added and the mixture stirred for 48 h. The mixture was concentrated and the crude product thus obtained purified by preparative HPLC (C18 reverse phase column, elution with a water/MeCN gradient with 0.1% TFA). The fractions containing the product were lyophilized to yield the pure product as its trifluoroacetate salt. Yield: 50 mg MS(ES+): m/e=623.

Example 665

4-{2-[(4-{2-[(S)-2-(3,4-Dihydro-2H-quinoline-1-carbonyl)-pyrrolidin-1-yl]-2-oxo-ethoxy}-7-methyl-quinoline-2-carbonyl)-amino]-acetyl}-piperazine-1-carboxylic acid butyl ester The title compound was prepared by adapting the procedures described in example 435 with the difference that (3,4-Dihydro-2H-quinolin-1-yl)-(S)-pyrrolidin-2-yl-methanone was used instead of (S)-Pyrrolidine-2-carboxylic acid cyclobutylamide. MS (ES⁺): m/e=699.

Example 666

4-{2-[(4-{2-[(S)-2-(2,3-Dihydro-indole-1-carbonyl)-pyrrolidin-1-yl]-2-oxo-ethoxy}-7-methyl-quinoline-2-carbonyl)-amino]-acetyl}-piperazine-1-carboxylic acid butyl ester The title compound was prepared by adapting the procedures described in example 435 with the difference that (2,3-Dihydro-indol-1-yl)-(S)-pyrrolidin-2-yl-methanone was used instead of (S)-Pyrrolidine-2-carboxylic acid cyclobutylamide. MS (ES⁺): m/e=685.

Example 667

4-[2-({4-[2-((S)-4-Cyclobutylcarbamoyl-oxazolidin-3-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that (S)-Oxazolidine-4-carboxylic acid cyclobutylamide was used instead of (S)-Pyrrolidine-2-carboxylic acid cyclobutylamide. MS (ES⁺): m/e=639.

Example 668

4-[2-({4-[2-(3-Dimethylamino-pyrrolidin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that Dimethyl-pyrrolidin-3-yl-amine was used instead of (S)-Pyrrolidine-2-carboxylic acid cyclobutylamide. MS (ES⁺): m/e=583.

Example 669

4-{2-[(7-Methyl-4-{2-oxo-2-[(S)-2-(1H-tetrazol-5-ylmethyl)-pyrrolidin-1-yl]-ethoxy}-quinoline-2-carbonyl)-amino]-acetyl}-piperazine-1-carboxylic acid butyl ester The title compound was prepared by adapting the procedures described in example 435 with the difference that 5-(S)-1-Pyrrolidin-2-ylmethyl-1H-tetrazole was used instead of (S)-Pyrrolidine-2-carboxylic acid cyclobutylamide. MS (ES⁺): m/e=622.

Example 670

4-[2-({7-Methyl-4-[2-oxo-2-(1-oxo-2,7-diaza-spiro[4.5]dec-7-yl)-ethoxy]-quinoline-2-carbonyl}-amino)-acetyl]-piperazine-1-carboxylic acid butyl ester The title compound was prepared by adapting the procedures described in example 435 with the difference that 2,7-Diaza-spiro[4.5]decan-1-one was used instead of (S)-Pyrrolidine-2-carboxylic acid cyclobutylamide. MS (ES⁺): m/e=623.

Example 671

4-[2-({4-[2-(3-Dimethylamino-piperidin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that Dimethyl-piperidin-3-yl-amine was used instead of (S)-Pyrrolidine-2-carboxylic acid cyclobutylamide. MS (ES⁺): m/e=597.

Example 672

4-[2-({4-[2-(4-Cyclobutyl-piperazin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that 1-Cyclobutyl-piperazine was used instead of (S)-Pyrrolidine-2-carboxylic acid cyclobutylamide. MS (ES⁺): m/e=609.

Example 673

4-[2-({4-[2-((S)-2-Cyclobutylcarbamoyl-pyrrolidin-1-yl)-2-oxo-ethoxy]-quinoline-2-carbonyl}-amino)-acetyl]-piperazine-1-carboxylic acid butyl ester (i) 4-(2-Benzyloxycarbonylamino-acetyl)-piperazine-1-carboxylic acid butyl ester To a solution of 5.62 g Z-Gly-OH in 100 ml DMF were added 13.7 ml N-ethylmorpholine, 8.8 g TOTU and 5.0 g 1-butoxycarbonylpiperazine. After stirring for 12 h, aqueous $NaHCO_3$ was added and the reaction mixture was diluted with ethyl acetate and washed with aqueous LiCl (4%) and 0.1 M HCl. The crude product obtained after evaporation of the solvent was purified by flash chromatography on silica using an ethyl acetate/heptane gradient. Yield: 6.34 g (ii) 4-(2-Amino-acetyl)-piperazine-1-carboxylic acid butyl ester To a solution of 6.34 g 4-(2-Benzyloxycarbonylamino-acetyl)-piperazine-1-carboxylic acid butyl ester in 120 ml ethanol were added 200 mg Pd/C (10%) and the suspension stirred under an atmosphere of hydrogen (3 bar) for 12 h. The reaction mixture was filtrated over a plug of Celite®, washed with ethanol and concentrated. Yield: 4.47 g colorless solid (iii) 4-[2-({4-[2-((S)-2-Cyclobutylcarbamoyl-pyrrolidin-1-yl)-2-oxo-ethoxy]-quinoline-2-carbonyl}-amino)-acetyl]-piperazine-1-carboxylic acid butyl ester To a solution of 100 mg 4-[2-((S)-2-Cyclobutylcarbamoyl-pyrrolidin-1-yl)-2-oxo-ethoxy]-quinoline-2-carboxylic acid in 5 ml DMF were added 66 µl DIPEA and 96 mg HATU. After 5 minutes 61 mg 4-(2-Amino-acetyl)piperazine-1-carboxylic acid butyl ester were added and the mixture stirred for 1 h. The mixture was concentrated and the crude product thus obtained purified by preparative HPLC (C18 reverse phase column, elution with a water/MeCN gradient with 0.1% TFA). The fractions containing the product were lyophilized to yield the pure product as its trifluoroacetate salt. Yield: 22 mg MS(ES+): m/e=623

Example 674

4-[2-({7-Chloro-4-[2-((S)-2-cyclobutylcarbamoyl-pyrrolidin-1-yl)-2-oxo-ethoxy]-quinoline-2-carbonyl}-amino)-acetyl]-piperazine-1-carboxylic acid butyl ester The title compound was prepared by adapting the procedures described in example 435 with the difference that 7-Chloro-4-hydroxy-quinoline-2-carboxylic acid ethyl ester was used instead of 4-Hydroxy-7-methyl-quinoline-2-carboxylic acid ethyl ester. MS (ES+): m/e=658, chloro pattern.

Example 675

4-[(S)-2-({4-[(R)-2-((S)-2-Cyclobutylcarbamoyl-pyrrolidin-1-yl)-1-methyl-2-oxo-ethoxy]-7-methyl-quinoline-2-carbonyl}-amino)-4-methoxycarbonyl-butyryl]-piperazine-1-carboxylic acid ethyl ester The title compound was prepared by adapting the procedures described in example 237 with the difference that 4-[(S)-4-Carboxy-2-({4-[(R)-2-((S)-2-cyclobutylcarbamoyl-pyrrolidin-1-yl)-1-methyl-2-oxo-ethoxy]-7-methyl-quinoline-2-carbonyl}-amino)-butyryl]-piperazine-1-carboxylic acid ethyl ester was used instead of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester. MS (ES+): m/e=709.

Example 676

4-[(S)-2-({4-[(R)-2-((S)-2-Cyclobutylcarbamoyl-pyrrolidin-1-yl)-1-methyl-2-oxo-ethoxy]-7-methyl-quinoline-2-carbonyl}-amino)-4-hydroxy-butyryl]-piperazine-1-carboxylic acid cyclobutyl ester (i) Piperazine-1,4-dicarboxylic acid benzyl ester cyclobutyl ester To a solution of 2.6 g triphosgene and 1.7 ml cyclobutanol in 40 ml dichloromethane were added 6.2 ml triethylamine dropwise at 0° C. After 30 minutes 4.4 ml benzyl 1-piperazinecarboxylate and 3.2 ml triethylamine were added at 0° C. The reaction mixture was allowed to warm to RT for 16 h. Excess triphosgene was destroyed by adding a solution of 2 g NaOH in 200 ml water and stirring for 2 h. The layers were separated, the organic layer dried over $MgSO_4$ and concentrated. The crude product thus obtained was purified by chromatography on silica using heptane/ethyl acetate 4/1 to 2/1 as eluent. Yield: 5.9 g.

(ii) Piperazine-1-carboxylic acid cyclobutyl ester

A suspension of 5.90 g Piperazine-1,4-dicarboxylic acid benzyl ester cyclobutyl ester and 0.25 g Pd/C (10%) in 50 ml ethyl acetate was stirred under an atmosphere of hydrogen (3 bar) for 12 h. The mixture was filtrated over a plug of Celite, washed with ethyl acetate and the combined wash solutions concentrated to give the title compound as colourless oil. Yield: 3.3 g.

(iii) 4-[(S)-2-({4-[(R)-2-((S)-2-Cyclobutylcarbamoyl-pyrrolidin-1-yl)-1-methyl-2-oxo-ethoxy]-7-methyl-quinoline-2-carbonyl}-amino)-4-hydroxy-butyryl]-piperazine-1-carboxylic acid cyclobutyl ester The title compound was prepared by adapting the procedures described in example 534 with the difference that Piperazine-1-carboxylic acid cyclobutyl ester was used instead of Piperazine-1-carboxylic acid butyl ester. MS (ES+): m/e=693.

Example 677

4-[2-({4-[2-((S)-2-Cyclobutylcarbamoyl-pyrrolidin-1-yl)-2-oxo-ethoxy]-6-fluoro-5-methyl-quinoline-2-carbonyl}-aminoacetyl]-piperazine-1-carboxylic acid butyl ester The title compound was prepared by adapting the procedures described in example 435 with the difference that 6-Fluoro-4-hydroxy-5-methyl-quinoline-2-carboxylic acid ethyl ester was used instead of 4-Hydroxy-7-methyl-quinoline-2-carboxylic acid ethyl ester. MS (ES+): m/e=655.

Example 678

4-[(S)-2-({4-[(R)-2-((S)-2-Cyclobutylcarbamoyl-pyrrolidin-1-yl)-1-methyl-2-oxo-ethoxy]-7-methyl-quinoline-2-carbonyl}-amino)-4-hydroxy-butyryl]-piperazine-1-carboxylic acid cyclopropylmethyl ester (i) Piperazine-1,4-dicarboxylic acid tert-butyl ester cyclopropylmethyl ester To a solution of 3.3 g triphosgene and 2 g Cyclopropyl-methanol in 40 ml dichloromethane were added 9.1 ml DIPEA dropwise at 0° C. After 1 h, 5.1 g Piperazine-1-carboxylic acid tert-butyl ester and 4.5 ml DIPEA in 7 ml were added at 0° C. The reaction mixture was allowed to warm to RT and stirred for 16 h. Excess triphosgene was destroyed by adding a solution of 2 g NaOH in 120 ml water and stirring for 2 h. The layers were separated and the aqueous layer was extracted with DCM. The combined organic layers were washed with 1M aqueous hydrochloric acid, dried over $MgSO_4$ and concentrated. The crude product thus obtained was purified was used in the next reaction step. Yield: 7.9 g.

(ii) Piperazine-1-carboxylic acid cyclopropylmethyl ester

To a solution of 7.9 g Piperazine-1,4-dicarboxylic acid tert-butyl ester cyclobutyl ester in 20 ml dichloromethane, 10 ml of TFA were added. After 16 h stirring at RT the solvents were removed and the residue was codistilled twice with toluene. The product was obtained as its trifluoroacetate salt. Yield: 11.7 g.

(iii) 4-[(S)-2-({4-[(R)-2-((S)-2-Cyclobutylcarbamoyl-pyrrolidin-1-yl)-1-methyl-2-oxo-ethoxy]-7-methyl-quinoline-2-carbonyl}-amino)-4-hydroxy-butyryl]-piperazine-1-carboxylic acid cyclopropylmethyl ester The title compound was prepared by adapting the procedures described in example 534 with the difference that Piperazine-1-carboxylic acid cyclopropylmethyl ester was used instead of Piperazine-1-carboxylic acid butyl ester. MS (ES+): m/e=693.

Example 679

4-[2-({4-[2-((S)-2-Cyclobutylcarbamoyl-pyrrolidin-1-yl)-2-oxo-ethoxy]-7-methyl-quinoline-2-carbonyl}-amino)-acetyl]-piperazine-1-carboxylic acid 3,3,3-trifluoro-propyl ester (i) Piperazine-1,4-dicarboxylic acid benzyl ester 3,3,3-trifluoro-propyl ester To a solution of 3.1 g triphosgene and 2.3 ml 3,3,3-trifluoropropan-1-ol in 70 ml dichloromethane were added 9.0 ml DIPEA dropwise at 0° C. After 30 minutes 5.1 ml benzyl 1-piperazinecarboxylate and 34.5 ml DIPEA were added at 0° C. The reaction mixture was allowed to warm to RT overnight. Excess triphosgene was destroyed by adding a solution of 2.5 g NaOH in 200 ml water and stirring for 2 h. The layers were separated, the organic layer dried over $MgSO_4$ and concentrated. The crude product thus obtained was purified by chromatography on silica using heptane/ethyl acetate 4/1 to 2/1 as eluent. Yield: 3.2 g.

(ii) Piperazine-1-carboxylic acid 3,3,3-trifluoro-propyl ester

To a solution of 3.2 g Piperazine-1,4-dicarboxylic acid benzyl ester 3,3,3-trifluoro-propyl ester in 60 ml ethanol were added 200 mg Pd/C (10%) and the suspension stirred under an atmosphere of hydrogen (3 bar) for 12 h. The reaction mixture was filtrated over a plug of Celite®, washed with ethanol and concentrated. Yield: 2.0 g colorless oil.

(iii) 4-(2-Benzyloxycarbonylamino-acetyl)-piperazine-1-carboxylic acid 3,3,3-trifluoro-propyl ester To a solution of 842 mg N-Benzyloxycarbonyl glycine were added 2.0 ml N-ethylmorpholine, 1.32 g TOTU and 910 mg Piperazine-1-carboxylic acid 3,3,3-trifluoro-propyl ester. After stirring for 48 h the reaction mixture was diluted with ethyl acetate and washed with aqueous LiCl (4%), 0.1 M HCl, saturated aqueous $NaHCO_3$ and brine. The crude product obtained was used without further purification. Yield: 1.63 g.

(iv) 4-(2-Amino-acetyl)-piperazine-1-carboxylic acid 3,3,3-trifluoro-propyl ester To a solution of 1.63 g 4-(2-Benzyloxycarbonylamino-acetyl)-piperazine-1-carboxylic acid 3,3,3-trifluoro-propyl ester in 40 ml ethanol were added 200 mg Pd/C (10%) and the suspension stirred under an atmosphere of hydrogen (3 bar) for 12 h. The reaction mixture was filtrated over a plug of Celite®, washed with ethanol and concentrated. Yield: 1.02 g colorless oil.

(v) 4-[2-({4-[2-((S)-2-Cyclobutylcarbamoyl-pyrrolidin-1-yl)-2-oxo-ethoxy]-7-methyl-quinoline-2-carbonyl}-amino)-acetyl]-piperazine-1-carboxylic acid 3,3,3-trifluoro-propyl ester To a solution of 983 mg 4-[2-((S)-2-Cyclobutylcarbamoyl-pyrrolidin-1-yl)-2-oxo-ethoxy]-7-methyl-quinoline-2-carboxylic acid in 15 ml DMF were added 816 µl DIPEA and 908 mg HATU. After 5 minutes 677 mg 4-(2-Amino-acetyl)-piperazine-1-carboxylic acid 3,3,3-trifluoro-propyl ester were added and the mixture stirred for 3 h. The mixture was concentrated, diluted with ethyl acetate and washed with aqueous LiCl (4%), 0.1 M HCl, saturated $NaHCO_3$ and brine. The crude product thus obtained was purified by preparative HPLC (C18 reverse phase column, elution with a water/MeCN gradient with 0.1% TFA). The fractions containing the product were lyophilized to yield the pure product as its trifluoroacetate salt. The latter one was dissolved in DCM, extracted once with each saturated aqueous $NaHCO_3$ and brine, followed by evaporation of the solvent to give the title compound. Yield: 800 mg MS(ES+): m/e=677.

Example 680

4-[2-({6-Chloro-4-[2-((S)-2-cyclobutylcarbamoyl-pyrrolidin-1-yl)-2-oxo-ethoxy]-7-methyl-quinoline-2-carbonyl}-aminoyacetyl]-piperazine-1-carboxylic acid butyl ester (i) 6-Chloro-4-hydroxy-7-methyl-quinoline-2-carboxylic acid ethyl ester To a solution of 3.5 g of 4-chloro-3-methylaniline in 30 ml of methanol, 4.2 g of but-2-ynedioic acid diethyl ester were added dropwise over 30 min at 0° C. and stirred for 3 h at RT. Then, the solvents were removed under reduced pressure and the residue was dissolved in 70 ml of Dowtherm® and heated to 250° C. for 2 h. Then, the reaction mixture was allowed to cool to RT and 300 ml of n-heptane were added to precipitate the crude product, which was collected by filtration. The title compound was purified by chromatography on silica gel eluting with a gradient of n-heptane/ethyl acetate. The fractions containing the product were combined and the solvent evaporated under reduced pressure. Yield: 1.1 g.

As a second fraction the regioisomeric product 6-Chloro-4-hydroxy-5-methyl-quinoline-2-carboxylic acid ethyl ester was isolated. Yield: 0.4 g.

(ii) 6-Chloro-4-[2-((S)-2-cyclobutylcarbamoyl-pyrrolidin-1-yl)-2-oxo-ethoxy]-7-methyl-quinoline-2-carboxylic acid ethyl ester To a solution of 1.1 g 6-Chloro-4-hydroxy-7-methyl-quinoline-2-carboxylic acid ethyl ester in 25 ml DMF were added 2.7 g of cesium carbonate followed by dropwise addition of a solution of 1.8 g (S)-1-(2-Bromo-acetyl)-pyrrolidine-2-carboxylic acid cyclobutylamide in 25 ml DMF over a period of 3 h. After this time another portion of cesium carbonate (700 mg) and (S)-1-(2-Bromo-acetyl)-pyrrolidine-2-carboxylic acid cyclobutylamide (700 mg) were added over 1.5 h. The mixture was evaporated, diluted with DCM and washed with aqueous LiCl (4%). The crude product obtained after evaporation of the solvent was pure enough for the subsequent transformation. Yield: 3.3 g.

(iii) 6-Chloro-4-[2-((S)-2-cyclobutylcarbamoyl-pyrrolidin-1-yl)-2-oxo-ethoxy]-7-methyl-quinoline-2-carboxylic acid To a solution of 3.2 g 6-Chloro-4-[2-((S)-2-cyclobutylcarbamoyl-pyrrolidin-1-yl)-2-oxo-ethoxy]-7-methyl-quinoline-2-carboxylic acid ethyl ester in 20 ml THF were added 6.7 ml aqueous NaOH (1 M) at 0° C. After 4 h the mixture was brought to pH 4 by using Amberlite IR-120 ion exchange resin. The reaction mixture was filtered and concentrated and the crude product obtained used in the next step without further purification. Yield: 2.78 g.

(iv) 4-[2-({6-Chloro-4-[2-((S)-2-cyclobutylcarbamoyl-pyrrolidin-1-yl)-2-oxo-ethoxy]-7-methyl-quinoline-2-carbonyl}-aminoyacetyl]-piperazine-1-carboxylic acid butyl ester To a solution of 1.2 g 6-Chloro-4-[2-((S)-2-cyclobutylcarbamoyl-pyrrolidin-1-yl)-2-oxo-ethoxy]-7-methyl-quinoline-2-carboxylic acid in 43 ml DMF were added 703 μl DIPEA and 1.0 g HATU. After 5 minutes 655 mg 4-(2-Amino-acetyl)piperazine-1-carboxylic acid butyl ester were added and the mixture stirred for 2 h. The mixture was concentrated, diluted with ethyl acetate and washed with aqueous LiCl (4%), 0.1 M HCl, saturated aqueous NaHCO₃ and brine. The crude product thus obtained was purified by preparative HPLC (C18 reverse phase column, elution with a water/MeCN gradient with 0.1% TFA). The fractions containing the product were lyophilized to yield the pure product as its trifluoroacetate salt. The latter one was dissolved in DCM, extracted once with each saturated aqueous NaHCO₃ and brine, followed by evaporation of the solvent to give the title compound. Yield: 470 mg MS(ES+): m/e=672, chloro pattern.

Example 681

4-[(S)-2-({4-[(R)-2-((S)-2-Cyclobutylcarbamoyl-pyrrolidin-1-yl)-1-methyl-2-oxo-ethoxy]-7-methyl-quinoline-2-carbonyl}-amino)-4-(1H-tetrazol-5-yl)-butyryl]-piperazine-1-carboxylic acid butyl ester (i) 4-Hydroxy-7-methyl-quinoline-2-carboxylic acid methyl ester 4-Hydroxy-7-methyl-quinoline-2-carboxylic acid (1.00 g) was suspended in 20 ml HCl (4 M in MeOH) and stirred until LCMS indicated complete conversion to the methyl ester. The reaction mixture was concentrated and the residue obtained codistilled twice with toluene to give the crude product as hydrochloride salt. Yield: 1.24 g.

(ii) 4-((R)-1-Benzyloxycarbonyl-ethoxy)-7-methyl-quinoline-2-carboxylic acid methyl ester To a solution of 1.00 g 4-Hydroxy-7-methyl-quinoline-2-carboxylic acid methyl ester hydrochloride and 0.83 g benzyl-L-lactate in 30 ml THF were added 1.81 g triphenylphosphine and 1.20 g diethylazodicarboxylate. After 2 h LCMS indicated complete conversion and water was added to the reaction mixture which was subsequently extracted with ethyl acetate. The residue obtained after evaporation of the solvent was purified by flash chromatography on silica using an ethyl acetate/heptane gradient. Yield: 1.80 g.

(iii) 4-((R)-1-Carboxy-ethoxy)-7-methyl-quinoline-2-carboxylic acid

To a solution of 1.80 g 4-((R)-1-Benzyloxycarbonyl-ethoxy)-7-methyl-quinoline-2-carboxylic acid methyl ester in 15 ml ethanol were added 200 mg Pd/C (10%) and the suspension stirred under an atmosphere of hydrogen (5 bar) for 18 h. Then, the reaction mixture was filtrated over a plug of Celite®, washed with ethanol and concentrated. Yield: 1.30 g colorless oil.

(iv) 4-[(R)-2-((S)-2-Cyclobutylcarbamoyl-pyrrolidin-1-yl)-1-methyl-2-oxo-ethoxy]-7-methyl-quinoline-2-carboxylic acid methyl ester To a solution of 1.30 g 4-((R)-1-Carboxy-ethoxy)-7-methyl-quinoline-2-carboxylic acid in 10 ml DCM, 1.24 g pentafluorophenol and 1.29 g EDC were added. The mixture was stirred under exclusion of moisture until LCMS indicated complete conversion to the corresponding pentafluorophenolester. (S)-Pyrrolidine-2-carboxylic acid cyclobutylamide hydrochloride (1.10 g) was mixed with 1.1 ml N-ethylmorpholine and 5 ml DCM and this mixture added dropwise to the solution of the pentafluorophenolester. After 12 h the reaction mixture was diluted with water and extracted with DCM. The crude product obtained after evaporation of the solvent was purified by flash chromatography on silica eluting with ethyl acetate/heptane gradient. Yield: 1.40 g.

(v) 4-[(R)-2-((S)-2-Cyclobutylcarbamoyl-pyrrolidin-1-yl)-1-methyl-2-oxo-ethoxy]-7-methyl-quinoline-2-carboxylic acid To a solution of 6.30 g 4-[(R)-2-((S)-2-Cyclobutylcarbamoyl-pyrrolidin-1-yl)-1-methyl-2-oxo-ethoxy]-7-methyl-quinoline-2-carboxylic acid methyl ester in 14 ml THF were added 14.3 ml aqueous NaOH (1 M) and the reaction mixture was stirred for 4 h at RT. The reaction mixture was acidified with 15 ml 1 M HCl, concentrated to a volume of 25 ml and extracted with DCM to give the crude product after evaporation of the solvent. Yield: 5.00 g (vi) 4-[(S)-2-({4-[(R)-2-((S)-2-Cyclobutylcarbamoyl-pyrrolidin-1-yl)-1-methyl-2-oxo-ethoxy]-7-methyl-quinoline-2-carbonyl}-amino)-4-(1H-tetrazol-5-yl)-butyryl]-piperazine-1-carboxylic acid butyl ester To a solution of 570 mg 4-[(R)-2-((S)-2-Cyclobutylcarbamoyl-pyrrolidin-1-yl)-1-methyl-2-oxo-ethoxy]-7-methyl-quinoline-2-carboxylic acid in 5 ml DMF were added 1.2 ml DIPEA and 510 mg HATU. After 5 minutes 1.2 g 4-[(S)-2-amino-4-(2H-tetrazol-5-yl)-butyryl]-piperazine-1-carboxylic acid butyl ester hydrotrifluoroacetate were added and the mixture stirred for 3 h. The reaction mixture was concentrated, the residue obtained diluted with DCM and subsequently washed with aqueous LiCl (4%), 0.1 M HCl and brine. The crude product obtained after evaporation of the solvent was purified by preparative HPLC (C18 reverse phase column, elution with a water/MeCN gradient with 0.1% TFA). The fractions containing the product were lyophilized to yield the pure product as its trifluoroacetate salt. The latter one was transformed to the hydrochloride salt by taking it up twice in water containing 1 M HCl (2 equivalents) and lyophilisation. Yield: 395 mg MS(ES+): m/e=747.

Example 682

4-[(S)-2-({4-[(S)-2-((S)-2-Cyclobutylcarbamoyl-pyrrolidin-1-yl)-1-methyl-2-oxo-ethoxy]-7-methyl-quinoline-2-carbonyl}-amino)-4-(1H-tetrazol-5-yl)-butyryl]-piperazine-1-carboxylic acid butyl ester The title compound was isolated during the preparation of example 681 as a diastereoisomeric by-product of 4-[(S)-2-({4-[(S)-2-((S)-2-Cyclobutylcarbamoyl-pyrrolidin-1-yl)-1-methyl-2-oxo-ethoxy]-7-methyl-quinoline-2-carbonyl}-amino)-4-(1H-tetrazol-5-yl)-butyryl]-piperazine-1-carboxylic acid butyl ester. Yield: 175 mg MS(ES+): m/e=747.

Example 683

4-[(S)-4-Hydroxy-2-({7-methyl-4-[2-oxo-2-((S)-2-phenyl-pyrrolidin-1-yl)-ethoxy]-quinoline-2-carbonyl}-amino)-butyryl]piperazine-1-carboxylic acid butyl ester The title compound was prepared by adapting the procedures described in example 354 with the difference that (S)-2-Phenyl-pyrrolidine was used instead of (S)-Pyrrolidine-2-carboxylic acid cyclobutylamide. MS (ES+): m/e=660.

Example 684

4-[2-({4-[2-((S)-2-Cyclobutylcarbamoyl-pyrrolidin-1-yl)-2-oxo-ethoxy]-6,7-difluoro-quinoline-2-carbonyl}-amino)-acetyl]-piperazine-1-carboxylic acid butyl ester The title compound was prepared by adapting the procedures described in example 659 with the difference that 6,7-Difluoro-4-hydroxy-quinoline-2-carboxylic acid ethyl ester was used instead of 4-Hydroxy-6,7-dimethyl-quinoline-2-carboxylic acid. MS (ES+): m/e=659.

Example 685

4-[2-({7-Cyano-4-[2-((S)-2-cyclobutylcarbamoyl-pyrrolidin-1-yl)-2-oxo-ethoxy]-quinoline-2-carbonyl}-amino)-acetyl]-piperazine-1-carboxylic acid butyl ester The title compound was prepared by adapting the procedures described in example 659 with the difference that 7-Cyano-4-hydroxy-quinoline-2-carboxylic acid ethyl ester was used instead of 4-Hydroxy-6,7-dimethyl-quinoline-2-carboxylic acid. MS (ES+): m/e=648.

Example 686

4-{(S)-4-Carboxy-2-[(4-{2-[(S)-2-(4-fluoro-phenyl)-pyrrolidin-1-yl]-2-oxo-ethoxy}-7-methyl-quinoline-2-carbonyl)-amino]-butyryl}-piperazine-1-carboxylic acid butyl ester The title compound was prepared by adapting the procedures described in example 303 with the difference that (S)-2-(4-Fluoro-phenyl)-pyrrolidine was used instead of (S)-Pyrrolidine-2-carboxylic acid cyclobutylamide. MS (ES+): m/e=706.

Example 687

4-{(S)-4-Carboxy-2-[(4-{2-[(S)-2-(4-fluoro-phenyl)-pyrrolidin-1-yl]-2-oxo-ethoxy}-6,7-dimethyl-quinoline-2-carbonyl)-amino]-butyryl}-piperazine-1-carboxylic acid butyl ester The title compound was prepared by adapting the procedures described in example 303 with the difference that (S)-2-(4-Fluoro-phenyl)-pyrrolidine and 4-Hydroxy-6,7-dimethyl-quinoline-2-carboxylic acid was used instead of (S)-Pyrrolidine-2-carboxylic acid cyclobutylamide and 4-Hydroxy-7-methyl-quinoline-2-carboxylic acid. MS (ES+): m/e=720.

Example 688

4-[2-({4-[2-((2S,4R)-4-Cyano-2-cyclopropylcarbamoyl-pyrrolidin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that (2S,4R)-4-Cyano-pyrrolidine-2-carboxylic acid cyclopropylamide was used instead of (S)-Pyrrolidine-2-carboxylic acid cyclobutylamide. MS (ES+): m/e=648.

Example 689

4-[2-({4-[2-((2S,4R)-2-Cyclobutylcarbamoyl-4-hydroxy-pyrrolidin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that (2S,4R)-4-Hydroxy-pyrrolidine-2-carboxylic acid cyclobutylamide was used instead of (S)-Pyrrolidine-2-carboxylic acid cyclobutylamide. MS (ES⁺): m/e=653.

Example 690

4-{2-[(7-Methyl-4-{2-oxo-2-[(S)-2-(1H-tetrazol-5-yl)-pyrrolidin-1-yl]-ethoxy}-quinoline-2-carbonyl)-amino]-acetyl}-piperazine-1-carboxylic acid butyl ester (i) (S)-2-Benzylcarbamoyl-pyrrolidine-1-carboxylic acid benzyl ester To a solution of 5.00 g Z-Pro-OH in 50 ml DMF were added 3.84 g EDC, 2.73 g HOAt, 7.3 ml DIPEA and 2.2 ml benzylamine at 0° C. After stirring for 2 h the reaction mixture was concentrated, the residue was dissolved in dichloromethane and subsequently extracted with aqueous LiCl (4%), 0.1 M HCl and saturated NaHCO₃. The crude product obtained after evaporation of the solvent was pure enough for the subsequent transformation. Yield: 7.11 g colorless amorphous solid.

(ii) (S)-2-(1-Benzyl-1H-tetrazol-5-yl)-pyrrolidine-1-carboxylic acid benzyl ester To a suspension of 1.50 g (S)-2-Benzylcarbamoyl-pyrrolidine-1-carboxylic acid benzyl ester and 2.91 g triphenylphosphine in 30 ml acetonitrile were added dropwise at 0° C. 2.3 ml diisopropylazodicarboxylate and after 2 minutes 1.5 ml trimethylsilylazide over a period of 20 minutes. After 30 minutes the mixture was allowed to warm to RT and stirred for 12 h. The mixture was cooled to 0° C. and 1.5 ml aqueous sodium nitrite (2.9 M) were added, after 30 minutes a solution of 2.4 g ceric ammonium nitrate in 15 ml water was added and stirred for another 20 minutes. After this time the mixture was poured into ice and extracted twice with dichloromethane.

The crude product thus obtained after evaporation of the solvent was purified by flash chromatography on silica eluting with ethyl acetate/heptane gradient. Yield: 494 mg colorless foam.

(iii) (S)-5-Pyrrolidin-2-yl-1H-tetrazole

To a solution of 494 mg (S)-2-(1-Benzyl-1H-tetrazol-5-yl)-pyrrolidine-1-carboxylic acid benzyl ester in 50 ml ethanol were added 100 mg Pd(OH)₂/C (10%) and the suspension stirred under an atmosphere of hydrogen (4 bar) for 6 h. The reaction mixture was filtrated over a plug of Celite® and washed with ethanol. Yield: 173 mg colorless foam.

(iv) 4-{2-[(7-Methyl-4-{2-oxo-2-[(S)-2-(1H-tetrazol-5-yl)-pyrrolidin-1-yl]-ethoxy}-quinoline-2-carbonyl)-amino]-acetyl}-piperazine-1-carboxylic acid butyl ester The title compound was prepared by adapting the procedures described in example 435 with the difference that (S)-5-Pyrrolidin-2-yl-1H-tetrazole was used instead of (S)-Pyrrolidine-2-carboxylic acid cyclobutylamide. MS (ES⁺): m/e=608.

Example 691

4-{(S)-4-Carboxy-2-[(4-{(R)-2-[(S)-2-(4-fluorophenyl)-pyrrolidin-1-yl]-1-methyl-2-oxo-ethoxy}-7-methyl-quinoline-2-carbonyl)-amino]-butyryl}-piperazine-1-carboxylic acid butyl ester (i) Piperazine-1,4-dicarboxylic acid butyl ester tert-butyl ester To a solution of 15 g of Piperazine-1-carboxylic acid tert-butyl ester in 200 ml of DCM, 18 g of triethylamine was added and the mixture was cooled to 0° C. Then, 12.1 g of butyl chloroformate was slowly added. After the addition was completed the reaction mixture was allowed to warm to RT and to stir for 16 h. Then, 200 ml of DCM was added and the organic phase was washed two times with 0.1M aqueous hydrochloric acid and the with saturated aqueous sodium hydrogen carbonate solution. The organic phase was dried over MgSO₄ and the solvents were removed under reduced pressure. The crude product was pure enough for the next reaction step. Yield: 21.9 g.

(ii) Piperazine-1-carboxylic acid butyl ester

To a solution of 21.9 g of Piperazine-1,4-dicarboxylic acid butyl ester tert-butyl ester from the preceding reaction step (i) in 20 ml of DCM, 30 ml of TFA was slowly added at RT. After 16 h, 200 ml of toluene was added and the solvents were removed under reduced pressure. The isolated crude product was obtained as its trifluoroacetate salt and was pure enough for the next reaction step. Yield: 23 g.

(iii) 4-((S)-2-Benzyloxycarbonylamino-4-tert-butoxycarbonyl-butyryl)-piperazine-1-carboxylic acid butyl ester To a solution of 22.4 g of (S)-2-Benzyloxycarbonylaminopentanedioic acid 5-tert-butyl ester, 30.7 g of NEM and 21.8 g of TOTU in 75 ml of DMF, 20 g of Piperazine-1-carboxylic acid butyl ester trifluoroacetate was added at RT and stirred for 16 h. The reaction mixture was then diluted with saturated aqueous sodium hydrogen carbonate solution and then extracted with 300 ml of ethyl acetate. The organic phase was washed with diluted saturated aqueous sodium hydrogen carbonate solution and dried over MgSO₄. The solvents were removed under reduced pressure. The crude product was purified by chromatography on silica gel eluting with n-heptane/ethyl acetate (1/1). The fractions containing the product were combined and the solvent evaporated under reduced pressure. Yield: 33.4 g.

(iv) 4-((S)-2-Amino-4-tert-butoxycarbonyl-butyryl)-piperazine-1-carboxylic acid butyl ester A solution of 33.4 g of 4-((S)-2-Benzyloxycarbonylamino-4-tert-butoxycarbonyl-butyryl)-piperazine-1-carboxylic acid ethyl ester in 130 ml of ethanol was purged with argon. Then, 3.3 g of Pd/C (5-10%) was added and the mixture stirred under a hydrogen atmosphere (3 bar). After 6 h the reaction mixture was filtered through a pad of celite and the solvents were removed under reduced pressure. After drying under reduced pressure the product was pure enough for the next reaction step. Yield: 17.3 g.

(v) 4-{(S)-4-tert-Butoxycarbonyl-2-[(4-hydroxy-7-methyl-quinoline-2-carbonyl)-amino]-butyryl}-piperazine-1-carboxylic acid butyl ester To a solution of 5.0 g of 4-Hydroxy-7-methyl-quinoline-2-carboxylic acid and 9.1 g of 4-((S)-2-Amino-4-tert-butoxycarbonyl-butyryl)-piperazine-1-carboxylic acid butyl ester in 50 ml of DMF, 3.7 g of HOBT and 4.7 g of EDC was added and the reaction mixture was stirred for 4 h at RT. Then, the reaction mixture was diluted with water and extracted with ethyl acetate. The combined organic phases were dried over MgSO$_4$ and the solvents were removed under reduced pressure. The isolated crude product was used in the next reaction step. Yield: 12.6 g.

(vi) 4-((S)-2-{[4-((R)-1-Benzyloxycarbonyl-ethoxy)-7-methyl-quinoline-2-carbonyl]-amino}-4-tert-butoxycarbonyl-butyryl)-piperazine-1-carboxylic acid butyl ester To a solution of 2 g 4-{(S)-4-tert-Butoxycarbonyl-2-[(4-hydroxy-7-methyl-quinoline-2-carbonyl)-amino]-butyryl}-piperazine-1-carboxylic acid butyl ester and 647 mg benzyl-L-lactate in 25 ml THF were added 1.4 g triphenylphosphine and 938 mg diethylazodicarboxylate. After stirring for 16 h at RT LCMS indicated complete conversion and water was added to the reaction mixture which was subsequently extracted with ethyl acetate. The residue obtained after evaporation of the solvent was purified by flash chromatography on silica using an ethyl acetate/heptane gradient. Yield: 1.7 g.

(vii) 4-((S)-4-tert-Butoxycarbonyl-2-{[4-((R)-1-carboxy-ethoxy)-7-methyl-quinoline-2-carbonyl]-amino}-butyryl)-piperazine-1-carboxylic acid butyl ester To a solution of 1.7 g 4-((S)-2-{[4-((R)-1-Benzyloxycarbonyl-ethoxy)-7-methyl-quinoline-2-carbonyl]-amino}-4-tert-butoxycarbonyl-butyrylypiperazine-1-carboxylic acid butyl ester in 30 ml ethanol were added 170 mg Pd/C (10%) and the suspension stirred under an atmosphere of hydrogen (4 bar) for 16 h. Then, the reaction mixture was filtrated over a plug of Celite®, washed with ethanol and then concentrated under reduced pressure. Yield: 1.3 g colorless solid.

(viii) 4-{(S)-4-tert-Butoxycarbonyl-2-[(4-{(R)-2-[(S)-2-(4-fluoro-phenyl)-pyrrolidin-1-yl]-1-methyl-2-oxo-ethoxy}-7-methyl-quinoline-2-carbonylamino]-butyryl}-piperazine-1-carboxylic acid butyl ester To a solution of 600 mg of 4-((S)-4-tert-Butoxycarbonyl-2-{[4-((R)-1-carboxy-ethoxy)-7-methyl-quinoline-2-carbonyl]-amino}-butyrylypiperazine-1-carboxylic acid butyl ester in 5 ml of DCM, 274 mg of EDC, 263 mg of pentafluorophenol was added and the reaction mixture was stirred for 2 h. Then, 192 mg of (S)-2-(4-Fluoro-phenyl)-pyrrolidine hydrochloride and 220 mg of NEM in 2 ml of DCM was added. After 16 h the reaction mixture was diluted with water. After filtration through a chem Elut® cartridge by eluting with DCM the solvents were removed under reduced pressure. The crude product was used in the next reaction step. Yield: 790 mg.

(iix) 4-{(S)-4-Carboxy-2-[(4-{(R)-2-[(S)-2-(4-fluoro-phenyl)-pyrrolidin-1-yl]-1-methyl-2-oxo-ethoxy}-7-methyl-quinoline-2-carbonylamino]-butyryl}-piperazine-1-carboxylic acid butyl ester To a solution of 790 mg of 4-{(S)-4-tert-Butoxycarbonyl-2-[(4-{(R)-2-[(S)-2-(4-fluoro-phenyl)-pyrrolidin-1-yl]-1-methyl-2-oxo-ethoxy}-7-methyl-quinoline-2-carbonylamino]-butyryl}-piperazine-1-carboxylic acid butyl ester in 5 ml of DCM, 0.6 ml of TFA was added at RT. After 3 h 20 ml of toluene was added and the solvents were removed under reduced pressure. The residue was purified by preparative HPLC (C18 reverse phase column, elution with a water/MeCN gradient with 0.1% TFA). The fractions containing the product were evaporated and lyophilized to yield a white solid. The product was obtained as its trifluoroacetate salt. The product was dissolved in DCM and washed with saturated aqueous sodium hydrogen carbonate solution and water. The organic phase dried over MgSO$_4$. The solvents were removed under reduced pressure. The residue was dissolved in water/acetonitrile and lyophilized to yield the product as a white solid. Yield: 414 mg MS(ES+): m/e=720.

Example 692

4-[2-({4-[2-((2S,4R)-4-Cyano-2-cyclobutylcarbamoyl-pyrrolidin-1-yl)-2-oxo-ethoxy]-7-methyl-quinoline-2-carbonyl}-amino)-acetyl]-piperazine-1-carboxylic acid butyl ester The title compound was prepared by adapting the procedures described in example 435 with the difference that (2S,4R)-4-Cyano-pyrrolidine-2-carboxylic acid cyclobutylamide was used instead of (S)-Pyrrolidine-2-carboxylic acid cyclobutylamide. MS (ES$^+$): m/e=662.

Example 693

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(2-methyl-2H-tetrazol-5-yl)-butyryl]-piperazine-1-carboxylic acid butyl ester (i) 4-[(S)-2-tert-Butoxycarbonylamino-4-(2-methyl-2H-tetrazol-5-yl)-butyryl]-piperazine-1-carboxylic acid butyl ester To a solution of 1.559 g 4-[(S)-2-tert-Butoxycarbonylamino-4-(2H-tetrazol-5-yl)-butyryl]-piperazine-1-carboxylic acid butyl ester in a mixture of 30 ml DCM and 7 ml MeOH were added 1.77 ml TMS-diazomethane (2 M in diethylether) at 0° C. After 12 h another 0.4 ml TMS-diazomethane were added before the reaction was quenched with 2 drops of acetic acid. The mixture was evaporated and the residue obtained purified by flash chromatography on silica using an ethyl acetate/heptane gradient. Yield: 806 mg As a second fraction the regioisomeric 4-[(S)-2-tert-Butoxycarbonylamino-4-(1-methyl-1H-tetrazol-5-yl)-butyryl]-piperazine-1-carboxylic acid butyl ester was isolated. Yield: 315 mg.

(ii) 4-[(S)-2-Amino-4-(2-methyl-2H-tetrazol-5-yl)-butyryl]-piperazine-1-carboxylic acid butyl ester hydrotrifluoroacetate To a solution of 806 mg 4-[(S)-2-tert-Butoxycarbonylamino-4-(2-methyl-2H-tetrazol-5-yl)-butyryl]-piperazine-1-carboxylic acid butyl ester in 8 ml dichloromethane were added 1.3 ml TFA. After 12 h stirring at RT the solvents were removed and the residue was codistilled twice with toluene. Yield: 1.18 g.

(iii) 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(2-methyl-2H-tetrazol-5-yl)-butyryl]-piperazine-1-carboxylic acid butyl ester To a solution of 731 mg 4-[2-((S)-2-Cyclobutylcarbamoyl-pyrrolidin-1-yl)-2-oxo-ethoxy]-7-methyl-quinoline-2-carboxylic acid in 8 ml DMF were added 929 µl DIPEA, 242 mg HOBt and 341 mg EDC. After 5 minutes 830 mg 4-[(S)-2-Amino-4-(2-methyl-2H-tetrazol-5-yl)-butyryl]-piperazine-1-carboxylic acid butyl ester hydrotrifluoroacetate were added and the mixture stirred for 12 h. The mixture was concentrated, diluted with DCM and washed with aqueous LiCl (4%), saturated aqueous NaHCO$_3$ and brine. The crude product thus obtained was purified by preparative HPLC (C18 reverse phase column, elution with a water/MeCN gradient with 0.1% TFA). The fractions containing the product were lyophilized to yield the pure product as its trifluoroacetate salt. The latter one was dissolved in DCM, extracted once with each saturated aqueous NaHCO$_3$ and brine, followed by evaporation of the solvent to give the title compound. Yield: 566 mg MS(ES+): m/e=747.

Example 694

4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(1-methyl-1H-tetrazol-5-yl)-butyryl]-piperazine-1-carboxylic acid butyl ester (i) 4-[(S)-2-Amino-4-(1-methyl-1H-tetrazol-5-yl)-butyryl]-piperazine-1-carboxylic acid butyl ester hydrotrifluoroacetate To a solution of 315 mg 4-[(S)-2-tert-Butoxycarbonylamino-4-(1-methyl-1H-tetrazol-5-yl)-butyryl]-piperazine-1-carboxylic acid butyl ester in 5 ml dichloromethane were added 0.5 ml TFA. After 12 h stirring at RT the solvents were removed and the residue was codistilled twice with toluene. Yield: 0.41 g.

(ii) 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(1-methyl-1H-tetrazol-5-yl)-butyryl]-piperazine-1-carboxylic acid butyl ester To a solution of 285 mg 4-[2-((S)-2-Cyclobutylcarbamoyl-pyrrolidin-1-yl)-2-oxo-ethoxy]-7-methyl-quinoline-2-carboxylic acid in 3 ml DMF were added 362 µl DIPEA, 94 mg HOAt and 133 mg EDC. After 5 minutes 324 mg 4-[(S)-2-Amino-4-(1-methyl-1H-tetrazol-5-yl)-butyryl]-piperazine-1-carboxylic acid butyl ester hydrotrifluoroacetate were added and the mixture stirred for 12 h. The mixture was concentrated, diluted with DCM and washed with aqueous LiCl (4%), saturated aqueous NaHCO$_3$ and brine. The crude product thus obtained was purified by preparative HPLC (C18 reverse phase column, elution with a water/MeCN gradient with 0.1% TFA). The fractions containing the product were lyophilized to yield the pure product as its trifluoroacetate salt. The latter one was dissolved in DCM, extracted once with each saturated aqueous NaHCO$_3$ and brine, followed by evaporation of the solvent to give the title compound. Yield: 100 mg MS(ES+): m/e=747.

Example 695

4-{2-[(7-Methyl-4-{2-[(S)-2-(1-methyl-azetidin-3-ylcarbamoyl)-pyrrolidin-1-yl]-2-oxo-ethoxyl}-quinoline-2-carbonyl)-amino]-acetyl}-piperazine-1-carboxylic acid butyl ester The title compound was prepared by adapting the procedures described in example 435 with the difference that (S)-Pyrrolidine-2-carboxylic acid (1-methyl-azetidin-3-yl)amide was used instead of (S)-Pyrrolidine-2-carboxylic acid cyclobutylamide. MS (ES+): m/e=652.

Example 696

4-{2-[(7-Methyl-4-{2-[(S)-2-(4-methyl-piperazine-1-carbonyl)-pyrrolidin-1-yl]-2-oxo-ethoxyl}-quinoline-2-carbonyl)-amino]-acetyl}-piperazine-1-carboxylic acid butyl ester The title compound was prepared by adapting the procedures described in example 435 with the difference that (4-Methyl-piperazin-1-yl)-(S)-pyrrolidin-2-yl-methanone was used instead of (S)-Pyrrolidine-2-carboxylic acid cyclobutylamide. MS (ES+): m/e=666.

Example 697

4-[(S)-2-({4-[2-((S)-2-Cyclobutylcarbamoyl-pyrrolidin-1-yl)-2-oxo-ethoxy]-7-methyl-quinoline-2-carbonyl}-amino)-3-(1H-[1,2,3]triazol-4-yl)-propionyl]-piperazine-1-carboxylic acid butyl ester (i) (S)-3-(1-Benzyl-1H-[1,2,3]triazol-4-yl)-2-tert-butoxycarbonylamino-propionic acid A mixture of 430 mg Boc-L-propargylglycine, 269 mg benzyl azide, 36 mg copper(II)acetate and 80 mg sodium ascorbate in 15 ml water/t-BuOH (1:1) was stirred for 12 h at RT. The reaction mixture was diluted with ethyl acetate, washed with brine (2×) and the aqueous phase reextracted with ethyl acetate. The crude product obtained after evaporation of the solvent was pure enough for the subsequent transformation. Yield: 855 mg.

(ii) 4-[(S)-3-(1-Benzyl-1H-[1,2,3]triazol-4-yl)-2-tert-butoxycarbonylamino-propionyl]-piperazine-1-carboxylic acid butyl ester To a solution of 836 mg (S)-3-(1-Benzyl-1H-[1,2,3]triazol-4-yl)-2-tert-butoxycarbonylamino-propionic acid in 20 ml DMF were added 0.61 ml N-ethylmorpholine, 0.79 g TOTU and 449 mg Piperazine-1-carboxylic acid butyl ester. After stirring for 2 h the reaction mixture was concentrated, diluted with ethyl acetate and washed with aqueous LiCl (4%), 0.1 M HCl, saturated aqueous NaHCO$_3$ and brine. The crude product obtained was used without further purification. Yield: 1.14 g.

(iii) 4-[(S)-2-tert-Butoxycarbonylamino-3-(1H-[1,2,3]triazol-4-yl)-propionyl]-piperazine-1-carboxylic acid butyl ester Debenzylation of 4-[(S)-3-(1-Benzyl-1H-[1,2,3]triazol-4-yl)-2-tert-butoxycarbonylamino-propionyl]-piperazine-1-carboxylic acid butyl ester (1.14 g) was performed using the H-Cube® (Thales Nanotechnology). Parameters were chosen as follows: 0.05 M solution in MeOH, Pd(OH)$_2$/C, 60° C., 30 bar. Yield: 739 mg colorless foam.

(iv) 4-[(S)-2-Amino-3-(1H-[1,2,3]triazol-4-yl)-propionyl]-piperazine-1-carboxylic acid butyl ester hydrotrifluoroacetate To a solution of 739 mg 4-[(S)-2-tert-Butoxycarbonylamino-3-(1H-[1,2,3]triazol-4-yl)-propionyl]-piperazine-1-carboxylic acid butyl ester in 8 ml dichloromethane were added 1.3 ml TFA. After 12 h stirring at RT the solvents were removed and the residue was codistilled twice with toluene. Yield: 1.32 g.

(v) 4-[(S)-2-({4-[2-((S)-2-Cyclobutylcarbamoyl-pyrrolidin-1-yl)-2-oxo-ethoxy]-7-methyl-quinoline-2-carbonyl}-amino)-3-(1H-[1,2,3]triazol-4-yl)-propionyl]-piperazine-1-carboxylic acid butyl ester To a solution of 358 mg 4-[2-((S)-2-Cyclobutylcarbamoyl-pyrrolidin-1-yl)-2-oxo-ethoxy]-7-methyl-quinoline-2-carboxylic acid in 10 ml DMF were added 455 μl DIPEA, 118 mg HOAt and 167 mg EDC. After 5 minutes 381 mg 4-[(S)-2-Amino-3-(1H-[1,2,3]triazol-4-yl)-propionyl]-piperazine-1-carboxylic acid butyl ester hydrotrifluoroacetate were added and the mixture stirred for 12 h. The mixture was concentrated, diluted with DCM and washed with aqueous LiCl (4%), saturated aqueous NaHCO$_3$, 0.1 M HCl and brine. The crude product thus obtained was purified by preparative HPLC (C18 reverse phase column, elution with a water/MeCN gradient with 0.1% TFA). The fractions containing the product were lyophilized to yield the pure product as its trifluoroacetate salt. The latter one was dissolved in DCM, extracted once with each saturated aqueous NaHCO$_3$ and brine, followed by evaporation of the solvent to give the title compound. Yield: 200 mg MS(ES+): m/e=718.

Example 698

4-[(S)-2-({4-[2-((S)-2-Cyclobutylcarbamoyl-pyrrolidin-1-yl)-2-oxo-ethoxy]-7-methyl-quinoline-2-carbonyl}-amino)-3-(3-hydroxy-5-methyl-isoxazol-4-yl)-propionyl]-piperazine-1-carboxylic acid butyl ester

(i) (S)-2-tert-Butoxycarbonylamino-3-(3-hydroxy-5-methyl-isoxazol-4-yl)-propionic acid To a solution of 50 mg (S)-2-Amino-3-(3-hydroxy-5-methyl-isoxazol-4-yl)-propionic acid in 2 ml dioxane were added at 0° C. 70 mg di-tert-butyl dicarbonate and a solution of 44 mg NaHCO$_3$ in 1 ml water. After stirring for 12 h the mixture was acidified to pH3 using aqueous ascorbic acid (10%) before being extracted with DCM. The crude product obtained after evaporation of the solvent was used in the next step without further purification. Yield: 110 mg.

(ii) 4-[(S)-2-tert-Butoxycarbonylamino-3-(3-hydroxy-5-methyl-isoxazol-4-yl)-propionyl]-piperazine-1-carboxylic acid butyl ester To a solution of 110 mg (S)-2-tert-Butoxycarbonylamino-3-(3-hydroxy-5-methyl-isoxazol-4-yl)-propionic acid in 2 ml DMF were added 0.07 ml DIPEA, 107 mg HATU and 50 mg Piperazine-1-carboxylic acid butyl ester. After stirring for 2 h the reaction mixture was concentrated, diluted with DCM and washed with aqueous LiCl (4%). The crude product obtained was used without further purification. Yield: 146 mg.

(iii) 4-[(S)-2-Amino-3-(3-hydroxy-5-methyl-isoxazol-4-yl)-propionyl]-piperazine-1-carboxylic acid butyl ester hydrotrifluoroacetate To a solution of 146 mg 4-[(S)-2-tert-Butoxycarbonylamino-3-(3-hydroxy-5-methyl-isoxazol-4-yl)-propionyl]-piperazine-1-carboxylic acid butyl ester in 5 ml dichloromethane were added 0.4 ml TFA. After 12 h stirring at RT the solvents were removed and the residue was codistilled twice with toluene. Yield: 156 mg.

(iv) 4-[(S)-2-({4-[2-((S)-2-Cyclobutylcarbamoyl-pyrrolidin-1-yl)-2-oxo-ethoxy]-7-methyl-quinoline-2-carbonyl}-amino)-3-(3-hydroxy-5-methyl-isoxazol-4-yl)-propionyl]-piperazine-1-carboxylic acid butyl ester To a solution of 111 mg 4-[2-((S)-2-Cyclobutylcarbamoyl-pyrrolidin-1-yl)-2-oxo-ethoxy]-7-methyl-quinoline-2-carboxylic acid in 4 ml DMF were added 140 μl DIPEA and 102 mg HATU. After 5 minutes 156 mg 4-[(S)-2-Amino-3-(3-hydroxy-5-methyl-isoxazol-4-yl)-propionyl]-piperazine-1-carboxylic acid butyl ester hydrotrifluoroacetate were added and the mixture stirred for 1 h. The mixture was concentrated and the crude product thus obtained was purified by preparative HPLC (C18 reverse phase column, elution with a water/MeCN gradient with 0.1% TFA). The fractions containing the product were lyophilized to yield the pure product as its trifluoroacetate salt. Yield: 59 mg MS(ES+): m/e=748.

Example 699

4-[(S)-4-Ethoxycarbonyl-2-({7-methyl-4-[2-oxo-2-((S)-2-phenyl-pyrrolidin-1-yl)-ethoxy]-quinoline-2-carbonyl}-amino)-butyryl]-piperazine-1-carboxylic acid butyl ester The title compound was prepared by adapting the procedures described in example 58 with the difference that 4-[(S)-4-Carboxy-2-({7-methyl-4-[2-oxo-2-((S)-2-phenyl-pyrrolidin-1-yl)-ethoxy]-quinoline-2-carbonyl}-amino)-butyryl]-piperazine-1-carboxylic acid butyl ester was used instead of 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester. MS (ES+): m/e=716.

Example 700

4-{2-[(7-Methyl-4-{2-oxo-2-[(S)-2-(2,2,2-trifluoro-ethylcarbamoyl)-pyrrolidin-1-yl]-ethoxy}-quinoline-2-carbonyl)-amino]-acetyl}-piperazine-1-carboxylic acid butyl ester The title compound was prepared by adapting the procedures described in example 435 with the difference that (S)-Pyrrolidine-2-carboxylic acid (2,2,2-trifluoro-ethyl)-amide was used instead of (S)-Pyrrolidine-2-carboxylic acid cyclobutylamide. MS (ES+): m/e=665.

Example 701

4-[(S)-2-({4-[2-(3,3-Difluoro-pyrrolidin-1-yl)-2-oxo-ethoxy]-7-methyl-quinoline-2-carbonyl}-amino)-4-(2H-tetrazol-5-yl)-butyryl]-piperazine-1-carboxylic acid butyl ester

(i) 4-Benzyloxycarbonylmethoxy-7-methyl-quinoline-2-carboxylic acid methyl ester To a solution of 5.00 g 4-Hydroxy-7-methyl-quinoline-2-carboxylic acid methyl ester in 35 ml of DMF, 8.25 g of cesium carbonate and 5.80 g of Bromo-acetic acid benzyl ester were added and the reaction mixture was stirred for 12 h at RT. Then, the reaction mixture was diluted with water and extracted with ethyl acetate. The organic phase was dried over MgSO$_4$ and the solvents were removed under reduced pressure. The isolated crude product was pure enough for the next reaction step. Yield: 10.00 g.

(ii) 4-Carboxymethoxy-7-methyl-quinoline-2-carboxylic acid methyl ester

To a solution of 3.00 g 4-Benzyloxycarbonylmethoxy-7-methyl-quinoline-2-carboxylic acid methyl ester in 50 ml ethanol were added under argon 0.3 g Pd/C (10%) and the suspension was stirred under an atmosphere of hydrogen (3 bar) for 16 h. The suspension was filtered over a plug of Celite® and washed with ethanol. The crude product was obtained after evaporation of the solvent. Yield: 1.90 g.

(iii) 4-[2-(3,3-Difluoro-pyrrolidin-1-yl)-2-oxo-ethoxy]-7-methyl-quinoline-2-carboxylic acid methyl ester To a solution of 900 mg 4-Carboxymethoxy-7-methyl-quinoline-2-carboxylic acid methyl ester in 5 ml DMF were added 902 mg pentafluorophenol and 940 mg EDC. The mixture was stirred under exclusion of moisture until LCMS indicated complete conversion to the corresponding pentafluorophenolester. 3,3-Difluoropyrrolidine hydrochloride (455 mg) was mixed with 1.2 ml N-ethylmorpholine and 5 ml DMF and this mixture added dropwise to the solution of the pentafluorophenolester. After 12 h the reaction mixture was diluted with DCM and washed with aqueous LiCl (4%), saturated aqueous NaHCO$_3$ and brine. The crude product obtained after evaporation of the solvent was purified by flash chromatography on silica eluting with ethyl acetate/heptane gradient. Yield: 815 mg.

(iv) 4-[2-(3,3-Difluoro-pyrrolidin-1-yl)-2-oxo-ethoxy]-7-methyl-quinoline-2-carboxylic acid To a solution of 815 mg 4-[2-(3,3-Difluoro-pyrrolidin-1-yl)-2-oxo-ethoxy]-7-methyl-quinoline-2-carboxylic acid methyl ester in 8 ml THF were added 2.2 ml aqueous NaOH (1 M) at 0° C. After 2 h the mixture was brought to pH 4 by using Amberlite IR-120 ion exchange resin. The reaction mixture was filtered and concentrated and the crude product obtained used in the next step without further purification. Yield: 658 mg.

(v) 4-[(S)-2-({4-[2-(3,3-Difluoro-pyrrolidin-1-yl)-2-oxo-ethoxy]-7-methyl-quinoline-2-carbonyl}-amino)-4-(2H-tetrazol-5-yl)-butyryl]-piperazine-1-carboxylic acid butyl ester To a solution of 658 mg 4-[2-(3,3-Difluoro-pyrrolidin-1-yl)-2-oxo-ethoxy]-7-methyl-quinoline-2-carboxylic acid in 20 ml DMF were added 1.3 ml DIPEA, 302 mg HOBt and 378 mg EDC. After 5 minutes 302 mg 4-[(S)-2-amino-4-(2H-tetrazol-5-yl)-butyryl]-piperazine-1-carboxylic acid butyl ester hydrotrifluoroacetate were added and the mixture stirred for 24 h. The mixture was concentrated, diluted with DCM and washed with aqueous LiCl (4%) and 0.1 M HCl. The crude product thus obtained was purified by preparative HPLC (C18 reverse phase column, elution with a water/MeCN gradient with 0.1% TFA). The fractions containing the product were lyophilized to yield the pure product as its trifluoroacetate salt. The latter one was transformed to the hydrochloride salt by taking it up twice in water containing 1 M HCl (2 equivalents) and lyophilisation. Yield: 518 mg MS(ES+): m/e=672.

Example 702

4-[(S)-2-({4-[2-((R)-3-Hydroxy-pyrrolidin-1-yl)-2-oxo-ethoxy]-7-methyl-quinoline-2-carbonyl}-amino)-4-(2H-tetrazol-5-yl)-butyryl]-piperazine-1-carboxylic acid butyl ester

(i) 4-[2-((R)-3-Hydroxy-pyrrolidin-1-yl)-2-oxo-ethoxy]-7-methyl-quinoline-2-carboxylic acid methyl ester To a solution of 1000 mg 4-Carboxymethoxy-7-methyl-quinoline-2-carboxylic acid methyl ester in 5 ml DMF were added 956 mg pentafluorophenol and 994 mg EDC. The mixture was stirred under exclusion of moisture until LCMS indicated complete conversion to the corresponding pentafluorophenolester. (R)-3-hydroxypyrrolidine (287 mg) was mixed with 1.3 ml N-ethylmorpholine and 5 ml DMF and this mixture added dropwise to the solution of the pentafluorophenolester. After 12 h the reaction mixture was diluted with DCM and washed with aqueous LiCl (4%) and saturated aqueous NaHCO$_3$. The crude product obtained after evaporation of the solvent was purified by flash chromatography on silica eluting with ethyl acetate/methanol gradient. Yield: 996 mg.

(ii) 4-[2-((R)-3-Hydroxy-pyrrolidin-1-yl)-2-oxo-ethoxy]-7-methyl-quinoline-2-carboxylic acid To a solution of 996 mg 4-[2-((R)-3-Hydroxy-pyrrolidin-1-yl)-2-oxo-ethoxy]-7-methyl-quinoline-2-carboxylic acid methyl ester in 10 ml THF were added 2.8 ml aqueous NaOH (1 M) at 0° C. After 2 h the mixture was brought to pH 4 by using Amberlite IR-120 ion exchange resin. The reaction mixture was filtered and concentrated and the crude product obtained used in the next step without further purification. Yield: 700 mg

(iii) 4-[(S)-2-({4-[2-((R)-3-Hydroxy-pyrrolidin-1-yl)-2-oxo-ethoxy]-7-methyl-quinoline-2-carbonyl}-amino)-4-(2H-tetrazol-5-yl)-butyryl]-piperazine-1-carboxylic acid butyl ester To a solution of 400 mg 4-[2-((R)-3-Hydroxy-pyrrolidin-1-yl)-2-oxo-ethoxy]-7-methyl-quinoline-2-carboxylic acid in 20 ml DMF were added 0.8 ml DIPEA, 195 mg HOBt and 243 mg EDC. After 5 minutes 915 mg 4-[(S)-2-amino-4-(2H-tetrazol-5-yl)-butyryl]-piperazine-1-carboxylic acid butyl ester hydrotrifluoroacetate were added and the mixture stirred for 24 h. The mixture was concentrated, diluted with DCM and washed with aqueous LiCl (4%) and 0.1 M HCl. The crude product thus obtained was purified by preparative HPLC (C18 reverse phase column, elution with a water/MeCN gradient with 0.1% TFA). The fractions containing the product were lyophilized to yield the pure product as its trifluoroacetate salt. The latter one was transformed to the hydrochloride salt by taking it up twice in water containing 1 M HCl (2 equivalents) and lyophilisation. Yield: 245 mg MS(ES+): m/e=652.

Example 703

4-[(S)-2-({4-[2-(4-Methoxy-piperidin-1-yl)-2-oxo-ethoxy]-7-methyl-quinoline-2-carbonyl}-amino)-4-(2H-tetrazol-5-yl)-butyryl]-piperazine-1-carboxylic acid butyl ester (i) 4-[2-(4-Methoxy-piperidin-1-yl)-2-oxo-ethoxy]-7-methyl-quinoline-2-carboxylic acid methyl ester To a solution of 1000 mg 4-Carboxymethoxy-7-methyl-quinoline-2-carboxylic acid methyl ester in 5 ml DMF were added 956 mg pentafluorophenol and 994 mg EDC. The mixture was stirred under exclusion of moisture until LCMS indicated complete conversion to the corresponding pentafluorophenolester. 4-methoxypiperidine (379 mg) was mixed with 1.3 ml N-ethylmorpholine and 10 ml DMF and this mixture added dropwise to the solution of the pentafluorophenolester. After 12 h the reaction mixture was diluted with DCM and washed with aqueous LiCl (4%) and saturated aqueous NaHCO$_3$. The crude product obtained after evaporation of the solvent was purified by flash chromatography on silica eluting with ethyl acetate/heptane gradient. Yield: 980 mg.

(ii) 4-[2-(4-Methoxy-piperidin-1-yl)-2-oxo-ethoxy]-7-methyl-quinoline-2-carboxylic acid To a solution of 980 mg 4-[2-(4-Methoxy-piperidin-1-yl)-2-oxo-ethoxy]-7-methyl-quinoline-2-carboxylic acid methyl ester in 10 ml THF were added 2.5 ml aqueous NaOH (1 M) at 0° C. After 2 h the mixture was brought to pH 4 by using Amberlite IR-120 ion exchange resin. The reaction mixture was filtered and concentrated and the crude product obtained used in the next step without further purification. Yield: 800 mg.

(iii) 4-[(S)-2-({4-[2-(4-Methoxy-piperidin-1-yl)-2-oxo-ethoxy]-7-methyl-quinoline-2-carbonyl}-amino)-4-(2H-tetrazol-5-yl)-butyryl]-piperazine-1-carboxylic acid butyl ester To a solution of 400 mg 4-[2-(4-Methoxy-piperidin-1-yl)-2-oxo-ethoxy]-7-methyl-quinoline-2-carboxylic acid in 20 ml DMF were added 0.8 ml DIPEA, 180 mg HOBt and 225 mg EDC. After 5 minutes 843 mg 4-[(S)-2-amino-4-(2H-tetrazol-5-yl)-butyryl]-piperazine-1-carboxylic acid butyl ester hydrotrifluoroacetate were added and the mixture stirred for 24 h. The mixture was concentrated, diluted with DCM and washed with aqueous LiCl (4%) and 0.1 M HCl. The crude product thus obtained was purified by preparative HPLC (C18 reverse phase column, elution with a water/MeCN gradient with 0.1% TFA). The fractions containing the product were lyophilized to yield the pure product as its trifluoroacetate salt. The latter one was transformed to the hydrochloride salt by taking it up twice in water containing 1 M HCl (2 equivalents) and lyophilisation. Yield: 320 mg MS(ES+): m/e=680.

Example 704

4-[(S)-2-({4-[2-((S)-2-Cyano-pyrrolidin-1-yl)-2-oxo-ethoxy]-7-methyl-quinoline-2-carbonyl}-amino)-4-(2H-tetrazol-5-yl)-butyryl]-piperazine-1-carboxylic acid butyl ester (i) 4-[2-((S)-2-Cyano-pyrrolidin-1-yl)-2-oxo-ethoxy]-7-methyl-quinoline-2-carboxylic acid methyl ester To a solution of 1000 mg 4-Carboxymethoxy-7-methyl-quinoline-2-carboxylic acid methyl ester in 5 ml DMF were added 956 mg pentafluorophenol and 994 mg EDC. The mixture was stirred under exclusion of moisture until LCMS indicated complete conversion to the corresponding pentafluorophenolester. (S)-2-Cyano-pyrrolidine hydrochloride (437 mg) was mixed with 1.3 ml N-ethylmorpholine and 10 ml DMF and this mixture added dropwise to the solution of the pentafluorophenolester. After 12 h the reaction mixture was diluted with DCM and washed with aqueous LiCl (4%) and saturated aqueous NaHCO$_3$. The crude product obtained after evaporation of the solvent was purified by flash chromatography on silica eluting with ethyl acetate/heptane gradient. Yield: 772 mg.

(ii) 4-[2-((S)-2-Cyano-pyrrolidin-1-yl)-2-oxo-ethoxy]-7-methyl-quinoline-2-carboxylic acid To a solution of 772 mg 4-[2-((S)-2-Cyano-pyrrolidin-1-yl)-2-oxo-ethoxy]-7-methyl-quinoline-2-carboxylic acid methyl ester in 10 ml THF were added 2.1 ml aqueous NaOH (1 M) at 0° C. After 2 h the mixture was brought to pH 4 by using Amberlite IR-120 ion exchange resin. The reaction mixture was filtered and concentrated and the crude product purified by preparative HPLC (C18 reverse phase column, elution with a water/MeCN gradient with 0.1% TFA). The fractions containing the product were lyophilized to yield the pure product. Yield: 310 mg.

(iii) 4-[(S)-2-({4-[2-((S)-2-Cyano-pyrrolidin-1-yl)-2-oxo-ethoxy]-7-methyl-quinoline-2-carbonyl}-amino)-4-(2H-tetrazol-5-yl)-butyryl]-piperazine-1-carboxylic acid butyl ester To a solution of 160 mg 4-[2-((S)-2-Cyano-pyrrolidin-1-yl)-2-oxo-ethoxy]-7-methyl-quinoline-2-carboxylic acid in 10 ml DMF were added 0.33 ml DIPEA, 76 mg HOBt and 95 mg EDC. After 5 minutes 428 mg 4-[(S)-2-amino-4-(2H-tetrazol-5-yl)-butyryl]-piperazine-1-carboxylic acid butyl ester hydrotrifluoroacetate were added and the mixture stirred for 24 h. The mixture was concentrated, diluted with DCM and washed with aqueous LiCl (4%) and 0.1 M HCl. The crude product thus obtained was purified by preparative HPLC (C18 reverse phase column, elution with a water/MeCN gradient with 0.1% TFA). The fractions containing the product were lyophilized to yield the pure product as its trifluoroacetate salt. The latter one was transformed to the hydrochloride salt by taking it up twice in water containing 1 M HCl (2 equivalents) and lyophilisation. Yield: 118 mg MS(ES+): m/e=661.

Example 705

4-[(R)-2-({4-[2-((2S,4S)-2-Cyclobutylcarbamoyl-4-hydroxy-pyrrolidin-1-yl)-2-oxo-ethoxy]-7-methyl-quinoline-2-carbonyl}-amino)-3-fluoro-propionyl]-piperazine-1-carboxylic acid butyl ester (i) (2S,4S)-2-Cyclobutylcarbamoyl-4-hydroxy-pyrrolidine-1-carboxylic acid tert-butyl ester To a solution of 4.98 g N-Boc-cis-4-hydroxy-L-proline in 50 ml DMF were added 4.13 g EDC, 2.93 g HOAt, 3.75 ml DIPEA and 1.53 g cyclobutylamine at 0° C. After stirring for 2 h the reaction mixture was concentrated, the residue was dissolved in ethyl acetate and subsequently extracted with aqueous LiCl (4%), 0.1 M HCl and saturated aqueous NaHCO$_3$. The crude product obtained after evaporation of the solvent was pure enough for the subsequent transformation. Yield: 3.32 g colorless amorphous solid.

(ii) (2S,4S)-4-Hydroxy-pyrrolidine-2-carboxylic acid cyclobutylamide hydrotrifluoroacetate To a solution of 463 mg (2S,4S)-2-Cyclobutylcarbamoyl-4-hydroxy-pyrrolidine-1-carboxylic acid tert-butyl ester in 8 ml dichloromethane were added 1.2 ml TFA. After 5 h stirring at RT the solvents were removed and the residue was codistilled twice with toluene. Yield: 463 mg.

(iii) 4-[2-((2S,4S)-2-Cyclobutylcarbamoyl-4-hydroxy-pyrrolidin-1-yl)-2-oxo-ethoxy]-7-methyl-quinoline-2-carboxylic acid ethyl ester To a solution of 976 mg 4-Carboxymethoxy-7-methyl-quinoline-2-carboxylic acid ethyl ester in 5 ml DMF were added 932 mg pentafluorophenol and 970 mg EDC. The mixture was stirred under exclusion of moisture until LCMS indicated complete conversion to the corresponding pentafluorophenolester. (2S,4S)-4-Hydroxy-pyrrolidine-2-carboxylic acid cyclobutylamide hydrotrifluoroacetate (437 mg) was mixed with 1.3 ml N-ethylmorpholine and 10 ml DMF and this mixture added dropwise to the solution of the pentafluorophenolester. After 12 h the reaction mixture was diluted with DCM and washed with aqueous LiCl (4%) and saturated aqueous NaHCO$_3$. The crude product obtained after evaporation of the solvent was purified by preparative HPLC (C18 reverse phase column, elution with a water/MeCN gradient with 0.1% TFA). The fractions containing the product were lyophilized to yield the pure product as its trifluoroacetate salt. Yield: 109 mg.

(iv) 4-[2-((2S,4S)-2-Cyclobutylcarbamoyl-4-hydroxy-pyrrolidin-1-yl)-2-oxo-ethoxy]-7-methyl-quinoline-2-carboxylic acid To a solution of 109 mg 4-[2-((2S,4S)-2-Cyclobutylcarbamoyl-4-hydroxy-pyrrolidin-1-yl)-2-oxo-ethoxy]-7-methyl-quinoline-2-carboxylic acid ethyl ester in 1 ml THF were added 0.24 ml aqueous NaOH (1 M) at 0° C. After 4 h the mixture was brought to pH 4 by adding 1 N HCl and the reaction mixture was concentrated to give the crude product. Yield: 147 mg.

(v) 4-[(R)-2-({4-[2-((2S,4S)-2-Cyclobutylcarbamoyl-4-hydroxy-pyrrolidin-1-yl)-2-oxo-ethoxy]-7-methyl-quinoline-2-carbonyl}-amino)-3-fluoro-propionyl]-piperazine-1-carboxylic acid butyl ester To a solution of 147 mg 4-[2-((2S,4S)-2-Cyclobutylcarbamoyl-4-hydroxy-pyrrolidin-1-yl)-2-oxo-ethoxy]-7-methyl-quinoline-2-carboxylic acid in 3 ml DMF were added 0.18 ml DIPEA and 131 mg HATU. After 5 minutes 134 mg 4-((R)-2-Amino-3-fluoro-propionyl)-piperazine-1-carboxylic acid butyl ester hydrotrifluoroacetate were added and the mixture stirred for 24 h. The mixture was concentrated, diluted with DCM and washed with aqueous LiCl (4%) and 0.1 M HCl. The crude product thus obtained was purified by preparative HPLC (C18 reverse phase column, elution with a water/MeCN gradient with 0.1% TFA). The fractions containing the product were lyophilized to yield the pure product as its trifluoroacetate salt. Yield: 30 mg MS(ES+): m/e=685.

Example 706

4-((R)-3-Fluoro-2-{[7-methyl-4-(2-oxo-2-piperazin-1-yl-ethoxy)-quinoline-2-carbonyl]-amino}-propionyl)-piperazine-1-carboxylic acid butyl ester (i) 4-[2-(4-tert-Butoxycarbonyl-piperazin-1-yl)-2-oxo-ethoxy]-7-methyl-quinoline-2-carboxylic acid ethyl ester To a solution of 990 mg 4-Carboxymethoxy-7-methyl-quinoline-2-carboxylic acid ethyl ester in 5 ml DMF were added 945 mg pentafluorophenol and 984 mg EDC. The mixture was stirred under exclusion of moisture until LCMS indicated complete conversion to the corresponding pentafluorophenolester. Tert-Butyl 1-piperazinecarboxylate (437 mg) was mixed with 0.8 ml N-ethylmorpholine and 10 ml DMF and this mixture added dropwise to the solution of the pentafluorophenolester. After 12 h the reaction mixture was diluted with DCM and washed with aqueous LiCl (4%) and saturated aqueous NaHCO$_3$. The crude product obtained after evaporation of the solvent was purified by flash chromatography on silica eluting with ethyl acetate/heptane gradient. Yield: 988 mg.

(ii) 4-[2-(4-tert-Butoxycarbonyl-piperazin-1-yl)-2-oxo-ethoxy]-7-methyl-quinoline-2-carboxylic acid To a solution of 988 mg 4-[2-(4-tert-Butoxycarbonyl-piperazin-1-yl)-2-oxo-ethoxy]-7-methyl-quinoline-2-carboxylic acid ethyl ester in 10 ml THF were added 2.2 ml aqueous NaOH (1 M) at 0° C. After 2 h the mixture was brought to pH 4 by using Amberlite IR-120 ion exchange resin. The reaction mixture was filtered and concentrated and the crude product obtained used in the next step without further purification. Yield: 925 mg.

(iii) 4-[(R)-3-Fluoro-2-({7-methyl-4-[2-(4-tert-Butoxycarbonyl-piperazin-1-yl)-2-oxo-ethoxy]-quinoline-2-carbonyl}-amino)-propionyl]-piperazine-1-carboxylic acid butyl ester To a solution of 452 mg 4-[2-(4-tert-Butoxycarbonyl-piperazin-1-yl)-2-oxo-ethoxy]-7-methyl-quinoline-2-carboxylic acid in 15 ml DMF were added 0.54 ml DIPEA and 400 mg HATU. After 5 minutes 410 mg 4-((R)-2-Amino-3-fluoro-propionyl)-piperazine-1-carboxylic acid butyl ester hydrotrifluoroacetate were added and the mixture stirred for 24 h. The mixture was concentrated, diluted with DCM and washed with aqueous LiCl (4%), saturated aqueous NaHCO$_3$ and 0.1 M HCl. The crude product thus obtained after evaporation of the solvent was used in the next step without further purification. Yield: 1.28 g.

(iv) 4-((R)-3-Fluoro-2-{[7-methyl-4-(2-oxo-2-piperazin-1-yl-ethoxy)-quinoline-2-carbonyl]-amino}-propionyl)-piperazine-1-carboxylic acid butyl ester To a solution of 1.28 g 4-[(R)-3-Fluoro-2-({7-methyl-4-[2-(4-tert-Butoxycarbonyl-piperazin-1-yl)-2-oxo-ethoxy]-quinoline-2-carbonyl}-amino)-propionyl]-piperazine-1-carboxylic acid butyl ester in 10 ml dichloromethane were added 2 ml TFA. After 24 h stirring at RT the solvents were removed and the residue was codistilled twice with toluene. The crude product thus obtained was purified by preparative HPLC (C18 reverse phase column, elution with a water/MeCN gradient with 0.1% TFA). The fractions containing the product were lyophilized to yield the pure product as its trifluoroacetate salt. Yield: 219 mg MS(ES+): m/e=587.

Example 707

4-[(S)-4-Carboxy-2-({4-[2-((R)-2-hydroxymethyl-pyrrolidin-1-yl)-2-oxo-ethoxy]-7-methyl-quinoline-2-carbonyl}-amino)-butyryl]-piperazine-1-carboxylic acid ethyl ester The title compound was prepared by adapting the procedures described in example 3 with the difference that (R)-1-Pyrrolidin-2-yl-methanol was used instead of (S)-Pyrrolidine-2-carboxylic acid cyclopropylamide hydrochloride. MS (ES$^+$): m/e=614.

Example 708

4-[2-({4-[2-((S)-2-tert-Butylcarbamoyl-pyrrolidin-1-yl)-2-oxo-ethoxy]-quinoline-2-carbonyl}-amino)-acetyl]-piperazine-1-carboxylic acid butyl ester

(i) 4-{2-[(4-Hydroxy-quinoline-2-carbonyl)-amino]-acetyl}-piperazine-1-carboxylic acid butyl ester To a solution of 9.5 g of 4-Hydroxy-quinoline-2-carboxylic acid and 12.2 g of 4-(2-Amino-acetyl)-piperazine-1-carboxylic acid butyl ester in 110 ml of DMF, 7.7 g of HOBT and 9.6 g of EDC was added and the reaction mixture was stirred for 16 h at RT. Then, the reaction mixture was diluted with water and extracted with DCM. The combined organic phases were dried over MgSO$_4$ and the solvents were removed under reduced pressure. The isolated crude product was used in the next reaction step. Yield: 23 g.

(ii) 4-{2-[(4-Benzyloxycarbonylmethoxy-quinoline-2-carbonyl)-amino]-acetyl}-piperazine-1-carboxylic acid butyl ester To a solution of 10 g 4-{2-[(4-Hydroxy-quinoline-2-carbonyl)-amino]acetyl}-piperazine-1-carboxylic acid butyl ester in 41 ml of DMF, 8.6 g of cesium carbonate and 6.1 g of Bromo-acetic acid benzyl ester were added and the reaction mixture was stirred for 16 h at RT. Then, the reaction mixture was diluted with water and extracted with ethyl acetate. The organic phase was dried over MgSO$_4$ and the solvents were removed under reduced pressure. The crude product was purified by chromatography on silica gel eluting with a gradient of n-heptane/ethyl acetate. The fractions containing the product were combined and the solvent evaporated under reduced pressure. Yield: 5.2 g.

(iii) 4-{2-[(4-Carboxymethoxy-quinoline-2-carbonyl)-amino]-acetyl}-piperazine-1-carboxylic acid butyl ester To a solution of 5.2 g 4-{2-[(4-Benzyloxycarbonylmethoxy-quinoline-2-carbonyl)-amino]acetyl}-piperazine-1-carboxylic acid butyl ester in 120 ml ethyl acetate and 16 ml DMF were added under argon 530 mg Pd/C (10%) and the suspension was stirred under an atmosphere of hydrogen (5 bar) for 3 h. The suspension was filtered over a plug of Celite® and washed with DMF. The crude product was obtained after evaporation of the solvent and used in the next reaction step without further purification. Yield: 4.4 g.

(iv) 4-[2-({4-[2-((S)-2-tert-Butylcarbamoyl-pyrrolidin-1-yl)-2-oxo-ethoxy]-quinoline-2-carbonyl}-amino)-acetyl]-piperazine-1-carboxylic acid butyl ester To a solution of 100 mg of 4-{2-[(4-Carboxymethoxy-quinoline-2-carbonyl)-amino]-acetyl}-piperazine-1-carboxylic acid butyl ester in 2 ml of DMF, 48 mg of EDC, 47 mg of pentafluorophenol was added and the reaction mixture was stirred for 2 h. Then, 37 mg of (S)-Pyrrolidine-2-carboxylic acid tert-butylamide and 37 mg of NEM in 2 ml of DMF was added. After 16 h the reaction mixture was diluted with water. After filtration through a chem Elut® cartridge by eluting with DCM the solvents were removed under reduced pressure. The residue was purified by preparative HPLC (C18 reverse phase column, elution with a water/MeCN gradient with 0.1% TFA). The fractions containing the product were lyophilized to yield the pure product as its trifluoroacetate salt. Yield: 52 mg MS(ES+): m/e=625.

Example 709

4-[2-({4-[2-((S)-2-Methylcarbamoyl-pyrrolidin-1-yl)-2-oxo-ethoxy]-quinoline-2-carbonyl}-amino)-acetyl]-piperazine-1-carboxylic acid butyl ester The title compound was prepared by adapting the procedures described in example 708 with the difference that (S)-Pyrrolidine-2-carboxylic acid methylamide was used instead of (S)-Pyrrolidine-2-carboxylic acid tert-butylamide. MS (ES$^+$): m/e=583.

Example 710

4-[2-({4-[2-((S)-2-Ethylcarbamoyl-pyrrolidin-1-yl)-2-oxo-ethoxy]-quinoline-2-carbonyl}-amino)-acetyl]-piperazine-1-carboxylic acid butyl ester The title compound was prepared by adapting the procedures described in example 708 with the difference that (S)-Pyrrolidine-2-carboxylic acid ethylamide was used instead of (S)-Pyrrolidine-2-carboxylic acid tert-butylamide. MS (ES$^+$): m/e=597.

Example 711

4-[2-({4-[2-Oxo-2-(1-oxo-2,7-diaza-spiro[4.5]dec-7-yl)-ethoxy]-quinoline-2-carbonyl}-amino)-acetyl]-piperazine-1-carboxylic acid butyl ester The title compound was prepared by adapting the procedures described in example 708 with the difference that 2,7-

Diaza-spiro[4.5]decan-1-one was used instead of (S)-Pyrrolidine-2-carboxylic acid tert-butylamide. MS (ES+): m/e=609.

Example 712

4-[2-({4-[2-Oxo-2-(3-oxo-piperazin-1-yl)-ethoxy]-quinoline-2-carbonyl}-amino)-acetyl]-piperazine-1-carboxylic acid butyl ester The title compound was prepared by adapting the procedures described in example 708 with the difference that Piperazin-2-one was used instead of (S)-Pyrrolidine-2-carboxylic acid tert-butylamide. MS (ES+): m/e=555.

Example 713

4-{2-[(4-{2-[4-(2-Hydroxy-ethyl)-piperazin-1-yl]-2-oxo-ethoxy]-quinoline-2-carbonyl)-amino]-acetyl}-piperazine-1-carboxylic acid butyl ester The title compound was prepared by adapting the procedures described in example 708 with the difference that 2-Piperazin-1-yl-ethanol was used instead of (S)-Pyrrolidine-2-carboxylic acid tert-butylamide. MS (ES+): m/e=585.

Example 714

4-[2-({4-[2-((S)-2-Cyano-pyrrolidin-1-yl)-2-oxo-ethoxy]-quinoline-2-carbonyl}-amino)-acetyl]-piperazine-1-carboxylic acid butyl ester The title compound was prepared by adapting the procedures described in example 708 with the difference that (S)-Pyrrolidine-2-carbonitrile was used instead of (S)-Pyrrolidine-2-carboxylic acid tert-butylamide. MS (ES+): m/e=551.

Example 715

4-[2-({4-[2-(5,6-Dihydro-8H-[1,2,4]triazolo[4,3-a]pyrazin-7-yl)-2-oxo-ethoxy]-quinoline-2-carbonyl}-aminoacetyl]-piperazine-1-carboxylic acid butyl ester The title compound was prepared by adapting the procedures described in example 708 with the difference that 5,6,7,8-Tetrahydro-[1,2,4]triazolo[4,3-a]pyrazine was used instead of (S)-Pyrrolidine-2-carboxylic acid tert-butylamide. MS (ES+): m/e=579.

Example 716

4-[2-({4-[2-((2S,4S)-2-Cyano-4-fluoro-pyrrolidin-1-yl)-2-oxo-ethoxy]-quinoline-2-carbonyl}-amino)-acetyl]-piperazine-1-carboxylic acid butyl ester The title compound was prepared by adapting the procedures described in example 708 with the difference that (2S,4S)-4-Fluoro-pyrrolidine-2-carbonitrile was used instead of (S)-Pyrrolidine-2-carboxylic acid tert-butylamide. MS (ES+): m/e=569.

Example 717

4-[2-({4-[2-(2-Methyl-octahydro-pyrrolo[3,4-c]pyridin-5-yl)-2-oxo-ethoxy]-quinoline-2-carbonyl}-aminoyacetyl]-piperazine-1-carboxylic acid butyl ester The title compound was prepared by adapting the procedures described in example 708 with the difference that 2-Methyl-octahydro-pyrrolo[3,4-c]pyridine was used instead of (S)-Pyrrolidine-2-carboxylic acid tert-butylamide. MS (ES+): m/e=595.

Example 718

4-[2-({4-[(R)-2-((S)-2-Cyano-pyrrolidin-1-yl)-1-methyl-2-oxo-ethoxy]-7-methyl-quinoline-2-carbonyl}-amino)-acetyl]-piperazine-1-carboxylic acid butyl ester (i) 4-{2-[(4-Hydroxy-7-methyl-quinoline-2-carbonyl)-amino]-acetyl}-piperazine-1-carboxylic acid butyl ester To a solution of 6.0 g of 4-Hydroxy-7-methyl-quinoline-2-carboxylic acid and 7.1 g of 4-(2-Amino-acetyl)-piperazine-1-carboxylic acid butyl ester in 61 ml of DMF, 8.5 g NEM, 5.0 g of HOBT and 6.2 g of EDC was added and the reaction mixture was stirred for 4 h at RT. Then, the reaction mixture was diluted with water and extracted with DCM. The combined organic phases were dried over MgSO$_4$ and the solvents were removed under reduced pressure. The isolated crude product was used in the next reaction step. Yield: 10.7 g.

(ii) 4-(2-{[4-((R)-1-Benzyloxycarbonyl-ethoxy)-7-methyl-quinoline-2-carbonyl]amino}-acetyl)-piperazine-1-carboxylic acid butyl ester To a solution of 6 g 4-{2-[(4-Hydroxy-7-methyl-quinoline-2-carbonyl)-amino]-acetyl}-piperazine-1-carboxylic acid butyl ester and 2.5 g benzyl-L-lactate in 97 ml THF were added 5.5 g triphenylphosphine and 3.6 g diethylazodicarboxylate. After stirring for 16 h at RT LCMS indicated complete conversion and water was added to the reaction mixture which was then extracted with ethyl acetate. The residue obtained after evaporation of the solvent was purified by flash chromatography on silica using an ethyl acetate/heptane gradient. Yield: 5.5 g (iii) 4-(2-{[4-((R)-1-Carboxy-ethoxy)-7-methyl-quinoline-2-carbonyl]-amino}-acetyl)-piperazine-1-carboxylic acid butyl ester To a solution of 6 g 4-((R)-1-Benzyloxycarbonyl-ethoxy)-7-methyl-quinoline-2-carboxylic acid methyl ester in 50 ml ethanol were added 500 mg Pd/C (10%) and the suspension stirred under an atmosphere of hydrogen (4 bar) for 16 h. Then, the reaction mixture was filtrated over a plug of Celite®, washed with ethanol and DMF and then concentrated under reduced pressure. Yield: 4.5 g colorless solid.

(iv) 4-[2-({4-[(R)-2-((S)-2-Cyano-pyrrolidin-1-yl)-1-methyl-2-oxo-ethoxy]-7-methyl-quinoline-2-carbonyl}-aminoyacetyl]-piperazine-1-carboxylic acid butyl ester To a solution of 700 mg of 4-(2-{[4-((R)-1-Carboxy-ethoxy)-7-methyl-quinoline-2-carbonyl]-amino}-acetyl)-piperazine-1-carboxylic acid butyl ester in 5 ml of DCM, 402 mg of EDC, 386 mg of pentafluorophenol was added and the reaction mixture was stirred for 2 h. Then, 150 mg of (S)-Pyrrolidine-2-carbonitrile and 319 mg of NEM in 2 ml of DCM was added. After 16 h the reaction mixture was diluted with water. After filtration through a chem Elut® cartridge by eluting with DCM the solvents were removed under reduced pressure. The residue was purified by preparative HPLC (C18 reverse phase column, elution with a water/MeCN gradient with 0.1% TFA). The fractions containing the product were lyophilized to yield the pure product as its trifluoroacetate salt. The product was dissolved in DCM and washed with saturated aqueous sodium hydrogen carbonate solution and water. The organic phase dried over $MgSO_4$. The solvents were removed under reduced pressure. The residue was dissolved was in water/acetonitrile and lyophilized to yield the product as a white solid. Yield: 103 mg MS(ES+): m/e=579.

Example 719

4-[2-({4-[(R)-2-(3-Hydroxy-azetidin-1-yl)-1-methyl-2-oxo-ethoxy]-7-methyl-quinoline-2-carbonyl}-amino)-acetyl]-piperazine-1-carboxylic acid butyl ester The title compound was prepared by adapting the procedures described in example 718 with the difference that Azetidin-3-ol was used instead of (S)-Pyrrolidine-2-carbonitrile. MS (ES$^+$): m/e=656.

Example 720

4-[2-({4-[(R)-2-(3,3-Difluoro-pyrrolidin-1-yl)-1-methyl-2-oxo-ethoxy]-7-methyl-quinoline-2-carbonyl}-amino)-acetyl]-piperazine-1-carboxylic acid butyl ester The title compound was prepared by adapting the procedures described in example 718 with the difference that 3,3-Difluoro-pyrrolidine was used instead of (S)-Pyrrolidine-2-carbonitrile. MS (ES$^+$): m/e=590.

Example 721

4-[2-({7-Methyl-4-[(R)-1-methyl-2-(2-methyl-octahydro-pyrrolo[3,4-c]pyridin-5-yl)-2-oxo-ethoxy]-quinoline-2-carbonyl}-amino)-acetyl]-piperazine-1-carboxylic acid butyl ester The title compound was prepared by adapting the procedures described in example 718 with the difference that 2-Methyl-octahydro-pyrrolo[3,4-c]pyridine was used instead of (S)-Pyrrolidine-2-carbonitrile. MS (ES$^+$): m/e=623.

Example 722

4-[2-({4-[(R)-2-((2S,4R)-4-Cyano-2-cyclobutylcarbamoyl-pyrrolidin-1-yl)-1-methyl-2-oxo-ethoxy]-7-methyl-quinoline-2-carbonyl}-amino)-acetyl]-piperazine-1-carboxylic acid butyl ester The title compound was prepared by adapting the procedures described in example 718 with the difference that (2S,4R)-4-Cyano-pyrrolidine-2-carboxylic acid cyclobutylamide was used instead of (S)-Pyrrolidine-2-carbonitrile. MS (ES$^+$): m/e=676.

Example 723

4-[2-({4-[2-((2S,4R)-4-Cyano-2-cyclobutylcarbamoyl-pyrrolidin-1-yl)-2-oxo-ethoxy]-6,7-dimethyl-quinoline-2-carbonyl}-amino)-acetyl]-piperazine-1-carboxylic acid butyl ester The title compound was prepared by adapting the procedures described in example 435 with the difference that 4-Hydroxy-6,7-dimethyl-quinoline-2-carboxylic acid and (2S,4R)-4-Cyano-pyrrolidine-2-carboxylic acid cyclobutylamide was used instead of 4-Hydroxy-7-methyl-quinoline-2-carboxylic acid and (S)-Pyrrolidine-2-carboxylic acid cyclobutylamide. MS (ES$^+$): m/e=676.

Example 724

4-[2-({7-Chloro-4-[2-((2S,4R)-4-cyano-2-cyclobutylcarbamoyl-pyrrolidin-1-yl)-2-oxo-ethoxy]-quinoline-2-carbonyl}-amino)-acetyl]-piperazine-1-carboxylic acid butyl ester The title compound was prepared by adapting the procedures described in example 435 with the difference that 7-Chloro-4-hydroxy-quinoline-2-carboxylic acid and (2S,4R)-4-Cyano-pyrrolidine-2-carboxylic acid cyclobutylamide was used instead of 4-Hydroxy-7-methyl-quinoline-2-carboxylic acid and (S)-Pyrrolidine-2-carboxylic acid cyclobutylamide. MS (ES$^+$): m/e=682, chloro pattern.

Pharmacological Testing

The ability of the compounds of the formula I to inhibit the P2Y12 receptor can be assessed by determining the concentration of the compound of the formula I that binds to the human P2Y12 Recombinant Cell Membrane Binding Assay with 33P 2MeS-ADP.

Human P2Y12 Recombinant Cell Membrane Binding Assay

The ability of a test compound to bind to the P2Y12 receptor was evaluated in a recombinant cell membrane binding assay. In this competitive binding assay, the test compound competed against a radiolabeled agonist for binding to the P2Y12 receptor, expressed on the cell membrane. Inhibition of binding of the labeled material was measured and correlated to the amount and potency of the test compound. This binding assay is a modification of the procedure described by Takasaki, J. et. al, Mol. Pharmacol., 2001, Vol. 60, pg. 432.

As source of P2Y12, a membrane preparation was prepared from Chinese Hamster Ovary (CHO) cells with recombinant expression of the human P2Y12 receptor according to standard procedures.

To a 96-well microtiter plate the following were added: a) 24 µl of assay buffer (10 mM HEPES, 138 mM NaCl, 2.9 mN KCl, 12 mM $NaHCO_3$, 1 mM EDTA-Na, 0.1% BSA, pH 7.4) b) 1 µL compound in DMSO c) 50 µL P2Y12 CHO membrane (20 µg/ml) and after 15 min at RT d) 25 µL of 1.61 nM 33P 2MeS-ADP (Perkin Elmer NEN custom synthesis, specific activity ~2100 Ci/mmol) made in assay buffer.

After 20 min incubation at RT samples were transferred to 96-well microtiter filter plates (Millipore HTS GF/B), pre-wetted for 20 min with 300 µL of stop buffer (10 mM HEPES, 138 mM NaCl pH 7.4) and then filtered through completely with a Millipore plate vacuum. Next, wells were washed four times with 400 µl/well of stop buffer on a plate vacuum. The plate was disassembled and allowed to air dry overnight with the filter side up over night. The filter plates were snapped into adapter plates and 0.1 mL of Microscint 20 Scintillation Fluid (Perkin Elmer #6013621) was added to each well. The top of the filter plate was sealed with plastic plate covers. The sealed filter plate were incubated 2 hours at RT. A Microbeta Scintillation Counter was used to measure counts. The binding of compound is expressed as a % inhibition of specific binding, defined by subtraction of the background with 1 mM ADP.

Compounds were diluted as 10 mM DMSO stocks and tested in a four-point, five-fold dilution series run in triplicate beginning at 10 µM, final concentration. Data were analyzed using a four-parameter curve fit with a fixed minimum and maximum experimentally defined as the average positive and negative controls on each plate.

The $IC_{50}$ data of the above described human P2Y12 recombinant cell membrane binding assay for exemplary compounds of the present invention are shown in table 1.

TABLE 1

| Example | IC50 [mikro M] |
|---------|----------------|
| 11 | 0.132 |
| 57 | 0.008 |
| 121 | 0.067 |
| 182 | 0.017 |
| 196 | 0.065 |
| 216 | 0.083 |
| 246 | 0.071 |
| 253 | 0.028 |
| 270 | 0.009 |
| 296 | 0.012 |
| 300 | 0.005 |
| 334 | 0.102 |
| 354 | 0.004 |
| 424 | 0.033 |
| 490 | 0.005 |
| 511 | 0.021 |
| 528 | 0.004 |
| 600 | 0.008 |
| 673 | 0.005 |
| 679 | 0.003 |

Inhibition of Human Platelet Aggregation

Alternatively to a binding assay which measures a compound's ability to bind to the P2Y12 receptor, the effect on cellular function was also determined. This ability of the compound was evaluated in two platelet aggregation assays: in 96-well plates and with the "Born"-method using single cuvettes.

96-Well Assay:

Whole blood was collected from healthy volunteers using 20 ml syringes containing 2 ml of ACD-A Aqua-Citrat-Dextrose-A, Fresenius). The anticoagulated whole blood was transferred into 15 ml polypropylene conical tubes (10 ml per tube). The tubes were centrifuged for 15 minutes at 150×g at RT without using the centrifuge brake. This procedure leads to a pellet of cellular components and a supernatant of platelet rich plasma (PRP). The PRP layer was collected from each tube and pooled for each donor. To avoid carry over of cellular components following centrifugation, approximately 5 ml of PRP was left in the tube. The platelet concentration was determined using a Coulter Counter.

The 15 ml tubes containing the pellet of cellular components were centrifuged again for 10 minutes at 1940×g. This pelleted out most particulate blood constituents remaining, leaving a layer of Platelet Poor Plasma (PPP). The PPP was collected for each donor. The PRP layer, previously set aside, was diluted with PPP to a final concentration of approximately 3×E8 platelets/ml with the PPP.

The human platelet aggregation assay is performed in 96-well plates using a microtiter plate reader (SpectraMax Plus 384 with SoftMax Pro software from Molecular Devices).

In the plate 15 µl of test compound at 10× final concentration in NaCl is mixed with 120 µl fresh PRP and incubated for 5 minutes. Following that incubation period, 15 µl of 40 µM ADP is added to the reaction mix. This addition of ADP is sufficient to induce aggregation in the absence of an inhibitor. The plates are then transferred to the microplate reader and aggregation is measured over 20 minutes. The instrument settings include: Absorbance at 650 nm, run time 20 minutes with readings in 1-minute intervals and 50 seconds shaking between readings all performed at 37° C. Results of the assay are expressed as % inhibition, and are calculated using area under curve (AUC) of the absorbance over 20 minutes.

The $IC_{50}$ data of the above described platelet aggregation 96-well assay using human platelet rich plasma for exemplary compounds of the present invention are shown in table 2.

TABLE 2

| Example | IC50 [mikro M] |
|---------|----------------|
| 10 | 0.18 |
| 179 | 0.03 |
| 308 | 0.06 |
| 308 | 0.06 |
| 460 | 0.073 |
| 472 | 0.065 |

"Born"-Method:

Whole blood was collected from healthy volunteers using 20 ml syringes containing 2 ml of buffered Citrate. The anticoagulated whole blood was transferred into 15 ml polypropylene conical tubes (10 ml per tube). The tubes were centrifuged for 15 minutes at 340×g at RT without using the centrifuge brake. This procedure leads to a pellet of cellular components and a supernatant of platelet rich plasma (PRP). The PRP layer was collected from each tube and pooled for each donor. To avoid carry over of cellular components following centrifugation, approximately 5 ml of PRP was left in the tube. The platelet concentration was determined using a Coulter Counter.

The 15 ml tubes containing the pellet of cellular components were centrifuged again for 10 minutes at 1940×g. This pelleted out most particulate blood constituents remaining, leaving a layer of Platelet Poor Plasma (PPP). The PPP was collected for each donor. The PRP layer, previously set aside, was diluted with PPP to a final concentration of approximately 3×E8 platelets/ml with the PPP.

The human platelet aggregation assay is performed in single use cuvettes using the platelet aggregation profiler (PAP-4 or -8, Bio/Data corporation).

In the assay cuvette 4 µl of test compound at 100× final concentration in DMSO is mixed with 392 µl fresh PRP and incubated for 2 minutes at 37° C. with 1.200 rpm stirring. Following that incubation period, 4 µl of 250 µM ADP is added to the reaction mix. This addition of ADP is sufficient to induce aggregation in the absence of an inhibitor. After that aggregation is measured over 6 minutes at 37° C. with 1.200 rpm stirring. Results of the assay are expressed as % inhibition, and are calculated using maximum aggregation (Tmax) or area under curve (AUC) of the absorbance over 6 minutes.

The $IC_{50}$ data of the above described platelet aggregation assay using human platelet rich plasma for exemplary compounds of the present invention are shown in table 3.

TABLE 3

| Example | $IC_{50}$ [mikro M] |
|---------|----------------|
| 3 | 0.18 |
| 17 | 0.24 |
| 18 | 0.16 |
| 50 | 0.59 |
| 71 | 0.31 |
| 75 | 0.19 |
| 294 | 0.03 |
| 317 | 0.29 |
| 435 | 0.030 |
| 481 | 0.08 |
| 521 | 0.12 |

TABLE 3-continued

| Example | IC$_{50}$ [mikro M] |
|---|---|
| 594 | 0.020 |
| 660 | 0.094 |
| 689 | 0.0006 |
| 693 | 0.077 |

What is claimed is:

1. A compound of formula I,

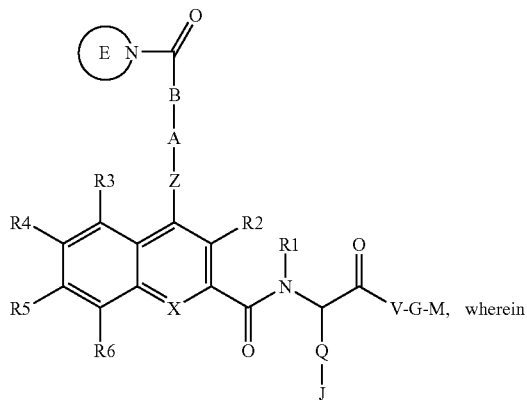

(I)

E is a heterocyclic residue selected from aza-bicycloheptane, aza-bicyclohexane, aza-bicyclooctane, aza-spiroheptane, aza-spirohexane, aza-spirooctane, aza-spiropentane, azepane, azepine, azetidine, aziridine, decahydro-quinoline, diaza-bicyclohexane, diaza-bicycloheptane, 2,5-Diaza-bicyclo[2.2.1]heptane, 1,2-diazapane, 2,7-diaza-spiro[4.5]decane, 2,8-diaza-spiro[4.5]decane, diaza-spirohexane, diaza-spirooctane, diaza-spiropentane, diaza-spiroheptane, 1,3-diazepane, 1,4-diazepane, 1,2-diazepine, 1,3-diazepine, 1,4-diazepine, dihydroazepine, 2,3-dihydro-1H-indole, 3,4-dihydro-1H-isoquinoline, 4,7-dihydro-5H-isoxazolo[5,4-c]pyridine, 6,7-dihydro-4H-isoxazolo[4,5-c]pyridine, dihydro-pyridazine, dihydro-oxazepine, 6,7-dihydro-4H-oxazolo[5,4-c]pyridine, 4,6-dihydro-1H-pyrrolo[3,4-c]pyrazol, 4,6-dihydro-4H-pyrrolo[3,4-d]thiazole, 6,7-dihydro-4H-thiazolo[5,4-c]pyridine, 4,7-dihydro-5H-thieno[2,3-c]pyridine, 5,6-Dihydro-8H-[1,2,4]triazolo[4,3-a]pyrazin, dioxazole, hexahydro-cyclopenta[c]pyrroline, hexahydro-pyridazine, hexahydro-pyrrolo[1,2-a]pyrazin, hexahydro-pyrrolo[3,4-b]pyrrol, Hexahydro-pyrrolo[1,2-a]pyrazin, imidazoline, imidazolidine, indole, isoquinoline, isothiazolidine, isothiazoline, isoxazoline, isoxazolidine, ketopiperazine, morpholine, octahydro-cyclopenta[c]pyrrole, octahydro-indole, octahydro-pyrrolo[3,4-b]pyridine, octahydro-pyrrolo[3,4-c]pyridine, 1,4-oxazepane, oxazepine, 1,2-oxa-thiepane, 1,2-oxazine, 1,3-oxazine, 1,4-oxazine, oxazolidine, piperazine, piperidine, pyrazine, pyrazoline, pyrazolidine, pyridazine, pyrrolidine, pyrrolidinone, pyrroline, tetrahydropyridine, tetrahydro-azepine, 1,2,3,4-tetrahydro-isoquinoline, 4,5,6,7-tetrahydro-isoxazolo[4,5-c]pyridine, 1,2,3,4-tetrahydropyrazine, 1,4,6,7-tetrahydro-pyrazolo[4,3-c]pyridine, 4,5,6,7-tetrahydro-1H-pyrazolo[4,3-c]pyridine, tetrahydro-pyridazine, 3,5,7,8-tetrahydro-4H-pyrido[4,3-d]pyrimidine, 4,5,6,6a-tetrahydro-3aH-pyrrolo[3,4-d]isoxazole, 1,2,3,4-tetrahydro-quinoline, 4,5,6,7-tetrahydro-thieno[2,3-c]pyridine, 1,4,6,7-tetrahydro-thiazolo[5,4-c]pyridine, 4,5,6,7-tetrahydro-thieno[3,2-c]pyridine, tetrazine, tetrazole, thiadiazine, 1,2-thiazine, 1,3-thiazine, 1,4-thiazine, 1,3-thiazole, thiazolidine, thiazoline, thietan, thiomorpholine, 1,3,8-triaza-spiro[4.5]decane, triaza-spirooctane, triazepane, 1,2,4-triazinane and 1,3,5-triazinane, wherein said heterocyclic residue is bond by its nitrogen atom to the carbonyl carbon atom and wherein said heterocyclic residue is unsubstituted or mono-, di- or trisubstituted independently of one another by R7, X is selected from nitrogen atom or C—R8, Q is selected from 1) a covalent bond,
2) —(C$_0$-C$_4$)-alkylene-CH(OH)—(C$_0$-C$_4$)-alkylene-,
3) —(C$_0$-C$_4$)-alkylene-O—(C$_0$-C$_4$)-alkylene-,
4) —(C$_0$-C$_4$)-alkylene-O—C(O)—N(R10)-(C$_0$-C$_4$)-alkylene-,
5) —(C$_0$-C$_4$)-alkylene-C(O)—(C$_0$-C$_4$)-alkylene-,
6) —(C$_0$-C$_4$)-alkylene-C(O)—O—(C$_0$-C$_4$)-alkylene-,
7) —(C$_0$-C$_4$)-alkylene-C(O)—NR10—,
8) —(C$_0$-C$_4$)-alkylene-N(R$^{10}$)—(C$_0$-C$_4$)-alkylene-,
9) —(C$_0$-C$_4$)-alkylene-N(R10)-C(O)—(C$_0$-C$_4$)-alkylene-,
10) —(C$_0$-C$_4$)-alkylene-N(R10)-C(O)—O—(C$_0$-C$_4$)-alkylene-,
11) —(C$_0$-C$_4$)-alkylene-N(R10)-C(O)—N(R10)-(C$_0$-C$_4$)-alkylene-,
12) —(C$_0$-C$_4$)-alkylene-N(R10)-SO$_2$—(C$_0$-C$_4$)-alkylene-,
13) —(C$_0$-C$_4$)-alkylene-N(R10)-SO$_2$—NR10-(C$_0$-C$_4$)-alkylene-,
14) —(C$_0$-C$_4$)-alkylene-S—(C$_0$-C$_4$)-alkylene-,
15) —(C$_0$-C$_4$)-alkylene-SO$_2$—(C$_0$-C$_4$)-alkylene-,
16) —(C$_0$-C$_4$)-alkylene-(C$_3$-C$_8$)-cycloalkyl-(C$_0$-C$_4$)-alkylene-, or
17) —(C$_0$-C$_4$)-alkylene-(C$_3$-C$_{15}$)-heterocyclyl-(C$_0$-C$_4$)-alkylene-, wherein heterocyclyl is selected from acridinyl, azabenzimidazolyl, aza-bicycloheptanyl, aza-bicyclohexanyl, aza-bicyclooctanyl, 8-aza-bicyclo[3.2.1]octanyl, azaspirodecanyl, aza-spiroheptanyl, aza-spirohexanyl, aza-spirooctanyl, aza-spiropentanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydro-quinolinyl, diaza-bicyclohexanyl, diaza-bicycloheptanyl, 2,5-diaza-bicyclo[2.2.1]heptanyl, 1,2-diazapanyl, diaza-spirohexanyl, diaza-spirooctanyl, diaza-spiropentanyl, diaza-spiroheptanyl, 1,3-diazepanyl, 1,4-diazepanyl, 1,2-diazepinyl, 1,3-diazepinyl, 1,4-diazepinyl, dihydroazepinyl, 3,4-dihydro-2H-quinoline, dihydrofuro[2,3-b]-tetrahydrofuranyl, 2,3-dihydro-1H-indolyl, 3,4-dihydro-1H-isoquinolinyl, 6,7-dihydro-4H-isoxazolo[4,5-c]pyridinyl, dihydro-pyridazinyl, 4,5-dihydro-[1,3,4]oxadiazol, dihydro-oxazepinyl, 4,5-dihydrooxazolinyl, 4,6-dihydro-4H-pyrrolo[3,4-d]thiazolyl, 6,7-dihydro-4H-thiazolo[5,4-c]pyridinyl, 4,7-dihydro-5H-thieno[2,3-c]pyridinyl, 1,3-dioxanyl, dioxazolyl, dioxazinyl, 1,3-dioxolanyl, 1,3-dioxolenyl, 3,3-dioxo[1,3,4]oxathiazinyl, 6H-1,5,2-dithiazinyl, furanyl, furazanyl, hexahydro-pyridazine, hexahydro-cyclopenta[c]pyrroline, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydro-cyclopenta[c]pyrrolyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 1H-pyrrolopyridinyl, 2H-pyrrolyl, pyrrolyl, quinazolinyl, quinolinyl, 4H-quinolizinyl, quinoxalinyl, quinuclidinyl, tetrahydrofuranyl, 1,2,3,4-tetrahydroisoquinolinyl, 4,5,6,7-tetrahydro-isoxazolo[4,5-c]pyridinyl, tetrahydropyranyl, 1,2,3,4-tetrahydropyrazinyl, 4,5,6,7-tetrahydro-1H-pyrazolo[4,3-c]pyridinyl, tetrahydro-pyridazinyl, tetrahydro-pyridinyl, 4,5,6,6a-tetrahydro-3aH-pyrrolo[3,4-d]isoxazolyl, 1,2,3,4-tetrahydro-quinolinyl, 4,5,6,7-tetrahydro-thieno[2,3-c]pyridinyl, 1,4,6,7-tetrahydro-thiazolo[5,4-c]pyridinyl, 4,5,6,7-tetrahydro-thieno[3,2-c]pyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, triaza-spirooctanyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl, and xanthenyl, and wherein said —($C_3$-$C_{15}$)-heterocyclyl is unsubstituted or mono-, di- or trisubstituted independently of one another by R14; and wherein the alkyl residues are unsubstituted or mono-, di- or trisubstituted independently of one another by halogen, —$NH_2$, —OH; or —($C_3$-$C_6$)-cycloalkyl, wherein cycloalkyl is unsubstituted or mono-, di- or trisubstituted independently of one another by halogen, —$NH_2$ or —OH;

J is
1) a hydrogen atom,
2) —($C_1$-$C_6$)-alkyl, wherein alkyl is unsubstituted or mono-, di- or trisubstituted independently of one another by R13,
3) —($C_0$-$C_4$)-alkylene-C(O)—R11,
4) —($C_0$-$C_4$)-alkylene-C(O)—O—R11,
5) —($C_0$-$C_4$)-alkylene-C(O)—O—($C_1$-$C_4$)-alkylene-O—C(O)—R17, wherein —($C_1$-$C_4$)-alkylene is unsubstituted or mono-, di- or trisubstituted independently of one another by R15,
6) —($C_0$-$C_4$)-alkylene-C(O)—O—($C_1$-$C_4$)-alkylene-O—C(O)—O—R17, wherein —($C_1$-$C_4$)-alkylene is unsubstituted or mono-, di- or trisubstituted independently of one another by R15,
7) —($C_0$-$C_4$)-alkylene-C(O)—N(R11)-R13
8) —($C_0$-$C_4$)-alkylene-N(R11)-R13,
9) —($C_0$-$C_4$)-alkylene-N(R10)-$SO_2$—R10,
10) —($C_0$-$C_4$)-alkylene-$SO_s$—R11, wherein s is 1 or 2,
11) —($C_0$-$C_4$)-alkylene-$SO_t$—N(R11)-R12, wherein t is 1 or 2,
12) —($C_0$-$C_4$)-alkylene-$SO_w$—N(R11)-R13, wherein w is 1 or 2,
13) —($C_0$-$C_4$)-alkylene-R22,
14) —($C_0$-$C_4$)-alkylene-($C_3$-$C_8$)-cycloalkyl, wherein cycloalkyl is unsubstituted or mono-, di- or trisubstituted independently of one another by R13,
15) —($C_0$-$C_4$)-alkylene-($C_6$-$C_{14}$)-aryl, wherein aryl is selected from phenyl, naphthyl, biphenylyl, indanyl, anthryl and fluorenyl and aryl is unsubstituted or mono-, di- or trisubstituted independently of one another by R13, or
16) —($C_0$-$C_4$)-alkylene-($C_3$-$C_{15}$)-heterocyclyl, wherein —($C_3$-$C_{15}$)-heterocyclyl is as defined above and is unsubstituted or mono-, di- or trisubstituted independently of one another by R13, R1 is a hydrogen atom, —($C_1$-$C_4$)-alkyl, wherein alkyl is unsubstituted or substituted one to three times by R13; —($C_1$-$C_3$)-alkylene-C(O)—NH—R10 or —($C_1$-$C_3$)-alkylene-C(O)—O—R10, Z is
1) —($C_0$-$C_8$)-alkylene-,
2) —($C_2$-$C_{10}$)-alkenyl-,
3) —($C_2$-$C_{10}$)-alkynyl-,
4) —($C_0$-$C_4$)-alkylene-O—($C_0$-$C_4$)-alkylene-,
5) —($C_0$-$C_4$)-alkylene-O—C(O)—N(R10)-($C_0$-$C_4$)-alkylene-,
6) —($C_0$-$C_4$)-alkylene-C(O)—($C_0$-$C_4$)-alkylene-,
7) —($C_0$-$C_4$)-alkylene-N(R10)-C(O)—($C_0$-$C_4$)-alkylene-,
8) —($C_0$-$C_4$)-alkylene-N(R10)-C(O)—O—($C_0$-$C_4$)-alkylene-,
9) —($C_0$-$C_4$)-alkylene-N(R10)-C(O)—N(R10)-($C_0$-$C_4$)-alkylene-,
10) —($C_0$-$C_4$)-alkylene-N(R10)-($C_0$-$C_4$)-alkylene-,
11) —($C_0$-$C_4$)-alkylene-S—($C_0$-$C_4$)-alkylene-,
12) —($C_0$-$C_4$)-alkylene-S(O)—($C_0$-$C_4$)-alkylene-,
13) —($C_0$-$C_4$)-alkylene-$SO_2$—($C_0$-$C_4$)-alkylene-, or
14) —($C_0$-$C_4$)-alkylene-($C_3$-$C_8$)-cycloalkyl-($C_0$-$C_4$)-alkylene-, A is a covalent bond, —($C_3$-$C_8$)-alkylene, —($C_3$-$C_8$)-cycloalkylene or —($C_3$-$C_{15}$)-heterocyclyl, wherein —($C_3$-$C_{15}$)-heterocyclyl is as defined above, B is
1) a covalent bond,
2) —($C_2$-$C_{10}$)-alkenyl-,
3) —($C_2$-$C_{10}$)-alkynyl-,
4) —($C_0$-$C_4$)-alkylene-CH(OH)—($C_0$-$C_4$)-alkylene-,
5) —($C_0$-$C_4$)-alkylene-O—($C_0$-$C_4$)-alkylene-,
6) —($C_0$-$C_4$)-alkylene-O—C(O)—N(R10)-($C_0$-$C_4$)-alkylene-,
7) —($C_0$-$C_4$)-alkylene-C(O)—($C_0$-$C_4$)-alkylene-,
8) —($C_0$-$C_4$)-alkylene-C(O)—O—($C_0$-$C_4$)-alkylene-,
9) —($C_0$-$C_4$)-alkylene-C(O)—N(R10)-,
10) —($C_0$-$C_4$)-alkylene-N(R10)-($C_0$-$C_4$)-alkylene-,
11) —($C_0$-$C_4$)-alkylene-N(R10)-C(O)—($C_0$-$C_4$)-alkylene-,
12) —($C_0$-$C_4$)-alkylene-N(R10)-C(O)—O—($C_0$-$C_4$)-alkylene-,
13) —($C_0$-$C_4$)-alkylene-N(R10)-C(O)—N(R10)-($C_0$-$C_4$)-alkylene-,
14) —($C_0$-$C_4$)-alkylene-N(R10)-$SO_2$—($C_0$-$C_4$)-alkylene-,
15) —($C_0$-$C_4$)-alkylene-N(R10)-$SO_2$—N(R10)-($C_0$-$C_4$)-alkylene-,
16) —($C_0$-$C_4$)-alkylene-S—($C_0$-$C_4$)-alkylene-,
17) —($C_0$-$C_4$)-alkylene-S(O)—($C_0$-$C_4$)-alkylene-,
18) —($C_0$-$C_4$)-alkylene-$SO_2$—($C_0$-$C_4$)-alkylene-,
19) —($C_0$-$C_4$)-alkylene-$SO_2$—N(R10)-($C_0$-$C_4$)-alkylene-, 20) —($C_0$-$C_4$)-alkylene-($C_3$-$C_8$)-cycloalkyl-($C_0$-$C_4$)-alkylene-, or
21) —($C_0$-$C_4$)-alkylene-($C_3$-$C_{15}$)-heterocyclyl-($C_0$-$C_4$)-alkylene-, wherein —($C_3$-$C_{15}$)-heterocyclyl is as defined above, wherein said heterocyclyl is unsubstituted or mono-, di- or trisubstituted independently of one another by R14, and wherein the alkyl residues are unsubstituted or mono-, di- or trisubstituted independently of one another by halogen, —$NH_2$, —OH; or —($C_3$-$C_6$)-cycloalkyl, wherein cycloalkyl is unsubstituted or mono-, di- or trisubstituted independently of one another by halogen, —$NH_2$ or —OH;

R14 is halogen, —OH, =O, —($C_1$-$C_8$)-alkyl, —($C_1$-$C_4$)-alkoxy, —$NO_2$, —CN, —$NH_2$, —S—R18, —($C_1$-$C_4$)-alkylene-C(O)—OH, —C(O)—O—($C_1$-$C_4$)-alkyl, —($C_1$-$C_4$)-alkylene-C(O)—$NH_2$, —($C_0$-$C_8$)-alkylene-$SO_2$—($C_1$-$C_4$)-alkyl, —($C_0$-$C_8$)-alkylene-$SO_2$—($C_1$-$C_3$)-fluoroalkyl, —($C_0$-$C_8$)-alkylene-$SO_2$—N(R18)-R21, —($C_1$-$C_4$)-alkylene-C(O)—NH—($C_1$-$C_8$)-alkyl, —($C_1$-$C_4$)-alkylene-C(O)—N—[($C_1$-$C_8$)-alkyl]$_2$, —N(R18)-C(O)—NH—($C_1$-$C_8$)-alkyl, —N(R18)-C(O)—NH—[($C_1$-$C_8$)-alkyl]$_2$, —($C_2$-$C_{10}$)-alkenyl, or —($C_2$-$C_{10}$)-alkynyl, wherein R18 and R21 are independently from each other hydrogen atom, —($C_1$-$C_3$)-fluoroalkyl or —($C_1$-$C_6$)-alkyl, V is —($C_3$-$C_{15}$)-heterocyclyl or —N(R1)-($C_3$-$C_{15}$)-heterocyclyl, wherein —($C_3$-$C_{15}$)-heterocyclyl is as defined above and is unsubstituted or mono-, di- or trisubstituted independently of one another by R14, G is
1) a covalent bond,
2) —($C_0$-$C_4$)-alkylene-CH(OH)—($C_0$-$C_4$)-alkylene-,
3) —($C_0$-$C_4$)-alkylene-O—($C_0$-$C_4$)-alkylene-,
4) —($C_0$-$C_4$)-alkylene-O—C(O)—N(R10)-($C_0$-$C_4$)-alkylene-,
5) —($C_0$-$C_4$)-alkylene-C(O)—($C_0$-$C_4$)-alkylene-,
6) —($C_0$-$C_4$)-alkylene-C(O)—O—($C_0$-$C_4$)-alkylene-,
7) —($C_0$-$C_4$)-alkylene-C(O)—N(R10)-,
8) —($C_0$-$C_4$)-alkylene-N(R10)-($C_0$-$C_4$)-alkylene-,
9) —($C_0$-$C_4$)-alkylene-N(R10)-C(O)—($C_0$-$C_4$)-alkylene-,
10) —($C_0$-$C_4$)-alkylene-N(R10)-C(O)—O—($C_0$-$C_4$)-alkylene-,
11) —($C_0$-$C_4$)-alkylene-N(R10)-C(O)—N(R10)-($C_0$-$C_4$)-alkylene-,
12) —($C_0$-$C_4$)-alkylene-N(R10)-$SO_2$—($C_0$-$C_4$)-alkylene-,
13) —($C_0$-$C_4$)-alkylene-N(R10)-$SO_2$—N(R10)-($C_0$-$C_4$)-alkylene-,
14) —($C_0$-$C_4$)-alkylene-S—($C_0$-$C_4$)-alkylene-,
15) —($C_0$-$C_4$)-alkylene-S(O)—($C_0$-$C_4$)-alkylene-,
16) —($C_0$-$C_4$)-alkylene-$SO_2$—($C_0$-$C_4$)-alkylene-,
17) —($C_0$-$C_4$)-alkylene-$SO_2$—N(R10)-($C_0$-$C_4$)-alkylene-, or
18) —($C_0$-$C_4$)-alkylene-($C_3$-$C_8$)-cycloalkyl-($C_0$-$C_4$)-alkylene-, and wherein the alkyl residues are unsubstituted or mono-, di- or trisubstituted independently of one another by halogen, —$NH_2$, —OH; or —($C_3$-$C_6$)-cycloalkyl, wherein cycloalkyl is unsubstituted or mono-, di- or trisubstituted independently of one another by halogen, —$NH_2$ or —OH;

M is
1) a hydrogen atom,
2) —($C_1$-$C_8$)-alkyl, wherein alkyl is unsubstituted or mono-, di- or trisubstituted independently of one another by R14,
3) —C(O)—N(R11)-R12,
4) —C(O)—O—R12,
5) —($C_1$-$C_8$)-alkylen-N(R10)$_2$, 6) —($C_6$-$C_{14}$)-aryl, wherein aryl is as defined above and is unsubstituted or mono-, di- or trisubstituted independently of one another by R14,
7) —($C_3$-$C_8$)-cycloalkyl, wherein said cycloalkyl is unsubstituted or mono-, di- or trisubstituted independently of one another by R14, or
8) a 3- to 7-membered heterocyclyl, containing 1, 2, 3 or 4 heteroatoms chosen from nitrogen, sulfur or oxygen, selected from azepine, azetidine, aziridine, azirine, 1,4-diazepane, 1,2-diazepine, 1,3-diazepine, 1,4-diazepine, diaziridine, diazirine, dihydroimidazolone, dioxazole, dioxazine, dioxole, 1,3-dioxolene, 1,3-dioxolane, furan, imidazole, imidazoline, imidazolidine, imidazolidinone, isothiazole, isothiazolidine, isothiazoline, isoxazole, isoxazoline, isoxazolidine, morpholine, 1,2-oxathiepane, 1,2-oxathiolane, 1,4-oxazepane, 1,2-oxazine, 1,3-oxazine, 1,4-oxazine, oxazolone, oxazole, [1,3,4] oxathiazinane 3,3-dioxide, oxaziridine, oxazolidinone, oxetan, oxirane, piperazine, piperidine, pyran, pyrazine, pyrazole, pyrazoline, pyrazolidine, pyridazine, pyridine, pyridinone, pyrimidine, pyrimidine-2,4-dione, pyrrole, pyrrolidine, pyrrolidinone, pyrroline, tetrahydrofuran, tetrahydropyran, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiomorpholine 1,1-dioxide thiopyran, 1,2,3-triazine, 1,2,4-triazine, 1,3,5-triazine, 1,2,3-triazole and 1,2,4-triazole, wherein said cyclic residue is unsubstituted or mono-, di- or trisubstituted independently of one another by R14, R2, R3, R4, R5, R6 and R8 are independently of one another selected from
1) a hydrogen atom,
2) —($C_1$-$C_6$)-alkyl, wherein alkyl is unsubstituted or mono-, di- or trisubstituted independently of one another by R13,
3) —($C_0$-$C_4$)-alkylene-O—R10,
4) halogen,
5) —($C_1$-$C_3$)-fluoroalkyl,
6) —CN or
7) phenyl, wherein phenyl is unsubstituted or mono-, di- or trisubstituted independently of one another by R13, or R3 and R4, R4 and R5 or R5 and R6 are each time both —O—R10 and form together with the atoms which they are attached to a 1,3-dioxole ring or 2,3-dihydro-[1,4]dioxine ring, which is unsubstituted or substituted one, two, three or four times by R13, R3 and R4, R4 and R5 or R5 and R6 form together with the atoms which they are attached to a cyclopentyl or cyclohexyl, which is unsubstituted or substituted one, two, three or four times by R13, R7 is
1) a hydrogen atom,
2) halogen,
3) —($C_1$-$C_6$)-alkyl, wherein alkyl is unsubstituted or mono-, di- or trisubstituted independently of one another by R13, 4) =O,
5) —($C_1$-$C_3$)-fluoroalkyl,
6) —($C_0$-$C_4$)-alkylene-O—R19, wherein R19 is
a) hydrogen atom,
b) —($C_1$-$C_4$)-alkyl, wherein alkyl is unsubstituted or mono-, di- or trisubstituted independently of one another by R13,
c) —($C_3$-$C_8$)-cycloalkyl, wherein alkyl is unsubstituted or mono-, di- or trisubstituted independently of one another by R13,
d) phenyl, wherein phenyl is unsubstituted or mono-, di- or trisubstituted independently of one another by R13,
e) —$CF_3$, or
f) —$CHF_2$,
7) —$NO_2$,
8) —CN,
9) —($C_0$-$C_4$)-alkylene-O—$CH_2$—($C_1$-$C_3$)-fluoroalkylene-$CH_2$—O—($C_1$-$C_4$)-alkyl,
10) —($C_0$-$C_4$)-alkylene-C(O)—R11,
11) —($C_0$-$C_4$)-alkylene-C(O)—O—R11,
12) —($C_0$-$C_4$)-alkylene-C(O)—O—($C_1$-$C_4$)-alkylene-O—C(O)—R17, wherein —($C_1$-$C_4$)-alkylene is unsubstituted or mono-, di- or trisubstituted independently of one another by R15,
13) —($C_0$-$C_4$)-alkylene-C(O)—O—($C_1$-$C_4$)-alkylene-O—C(O)—O—R17, wherein
—($C_1$-$C_4$)-alkylene is unsubstituted or mono-, di- or trisubstituted independently of one another by R15,
14) —($C_0$-$C_4$)-alkylene-C(O)—N(R11)-R12,
15) —($C_0$-$C_4$)-alkylene-C(O)—N(R11)-R13,
16) —($C_0$-$C_4$)-alkylene-C(O)—N[($C_0$-$C_4$)-alkylene]-R13, wherein alkyl and cycloalkyl are unsubstituted or mono-, di- or trisubstituted independently of one another by R13,
17) —($C_0$-$C_4$)-alkylene-C(O)—N[($C_0$-$C_4$)-alkylene-($C_3$-$C_8$)-cycloalkyl]-R13, wherein alkyl and cycloalkyl is unsubstituted or mono-, di- or trisubstituted independently of one another by R13,
18) —($C_0$-$C_4$)-alkylene-N(R11)-R12,
19) —($C_0$-$C_4$)-alkylene-N(R11)-R13,
20) —($C_0$-$C_4$)-alkylene-N(R10)-$SO_2$—R10,
21) —($C_0$-$C_4$)-alkylene-S—R10,
22) —($C_0$-$C_4$)-alkylene-$SO_s$—R11, wherein s is 1 or 2,
23) —($C_0$-$C_4$)-alkylene-$SO_t$—N(R11)-R12, wherein t is 1 or 2,
24) —($C_0$-$C_4$)-alkylene-$SO_w$—N(R11)-R13, wherein w is 1 or 2,
25) —($C_0$-$C_4$)-alkylene-$SO_u$—($C_0$-$C_4$)-alkylene-C(O)—O—R10, wherein u is 1 or 2,
26) —($C_0$-$C_4$)-alkylene-($C_3$-$C_8$)-cycloalkyl, wherein cycloalkyl is unsubstituted or mono-, di- or trisubstituted independently of one another by R13,
27) —($C_0$-$C_4$)-alkylene-($C_6$-$C_{14}$)-aryl, wherein aryl is selected from phenyl, naphthyl, biphenylyl, indanyl, anthryl or fluorenyl; and wherein aryl is unsubstituted or mono-, di- or trisubstituted independently of one another by R13, or
28) —($C_0$-$C_4$)-alkylene-($C_3$-$C_{15}$)-heterocyclyl, wherein —($C_3$-$C_{15}$)-heterocyclyl is as defined above and is unsubstituted or mono-, di- or trisubstituted independently of one another by R13,
29) —($C_0$-$C_4$)-alkylene-O—($C_0$-$C_4$)-alkylene-($C_6$-$C_{14}$)-aryl, wherein aryl is unsubstituted or mono-, di- or trisubstituted independently of one another by R13,
30) —($C_0$-$C_4$)-alkylene-O—($C_0$-$C_4$)-alkylene-($C_3$-$C_{15}$)-heterocyclyl, wherein —($C_3$-$C_{15}$)-heterocyclyl is un-substituted or mono-, di- or trisubstituted independently of one another by R13,
31) —($C_0$-$C_4$)-alkylene-N(R13)-($C_0$-$C_4$)-alkylene-($C_6$-$C_{14}$)-aryl, wherein aryl is unsubstituted or mono-, di- or trisubstituted independently of one another by R13, or
32) —($C_0$-$C_4$)-alkylene-N(R13)-($C_0$-$C_4$)-alkylene-($C_3$-$C_{15}$)-heterocyclyl, wherein —($C_3$-$C_{15}$)-heterocyclyl is un-substituted or mono-, di- or trisubstituted independently of one another by R13,
R11 and R12 are independently of one another identical or different and are
1) a hydrogen atom,
2) —($C_1$-$C_6$)-alkyl, wherein alkyl is unsubstituted or mono-, di- or trisubstituted independently of one another by R13,
3) —($C_0$-$C_6$)-alkylene-($C_3$-$C_8$)-cycloalkyl, wherein alkylene and cycloalkyl independently from one another are unsubstituted or mono-, di- or trisubstituted independently of one another by R13,
4) —$SO_t$—R10, wherein t is 1 or 2,
5) —($C_0$-$C_6$)-alkylene-($C_6$-$C_{14}$)-aryl, wherein aryl is as defined above and alkylene and aryl independently from one another are unsubstituted or mono-, di- or trisubstituted by R13,
6) —($C_1$-$C_3$)-fluoroalkyl,
7) —O—R17, or
8) —($C_0$-$C_6$)-alkylene-($C_3$-$C_{15}$)-heterocyclyl, wherein —($C_3$-$C_{15}$)-heterocyclyl is as defined above and alkylene and heterocyclyl independently from one another are unsubstituted or mono-, di- or trisubstituted by R13, or
R11 and R12 together with the nitrogen atom to which they are bonded form a 4- to 8-membered monocyclic heterocyclic ring, which is selected from aza-bicycloheptane, aza-bicyclohexane, aza-spiroheptane, aza-spirohexane, aza-spirooctane, aza-spiropentane, azepane, azepine, azetidine, diaza-bicycloheptane, diaza-bicyclohexane, diaza-spiroheptane, diaza-spirohexane, diaza-spiropentane, diaza-spirooctane 1,2-diazapane, 1,3-diazepane, 1,4-diazepane, 1,2-diazepine, 1,3-diazepine, 1,4-diazepine, dihydroazepine, dihydro-oxazepine, dihydro-pyridazine, dioxazole, hexahydro-pyridazine, imidazoline, imidazolidine, isothiazolidine, isothiazoline, isoxazoline, isoxazolidine, ketopiperazine, morpholine, 1,4-oxazepane, 1,2-oxa-thiepane, oxazepine, 1,2-oxazine, 1,3-oxazine, 1,4-oxazine, piperazine, piperidine, pyrazine, pyrazoline, pyrazolidine, pyridazine, pyrrolidine, pyrrolidinone, pyrroline, tetrahydro-azepine, 1,2,3,4-tetrahydropyrazine, tetrahydropyridine, tetrazine, tetrazole, thiadiazine, 1,2-thiazine, 1,3-thiazine, 1,4-thiazine, 1,3-thiazole, thiazolidine, thiazoline, thietan, thiomorpholine, triazepane, 1,2,4-triazinane and 1,3,5-triazinane; wherein said heterocyclic ring is unsubstituted or mono-, di- or trisubstituted independently of one another by R13,
R13 is halogen, —$NO_2$, —CN, =O, —OH, —$CF_3$, —C(O)—O—R10, —C(O)—N(R10)-R20, —N(R10)-R20, —($C_3$-$C_8$)-cycloalkyl, —($C_2$-$C_{10}$)-alkenyl-, —($C_2$-$C_{10}$)-alkynyl-, —O—$CF_3$, —Si—($CH_3$)$_3$, —($C_0$-$C_4$)-alkylene-O—R10, —N(R10)-S(O)$_u$—R10, wherein u is 1 or 2, —$SO_r$—R10, wherein r is 1 or 2, —S(O)$_v$—N(R10)-R20, wherein v is 1 or 2, —S—R10, —C(O)—R10, —($C_1$-$C_8$)-alkyl, —($C_1$-$C_8$)-alkoxy, phenyl, phenyloxy-, —($C_1$-$C_8$)-alkoxy-phenyl, —($C_0$-$C_4$)-alkylene-C(O)—O—C(R15,R16)-O—C(O)—R17, —O—R15, —NH—C(O)—NH—R10, —($C_0$-$C_4$)-alkylene-C(O)—O—C(R15,R16)-O—C(O)—O—

R17, —($C_1$-$C_3$)-fluoroalkyl, —NH—C(O)—O—R10 or —($C_0$-$C_4$)-alkylene-R22,

R10 and R20 are independently of one another hydrogen, —($C_1$-$C_4$)-alkyl, —($C_1$-$C_4$)-alkyl-OH, —($C_0$-$C_4$)-alkylene-O—($C_1$-$C_4$)-alkyl or —($C_1$-$C_3$)-fluoroalkyl, R15 and R16 are independently of one another hydrogen atom, —($C_1$-$C_6$)-alkyl, or together with the carbon atom to which they are bonded form a —($C_3$-$C_6$)-cycloalkyl, which is unsubstituted or mono, di- or trisubstituted by R10, R17 is hydrogen atom, —($C_1$-$C_6$)-alkyl, —($C_1$-$C_6$)-alkyl-OH, —($C_1$-$C_6$)-alkylene-O—($C_1$-$C_6$)-alkyl, —($C_0$-$C_6$)-alkylene-($C_3$-$C_8$)-cycloalkyl or —($C_1$-$C_6$)-alkylene-O—($C_1$-$C_6$)-alkylene-($C_3$-$C_8$)-cycloalkyl, wherein said cycloalkyl ring is unsubstituted or substituted one, two or three times by —OH, —O—($C_1$-$C_4$)-alkyl or R10, and R22 is a residue from the following list:

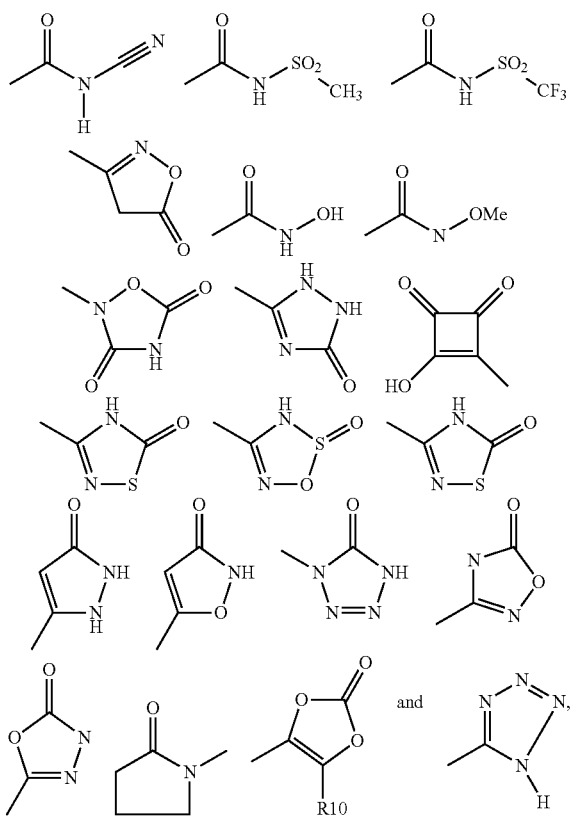

wherein Me is methyl, in all its stereoisomeric forms and mixtures thereof in any ratio, and its physiologically tolerable salts.

2. A compound as claimed in claim 1, wherein

E is a heterocyclic residue selected from aza-bicycloheptane, aza-bicyclohexane, aza-bicyclooctane, aza-spiroheptane, aza-spirohexane, aza-spirooctane, aza-spiropentane, azepane, azepine, azetidine, aziridine, decahydro-quinoline, diaza-bicyclohexane, diaza-bicycloheptane, 2,5-Diaza-bicyclo[2.2.1]heptane, 1,2-diazapane, 2,7-diaza-spiro[4.5]decane, 2,8-diaza-spiro[4.5]decane, diaza-spirohexane, diaza-spirooctane, diaza-spiropentane, diaza-spiroheptane, 1,3-diazepane, 1,4-diazepane, 1,2-diazepine, 1,3-diazepine, 1,4-diazepine, dihydroazepine, 2,3-dihydro-1H-indole, 3,4-dihydro-1H-isoquinoline, 4,7-dihydro-5H-isoxazolo[5,4-c]pyridine, 6,7-dihydro-4H-isoxazolo[4,5-c]pyridine, dihydro-pyridazine, dihydro-oxazepine, 6,7-dihydro-4H-oxazolo[5,4-c]pyridine, 4,6-dihydro-1H-pyrrolo[3,4-c]pyrazol, 4,6-dihydro-4H-pyrrolo[3,4-d]thiazole, 6,7-dihydro-4H-thiazolo[5,4-c]pyridine, 4,7-dihydro-5H-thieno[2,3-c]pyridine, 5,6-dihydro-8H-[1,2,4]triazolo[4,3-a]pyrazin, dioxazole, hexahydro-cyclopenta[c]pyrroline, hexahydro-pyridazine, hexahydro-pyrrolo[1,2-a]pyrazin, hexahydro-pyrrolo[3,4-b]pyrrol, Hexahydro-pyrrolo[1,2-a]pyrazin, imidazoline, imidazolidine, indole, isoquinoline, isothiazolidine, isothiazoline, isoxazoline, isoxazolidine, ketopiperazine, morpholine, octahydro-cyclopenta[c]pyrrole, octahydro-indole, octahydro-pyrrolo[3,4-b]pyridine, octahydro-pyrrolo[3,4-c]pyridine, 1,4-oxazepane, oxazepine, 1,2-oxa-thiepane, 1,2-oxazine, 1,3-oxazine, 1,4-oxazine, oxazolidine, piperazine, piperidine, pyrazine, pyrazoline, pyrazolidine, pyridazine, pyrrolidine, pyrrolidinone, pyrroline, tetrahydropyridine, tetrahydro-azepine, 1,2,3,4-tetrahydro-isoquinoline, 4,5,6,7-tetrahydro-isoxazolo[4,5-c]pyridine, 1,2,3,4-tetrahydropyrazine, 1,4,6,7-tetrahydro-pyrazolo[4,3-c]pyridine, 4,5,6,7-tetrahydro-1H-pyrazolo[4,3-c]pyridine, tetrahydro-pyridazine, 3,5,7,8-tetrahydro-4H-pyrido[4,3-d]pyrimidine, 4,5,6,6a-tetrahydro-3aH-pyrrolo[3,4-d]isoxazole, 1,2,3,4-tetrahydro-quinoline, 4,5,6,7-tetrahydro-thieno[2,3-c]pyridine, 1,4,6,7-tetrahydro-thiazolo[5,4-c]pyridine, 4,5,6,7-tetrahydro-thieno[3,2-c]pyridine, tetrazine, tetrazole, thiadiazine, 1,2-thiazine, 1,3-thiazine, 1,4-thiazine, 1,3-thiazole, thiazolidine, thiazoline, thietan, thiomorpholine, 1,3,8-triaza-spiro[4.5]decane, triaza-spirooctane, triazepane, 1,2,4-triazinane and 1,3,5-triazinane, wherein said heterocyclic residue is bond by its nitrogen atom to the carbonyl carbon atom and wherein said heterocyclic residue is unsubstituted or mono-, di- or trisubstituted independently of one another by R7, X is a nitrogen atom, Q is 1) a covalent bond,
2) —($C_0$-$C_4$)-alkylene-CH(OH)—($C_0$-$C_4$)-alkylene-,
3) —($C_0$-$C_4$)-alkylene-O—($C_0$-$C_4$)-alkylene-,
4) —($C_0$-$C_4$)-alkylene-C(O)—($C_0$-$C_4$)-alkylene-,
5) —($C_0$-$C_4$)-alkylene-C(O)—O—($C_0$-$C_4$)-alkylene-,
6) —($C_0$-$C_4$)-alkylene-C(O)—N(R10)-,
7) —($C_0$-$C_4$)-alkylene-N(R10)-($C_0$-$C_4$)-alkylene-,
8) —($C_0$-$C_4$)-alkylene-N(R10)-C(O)—($C_0$-$C_4$)-alkylene-,
9) —($C_0$-$C_4$)-alkylene-N(R10)-C(O)—O—($C_0$-$C_4$)-alkylene-,
10) —($C_0$-$C_4$)-alkylene-N(R10)-C(O)—N(R10)-($C_0$-$C_4$)-alkylene-,
11) —($C_0$-$C_4$)-alkylene-S—($C_0$-$C_4$)-alkylene-,
12) —($C_0$-$C_4$)-alkylene-$SO_2$—($C_0$-$C_4$)-alkylene-,
13) —($C_0$-$C_4$)-alkylene-($C_3$-$C_6$)-cycloalkyl-($C_0$-$C_4$)-alkylene-, or
14) —($C_0$-$C_4$)-alkylene-($C_3$-$C_{15}$)-heterocyclyl-($C_0$-$C_4$)-alkylene-, wherein —($C_3$-$C_{15}$)-heterocyclyl is selected from acridinyl, azabenzimidazolyl, aza-bicycloheptanyl, aza-bicyclohexanyl, aza-bicyclooctanyl, 8-aza-bicyclo[3.2.1]octanyl, azaspirodecanyl, aza-spiroheptanyl, aza-spirohexanyl, aza-spirooctanyl, aza-spiropentanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydro-quinolinyl, diaza-bicyclohexanyl, diaza-bicycloheptanyl, 2,5-diaza-bicyclo[2.2.1]heptanyl, 1,2-diazapanyl, diaza-spirohexanyl, diaza-spirooctanyl, diaza-spiropentanyl, diaza-spiroheptanyl, 1,3-diazepanyl, 1,4-diazepanyl, 1,2-diazepinyl, 1,3-diazepinyl, 1,4-diazepinyl, dihydroazepinyl, 3,4-dihydro-2H-quinoline, dihydrofuro[2,3-b]-tetrahydrofuranyl, 2,3-dihydro-1H-indolyl, 3,4-dihydro-1H-isoquinolinyl, 6,7-dihydro-4H-isoxazolo[4,5-c]pyridinyl, dihydro-pyridazinyl, 4,5-dihydro-[1,3,4]oxadiazol, dihydro-oxazepinyl, 4,5-dihydrooxazolinyl, 4,6-dihydro-4H-pyrrolo[3,4-d]thiazolyl, 6,7-dihydro-4H-thiazolo[5,4-c]pyridinyl, 4,7-dihydro-5H-thieno[2,3-c]pyridinyl, 1,3-dioxanyl, dioxazolyl, dioxazinyl, 1,3-dioxolanyl, 1,3-dioxolenyl, 3,3-dioxo[1,3,4]oxathiazinyl, 6H-1,5,2-dithiazinyl, furanyl, furazanyl, hexahydro-pyridazine, hexahydro-cyclopenta[c]pyrroline, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydro-cyclopenta[c]pyrrolyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 1H-pyrrolopyridinyl, 2H-pyrrolyl, pyrrolyl, quinazolinyl, quinolinyl, 4H-quinolizinyl, quinoxalinyl, quinuclidinyl, tetrahydrofuranyl, 1,2,3,4-tetrahydro-isoquinolinyl, 4,5,6,7-tetrahydro-isoxazolo[4,5-c]pyridinyl, tetrahydropyranyl, 1,2,3,4-tetrahydropyrazinyl, 4,5,6,7-tetrahydro-1H-pyrazolo[4,3-c]pyridinyl, tetrahydro-pyridazinyl, tetrahydro-pyridinyl, 4,5,6,6a-tetrahydro-3aH-pyrrolo[3,4-d]isoxazolyl, 1,2,3,4-tetrahydro-quinolinyl, 4,5,6,7-tetrahydro-thieno[2,3-c]pyridinyl, 1,4,6,7-tetrahydro-thiazolo[5,4-c]pyridinyl, 4,5,6,7-tetrahydro-thieno[3,2-c]pyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, triaza-spirooctanyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl, and xanthenyl, and wherein —$(C_3-C_{15})$-heterocyclyl is unsubstituted or mono-, di- or trisubstituted independently of one another by R14; and wherein the alkyl residues are unsubstituted or mono-, di- or trisubstituted independently of one another by halogen, —$NH_2$, —OH; or —$(C_3-C_6)$-cycloalkyl, wherein cycloalkyl is unsubstituted or mono-, di- or trisubstituted independently of one another by halogen, —$NH_2$ or —OH;

J is
1) a hydrogen atom,
2) —$(C_1-C_6)$-alkyl, wherein alkyl is unsubstituted or mono-, di- or trisubstituted independently of one another by R13,
3) —$(C_0-C_4)$-alkylene-C(O)—R11,
4) —$(C_0-C_4)$-alkylene-C(O)—O—R11,
5) —$(C_0-C_4)$-alkylene-C(O)—O—$(C_1-C_4)$-alkylene-O—C(O)—R17, wherein —$(C_1-C_4)$-alkylene is unsubstituted or mono-, di- or trisubstituted independently of one another by R15,
6) —$(C_0-C_4)$-alkylene-C(O)—O—$(C_1-C_4)$-alkylene-O—C(O)—O—R17, wherein
—$(C_1-C_4)$-alkylene is unsubstituted or mono-, di- or trisubstituted independently of one another by R15,
7) —$(C_0-C_4)$-alkylene-C(O)—N(R11)-R13,
8) —$(C_0-C_4)$-alkylene-N(R11)-R13,
9) —$(C_0-C_4)$-alkylene-N(R10)-$SO_2$—R10,
10) —$(C_0-C_4)$-alkylene-$SO_s$—R11, wherein s is 1 or 2,
11) —$(C_0-C_4)$-alkylene-$SO_t$—N(R11)-R12, wherein t is 1 or 2,
12) —$(C_0-C_4)$-alkylene-$SO_w$—N(R11)-R13, wherein w is 1 or 2,
13) —$(C_0-C_4)$-alkylene-R22,
14) —$(C_0-C_4)$-alkylene-$(C_3-C_6)$-cycloalkyl, wherein cycloalkyl is unsubstituted or 5 mono-, di- or trisubstituted independently of one another by R13,
15) —$(C_0-C_4)$-alkylene-$(C_6-C_{14})$-aryl, wherein aryl is selected from phenyl or indanyl, and aryl is unsubstituted or mono-, di- or trisubstituted independently of one another by R13, or
16) —$(C_0-C_4)$-alkylene-$(C_3-C_{15})$-heterocyclyl, wherein heterocyclyl is as defined above and is unsubstituted or mono-, di- or trisubstituted independently of one another by R13, R1 is a hydrogen atom, —$(C_1-C_4)$-alkyl, wherein alkyl is unsubstituted or substituted one to three times by R13;
—$(C_1-C_3)$-alkylene-C(O)—NH—R10 or
—$(C_1-C_3)$-alkylene-C(O)—O—R10, Z is
1) —$(C_0-C_8)$-alkylene-,
2) —$(C_2-C_{10})$-alkenyl-,
3) —$(C_2-C_{10})$-alkynyl-,
4) —$(C_0-C_4)$-alkylene-O—$(C_0-C_4)$-alkylene-,
5) —$(C_0-C_4)$-alkylene-O—C(O)—N(R10)-$(C_0-C_4)$-alkylene-,
6) —$(C_0-C_4)$-alkylene-C(O)—$(C_0-C_4)$-alkylene-,
7) —$(C_0-C_4)$-alkylene-N(R10)-C(O)—$(C_0-C_4)$-alkylene-,
8) —$(C_0-C_4)$-alkylene-N(R10)-C(O)—O—$(C_0-C_4)$-alkylene-,
9) —$(C_0-C_4)$-alkylene-N(R10)-C(O)—N(R10)-$(C_0-C_4)$-alkylene-,
10) —$(C_0-C_4)$-alkylene-N(R10)-$(C_0-C_4)$-alkylene-,
11) —$(C_0-C_4)$-alkylene-S—$(C_0-C_4)$-alkylene-,
12) —$(C_0-C_4)$-alkylene-S(O)—$(C_0-C_4)$-alkylene-,
13) —$(C_0-C_4)$-alkylene-$SO_2$—$(C_0-C_4)$-alkylene-, or
14) —$(C_0-C_4)$-alkylene-$(C_3-C_8)$-cycloalkyl-$(C_0-C_4)$-alkylene-, A is selected from a covalent bond, —$(C_3-C_8)$-alkylene, —$(C_3-C_8)$-cycloalkylene or —$(C_3-C_{15})$-heterocyclyl, wherein —$(C_3-C_{15})$-heterocyclyl is as defined above, B is
1) a covalent bond,
2) —$(C_2-C_{10})$-alkenyl-,
3) —$(C_2-C_{10})$-alkynyl-,
4) —$(C_0-C_4)$-alkylene-CH(OH)—$(C_0-C_4)$-alkylene-,
5) —$(C_0-C_4)$-alkylene-O—$(C_0-C_4)$-alkylene-, 6) —(C₀-C₄)-alkylene-O—C(O)—N(R10)-(C₀-C₄)-alkylene-,
7) —(C₀-C₄)-alkylene-C(O)—(C₀-C₄)-alkylene-,
8) —(C₀-C₄)-alkylene-C(O)—O—(C₀-C₄)-alkylene-,
9) —(C₀-C₄)-alkylene-C(O)—N(R10)-,
10) —(C₀-C₄)-alkylene-N(R10)-(C₀-C₄)-alkylene-,
11) —(C₀-C₄)-alkylene-N(R10)-C(O)—(C₀-C₄)-alkylene-,
12) —(C₀-C₄)-alkylene-N(R10)-C(O)—O—(C₀-C₄)-alkylene-,
13) —(C₀-C₄)-alkylene-N(R10)-C(O)—N(R10)-(C₀-C₄)-alkylene-,
14) —(C₀-C₄)-alkylene-N(R10)-SO₂—(C₀-C₄)-alkylene-,
15) —(C₀-C₄)-alkylene-N(R10)-SO₂—N(R10)-(C₀-C₄)-alkylene-,
16) —(C₀-C₄)-alkylene-S—(C₀-C₄)-alkylene-,
17) —(C₀-C₄)-alkylene-S(O)—(C₀-C₄)-alkylene-,
18) —(C₀-C₄)-alkylene-SO₂—(C₀-C₄)-alkylene-,
19) —(C₀-C₄)-alkylene-SO₂—N(R10)-(C₀-C₄)-alkylene-,
20) —(C₀-C₄)-alkylene-(C₃-C₈)-cycloalkyl-(C₀-C₄)-alkylene-, or
21) —(C₀-C₄)-alkylene-(C₃-C₁₅)-heterocyclyl-(C₀-C₄)-alkylene-, wherein heterocyclyl is as defined above, wherein —(C₃-C₁₅)-heterocyclyl is unsubstituted or mono-, di- or trisubstituted independently of one another by R14, and wherein the alkyl residues are unsubstituted or mono-, di- or trisubstituted independently of one another by halogen, —NH₂, —OH; or —(C₃-C₆)-cycloalkyl, wherein cycloalkyl is unsubstituted or mono-, di- or trisubstituted independently of one another by halogen, —NH₂ or —OH;

R14 is halogen, —OH, =O, —(C₁-C₈)-alkyl, —(C₁-C₄)-alkoxy, —NO₂, —CN, —NH₂, —S—R18, —(C₁-C₄)-alkylene-C(O)—OH, —C(O)—O—(C₁-C₄)-alkyl, —(C₁-C₄)-alkylene-C(O)—NH₂, —(C₀-C₈)-alkylene-SO₂—(C₁-C₄)-alkyl, —(C₀-C₈)-alkylene-SO₂—(C₁-C₃)-fluoroalkyl, —(C₀-C₈)-alkylene-SO₂—N(R18)-R21, —(C₁-C₄)-alkylene-C(O)—NH—(C₁-C₈)-alkyl, —(C₁-C₄)-alkylene-C(O)—N—[(C₁-C₈)-alkyl]₂, —N(R18)-C(O)—NH—(C₁-C₈)-alkyl, —N(R18)-C(O)—NH—[(C₁-C₈)-alkyl]₂, —(C₂-C₁₀)-alkenyl, or —(C₂-C₁₀)-alkynyl, wherein R18 and R21 are independently from each other hydrogen atom, —(C₁-C₃)-fluoroalkyl or —(C₁-C₆)-alkyl, V is —(C₃-C₁₅)-heterocyclyl or —N(R1)-(C₃-C₁₅)-heterocyclyl, wherein —(C₃-C₁₅)-heterocyclyl is as defined above and is unsubstituted or mono-, di- or trisubstituted independently of one another by R14, G is
1) a covalent bond,
2) —(C₀-C₄)-alkylene-O—(C₀-C₄)-alkylene-,
3) —(C₀-C₄)-alkylene-O—C(O)—N(R10)-(C₀-C₄)-alkylene-,
4) —(C₀-C₄)-alkylene-C(O)—(C₀-C₄)-alkylene-,
5) —(C₀-C₄)-alkylene-C(O)—O—(C₀-C₄)-alkylene-,
6) —(C₀-C₄)-alkylene-C(O)—N(R10)-,
7) —(C₀-C₄)-alkylene-N(R10)-(C₀-C₄)-alkylene-,
8) —(C₀-C₄)-alkylene-N(R10)-C(O)—(C₀-C₄)-alkylene-,
9) —(C₀-C₄)-alkylene-N(R10)-C(O)—O—(C₀-C₄)-alkylene-,
10) —(C₀-C₄)-alkylene-N(R10)-C(O)—N(R10)-(C₀-C₄)-alkylene-,
11) —(C₀-C₄)-alkylene-N(R10)-SO₂—(C₀-C₄)-alkylene-,
12) —(C₀-C₄)-alkylene-N(R10)-SO₂—N(R10)-(C₀-C₄)-alkylene-,
13) —(C₀-C₄)-alkylene-SO₂—(C₀-C₄)-alkylene-, or
14) —(C₀-C₄)-alkylene-SO₂—N(R10)-(C₀-C₄)-alkylene-, and wherein the alkyl residues are unsubstituted or mono-, di- or trisubstituted independently of one another by halogen, —NH₂, —OH; or —(C₃-C₆)-cycloalkyl, wherein cycloalkyl is unsubstituted or mono-, di- or trisubstituted independently of one another by halogen, —NH₂ or —OH;

M is
1) a hydrogen atom,
2) —(C₁-C₈)-alkyl, wherein alkyl is unsubstituted or mono-, di- or trisubstituted independently of one another by R14,
3) —C(O)—N(R11)-R12,
4) —C(O)—O—R12,
5) —(C₁-C₈)-alkylene-N(R10)₂, 6) —(C₆-C₁₄)-aryl, wherein aryl is selected from phenyl, naphthyl, biphenylyl, indanyl, anthryl and fluorenyl and aryl is unsubstituted or mono-, di- or trisubstituted independently of one another by R14,
7) —(C₃-C₈)-cycloalkyl, wherein said cycloalkyl is unsubstituted or mono-, di- or trisubstituted independently of one another by R14, or
8) a 3- to 7-membered heterocyclyl, containing 1, 2, 3 or 4 heteroatoms chosen from nitrogen, sulfur or oxygen, selected from azepine, azetidine, aziridine, azirine, 1,4-diazepane, 1,2-diazepine, 1,3-diazepine, 1,4-diazepine, diaziridine, diazirine, dihydroimidazolone, dioxazole, dioxazine, dioxole, 1,3-dioxolene, 1,3-dioxolane, furan, imidazole, imidazoline, imidazolidine, imidazolidinone, isothiazole, isothiazolidine, isothiazoline, isoxazole, isoxazoline, isoxazolidine, morpholine, 1,2-oxathiepane, 1,2-oxathiolane, 1,4-oxazepane, 1,2-oxazine, 1,3-oxazine, 1,4-oxazine, oxazolone, oxazole, [1,3,4]oxathiazinane 3,3-dioxide, oxaziridine, oxazolidinone, oxetan, oxirane, piperazine, piperidine, pyran, pyrazine, pyrazole, pyrazoline, pyrazolidine, pyridazine, pyridine, pyridinone, pyrimidine, pyrimidine-2,4-dione, pyrrole, pyrrolidine, pyrrolidinone, pyrroline, tetrahydrofuran, tetrahydropyran, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiomorpholine-1,1-dioxide, thiopyran, 1,2,3-triazine, 1,2,4-triazine, 1,3,5-triazine, 1,2,3-triazole and 1,2,4-triazole, wherein said cyclic residue is unsubstituted or mono-, di- or trisubstituted independently of one another by R14, R2, R3, R4, R5 and R6 are independently of one another selected from
1) a hydrogen atom,
2) —(C₁-C₆)-alkyl, wherein alkyl is unsubstituted or mono-, di- or trisubstituted independently of one another by R13,
3) —(C₀-C₄)-alkylene-O—R10,
4) halogen,
5) —(C₁-C₃)-fluoroalkyl,
6) —CN or
7) phenyl, wherein phenyl is unsubstituted or mono-, di- or trisubstituted independently of one another by R13, or R3 and R4, R4 and R5 or R5 and R6 are each time both —O—R10 and form together with the atoms which they are attached to a 1,3-dioxole ring or 2,3-dihydro-[1,4]

dioxine ring, which is unsubstituted or substituted one, two, three or four times by R13, R3 and R4, R4 and R5 or R5 and R6 form together with the atoms which they are attached to a cyclopentyl or cyclohexyl, which is unsubstituted or substituted one, two, three or four times by R13, R7 is
1) a hydrogen atom,
2) halogen,
3) —($C_1$-$C_6$)-alkyl, wherein alkyl is unsubstituted or mono-, di- or trisubstituted independently of one another by R13,
4) =O,
5) —($C_1$-$C_3$)-fluoroalkyl,
6) —($C_0$-$C_4$)-alkylene-O—R19, wherein R19 is
   a) a hydrogen atom,
   b) —($C_1$-$C_4$)-alkyl, wherein alkyl is unsubstituted or mono-, di- or trisubstituted independently of one another by R13,
   c) —($C_3$-$C_8$)-cycloalkyl, wherein alkyl is unsubstituted or mono-, di- or trisubstituted independently of one another by R13,
   d) phenyl, wherein phenyl is unsubstituted or mono-, di- or trisubstituted independently of one another by R13,
   e) —$CF_3$, or
   f) —$CHF_2$,
7) —$NO_2$,
8) —CN,
9) —($C_0$-$C_4$)-alkylene-O—$CH_2$—($C_1$-$C_3$)-fluoroalkylene-$CH_2$—O—($C_1$-$C_4$)-alkyl,
10) —($C_0$-$C_4$)-alkylene-C(O)—R11,
11) —($C_0$-$C_4$)-alkylene-C(O)—O—R11,
12) —($C_0$-$C_4$)-alkylene-C(O)—O—($C_1$-$C_4$)-alkylene-O—C(O)—R17, wherein —($C_1$-$C_4$)-alkylene is unsubstituted or mono-, di- or trisubstituted independently of one another by R15,
13) —($C_0$-$C_4$)-alkylene-C(O)—O—($C_1$-$C_4$)-alkylene-O—C(O)—O—R17, wherein —($C_1$-$C_4$)-alkylene is unsubstituted or mono-, di- or trisubstituted independently of one another by R15,
14) —($C_0$-$C_4$)-alkylene-C(O)—N(R11)-R12,
15) —($C_0$-$C_4$)-alkylene-C(O)—N(R11)-R13,
16) —($C_0$-$C_4$)-alkylene-C(O)—N[($C_0$-$C_4$)-alkylene]-R13, wherein alkyl and cycloalkyl are unsubstituted or mono-, di- or trisubstituted independently of one another by R13,
17) —($C_0$-$C_4$)-alkylene-C(O)—N[($C_0$-$C_4$)-alkylene-($C_3$-$C_8$)-cycloalkyl]-R13, wherein alkyl and cycloalkyl is unsubstituted or mono-, di- or trisubstituted independently of one another by R13,
18) —($C_0$-$C_4$)-alkylene-N(R11)-R12,
19) —($C_0$-$C_4$)-alkylene-N(R11)-R13,
20) —($C_0$-$C_4$)-alkylene-N(R10)-$SO_2$—R10,
21) —($C_0$-$C_4$)-alkylene-S—R10,
22) —($C_0$-$C_4$)-alkylene-$SO_s$—R11, wherein s is 1 or 2,
23) —($C_0$-$C_4$)-alkylene-$SO_t$—N(R11)-R12, wherein t is 1 or 2,
24) —($C_0$-$C_4$)-alkylene-$SO_w$—N(R11)-R13, wherein w is 1 or 2,
25) —($C_0$-$C_4$)-alkylene-$SO_u$—($C_0$-$C_4$)-alkylene-C(O)—O—R10, wherein u is 1 or 2,
26) —($C_0$-$C_4$)-alkylene-($C_3$-$C_8$)-cycloalkyl, wherein cycloalkyl is unsubstituted or mono-, di- or trisubstituted independently of one another by R13,
27) —($C_0$-$C_4$)-alkylene-($C_6$-$C_{14}$)-aryl, wherein aryl is selected from phenyl, naphthyl, biphenylyl, indanyl, anthryl or fluorenyl; and wherein aryl is unsubstituted or mono-, di- or trisubstituted independently of one another by R13, or
28) —($C_0$-$C_4$)-alkylene-($C_3$-$C_{15}$)-heterocyclyl, wherein heterocyclyl is as defined above and is unsubstituted or mono-, di- or trisubstituted independently of one another by R13,
29) —($C_0$-$C_4$)-alkylene-O—($C_0$-$C_4$)-alkylene-($C_6$-$C_{14}$)-aryl, wherein aryl is unsubstituted or mono-, di- or trisubstituted independently of one another by R13,
30) —($C_0$-$C_4$)-alkylene-O—($C_0$-$C_4$)-alkylene-($C_3$-$C_{15}$)-heterocyclyl, wherein heterocyclyl is un-substituted or mono-, di- or trisubstituted independently of one another by R13,
31) —($C_0$-$C_4$)-alkylene-N(R13)-($C_0$-$C_4$)-alkylene-($C_6$-$C_{14}$)-aryl, wherein aryl is unsubstituted or mono-, di- or trisubstituted independently of one another by R13, or
32) —($C_0$-$C_4$)-alkylene-N(R13)-($C_0$-$C_4$)-alkylene-($C_3$-$C_{15}$)-heterocyclyl, wherein heterocyclyl is un-substituted or mono-, di- or trisubstituted independently of one another by R13, R11 and R12 are independently of one another identical or different and are
1) a hydrogen atom,
2) —($C_1$-$C_6$)-alkyl, wherein alkyl is unsubstituted or mono-, di- or trisubstituted independently of one another by R13,
3) —($C_0$-$C_6$)-alkylene-($C_3$-$C_8$)-cycloalkyl, wherein alkylene and cycloalkyl independently from one another are unsubstituted or mono-, di- or trisubstituted independently of one another by R13,
4) —$SO_t$—R10, wherein t is 1 or 2,
5) —($C_0$-$C_6$)-alkylene-($C_6$-$C_{14}$)-aryl, wherein aryl is as defined above and alkylene and aryl independently from one another are unsubstituted or mono-, di- or trisubstituted by R13,
6) —($C_1$-$C_3$)-fluoroalkyl,
7) —O—R17, or
8) —($C_0$-$C_6$)-alkylene-($C_3$-$C_{15}$)-heterocyclyl, wherein heterocyclyl is as defined above and alkylene and heterocyclyl independently from one another are unsubstituted or mono-, di- or trisubstituted by R13, or R11 and R12 together with the nitrogen atom to which they are bonded form a 4- to 8-membered monocyclic heterocyclic ring, which is selected from aza-bicycloheptane, aza-bicyclohexane, aza-spiroheptane, aza-spirohexane, aza-spirooctane, aza-spiropentane, azepane, azepine, azetidine, diaza-bicycloheptane, diaza-bicyclohexane, diaza-spiroheptane, diaza-spirohexane, diaza-spiropentane, diaza-spirooctane 1,2-diazapane, 1,3-diazepane, 1,4-diazepane, 1,2-diazepine, 1,3-diazepine, 1,4-diazepine, dihydroazepine, dihydro-oxazepine, dihydro-pyridazine, dioxazole, hexahydro-pyridazine, imidazoline, imidazolidine, isothiazolidine, isothiazoline, isoxazoline, isoxazolidine, ketopiperazine, morpholine, 1,4-oxazepane, 1,2-oxa-thiepane, oxazepine, 1,2-oxazine, 1,3-oxazine, 1,4-oxazine, piperazine, piperidine, pyrazine, pyrazoline, pyrazolidine, pyridazine, pyrrolidine, pyrrolidinone, pyrroline, tetrahydro-azepine, 1,2,3,4-tetrahydropyrazine, tetrahydropyridine, tetrazine, tetrazole, thiadiazine, 1,2-thiazine, 1,3-thiazine, 1,4-thiazine, 1,3-thiazole, thiazolidine, thiazoline, thietan, thiomorpholine, triazepane, 1,2,4-triazinane and 1,3,5-triazinane; wherein said heterocyclic ring is unsubstituted or mono-, di- or trisubstituted independently of one another by R13, R13 is halogen, —NO$_2$, —CN, =O, —OH, —CF$_3$, —C(O)—O—R10, —C(O)—N(R10)-R20, —N(R10)-R20, —(C$_3$-C$_8$)-cycloalkyl, —(C$_2$-C$_{10}$)-alkenyl-, —(C$_2$-C$_{10}$)-alkynyl-, —O—CF$_3$, —Si—(CH$_3$)$_3$, —(C$_0$-C$_4$)-alkylene-O—R10, —N(R10)-S(O)$_u$—R10, wherein u is 1 or 2, —SO$_r$—R10, wherein r is 1 or 2, —S(O)$_v$—N(R10)-R20, wherein v is 1 or 2, —S—R10, —C(O)—R10, —(C$_1$-C$_8$)-alkyl, —(C$_1$-C$_8$)-alkoxy, phenyl, phenyloxy-, —(C$_1$-C$_8$)-alkoxy-phenyl, —(C$_0$-C$_4$)-alkylene-C(O)—O—C(R15, R16)-O—C(O)—R17, O—R15, —NH—C(O)—NH—R10, —(C$_0$-C$_4$)-alkylene-C(O)—O—C(R15,R16)-O—C(O)—O—R17, —(C$_1$-C$_3$)-fluoroalkyl, —NH—C(O)—O—R10, or —(C$_0$-C$_4$)-alkylene-R22, R10 and R20 are independently of one another hydrogen, —(C$_1$-C$_4$)-alkyl, —(C$_1$-C$_4$)-alkyl-OH, —(C$_0$-C$_4$)-alkylene-O—(C$_1$-C$_4$)-alkyl or —(C$_1$-C$_3$)-fluoroalkyl, R15 and R16 are independently of one another hydrogen atom or —(C$_1$-C$_6$)-alkyl, or together with the carbon atom to which they are bonded form a —(C$_3$-C$_6$)-cycloalkyl, which is unsubstituted or mono, di- or trisubstituted by R10, R17 is hydrogen atom, —(C$_1$-C$_6$)-alkyl, —(C$_1$-C$_6$)-alkyl-OH, —(C$_1$-C$_6$)-alkylene-O—(C$_1$-C$_6$)-alkyl, —(C$_{10}$-C$_{16}$)-alkylene-(C$_3$-C$_8$)-cycloalkyl or —(C$_1$-C$_6$)-alkylene-O—(C$_1$-C$_6$)-alkylene-(C$_3$-C$_8$)-cycloalkyl, wherein said cycloalkyl ring is unsubstituted or substituted one, two or three times by —OH, —O—(C$_1$-C$_4$)-alkyl or R10, and R22 is a residue from the following list:

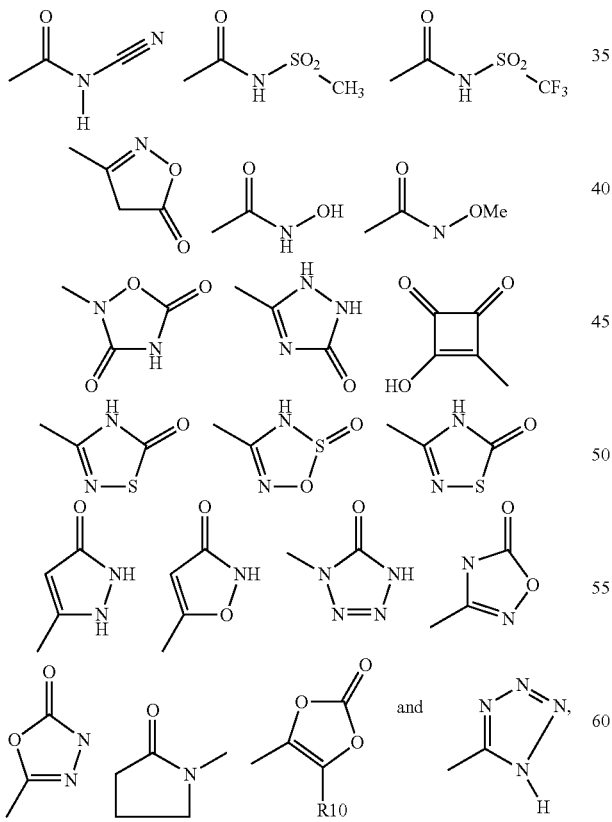

wherein Me is methyl,
in all its stereoisomeric forms and mixtures thereof in any ratio, and its physiologically tolerable salts.

3. A compound as claimed in claim 1, of formula Ia

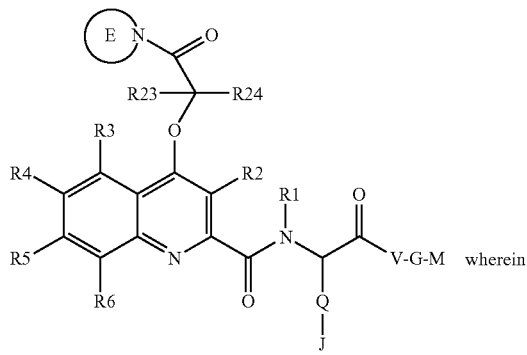

(Ia)

E is a heterocyclic residue selected from aza-bicycloheptane, aza-bicyclohexane, aza-bicyclooctane, aza-spiroheptane, aza-spirohexane, aza-spirooctane, aza-spiropentane, azepane, azepine, azetidine, aziridine, decahydro-quinoline, diaza-bicyclohexane, diaza-bicycloheptane, 2,5-Diaza-bicyclo[2.2.1]heptane, 1,2-diazapane, 2,7-diaza-spiro[4.5]decane, 2,8-diaza-spiro[4.5]decane, diaza-spirohexane, diaza-spirooctane, diaza-spiropentane, diaza-spiroheptane, 1,3-diazepane, 1,4-diazepane, 1,2-diazepine, 1,3-diazepine, 1,4-diazepine, dihydroazepine, 2,3-dihydro-1H-indole, 3,4-dihydro-1H-isoquinoline, 4,7-dihydro-5H-isoxazolo[5,4-c]pyridine, 6,7-dihydro-4H-isoxazolo[4,5-c]pyridine, dihydro-pyridazine, dihydro-oxazepine, 6,7-dihydro-4H-oxazolo[5,4-c]pyridine, 4,6-dihydro-1H-pyrrolo[3,4-c]pyrazol, 4,6-dihydro-4H-pyrrolo[3,4-d]thiazole, 6,7-dihydro-4H-thiazolo[5,4-c]pyridine, 4,7-dihydro-5H-thieno[2,3-c]pyridine, 5,6-Dihydro-8H-[1,2,4]triazolo[4,3-a]pyrazin, dioxazole, hexahydro-cyclopenta[c]pyrroline, hexahydro-pyridazine, hexahydro-pyrrolo[1,2-a]pyrazin, hexahydro-pyrrolo[3,4-b]pyrrol, Hexahydro-pyrrolo[1,2-a]pyrazin, imidazoline, imidazolidine, indole, isoquinoline, isothiazolidine, isothiazoline, isoxazoline, isoxazolidine, ketopiperazine, morpholine, octahydro-cyclopenta[c]pyrrole, octahydroindole, octahydro-pyrrolo[3,4-b]pyridine, octahydropyrrolo[3,4-c]pyridine, 1,4-oxazepane, oxazepine, 1,2-oxa-thiepane, 1,2-oxazine, 1,3-oxazine, 1,4-oxazine, oxazolidine, piperazine, piperidine, pyrazine, pyrazoline, pyrazolidine, pyridazine, pyrrolidine, pyrrolidinone, pyrroline, tetrahydropyridine, tetrahydro-azepine, 1,2,3,4-tetrahydro-isoquinoline, 4,5,6,7-tetrahydro-isoxazolo[4,5-c]pyridine, 1,2,3,4-tetrahydropyrazine, 1,4,6,7-tetrahydro-pyrazolo[4,3-c]pyridine, 4,5,6,7-tetrahydro-1H-pyrazolo[4,3-c]pyridine, tetrahydro-pyridazine, 3,5,7,8-tetrahydro-4H-pyrido[4,3-d]pyrimidine, 4,5,6,6a-tetrahydro-3aH-pyrrolo[3,4-d]isoxazole, 1,2,3,4-tetrahydro-quinoline, 4,5,6,7-tetrahydro-thieno[2,3-c]pyridine, 1,4,6,7-tetrahydro-thiazolo[5,4-c]pyridine, 4,5,6,7-tetrahydro-thieno[3,2-c]pyridine, tetrazine, tetrazole, thiadiazine, 1,2-thiazine, 1,3-thiazine, 1,4-thiazine, 1,3-thiazole, thiazolidine, thiazoline, thietan, thiomorpholine, 1,3,8-triaza-spiro[4.5]decane, triaza-spirooctane, triazepane, 1,2,4-triazinane and 1,3,5-triazinane, wherein said heterocyclic residue is bond by its nitrogen atom to the carbonyl carbon atom and wherein said heterocyclic residue is mono-, di- or trisubstituted independently of one another by R7, Q is
1) a covalent bond,
2) —($C_0$-$C_4$)-alkylene-CH(OH)—($C_0$-$C_4$)-alkylene-,
3) —($C_0$-$C_4$)-alkylene-O—($C_0$-$C_4$)-alkylene-,
4) —($C_0$-$C_4$)-alkylene-C(O)—($C_0$-$C_4$)-alkylene-,
5) —($C_0$-$C_4$)-alkylene-C(O)—O—($C_0$-$C_4$)-alkylene-,
6) —($C_0$-$C_4$)-alkylene-C(O)—N(R10)-,
7) —($C_0$-$C_4$)-alkylene-N(R10)-($C_0$-$C_4$)-alkylene-,
8) —($C_0$-$C_4$)-alkylene-N(R10)-C(O)—($C_0$-$C_4$)-alkylene-,
9) —($C_0$-$C_4$)-alkylene-N(R10)-C(O)—O—($C_0$-$C_4$)-alkylene-,
10) —($C_0$-$C_4$)-alkylene-N(R10)-C(O)—N(R10)-($C_0$-$C_4$)-alkylene-,
11) —($C_0$-$C_4$)-alkylene-S—($C_0$-$C_4$)-alkylene-,
12) —($C_0$-$C_4$)-alkylene-$SO_2$—($C_0$-$C_4$)-alkylene-,
13) —($C_0$-$C_4$)-alkylene-($C_3$-$C_6$)-cycloalkyl-($C_0$-$C_4$)-alkylene-, or
14) —($C_0$-$C_4$)-alkylene-($C_3$-$C_{15}$)-heterocyclyl-($C_0$-$C_4$)-alkylene-, wherein —($C_3$-$C_{15}$)-heterocyclyl is selected from acridinyl, azabenzimidazolyl, aza-bicycloheptanyl, aza-bicyclohexanyl, aza-bicyclooctanyl, 8-aza-bicyclo[3.2.1]octanyl, azaspirodecanyl, aza-spirohepta-nyl, aza-spirohexanyl, aza-spirooctanyl, aza-spiropentanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benziso-thiazolyl, carbazolyl, 4aH-carbazolyl, carbolinyl, chromanyl, chromenyl, cinnolinyl, decahydro-quinolinyl, diaza-bicyclohexanyl, diaza-bicycloheptanyl, 2,5-Diaza-bicyclo[2.2.1]heptanyl, 1,2-diazapanyl, diaza-spirohexanyl, diaza-spirooctanyl, diaza-spiropentanyl, diaza-spiroheptanyl, 1,3-diazepanyl, 1,4-diazepanyl, 1,2-diazepinyl, 1,3-diazepinyl, 1,4-diazepinyl, dihydroazepinyl, 3,4-dihydro-2H-quinoline, dihydrofuro[2,3-b]-tetrahydrofuranyl, 2,3-dihydro-1H-indolyl, 3,4-dihydro-1H-isoquinolinyl, 6,7-dihydro-4H-isoxazolo[4,5-c]pyridinyl, dihydro-pyridazinyl, 4,5-dihydro-[1,3,4]oxadiazol, dihydro-oxazepinyl, 4,5-dihydrooxazolinyl, 4,6-dihydro-4H-pyrrolo[3,4-d]thiazolyl, 6,7-dihydro-4H-thiazolo[5,4-c]pyridinyl, 4,7-dihydro-5H-thieno[2,3-c]pyridinyl, 1,3-dioxanyl, dioxazolyl, dioxazinyl, 1,3-dioxolanyl, 1,3-dioxolenyl, 3,3-dioxo[1,3,4]oxathiazinyl, furanyl, furazanyl, hexahydro-pyridazine, hexahydro-cyclopenta[c]pyrroline, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydro-cyclopenta[c]pyrrolyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 1H-pyrrolopyridinyl, 2H-pyrrolyl, pyrrolyl, quinazolinyl, quinolinyl, 4H-quinolizinyl, quinoxalinyl, quinuclidinyl, tetrahydrofuranyl, 1,2,3,4-tetrahydroisoquinolinyl, 4,5,6,7-tetrahydro-isoxazolo[4,5-c]pyridinyl, tetrahydropyranyl, 1,2,3,4-tetrahydropyrazinyl, 4,5,6,7-tetrahydro-1H-pyrazolo[4,3-c]pyridinyl, tetrahydro-pyridazinyl, tetrahydro-pyridinyl, 4,5,6,6a-tetrahydro-3aH-pyrrolo[3,4-d]isoxazolyl, 1,2,3,4-tetrahydro-quinolinyl, 4,5,6,7-tetrahydro-thieno[2,3-c]pyridinyl, 1,4,6,7-tetrahydro-thiazolo[5,4-c]pyridinyl, 4,5,6,7-tetrahydro-thieno[3,2-c]pyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, triaza-spirooctanyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl, and xanthenyl, and wherein —($C_3$-$C_{15}$)-heterocyclyl is unsubstituted or mono-, di- or trisubstituted independently of one another by R14; and wherein the alkyl residues are unsubstituted or mono-, di- or trisubstituted independently of one another by halogen, —$NH_2$, —OH; or —($C_3$-$C_6$)-cycloalkyl, wherein cycloalkyl is unsubstituted or mono-, di- or trisubstituted independently of one another by halogen, —$NH_2$ or —OH;

J is
1) a hydrogen atom,
2) —($C_1$-$C_6$)-alkyl, wherein alkyl is unsubstituted or mono-, di- or trisubstituted independently of one another by R13,
3) —($C_0$-$C_4$)-alkylene-C(O)—R11,
4) —($C_0$-$C_4$)-alkylene-C(O)—O—R11,
5) —($C_0$-$C_4$)-alkylene-C(O)—O—($C_1$-$C_4$)-alkylene-O—C(O)—R17, wherein —($C_1$-$C_4$)-alkylene is unsubstituted or mono-, di- or trisubstituted independently of one another by R15,
6) —($C_0$-$C_4$)-alkylene-C(O)—O—($C_1$-$C_4$)-alkylene-O—C(O)—O—R17, wherein —($C_1$-$C_4$)-alkylene is unsubstituted or mono-, di- or trisubstituted independently of one another by R15,
7) —($C_0$-$C_4$)-alkylene-C(O)—N(R11)-R13
8) —($C_0$-$C_4$)-alkylene-N(R11)-R13,
9) —($C_0$-$C_4$)-alkylene-N(R10)-$SO_2$—R10,
10) —($C_0$-$C_4$)-alkylene-$SO_s$—R11, wherein s is 1 or 2,
11) —($C_0$-$C_4$)-alkylene-$SO_t$—N(R11)-R12, wherein t is 1 or 2,
12) —($C_0$-$C_4$)-alkylene-$SO_w$—N(R11)-R13, wherein w is 1 or 2,
13) —($C_0$-$C_4$)-alkylene-R22,
14) —($C_0$-$C_4$)-alkylene-($C_3$-$C_6$)-cycloalkyl, wherein cycloalkyl is unsubstituted or mono-, di- or trisubstituted independently of one another by R13,
15) —($C_0$-$C_4$)-alkylene-($C_6$-$C_{14}$)-aryl, wherein aryl is selected from phenyl or indanyl, and aryl is unsubstituted or mono-, di- or trisubstituted independently of one another by R13, or
16) —($C_0$-$C_4$)-alkylene-($C_3$-$C_{15}$)-heterocyclyl, wherein —($C_3$-$C_{15}$)-heterocyclyl is as defined above and is unsubstituted or mono-, di- or trisubstituted independently of one another by R13, V is —($C_3$-$C_{15}$)-heterocyclyl or —N(R1)-($C_3$-$C_{15}$)-heterocyclyl, wherein —($C_3$-$C_{15}$)-heterocyclyl is as defined above and is unsubstituted or mono-, di- or trisubstituted independently of one another by R14, G is
1) a covalent bond,
2) —$(C_0\text{-}C_4)$-alkylene-O—$(C_0\text{-}C_4)$-alkylene-,
3) —$(C_0\text{-}C_4)$-alkylene-O—C(O)—N(R10)-$(C_0\text{-}C_4)$-alkylene-,
4) —$(C_0\text{-}C_4)$-alkylene-C(O)—$(C_0\text{-}C_4)$-alkylene-,
5) —$(C_0\text{-}C_4)$-alkylene-C(O)—O—$(C_0\text{-}C_4)$-alkylene-,
6) —$(C_0\text{-}C_4)$-alkylene-C(O)—N(R10)-,
7) —$(C_0\text{-}C_4)$-alkylene-N(R10)-$(C_0\text{-}C_4)$-alkylene-,
8) —$(C_0\text{-}C_4)$-alkylene-N(R10)-C(O)—$(C_0\text{-}C_4)$-alkylene-,
9) —$(C_0\text{-}C_4)$-alkylene-N(R10)-C(O)—O—$(C_0\text{-}C_4)$-alkylene-,
10) —$(C_0\text{-}C_4)$-alkylene-N(R10)-C(O)—N(R10)-$(C_0\text{-}C_4)$-alkylene-,
11) —$(C_0\text{-}C_4)$-alkylene-N(R10)-$SO_2$—$(C_0\text{-}C_4)$-alkylene-,
12) —$(C_0\text{-}C_4)$-alkylene-N(R10)-$SO_2$—N(R10)-$(C_0\text{-}C_4)$-alkylene-,
13) —$(C_0\text{-}C_4)$-alkylene-$SO_2$—$(C_0\text{-}C_4)$-alkylene-, or
14) —$(C_0\text{-}C_4)$-alkylene-$SO_2$—N(R10)-$(C_0\text{-}C_4)$-alkylene-,
and wherein the alkyl residues are unsubstituted or mono-, di- or trisubstituted independently of one another by halogen, —$NH_2$, —OH; or —$(C_3\text{-}C_6)$-cycloalkyl, wherein cycloalkyl is unsubstituted or mono-, di- or trisubstituted independently of one another by halogen, —$NH_2$ or —OH;

M is
1) a hydrogen atom,
2) —$(C_1\text{-}C_8)$-alkyl, wherein alkyl is unsubstituted or mono-, di- or trisubstituted independently of one another by R14,
3) —C(O)—N(R11)-R12,
4) —C(O)—O—R12,
5) —$(C_1\text{-}C_8)$-alkylene-N(R10)$_2$,
6) —$(C_6\text{-}C_{14})$-aryl, wherein aryl is selected from phenyl, naphthyl, biphenylyl, indanyl, anthryl and fluorenyl and aryl is unsubstituted or mono-, di- or trisubstituted independently of one another by R14,
7) —$(C_3\text{-}C_6)$-cycloalkyl, wherein said cycloalkyl is unsubstituted or mono-, di- or trisubstituted independently of one another by R14, or
8) a 3- to 7-membered heterocyclyl, containing 1, 2, 3 or 4 heteroatoms chosen from nitrogen, sulfur or oxygen, selected from azepine, azetidine, aziridine, azirine, 1,4-diazepane, 1,2-diazepine, 1,3-diazepine, 1,4-diazepine, diaziridine, diazirine, dihydroimidazolone, dioxazole, dioxazine, dioxole, 1,3-dioxolene, 1,3-dioxolane, furan, imidazole, imidazoline, imidazolidine, imidazolidinone, isothiazole, isothiazolidine, isothiazoline, isoxazole, isoxazoline, isoxazolidine, morpholine, 1,2-oxathiepane, 1,2-oxathiolane, 1,4-oxazepane, 1,2-oxazine, 1,3-oxazine, 1,4-oxazine, oxazolone, oxazole, [1,3,4] oxathiazinane 3,3-dioxide, oxaziridine, oxazolidinone, oxetan, oxirane, piperazine, piperidine, pyran, pyrazine, pyrazole, pyrazoline, pyrazolidine, pyridazine, pyridine, pyridinone, pyrimidine, pyrimidine-2,4-dione, pyrrole, pyrrolidine, pyrrolidinone, pyrroline, tetrahydrofuran, tetrahydropyran, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiomorpholine 1,1-dioxide thiopyran, 1,2,3-triazine, 1,2,4-triazine, 1,3,5-triazine, 1,2,3-triazole and 1,2,4-triazole, wherein said cyclic residue is unsubstituted or mono-, di- or trisubstituted independently of one another by R14, R1 is a hydrogen atom, —$(C_1\text{-}C_4)$-alkyl, wherein alkyl is unsubstituted or substituted one to three times by R13;
—$(C_1\text{-}C_3)$-alkylene-C(O)—NH—R10 or
—$(C_1\text{-}C_3)$-alkylene-C(O)—O—R10, R2, R3, R4, R5 and R6 are independently of one another selected from
1) a hydrogen atom,
2) —$(C_1\text{-}C_6)$-alkyl, wherein alkyl is unsubstituted or mono-, di- or trisubstituted independently of one another by R13,
3) —$(C_0\text{-}C_4)$-alkylene-O—R10,
4) halogen,
5) —$(C_1\text{-}C_3)$-fluoroalkyl,
6) —CN or
7) phenyl, wherein phenyl is unsubstituted or mono-, di- or trisubstituted independently of one another by R13, or
R3 and R4, R4 and R5 or R5 and R6 are each time both —O—R10 and form together with the atoms which they are attached to a 1,3-dioxole ring or 2,3-dihydro-[1,4] dioxine ring, which is unsubstituted or substituted one, two, three or four times by R13,
R3 and R4, R4 and R5 or R5 and R6 form together with the atoms which they are attached to a cyclopentyl or cyclohexyl, which is unsubstituted or substituted one, two, three or four times by R13, R7 is
1) a hydrogen atom,
2) halogen,
3) —$(C_1\text{-}C_6)$-alkyl, wherein alkyl is unsubstituted or mono-, di- or trisubstituted independently of one another by R13,
4) =O,
5) —$(C_1\text{-}C_3)$-fluoroalkyl,
6) —$(C_0\text{-}C_4)$-alkylene-O—R19, wherein R19 is
a) hydrogen atom,
b) —$(C_1\text{-}C_4)$-alkyl, wherein alkyl is unsubstituted or mono-, di- or trisubstituted independently of one another by R13,
c) —$(C_3\text{-}C_8)$-cycloalkyl, wherein alkyl is unsubstituted or mono-, di- or trisubstituted independently of one another by R13,
d) phenyl, wherein phenyl is unsubstituted or mono-, di- or trisubstituted independently of one another by R13,
e) —$CF_3$, or
f) —$CHF_2$,
7) —$NO_2$,
8) —CN,
9) —$(C_0\text{-}C_4)$-alkylene-O—$CH_2$—$(C_1\text{-}C_3)$-fluoroalkylene-$CH_2$—O—$(C_1\text{-}C_4)$-alkyl,
10) —$(C_0\text{-}C_4)$-alkylene-C(O)—R11,
11) —$(C_0\text{-}C_4)$-alkylene-C(O)—O—R11,
12) —$(C_0\text{-}C_4)$-alkylene-C(O)—O—$(C_1\text{-}C_4)$-alkylene-O—C(O)—R17, wherein —$(C_1\text{-}C_4)$-alkylene is unsubstituted or mono-, di- or trisubstituted independently of one another by R15,
13) —$(C_0\text{-}C_4)$-alkylene-C(O)—O—$(C_1\text{-}C_4)$-alkylene-O—C(O)—O—R17, wherein
—$(C_1\text{-}C_4)$-alkylene is unsubstituted or mono-, di- or trisubstituted independently of one another by R15,
14) —$(C_0\text{-}C_4)$-alkylene-C(O)—N(R11)-R12,
15) —$(C_0\text{-}C_4)$-alkylene-C(O)—N(R11)-R13,
16) —$(C_0\text{-}C_4)$-alkylene-C(O)—N[$(C_0\text{-}C_4)$-alkylene]-R13, wherein alkyl and cycloalkyl are unsubstituted or mono-, di- or trisubstituted independently of one another by R13,
17) —$(C_0\text{-}C_4)$-alkylene-C(O)—N[$(C_0\text{-}C_4)$-alkylene-$(C_3\text{-}C_8)$-cycloalkyl]-R13, wherein alkyl and cycloalkyl is unsubstituted or mono-, di- or trisubstituted independently of one another by R13, 18) —$(C_0$-$C_4)$-alkylene-N(R11)-R12,
19) —$(C_0$-$C_4)$-alkylene-N(R11)-R13,
20) —$(C_0$-$C_4)$-alkylene-N(R10)-$SO_2$—R10,
21) —$(C_0$-$C_4)$-alkylene-S—R10,
22) —$(C_0$-$C_4)$-alkylene-$SO_s$—R11, wherein s is 1 or 2,
23) —$(C_0$-$C_4)$-alkylene-$SO_t$—N(R11)-R12, wherein t is 1 or 2,
24) —$(C_0$-$C_4)$-alkylene-$SO_w$—N(R11)-R13, wherein w is 1 or 2,
25) —$(C_0$-$C_4)$-alkylene-$SO_u$—$(C_0$-$C_4)$-alkylene-C(O)—O—R10, wherein u is 1 or 2,
26) —$(C_0$-$C_4)$-alkylene-$(C_3$-$C_6)$-cycloalkyl, wherein cycloalkyl is unsubstituted or mono-, di- or trisubstituted independently of one another by R13,
27) —$(C_0$-$C_4)$-alkylene-$(C_6$-$C_{14})$-aryl, wherein aryl is selected from phenyl, naphthyl, biphenylyl, indanyl, anthryl or fluorenyl; and wherein aryl is unsubstituted or mono-, di- or trisubstituted independently of one another by R13,
28) —$(C_0$-$C_4)$-alkylene-$(C_3$-$C_{15})$-heterocyclyl, wherein heterocyclyl is as defined above and is unsubstituted or mono-, di- or trisubstituted independently of one another by R13,
29) —$(C_0$-$C_4)$-alkylene-O—$(C_0$-$C_4)$-alkylene-$(C_6$-$C_{14})$-aryl, wherein aryl is unsubstituted or mono-, di- or trisubstituted independently of one another by R13,
30) —$(C_0$-$C_4)$-alkylene-O—$(C_0$-$C_4)$-alkylene-$(C_3$-$C_{15})$-heterocyclyl, wherein heterocyclyl is un-substituted or mono-, di- or trisubstituted independently of one another by R13,
31) —$(C_0$-$C_4)$-alkylene-N(R13)-$(C_0$-$C_4)$-alkylene-$(C_6$-$C_{14})$-aryl, wherein aryl is unsubstituted or mono-, di- or trisubstituted independently of one another by R13, or
32) —$(C_0$-$C_4)$-alkylene-N(R13)-$(C_0$-$C_4)$-alkylene-$(C_3$-$C_{15})$-heterocyclyl, wherein heterocyclyl is un-substituted or mono-, di- or trisubstituted independently of one another by R13, R11 and R12 are independently of one another identical or different and are 1) a hydrogen atom,
2) —$(C_1$-$C_6)$-alkyl, wherein alkyl is unsubstituted or mono-, di- or trisubstituted independently of one another by R13,
3) —$(C_0$-$C_6)$-alkylene-$(C_3$-$C_8)$-cycloalkyl, wherein alkylene and cycloalkyl independently from one another are unsubstituted or mono-, di- or trisubstituted independently of one another by R13,
4) —$SO_t$—R10, wherein t is 1 or 2,
5) —$(C_0$-$C_6)$-alkylene-$(C_6$-$C_{14})$-aryl, wherein aryl is as defined above and alkylene and aryl independently from one another are unsubstituted or mono-, di- or trisubstituted by R13,
6) —$(C_1$-$C_3)$-fluoroalkyl,
7) —O—R17, or
8) —$(C_0$-$C_6)$-alkylene-$(C_3$-$C_{15})$-heterocyclyl, wherein —$(C_3$-$C_{15})$-heterocyclyl is as defined above and alkylene and heterocyclyl independently from one another are unsubstituted or mono-, di- or trisubstituted by R13, or R11 and R12 together with the nitrogen atom to which they are bonded form a 4- to 8-membered monocyclic heterocyclic ring, which is selected from aza-bicycloheptane, aza-bicyclohexane, aza-spiroheptane, aza-spirohexane, aza-spirooctane, aza-spiropentane, azepane, azepine, azetidine, diaza-bicycloheptane, diaza-bicyclohexane, diaza-spiroheptane, diaza-spirohexane, diaza-spiropentane, diaza-spirooctane 1,2-diazapane, 1,3-diazepane, 1,4-diazepane, 1,2-diazepine, 1,3-diazepine, 1,4-diazepine, dihydroazepine, dihydro-oxazepine, dihydro-pyridazine, dioxazole, hexahydro-pyridazine, imidazoline, imidazolidine, isothiazolidine, isothiazoline, isoxazoline, isoxazolidine, ketopiperazine, morpholine, 1,4-oxazepane, 1,2-oxa-thiepane, oxazepine, 1,2-oxazine, 1,3-oxazine, 1,4-oxazine, piperazine, piperidine, pyrazine, pyrazoline, pyrazolidine, pyridazine, pyrrolidine, pyrrolidinone, pyrroline, tetrahydro-azepine, 1,2,3,4-tetrahydropyrazine, tetrahydropyridine, tetrazine, tetrazole, thiadiazine, 1,2-thiazine, 1,3-thiazine, 1,4-thiazine, 1,3-thiazole, thiazolidine, thiazoline, thietan, thiomorpholine, triazepane, 1,2,4-triazinane and 1,3,5-triazinane; wherein said heterocyclic ring is unsubstituted or mono-, di- or trisubstituted independently of one another by R13, R13 is halogen, —$NO_2$, —CN, =O, —OH, —$CF_3$, —C(O)—O—R10, —C(O)—N(R10)-R20, —N(R10)-R20, —$(C_3$-$C_8)$-cycloalkyl, —$(C_2$-$C_{10})$-alkenyl-, —$(C_2$-$C_{10})$-alkynyl-, —O—$CF_3$, —Si—$(CH_3)_3$, —$(C_0$-$C_4)$-alkylene-O—R10, —N(R10)-S(O)$_u$—R10, wherein u is 1 or 2, —$SO_r$—R10, wherein r is 1 or 2, —S(O)$_v$—N(R10)-R20, wherein v is 1 or 2, —S—R10, —C(O)—R10, —$(C_1$-$C_8)$-alkyl, —$(C_1$-$C_8)$-alkoxy, phenyl, phenyloxy-, —$(C_1$-$C_8)$-alkoxy-phenyl, —$(C_0$-$C_4)$-alkylene-C(O)—O—C(R15,R16)-O—C(O)—R17, —O—R15, —NH—C(O)—NH—R10, —$(C_0$-$C_4)$-alkylene-C(O)—O—C(R15,R16)-O—C(O)—O—R17, —$(C_1$-$C_3)$-fluoroalkyl, hydrogen, —NH—C(O)—O—R10, or —$(C_0$-$C_4)$-alkylene-R22, R10 and R20 are independently of one another hydrogen, —$(C_1$-$C_4)$-alkyl, —$(C_1$-$C_4)$-alkyl-OH, —$(C_0$-$C_4)$-alkylene-O—$(C_1$-$C_4)$-alkyl or —$(C_1$-$C_3)$-fluoroalkyl, R14 is halogen, —OH, =O, —$(C_1$-$C_8)$-alkyl, —$(C_1$-$C_4)$-alkoxy, —$NO_2$, —CN, —$NH_2$, —S—R18, —$(C_1$-$C_4)$-alkylene-C(O)—OH, —C(O)—O—$(C_1$-$C_4)$-alkyl, —$(C_1$-$C_4)$-alkylene-C(O)—$NH_2$, —$(C_0$-$C_8)$-alkylene-$SO_2$—$(C_1$-$C_4)$-alkyl, —$(C_0$-$C_8)$-alkylene-$SO_2$—$(C_1$-$C_3)$-fluoro alkyl, —$(C_0$-$C_8)$-alkylene-$SO_2$—N(R18)-R21, —$(C_1$-$C_4)$-alkylene-C(O)—NH—$(C_1$-$C_8)$-alkyl, —$(C_1$-$C_4)$-alkylene-C(O)—N—[$(C_1$-$C_8)$-alkyl]$_2$, —N(R18)-C(O)—NH—$(C_1$-$C_8)$-alkyl, hydrogen, —N(R18)-C(O)—NH—[$(C_1$-$C_8)$-alkyl]$_2$, —$(C_2$-$C_{10})$-alkenyl, or —$(C_2$-$C_{10})$-alkynyl, wherein R18 and R21 are independently from each other hydrogen atom, —$(C_1$-$C_3)$-fluoroalkyl or —$(C_1$-$C_6)$-alkyl, R15 and R16 are independently of one another hydrogen atom or —$(C_1$-$C_6)$-alkyl, or together with the carbon atom to which they are bonded form a —$(C_3$-$C_6)$-cycloalkyl, which is unsubstituted or mono, di- or trisubstituted by R10, R17 is hydrogen atom, —$(C_1$-$C_6)$-alkyl, —$(C_1$-$C_6)$-alkyl-OH, —$(C_1$-$C_6)$-alkylene-O—$(C_1$-$C_6)$-alkyl, —$(C_0$-$C_6)$-alkylene-$(C_3$-$C_8)$-cycloalkyl or —$(C_1$-$C_6)$-alkylene-O—$(C_1$-$C_6)$-alkylene-$(C_3$-$C_8)$-cycloalkyl, wherein each cycloalkyl ring is unsubstituted or substituted one, two or three times by —OH, —O—$(C_1$-$C_4)$-alkyl or R10, and R22 is a residue from the following list:

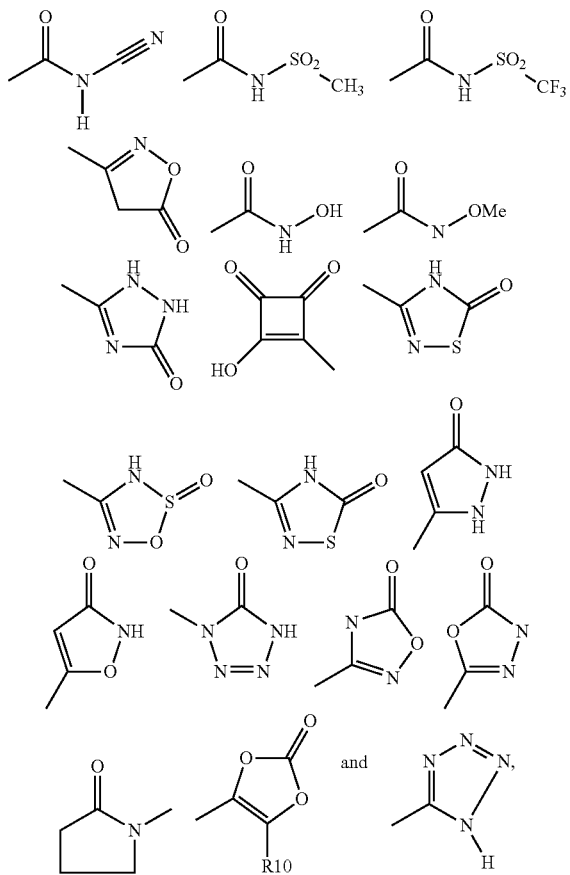

wherein
Me is methyl,
R23 and R24 are independently of one another selected from hydrogen atom or methyl,
in all its stereoisomeric forms and mixtures thereof in any ratio, and its physiologically tolerable salts.

4. A compound as claimed in claim 3, wherein
E is a heterocyclic residue selected from aza-bicyclohexane, aza-bicyclooctane, azetidine, aziridine, decahydroquinoline, 2,5-diaza-bicyclo[2.2.1]heptane, 1,4-diazepane, 2,7-diaza-spiro[4.5]decane, 2,8-diaza-spiro[4.5]decane, 2,3-dihydro-1H-indole, 4,7-dihydro-5H-isoxazolo[5,4-c]pyridine, 6,7-dihydro-4H-oxazolo[5,4-c]pyridine, 4,6-dihydro-1H-pyrrolo[3,4-c]pyrazol, 4,6-dihydro-4H-pyrrolo[3,4-d]thiazole, 5,6-Dihydro-8H-[1,2,4]triazolo[4,3-a]pyrazin, hexahydro-pyrrolo[1,2-a]pyrazin, hexahydro-pyrrolo[3,4-b]pyrrol, Hexahydro-pyrrolo[1,2-a]pyrazin, imidazolidine, morpholine, indole, octahydro-cyclopenta[c]pyrrole, octahydro-indole, octahydro-pyrrolo[3,4-b]pyridine, octahydro-pyrrolo[3,4-c]pyridine, oxazolidine, piperazine, piperidine, pyrazolidine, pyrrolidine, 1,4,6,7-tetrahydro-pyrazolo[4,3-c]pyridine, 1,2,3,4-tetrahydro-isoquinoline, 4,5,6,7-tetrahydro-isoxazolo[4,5-c]pyridine, 4,5,6,7-tetrahydro-1H-pyrazolo[4,3-c]pyridine, 3,5,7,8-tetrahydro-4H-pyrido[4,3-d]pyrimidine, 4,5,6,6a-tetrahydro-3aH-pyrrolo[3,4-d]isoxazole, 1,2,3,4-tetrahydro-quinoline, 4,5,6,7-tetrahydro-thieno[2,3-c]pyridine, 4,5,6,7-tetrahydro-thieno[3,2-c]pyridine, 4,5,6,7-tetrahydro-thiazolo[5,4-c]pyridine, 1,3,8-triaza-spiro[4.5]decane or triaza-spirooctane, wherein said heterocyclic residue is mono-, di- or trisubstituted independently of one another by R7, Q is
1) a covalent bond,
2) —($C_0$-$C_4$)-alkylene-CH(OH)—,
3) —($C_0$-$C_4$)-alkylene-C(O)—N(R10)-,
4) —($C_1$-$C_3$)-alkylene-C(O)—O—,
5) —($C_1$-$C_3$)-alkylene-O— or
6) —($C_1$-$C_3$)-alkylene-S(O)$_2$—, J is
1) a hydrogen atom,
2) —($C_1$-$C_6$)-alkyl,
3) —($C_0$-$C_4$)-alkylene-C(O)—R11,
4) —($C_0$-$C_4$)-alkylene-C(O)—O—R11,
5) —($C_0$-$C_4$)-alkylene-N(R11)-R13,
6) —($C_0$-$C_2$)-alkylene-($C_3$-$C_6$)-cycloalkyl,
7) —($C_0$-$C_2$)-alkylene-($C_6$-$C_{14}$)-aryl, wherein aryl is selected from phenyl or indanyl, or
8) —($C_0$-$C_4$)-alkylene-($C_3$-$C_{15}$)-heterocyclyl, wherein —($C_3$-$C_{15}$)-heterocyclyl is azetidinyl, benzimidazolyl, 2,3-dihydro-1H-indolyl, 4,5-dihydro-[1,3,4]oxadiazolyl, 3,4-dihydro-2H-quinolinyl, 1,3-dioxanyl, 1,3-dioxolanyl, isoxazolyl, furanyl, morpholinyl, oxadiazolyl, oxazolidinyl, oxetanyl, piperidinyl, pyridyl, pyrimidinyl, pyrrolidinyl, tetrahydrofuranyl, tetrahydropyranyl, tetrazolyl, thiazolyl or thiophenyl, wherein heterocyclyl is unsubstituted or mono- or di-substituted independently of one another by R13, V is azetidinyl, aminoazetidinyl, piperazinyl, piperidinyl or pyrrolidinyl, G and M together form a —C(O)—($C_0$-$C_4$)-alkyl, —C(O)—O—($C_2$-$C_6$)-alkyl or —N(R10)-C(O)—O—($C_2$-$C_6$)-alkyl, or G is a direct bond and M is a phenyl residue, which is unsubstituted or substituted by Cl, F or Br, R1 is a hydrogen atom, methyl or ethyl,
R2, R3, R4, R5 and R6 are independently of one another selected from
hydrogen atom, Cl, F, Br, —CN, —O—$CH_3$, —O—$CH_2$—$CH_3$, methyl, ethyl, propyl or butyl, or
R3 and R4, R4 and R5 or R5 and R6 form together with the atoms which they are attached to a cyclohexyl ring, R7 is
1) a hydrogen atom,
2) halogen,
3) —($C_1$-$C_6$)-alkyl, wherein alkyl is unsubstituted or mono-, di- or trisubstituted independently of one another by R13,
4) =O,
5) —($C_1$-$C_3$)-fluoroalkyl,
6) —($C_0$-$C_4$)-alkylene-O—R19, wherein R19 is
a) hydrogen atom,
b) —($C_1$-$C_4$)-alkyl, wherein alkyl is unsubstituted or mono-, di- or trisubstituted independently of one another by R13,
c) phenyl, wherein phenyl is unsubstituted or mono-, di- or trisubstituted independently of one another by R13,
d) —$CF_3$, or
e) —$CHF_2$,
7) —$NO_2$,
8) —CN,
9) —($C_0$-$C_4$)-alkylene-O—$CH_2$—($C_1$-$C_3$)-fluoroalkylene-$CH_2$—O—($C_1$-$C_4$)-alkyl,
10) —($C_0$-$C_4$)-alkylene-C(O)—R11,
11) —($C_0$-$C_4$)-alkylene-C(O)—O—R11, 12) —($C_0$-$C_4$)-alkylene-C(O)—O—($C_1$-$C_4$)-alkylene-O—C(O)—R17, wherein —($C_1$-$C_4$)-alkylene is unsubstituted or mono-, di- or trisubstituted independently of one another by R15,
13) —($C_0$-$C_4$)-alkylene-C(O)—O—($C_1$-$C_4$)-alkylene-O—C(O)—O—R17, wherein —($C_1$-$C_4$)-alkylene is unsubstituted or mono-, di- or trisubstituted independently of one another by R15,
14) —($C_0$-$C_4$)-alkylene-C(O)—N(R11)-R12,
15) —($C_0$-$C_4$)-alkylene-C(O)—N(R11)-R13,
16) —($C_0$-$C_4$)-alkylene-C(O)—N[($C_0$-$C_4$)-alkylene]-R13, wherein alkyl and cycloalkyl are unsubstituted or mono-, di- or trisubstituted independently of one another by R13,
17) —($C_0$-$C_4$)-alkylene-C(O)—N[($C_0$-$C_4$)-alkylene-($C_3$-$C_8$)-cycloalkyl]-R13, wherein alkyl and cycloalkyl is unsubstituted or mono-, di- or trisubstituted independently of one another by R13
18) —($C_0$-$C_4$)-alkylene-N(R11)-R12,
19) —($C_0$-$C_4$)-alkylene-N(R11)-R13,
20) —($C_0$-$C_4$)-alkylene-N(R10)-$SO_2$—R10,
21) —($C_0$-$C_4$)-alkylene-S—R10,
22) —($C_0$-$C_4$)-alkylene-$SO_s$—R11, wherein s is 1 or 2,
23) —($C_0$-$C_4$)-alkylene-$SO_t$—N(R11)-R12, wherein t is 1 or 2,
24) —($C_0$-$C_4$)-alkylene-$SO_s$,—N(R11)-R13, wherein w is 1 or 2,
25) —($C_0$-$C_4$)-alkylene-$SO_u$—($C_0$-$C_4$)-alkylene-C(O)—O—R10, wherein u is 1 or 2,
26) —($C_0$-$C_4$)-alkylene-($C_3$-$C_6$)-cycloalkyl, wherein cycloalkyl is unsubstituted or mono-, di- or trisubstituted independently of one another by R13,
27) —($C_0$-$C_4$)-alkylene-($C_6$-$C_{14}$)-aryl, wherein aryl is selected from phenyl, naphthyl, biphenylyl, indanyl, anthryl or fluorenyl; and wherein aryl is unsubstituted or mono-, di- or trisubstituted independently of one another by R13,
28) —($C_0$-$C_4$)-alkylene-($C_3$-$C_{15}$)-heterocyclyl, wherein —($C_3$-$C_{15}$)-heterocyclyl is selected from the group consisting of azetidinyl, benzimidazolyl, 2,3-dihydro-1H-indolyl, 4,5-dihydro-[1,3,4]oxadiazolyl, 3,4-dihydro-2H-quinolinyl, 1,3-dioxanyl, 1,3-dioxolanyl, furanyl, morpholinyl, oxadiazolyl, oxazolidinyl, oxetanyl, piperidinyl, pyridyl, pyrimidinyl, pyrrolidinyl, tetrahydrofuranyl, tetrahydropyranyl, tetrazolyl, thiazolyl or thiophenyl, and is unsubstituted or mono-, di- or trisubstituted independently of one another by R13,
29) —($C_0$-$C_4$)-alkylene-O—($C_0$-$C_4$)-alkylene-($C_6$-$C_{14}$)-aryl, wherein aryl is as defined above and is unsubstituted or mono-, di- or trisubstituted independently of one another by R13,
30) —($C_0$-$C_4$)-alkylene-O—($C_0$-$C_4$)-alkylene-($C_3$-$C_{15}$)-heterocyclyl, wherein —($C_3$-$C_{15}$)-heterocyclyl is as defined above and is un-substituted or mono-, di- or trisubstituted independently of one another by R13,
31) —($C_0$-$C_4$)-alkylene-N(R13)-($C_0$-$C_4$)-alkylene-($C_6$-$C_{14}$)-aryl, wherein aryl is as defined above and is unsubstituted or mono-, di- or trisubstituted independently of one another by R13, or
32) —($C_0$-$C_4$)-alkylene-N(R13)-($C_0$-$C_4$)-alkylene-($C_3$-$C_{15}$)-heterocyclyl, wherein —($C_3$-$C_{15}$)-heterocyclyl is as defined above and is un-substituted or mono-, di- or trisubstituted independently of one another by R13,
R10 is hydrogen atom or —($C_1$-$C_4$)-alkyl,
R11 and R12 are independently of one another identical or different and are
1) a hydrogen atom,
2) —($C_1$-$C_4$)-alkyl, wherein alkyl is unsubstituted or mono- or di-substituted independently of one another by R13,
3) —($C_1$-$C_3$)-fluoroalkyl,
4) —($C_0$-$C_4$)-alkylene-($C_3$-$C_6$)-cycloalkyl, wherein cycloalkyl is unsubstituted or mono- or di-substituted independently of one another by R13,
5) —($C_0$-$C_4$)-alkylene-($C_3$-$C_{15}$)-heterocyclyl, wherein —($C_3$-$C_{15}$)-heterocyclyl is azetidinyl, benzimidazolyl, 2,3-dihydro-1H-indolyl, 4,5-dihydro-[1,3,4]oxadiazolyl, 3,4-dihydro-2H-quinolinyl, 1,3-dioxanyl, 1,3-dioxolanyl, furanyl, morpholinyl, oxadiazolyl, oxazolidinyl, oxetanyl, piperidinyl, pyridyl, pyrimidinyl, pyrrolidinyl, tetrahydrofuranyl, tetrahydropyranyl, tetrazolyl, thiazolyl or thiophenyl, or R11 and R12 together with the nitrogen atom to which they are bonded form a 4- to 8-membered monocyclic heterocyclic ring selected from azetidine, piperidine, pyrrolidine or morpholine,
R13 is F, Cl, Br, —CN, =O, —OH, —$CF_3$, —C(O)—O—R10, —($C_3$-$C_6$)-cycloalkyl, —($C_0$-$C_4$)-alkylene-O—R10, —C(O)—R10, —($C_1$-$C_4$)-alkyl or phenyl,
R15 is hydrogen atom or —($C_1$-$C_6$)-alkyl,
R17 is hydrogen atom or —($C_1$-$C_6$)-alkyl,
R23 and R24 are independently of one another selected from hydrogen atom or methyl,
in all its stereoisomeric forms and mixtures thereof in any ratio, and its physiologically tolerable salts.

5. A compound as claimed in claim 3, wherein
E is a heterocyclic residue selected from aza-bicyclohexane, aza-bicyclooctane, azetidine, aziridine, decahydroquinoline, 2,5-diaza-bicyclo[2.2.1]heptane, 1,4-diazepane, 2,7-diaza-spiro[4.5]decane, 2,8-diaza-spiro[4.5]decane, 2,3-dihydro-1H-indole, 4,7-dihydro-5H-isoxazolo[5,4-c]pyridine, 6,7-dihydro-4H-oxazolo[5,4-c]pyridine, 4,6-dihydro-1H-pyrrolo[3,4-c]pyrazol, 4,6-dihydro-4H-pyrrolo[3,4-d]thiazole, 5,6-dihydro-8H-[1,2,4]triazolo[4,3-a]pyrazin, hexahydro-pyrrolo[1,2-a]pyrazin, hexahydro-pyrrolo[3,4-b]pyrrol, Hexahydro-pyrrolo[1,2-a]pyrazin, imidazolidine, morpholine, indole, octahydro-cyclopenta[c]pyrrole, octahydro-indole, octahydro-pyrrolo[3,4-b]pyridine, octahydro-pyrrolo[3,4-c]pyridine, oxazolidine, piperazine, piperidine, pyrazolidine, pyrrolidine, 1,4,6,7-tetrahydro-pyrazolo[4,3-c]pyridine, 1,2,3,4-tetrahydro-isoquinoline, 4,5,6,7-tetrahydro-isoxazolo[4,5-c]pyridine, 4,5,6,7-tetrahydro-1H-pyrazolo[4,3-c]pyridine, 3,5,7,8-tetrahydro-4H-pyrido[4,3-d]pyrimidine, 4,5,6,6a-tetrahydro-3aH-pyrrolo[3,4-d]isoxazole, 1,2,3,4-tetrahydro-quinoline, 4,5,6,7-tetrahydro-thieno[2,3-c]pyridine, 4,5,6,7-tetrahydro-thieno[3,2-c]pyridine, 4,5,6,7-tetrahydro-thiazolo[5,4-c]pyridine, 1,3,8-triaza-spiro[4.5]decane or triaza-spirooctane, wherein said heterocyclic residue is mono-, di- or trisubstituted independently of one another by R7,
Q is
1) a covalent bond,
2) —($C_0$-$C_4$)-alkylene-CH(OH)—,
3) —($C_0$-$C_4$)-alkylene-C(O)—N(R10)-,
4) —($C_1$-$C_3$)-alkylene-C(O)—O—,
5) —($C_1$-$C_3$)-alkylene-O— or
6) —($C_1$-$C_3$)-alkylene-S(O)$_2$—, J is
1) a hydrogen atom,
2) —($C_1$-$C_6$)-alkyl,
3) —($C_0$-$C_4$)-alkylene-C(O)—R11,
4) —($C_0$-$C_4$)-alkylene-C(O)—O—R11,
5) —($C_0$-$C_4$)-alkylene-N(R11)-R13,
6) —($C_0$-$C_2$)-alkylene-($C_3$-$C_6$)-cycloalkyl,
7) —($C_0$-$C_2$)-alkylene-phenyl or
8) —($C_0$-$C_4$)-alkylene-($C_3$-$C_{15}$)-heterocyclyl, wherein —($C_3$-$C_{15}$)-heterocyclyl is azetidinyl, benzimidazolyl, 2,3-dihydro-1H-indolyl, 4,5-dihydro-[1,3,4]oxadiazolyl, 3,4-dihydro-2H-quinolinyl, 1,3-dioxanyl, 1,3-dioxolanyl, indanyl, isoxazolyl, furanyl, morpholinyl, oxadiazolyl, oxazolidinyl, oxetanyl, piperidinyl, pyridyl, pyrimidinyl, pyrrolidinyl, tetrahydrofuranyl, tetrahydropyranyl, tetrazolyl, thiazolyl or thiophenyl, wherein heterocyclyl is unsubstituted or mono- or di-substituted independently of one another by R13,
V is a piperazinyl, piperidinyl, azetidinyl or aminoazetidinyl,
G and M together form a —C(O)—($C_0$-$C_4$)-alkyl, —C(O)—O—($C_2$-$C_4$)-alkyl or —N(R10)-C(O)—O—($C_2$-$C_4$)-alkyl, or
G is a direct bond and M is a phenyl residue, which is unsubstituted or substituted by Cl, F or Br,
R1 is a hydrogen atom, methyl or ethyl,
R2, R3, R4, R5 and R6 are independently of one another selected from hydrogen atom, Cl, F, Br, —CN, —O—$CH_3$, —O—$CH_2$—$CH_3$, methyl, ethyl, propyl or butyl, or
R3 and R4, R4 and R5 or R5 and R6 form together with the atoms which they are attached to a cyclohexyl ring,
R7 is
1) hydrogen atom,
2) Cl, F or Br,
3) —($C_1$-$C_4$)-alkyl,
4) =O,
5) —($C_1$-$C_3$)-fluoroalkyl,
6) —($C_0$-$C_2$)-alkylene-OH,
7) —($C_0$-$C_2$)-alkylene-O—($C_1$-$C_4$)-alkyl,
8) —($C_0$-$C_2$)-alkylene-O—$CF_3$,
9) —CN,
10) —C(O)—R11,
11) —($C_0$-$C_2$)-alkylene-C(O)—O—R11,
12) —($C_0$-$C_2$)-alkylene-C(O)—N(R11)-R12,
13) —N(R11)-R12,
14) —N(R11)-R13,
15) —$SO_2$—($C_1$-$C_4$)-alkyl,
16) —($C_0$-$C_4$)-alkyl-($C_3$-$C_6$)-cycloalkyl,
17) phenyl,
18) —($C_0$-$C_4$)-alkylene-($C_3$-$C_{15}$)-heterocyclyl, wherein —($C_3$-$C_{15}$)-heterocyclyl is azetidinyl, benzimidazolyl, 2,3-dihydro-1H-indolyl, 4,5-dihydro-[1,3,4]oxadiazolyl, 3,4-dihydro-2H-quinolinyl, 1,3-dioxanyl, 1,3-dioxolanyl, furanyl, morpholinyl, oxadiazolyl, oxazolidinyl, oxetanyl, piperidinyl, pyridyl, pyrimidinyl, pyrrolidinyl, tetrahydrofuranyl, tetrahydropyranyl, tetrazolyl, thiazolyl or thiophenyl, or
19) —O-phenyl, wherein phenyl is unsubstituted or mono- or di-substituted independently of one another by R13,
R10 is hydrogen atom or —($C_1$-$C_4$)-alkyl,
R11 and R12 are independently of one another identical or different and are
1) a hydrogen atom,
2) —($C_1$-$C_4$)-alkyl, wherein alkyl is unsubstituted or mono- or di-substituted independently of one another by R13,
3) —($C_1$-$C_3$)-fluoroalkyl,
4) —($C_0$-$C_4$)-alkylene-($C_3$-$C_6$)-cycloalkyl, wherein cycloalkyl is unsubstituted or mono- or di-substituted independently of one another by R13,
5) phenyl or
6) —($C_0$-$C_4$)-alkylene-($C_3$-$C_{15}$)-heterocyclyl, wherein —($C_3$-$C_{15}$)-heterocyclyl is azetidinyl, benzimidazolyl, 2,3-dihydro-1H-indolyl, 4,5-dihydro-[1,3,4]oxadiazolyl, 3,4-dihydro-2H-quinolinyl, 1,3-dioxanyl, 1,3-dioxolanyl, furanyl, morpholinyl, oxadiazolyl, oxazolidinyl, oxetanyl, piperidinyl, pyridyl, pyrimidinyl, pyrrolidinyl, tetrahydrofuranyl, tetrahydropyranyl, tetrazolyl, thiazolyl or thiophenyl,
R13 is F, Cl, Br, —CN, =O, —OH, —$CF_3$, —C(O)—O—R10, —($C_3$-$C_6$)-cycloalkyl, —($C_0$-$C_4$)-alkylene-O—R10, —C(O)—R10, —($C_1$-$C_4$)-alkyl or phenyl,
R23 and R24 are independently of one another selected from hydrogen atom or methyl,
in all its stereoisomeric forms and mixtures thereof in any ratio, and its physiologically tolerable salts.

6. A compound as claimed in claim 1, wherein the compound is
4-[(S)-4-Carboxy-2-({4-[2-(4-hydroxy-2-methoxycarbonyl-pyrrolidin-1-yl)-2-oxo-ethoxy]-7-methyl-quinoline-2-carbonyl}-amino)-butyryl]-piperazine-1-carboxylic acid ethyl ester, 4-[(S)-4-Carboxy-2-({7-methyl-4-[2-oxo-2-(2-oxo-pyrrolidin-1-yl)-ethoxy]-quinoline-2-carbonyl}-amino)-butyryl]-piperazine-1-carboxylic acid ethyl ester,
4-[(S)-4-Carboxy-2-({4-[2-((S)-2-cyclopropylcarbamoyl-pyrrolidin-1-yl)-2-oxo-ethoxy]-7-methyl-quinoline-2-carbonyl}-amino)-butyryl]-piperazine-1-carboxylic acid ethyl ester,
4-[(S)-4-Carboxy-2-({7-methyl-4-[2-oxo-2-(3-oxo-piperazin-1-yl)-ethoxy]-quinoline-2-carbonyl}-amino)-butyryl]-piperazine-1-carboxylic acid ethyl ester,
4-[(S)-4-Carboxy-2-({4-[2-(3-carboxy-azetidin-1-yl)-2-oxo-ethoxy]-7-methyl-quinoline-2-carbonyl}-amino)-butyryl]-piperazine-1-carboxylic acid ethyl ester, 4-[(S)-4-Carboxy-2-({4-[2-((2S,3S)-2-carboxy-3-hydroxy-pyrrolidin-1-yl)-2-oxo-ethoxy]-7-methyl-quinoline-2-carbonyl}-amino)-butyryl]-piperazine-1-carboxylic acid ethyl ester, 4-[(S)-4-Carboxy-2-({4-[2-((2S,4R)-2-ethoxycarbonyl-4-hydroxy-pyrrolidin-1-yl)-2-oxo-ethoxy]-7-methyl-quinoline-2-carbonyl}-amino)-butyryl]-piperazine-1-carboxylic acid ethyl ester,
4-[(S)-4-Carboxy-2-({4-[2-((R)-3-hydroxy-pyrrolidin-1-yl)-2-oxo-ethoxy]-7-methyl-quinoline-2-carbonyl}-amino)-butyryl]-piperazine-1-carboxylic acid ethyl ester,
4-[(S)-4-Carboxy-2-({4-[2-((S)-3-hydroxy-pyrrolidin-1-yl)-2-oxo-ethoxy]-7-methyl-quinoline-2-carbonyl}-amino)-butyryl]-piperazine-1-carboxylic acid ethyl ester,
4-[(S)-4-Carboxy-2-({4-[2-(4-hydroxy-piperidin-1-yl)-2-oxo-ethoxy]-7-methyl-quinoline-2-carbonyl}-amino)-butyryl]-piperazine-1-carboxylic acid ethyl ester,
4-[(S)-4-Carboxy-2-({4-[2-((S)-2-ethoxycarbonyl-pyrrolidin-1-yl)-2-oxo-ethoxy]-7-methyl-quinoline-2-carbonyl}-amino)-butyryl]-piperazine-1-carboxylic acid ethyl ester,
4-[(S)-4-Carboxy-2-({4-[2-((2R,4R)-2-carboxy-4-hydroxy-pyrrolidin-1-yl)-2-oxo-ethoxy]-7-methyl-quinoline-2-carbonyl}-amino)-butyryl]-piperazine-1-carboxylic acid ethyl ester, 4-[(S)-4-Carboxy-2-({4-[2-(3-hydroxy-azetidin-1-yl)-2-oxo-ethoxy]-7-methyl-quinoline-2-carbonyl}-amino)-butyryl]-piperazine-1-carboxylic acid ethyl ester, 4-[(S)-4-Carboxy-2-({4-[2-((S)-2-methoxycarbonyl-pyrrolidin-1-yl)-2-oxo-ethoxy]-7-methyl-quinoline-2-carbonyl}-amino)-butyryl]-piperazine-1-carboxylic acid ethyl ester, 4-[(S)-4-Carboxy-2-({4-[2-((S)-2-carboxy-azetidin-1-yl)-2-oxo-ethoxy]-7-methyl-quinoline-2-carbonyl}-amino)-butyryl]-piperazine-1-carboxylic acid ethyl ester, 4-[(S)-4-Ethoxycarbonyl-2-({7-methyl-4-[2-oxo-2-(2-oxo-pyrrolidin-1-yl)-ethoxy]-quinoline-2-carbonyl}-amino)-butyryl]-piperazine-1-carboxylic acid ethyl ester, 4-[(S)-4-Carboxy-2-({4-[2-((S)-2-carboxy-pyrrolidin-1-yl)-2-oxo-ethoxy]-7-methyl-quinoline-2-carbonyl}-amino)-butyryl]-piperazine-1-carboxylic acid ethyl ester, 4-[(S)-4-Carboxy-2-({4-[2-(3-methanesulfonyl-pyrrolidin-1-yl)-2-oxo-ethoxy]-7-methyl-quinoline-2-carbonyl}-amino)-butyryl]-piperazine-1-carboxylic acid ethyl ester, 4-[(S)-4-Carboxy-2-({4-[2-(3-carboxy-pyrrolidin-1-yl)-2-oxo-ethoxy]-7-methyl-quinoline-2-carbonyl}-amino)-butyryl]-piperazine-1-carboxylic acid ethyl ester, 4-[(S)-4-Carboxy-2-({4-[2-((3S,4S)-3,4-dihydroxy-pyrrolidin-1-yl)-2-oxo-ethoxy]-7-methyl-quinoline-2-carbonyl}-amino)-butyryl]-piperazine-1-carboxylic acid ethyl ester, 4-[(S)-4-Carboxy-2-({7-methyl-4-[2-oxo-2-(2-oxo-oxazolidin-3-yl)-ethoxy]-quinoline-2-carbonyl}-amino)-butyryl]-piperazine-1-carboxylic acid ethyl ester, 4-[(S)-4-Carboxy-2-({4-[2-(3-cyclopropylcarbamoyl-azetidin-1-yl)-2-oxo-ethoxy]-7-methyl-quinoline-2-carbonyl}-amino)-butyryl]-piperazine-1-carboxylic acid ethyl ester, 4-[(S)-4-Carboxy-2-({4-[2-((R)-2-cyclopropylcarbamoyl-azetidin-1-yl)-2-oxo-ethoxy]-7-methyl-quinoline-2-carbonyl}-amino)-butyryl]-piperazine-1-carboxylic acid ethyl ester, 4-[(S)-2-({4-[2-((S)-2-Cyclopropylcarbamoyl-pyrrolidin-1-yl)-2-oxo-ethoxy]-7-methyl-quinoline-2-carbonyl}-amino)-4-ethoxycarbonyl-butyryl]-piperazine-1-carboxylic acid ethyl ester, 4-[(S)-4-Carboxy-2-({4-[2-((S)-2-ethylcarbamoyl-pyrrolidin-1-yl)-2-oxo-ethoxy]-7-methyl-quinoline-2-carbonyl}-amino)-butyryl]-piperazine-1-carboxylic acid ethyl ester, 4-[(S)-4-Carboxy-2-({4-[2-((S)-2-cyclopropylcarbamoyl-pyrrolidin-1-yl)-1,1-dimethyl-2-oxo-ethoxy]-7-methyl-quinoline-2-carbonyl}-amino)-butyryl]-piperazine-1-carboxylic acid ethyl ester, 4-[(S)-4-Carboxy-2-({4-[2-((S)-2-dimethylcarbamoyl-pyrrolidin-1-yl)-2-oxo-ethoxy]-7-methyl-quinoline-2-carbonyl}-amino)-butyryl]-piperazine-1-carboxylic acid ethyl ester, 4-[(S)-2-({4-[2-((S)-2-Carbamoyl-pyrrolidin-1-yl)-2-oxo-ethoxy]-7-methyl-quinoline-2-carbonyl}-amino)-4-carboxy-butyryl]-piperazine-1-carboxylic acid ethyl ester, 4-[(S)-4-Carboxy-2-({4-[2-((S)-3-cyclopropylcarbamoyl-pyrrolidin-1-yl)-2-oxo-ethoxy]-7-methyl-quinoline-2-carbonyl}-amino)-butyryl]-piperazine-1-carboxylic acid ethyl ester, 4-[(S)-4-Carboxy-2-({4-[2-((R)-3-cyclopropylcarbamoyl-pyrrolidin-1-yl)-2-oxo-ethoxy]-7-methyl-quinoline-2-carbonyl}-amino)-butyryl]-piperazine-1-carboxylic acid ethyl ester, 4-[(S)-4-Carboxy-2-({4-[2-((S)-2-hydroxymethyl-pyrrolidin-1-yl)-2-oxo-ethoxy]-7-methyl-quinoline-2-carbonyl}-amino)-butyryl]-piperazine-1-carboxylic acid ethyl ester, 4-{(S)-4-Carboxy-2-[(7-methyl-4-{2-oxo-2-[(S)-2-(2,2,2-trifluoro-ethylcarbamoyl)-pyrrolidin-1-yl]-ethoxy}-quinoline-2-carbonyl)-amino]-butyryl}-piperazine-1-carboxylic acid ethyl ester, 4-[(S)-4-Carboxy-2-({4-[2-(4-methoxy-piperidin-1-yl)-2-oxo-ethoxy]-7-methyl-quinoline-2-carbonyl}-amino)-butyryl]-piperazine-1-carboxylic acid ethyl ester, 4-[(S)-4-Carboxy-2-({7-methyl-4-[2-oxo-2-(3-oxo-pyrazolidin-1-yl)-ethoxy]-quinoline-2-carbonyl}-amino)-butyryl]-piperazine-1-carboxylic acid ethyl ester, 4-[(S)-4-Carboxy-2-({4-[2-(2-hydroxymethyl-morpholin-4-yl)-2-oxo-ethoxy]-7-methyl-quinoline-2-carbonyl}-amino)-butyryl]-piperazine-1-carboxylic acid ethyl ester, 4-[(S)-4-Carboxy-2-({7-methyl-4-[2-oxo-2-((1S,5R)-3-oxo-8-aza-bicyclo[3.2.1]oct-8-yl)-ethoxy]-quinoline-2-carbonyl}-amino)-butyryl]-piperazine-1-carboxylic acid ethyl ester, 4-[(S)-4-Carboxy-2-({7-methyl-4-[2-oxo-2-(5-oxo-[1,4]diazepan-1-yl)-ethoxy]-quinoline-2-carbonyl}-amino)-butyryl]-piperazine-1-carboxylic acid ethyl ester, 4-[(S)-4-Carboxy-2-({4-[2-(4-ethoxycarbonyl-piperidin-1-yl)-2-oxo-ethoxy]-7-methyl-quinoline-2-carbonyl}-amino)-butyryl]-piperazine-1-carboxylic acid ethyl ester, 4-[(S)-4-Carboxy-2-({4-[2-(4-ethoxy-piperidin-1-yl)-2-oxo-ethoxy]-7-methyl-quinoline-2-carbonyl}-amino)-butyryl]-piperazine-1-carboxylic acid ethyl ester, 4-((S)-4-Carboxy-2-{[7-methyl-4-(2-morpholin-4-yl-2-oxo-ethoxy)-quinoline-2-carbonyl]-amino}-butyryl)-piperazine-1-carboxylic acid ethyl ester, 4-[(S)-4-Carboxy-2-({4-[2-(3-hydroxy-piperidin-1-yl)-2-oxo-ethoxy]-7-methyl-quinoline-2-carbonyl}-amino)-butyryl]-piperazine-1-carboxylic acid ethyl ester, 4-[(S)-4-Carboxy-2-({4-[2-(4-carboxy-piperidin-1-yl)-2-oxo-ethoxy]-7-methyl-quinoline-2-carbonyl}-amino)-butyryl]-piperazine-1-carboxylic acid ethyl ester, 4-[(S)-4-Carboxy-2-({4-[2-((R)-3-hydroxy-piperidin-1-yl)-2-oxo-ethoxy]-7-methyl-quinoline-2-carbonyl}-amino)-butyryl]-piperazine-1-carboxylic acid ethyl ester, 4-[(S)-4-Carboxy-2-({4-[2-(2,2-dimethyl-3-oxo-piperazin-1-yl)-2-oxo-ethoxy]-7-methyl-quinoline-2-carbonyl}-amino)-butyryl]-piperazine-1-carboxylic acid ethyl ester, 4-[(S)-4-Carboxy-2-({4-[2-((S)-2-carboxy-piperidin-1-yl)-2-oxo-ethoxy]-7-methyl-quinoline-2-carbonyl}-amino)-butyryl]-piperazine-1-carboxylic acid ethyl ester, 4-[(S)-4-Carboxy-2-({4-[2-((R)-2-carboxy-piperidin-1-yl)-2-oxo-ethoxy]-7-methyl-quinoline-2-carbonyl}-amino)-butyryl]-piperazine-1-carboxylic acid ethyl ester, 4-[(S)-4-Carboxy-2-({4-[2-((S)-2-methoxymethyl-pyrrolidin-1-yl)-2-oxo-ethoxy]-7-methyl-quinoline-2-carbonyl}-amino)-butyryl]-piperazine-1-carboxylic acid ethyl ester, 4-[(S)-4-Carboxy-2-({4-[2-(4-cyclopropylcarbamoyl-piperidin-1-yl)-2-oxo-ethoxy]-7-methyl-quinoline-2-carbonyl}-amino)-butyryl]-piperazine-1-carboxylic acid ethyl ester, 4-[(S)-4-Carboxy-2-({4-[2-((R)-2-cyclopropylcarbamoyl-piperidin-1-yl)-2-oxo-ethoxy]-7-methyl-quinoline-2-carbonyl}-amino)-butyryl]-piperazine-1-carboxylic acid ethyl ester, 4-[(S)-4-Carboxy-2-({4-[2-((S)-3-hydroxymethyl-pyrrolidin-1-yl)-2-oxo-ethoxy]-7-methyl-quinoline-2-carbonyl}-amino)-butyryl]-piperazine-1-carboxylic acid ethyl ester, 4-[(S)-4-Carboxy-2-({4-[2-((R)-3-hydroxymethyl-pyrrolidin-1-yl)-2-oxo-ethoxy]-7-methyl-quinoline-2-carbonyl}-amino)-butyryl]-piperazine-1-carboxylic acid ethyl ester, 4-[(S)-4-Carboxy-2-({4-[2-(2-carboxy-4,4-difluoro-pyrrolidin-1-yl)-2-oxo-ethoxy]-7-methyl-quinoline-2-carbonyl}-amino)-butyryl]-piperazine-1-carboxylic acid ethyl ester, 4-[(S)-4-Carboxy-2-({7-methyl-4-[2-oxo-2-(3-oxo-pyrrolidin-1-yl)-ethoxy]-quinoline-2-carbonyl}-amino)-butyryl]-piperazine-1-carboxylic acid ethyl ester, 4-[(S)-4-Carboxy-2-({4-[2-((S)-2-cyclopropylcarbamoyl-piperidin-1-yl)-2-oxo-ethoxy]-7-methyl-quinoline-2-carbonyl}-amino)-butyryl]-piperazine-1-carboxylic acid ethyl ester, 4-[(S)-4-Carboxy-2-({4-[2-(3-cyclopropylcarbamoyl-piperidin-1-yl)-2-oxo-ethoxy]-7-methyl-quinoline-2-carbonyl}-amino)-butyryl]-piperazine-1-carboxylic acid ethyl ester, 4-[(S)-4-Carboxy-2-({4-[2-((S)-2-cyclopropylcarbamoyl-pyrrolidin-1-yl)-2-oxo-ethoxy]-5,7-dimethyl-quinoline-2-carbonyl}-amino)-butyryl]-piperazine-1-carboxylic acid ethyl ester, 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-ethoxycarbonyl-butyryl]-piperazine-1-carboxylic acid ethyl ester, 4-[(S)-4-Carboxy-2-({4-[2-((S)-2-cyclopropylcarbamoyl-pyrrolidin-1-yl)-2-oxo-ethoxy]-6-fluoro-7-methyl-quinoline-2-carbonyl}-amino)-butyryl]-piperazine-1-carboxylic acid ethyl ester, 4-[(S)-4-Carboxy-2-({4-[2-((R)-2-ethoxycarbonyl-pyrrolidin-1-yl)-2-oxo-ethoxy]-7-methyl-quinoline-2-carbonyl}-amino)-butyryl]-piperazine-1-carboxylic acid ethyl ester, 4-[(S)-2-({4-[2-((R)-2-Carbamoyl-pyrrolidin-1-yl)-2-oxo-ethoxy]-7-methyl-quinoline-2-carbonyl}-amino)-4-carboxy-butyryl]-piperazine-1-carboxylic acid ethyl ester, 4-[(S)-4-Carboxy-2-({4-[2-((S)-2-carboxy-2-methyl-pyrrolidin-1-yl)-2-oxo-ethoxy]-7-methyl-quinoline-2-carbonyl}-amino)-butyryl]-piperazine-1-carboxylic acid ethyl ester, 4-{(S)-4-Carboxy-2-[(4-{2-[(S)-2-(cyclopropylmethylcarbamoyl)-pyrrolidin-1-yl]-2-oxo-ethoxy}-7-methyl-quinoline-2-carbonyl)-amino]-butyryl}-piperazine-1-carboxylic acid ethyl ester, 4-[(S)-4-Carboxy-2-({4-[2-((S)-2-isopropylcarbamoyl-pyrrolidin-1-yl)-2-oxo-ethoxy]-7-methyl-quinoline-2-carbonyl}-amino)-butyryl]-piperazine-1-carboxylic acid ethyl ester, 4-{(S)-4-Carboxy-2-[(4-{2-[(S)-2-(2,2-difluoro-ethylcarbamoyl)-pyrrolidin-1-yl]-2-oxo-ethoxy}-7-methyl-quinoline-2-carbonyl)-amino]-butyryl}-piperazine-1-carboxylic acid ethyl ester, 4-{(S)-4-Carboxy-2-[(4-{2-[(S)-2-(2-fluoro-ethylcarbamoyl)-pyrrolidin-1-yl]-2-oxo-ethoxy}-7-methyl-quinoline-2-carbonyl)-amino]-butyryl}-piperazine-1-carboxylic acid ethyl ester, 4-[(S)-4-Carboxy-2-({4-[2-((R)-2-cyclopropylcarbamoyl-pyrrolidin-1-yl)-2-oxo-ethoxy]-7-methyl-quinoline-2-carbonyl}-amino)-butyryl]-piperazine-1-carboxylic acid ethyl ester, 4-[(S)-4-Carboxy-2-({4-[2-(4,4-dimethyl-oxazolidin-3-yl)-2-oxo-ethoxy]-7-methyl-quinoline-2-carbonyl}-amino)-butyryl]-piperazine-1-carboxylic acid ethyl ester, 4-[(S)-4-Ethoxycarbonyl-2-({4-[2-(4-hydroxy-piperidin-1-yl)-2-oxo-ethoxy]-7-methyl-quinoline-2-carbonyl}-amino)-butyryl]-piperazine-1-carboxylic acid ethyl ester, 4-[(S)-4-Carboxy-2-({7-methyl-4-[2-oxo-2-((S)-2-propylcarbamoyl-pyrrolidin-1-yl)-ethoxy]-quinoline-2-carbonyl}-amino)-butyryl]-piperazine-1-carboxylic acid ethyl ester, 4-[(S)-4-Carboxy-2-({4-[2-(4-hydroxy-2-methoxycarbonyl-pyrrolidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-oxo-2-(2-oxo-pyrrolidin-1-yl)-ethoxy]-quinoline-2-carbonyl}-amino)-butyryl]-piperazine-1-carboxylic acid ethyl ester, 4-[(S)-4-Carboxy-2-({4-[2-((S)-2-cyclopropylcarbamoyl-pyrrolidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-((R)-3-hydroxy-pyrrolidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-((2S,4R)-2-ethoxycarbonyl-4-hydroxy-pyrrolidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-((S)-2-carboxy-pyrrolidin-1-yl)-2-oxo-ethoxy]-quinoline-2-carbonyl}-amino)-butyryl]-piperazine-1-carboxylic acid ethyl ester, 4-[(S)-4-Carboxy-2-({-[2-((2S,4R)-2-carboxy-4-hydroxy-pyrrolidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-((2S,3S)-2-carboxy-3-hydroxy-pyrrolidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-((S)-2-carboxy-azetidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-(2,4-dioxo-1,3,8-triaza-spiro[4.5]dec-8-yl)-2-oxo-ethoxy]-quinoline-2-carbonyl}-amino)-butyryl]-piperazine-1-carboxylic acid ethyl ester, 4-[(S)-2-({4-[2-(3-Acetylamino-pyrrolidin-1-yl)-2-oxo-ethoxy]-quinoline-2-carbonyl}-amino)-4-carboxy-butyryl]-piperazine-1-carboxylic acid ethyl ester, 4-(2-{2-[(S)-3-Carboxy-1-(4-ethoxycarbonyl-piperazine-1-carbonyl)-propylcarbamoyl]-quinolin-4-yloxy}-acetyl)-piperazine-1-carboxylic acid ethyl ester, 4-[(S)-4-Carboxy-2-({4-[2-(4-ethyl-piperazin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-((2S,4S)-2-carboxy-4-hydroxy-pyrrolidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-(3-methanesulfonyl-pyrrolidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-oxo-2-(3-oxo-piperazin-1-yl)-ethoxy]-quinoline-2-carbonyl}-amino)-butyryl]-piperazine-1-carboxylic acid ethyl ester, 4-{(S)-4-Carboxy-2-[(4-{2-[4-(2-hydroxy-ethyl)-piperazin-1-yl]-2-oxo-ethoxy}-quinoline-2-carbonyl)-amino]-butyryl}-piperazine-1-carboxylic acid ethyl ester, 4-[(S)-2-({4-[2-(4-Acetyl-piperazin-1-yl)-2-oxo-ethoxy]-quinoline-2-carbonyl}-amino)-4-carboxy-butyryl]-piperazine-1-carboxylic acid ethyl ester, 4-[(S)-4-Carboxy-2-({4-[2-((2R,4R)-2-carboxy-4-hydroxy-pyrrolidin-1-yl)-2-oxo-ethoxy]-quinoline-2-carbonyl}-amino)-butyryl]-piperazine-1-carboxylic acid ethyl ester, 4-[(S)-2-({4-[2-(3-Amino-azetidin-1-yl)-2-oxo-ethoxy]-quinoline-2-carbonyl}-amino)-4-carboxy-butyryl]-piperazine-1-carboxylic acid ethyl ester, 4-[(S)-4-Carboxy-2-({4-[2-(3-hydroxy-azetidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-((2S,4R)-4-hydroxy-2-methoxycarbonyl-pyrrolidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-(3-carboxy-azetidin-1-yl)-2-oxo-ethoxy]-quinoline-2-carbonyl}-amino)-butyryl]-piperazine-1-carboxylic acid ethyl ester, 3-(2-{2-[(S)-3-Carboxy-1-(4-ethoxycarbonyl-piperazine-1-carbonyl)-propylcarbamoyl]-quinolin-4-yloxy}-acetyl)-3-aza-bicyclo[3.1.0]hexane-6-carboxylic acid ethyl ester, 4-[(S)-4-Carboxy-2-({4-[2-((S)-2-ethoxycarbonyl-pyrrolidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-(4-carboxymethyl-piperazin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-((S)-2-methoxycarbonyl-pyrrolidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-(3-methoxycarbonylmethanesulfonyl-azetidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-((3R,4R)-3,4-dihydroxy-pyrrolidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-((3S,4S)-3,4-dihydroxy-pyrrolidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-((S)-3-hydroxy-2-oxo-pyrrolidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-(4-hydroxy-piperidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-(3-carboxy-pyrrolidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-((S)-3-hydroxy-pyrrolidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-((2S,4S)-4-hydroxy-2-methoxycarbonyl-pyrrolidin-1-yl)-2-oxo-ethoxy]-quinoline-2-carbonyl}-amino)-butyryl]-piperazine-1-carboxylic acid ethyl ester, 4-[(S)-4-Ethoxycarbonyl-2-({4-[2-oxo-2-(2-oxo-pyrrolidin-1-yl)-ethoxy]-quinoline-2-carbonyl}-amino)-butyryl]-piperazine-1-carboxylic acid ethyl ester, 4-[(S)-2-({4-[2-((S)-2-Cyclopropylcarbamoyl-pyrrolidin-1-yl)-2-oxo-ethoxy]-quinoline-2-carbonyl}-amino)-4-ethoxycarbonyl-butyryl]-piperazine-1-carboxylic acid ethyl ester, 4-[(S)-4-Carboxy-2-({4-[2-((S)-2-dimethylcarbamoyl-pyrrolidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-((S)-2-ethylcarbamoyl-pyrrolidin-1-yl)-2-oxo-ethoxy]-quinoline-2-carbonyl}-amino)-butyryl]-piperazine-1-carboxylic acid ethyl ester, 4-[(S)-2-({4-[2-((S)-2-Carbamoyl-pyrrolidin-1-yl)-2-oxo-ethoxy]-quinoline-2-carbonyl}-amino)-4-carboxy-butyryl]-piperazine-1-carboxylic acid ethyl ester, 4-[(S)-4-Carboxy-2-({4-[2-(3-cyclopropylcarbamoyl-azetidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-((S)-3-cyclopropylcarbamoyl-pyrrolidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-((R)-3-cyclopropylcarbamoyl-pyrrolidin-1-yl)-2-oxo-ethoxy]-quinoline-2-carbonyl}-amino)-butyryl]-piperazine-1-carboxylic acid ethyl ester, 4-{(S)-4-Carboxy-2-[(4-{2-[(S)-2-(2,2-difluoro-ethylcarbamoyl)-pyrrolidin-1-yl]-2-oxo-ethoxy}-quinoline-2-carbonyl)-amino]-butyryl}-piperazine-1-carboxylic acid ethyl ester, 4-{(S)-4-Carboxy-2-[(4-{2-[(S)-2-(2-fluoro-ethylcarbamoyl)-pyrrolidin-1-yl]-2-oxo-ethoxy}-quinoline-2-carbonyl)-amino]-butyryl}-piperazine-1-carboxylic acid ethyl ester, 4-[(S)-4-Carboxy-2-({4-[2-oxo-2-((1S,5R)-3-oxo-8-aza-bicyclo[3.2.1]oct-8-yl)-ethoxy]-quinoline-2-carbonyl}-amino)-butyryl]-piperazine-1-carboxylic acid ethyl ester, 4-[(S)-4-Carboxy-2-({4-[2-(2-hydroxymethyl-morpholin-4-yl)-2-oxo-ethoxy]-quinoline-2-carbonyl}-amino)-butyryl]-piperazine-1-carboxylic acid ethyl ester, 4-[(S)-4-Carboxy-2-({4-[2-((R)-3-hydroxy-piperidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-oxo-2-(3-oxo-pyrazolidin-1-yl)-ethoxy]-quinoline-2-carbonyl}-amino)-butyryl]-piperazine-1-carboxylic acid ethyl ester,
4-[(S)-4-Carboxy-2-({4-[2-(4-methoxy-piperidin-1-yl)-2-oxo-ethoxy]-quinoline-2-carbonyl}-amino)-butyryl]-piperazine-1-carboxylic acid ethyl ester,
4-{(S)-4-Carboxy-2-[(4-{2-oxo-2-[(S)-2-(2,2,2-trifluoro-ethylcarbamoyl)-pyrrolidin-1-yl]-ethoxy}-quinoline-2-carbonyl)-amino]-butyryl}-piperazine-1-carboxylic acid ethyl ester,
4-[(S)-4-Carboxy-2-({4-[2-((S)-2-hydroxymethyl-pyrrolidin-1-yl)-2-oxo-ethoxy]-quinoline-2-carbonyl}-amino)-butyryl]-piperazine-1-carboxylic acid ethyl ester,
4-[(S)-4-Carboxy-2-({4-[2-(4-cyclopropylcarbamoyl-piperidin-1-yl)-2-oxo-ethoxy]-quinoline-2-carbonyl}-amino)-butyryl]-piperazine-1-carboxylic acid ethyl ester,
4-[(S)-4-Carboxy-2-({4-[2-((S)-2-cyclopropylcarbamoyl-piperidin-1-yl)-2-oxo-ethoxy]-quinoline-2-carbonyl}-amino)-butyryl]-piperazine-1-carboxylic acid ethyl ester,
4-[(S)-4-Carboxy-2-({4-[2-((S)-3-hydroxymethyl-pyrrolidin-1-yl)-2-oxo-ethoxy]-quinoline-2-carbonyl}-amino)-butyryl]-piperazine-1-carboxylic acid ethyl ester,
4-[(S)-4-Carboxy-2-({4-[2-((R)-3-hydroxymethyl-pyrrolidin-1-yl)-2-oxo-ethoxy]-quinoline-2-carbonyl}-amino)-butyryl]-piperazine-1-carboxylic acid ethyl ester,
4-((S)-4-Carboxy-2-{[4-(2-morpholin-4-yl-2-oxo-ethoxy)-quinoline-2-carbonyl]-amino}-butyryl)-piperazine-1-carboxylic acid ethyl ester,
4-[(S)-4-Carboxy-2-({4-[2-(4-ethoxy-piperidin-1-yl)-2-oxo-ethoxy]-quinoline-2-carbonyl}-amino)-butyryl]-piperazine-1-carboxylic acid ethyl ester,
4-[(S)-4-Carboxy-2-({4-[2-(4-carboxy-piperidin-1-yl)-2-oxo-ethoxy]-quinoline-2-carbonyl}-amino)-butyryl]-piperazine-1-carboxylic acid ethyl ester,
4-[(S)-4-Carboxy-2-({4-[2-(4-ethoxycarbonyl-piperidin-1-yl)-2-oxo-ethoxy]-quinoline-2-carbonyl}-amino)-butyryl]-piperazine-1-carboxylic acid ethyl ester,
4-[(S)-4-Carboxy-2-({4-[2-oxo-2-(5-oxo-[1,4]diazepan-1-yl)-ethoxy]-quinoline-2-carbonyl}-amino)-butyryl]-piperazine-1-carboxylic acid ethyl ester,
4-[(S)-4-Carboxy-2-({4-[2-(3-cyclopropylcarbamoyl-piperidin-1-yl)-2-oxo-ethoxy]-quinoline-2-carbonyl}-amino)-butyryl]-piperazine-1-carboxylic acid ethyl ester,
4-[(S)-4-Carboxy-2-({4-[2-((R)-2-cyclopropylcarbamoyl-piperidin-1-yl)-2-oxo-ethoxy]-quinoline-2-carbonyl}-amino)-butyryl]-piperazine-1-carboxylic acid ethyl ester,
4-[(S)-4-Carboxy-2-({4-[2-oxo-2-(3-oxo-pyrrolidin-1-yl)-ethoxy]-quinoline-2-carbonyl}-amino)-butyryl]-piperazine-1-carboxylic acid ethyl ester,
4-[(S)-4-Carboxy-2-({4-[2-(2-carboxy-4,4-difluoro-pyrrolidin-1-yl)-2-oxo-ethoxy]-quinoline-2-carbonyl}-amino)-butyryl]-piperazine-1-carboxylic acid ethyl ester,
4-[(S)-4-Carboxy-2-({4-[2-(3-hydroxy-piperidin-1-yl)-2-oxo-ethoxy]-quinoline-2-carbonyl}-amino)-butyryl]-piperazine-1-carboxylic acid ethyl ester,
4-[(S)-4-Carboxy-2-({4-[2-((S)-2-carboxy-piperidin-1-yl)-2-oxo-ethoxy]-quinoline-2-carbonyl}-amino)-butyryl]-piperazine-1-carboxylic acid ethyl ester,
4-[(S)-4-Carboxy-2-({4-[2-((R)-2-carboxy-piperidin-1-yl)-2-oxo-ethoxy]-quinoline-2-carbonyl}-amino)-butyryl]-piperazine-1-carboxylic acid ethyl ester,
4-[(S)-4-Carboxy-2-({4-[2-((S)-2-methoxymethyl-pyrrolidin-1-yl)-2-oxo-ethoxy]-quinoline-2-carbonyl}-amino)-butyryl]-piperazine-1-carboxylic acid ethyl ester,
4-[(S)-4-Carboxy-2-({6-chloro-4-[2-((S)-2-cyclopropylcarbamoyl-pyrrolidin-1-yl)-2-oxo-ethoxy]-quinoline-2-carbonyl}-amino)-butyryl]-piperazine-1-carboxylic acid ethyl ester,
4-[(S)-4-Carboxy-2-({4-[2-((S)-2-cyclopropylcarbamoyl-pyrrolidin-1-yl)-2-oxo-ethoxy]-6-methyl-quinoline-2-carbonyl}-amino)-butyryl]-piperazine-1-carboxylic acid ethyl ester,
4-[(S)-4-Carboxy-2-({4-[2-((S)-2-cyclopropylcarbamoyl-pyrrolidin-1-yl)-2-oxo-ethoxy]-5-methyl-quinoline-2-carbonyl}-amino)-butyryl]-piperazine-1-carboxylic acid ethyl ester,
4-[(S)-4-Carboxy-2-({4-[2-((S)-2-cyclobutylcarbamoyl-pyrrolidin-1-yl)-2-oxo-ethoxy]-quinoline-2-carbonyl}-amino)-butyryl]-piperazine-1-carboxylic acid ethyl ester,
4-[(S)-4-Carboxy-2-({4-[2-((R)-2-ethoxycarbonyl-pyrrolidin-1-yl)-2-oxo-ethoxy]-quinoline-2-carbonyl}-amino)-butyryl]-piperazine-1-carboxylic acid ethyl ester,
4-[(S)-2-({4-[2-((R)-2-Carbamoyl-pyrrolidin-1-yl)-2-oxo-ethoxy]-quinoline-2-carbonyl}-amino)-4-carboxy-butyryl]-piperazine-1-carboxylic acid ethyl ester,
4-[(S)-4-Carboxy-2-({4-[2-((S)-2-carboxy-2-methyl-pyrrolidin-1-yl)-2-oxo-ethoxy]-quinoline-2-carbonyl}-amino)-butyryl]-piperazine-1-carboxylic acid ethyl ester,
4-{(S)-4-Carboxy-2-[(4-{2-[(S)-2-(cyclopropylmethyl-carbamoyl-pyrrolidin-1-yl]-2-oxo-ethoxy}-quinoline-2-carbonyl)-amino]-butyryl}-piperazine-1-carboxylic acid ethyl ester,
4-[(S)-4-Carboxy-2-({4-[2-((S)-2-isopropylcarbamoyl-pyrrolidin-1-yl)-2-oxo-ethoxy]-quinoline-2-carbonyl}-amino)-butyryl]-piperazine-1-carboxylic acid ethyl ester,
4-[(S)-4-Carboxy-2-({4-[2-((R)-2-cyclopropylcarbamoyl-pyrrolidin-1-yl)-2-oxo-ethoxy]-quinoline-2-carbonyl}-amino)-butyryl]-piperazine-1-carboxylic acid ethyl ester,
4-[(S)-4-Carboxy-2-({4-[2-(4,4-dimethyl-oxazolidin-3-yl)-2-oxo-ethoxy]-quinoline-2-carbonyl}-amino)-butyryl]-piperazine-1-carboxylic acid ethyl ester,
4-[(S)-4-Carboxy-2-({4-[2-oxo-2-((S)-2-propylcarbamoyl-pyrrolidin-1-yl)-ethoxyl]-quinoline-2-carbonyl}-amino)-butyryl]-piperazine-1-carboxylic acid ethyl ester,
4-[(S)-4-Carboxy-2-({4-[2-((R)-2-hydroxymethyl-pyrrolidin-1-yl)-2-oxo-ethoxy]-quinoline-2-carbonyl}-amino)-butyryl]-piperazine-1-carboxylic acid ethyl ester,
4-((S)-4-Carboxy-2-{[4-(3-carboxy-azetidine-1-carbonyl)-quinoline-2-carbonyl]-amino}-butyryl)-piperazine-1-carboxylic acid ethyl ester,
4-((S)-2-{[4-(Azetidine-1-carbonyl)-quinoline-2-carbonyl]-amino}-4-carboxy-butyryl)-piperazine-1-carboxylic acid ethyl ester,
4-((S)-4-Carboxy-2-{[4-(morpholine-4-carbonyl)-quinoline-2-carbonyl]-amino}-butyryl)-piperazine-1-carboxylic acid ethyl ester, 4-((S)-4-Carboxy-2-{[4-((S)-2-carboxy-azetidine-1-carbonyl)-quinoline-2-carbonyl]-amino}-butyryl)-piperazine-1-carboxylic acid ethyl ester, 4-((S)-4-Carboxy-2-{[4-(2-carboxy-pyrrolidine-1-carbonyl)-quinoline-2-carbonyl]-amino}-butyryl)-piperazine-1-carboxylic acid ethyl ester, 4-((S)-4-Carboxy-2-{[4-(3-hydroxy-azetidine-1-carbonyl)-quinoline-2-carbonyl]-amino}-butyryl)-piperazine-1-carboxylic acid ethyl ester, 4-((S)-4-Carboxy-2-{[4-(2-methoxycarbonyl-aziridine-1-carbonyl)-quinoline-2-carbonyl]-amino}-butyryl)-piperazine-1-carboxylic acid ethyl ester, 4-[(S)-4-Carboxy-2-({4-[2-(2-carboxy-4-hydroxy-pyrrolidin-1-yl)-2-oxo-ethoxy]-quinoline-2-carbonyl}-amino)-butyryl]-piperazine-1-carboxylic acid ethyl ester, 4-[(S)-4-Carboxy-2-({7-fluoro-4-[2-(4-hydroxy-piperidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-((S)-2-cyclobutylcarbamoyl-pyrrolidin-1-yl)-2-oxo-ethoxy]-8-fluoro-quinoline-2-carbonyl}-amino)-butyryl]-piperazine-1-carboxylic acid ethyl ester, 4-[(S)-4-Carboxy-2-({4-[2-((S)-2-cyclobutylcarbamoyl-pyrrolidin-1-yl)-2-oxo-ethoxy]-7-fluoro-quinoline-2-carbonyl}-amino)-butyryl]-piperazine-1-carboxylic acid ethyl ester, 4-[(S)-4-Carboxy-2-({4-[2-((S)-2-ethylcarbamoyl-pyrrolidin-1-yl)-2-oxo-ethoxy]-7-fluoro-quinoline-2-carbonyl}-amino)-butyryl]-piperazine-1-carboxylic acid ethyl ester, 4-[(S)-4-Carboxy-2-({4-[2-((S)-2-cyclobutylcarbamoyl-azetidin-1-yl)-2-oxo-ethoxy]-7-fluoro-quinoline-2-carbonyl}-amino)-butyryl]-piperazine-1-carboxylic acid ethyl ester, 4-[(S)-4-Carboxy-2-({4-[2-((S)-2-cyclopropylcarbamoyl-pyrrolidin-1-yl)-2-oxo-ethoxy]-7-fluoro-quinoline-2-carbonyl}-amino)-butyryl]-piperazine-1-carboxylic acid ethyl ester, 4-[(S)-4-Carboxy-2-({4-[2-((S)-2-cyclobutylcarbamoyl-azetidin-1-yl)-2-oxo-ethoxy]-8-fluoro-quinoline-2-carbonyl}-amino)-butyryl]-piperazine-1-carboxylic acid ethyl ester, 4-[(S)-4-Carboxy-2-({4-[2-((S)-2-ethylcarbamoyl-pyrrolidin-1-yl)-2-oxo-ethoxy]-8-fluoro-quinoline-2-carbonyl}-amino)-butyryl]-piperazine-1-carboxylic acid ethyl ester, 4-[(S)-4-Carboxy-2-({4-[2-((S)-2-cyclopropylcarbamoyl-pyrrolidin-1-yl)-2-oxo-ethoxy]-8-fluoro-quinoline-2-carbonyl}-amino)-butyryl]-piperazine-1-carboxylic acid ethyl ester, 4-[(S)-4-Carboxy-2-({8-fluoro-4-[2-(4-hydroxy-piperidin-1-yl)-2-oxo-ethoxy]-quinoline-2-carbonyl}-amino)-butyryl]-piperazine-1-carboxylic acid ethyl ester, 4-[(S)-4-Carboxy-2-({6-fluoro-4-[2-(4-hydroxy-piperidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-((S)-2-ethylcarbamoyl-pyrrolidin-1-yl)-2-oxo-ethoxy]-6-fluoro-quinoline-2-carbonyl}-amino)-butyryl]-piperazine-1-carboxylic acid ethyl ester, 4-[(S)-4-Carboxy-2-({4-[2-((S)-2-cyclopropylcarbamoyl-pyrrolidin-1-yl)-2-oxo-ethoxy]-5-fluoro-quinoline-2-carbonyl}-amino)-butyryl]-piperazine-1-carboxylic acid ethyl ester, 4-[(S)-4-Carboxy-2-({4-[2-((S)-2-cyclobutylcarbamoyl-pyrrolidin-1-yl)-2-oxo-ethoxy]-5-fluoro-quinoline-2-carbonyl}-amino)-butyryl]-piperazine-1-carboxylic acid ethyl ester, 4-[(S)-4-Carboxy-2-({4-[2-((S)-2-cyclopropylcarbamoyl-pyrrolidin-1-yl)-2-oxo-ethoxy]-6-fluoro-quinoline-2-carbonyl}-amino)-butyryl]-piperazine-1-carboxylic acid ethyl ester, 4-[(S)-4-Carboxy-2-({4-[2-((S)-2-cyclobutylcarbamoyl-pyrrolidin-1-yl)-2-oxo-ethoxy]-6-fluoro-quinoline-2-carbonyl}-amino)-butyryl]-piperazine-1-carboxylic acid ethyl ester, 4-[(S)-4-Carboxy-2-({4-[2-((S)-2-cyclobutylcarbamoyl-azetidin-1-yl)-2-oxo-ethoxy]-6-fluoro-quinoline-2-carbonyl}-amino)-butyryl]-piperazine-1-carboxylic acid ethyl ester, 4-[(S)-4-Carboxy-2-({5-fluoro-4-[2-(4-hydroxy-piperidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-((S)-2-ethylcarbamoyl-pyrrolidin-1-yl)-2-oxo-ethoxy]-5-fluoro-quinoline-2-carbonyl}-amino)-butyryl]-piperazine-1-carboxylic acid ethyl ester, 4-[(S)-4-Carboxy-2-({4-[2-((S)-2-cyclobutylcarbamoyl-azetidin-1-yl)-2-oxo-ethoxy]-5-fluoro-quinoline-2-carbonyl}-amino)-butyryl]-piperazine-1-carboxylic acid ethyl ester, 4-{(S)-2-[(4-{2-[(S)-2-(Azetidine-1-carbonyl)-pyrrolidin-1-yl]-2-oxo-ethoxy}-7-methyl-quinoline-2-carbonyl)-amino]-4-carboxy-butyryl}-piperazine-1-carboxylic acid ethyl ester, 4-{(S)-4-Carboxy-2-[(7-methyl-4-{2-oxo-2-[(S)-2-(pyrrolidine-1-carbonyl)-pyrrolidin-1-yl]-ethoxy}-quinoline-2-carbonyl)-amino]-butyryl}-piperazine-1-carboxylic acid ethyl ester, 4-{(S)-4-Carboxy-2-[(7-methyl-4-{2-oxo-2-[(S)-2-(piperidine-1-carbonyl)-pyrrolidin-1-yl]-ethoxy}-quinoline-2-carbonyl)-amino]-butyryl}-piperazine-1-carboxylic acid ethyl ester, 4-[(S)-4-Carboxy-2-({4-[2-((S)-2-cyclopentylcarbamoyl-pyrrolidin-1-yl)-2-oxo-ethoxy]-7-methyl-quinoline-2-carbonyl}-amino)-butyryl]-piperazine-1-carboxylic acid ethyl ester, 4-[(S)-4-Carboxy-2-({4-[2-((S)-2-cyclopropylcarbamoyl-pyrrolidin-1-yl)-2-oxo-ethoxy]-7,8,9,10-tetrahydro-benzo[h]quinoline-2-carbonyl}-amino)-butyryl]-piperazine-1-carboxylic acid ethyl ester, 4-[(S)-3-Carboxy-2-({4-[(S)-2-((S)-2-cyclopentylcarbamoyl-pyrrolidin-1-yl)-1-methyl-2-oxo-ethoxy]-7-methyl-quinoline-2-carbonyl}-amino)-propionyl]-piperazine-1-carboxylic acid ethyl ester, 4-[(S)-3-Carboxy-2-({4-[(S)-2-((S)-2-cyclopentylcarbamoyl-azetidin-1-yl)-1-methyl-2-oxo-ethoxy]-7-methyl-quinoline-2-carbonyl}-amino)-propionyl]-piperazine-1-carboxylic acid ethyl ester, 4-[(S)-3-Carboxy-2-({4-[(S)-2-((S)-2-cyclopropylcarbamoyl-pyrrolidin-1-yl)-1-methyl-2-oxo-ethoxy]-7-methyl-quinoline-2-carbonyl}-amino)-propionyl]-piperazine-1-carboxylic acid ethyl ester, 4-[(S)-3-Carboxy-2-({4-[(S)-2-((S)-2-ethylcarbamoyl-pyrrolidin-1-yl)-1-methyl-2-oxo-ethoxy]-7-methylquinoline-2-carbonyl}-amino)-propionyl]-piperazine-1-carboxylic acid ethyl ester, 4-[(S)-3-Carboxy-2-({4-[(S)-2-(4-hydroxy-piperidin-1-yl)-1-methyl-2-oxo-ethoxy]-7-methyl-quinoline-2-carbonyl}-amino)-propionyl]-piperazine-1-carboxylic acid ethyl ester, 4-[(S)-3-Carboxy-2-({4-[(S)-2-((S)-2-hydroxymethyl-pyrrolidin-1-yl)-1-methyl-2-oxo-ethoxy]-7-methyl-quinoline-2-carbonyl}-amino)-propionyl]-piperazine-1-carboxylic acid ethyl ester, 4-[(S)-3-Carboxy-2-({4-[(S)-2-((S)-3-hydroxymethyl-pyrrolidin-1-yl)-1-methyl-2-oxo-ethoxy]-7-methyl-quinoline-2-carbonyl}-amino)-propionyl]-piperazine-1-carboxylic acid ethyl ester, 4-[(S)-3-Carboxy-2-({4-[(S)-2-((S)-2-cyclobutylcarbamoyl-azetidin-1-yl)-1-methyl-2-oxo-ethoxy]-7-methyl-quinoline-2-carbonyl}-amino)-propionyl]-piperazine-1-carboxylic acid ethyl ester, 4-[(S)-3-Carboxy-2-({4-[(S)-2-((S)-2-isopropylcarbamoyl-pyrrolidin-1-yl)-1-methyl-2-oxo-ethoxy]-7-methyl-quinoline-2-carbonyl}-amino)-propionyl]-piperazine-1-carboxylic acid ethyl ester, 4-[(S)-4-Carboxy-2-({4-[2-((S)-2-cyclopentylcarbamoyl-azetidin-1-yl)-2-oxo-ethoxy]-7-methyl-quinoline-2-carbonyl}-amino)-butyryl]-piperazine-1-carboxylic acid ethyl ester, 4-[(S)-4-Carboxy-2-({4-[2-((S)-2-ethylcarbamoyl-pyrrolidin-1-yl)-2-oxo-ethoxy]-6,7-difluoro-quinoline-2-carbonyl}-amino)-butyryl]-piperazine-1-carboxylic acid ethyl ester, 4-[(S)-4-Carboxy-2-({4-[2-((S)-2-cyclobutylcarbamoyl-pyrrolidin-1-yl)-2-oxo-ethoxy]-6,7-difluoro-quinoline-2-carbonyl}-amino)-butyryl]-piperazine-1-carboxylic acid ethyl ester, 4-[(S)-3-Carboxy-2-({4-[2-((S)-2-ethylcarbamoyl-pyrrolidin-1-yl)-2-oxo-ethoxy]-7-methyl-quinoline-2-carbonyl}-amino)-propionyl]-piperazine-1-carboxylic acid ethyl ester, 4-[(S)-3-Carboxy-2-({4-[2-((S)-2-isopropylcarbamoyl-pyrrolidin-1-yl)-2-oxo-ethoxy]-7-methyl-quinoline-2-carbonyl}-amino)-propionyl]-piperazine-1-carboxylic acid ethyl ester, 4-[(S)-3-Carboxy-2-({4-[2-((S)-2-cyclopentylcarbamoyl-pyrrolidin-1-yl)-2-oxo-ethoxy]-7-methyl-quinoline-2-carbonyl}-amino)-propionyl]-piperazine-1-carboxylic acid ethyl ester, 4-{(S)-3-Carboxy-2-[(4-{2-[(S)-2-(cyclopropylmethyl-carbamoyl)-pyrrolidin-1-yl]-2-oxo-ethoxy}-7-methyl-quinoline-2-carbonyl)-amino]-propionyl}-piperazine-1-carboxylic acid ethyl ester, 4-[(S)-3-Carboxy-2-({4-[2-((S)-2-cyclopentylcarbamoyl-azetidin-1-yl)-2-oxo-ethoxy]-7-methyl-quinoline-2-carbonyl}-amino)-propionyl]-piperazine-1-carboxylic acid ethyl ester, 4-[(S)-3-Carboxy-2-({4-[2-((S)-2-cyclopentylcarbamoyl-azetidin-1-yl)-2-oxo-ethoxy]-quinoline-2-carbonyl}-amino)-propionyl]-piperazine-1-carboxylic acid ethyl ester, 4-[(S)-3-Carboxy-2-({4-[2-((S)-2-cyclopropylcarbamoyl-pyrrolidin-1-yl)-2-oxo-ethoxy]-7-methyl-quinoline-2-carbonyl}-amino)-propionyl]-piperazine-1-carboxylic acid ethyl ester, 4-[(S)-3-Carboxy-2-({7-methyl-4-[2-oxo-2-((S)-2-propylcarbamoyl-pyrrolidin-1-yl)-ethoxy]-quinoline-2-carbonyl}-amino)-propionyl]-piperazine-1-carboxylic acid ethyl ester, 4-[(S)-3-Carboxy-2-({4-[2-((S)-2-cyclopentylcarbamoyl-pyrrolidin-1-yl)-2-oxo-ethoxy]-quinoline-2-carbonyl}-amino)-propionyl]-piperazine-1-carboxylic acid ethyl ester, 4-[(S)-4-Carboxy-2-({4-[2-((S)-2-ethylcarbamoyl-pyrrolidin-1-yl)-2-oxo-ethoxy]-7-methoxy-quinoline-2-carbonyl}-amino)-butyryl]-piperazine-1-carboxylic acid ethyl ester, 4-[(S)-4-Carboxy-2-({4-[2-((S)-2-cyclobutylcarbamoyl-pyrrolidin-1-yl)-2-oxo-ethoxy]-7-methoxy-quinoline-2-carbonyl}-amino)-butyryl]-piperazine-1-carboxylic acid ethyl ester, 4-[(S)-4-Carboxy-2-({7-ethyl-4-[2-((S)-2-ethylcarbamoyl-pyrrolidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-((S)-2-cyclobutylcarbamoyl-pyrrolidin-1-yl)-2-oxo-ethoxy]-7-ethyl-quinoline-2-carbonyl}-amino)-butyryl]-piperazine-1-carboxylic acid ethyl ester, 4-[(S)-4-Carboxy-2-({4-[2-((S)-2-cyclopropylcarbamoyl-pyrrolidin-1-yl)-2-oxo-ethoxy]-7-ethyl-quinoline-2-carbonyl}-amino)-butyryl]-piperazine-1-carboxylic acid ethyl ester, 4-[(S)-4-Carboxy-2-({4-[2-((S)-2-ethylcarbamoyl-pyrrolidin-1-yl)-2-oxo-ethoxy]-6-fluoro-5-methyl-quinoline-2-carbonyl}-amino)-butyryl]-piperazine-1-carboxylic acid ethyl ester, 4-[(S)-4-Carboxy-2-({4-[2-((S)-2-cyclobutylcarbamoyl-pyrrolidin-1-yl)-2-oxo-ethoxy]-6-fluoro-5-methyl-quinoline-2-carbonyl}-amino)-butyryl]-piperazine-1-carboxylic acid ethyl ester, 4-[(S)-4-Carboxy-2-({4-[2-((S)-2-cyclopropylcarbamoyl-pyrrolidin-1-yl)-2-oxo-ethoxy]-6-ethoxy-quinoline-2-carbonyl}-amino)-butyryl]-piperazine-1-carboxylic acid ethyl ester, 4-[(S)-4-Carboxy-2-({6-ethoxy-4-[2-((S)-2-ethylcarbamoyl-pyrrolidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-((S)-2-cyclobutylcarbamoyl-pyrrolidin-1-yl)-2-oxo-ethoxy]-6-ethoxy-quinoline-2-carbonyl}-amino)-butyryl]-piperazine-1-carboxylic acid ethyl ester, 4-(S)-4-Carbamoyl-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester, 4-{(S)-4-Carboxy-2-[(6-fluoro-7-methyl-4-{2-oxo-2-[((S)-2-(pyrrolidine-1-carbonyl)-pyrrolidin-1-yl]-ethoxy}-quinoline-2-carbonyl)-amino]-butyryl}-piperazine-1-carboxylic acid ethyl ester, 4-[(S)-4-Carboxy-2-({4-[2-((S)-2-ethylcarbamoyl-pyrrolidin-1-yl)-2-oxo-ethoxy]-6-fluoro-7-methyl-quinoline-2-carbonyl}-amino)-butyryl]-piperazine-1-carboxylic acid ethyl ester, 4-[(S)-4-Carboxy-2-({4-[2-((S)-2-cyclobutylcarbamoyl-pyrrolidin-1-yl)-2-oxo-ethoxy]-6-fluoro-7-methyl-quinoline-2-carbonyl}-amino)-butyryl]-piperazine-1-carboxylic acid ethyl ester, 4-{(S)-4-Carboxy-2-[(7-fluoro-4-{2-oxo-2-[(S)-2-(pyrrolidine-1-carbonyl)-pyrrolidin-1-yl]-ethoxy}-quinoline-2-carbonyl)-amino]-butyryl}-piperazine-1-carboxylic acid ethyl ester, 4-[(S)-4-Carboxy-2-({7-fluoro-4-[2-oxo-2-((S)-2-propyl-carbamoyl-pyrrolidin-1-yl)-ethoxy]-quinoline-2-carbonyl}-amino)-butyryl]-piperazine-1-carboxylic acid ethyl ester, 4-[(S)-4-Ethoxycarbonyl-2-({7-fluoro-4-[2-oxo-2-((S)-2-propylcarbamoyl-pyrrolidin-1-yl)-ethoxy]-quinoline-2-carbonyl}-amino)-butyryl]-piperazine-1-carboxylic acid ethyl ester, 4-[(S)-4-Ethoxycarbonyl-2-({4-[2-((S)-2-ethylcarbamoyl-pyrrolidin-1-yl)-2-oxo-ethoxy]-7-fluoro-quinoline-2-carbonyl}-amino)-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-fluoro-quinoline-2-carbonyl}-amino)-4-ethoxycarbonyl-butyryl]-piperazine-1-carboxylic acid ethyl ester, 4-{(S)-4-Carboxy-2-[(4-{2-[(S)-2-(ethyl-methyl-carbamoyl)-pyrrolidin-1-yl]-2-oxo-ethoxy}-7-methyl-quinoline-2-carbonyl)-amino]-butyryl}-piperazine-1-carboxylic acid ethyl ester, 4-[(S)-3-Carboxy-2-({4-[(R)-2-((S)-2-cyclobutylcarbamoyl-pyrrolidin-1-yl)-1-methyl-2-oxo-ethoxy]-7-methyl-quinoline-2-carbonyl}-amino)-propionyl]-piperazine-1-carboxylic acid ethyl ester, 4-{(S)-3-Carboxy-2-[(7-methyl-4-(R)-1-methyl-2-oxo-2-[(S)-2-(pyrrolidine-1-carbonyl)-pyrrolidin-1-yl)-ethoxy]-quinoline-2-carbonyl)-amino]-propionyl}-piperazine-1-carboxylic acid ethyl ester, 4-[(S)-3-Carboxy-2-({7-methyl-4-[(R)-1-methyl-2-oxo-2-((S)-2-propylcarbamoyl-pyrrolidin-1-yl)-ethoxy]-quinoline-2-carbonyl}-amino)-propionyl]-piperazine-1-carboxylic acid ethyl ester, 4-[(S)-3-Carboxy-2-({4-[(R)-2-((S)-2-cyclopropylcarbamoyl-pyrrolidin-1-yl)-1-methyl-2-oxo-ethoxy]-7-methyl-quinoline-2-carbonyl}-amino)-propionyl]-piperazine-1-carboxylic acid ethyl ester, 4-[(S)-3-Carboxy-2-({4-[(R)-2-((S)-2-cyclobutylcarbamoyl-azetidin-1-yl)-1-methyl-2-oxo-ethoxy]-7-methyl-quinoline-2-carbonyl}-amino)-propionyl]-piperazine-1-carboxylic acid ethyl ester, 4-[(S)-3-Carboxy-2-({4-[(R)-2-((S)-3-hydroxymethyl-pyrrolidin-1-yl)-1-methyl-2-oxo-ethoxy]-7-methyl-quinoline-2-carbonyl}-amino)-propionyl]-piperazine-1-carboxylic acid ethyl ester, 4-[(S)-4-Ethoxycarbonyl-2-({4-[2-((S)-2-ethylcarbamoyl-pyrrolidin-1-yl)-2-oxo-ethoxy]-6-fluoro-7-methyl-quinoline-2-carbonyl}-amino)-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-ethylcarbamoyl-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-dimethylcarbamoyl-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-methylcarbamoyl-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-cyclopropylcarbamoyl-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-methoxycarbonyl-butyryl]-piperazine-1-carboxylic acid ethyl ester, 4-[(S)-4-Butoxycarbonyl-2-({4-[2-((S)-2-cyclobutyl carbamoyl-pyrrolidin-1-yl)-2-oxo-ethoxy]-7-methyl-quinoline-2-carbonyl}-amino)-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-pentyloxycarbonyl-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-isopropoxycarbonyl-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(1-ethyl-propoxycarbonyl)-butyryl]-piperazine-1-carboxylic acid ethyl ester, 4-[(S)-4-Cyclobutoxycarbonyl-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-cyclopentyloxycarbonyl-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-cyclopropylmethoxycarbonyl-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(indan-5-yloxycarbonyl)-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-cyclopentylmethoxycarbonyl-butyryl]-piperazine-1-carboxylic acid ethyl ester, 4-[(S)-2-({4-[2-((S)-2-Cyclopropylcarbamoyl-pyrrolidin-1-yl)-2-oxo-ethoxy]-7-fluoro-quinoline-2-carbonyl}-amino)-4-ethoxycarbonyl-butyryl]-piperazine-1-carboxylic acid ethyl ester, 4-{(S)-4-Ethoxycarbonyl-2-[(7-fluoro-4-{2-oxo-2-[(S)-2-(pyrrolidine-1-carbonyl)-pyrrolidin-1-yl]-ethoxy}-quinoline-2-carbonyl)-amino]-butyryl}-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(2-morpholin-4-yl-ethoxycarbonyl)-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(1-morpholin-4-ylmethyl-propoxycarbonyl)-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-cyclohexyloxycarbonyl-butyryl]-piperazine-1-carboxylic acid ethyl ester, 4-[(S)-4-Benzyloxycarbonyl-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-isobutoxycarbonyl-butyryl]-piperazine-1-carboxylic acid ethyl ester, 4-[(S)-2-({4-[2-((S)-2-Cyclopropylcarbamoyl-pyrrolidin-1-yl)-2-oxo-ethoxy]-6-fluoro-7-methyl-quinoline-2-carbonyl}-amino)-4-ethoxycarbonyl-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-6-fluoro-7-methyl-quinoline-2-carbonyl}-amino)-4-ethoxycarbonyl-butyryl]-piperazine-1-carboxylic acid ethyl ester, 4-{(S)-4-Ethoxycarbonyl-2-[(6-fluoro-7-methyl-4-{2-oxo-2-[(S)-2-(pyrrolidine-1-carbonyl)-pyrrolidin-1-yl]-ethoxy}-quinoline-2-carbonyl)-amino]-butyryl}-piperazine-1-carboxylic acid ethyl ester, 4-{(S)-4-Ethoxycarbonyl-2-[(7-methyl-4-{2-oxo-2-[(S)-2-(pyrrolidine-1-carbonyl)-pyrrolidin-1-yl]-ethoxy}-quinoline-2-carbonyl)-amino]-butyryl}-piperazine-1-carboxylic acid ethyl ester, 4-[(S)-3-Carboxy-2-({4-[2-((S)-2-cyclobutylcarbamoyl-pyrrolidin-1-yl)-2-oxo-ethoxy]-5-fluoro-quinoline-2-carbonyl}-amino)-propionyl]-piperazine-1-carboxylic acid ethyl ester, 4-[(S)-3-Carboxy-2-({5-fluoro-4-[2-oxo-2-((S)-2-propyl-carbamoyl-pyrrolidin-1-yl)-ethoxy]-quinoline-2-carbonyl}-amino)-propionyl]-piperazine-1-carboxylic acid ethyl ester, 4-[(S)-4-Carboxy-2-({5-fluoro-7-methyl-4-[2-oxo-2-((S)-2-propylcarbamoyl-pyrrolidin-1-yl)-ethoxy]-quinoline-2-carbonyl}-amino)-butyryl]-piperazine-1-carboxylic acid ethyl ester, 4-{(S)-4-Carboxy-2-[(5-fluoro-7-methyl-4-{2-oxo-2-[(S)-2-(pyrrolidine-1-carbonyl)-pyrrolidin-1-yl]-ethoxy}-quinoline-2-carbonyl)-amino]-butyryl}-piperazine-1-carboxylic acid ethyl ester, 4-[(S)-4-Carboxy-2-({4-[2-((S)-2-cyclobutylcarbamoyl-pyrrolidin-1-yl)-2-oxo-ethoxy]-5-fluoro-7-methyl-quinoline-2-carbonyl}-amino)-butyryl]-piperazine-1-carboxylic acid ethyl ester, 4-{(S)-3-Carboxy-2-[(7-methyl-4-{2-oxo-2-[(S)-2-(pyrrolidine-1-carbonyl)-pyrrolidin-1-yl]-ethoxy}-quinoline-2-carbonyl)-amino]-propionyl}-piperazine-1-carboxylic acid ethyl ester, 4-[(S)-2-({4-[2-((S)-2-Cyclopentylcarbamoyl-pyrrolidin-1-yl)-2-oxo-ethoxy]-7-methyl-quinoline-2-carbonyl}-amino)-4-ethoxycarbonyl-butyryl]-piperazine-1-carboxylic acid ethyl ester, 4-[(S)-3-Carboxy-2-({4-[2-((S)-2-cyclobutylcarbamoyl-pyrrolidin-1-yl)-2-oxo-ethoxy]-7-fluoro-quinoline-2-carbonyl}-amino)-propionyl]-piperazine-1-carboxylic acid ethyl ester, 4-[(S)-3-Carboxy-2-({5-fluoro-7-methyl-4-[2-oxo-2-((S)-2-propylcarbamoyl-pyrrolidin-1-yl)-ethoxy]-quinoline-2-carbonyl}-amino)-propionyl]-piperazine-1-carboxylic acid ethyl ester, 4-{(S)-3-Carboxy-2-[(5-fluoro-7-methyl-4-{2-oxo-2-[(S)-2-(pyrrolidine-1-carbonyl)-pyrrolidin-1-yl]-ethoxy}-quinoline-2-carbonyl)-amino]-propionyl}-piperazine-1-carboxylic acid ethyl ester, 4-[(S)-3-Carboxy-2-({4-[2-((S)-2-cyclobutylcarbamoyl-pyrrolidin-1-yl)-2-oxo-ethoxy]-5-fluoro-7-methyl-quinoline-2-carbonyl}-amino)-propionyl]-piperazine-1-carboxylic acid ethyl ester, 4-{(S)-3-Carboxy-2-[(5-fluoro-4-{2-oxo-2-[(S)-2-(pyrrolidine-1-carbonyl)-pyrrolidin-1-yl]-ethoxy}-quinoline-2-carbonyl)-amino]-propionyl}-piperazine-1-carboxylic acid ethyl ester, 4-[(S)-3-Carboxy-2-({4-[2-((S)-2-cyclobutylcarbamoyl-pyrrolidin-1-yl)-2-oxo-ethoxy]-6-fluoro-7-methyl-quinoline-2-carbonyl}-amino)-propionyl]-piperazine-1-carboxylic acid ethyl ester, 4-{(S)-4-Ethoxycarbonyl-2-[(5-fluoro-7-methyl-4-{2-oxo-2-[(S)-2-(pyrrolidine-1-carbonyl)-pyrrolidin-1-yl]-ethoxy}-quinoline-2-carbonyl)-amino]-butyryl}-piperazine-1-carboxylic acid ethyl ester, 4-[(S)-2-({4-[2-((S)-2-Cyclobutylcarbamoyl-pyrrolidin-1-yl)-2-oxo-ethoxy]-5-fluoro-7-methyl-quinoline-2-carbonyl}-amino)-4-ethoxycarbonyl-butyryl]-piperazine-1-carboxylic acid ethyl ester, 4-{(S)-3-Carboxy-2-[(4-{2-[(S)-2-(ethyl-methyl-carbamoyl)-pyrrolidin-1-yl]-2-oxo-ethoxy}-7-methyl-quinoline-2-carbonyl)-amino]-propionyl}-piperazine-1-carboxylic acid ethyl ester, 4-[(S)-4-Carboxy-2-({4-[(R)-2-((S)-2-cyclobutylcarbamoyl-pyrrolidin-1-yl)-1-methyl-2-oxo-ethoxy]-7-methyl-quinoline-2-carbonyl}-amino)-butyryl]-piperazine-1-carboxylic acid ethyl ester, 4-[(S)-4-Ethoxycarbonyl-2-({5-fluoro-7-methyl-4-[2-oxo-2-((S)-2-propylcarbamoyl-pyrrolidin-1-yl)-ethoxy]-quinoline-2-carbonyl}-amino)-butyryl]-piperazine-1-carboxylic acid ethyl ester, 4-{(S)-3-Carboxy-2-[(6-fluoro-7-methyl-4-{2-oxo-2-[(S)-2-(pyrrolidine-1-carbonyl)-pyrrolidin-1-yl]-ethoxy}-quinoline-2-carbonyl)-amino]-propionyl}-piperazine-1-carboxylic acid ethyl ester, 4-[(S)-3-Carboxy-2-({4-[2-((S)-2-ethylcarbamoyl-pyrrolidin-1-yl)-2-oxo-ethoxy]-7-fluoro-quinoline-2-carbonyl}-amino)-propionyl]-piperazine-1-carboxylic acid ethyl ester, 4-[(S)-3-Carboxy-2-({7-fluoro-4-[2-oxo-2-((S)-2-propyl-carbamoyl-pyrrolidin-1-yl)-ethoxy]-quinoline-2-carbonyl}-amino)-propionyl]-piperazine-1-carboxylic acid ethyl ester, 4-[(S)-3-Carboxy-2-({4-[2-((S)-2-cyclopropylcarbamoyl-pyrrolidin-1-yl)-2-oxo-ethoxy]-7-fluoro-quinoline-2-carbonyl}-amino)-propionyl]-piperazine-1-carboxylic acid ethyl ester, 4-[(S)-4-Carboxy-2-({4-[2-((S)-2-cyclopropylcarbamoyl-pyrrolidin-1-yl)-2-oxo-ethoxy]-naphthalene-2-carbonyl}-amino)-butyryl]-piperazine-1-carboxylic acid ethyl ester, 4-{(S)-4-Carboxy-2-[(6,7-dimethyl-4-{2-oxo-2-[(S)-2-(pyrrolidine-1-carbonyl)-pyrrolidin-1-yl]-ethoxy}-quinoline-2-carbonyl)-amino]-butyryl}-piperazine-1-carboxylic acid ethyl ester, 4-{(S)-4-Ethoxycarbonyl-2-[(7-methyl-4-{2-oxo-2-[(S)-2-(2,2,2-trifluoro-ethylcarbamoyl)-pyrrolidin-1-yl]-ethoxy}-quinoline-2-carbonyl)-amino]-butyryl}-piperazine-1-carboxylic acid ethyl ester, 4-{(S)-2-[(4-{2-[(S)-2-(Cyclopropylmethyl-carbamoyl)-pyrrolidin-1-yl]-2-oxo-ethoxy}-7-methyl-quinoline-2-carbonyl)-amino]-4-ethoxycarbonyl-butyryl}-piperazine-1-carboxylic acid ethyl ester, 4-[(S)-4-Ethoxycarbonyl-2-({7-methyl-4-[2-oxo-2-((S)-2-propylcarbamoyl-pyrrolidin-1-yl)-ethoxy]-quinoline-2-carbonyl}-amino)-butyryl]-piperazine-1-carboxylic acid ethyl ester, 4-[(S)-4-Carboxy-2-({6,7-dimethyl-4-[2-oxo-2-((S)-2-propylcarbamoyl-pyrrolidin-1-yl)-ethoxy]-quinoline-2-carbonyl}-amino)-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-5-fluoro-quinoline-2-carbonyl}-amino)-4-ethoxycarbonyl-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-6-fluoro-quinoline-2-carbonyl}-amino)-4-ethoxycarbonyl-butyryl]-piperazine-1-carboxylic acid ethyl ester, 4-{(S)-4-Carboxy-2-[(5,6-difluoro-4-[2-oxo-2-[(S)-2-(pyrrolidine-1-carbonyl)-pyrrolidin-1-yl]-ethoxy]-quinoline-2-carbonyl)-amino]-butyryl}-piperazine-1-carboxylic acid ethyl ester, 4-[(S)-4-Carboxy-2-({4-[2-((S)-2-cyclobutylcarbamoyl-pyrrolidin-1-yl)-2-oxo-ethoxy]-5,6-difluoro-quinoline-2-carbonyl}-amino)-butyryl]-piperazine-1-carboxylic acid ethyl ester, 4-[(S)-4-Carboxy-2-({5,6-difluoro-4-[2-oxo-2-((S)-2-propylcarbamoyl-pyrrolidin-1-yl)-ethoxy]-quinoline-2-carbonyl}-amino)-butyryl]-piperazine-1-carboxylic acid ethyl ester, 4-[(S)-4-Carboxy-2-({4-[2-((S)-2-cyclobutylcarbamoyl-pyrrolidin-1-yl)-2-oxo-ethoxy]-6,7-dimethyl-quinoline-2-carbonyl}-amino)-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-6-fluoro-5-methyl-quinoline-2-carbonyl}-amino)-4-ethoxycarbonyl-butyryl]-piperazine-1-carboxylic acid ethyl ester, 4-[(S)-2-({4-[(R)-2-((S)-2-Cyclobutylcarbamoyl-pyrrolidin-1-yl)-1-methyl-2-oxo-ethoxy]-7-methyl-quinoline-2-carbonyl}-amino)-4-ethoxycarbonyl-butyryl]-piperazine-1-carboxylic acid ethyl ester, 4-[(S)-4-Carboxy-2-({4-[(R)-2-((S)-2-cyclopentylcarbamoyl-pyrrolidin-1-yl)-1-methyl-2-oxo-ethoxy]-7-methyl-quinoline-2-carbonyl}-amino)-butyryl]-piperazine-1-carboxylic acid ethyl ester, 4-[(S)-2-({4-[(R)-2-((S)-2-Cyclopentylcarbamoyl-pyrrolidin-1-yl)-1-methyl-2-oxo-ethoxy]-7-methyl-quinoline-2-carbonyl}-amino)-4-ethoxycarbonyl-butyryl]-piperazine-1-carboxylic acid ethyl ester, 4-{(S)-4-Carboxy-2-[(7-methyl-4-{(R)-1-methyl-2-oxo-2-[(S)-2-(piperidine-1-carbonyl)-pyrrolidin-1-yl]-ethoxy}-quinoline-2-carbonyl)-amino]-butyryl}-piperazine-1-carboxylic acid ethyl ester, 4-{(S)-4-Ethoxycarbonyl-2-[(7-methyl-4-{(R)-1-methyl-2-oxo-2-[(S)-2-(piperidine-1-carbonyl)-pyrrolidin-1-yl]-ethoxy}-quinoline-2-carbonyl)-amino]-butyryl}-piperazine-1-carboxylic acid ethyl ester, 4-[(S)-4-Carboxy-2-({7-methyl-4-[(R)-1-methyl-2-oxo-2-((S)-2-propylcarbamoyl-pyrrolidin-1-yl)-ethoxy]-quinoline-2-carbonyl}-amino)-butyryl]-piperazine-1-carboxylic acid ethyl ester, 4-[(S)-4-Ethoxycarbonyl-2-({7-methyl-4-[(R)-1-methyl-2-oxo-2-((S)-2-propylcarbamoyl-pyrrolidin-1-yl)-ethoxy]-quinoline-2-carbonyl}-amino)-butyryl]-piperazine-1-carboxylic acid ethyl ester, 4-{(S)-4-Carboxy-2-[(4-{(R)-2-[(S)-2-(cyclopropylmethyl-carbamoyl)-pyrrolidin-1-yl]-1-methyl-2-oxo-ethoxy}-7-methyl-quinoline-2-carbonyl)-amino]-butyryl}-piperazine-1-carboxylic acid ethyl ester, 4-{(S)-2-[(4-{(R)-2-[(S)-2-(Cyclopropylmethyl-carbamoyl)-pyrrolidin-1-yl]-1-methyl-2-oxo-ethoxy}-7-methyl-quinoline-2-carbonyl)-amino]-4-ethoxycarbonyl-butyryl}-piperazine-1-carboxylic acid ethyl ester, 4-{(S)-4-Carboxy-2-[(4-{2-[(S)-2-(4,4-difluoro-piperidine-1-carbonyl)-pyrrolidin-1-yl]-2-oxo-ethoxy}-7-methyl-quinoline-2-carbonyl)-amino]-butyryl}-piperazine-1-carboxylic acid ethyl ester, 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid butyl ester, 4-[(S)-2-({4-[2-((S)-2-Cyclobutylcarbamoyl-pyrrolidin-1-yl)-2-oxo-ethoxy]-quinoline-2-carbonyl}-amino)-4-hydroxy-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-quinoline-2-carbonyl}-amino)-4-hydroxy-butyryl]-piperazine-1-carboxylic acid butyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-hydroxy-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-fluoro-quinoline-2-carbonyl}-amino)-4-ethoxycarbonyl-butyryl]-piperazine-1-carboxylic acid ethyl ester, 4-{(S)-4-Carboxy-2-[(4-{2-[(S)-2-(cyclobutylmethyl-carbamoyl)-pyrrolidin-1-yl]-2-oxo-ethoxy}-7-methyl-quinoline-2-carbonyl)-amino]-butyryl}-piperazine-1-carboxylic acid ethyl ester, 4-[(S)-4-Carboxy-2-({4-[2-(3,3-difluoro-pyrrolidin-1-yl)-2-oxo-ethoxy]-quinoline-2-carbonyl}-amino)-butyryl]-piperazine-1-carboxylic acid ethyl ester, 4-[(S)-2-({4-[2-(2-Butyl-pyrrolidin-1-yl)-2-oxo-ethoxy]-quinoline-2-carbonyl}-amino)-4-carboxy-butyryl]-piperazine-1-carboxylic acid ethyl ester, 4-[(S)-4-Carboxy-2-({4-[2-(4-cyclohexyl-3-oxo-piperazin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-(2-methyl-3-oxo-piperazin-1-yl)-2-oxo-ethoxy]-quinoline-2-carbonyl}-amino)-butyryl]-piperazine-1-carboxylic acid ethyl ester, 4-{(S)-4-Carboxy-2-[(4-{2-oxo-2-[4-(2-oxo-pyrrolidin-1-yl)-piperidin-1-yl]-ethoxy}-quinoline-2-carbonyl)-amino]-butyryl}-piperazine-1-carboxylic acid ethyl ester, 4-[(S)-4-Carboxy-2-({4-[2-oxo-2-(3-oxo-4-phenyl-piperazin-1-yl)-ethoxy]-quinoline-2-carbonyl}-amino)-butyryl]-piperazine-1-carboxylic acid ethyl ester, 4-[(S)-4-Carboxy-2-({4-[2-(4-isobutoxy-piperidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-(4-isopropoxy-piperidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-(2-furan-2-yl-pyrrolidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-((R)-2-cyano-pyrrolidin-1-yl)-2-oxo-ethoxy]-quinoline-2-carbonyl}-amino)-butyryl]-piperazine-1-carboxylic acid ethyl ester, 4-{(S)-4-Carboxy-2-[(4-{2-[4-(2-morpholin-4-yl-2-oxo-ethyl)-piperazin-1-yl]-2-oxo-ethoxy}-quinoline-2-carbonyl)-amino]-butyryl}-piperazine-1-carboxylic acid ethyl ester, 4-[(S)-4-Carboxy-2-({4-[2-((2S,4R)-4-hydroxy-2-methoxycarbonyl-piperidin-1-yl)-2-oxo-ethoxy]-quinoline-2-carbonyl}-amino)-butyryl]-piperazine-1-carboxylic acid ethyl ester, 4-{(S)-4-Carboxy-2-[(4-{2-[2-(5-methyl-furan-2-yl)-pyrrolidin-1-yl]-2-oxo-ethoxy}-quinoline-2-carbonyl)-amino]-butyryl}-piperazine-1-carboxylic acid ethyl ester, 4-[(S)-4-Carboxy-2-({4-[2-(2-methoxymethyl-piperidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-(4-morpholin-4-yl-piperidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-(4-isopropyl-piperazin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-(2-ethoxymethyl-pyrrolidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-(4-cyclopropanecarbonyl-piperazin-1-yl)-2-oxo-ethoxy]-quinoline-2-carbonyl}-amino)-butyryl]-piperazine-1-carboxylic acid ethyl ester, 4-((S)-4-Carboxy-2-{[4-(2-oxo-2-piperazin-1-yl-ethoxy)-quinoline-2-carbonyl]-amino}-butyryl)-piperazine-1-carboxylic acid ethyl ester, 4-[(S)-4-Carboxy-2-({4-[2-(4-ethanesulfonyl-piperazin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-oxo-2-((S)-2-trifluoromethyl-pyrrolidin-1-yl)-ethoxy]-quinoline-2-carbonyl}-amino)-butyryl]-piperazine-1-carboxylic acid ethyl ester, 4-{(S)-4-Carboxy-2-[(4-[2-oxo-2-[2-(tetrahydro-furan-2-yl)-piperidin-1-yl]-ethoxy}-quinoline-2-carbonyl)-amino]1-butyryl]-piperazine-1-carboxylic acid ethyl ester, 4-[(S)-4-Carboxy-2-({4-[2-(2-morpholin-4-ylmethyl-pyrrolidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-(2,2-dimethyl-3-oxo-piperazin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-(2-methylsulfanylmethyl-pyrrolidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-oxo-2-(2-phenyl-pyrrolidin-1-yl)-ethoxy]-quinoline-2-carbonyl}-amino)-butyryl]-piperazine-1-carboxylic acid ethyl ester, 4-[(S)-4-Carboxy-2-({4-[2-oxo-2-(2-thiazol-2-yl-pyrrolidin-1-yl)-ethoxy]-quinoline-2-carbonyl}-amino)-butyryl]-piperazine-1-carboxylic acid ethyl ester, 4-[(S)-4-Carboxy-2-({4-[2-(2-cyclopentyl-pyrrolidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-(3-methoxy-3a,4,6,6a-tetrahydro-pyrrolo[3,4-d]isoxazol-5-yl)-2-oxo-ethoxy]-quinoline-2-carbonyl}-amino)-butyryl]-piperazine-1-carboxylic acid ethyl ester, 4-[(S)-4-Carboxy-2-({4-[2-(4,4-difluoro-piperidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-((S)-2-cyano-pyrrolidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-oxo-2-(3-trifluoromethyl-pyrrolidin-1-yl)-ethoxy]-quinoline-2-carbonyl}-amino)-butyryl]-piperazine-1-carboxylic acid ethyl ester, 4-[(S)-4-Carboxy-2-({4-[2-oxo-2-(4-oxo-hexahydro-cyclopenta[c]pyrrol-2-yl)-ethoxy]-quinoline-2-carbonyl}-amino)-butyryl]-piperazine-1-carboxylic acid ethyl ester, 4-[(S)-4-Carboxy-2-({4-[2-oxo-2-(4-oxo-imidazolidin-1-yl)-ethoxy]-quinoline-2-carbonyl}-amino)-butyryl]-piperazine-1-carboxylic acid ethyl ester, (S)-4-({4-[2-((S)-2-Cyclobutylcarbamoyl-pyrrolidin-1-yl)-2-oxo-ethoxy]-quinoline-2-carbonyl}-amino)-5-[4-(3-methoxy-phenyl)-piperazin-1-yl]-5-oxo-pentanoic acid, 4-[(S)-5-Carboxy-2-({4-[2-((S)-2-cyclobutylcarbamoyl-pyrrolidin-1-yl)-2-oxo-ethoxy]-quinoline-2-carbonyl}-amino)-pentanoyl]-piperazine-1-carboxylic acid ethyl ester, 4-[(S)-2-({4-[2-((S)-2-Cyclobutylcarbamoyl-pyrrolidin-1-yl)-2-oxo-ethoxy]-quinoline-2-carbonyl}-amino)-4-methanesulfonyl-butyryl]-piperazine-1-carboxylic acid ethyl ester, 4-[(S)-4-Carboxy-2-({4-[2-((S)-2-methyl-3-oxo-piperazin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-oxo-2-(2-pyridin-3-yl-pyrrolidin-1-yl)-ethoxy]-quinoline-2-carbonyl}-amino)-butyryl]-piperazine-1-carboxylic acid ethyl ester, 4-((S)-4-Carboxy-2-{[4-((1S,4S)-2-2,5-diaza-bicyclo[2.2.1]hept-2-yl-2-oxo-ethoxy)-quinoline-2-carbonyl]-amino}-butyryl)-piperazine-1-carboxylic acid ethyl ester, 4-[(S)-2-({4-[2-((S)-3-Amino-pyrrolidin-1-yl)-2-oxo-ethoxy]-quinoline-2-carbonyl}-amino)-4-carboxy-butyryl]-piperazine-1-carboxylic acid ethyl ester, 4-{(S)-4-Carboxy-2-[(4-{2-[2-(1-methyl-piperidin-2-yl)-pyrrolidin-1-yl]-2-oxo-ethoxy}-quinoline-2-carbonyl)-amino]-butyryl}-piperazine-1-carboxylic acid ethyl ester, 4-[(S)-4-Carboxy-2-({4-[2-oxo-2-(3-pyridin-4-yl-pyrrolidin-1-yl)-ethoxy]-quinoline-2-carbonyl}-amino)-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-ethoxycarbonyl-butyryl]-piperazine-1-carboxylic acid butyl ester, 4-[(S)-4-Carboxy-2-({4-[2-((R)-2-methoxymethyl-pyrrolidin-1-yl)-2-oxo-ethoxy]-quinoline-2-carbonyl}-amino)-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-hydroxy-butyryl]-piperazine-1-carboxylic acid butyl ester, 4-[(S)-4-Carboxy-2-({4-[(R)-2-((S)-2-carboxy-pyrrolidin-1-yl)-1-methyl-2-oxo-ethoxy]-7-methyl-quinoline-2-carbonyl}-amino)-butyryl]-piperazine-1-carboxylic acid ethyl ester, 4-[(S)-4-Carboxy-2-({7-methyl-4-[(R)-1-methyl-2-oxo-2-(2-phenyl-pyrrolidin-1-yl)-ethoxy]-quinoline-2-carbonyl}-amino)-butyryl]-piperazine-1-carboxylic acid ethyl ester, 4-[(S)-4-Carboxy-2-({4-[2-oxo-2-(2-o-tolyl-pyrrolidin-1-yl)-ethoxy]-quinoline-2-carbonyl}-amino)-butyryl]-piperazine-1-carboxylic acid ethyl ester, 4-[(S)-4-Carboxy-2-({4-[2-oxo-2-(3-phenyl-pyrrolidin-1-yl)-ethoxy]-quinoline-2-carbonyl}-amino)-butyryl]-piperazine-1-carboxylic acid ethyl ester, 4-[(S)-4-Carboxy-2-({4-[2-(2-hydroxymethyl-2,3-dihydro-indol-1-yl)-2-oxo-ethoxy]-quinoline-2-carbonyl}-amino)-butyryl]-piperazine-1-carboxylic acid ethyl ester, 4-[(S)-2-({4-[2-(5-Acetyl-2,3-dihydro-indol-1-yl)-2-oxo-ethoxy]-quinoline-2-carbonyl}-amino)-4-carboxy-butyryl]-piperazine-1-carboxylic acid ethyl ester, (S)-1-(2-{2-[(S)-3-Carboxy-1-(4-ethoxycarbonyl-piperazine-1-carbonyl)-propylcarbamoyl]-quinolin-4-yloxy}-acetyl)-2,3-dihydro-1H-indole-2-carboxylic acid, 4-[(S)-4-Carboxy-2-({4-[2-(2-methyl-2,3-dihydro-indol-1-yl)-2-oxo-ethoxy]-quinoline-2-carbonyl}-amino)-butyryl]-piperazine-1-carboxylic acid ethyl ester, 4-[(S)-4-Carboxy-2-({4-[2-(2,3-dihydro-indol-1-yl)-2-oxo-ethoxy]-quinoline-2-carbonyl}-amino)-butyryl]-piperazine-1-carboxylic acid ethyl ester, 4-[(S)-4-Carboxy-2-({4-[2-((S)-3-hydroxymethyl-3,4-dihydro-1H-isoquinolin-2-yl)-2-oxo-ethoxy]-quinoline-2-carbonyl}-amino)-butyryl]-piperazine-1-carboxylic acid ethyl ester, 4-[(S)-4-Carboxy-2-({4-[2-(3,4-dihydro-1H-isoquinolin-2-yl)-2-oxo-ethoxy]-quinoline-2-carbonyl}-amino)-butyryl]-piperazine-1-carboxylic acid ethyl ester, 4-[(S)-4-Carboxy-2-({4-[2-(6-methoxy-3,4-dihydro-2H-quinolin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-(3,4-dihydro-2H-quinolin-1-yl)-2-oxo-ethoxy]-quinoline-2-carbonyl}-amino)-butyryl]-piperazine-1-carboxylic acid ethyl ester, 4-{(S)-4-Carboxy-2-[(4-{2-[2-(4-fluoro-phenyl)-pyrrolidin-1-yl]-2-oxo-ethoxy}-quinoline-2-carbonyl)-amino]-butyryl}-piperazine-1-carboxylic acid ethyl ester, 4-{(S)-4-Carboxy-2-[(4-{2-[2-(2-chloro-phenyl)-pyrrolidin-1-yl]-2-oxo-ethoxy]-quinoline-2-carbonyl}-amino]-butyryl}-piperazine-1-carboxylic acid ethyl ester, 4-[(S)-4-Carboxy-2-({4-[2-(4-methyl-3-oxo-piperazin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-(5-methyl-3-oxo-pyrazolidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-oxo-2-(2-pyridin-4-yl-pyrrolidin-1-yl)-ethoxy]-quinoline-2-carbonyl}-amino)-butyryl]-piperazine-1-carboxylic acid ethyl ester, 4-[(S)-4-Carboxy-2-({4-[2-(2-methyl-4,6-dihydro-pyrrolo[3,4-d]thiazol-5-yl)-2-oxo-ethoxy]-quinoline-2-carbonyl}-amino)-butyryl]-piperazine-1-carboxylic acid ethyl ester, 4-[(S)-4-Carboxy-2-({4-[2-oxo-2-(3-pyridin-2-yl-pyrrolidin-1-yl)-ethoxy]-quinoline-2-carbonyl}-amino)-butyryl]-piperazine-1-carboxylic acid ethyl ester, 4-[(S)-4-Carboxy-2-({4-[2-oxo-2-((R)-2-phenylaminomethyl-pyrrolidin-1-yl)-ethoxy]-quinoline-2-carbonyl}-amino)-butyryl]-piperazine-1-carboxylic acid ethyl ester, 4-[(S)-2-({4-[2-(2-Benzyloxymethyl-pyrrolidin-1-yl)-2-oxo-ethoxy]-quinoline-2-carbonyl}-amino)-4-carboxy-butyryl]-piperazine-1-carboxylic acid ethyl ester, 4-[(S)-4-Carboxy-2-({4-[2-(4,7-dihydro-5H-thieno[2,3-c]pyridin-6-yl)-2-oxo-ethoxy]-quinoline-2-carbonyl}-amino)-butyryl]-piperazine-1-carboxylic acid ethyl ester, 4-[(S)-4-Carboxy-2-({4-[2-(4-methyl-6,7-dihydro-4H-thieno[3,2-c]pyridin-5-yl)-2-oxo-ethoxy]-quinoline-2-carbonyl}-amino)-butyryl]-piperazine-1-carboxylic acid ethyl ester, 4-[(S)-4-Carboxy-2-({4-[2-oxo-2-(3-phenyl-6,7-dihydro-4H-isoxazolo[4,5-c]pyridin-5-yl)-ethoxy]-quinoline-2-carbonyl}-amino)-butyryl]-piperazine-1-carboxylic acid ethyl ester, 4-[(S)-2-({4-[2-(3-Benzyloxy-pyrrolidin-1-yl)-2-oxo-ethoxy]-quinoline-2-carbonyl}-amino)-4-carboxy-butyryl]-piperazine-1-carboxylic acid ethyl ester, 4-[(S)-4-Carboxy-2-({4-[2-oxo-2-(3-trifluoromethyl-1,4,6,7-tetrahydro-pyrazolo[4,3-c]pyridin-5-yl)-ethoxy]-quinoline-2-carbonyl}-amino)-butyryl]-piperazine-1-carboxylic acid ethyl ester, 4-[(S)-4-Carboxy-2-({4-[2-(2-isopropyl-pyrrolidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-oxo-2-(2-m-tolyl-pyrrolidin-1-yl)-ethoxy]-quinoline-2-carbonyl}-amino)-butyryl]-piperazine-1-carboxylic acid ethyl ester, 4-[(S)-4-Carboxy-2-({4-[2-oxo-2-((R)-3-phenyl-pyrrolidin-1-yl)-ethoxy]-quinoline-2-carbonyl}-amino)-butyryl]-piperazine-1-carboxylic acid ethyl ester, 4-[(S)-4-Carboxy-2-({4-[2-(2-isopropyl-4-methyl-3-oxo-piperazin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-(2-ethyl-pyrrolidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-oxo-2-(2-pyridin-2-yl-pyrrolidin-1-yl)-ethoxy]-quinoline-2-carbonyl}-amino)-butyryl]-piperazine-1-carboxylic acid ethyl ester, 4-[(S)-2-({4-[2-(2-tert-Butyl-pyrrolidin-1-yl)-2-oxo-ethoxy]-quinoline-2-carbonyl}-amino)-4-carboxy-butyryl]-piperazine-1-carboxylic acid ethyl ester, 4-{(S)-2-[(4-{2-[2-(1H-Benzoimidazol-2-yl)-pyrrolidin-1-yl]-2-oxo-ethoxy}-quinoline-2-carbonyl)-amino]-4-carboxy-butyryl}-piperazine-1-carboxylic acid ethyl ester, 4-[(S)-4-Carboxy-2-({4-[2-oxo-2-(3-phenylamino-pyrrolidin-1-yl)-ethoxy]-quinoline-2-carbonyl}-amino)-butyryl]-piperazine-1-carboxylic acid ethyl ester, 4-((S)-2-{[4-(2-[1,3']Bipyrrolidinyl-1'-yl-2-oxo-ethoxy)-quinoline-2-carbonyl]-amino}-4-carboxy-butyryl)-piperazine-1-carboxylic acid ethyl ester, 4-{(S)-4-Carboxy-2-[(4-{2-oxo-2-[(S)-2-(1H-tetrazol-5-ylmethyl)-pyrrolidin-1-yl]-ethoxy}-quinoline-2-carbonyl)-amino]-butyryl}-piperazine-1-carboxylic acid ethyl ester, 4-[(S)-4-Carboxy-2-({4-[2-oxo-2-(3-o-tolyloxy-pyrrolidin-1-yl)-ethoxy]-quinoline-2-carbonyl}-amino)-butyryl]-piperazine-1-carboxylic acid ethyl ester, 4-[(S)-4-Carboxy-2-({4-[2-(2-methyl-6,7-dihydro-4H-thiazolo[5,4-c]pyridin-5-yl)-2-oxo-ethoxy]-quinoline-2-carbonyl}-amino)-butyryl]-piperazine-1-carboxylic acid ethyl ester, 4-[(S)-2-({4-[2-(2-Butyl-4-methyl-3-oxo-piperazin-1-yl)-2-oxo-ethoxy]-quinoline-2-carbonyl}-amino)-4-carboxy-butyryl]-piperazine-1-carboxylic acid ethyl ester, 4-{(S)-4-Carboxy-2-[(4-{2-[2-(3-methoxy-phenyl)-pyrrolidin-1-yl]-2-oxo-ethoxy}-quinoline-2-carbonyl)-amino]-butyryl}-piperazine-1-carboxylic acid ethyl ester, 4-[(S)-4-Carboxy-2-({4-[2-(6-methyl-octahydro-pyrrolo[3,4-b]pyridin-1-yl)-2-oxo-ethoxy]-quinoline-2-carbonyl}-amino)-butyryl]-piperazine-1-carboxylic acid ethyl ester, 4-{(S)-4-Carboxy-2-[(4-{2-[2-(2-methoxy-phenyl)-pyrrolidin-1-yl]-2-oxo-ethoxy}-quinoline-2-carbonyl)-amino]-butyryl}-piperazine-1-carboxylic acid ethyl ester, 4-[(S)-4-Carboxy-2-({4-[2-(3-diethylamino-pyrrolidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-oxo-2-(3-o-tolyloxy-pyrrolidin-1-yl)-ethoxy]-quinoline-2-carbonyl}-amino)-butyryl]-piperazine-1-carboxylic acid ethyl ester, 4-{(S)-4-Carboxy-2-[(4-{2-[(S)-2-(cyclobutyl-methyl-carbamoyl)-pyrrolidin-1-yl]-2-oxo-ethoxy}-7-methyl-quinoline-2-carbonyl)-amino]-butyryl}-piperazine-1-carboxylic acid ethyl ester, 4-{(S)-2-[(4-{2-[(S)-2-(Cyclobutyl-methyl-carbamoyl)-pyrrolidin-1-yl]-2-oxo-ethoxy}-7-methyl-quinoline-2-carbonyl)-amino]-4-ethoxycarbonyl-butyryl}-piperazine-1-carboxylic acid ethyl ester, 4-[(S)-4-Carboxy-2-({4-[2-oxo-2-((R)-2-phenyl-pyrrolidin-1-yl)-ethoxy]-quinoline-2-carbonyl}-amino)-butyryl]-piperazine-1-carboxylic acid ethyl ester, 4-[(S)-4-Carboxy-2-({4-[2-oxo-2-((S)-2-phenyl-pyrrolidin-1-yl)-ethoxy]-quinoline-2-carbonyl}-amino)-butyryl]-piperazine-1-carboxylic acid ethyl ester, 4-{(S)-4-Carboxy-2-[(4-{2-[2-(2-fluoro-phenyl)-pyrrolidin-1-yl]-2-oxo-ethoxy}-quinoline-2-carbonyl)-amino]-butyryl}-piperazine-1-carboxylic acid ethyl ester, 4-{(S)-4-Carboxy-2-[(4-{2-[3-(2-fluoro-phenyl)-pyrrolidin-1-yl]-2-oxo-ethoxy}-quinoline-2-carbonyl)-amino]-butyryl}-piperazine-1-carboxylic acid ethyl ester, 4-{(S)-4-Carboxy-2-[(4-{2-[2-(2,4-dimethoxy-phenyl)-pyrrolidin-1-yl]-2-oxo-ethoxy}-quinoline-2-carbonyl)-amino]-butyryl}-piperazine-1-carboxylic acid ethyl ester, 4-[(S)-4-Carboxy-2-({4-[2-((2S,5R)-2-carboxy-5-phenyl-pyrrolidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-oxo-2-(2-p-tolyl-pyrrolidin-1-yl)-ethoxy]-quinoline-2-carbonyl}-amino)-butyryl]-piperazine-1-carboxylic acid ethyl ester, 4-{(S)-4-Carboxy-2-[(4-{2-[2-(3,4-difluoro-phenyl)-pyrrolidin-1-yl]-2-oxo-ethoxy}-quinoline-2-carbonyl)-amino]-butyryl}-piperazine-1-carboxylic acid ethyl ester, 4-{(S)-4-Carboxy-2-[(4-{2-[2-(3,4-dimethoxy-phenyl)-pyrrolidin-1-yl]-2-oxo-ethoxy}-quinoline-2-carbonyl)-amino]-butyryl}-piperazine-1-carboxylic acid ethyl ester, 4-[(S)-4-Carboxy-2-({4-[2-(2-ethyl-3-oxo-piperazin-1-yl)-2-oxo-ethoxy]-quinoline-2-carbonyl}-amino)-butyryl]-piperazine-1-carboxylic acid ethyl ester, 4-{(S)-4-Carboxy-2-[(4-{2-oxo-2-[3-(2-oxo-pyrrolidin-1-ylmethyl)-piperidin-1-yl]-ethoxy}-quinoline-2-carbonyl)-amino]-butyryl}-piperazine-1-carboxylic acid ethyl ester, 4-[(S)-4-Carboxy-2-({4-[2-oxo-2-(2-thiophen-2-yl-pyrrolidin-1-yl)-ethoxy]-quinoline-2-carbonyl}-amino)-butyryl]-piperazine-1-carboxylic acid ethyl ester, 4-[(S)-4-Carboxy-2-({4-[2-oxo-2-(2-pyrimidin-4-yl-pyrrolidin-1-yl)-ethoxy]-quinoline-2-carbonyl}-amino)-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-cyclohexylmethoxycarbonyl-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-cyclobutylmethoxycarbonyl-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-propoxycarbonyl-butyryl]-piperazine-1-carboxylic acid ethyl ester, 4-[(S)-4-Cyclobutoxycarbonyl-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-cyclopentylmethoxycarbonyl-butyryl]-piperazine-1-carboxylic acid butyl ester, 4-[(S)-4-Carboxy-2-({4-[2-oxo-2-(4-oxo-3,5,7,8-tetrahydro-4H-pyrido[4,3-d]pyrimidin-6-yl)-ethoxy]-quinoline-2-carbonyl}-amino)-butyryl]-piperazine-1-carboxylic acid ethyl ester, 4-{(S)-4-Carboxy-2-[(4-{2-[2-(3-chloro-phenyl)-pyrrolidin-1-yl]-2-oxo-ethoxy}-quinoline-2-carbonyl)-amino]-butyryl}-piperazine-1-carboxylic acid ethyl ester, 4-{(S)-4-Carboxy-2-[(4-{2-[2-(2,4-difluoro-phenyl)-pyrrolidin-1-yl]-2-oxo-ethoxy}-quinoline-2-carbonyl)-amino]-butyryl}-piperazine-1-carboxylic acid ethyl ester, 3-[(S)-4-Carboxy-2-({4-[2-((S)-2-cyclobutylcarbamoyl-pyrrolidin-1-yl)-2-oxo-ethoxy]-quinoline-2-carbonyl}-amino)-butyrylamino]-azetidine-1-carboxylic acid butyl ester, (S)-5-(4-Benzoyl-piperidin-1-yl)-4-({4-[2-((S)-2-cyclobutylcarbamoyl-pyrrolidin-1-yl)-2-oxo-ethoxy]-quinoline-2-carbonyl}-amino)-5-oxo-pentanoic acid, (S)-5-[4-(3-Chloro-benzoyl)-piperidin-1-yl]-4-({4-[2-((S)-2-cyclobutylcarbamoyl-pyrrolidin-1-yl)-2-oxo-ethoxy]-quinoline-2-carbonyl}-amino)-5-oxo-pentanoic acid, (S)-5-(4-Benzoyl-piperazin-1-yl)-4-({4-[2-((S)-2-cyclobutylcarbamoyl-pyrrolidin-1-yl)-2-oxo-ethoxy]-quinoline-2-carbonyl}-amino)-5-oxo-pentanoic acid, 4-[(S)-4-Carboxy-2-({4-[2-((2S,4R)-4-fluoro-2-methoxycarbonyl-pyrrolidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-(hexahydro-pyrrolo[3,4-b]pyrrol-5-yl)-2-oxo-ethoxy]-quinoline-2-carbonyl}-amino)-butyryl]-piperazine-1-carboxylic acid ethyl ester, 4-{(S)-2-[(4-{2-[2-(5-Bromo-pyridin-3-yl)-pyrrolidin-1-yl]-2-oxo-ethoxy}-quinoline-2-carbonyl)-amino]-4-carboxy-butyryl}-piperazine-1-carboxylic acid ethyl ester, (S)-5-(3-Butoxycarbonylamino-azetidin-1-yl)-4-({4-[2-((S)-2-cyclobutylcarbamoyl-pyrrolidin-1-yl)-2-oxo-ethoxy]-quinoline-2-carbonyl}-amino)-5-oxo-pentanoic acid, 4-{(S)-4-Carboxy-2-[(4-{2-[2-(3,4-dimethyl-phenyl)-pyrrolidin-1-yl]-2-oxo-ethoxy}-quinoline-2-carbonyl)-amino]-butyryl}-piperazine-1-carboxylic acid ethyl ester, 4-{(S)-4-Carboxy-2-[(4-{2-[2-(3,5-dimethyl-phenyl)-pyrrolidin-1-yl]-2-oxo-ethoxy}-quinoline-2-carbonyl)-amino]-butyryl}-piperazine-1-carboxylic acid ethyl ester, 4-{(S)-4-Carboxy-2-[(4-{2-[2-(2,4-dimethyl-phenyl)-pyrrolidin-1-yl]-2-oxo-ethoxy}-quinoline-2-carbonyl)-amino]-butyryl}-piperazine-1-carboxylic acid ethyl ester, 4-[2-({4-[2-((S)-2-Cyclobutylcarbamoyl-pyrrolidin-1-yl)-2-oxo-ethoxy]-7-methyl-quinoline-2-carbonyl}-amino)-acetyl]-piperazine-1-carboxylic acid butyl ester, 4-{(S)-4-Carboxy-2-[(4-{2-[2-(2,5-dimethyl-phenyl)-pyrrolidin-1-yl]-2-oxo-ethoxy}-quinoline-2-carbonyl)-amino]-butyryl}-piperazine-1-carboxylic acid ethyl ester, 4-[(S)-4-Carboxy-2-({4-[2-(3-hydroxy-4,7-dihydro-5H-isoxazolo[5,4-c]pyridin-6-yl)-2-oxo-ethoxy]-quinoline-2-carbonyl}-amino)-butyryl]-piperazine-1-carboxylic acid ethyl ester, 4-[(S)-4-Carboxy-2-({4-[2-oxo-2-(2-trifluoromethoxymethyl-pyrrolidin-1-yl)-ethoxy]-quinoline-2-carbonyl}-amino)-butyryl]-piperazine-1-carboxylic acid ethyl ester, 4-[(S)-4-Carboxy-2-({4-[2-(3-methoxy-pyrrolidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-((2S,4S)-4-fluoro-2-methoxycarbonyl-pyrrolidin-1-yl)-2-oxo-ethoxy]-quinoline-2-carbonyl}-amino)-butyryl]-piperazine-1-carboxylic acid ethyl ester, 4-[(S)-4-Carboxy-2-({4-[2-(4,6-dihydro-1H-pyrrolo[3,4-c]pyrazol-5-yl)-2-oxo-ethoxy]-quinoline-2-carbonyl}-amino)-butyryl]-piperazine-1-carboxylic acid ethyl ester, 4-{(S)-4-Carboxy-2-[(4-{2-[(S)-2-(5-methyl-pyridin-3-yl)-pyrrolidin-1-yl]-2-oxo-ethoxy}-quinoline-2-carbonyl)-amino]-butyryl}-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-5-hydroxy-pentanoyl]-piperazine-1-carboxylic acid butyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(2-cyclopentyl-ethoxycarbonyl)-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(tetrahydro-furan-3-ylmethoxycarbonyl)-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(3-methyl-oxetan-3-ylmethoxycarbonyl)-butyryl]-piperazine-1-carboxylic acid ethyl ester, 4-[(S)-4-((1R,4S)-1-Bicyclo[2.2.1]hept-2-ylmethoxycarbonyl)-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(3-ethyl-oxetan-3-ylmethoxycarbonyl)-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(tetrahydro-pyran-2-ylmethoxycarbonyl)-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(5-ethyl-[1,3]dioxan-5-ylmethoxycarbonyl)-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(2-oxo-[1,3]dioxolan-4-ylmethoxycarbonyl)-butyryl]-piperazine-1-carboxylic acid ethyl ester, 4-{(S)-2-({4-[2-((S)-2-Cyclobutylcarbamoyl-pyrrolidin-1-yl)-2-oxo-ethoxy]-7-methyl-quinoline-2-carbonyl}-amino)-4-[2-(2-hydroxy-ethylamino)-ethoxycarbonyl]-butyryl}-piperazine-1-carboxylic acid ethyl, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(3-methoxy-butoxycarbonyl)-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(tetrahydro-furan-2-ylmethoxycarbonyl)-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(3-dimethylamino-2,2-dimethyl-propoxycarbonyl)-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(2-dimethylamino-2-methyl-propoxycarbonyl)-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(2-morpholin-4-yl-ethoxycarbonyl)-butyryl]-piperazine-1-carboxylic acid ethyl ester, 4-[(S)-4-Carboxy-2-({4-[2-(4,6-dihydro-1H-pyrrolo[3,4-c]pyrazol-5-yl)-2-oxo-ethoxy]-7-methyl-quinoline-2-carbonyl}-amino)-butyryl]-piperazine-1-carboxylic acid butyl ester, 4-{(S)-4-Carboxy-2-[(4-{2-[2-(3,4-difluoro-phenyl)-pyrrolidin-1-yl]-2-oxo-ethoxy}-7-methyl-quinoline-2-carbonyl)-amino]-butyryl}-piperazine-1-carboxylic acid butyl ester, 4-[(S)-4-Carboxy-2-({4-[2-((S)-2-cyano-pyrrolidin-1-yl)-2-oxo-ethoxy]-7-methyl-quinoline-2-carbonyl}-amino)-butyryl]-piperazine-1-carboxylic acid butyl ester, 4-{(S)-4-Carboxy-2-[(4-{2-[2-(2,4-difluoro-phenyl)-pyrrolidin-1-yl]-2-oxo-ethoxy}-7-methyl-quinoline-2-carbonyl)-amino]-butyryl}-piperazine-1-carboxylic acid butyl ester, 4-[(S)-4-Carboxy-2-({4-[2-(2-furan-2-yl-pyrrolidin-1-yl)-2-oxo-ethoxy]-7-methyl-quinoline-2-carbonyl}-amino)-butyryl]-piperazine-1-carboxylic acid butyl ester, 4-[(S)-4-Carboxy-2-({7-methyl-4-[2-oxo-2-(4-oxo-3,5,7,8-tetrahydro-4H-pyrido[4,3-d]pyrimidin-6-yl)-ethoxy]-quinoline-2-carbonyl}-amino)-butyryl]-piperazine-1-carboxylic acid butyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(1-methyl-2-morpholin-4-yl-ethoxycarbonyl)-butyryl]-piperazine-1-carboxylic acid ethyl ester, 4-[(S)-2-({4-[(R)-2-((S)-2-Cyclobutylcarbamoyl-pyrrolidin-1-yl)-1-methyl-2-oxo-ethoxy]-7-methyl-quinoline-2-carbonyl}-amino)-4-cyclopentylmethoxycarbonyl-butyryl]-piperazine-1-carboxylic acid ethyl ester, 4-[(S)-4-Carboxy-2-({7-methyl-4-[2-oxo-2-(2-oxo-oxazolidin-3-yl)-ethoxy]-quinoline-2-carbonyl}-amino)-butyryl]-piperazine-1-carboxylic acid butyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(3-methoxy-propoxycarbonyl)-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(2-ethoxy-ethoxycarbonyl)-butyryl]-piperazine-1-carboxylic acid ethyl ester, 4-[(S)-4-Carboxy-2-({7-methyl-4-[2-oxo-2-(2-o-tolyl-pyrrolidin-1-yl)-ethoxy]-quinoline-2-carbonyl}-amino)-butyryl]-piperazine-1-carboxylic acid butyl ester, 4-[(S)-4-Carboxy-2-({4-[2-((S)-2-hydroxymethyl-pyrrolidin-1-yl)-2-oxo-ethoxy]-7-methyl-quinoline-2-carbonyl}-amino)-butyryl]-piperazine-1-carboxylic acid butyl ester, 4-[(S)-4-Carboxy-2-({4-[2-(3,3-difluoro-pyrrolidin-1-yl)-2-oxo-ethoxy]-7-methyl-quinoline-2-carbonyl}-amino)-butyryl]-piperazine-1-carboxylic acid butyl ester, 4-[(S)-4-Carboxy-2-({4-[2-(3-hydroxy-azetidin-1-yl)-2-oxo-ethoxy]-7-methyl-quinoline-2-carbonyl}-amino)-butyryl]-piperazine-1-carboxylic acid butyl ester, 4-[(S)-4-Carboxy-2-({7-methyl-4-[2-(4-methyl-3-oxo-piperazin-1-yl)-2-oxo-ethoxy]-quinoline-2-carbonyl}-amino)-butyryl]-piperazine-1-carboxylic acid butyl ester, 4-[(S)-4-Carboxy-2-({4-[2-(4-hydroxy-piperidin-1-yl)-2-oxo-ethoxy]-7-methyl-quinoline-2-carbonyl}-amino)-butyryl]-piperazine-1-carboxylic acid butyl ester, 4-[(S)-4-Carboxy-2-({7-methyl-4-[2-(5-methyl-3-oxo-pyrazolidin-1-yl)-2-oxo-ethoxy]-quinoline-2-carbonyl}-amino)-butyryl]-piperazine-1-carboxylic acid butyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(2-dimethylamino-ethoxycarbonyl)-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(2-isopropoxy-ethoxycarbonyl)-butyryl]-piperazine-1-carboxylic acid ethyl ester, 4-[(S)-4-Carboxy-2-({4-[2-((R)-3-hydroxy-pyrrolidin-1-yl)-2-oxo-ethoxy]-7-methyl-quinoline-2-carbonyl}-amino)-butyryl]-piperazine-1-carboxylic acid butyl ester, 4-{(S)-4-Carboxy-2-[(7-methyl-4-{2-[(S)-2-(5-methyl-pyridin-3-yl)-pyrrolidin-1-yl]-2-oxo-ethoxy}-quinoline-2-carbonyl)-amino]-butyryl}-piperazine-1-carboxylic acid butyl ester, 4-[(S)-4-Carboxy-2-({4-[2-((S)-3-hydroxy-pyrrolidin-1-yl)-2-oxo-ethoxy]-7-methyl-quinoline-2-carbonyl}-amino)-butyryl]-piperazine-1-carboxylic acid butyl ester, 4-[(S)-4-Carboxy-2-({7-methyl-4-[2-oxo-2-((S)-2-phenyl-pyrrolidin-1-yl)-ethoxy]-quinoline-2-carbonyl}-amino)-butyryl]-piperazine-1-carboxylic acid butyl ester, 4-[(S)-4-Carboxy-2-({4-[2-((S)-2-methoxymethyl-pyrrolidin-1-yl)-2-oxo-ethoxy]-7-methyl-quinoline-2-carbonyl}-amino)-butyryl]-piperazine-1-carboxylic acid butyl ester, 4-((S)-4-Carboxy-2-{[7-methyl-4-(2-oxo-2-piperazin-1-yl-ethoxy)-quinoline-2-carbonyl]-amino}-butyryl)-piperazine-1-carboxylic acid butyl ester, 4-{(S)-2-({4-[2-((S)-2-Cyclobutylcarbamoyl-pyrrolidin-1-yl)-2-oxo-ethoxy]-7-methyl-quinoline-2-carbonyl}-amino)-4-[2-(2-oxo-oxazolidin-3-yl)-ethoxycarbonyl]-butyryl}-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(5-methyl-[1,3]dioxan-5-ylmethoxycarbonyl)-butyryl]-piperazine-1-carboxylic acid ethyl ester, 4-[(S)-4-Carboxy-2-({4-[2-(3-methoxy-pyrrolidin-1-yl)-2-oxo-ethoxy]-7-methyl-quinoline-2-carbonyl}-amino)-butyryl]-piperazine-1-carboxylic acid butyl ester, 4-[(S)-4-Carboxy-2-({7-methyl-4-[2-oxo-2-(3-oxo-pyrazolidin-1-yl)-ethoxy]-quinoline-2-carbonyl}-amino)-butyryl]-piperazine-1-carboxylic acid butyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-methoxycarbonyl-butyryl]-piperazine-1-carboxylic acid butyl ester, 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid propyl ester, 4-[(S)-4-Carboxy-2-({4-[2-((S)-2-cyclobutylcarbamoyl-pyrrolidin-1-yl)-2-oxo-ethoxy]-7-methyl-quinoline-2-carbonyl}-amino)-butyryl]-piperazine-1-carboxylic acid cyclobutyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-methoxycarbonyl-butyryl]-piperazine-1-carboxylic acid propyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-methoxycarbonyl-butyryl]-piperazine-1-carboxylic acid cyclobutyl ester, 4-{(S)-4-Carboxy-2-[(4-{2-[2-(3-fluoro-phenyl)-pyrrolidin-1-yl]-2-oxo-ethoxy}-quinoline-2-carbonyl)-amino]-butyryl}-piperazine-1-carboxylic acid ethyl ester, 4-[(S)-4-Carboxy-2-({4-[2-oxo-2-(2-oxo-[1,4']bipiperidinyl-1'-yl)-ethoxy]-quinoline-2-carbonyl}-amino)-butyryl]-piperazine-1-carboxylic acid ethyl ester, 4-[(S)-4-Carboxy-2-({4-[2-(2-methyl-6,7-dihydro-4H-oxazolo[5,4-c]pyridin-5-yl)-2-oxo-ethoxy]-quinoline-2-carbonyl}-amino)-butyryl]-piperazine-1-carboxylic acid ethyl ester, 4-[(S)-4-Carboxy-2-({4-[2-oxo-2-((S)-2-phenylcarbamoyl-pyrrolidin-1-yl)-ethoxy]-quinoline-2-carbonyl}-amino)-butyryl]-piperazine-1-carboxylic acid ethyl ester, 4-[(S)-4-Carboxy-2-({4-[2-(1-methyl-4,6-dihydro-1H-pyrrolo[3,4-c]pyrazol-5-yl]-2-oxo-ethoxy]-quinoline-2-carbonyl}-amino)-butyryl]-piperazine-1-carboxylic acid ethyl ester, 4-{(S)-2-({4-[2-((S)-2-Cyclobutylcarbamoyl-pyrrolidin-1-yl)-2-oxo-ethoxy]-7-methyl-quinoline-2-carbonyl}-amino)-4-[2-(tetrahydro-pyran-4-yl)-ethoxycarbonyl]-butyryl}-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(3-hydroxy-3-methyl-butoxycarbonyl)-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(tetrahydro-pyran-3-ylmethoxycarbonyl)-butyryl]-piperazine-1-carboxylic acid ethyl ester, 4-[(S)-4-Carboxy-2-({7-methyl-4-[2-oxo-2-(3-oxo-piperazin-1-yl)-ethoxy]-quinoline-2-carbonyl}-amino)-butyryl]-piperazine-1-carboxylic acid butyl ester, 4-{(S)-4-Carboxy-2-[(4-{2-[2-(4-fluoro-phenyl)-pyrrolidin-1-yl]-2-oxo-ethoxy}-7-methyl-quinoline-2-carbonyl)-amino]-butyryl}-piperazine-1-carboxylic acid butyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(tetrahydro-pyran-4-ylmethoxycarbonyl)-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(2-hydroxy-2-methyl-butoxycarbonyl)-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(2-methyl-oxetan-2-ylmethoxycarbonyl)-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(3-ethyl-oxetan-3-ylmethoxycarbonyl)-butyryl]-piperazine-1-carboxylic acid butyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(tetrahydro-pyran-2-ylmethoxycarbonyl)-butyryl]-piperazine-1-carboxylic acid butyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(tetrahydro-furan-3-ylmethoxycarbonyl)-butyryl]-piperazine-1-carboxylic acid butyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(tetrahydro-furan-2-ylmethoxycarbonyl)-butyryl]-piperazine-1-carboxylic acid butyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(2-ethoxy-ethoxycarbonyl)-butyryl]-piperazine-1-carboxylic acid butyl ester, 4-[(S)-4-Carboxy-2-({4-[2-((S)-2-cyclobutylcarbamoyl-pyrrolidin-1-yl)-2-oxo-ethoxy]-7-methyl-naphthalene-2-carbonyl}-amino)-butyryl]-piperazine-1-carboxylic acid butyl ester, 4-[(S)-2-({4-[2-((S)-2-Cyclobutylcarbamoyl-pyrrolidin-1-yl)-2-oxo-ethoxy]-7-methyl-naphthalene-2-carbonyl}-amino)-4-methoxycarbonyl-butyryl]-piperazine-1-carboxylic acid butyl ester, 4-[(S)-2-({4-[2-((S)-2-Cyclobutylcarbamoyl-pyrrolidin-1-yl)-2-oxo-ethoxy]-7-methyl-naphthalene-2-carbonyl}-amino)-4-ethoxycarbonyl-butyryl]-piperazine-1-carboxylic acid butyl ester, 4-[(S)-3-Cyclobutyl-2-({4-[2-((S)-2-cyclobutylcarbamoyl-pyrrolidin-1-yl)-2-oxo-ethoxy]-7-methyl-quinoline-2-carbonyl}-amino)-propionyl]-piperazine-1-carboxylic acid butyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-butyryl]-piperazine-1-carboxylic acid butyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-3-cyclopropyl-propionyl]-piperazine-1-carboxylic acid butyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-3-methoxy-propionyl]-piperazine-1-carboxylic acid butyl ester, 4-[(S)-2-({4-[2-((S)-2-Cyclobutylcarbamoyl-pyrrolidin-1-yl)-2-oxo-ethoxy]-7-methyl-naphthalene-2-carbonyl}-amino)-4-cyclopentylmethoxycarbonyl-butyryl]-piperazine-1-carboxylic acid butyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-cyclopentylmethoxycarbonyl-butyryl]-piperazine-1-carboxylic acid cyclopropylmethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-cyclopentylmethoxycarbonyl-butyryl]-piperazine-1-carboxylic acid cyclobutyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-methoxy-butyryl]-piperazine-1-carboxylic acid butyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-2-cyclopropyl-acetyl]-piperazine-1-carboxylic acid butyl ester, 4-[(2S,3R)-2-({4-[2-((S)-2-Cyclobutylcarbamoyl-pyrrolidin-1-yl)-2-oxo-ethoxy]-7-methyl-quinoline-2-carbonyl}-amino)-3-methyl-pentanoyl]-piperazine-1-carboxylic acid butyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-3-hydroxy-3-methyl-butyryl]-piperazine-1-carboxylic acid butyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-3-ethoxy-propionyl]-piperazine-1-carboxylic acid butyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-hydroxy-butyryl]-piperazine-1-carboxylic acid cyclopropylmethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-hydroxy-butyryl]-piperazine-1-carboxylic acid cyclobutyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-3-hydroxy-propionyl]-piperazine-1-carboxylic acid butyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-propionyl]-piperazine-1-carboxylic acid butyl ester, 4-[(2S,3R)-2-({4-[2-((S)-2-Cyclobutylcarbamoyl-pyrrolidin-1-yl)-2-oxo-ethoxy]-7-methyl-quinoline-2-carbonyl}-amino)-3-methoxy-butyryl]-piperazine-1-carboxylic acid butyl ester, 4-[(S)-2-({4-[2-((S)-2-Cyclobutylcarbamoyl-pyrrolidin-1-yl)-2-oxo-ethoxy]-quinoline-2-carbonyl}-amino)-4-cyclopentylmethoxycarbonyl-butyryl]-piperazine-1-carboxylic acid butyl ester, 4-[2-({4-[2-((S)-2-Cyclobutylcarbamoyl-pyrrolidin-1-yl)-2-oxo-ethoxy]-7-methyl-quinoline-2-carbonyl}-amino)-2-(tetrahydro-furan-3-yl)-acetyl]-piperazine-1-carboxylic acid butyl ester, 4-[2-({4-[2-((S)-2-Cyclobutylcarbamoyl-pyrrolidin-1-yl)-2-oxo-ethoxy]-7-methyl-quinoline-2-carbonyl}-amino)-2-(tetrahydro-pyran-4-yl)-acetyl]-piperazine-1-carboxylic acid butyl ester, 4-[(S)-2-({4-[(R)-2-((S)-2-Cyclobutylcarbamoyl-pyrrolidin-1-yl)-1-methyl-2-oxo-ethoxy]-7-methyl-quinoline-2-carbonyl}-amino)-4-hydroxy-butyryl]-piperazine-1-carboxylic acid butyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-5-cyclopentylmethoxycarbonyl-pentanoyl]-piperazine-1-carboxylic acid ethyl ester, 4-{(S)-2-[(4-[2-[(S)-2-(Cyclobutyl-methyl-carbamoyl)-pyrrolidin-1-yl]-2-oxo-ethoxy}-7-methyl-quinoline-2-carbonyl)-amino]-4-(2-ethoxy-ethoxycarbonyl)-butyryl]-piperazine-1-carboxylic acid butyl ester, 4-[(S)-4-Cyclopentylmethoxycarbonyl-2-({4-[2-((S)-2-cyclopropylcarbamoyl-pyrrolidin-1-yl)-2-oxo-ethoxy]-7-methyl-quinoline-2-carbonyl}-amino)-butyryl]-piperazine-1-carboxylic acid butyl ester, 4-[(S)-2-[(4-{2-[(S)-2-(Cyclobutylmethyl-carbamoyl)-pyrrolidin-1-yl]-2-oxo-ethoxy}-7-methyl-quinoline-2-carbonyl)-amino]-4-(2-ethoxy-ethoxycarbonyl)-butyryl]-piperazine-1-carboxylic acid butyl ester, 4-{(S)-2-[(4-{2-[(S)-2-(Cyclobutylmethyl-carbamoyl)-pyrrolidin-1-yl]-2-oxo-ethoxy}-7-methyl-quinoline-2-carbonyl)-amino]-4-cyclopentylmethoxycarbonyl-butyryl]-piperazine-1-carboxylic acid butyl ester, 4-[(S)-4-(2-Ethoxy-ethoxycarbonyl)-2-({4-[2-((S)-2-methoxymethyl-pyrrolidin-1-yl)-2-oxo-ethoxy]-7-methyl-quinoline-2-carbonyl}-amino)-butyryl]-piperazine-1-carboxylic acid butyl ester, 4-[(S)-4-Cyclopentylmethoxycarbonyl-2-({4-[2-((R)-3-hydroxy-pyrrolidin-1-yl)-2-oxo-ethoxy]-7-methyl-quinoline-2-carbonyl}-amino)-butyryl]-piperazine-1-carboxylic acid butyl ester, 4-[(S)-4-(2-Ethoxy-ethoxycarbonyl)-2-({4-[2-((R)-3-hydroxy-pyrrolidin-1-yl)-2-oxo-ethoxy]-7-methyl-quinoline-2-carbonyl}-amino)-butyryl]-piperazine-1-carboxylic acid butyl ester, 4-[(S)-4-Cyclopentylmethoxycarbonyl-2-({4-[2-(3,3-difluoro-pyrrolidin-1-yl)-2-oxo-ethoxy]-7-methyl-quinoline-2-carbonyl}-amino)-butyryl]-piperazine-1-carboxylic acid butyl ester, 4-[(S)-2-({4-[2-(3,3-Difluoro-pyrrolidin-1-yl)-2-oxo-ethoxy]-7-methyl-quinoline-2-carbonyl}-amino)-4-(2-ethoxy-ethoxycarbonyl)-butyryl]-piperazine-1-carboxylic acid butyl ester, 4-[(2S,3S)-2-({4-[2-((S)-2-Cyclobutylcarbamoyl-pyrrolidin-1-yl)-2-oxo-ethoxy]-7-methyl-quinoline-2-carbonyl}-amino)-3-methyl-pentanoyl]-piperazine-1-carboxylic acid butyl ester, 4-[(S)-2-({6-[2-((S)-2-Cyclobutylcarbamoyl-pyrrolidin-1-yl)-2-oxo-ethoxy]-2,3-dihydro-1H-9-aza-cyclopenta[a]naphthalene-8-carbonyl}-amino)-4-cyclopentylmethoxycarbonyl-butyryl]-piperazine-1-carboxylic acid ethyl ester, 4-[(S)-2-({4-[2-((S)-2-Cyclopropylcarbamoyl-pyrrolidin-1-yl)-2-oxo-ethoxy]-7-methyl-quinoline-2-carbonyl}-amino)-4-(2-ethoxy-ethoxycarbonyl)-butyryl]-piperazine-1-carboxylic acid butyl ester, 4-[(S)-4-Cyclopentylmethoxycarbonyl-2-({4-[2-((S)-2-methoxymethyl-pyrrolidin-1-yl)-2-oxo-ethoxy]-7-methyl-quinoline-2-carbonyl}-amino)-butyryl]-piperazine-1-carboxylic acid butyl ester, 4-[(S)-4-Cyclopentylmethoxycarbonyl-2-({7-methyl-4-[2-oxo-2-((S)-2-phenyl-pyrrolidin-1-yl)-ethoxy]-quinoline-2-carbonyl}-amino)-butyryl]-piperazine-1-carboxylic acid butyl ester, 4-[(S)-4-(2-Ethoxy-ethoxycarbonyl)-2-({7-methyl-4-[2-oxo-2-((S)-2-phenyl-pyrrolidin-1-yl)-ethoxy]-quinoline-2-carbonyl}-amino)-butyryl]-piperazine-1-carboxylic acid butyl ester, 4-{(S)-2-[(4-{2-[(S)-2-(Cyclobutyl-methyl-carbamoyl)-pyrrolidin-1-yl]-2-oxo-ethoxy}-7-methyl-quinoline-2-carbonyl)-amino]-4-cyclopentylmethoxycarbonyl-butyryl}-piperazine-1-carboxylic acid butyl ester, 4-[2-({7-Methyl-4-[2-oxo-2-(3-oxo-piperazin-1-yl)-ethoxy]-quinoline-2-carbonyl}-amino)-acetyl]-piperazine-1-carboxylic acid butyl ester, 4-[2-({4-[2-(4,4-Difluoro-piperidin-1-yl)-2-oxo-ethoxy]-7-methyl-quinoline-2-carbonyl}-amino)-acetyl]-piperazine-1-carboxylic acid butyl ester, 4-[2-({4-[2-(3,3-Difluoro-pyrrolidin-1-yl)-2-oxo-ethoxy]-7-methyl-quinoline-2-carbonyl]-amino)-acetyl}-piperazine-1-carboxylic acid butyl ester, 4-[2-({4-[2-(4-Cyclopropylmethyl-piperazin-1-yl)-2-oxo-ethoxy]-7-methyl-quinoline-2-carbonyl}-amino)-acetyl]-piperazine-1-carboxylic acid butyl ester, 4-[2-({4-[2-((R)-3-Hydroxy-pyrrolidin-1-yl)-2-oxo-ethoxy]-7-methyl-quinoline-2-carbonyl}-amino)-acetyl]-piperazine-1-carboxylic acid butyl ester, 4-[2-({4-[2-(4-Isobutyl-piperazin-1-yl)-2-oxo-ethoxy]-7-methyl-quinoline-2-carbonyl}-amino)-acetyl]-piperazine-1-carboxylic acid butyl ester, 4-{2-[(7-Methyl-4-{2-[(S)-2-(5-methyl-pyridin-3-yl)-pyrrolidin-1-yl]-2-oxo-ethoxy}-quinoline-2-carbonyl)-amino]-acetyl}-piperazine-1-carboxylic acid butyl ester, 4-{2-[(4-{2-[2-(4-Fluoro-phenyl)-pyrrolidin-1-yl]-2-oxo-ethoxy}-7-methyl-quinoline-2-carbonyl)-amino]-acetyl}-piperazine-1-carboxylic acid butyl ester, 4-[2-({4-[2-(3-Hydroxy-azetidin-1-yl)-2-oxo-ethoxy]-7-methyl-quinoline-2-carbonyl}-amino)-acetyl]-piperazine-1-carboxylic acid butyl ester, 4-{2-[(4-{2-[2-(3,4-Difluoro-phenyl)-pyrrolidin-1-yl]-2-oxo-ethoxy}-7-methyl-quinoline-2-carbonyl)-amino]-acetyl}-piperazine-1-carboxylic acid butyl ester, 4-{2-[(4-{2-[2-(2,4-Difluoro-phenyl)-pyrrolidin-1-yl]-2-oxo-ethoxy}-7-methyl-quinoline-2-carbonyl)-amino]-acetyl}-piperazine-1-carboxylic acid butyl ester, 4-[2-({4-[2-((S)-2-Ethoxycarbonyl-pyrrolidin-1-yl)-2-oxo-ethoxy]-7-methyl-quinoline-2-carbonyl}-amino)-acetyl]-piperazine-1-carboxylic acid butyl ester, 4-[2-({4-[2-(3,3-Difluoro-piperidin-1-yl)-2-oxo-ethoxy]-7-methyl-quinoline-2-carbonyl}-amino)-acetyl]-piperazine-1-carboxylic acid butyl ester, 4-[2-({4-[2-((S)-2-Cyano-pyrrolidin-1-yl)-2-oxo-ethoxy]-7-methyl-quinoline-2-carbonyl}-amino)-acetyl]-piperazine-1-carboxylic acid butyl ester, 4-[2-({4-[2-(Hexahydro-pyrrolo[1,2-a]pyrazin-2-yl)-2-oxo-ethoxy]-7-methyl-quinoline-2-carbonyl}-amino)-acetyl]-piperazine-1-carboxylic acid butyl ester, 4-[2-({7-Methyl-4-[2-oxo-2-(4-oxo-3,5,7,8-tetrahydro-4H-pyrido[4,3-d]pyrimidin-6-yl)-ethoxy]-quinoline-2-carbonyl}-amino)-acetyl]piperazine-1-carboxylic acid butyl ester, 4-[2-({7-Methyl-4-[2-(4-methyl-piperazin-1-yl)-2-oxo-ethoxy]-quinoline-2-carbonyl}-amino)-acetyl]-piperazine-1-carboxylic acid butyl ester, 4-[2-({4-[2-((R)-2-Hydroxymethyl-pyrrolidin-1-yl)-2-oxo-ethoxy]-7-methyl-quinoline-2-carbonyl}-amino)-acetyl]-piperazine-1-carboxylic acid butyl ester, 4-[2-({7-Methyl-4-[2-(4-methoxycarbonyl-piperazin-1-yl)-2-oxo-ethoxy]-quinoline-2-carbonyl}-amino)-acetyl]-piperazine-1-carboxylic acid butyl ester, 4-[2-({4-[2-((S)-3-Hydroxy-pyrrolidin-1-yl)-2-oxo-ethoxy]-7-methyl-quinoline-2-carbonyl}-amino)-acetyl]-piperazine-1-carboxylic acid butyl ester, 4-{2-[(4-{2-[4-(2-Methoxy-ethyl)-piperazin-1-yl]-2-oxo-ethoxy}-7-methyl-quinoline-2-carbonyl)-amino]-acetyl}-piperazine-1-carboxylic acid butyl ester, 4-[2-({4-[2-(4,6-Dihydro-1H-pyrrolo[3,4-c]pyrazol-5-yl)-2-oxo-ethoxy]-7-methyl-quinoline-2-carbonyl}-amino)-acetyl]-piperazine-1-carboxylic acid butyl ester, 4-[2-({7-Methyl-4-[2-oxo-2-(3-oxo-pyrazolidin-1-yl)-ethoxy]-quinoline-2-carbonyl}-amino)-acetyl]-piperazine-1-carboxylic acid butyl ester, 4-[2-({7-Methyl-4-[2-(4-methyl-3-oxo-piperazin-1-yl)-2-oxo-ethoxy]-quinoline-2-carbonyl}-amino)-acetyl]-piperazine-1-carboxylic acid butyl ester, 4-[(S)-2-({4-[2-((S)-2-Cyclobutylcarbamoyl-4,4-difluoro-pyrrolidin-1-yl)-2-oxo-ethoxy]-7-methyl-quinoline-2-carbonyl}-amino)-4-(2-ethoxy-ethoxycarbonyl)-butyryl]-piperazine-1-carboxylic acid butyl ester, 4-{2-[(7-Methyl-4-{2-oxo-2-[(S)-2-(pyrrolidine-1-carbonyl)-pyrrolidin-1-yl]-ethoxy}-quinoline-2-carbonyl)-amino]-acetyl}-piperazine-1-carboxylic acid butyl ester, 4-{2-[(7-Methyl-4-{2-oxo-2-[4-(2,2,2-trifluoro-ethyl)-piperazin-1-yl]-ethoxy}-quinoline-2-carbonyl)-amino]-acetyl}-piperazine-1-carboxylic acid butyl ester, 4-[2-({4-[2-((S)-2-Carboxy-pyrrolidin-1-yl)-2-oxo-ethoxy]-7-methyl-quinoline-2-carbonyl}-amino)-acetyl]-piperazine-1-carboxylic acid butyl ester, 4-[2-({4-[2-(4-Cyclopropyl-piperazin-1-yl)-2-oxo-ethoxy]-7-methyl-quinoline-2-carbonyl}-amino)-acetyl]-piperazine-1-carboxylic acid butyl ester, 4-{2-[(4-{2-[4-(2-Hydroxy-ethyl)-piperazin-1-yl]-2-oxo-ethoxy}-7-methyl-quinoline-2-carbonyl)-amino]-acetyl}-piperazine-1-carboxylic acid butyl ester, 4-[2-({7-Methyl-4-[2-oxo-2-((S)-2-phenylcarbamoyl-pyrrolidin-1-yl)-ethoxy]-quinoline-2-carbonyl}-amino)-acetyl]-piperazine-1-carboxylic acid butyl ester, 4-[2-({4-[2-((S)-2-Cyclopropylcarbamoyl-pyrrolidin-1-yl)-2-oxo-ethoxy]-7-methyl-quinoline-2-carbonyl}-amino)-acetyl]-piperazine-1-carboxylic acid butyl ester, 4-[2-({4-[2-(3-Methoxy-pyrrolidin-1-yl)-2-oxo-ethoxy]-7-methyl-quinoline-2-carbonyl}-amino)-acetyl]-piperazine-1-carboxylic acid butyl ester, 4-[2-({4-[2-((S)-3-tert-Butoxycarbonylamino-pyrrolidin-1-yl)-2-oxo-ethoxy]-7-methyl-quinoline-2-carbonyl}-amino)-acetyl]-piperazine-1-carboxylic acid butyl ester, 4-{2-([7-Methyl-4-[2-(4-ethoxycarbonyl-piperazin-1-yl)-2-oxo-ethoxy]-quinoline-2-carbonyl]-amino)-acetyl}-piperazine-1-carboxylic acid butyl ester, 4-[2-({4-[2-(4-Hydroxy-piperidin-1-yl)-2-oxo-ethoxy]-7-methyl-quinoline-2-carbonyl}-amino)-acetyl]-piperazine-1-carboxylic acid butyl ester, 4-[2-({4-[2-(4-Ethyl-piperazin-1-yl)-2-oxo-ethoxy]-7-methyl-quinoline-2-carbonyl}-amino)-acetyl]-piperazine-1-carboxylic acid butyl ester, 4-(2-{[7-Methyl-4-(2-oxo-2-piperazin-1-yl-ethoxy)-quinoline-2-carbonyl]-amino}-acetyl)-piperazine-1-carboxylic acid butyl ester, 4-[2-({7-Methyl-4-[2-oxo-2-((S)-2-propylcarbamoyl-pyrrolidin-1-yl)-ethoxy]-quinoline-2-carbonyl}-amino)-acetyl]-piperazine-1-carboxylic acid butyl ester, 4-{2-[(4-{2-[(S)-2-(Cyclopropylmethyl-carbamoyl)-pyrrolidin-1-yl]-2-oxo-ethoxy}-7-methyl-quinoline-2-carbonyl)-amino]-acetyl}-piperazine-1-carboxylic acid butyl ester, 4-{2-[(7-Methyl-4-{2-oxo-2-[(S)-2-(piperidine-1-carbonyl)-pyrrolidin-1-yl]-ethoxy}-quinoline-2-carbonyl)-amino]-acetyl}-piperazine-1-carboxylic acid butyl ester, 4-{2-((4-{2-[(S)-2-(4,4-Difluoro-piperidine-1-carbonyl)-pyrrolidin-1-yl]-2-oxo-ethoxy}-7-methyl-quinoline-2-carbonyl)-amino]-acetyl}-piperazine-1-carboxylic acid butyl ester, 4-[2-({4-[2-((S)-2-Cyclopentylcarbamoyl-pyrrolidin-1-yl)-2-oxo-ethoxy]-7-methyl-quinoline-2-carbonyl}-amino)-acetyl]-piperazine-1-carboxylic acid butyl ester, 4-[2-({4-[2-(2-Furan-2-yl-pyrrolidin-1-yl)-2-oxo-ethoxy]-7-methyl-quinoline-2-carbonyl}-amino)-acetyl]-piperazine-1-carboxylic acid butyl ester, 4-[2-({7-Methyl-4-[2-oxo-2-(3-oxo-pyrrolidin-1-yl)-ethoxy]-quinoline-2-carbonyl}-amino)-acetyl]-piperazine-1-carboxylic acid butyl ester, 4-[2-({7-Methyl-4-[2-oxo-2-((S)-2-phenyl-pyrrolidin-1-yl)-ethoxy]-quinoline-2-carbonyl}-amino)-acetyl]-piperazine-1-carboxylic acid butyl ester, 4-[2-({4-[2-((S)-2-Methoxymethyl-pyrrolidin-1-yl)-2-oxo-ethoxy]-7-methyl-quinoline-2-carbonyl}-amino)-acetyl]-piperazine-1-carboxylic acid butyl ester, 4-{2-[(7-Methyl-4-{2-oxo-2-[(S)-2-(pyridin-2-ylcarbamoyl)-pyrrolidin-1-yl]-ethoxy}-quinoline-2-carbonyl)-amino]-acetyl}-piperazine-1-carboxylic acid butyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(2H-tetrazol-5-yl)-butyryl]-piperazine-1-carboxylic acid butyl ester, 4-[2-({4-[2-((2S,5S)-2,5-Bis-cyclobutylcarbamoyl-pyrrolidin-1-yl)-2-oxo-ethoxy]-7-methyl-quinoline-2-carbonyl}-amino)-acetyl]-piperazine-1-carboxylic acid butyl ester, 4-{(S)-4-Carboxy-2-[(4-{2-[(S)-2-(2,2-difluoro-cyclopropylcarbamoyl)-pyrrolidin-1-yl]-2-oxo-ethoxy}-7-methyl-quinoline-2-carbonyl)-amino]-butyryl}-piperazine-1-carboxylic acid butyl ester, 4-{2-[(4-{2-[(S)-2-(2,2-Difluoro-cyclopropylcarbamoyl)-pyrrolidin-1-yl]-2-oxo-ethoxy}-7-methyl-quinoline-2-carbonyl)-amino]-acetyl}-piperazine-1-carboxylic acid butyl ester, 4-[2-({4-[2-(5,6-Dihydro-8H-[1,2,4]triazolo[4,3-a]pyrazin-7-yl)-2-oxo-ethoxy]-7-methyl-quinoline-2-carbonyl}-amino)-acetyl]-piperazine-1-carboxylic acid butyl ester, 4-[2-({7-Methyl-4-[2-oxo-2-(2-o-tolyl-pyrrolidin-1-yl)-ethoxy]-quinoline-2-carbonyl}-amino)-acetyl]-piperazine-1-carboxylic acid butyl ester, 4-{2-[(4-{2-[(S)-2-(Ethyl-methyl-carbamoyl)-pyrrolidin-1-yl]-2-oxo-ethoxy}-7-methyl-quinoline-2-carbonyl)-amino]-acetyl}-piperazine-1-carboxylic acid butyl ester, 4-[(S)-2-({4-[2-((S)-2-Cyclobutylcarbamoyl-4,4-difluoro-pyrrolidin-1-yl)-2-oxo-ethoxy]-7-methyl-quinoline-2-carbonyl}-amino)-4-cyclopentylmethoxycarbonyl-butyryl]piperazine-1-carboxylic acid butyl ester, 4-[2-({4-[2-((S)-3-Amino-pyrrolidin-1-yl)-2-oxo-ethoxy]-7-methyl-quinoline-2-carbonyl}-amino)-acetyl]-piperazine-1-carboxylic acid butyl ester, 4-[2-({4-[2-((S)-2-Cyclobutylcarbamoyl-pyrrolidin-1-yl)-2-oxo-ethoxy]-7-methyl-quinoline-2-carbonyl}-amino)-acetyl]-piperazine-1-carboxylic acid cyclobutyl ester, 4-[2-({4-[2-((S)-2-Cyclobutylcarbamoyl-pyrrolidin-1-yl)-2-oxo-ethoxy]-7-methyl-quinoline-2-carbonyl}-amino)-acetyl]-piperazine-1-carboxylic acid cyclopropylmethyl ester, 4-[(S)-2-({4-[2-((S)-2-Cyclobutylcarbamoyl-pyrrolidin-1-yl)-2-oxo-ethoxy]-7-methoxy-quinoline-2-carbonyl}-amino)-4-cyclopentylmethoxycarbonyl-butyryl]-piperazine-1-carboxylic acid butyl ester, 4-[(R)-2-({4-[2-((S)-2-Cyclobutylcarbamoyl-pyrrolidin-1-yl)-2-oxo-ethoxy]-7-methyl-quinoline-2-carbonyl}-amino)-3-fluoro-propionyl]-piperazine-1-carboxylic acid ethyl ester, 4-[(R)-2-({4-[2-((S)-2-Cyclobutylcarbamoyl-pyrrolidin-1-yl)-2-oxo-ethoxy]-7-methyl-quinoline-2-carbonyl}-amino)-3-fluoro-propionyl]-piperazine-1-carboxylic acid butyl ester, 4-[2-({4-[2-((S)-2-Cyclobutylcarbamoyl-pyrrolidin-1-yl)-2-oxo-ethoxy]-7-methoxy-quinoline-2-carbonyl}-amino)-acetyl]-piperazine-1-carboxylic acid butyl ester, 3-(2-{2-[2-(4-Butoxycarbonyl-piperazin-1-yl)-2-oxo-ethylcarbamoyl]-7-methyl-quinolin-4-yloxy}-acetyl)-3-aza-bicyclo[3.1.0]hexane-6-carboxylic acid ethyl ester, 4-[2-({7-Methyl-4-[2-oxo-2-(2-trifluoromethoxymethyl-pyrrolidin-1-yl)-ethoxy]-quinoline-2-carbonyl}-amino)-acetyl]-piperazine-1-carboxylic acid butyl ester, 4-[2-({4-[2-(2,4-Dioxo-1,3,8-triaza-spiro[4.5]dec-8-yl)-2-oxo-ethoxy]-7-methyl-quinoline-2-carbonyl}-amino)-acetyl]-piperazine-1-carboxylic acid butyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(5-oxo-4,5-dihydro-[1,3,4]oxadiazol-2-yl)-butyryl]-piperazine-1-carboxylic acid ethyl ester, 4-[2-({4-[2-(3-Hydroxy-4,7-dihydro-5H-isoxazolo[5,4-c]pyridin-6-yl)-2-oxo-ethoxy]-7-methyl-quinoline-2-carbonyl}-amino)-acetyl]-piperazine-1-carboxylic acid butyl ester, 4-{2-[(4-{2-[2-(1H-Benzoimidazol-2-yl)-pyrrolidin-1-yl]-2-oxo-ethoxy}-7-methyl-quinoline-2-carbonyl)-amino]-acetyl}-piperazine-1-carboxylic acid butyl ester, 4-[2-({4-[(R)-2-((S)-2-Cyclobutylcarbamoyl-pyrrolidin-1-yl)-1-methyl-2-oxo-ethoxy]-7-methyl-quinoline-2-carbonyl}-amino)-acetyl]-piperazine-1-carboxylic acid butyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4,4-difluoro-butyryl]-piperazine-1-carboxylic acid ethyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4,4-difluoro-butyryl]-piperazine-1-carboxylic acid butyl ester, 4-{2-[(7-Methyl-4-{2-[(S)-2-(morpholine-4-carbonyl)-pyrrolidin-1-yl]-2-oxo-ethoxy}-quinoline-2-carbonyl)-amino]-acetyl}-piperazine-1-carboxylic acid butyl ester, 4-[2-({4-[2-((S)-2-Cyclobutylcarbamoyl-pyrrolidin-1-yl)-2-oxo-ethoxy]-7-methyl-quinoline-2-carbonyl}-methyl-amino)-acetyl]-piperazine-1-carboxylic acid butyl ester, 4-[2-({7-Methyl-4-[2-oxo-2-(6-oxo-hexahydro-pyrrolo[1,2-a]pyrazin-2-yl)-ethoxy]-quinoline-2-carbonyl}-amino)-acetyl]-piperazine-1-carboxylic acid butyl ester, 4-[2-({4-[2-(2,4-Dioxo-1,3,7-triaza-spiro[4.5]dec-7-yl)-2-oxo-ethoxy]-7-methyl-quinoline-2-carbonyl}-amino)-acetyl]-piperazine-1-carboxylic acid butyl ester, 4-[2-({7-Methyl-4-[2-oxo-2-(3-trifluoromethyl-4,6-dihydro-1H-pyrrolo[3,4-c]pyrazol-5-yl)-ethoxy]-quinoline-2-carbonyl}-amino)-acetyl]-piperazine-1-carboxylic acid butyl ester, 4-[2-({4-[2-((R)-3-Dimethylamino-pyrrolidin-1-yl)-2-oxo-ethoxy]-7-methyl-quinoline-2-carbonyl}-amino)-acetyl]-piperazine-1-carboxylic acid butyl ester, 4-[2-({7-Methyl-4-[2-oxo-2-((S)-2-trifluoromethyl-pyrrolidin-1-yl)-ethoxy]-quinoline-2-carbonyl}-amino)-acetyl]-piperazine-1-carboxylic acid butyl ester, 4-[2-({4-[2-((R)-3-Acetylamino-pyrrolidin-1-yl)-2-oxo-ethoxy]-7-methyl-quinoline-2-carbonyl}-amino)-acetyl]-piperazine-1-carboxylic acid butyl ester, 4-[2-({7-Methyl-4-[2-oxo-2-(2-trifluoromethyl-pyrrolidin-1-yl)-ethoxy]-quinoline-2-carbonyl}-amino)-acetyl]-piperazine-1-carboxylic acid butyl ester, 4-[2-({4-[2-((S)-3-Dimethylamino-pyrrolidin-1-yl)-2-oxo-ethoxy]-7-methyl-quinoline-2-carbonyl}-amino)-acetyl]-piperazine-1-carboxylic acid butyl ester, 4-(2-{[4-((R)-2-Hexahydro-pyrrolo[1,2-a]pyrazin-2-yl-2-oxo-ethoxy)-7-methyl-quinoline-2-carbonyl}-amino]-acetyl)-piperazine-1-carboxylic acid butyl ester, 4-{2-[(4-{2-[2-(1H-Indol-2-yl)-pyrrolidin-1-yl]-2-oxo-ethoxy}-7-methyl-quinoline-2-carbonyl)-amino]-acetyl}-piperazine-1-carboxylic acid butyl ester, 4-{2-[(7-Methyl-4-{2-[2-(3-methyl-[1,2,4]oxadiazol-5-yl)-pyrrolidin-1-yl]-2-oxo-ethoxy}-quinoline-2-carbonyl)-amino]-acetyl}-piperazine-1-carboxylic acid butyl ester, 4-[2-({4-[2-((2S,4S)-2-Cyano-4-fluoro-pyrrolidin-1-yl)-2-oxo-ethoxy]-7-methyl-quinoline-2-carbonyl}-amino)-acetyl]-piperazine-1-carboxylic acid butyl ester, (2S,3aR,7aR)-1-(2-{2-[2-(4-Butoxycarbonyl-piperazin-1-yl)-2-oxo-ethylcarbamoyl]-7-methyl-quinolin-4-yloxy}-acetyl)-octahydro-indole-2-carboxylic acid, 4-[2-({7-Methyl-4-[2-oxo-2-(3-trifluoromethyl-pyrrolidin-1-yl)-ethoxy]-quinoline-2-carbonyl}-amino)-acetyl]-piperazine-1-carboxylic acid butyl ester, 4-[2-({7-Methyl-4-[2-oxo-2-((R)-2-trifluoromethyl-pyrrolidin-1-yl)-ethoxy]-quinoline-2-carbonyl}-amino)-acetyl]-piperazine-1-carboxylic acid butyl ester, 4-[2-({4-[2-((2S,5R)-2-Carboxy-5-phenyl-pyrrolidin-1-yl)-2-oxo-ethoxy]-7-methyl-quinoline-2-carbonyl}-amino)-acetyl]-piperazine-1-carboxylic acid butyl ester, 4-[2-({7-Methyl-4-[2-(2-methyl-6,7-dihydro-4H-oxazolo[5,4-c]pyridin-5-yl)-2-oxo-ethoxy]-quinoline-2-carbonyl}-amino)-acetyl]-piperazine-1-carboxylic acid butyl ester, 4-[2-({4-[2-(3-Methanesulfonyl-pyrrolidin-1-yl)-2-oxo-ethoxy]-7-methyl-quinoline-2-carbonyl}-amino)-acetyl]-piperazine-1-carboxylic acid butyl ester, 4-[2-({4-[2-(3-Ethoxy-piperidin-1-yl)-2-oxo-ethoxy]-7-methyl-quinoline-2-carbonyl}-amino)-acetyl]-piperazine-1-carboxylic acid butyl ester, 4-[2-({7-Methyl-4-[2-oxo-2-(1-oxo-2,8-diaza-spiro[4.5]dec-8-yl)-ethoxy]-quinoline-2-carbonyl}-amino)-acetyl]-piperazine-1-carboxylic acid butyl ester, 4-[(S)-2-({4-[(R)-2-((S)-2-Cyclobutylcarbamoyl-pyrrolidin-1-yl)-1-methyl-2-oxo-ethoxy]-7-methyl-quinoline-2-carbonyl}-amino)-4-hydroxy-butyryl]-piperazine-1-carboxylic acid ethyl ester, 4-[2-({7-Methyl-4-[2-(1-methyl-4,6-dihydro-1H-pyrrolo[3,4-c]pyrazol-5-yl)-2-oxo-ethoxy]-quinoline-2-carbonyl}-amino)-acetyl]-piperazine-1-carboxylic acid butyl ester, 4-[2-({4-[2-((1R,4R)-5-Ethyl-2,5-diaza-bicyclo[2.2.1]hept-2-yl)-2-oxo-ethoxy]-7-methyl-quinoline-2-carbonyl}-amino)-acetyl]-piperazine-1-carboxylic acid butyl ester, 4-[2-({4-[2-((R)-3-tert-Butoxycarbonylamino-pyrrolidin-1-yl)-2-oxo-ethoxy]-7-methyl-quinoline-2-carbonyl}-amino)-acetyl]-piperazine-1-carboxylic acid butyl ester, 4-[2-({4-[2-(4-Cyanomethyl-piperazin-1-yl)-2-oxo-ethoxy]-7-methyl-quinoline-2-carbonyl}-amino)-acetyl]-piperazine-1-carboxylic acid butyl ester, 4-{2-[(4-{2-[3-(Acetyl-methyl-amino)-pyrrolidin-1-yl]-2-oxo-ethoxy}-7-methyl-quinoline-2-carbonyl)-amino]-acetyl}-piperazine-1-carboxylic acid butyl ester, 4-{2-[(7-Methyl-4-{2-[2-(6-methyl-pyridin-2-yl)-pyrrolidin-1-yl]-2-oxo-ethoxy}-quinoline-2-carbonyl)-amino]-acetyl}-piperazine-1-carboxylic acid butyl ester, 4-{2-[(7-Methyl-4-{2-oxo-2-[4-(pyrrolidine-1-carbonyl)-piperazin-1-yl]-ethoxy}-quinoline-2-carbonyl)-amino]-acetyl}-piperazine-1-carboxylic acid butyl ester, 4-[2-({4-[2-(3-Methoxy-piperidin-1-yl)-2-oxo-ethoxy]-7-methyl-quinoline-2-carbonyl}-amino)-acetyl]-piperazine-1-carboxylic acid butyl ester, 4-[2-({4-[2-(4-Methoxy-piperidin-1-yl)-2-oxo-ethoxy]-7-methyl-quinoline-2-carbonyl}-amino)-acetyl]-piperazine-1-carboxylic acid butyl ester, 4-[2-({4-[2-(4-Acetylamino-piperidin-1-yl)-2-oxo-ethoxy]-7-methyl-quinoline-2-carbonyl}-amino)-acetyl]-piperazine-1-carboxylic acid butyl ester, 4-[2-({4-[2-((S)-3-Acetylamino-pyrrolidin-1-yl)-2-oxo-ethoxy]-7-methyl-quinoline-2-carbonyl}-amino)-acetyl]-piperazine-1-carboxylic acid butyl ester, 4-[2-({7-Methyl-4-[2-(1-methyl-3-trifluoromethyl-1,4,6,7-tetrahydro-pyrazolo[4,3-c]pyridin-5-yl)-2-oxo-ethoxy]-quinoline-2-carbonyl}-amino)-acetyl]-piperazine-1-carboxylic acid butyl ester, 4-[2-({4-[2-((S)-2-Cyclobutylcarbamoyl-pyrrolidin-1-yl)-2-oxo-ethoxy]-6,7-dimethyl-quinoline-2-carbonyl}-amino)-acetyl]-piperazine-1-carboxylic acid butyl ester, 4-[2-({7-Methyl-4-[2-(2-methyl-octahydro-pyrrolo[3,4-c]pyridin-5-yl)-2-oxo-ethoxy]-quinoline-2-carbonyl}-amino)-acetyl]-piperazine-1-carboxylic acid butyl ester, 4-{2-[(7-Methyl-4-{2-oxo-2-[4-(pyrrolidine-1-carbonyl)-piperidin-1-yl]-ethoxy}-quinoline-2-carbonyl)-amino]-acetyl}-piperazine-1-carboxylic acid butyl ester, 4-[2-({4-[2-((2S,4R)-2-Ethoxycarbonyl-4-hydroxy-pyrrolidin-1-yl)-2-oxo-ethoxy]-7-methyl-quinoline-2-carbonyl}-amino)-acetyl]-piperazine-1-carboxylic acid butyl ester, 4-{2-[(7-Methyl-4-{2-[(S)-2-(4-methyl-piperidine-1-carbonyl)-pyrrolidin-1-yl]-2-oxo-ethoxy}-quinoline-2-carbonyl)-amino]-acetyl}-piperazine-1-carboxylic acid butyl ester, 4-[2-({4-[2-((S)-2-Cyclobutylcarbamoyl-pyrrolidin-1-yl)-2-oxo-ethoxy]-7-methyl-quinoline-2-carbonyl}-methyl-amino)-acetyl]-piperazine-1-carboxylic acid ethyl ester, 4-{2-[(4-{2-[(S)-2-(3,4-Dihydro-2H-quinoline-1-carbonyl)-pyrrolidin-1-yl]-2-oxo-ethoxy}-7-methyl-quinoline-2-carbonyl)-amino]-acetyl}-piperazine-1-carboxylic acid butyl ester, 4-{2-[(4-{2-[(S)-2-(2,3-Dihydro-indole-1-carbonyl)-pyrrolidin-1-yl]-2-oxo-ethoxy}-7-methyl-quinoline-2-carbonyl)-amino]-acetyl}-piperazine-1-carboxylic acid butyl ester, 4-[2-({4-[2-((S)-4-Cyclobutylcarbamoyl-oxazolidin-3-yl)-2-oxo-ethoxy]-7-methyl-quinoline-2-carbonyl}-amino)-acetyl]-piperazine-1-carboxylic acid butyl ester, 4-[2-({4-[2-(3-Dimethylamino-pyrrolidin-1-yl)-2-oxo-ethoxy]-7-methyl-quinoline-2-carbonyl}-amino)-acetyl]-piperazine-1-carboxylic acid butyl ester, 4-{2-[(7-Methyl-4-{2-oxo-2-[(S)-2-(1H-tetrazol-5-ylmethyl)-pyrrolidin-1-yl]-ethoxy}-quinoline-2-carbonyl)-amino]-acetyl}-piperazine-1-carboxylic acid butyl ester, 4-[2-({7-Methyl-4-[2-oxo-2-(1-oxo-2,7-diaza-spiro[4.5]dec-7-yl)-ethoxy]-quinoline-2-carbonyl}-amino)-acetyl]-piperazine-1-carboxylic acid butyl ester, 4-[2-({4-[2-(3-Dimethylamino-piperidin-1-yl)-2-oxo-ethoxy]-7-methyl-quinoline-2-carbonyl}-amino)-acetyl]-piperazine-1-carboxylic acid butyl ester, 4-[2-({4-[2-(4-Cyclobutyl-piperazin-1-yl)-2-oxo-ethoxy]-7-methyl-quinoline-2-carbonyl}-amino)-acetyl]-piperazine-1-carboxylic acid butyl ester, 4-[2-({4-[2-((S)-2-Cyclobutylcarbamoyl-pyrrolidin-1-yl)-2-oxo-ethoxy]-quinoline-2-carbonyl}-amino)-acetyl]-piperazine-1-carboxylic acid butyl ester, 4-[2-({7-Chloro-4-[2-((S)-2-cyclobutylcarbamoyl-pyrrolidin-1-yl)-2-oxo-ethoxy]-quinoline-2-carbonyl}-amino)-acetyl]-piperazine-1-carboxylic acid butyl ester, 4-[(S)-2-({4-[(R)-2-((S)-2-Cyclobutylcarbamoyl-pyrrolidin-1-yl)-1-methyl-2-oxo-ethoxy]-7-methyl-quinoline-2-carbonyl}-amino)-4-methoxycarbonyl-butyryl]-piperazine-1-carboxylic acid ethyl ester, 4-[(S)-2-({4-[(R)-2-((S)-2-Cyclobutylcarbamoyl-pyrrolidin-1-yl)-1-methyl-2-oxo-ethoxy]-7-methyl-quinoline-2-carbonyl}-amino)-4-hydroxy-butyryl]-piperazine-1-carboxylic acid cyclobutyl ester, 4-[2-({4-[2-((S)-2-Cyclobutylcarbamoyl-pyrrolidin-1-yl)-2-oxo-ethoxy]-6-fluoro-5-methyl-quinoline-2-carbonyl}-amino)-acetyl]-piperazine-1-carboxylic acid butyl ester, 4-[(S)-2-({4-[(R)-2-((S)-2-Cyclobutylcarbamoyl-pyrrolidin-1-yl)-1-methyl-2-oxo-ethoxy]-7-methyl-quinoline-2-carbonyl}-amino)-4-hydroxy-butyryl]-piperazine-1-carboxylic acid cyclopropylmethyl ester, 4-[2-({4-[2-((S)-2-Cyclobutylcarbamoyl-pyrrolidin-1-yl)-2-oxo-ethoxy]-7-methyl-quinoline-2-carbonyl}-amino)-acetyl]-piperazine-1-carboxylic acid 3,3,3-trifluoro-propyl ester, 4-[2-({6-Chloro-4-[2-((S)-2-cyclobutylcarbamoyl-pyrrolidin-1-yl)-2-oxo-ethoxy]-7-methyl-quinoline-2-carbonyl}-amino)-acetyl]-piperazine-1-carboxylic acid butyl ester, 4-[(S)-2-({4-[(R)-2-((S)-2-Cyclobutylcarbamoyl-pyrrolidin-1-yl)-1-methyl-2-oxo-ethoxy]-7-methyl-quinoline-2-carbonyl}-amino)-4-(1H-tetrazol-5-yl)-butyryl]-piperazine-1-carboxylic acid butyl ester, 4-[(S)-2-({4-[(S)-2-((S)-2-Cyclobutylcarbamoyl-pyrrolidin-1-yl)-1-methyl-2-oxo-ethoxy]-7-methyl-quinoline-2-carbonyl}-amino)-4-(1H-tetrazol-5-yl)-butyryl]-piperazine-1-carboxylic acid butyl ester, 4-[(S)-4-Hydroxy-2-({7-methyl-4-[2-oxo-2-((S)-2-phenyl-pyrrolidin-1-yl)-ethoxy]-quinoline-2-carbonyl}-amino)-butyryl]-piperazine-1-carboxylic acid butyl ester, 4-[2-({4-[2-((S)-2-Cyclobutylcarbamoyl-pyrrolidin-1-yl)-2-oxo-ethoxy]-6,7-difluoro-quinoline-2-carbonyl}-amino)-acetyl]-piperazine-1-carboxylic acid butyl ester, 4-[2-({7-Cyano-4-[2-((S)-2-cyclobutylcarbamoyl-pyrrolidin-1-yl)-2-oxo-ethoxy]-quinoline-2-carbonyl}-amino)-acetyl]-piperazine-1-carboxylic acid butyl ester, 4-{(S)-4-Carboxy-2-[(4-{2-[(S)-2-(4-fluoro-phenyl)-pyrrolidin-1-yl]-2-oxo-ethoxy}-7-methyl-quinoline-2-carbonyl)-amino]-butyryl}-piperazine-1-carboxylic acid butyl ester, 4-{(S)-4-Carboxy-2-[(4-{2-[(S)-2-(4-fluoro-phenyl)-pyrrolidin-1-yl]-2-oxo-ethoxy}-6,7-dimethyl-quinoline-2-carbonyl)-amino]-butyryl}-piperazine-1-carboxylic acid butyl ester, 4-[2-({4-[2-((2S,4R)-4-Cyano-2-cyclopropylcarbamoyl-pyrrolidin-1-yl)-2-oxo-ethoxy]-7-methyl-quinoline-2-carbonyl}-amino)-acetyl]-piperazine-1-carboxylic acid butyl ester, 4-[2-({4-[2-((2S,4R)-2-Cyclobutylcarbamoyl-4-hydroxy-pyrrolidin-1-yl)-2-oxo-ethoxy]-7-methyl-quinoline-2-carbonyl}-amino)-acetyl]-piperazine-1-carboxylic acid butyl ester, 4-{2-[(7-Methyl-4-{2-oxo-2-[(S)-2-(1H-tetrazol-5-yl)-pyrrolidin-1-yl]-ethoxy}-quinoline-2-carbonyl)-amino]-acetyl}-piperazine-1-carboxylic acid butyl ester, 4-{(S)-4-Carboxy-2-[(4-{(R)-2-[(S)-2-(4-fluoro-phenyl)-pyrrolidin-1-yl]-1-methyl-2-oxo-ethoxy}-7-methyl-quinoline-2-carbonyl)-amino]-butyryl}-piperazine-1-carboxylic acid butyl ester, 4-[2-({4-[2-((2S,4R)-4-Cyano-2-cyclobutylcarbamoyl-pyrrolidin-1-yl)-2-oxo-ethoxy]-7-methyl-quinoline-2-carbonyl}-amino)-acetyl]-piperazine-1-carboxylic acid butyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(2-methyl-2H-tetrazol-5-yl)-butyryl]-piperazine-1-carboxylic acid butyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-4-(1-methyl-1H-tetrazol-5-yl)-butyryl]-piperazine-1-carboxylic acid butyl ester, 4-{2-[(7-Methyl-4-{2-[(S)-2-(1-methyl-azetidin-3-ylcarbamoyl)-pyrrolidin-1-yl]-2-oxo-ethoxy}-quinoline-2-carbonyl)-amino]-acetyl]-piperazine-1-carboxylic acid butyl ester, 4-{2-[(7-Methyl-4-{2-[(S)-2-(4-methyl-piperazine-1-carbonyl)-pyrrolidin-1-yl]-2-oxo-ethoxy}-quinoline-2-carbonyl)-amino]-acetyl}-piperazine-1-carboxylic acid butyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-3-(1H-[1,2,3]triazol-4-yl)-propionyl]-piperazine-1-carboxylic acid butyl ester, 4-[(S)-2-({4-[2-((S)-2-Cyclobutylcarbamoyl-pyrrolidin-1-yl)-2-oxo-ethoxy]-7-methyl-quinoline-2-carbonyl}-amino)-3-(3-hydroxy-5-methyl-isoxazol-4-yl)-propionyl]-piperazine-1-carboxylic acid butyl ester, 4-[(S)-4-Ethoxycarbonyl-2-({7-methyl-4-[2-oxo-2-((S)-2-phenyl-pyrrolidin-1-yl)-ethoxy]-quinoline-2-carbonyl}-amino)-butyryl]-piperazine-1-carboxylic acid butyl ester, 4-{2-[(7-Methyl-4-{2-oxo-2-[(S)-2-(2,2,2-trifluoro-ethylcarbamoyl)-pyrrolidin-1-yl]-ethoxy}-quinoline-2-carbonyl)-amino]-acetyl}-piperazine-1-carboxylic acid butyl ester, 4-[(S)-2-({4-[2-(3,3-Difluoro-pyrrolidin-1-yl)-2-oxo-ethoxy]-7-methyl-quinoline-2-carbonyl}-amino)-4-(2H-tetrazol-5-yl)-butyryl]-piperazine-1-carboxylic acid butyl ester, 4-[(S)-2-({4-[2-((R)-3-Hydroxy-pyrrolidin-1-yl)-2-oxo-ethoxy]-7-methyl-quinoline-2-carbonyl}-amino)-4-(2H-tetrazol-5-yl)-butyryl]-piperazine-1-carboxylic acid butyl ester, 4-[(S)-2-({4-[2-(4-Methoxy-piperidin-1-yl)-2-oxo-ethoxy]-7-methyl-quinoline-2-carbonyl}-amino)-4-(2H-tetrazol-5-yl)-butyryl]-piperazine-1-carboxylic acid butyl ester, 4-[(S)-2-({4-[2-((S)-2-Cyano-pyrrolidin-1-yl)-2-oxo-ethoxy]-7-methyl-quinoline-2-carbonyl}-amino)-4-(2H-tetrazol-5-yl)-butyryl]-piperazine-1-carboxylic acid butyl ester, 4-[(R)-2-({4-[2-((2S,4S)-2-Cyclobutylcarbamoyl-4-hydroxy-pyrrolidin-1-yl)-2-oxo-ethoxy]-7-methyl-quinoline-2-carbonyl}-amino)-3-fluoro-propionyl]-piperazine-1-carboxylic acid butyl ester, 4-((R)-3-Fluoro-2-{[7-methyl-4-(2-oxo-2-piperazin-1-yl-ethoxy)-quinoline-2-carbonyl]-amino}-propionyl)-piperazine-1-carboxylic acid butyl ester, 4-[(S)-4-Carboxy-2-({4-[2-((R)-2-hydroxymethyl-pyrrolidin-1-yl)-2-oxo-ethoxy]-7-methyl-quinoline-2-carbonyl}-amino)-butyryl]-piperazine-1-carboxylic acid ethyl ester, 4-[2-({4-[2-((S)-2-tert-Butylcarbamoyl-pyrrolidin-1-yl)-2-oxo-ethoxy]-quinoline-2-carbonyl}-amino)-acetyl]-piperazine-1-carboxylic acid butyl ester, 4-[2-({4-[2-((S)-2-Methylcarbamoyl-pyrrolidin-1-yl)-2-oxo-ethoxy]-quinoline-2-carbonyl}-amino)-acetyl]-piperazine-1-carboxylic acid butyl ester, 4-[2-({4-[2-((S)-2-Ethylcarbamoyl-pyrrolidin-1-yl)-2-oxo-ethoxy]-quinoline-2-carbonyl}-amino)-acetyl]-piperazine-1-carboxylic acid butyl ester, 4-[2-({4-[2-Oxo-2-(1-oxo-2,7-diaza-spiro[4.5]dec-7-yl)-ethoxy]-quinoline-2-carbonyl}-amino)-acetyl]-piperazine-1-carboxylic acid butyl ester, 4-[2-({4-[2-oxo-2-(3-oxo-piperazin-1-yl)-ethoxy]-quinoline-2-carbonyl}-amino)-acetyl]-piperazine-1-carboxylic acid butyl ester, 4-{2-[(4-{2-[4-(2-Hydroxy-ethyl)-piperazin-1-yl]-2-oxo-ethoxy}-quinoline-2-carbonyl)-amino]-acetyl}-piperazine-1-carboxylic acid butyl ester, 4-[2-({4-[2-((S)-2-Cyano-pyrrolidin-1-yl)-2-oxo-ethoxy]-quinoline-2-carbonyl}-amino)-acetyl]-piperazine-1-carboxylic acid butyl ester, 4-[2-({4-[2-(5,6-Dihydro-8H-[1,2,4]triazolo[4,3-a]pyrazin-7-yl)-2-oxo-ethoxy]-quinoline-2-carbonyl}-amino)-acetyl]-piperazine-1-carboxylic acid butyl ester, 4-[2-({4-[2-((2S,4S)-2-Cyano-4-fluoro-pyrrolidin-1-yl)-2-oxo-ethoxy]-quinoline-2-carbonyl}-amino)-acetyl]-piperazine-1-carboxylic acid butyl ester, 4-[2-({4-[2-(2-Methyl-octahydro-pyrrolo[3,4-c]pyridin-5-yl)-2-oxo-ethoxy]-quinoline-2-carbonyl}-amino)-acetyl]-piperazine-1-carboxylic acid butyl ester, 4-[2-({4-[(R)-2-((S)-2-Cyano-pyrrolidin-1-yl)-1-methyl-2-oxo-ethoxy]-7-methyl-quinoline-2-carbonyl}-amino)-acetyl]-piperazine-1-carboxylic acid butyl ester, 4-[2-({4-[(R)-2-(3-Hydroxy-azetidin-1-yl)-1-methyl-2-oxo-ethoxy]-7-methyl-quinoline-2-carbonyl}-amino)-acetyl]-piperazine-1-carboxylic acid butyl ester, 4-[2-({4-[(R)-2-(3,3-Difluoro-pyrrolidin-1-yl)-1-methyl-2-oxo-ethoxy]-7-methyl-quinoline-2-carbonyl}-amino)-acetyl]-piperazine-1-carboxylic acid butyl ester, 4-[2-({7-Methyl-4-[(R)-1-methyl-2-(2-methyl-octahydro-pyrrolo[3,4-c]pyridin-5-yl)-2-oxo-ethoxy]-quinoline-2-carbonyl}-amino)-acetyl]-piperazine-1-carboxylic acid butyl ester, 4-[2-({4-[(R)-2-((2S,4R)-4-Cyano-2-cyclobutylcarbamoyl-pyrrolidin-1-yl)-1-methyl-2-oxo-ethoxy]-7-methyl-quinoline-2-carbonyl}-amino)-acetyl]-piperazine-1-carboxylic acid butyl ester, 4-[2-({4-[2-((2S,4R)-4-Cyano-2-cyclobutylcarbamoyl-pyrrolidin-1-yl)-2-oxo-ethoxy]-6,7-dimethyl-quinoline-2-carbonyl}-amino)-acetyl]-piperazine-1-carboxylic acid butyl ester, or 4-[2-({7-Chloro-4-[2-((2S,4R)-4-cyano-2-cyclobutylcarbamoyl-pyrrolidin-1-yl)-2-oxo-ethoxy]-quinoline-2-carbonyl}-amino)-acetyl]-piperazine-1-carboxylic acid butyl ester.

7. A process for the preparation of a compound of formula I as claimed in claim 1, which comprises reacting a compound of formula XI with a compound of formula VII to give a compound of formula II,

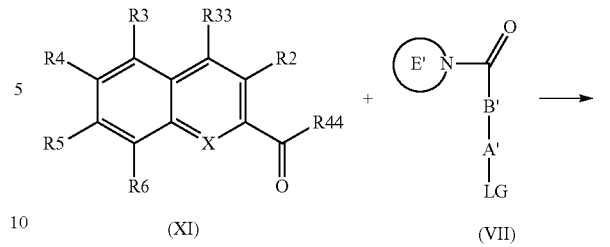

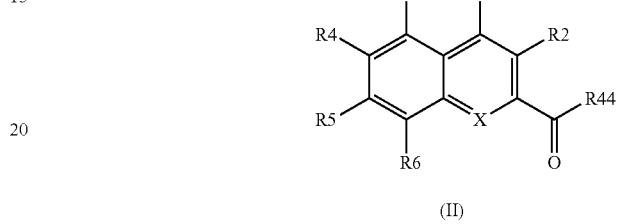

wherein the residues R2, R3, R4, R5, R6, X, A, B and E are as defined in formula I, R33 is oxygen, sulfur or nitrogen atom, LG is Cl, Br, J, tosyloxy, mesyloxy or trifluormethyl-sulfonyloxy, R44 is —OH or —($C_1$-$C_4$)-alkoxy and R43 is a compound of the formula VI or a precursor of a compound of the formula VI

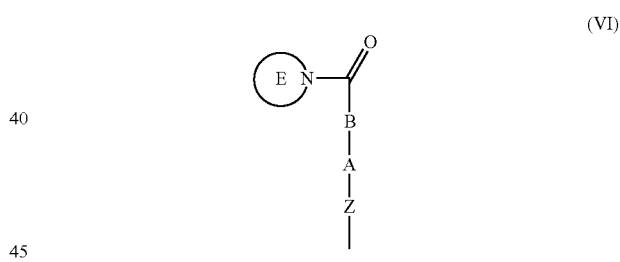

and reacting a compound of formula II with a compound of formula IV

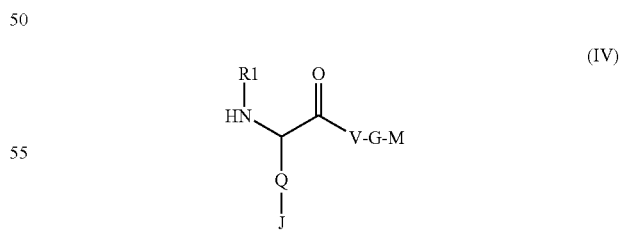

wherein R1, Q, J, V, G and M are as defined in claim 1, to give a compound of formula I.

8. A process for the preparation of a compound of formula I as claimed in claim 1, which comprises reacting a compound of formula XI with a compound of formula H-R45 to give a compound of formula XII, followed by a reaction of compound XII with LG-R43 to give a compound of formula III,

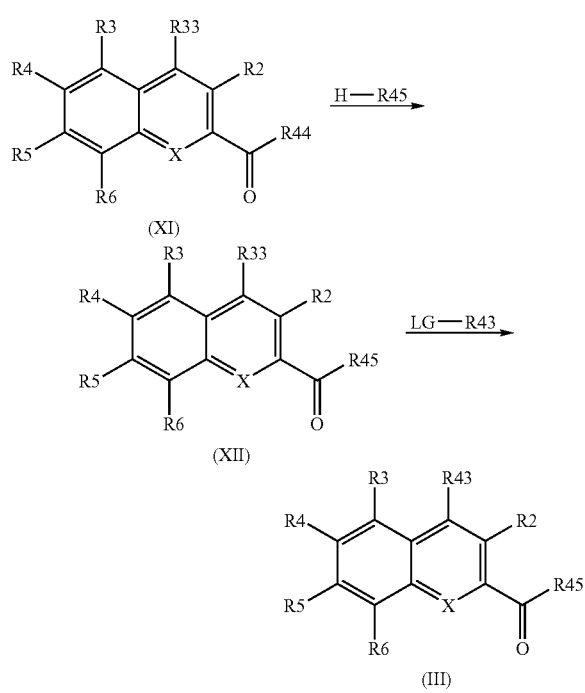

wherein the residues R2, R3, R4, R5, R6, X, A, B and E are as defined in claim 1, R33 is oxygen, sulfur or nitrogen atom, LG is Cl, Br, J, tosyloxy, mesyloxy or trifluormethyl-sulfonyloxy, R44 is —OH or —($C_1$-$C_4$)-alkoxy and R45 is a compound of the formula V or a precursor of a compound of the formula V

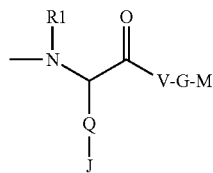

and R43 is a compound of formula VI or a precursor of a compound of the formula VI

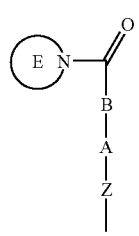

wherein R1, Q, J, V, G and M are as defined in claim 1, to give a compound of formula I.

9. A pharmaceutical composition, comprising at least one compound of as claimed in claim 1 in all its stereoisomeric forms and mixtures thereof in any ratio, and its physiologically tolerable salts, and a pharmaceutically acceptable carrier.

10. A pharmaceutical composition comprising a compound as claimed in claim 1 and a pharmaceutically acceptable carrier, in combination with
an anti-arrhythmic agent;
a K+ channel opener,
an antihypertensive agent;
a calcium channel blockers;
a diruetic;
a renin inhibitor;
an angiotensin-converting enzyme (ACE) inhibitor;
an angiotensin AT-I receptor antagonist such;
an ET-A receptor antagonist;
a dual ET-A/AT-I antagonist;
a neutral endopeptidase inhibitor (NEP);
a vasopepsidase inhibitor;
a dual NEP-ACE inhibitor;
a β-blocker;
a non-steroidal anti-inflammatory drug (NSAID);
a glycoprotein IIb/IIIa blocker;
a thromboxane-A2-receptor antagonist;
a thromboxane-A2-synthetase inhibitor;
a phosphodiesterase-III (PDE-III) inhibitor;
a PDE V inhibitors;
a protease-activated receptor 1 (PAR-I) antagonist;
an anticoagulant;
a direct acting thrombin inhibitor;
a factor VIIa inhibitor;
a factor Xa inhibitor;
a factor XIa inhibitor;
an inhibitor of activated procarboxypeptidase U (TAFIa);
an inhibitor of plasminogen activator inhibitor 1 (PAI-1);
a thrombin inhibitor;
a thrombolytic agent;
an anisoylated plasminogen streptokinase activator complex;
a urokinase;
a cardiac glycoside;
a mineralocorticoid receptor antagonist;
a cholesterol/lipid lowering agent;
a squalene synthetase inhibitor;
a fibrate;
a bile acid sequestrant such as questran;
an ACAT inhibitor;
an MTP inhibitors;
a lipooxygenase inhibitor;
nicotonic acid;
a fenofibric acid derivative;
probucol;
a choesterol absorption inhibitor;
a cholesterol ester transfer protein inhibitor;
an anti-diabetic agent;
an anti-depressant agent;
an anti-inflammatory agent;
an anti-osteoporosis agent;
an estrogen or estradiol;
an anti-obesity agent;
an anti-proliferative agent; or
an anti-ulcer and gastroesophageal reflux disease agent.

11. The pharmaceutical composition claimed in claim 10 wherein
the anti-arrhythmic agent is propafenone, carvadiol, propranolol, sotalol, dofetilide, amiodarone, azimilide, ibutilide, ditiazem or verapamil;
the K+ channel opener is an lAch inhibitor or an IKur inhibitor;
the antihypertensive agent is an alpha adrenergic blocker or a beta adrenergic blocker;

the calcium channel blocker is diltiazem, verapamil, nifedipine, amlodipine or mybefradil;

the diruetic is chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride or spironolactone;

the angiotensin-converting enzyme (ACE) inhibitor is captopril, zofenopril, fosinopril, enalapril, ceranopril, cilazopril, delapril, pentopril, quinapril, ramipril or lisinopril;

the angiotensin AT-I receptor antagonist is losartan, irbesartan or valsartan;

the ET-A receptor antagonist is sitaxsentan or atrsentan;

the dual NEP-ACE inhibitor is omapatrilat, gemopatrilat or nitrates;

the β-blocker is propanolol, nadolol, or carvedilol;

the non-steroidal anti-inflammatory drug (NSAID) is acetaminophen, aspirin, codeine, diclofenac, droxicam, fentaynl, ibuprofen, indomethacin, ketorolac-, mefenamate, morphine, naproxen, phenacetin, piroxicam, sufentanyl, sulfinpyrazone, or sulindac, or a pharmaceutically acceptable salt thereof;

the glycoprotein IIb/IIIa blocker is abciximab, eptifibatide, tirofiban, or integrelin;

the thromboxane-A2-receptor antagonist is ifetroban;

the phosphodiesterase-III (PDE-III) inhibitor is dipyridamole or cilostazol, the PDE V inhibitor is sildenafil;

the protease-activated receptor 1 (PAR-I) antagonist is SCH-530348, SCH-203099, SCH-529153, or SCH-205831, or a pharmaceutically acceptable salt thereof;

the anticoagulant is warfarin, unfractionated heparin or a low molecular weight heparin, or a synthetic pentasaccharide;

the direct acting thrombin inhibitor is hirudin or argatroban;

the factor Xa inhibitor is Arixtra™, apixaban, rivaroxaban, LY-517717, DU-176b, DX-9065a, or otamixaban;

the thrombin inhibitor is a boroarginine derivative, a boropeptide, a heparin, hirudin, argatroban, dabigatran or AZD-0837;

the thrombolytic agent is tissue plasminogen activator (TPA), anistreplase, urokinase, streptokinase, tenecteplase (TNK), or lanoteplase (nPA);

the urokinase is dual or single chain urokinase;

the cardiac glycoside is digitalis or ouabain;

the mineralocorticoid receptor antagonist is sprionolactone or eplirinone;

the cholesterol/lipid lowering agent is an HMG-CoA reductase inhibitor selected from pravastatin, lovastatin, atorvastatin, simvastatin, NK-104, itavastatin, nisvastatin, nisbastatin, ZD-4522, rosuvastatin, atavastatin or visastatin;

the bile acid sequestrants is questran;

the fenofibric acid derivative is gemfibrozil, clofibrat, fenofibrate or benzafibrate;

the cholesterol ester transfer protein inhibitors is CP-529414;

the anti-diabetic agent is metformin, a glucosidase inhibitor; insulin; a meglitinide; a sulfonylurea; a biguanide/glyburide combination, a thiozolidinedione, a PPAR-alpha agonist, a PPAR-gamma agonist, a PPAR alpha/gamma dual agonist, an SGLT2 inhibitor, an inhibitor of fatty acid binding protein (aP2), a glucagon-like peptide-1 (GLP-I), or a dipeptidyl peptidase IV (DPP4) inhibitor;

the anti-depressant agent is nefazodone or sertraline;

the anti-inflammatory agent is prednisone, dexamethasone, enbrel, a protein tyrosine kinase (PTK) inhibitor; a cyclooxygenase inhibitor, aspirin, indomethacin, ibuprofen, prioxicam, naproxen, celecoxib or rofecoxib;

the anti-osteoporosis agent is alendronate or raloxifene;

the anti-obesity agent is orlistat, a P2 inhibitor, a cannabinoid receptor CB1 antagonist, AVE-1625, SR-147778, or CP-945598;

the anti-anxiety agent is diazepam, lorazepam, buspirone, or hydroxyzine pamoate;

the anti-proliferative agent is cyclosporin A, paclitaxel, adriamycin; epithilones, cisplatin, or carboplatin; and the anti-ulcer and gastroesophageal reflux disease agent is famotidine, ranitidine, or omeprazole.

12. A method for treating abnormal thrombus formation, acute myocardial infarction, unstable angina, thromboembolism, acute vessel closure associated with thrombolytic therapy or percutaneous transluminal coronary angioplasty, transient ischemic attacks, stroke, intermittent claudication or bypass grafting of the coronary or peripheral arteries, vessel luminal narrowing, restenosis post coronary or venous angioplasty, maintenance of vascular access patency in long-term hemodialysis patients, pathologic thrombus formation occurring in the veins of the lower extremities following abdominal, knee or hip surgery, pathologic thrombus formation occurring in the veins of the lower extremities following abdominal, knee and hip surgery, a risk of pulmonary thromboembolism, or disseminated systemic intravascular coagulatopathy occurring in vascular systems during septic shock; or treatment or prophylaxis of coronary heart disease, myocardial infarction, angina pectoris, vascular restenosis, restenosis following angioplasty, adult respiratory distress syndrome, and disseminated intravascular clotting disorder, or treatment or prophylaxis of deep vein and proximal vein thrombosis, the method comprising administering to a patient in need thereof an effective dose of a compound as claimed in claim 1, in all its stereoisomeric forms and mixtures thereof in any ratio, or a physiologically tolerable salt thereof.

* * * * *